US012643857B2

(12) United States Patent
Imaizumi

(10) Patent No.: US 12,643,857 B2
(45) Date of Patent: Jun. 2, 2026

(54) LIGHT EMITTING ELEMENT AND POLYCYCLIC COMPOUND FOR THE SAME

(71) Applicant: Samsung Display Co., Ltd., Yongin-si (KR)

(72) Inventor: Taku Imaizumi, Yokohama (JP)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 1018 days.

(21) Appl. No.: 17/833,028

(22) Filed: Jun. 6, 2022

(65) Prior Publication Data

US 2023/0139741 A1 May 4, 2023

(30) Foreign Application Priority Data

Sep. 10, 2021 (KR) ........................ 10-2021-0121220

(51) Int. Cl.

*H01L 51/54* (2006.01)
*C07D 209/82* (2006.01)
*C07D 405/04* (2006.01)
*C07D 405/12* (2006.01)
*C07D 405/14* (2006.01)
*C07D 409/12* (2006.01)
*H10K 85/30* (2023.01)
*H10K 85/60* (2023.01)
*H10K 50/15* (2023.01)

(52) U.S. Cl.

CPC ......... *C07D 209/82* (2013.01); *C07D 405/04* (2013.01); *C07D 405/12* (2013.01); *C07D 405/14* (2013.01); *C07D 409/12* (2013.01); *H10K 85/321* (2023.02); *H10K 85/631* (2023.02); *H10K 85/6572* (2023.02); *H10K 85/6574* (2023.02); *H10K 85/6576* (2023.02); *H10K 50/15* (2023.02)

(58) Field of Classification Search

None

See application file for complete search history.

(56) References Cited

U.S. PATENT DOCUMENTS 10,263,196 B2 4/2019 Danz et al.
10,340,462 B2 7/2019 Kim et al.
10,957,862 B2 3/2021 Kim et al.
12,446,464 B2 10/2025 Sakamoto
2014/0131686 A1 5/2014 Kawakami et al.
2017/0077421 A1* 3/2017 Ihn ........................ C07D 209/88
2019/0157570 A1 5/2019 Sim et al.
2020/0295269 A1 9/2020 Lee et al.
2021/0094937 A1 4/2021 Ito et al.
2021/0139425 A1 5/2021 Sim et al.
2021/0305520 A1 9/2021 Thompson et al.
2021/0399234 A1 12/2021 Kim et al.

FOREIGN PATENT DOCUMENTS

| | | |
|---|---|---|
| CN | 103396285 | 11/2013 |
| CN | 105906547 | 8/2016 |
| CN | 107459478 | 12/2017 |
| CN | 109096268 A | 12/2018 |
| CN | 110981867 | 4/2020 |
| CN | 111057005 | 4/2020 |
| CN | 112794814 | 5/2021 |
| JP | 4552382 | 9/2010 |
| JP | 2014-116595 | 6/2014 |
| JP | 2018-505126 | 2/2018 |
| JP | 2019-96876 | 6/2019 |
| KR | 20170136842 A | 12/2017 |
| KR | 10-2019-0142466 | 12/2019 |
| KR | 20200065952 A | 6/2020 |
| KR | 1020200061903 A | 6/2020 |
| KR | 10-2021-0020829 | 2/2021 |
| KR | 1020210024363 A | 3/2021 |
| WO | 2017/005699 | 1/2017 |
| WO | 2019/189033 | 10/2019 |
| WO | 2019/197407 | 10/2019 |
| WO | 2020/043483 | 3/2020 |
| WO | 2020/220942 | 11/2020 |
| WO | 2021/045347 | 3/2021 |
| WO | WO-2021045347 A1 * | 3/2021 ........... H10K 85/649 |

OTHER PUBLICATIONS

Machine of translation of JP4552382 (Year: 2010).*
Machine translation of WO2021045347 (Year: 2021).*

* cited by examiner

*Primary Examiner* — Andrew K Bohaty
(74) *Attorney, Agent, or Firm* — CANTOR COLBURN LLP

(57) ABSTRACT

A light emitting element according to an embodiment includes a first electrode, a second electrode disposed on the first electrode, and at least one functional layer disposed between the first electrode and the second electrode and including a polycyclic compound according to an embodiment, thereby showing high efficiency and long-life characteristics.

20 Claims, 8 Drawing Sheets

LIGHT EMITTING ELEMENT AND POLYCYCLIC COMPOUND FOR THE SAME

CROSS-REFERENCE TO RELATED APPLICATION(S)

This application claims priority to and benefits of Korean Patent Application No. 10-2021-0121220 under 35 U.S.C. § 119, filed on Sep. 10, 2021 in the Korean Intellectual Property Office, the entire contents of which are incorporated herein by reference.

BACKGROUND

1. Technical Field

The disclosure herein relates to a polycyclic compound used in a hole transport region and a light emitting element including the same.

2. Description of the Related Art

Active development continues for a luminescence display as an image display. The luminescence display is different from a liquid crystal display and is a so-called self-luminescent type display in which holes and electrons respectively injected from a first electrode and a second electrode recombine in an emission layer, so that a light emitting material in the emission layer emits light to achieve display.

In the application of a light emitting element to a display, there is a demand for decreasing driving voltage and for increasing emission efficiency and device life, and continuous development is required on materials for a light emitting element which stably achieves such requirements.

In order to achieve a light emitting element with high efficiency, there is current development on a material for a hole transport layer which suppresses diffusion of exciton energy outside of an emission layer.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

The disclosure provides a light emitting element showing excellent emission efficiency and long-life characteristics.

The disclosure also provides a polycyclic compound which is a material for a light emitting element having high efficiency and long-life characteristics.

An embodiment provides a polycyclic compound which may be represented by Formula 1.

[Formula 1]

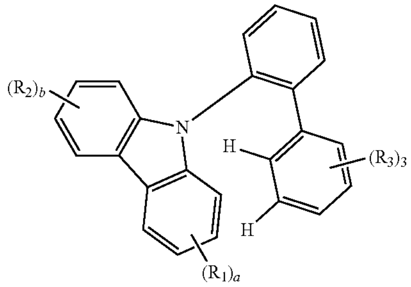

In Formula 1, $R_1$ and $R_2$ may each independently be a substituted or unsubstituted aryl group of 6 to 40 ring-forming carbon atoms, a substituted or unsubstituted heteroaryl group of 5 to 40 ring-forming carbon atoms, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted alkoxy group of 1 to 20 carbon atoms, a substituted or unsubstituted alkylthio group of 1 to 20 carbon atoms, a substituted or unsubstituted aryloxy group of 6 to 40 ring-forming carbon atoms, a substituted or unsubstituted arylthio group of 6 to 40 ring-forming carbon atoms, or a substituted or unsubstituted silyl group, a may be an integer from 0 to 4, b may be an integer from 1 to 4, and one of $R_3$ may be a group represented by Formula 2 and may be bonded to a ring at an ortho position, a meta position, or a para position with respect to a phenyl group bonded to a nitrogen atom of a carbazole group, and the remainder of $R_3$ may each independently be a hydrogen atom or a deuterium atom.

[Formula 2]

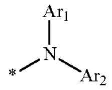

In Formula 2, $Ar_1$ and $Ar_2$ may each independently be a substituted or unsubstituted aryl group of 6 to 40 ring-forming carbon atoms, a substituted or unsubstituted heteroaryl group of 5 to 40 ring-forming carbon atoms, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted alkoxy group of 1 to 20 carbon atoms, a substituted or unsubstituted alkylthio group of 1 to 20 carbon atoms, a substituted or unsubstituted aryloxy group of 6 to 40 ring-forming carbon atoms, a substituted or unsubstituted arylthio group of 6 to 40 ring-forming carbon atoms, or a substituted or unsubstituted silyl group, or may be combined with an adjacent group to form a ring, or $Ar_1$ and $Ar_2$ may be combined with each other to form a ring, and —* is a bonding site to Formula 1. In case that an $R_3$ group represented by Formula 2 is bonded to a ring at an ortho position with respect to the phenyl group bonded to the nitrogen atom of the carbazole group, and $Ar_1$ and $Ar_2$ are combined with each other to form a ring, then a may be equal to or greater than 1, and $R_1$ and $R_2$ may not include alkyl groups, and in case that an $R_3$ group represented by Formula 2 is bonded to a ring at a para relationship with respect to the phenyl group bonded to the nitrogen atom of the carbazole group, and $Ar_1$ and $Ar_2$ are not combined with each other to form a ring, then a may be equal to or greater than 1. At least one hydrogen in Formula 1 or Formula 2 may be optionally substituted with deuterium.

In an embodiment, the polycyclic compound represented by Formula 1 may be represented by any one of Formula 1-1 to Formula 1-3.

[Formula 1-1]

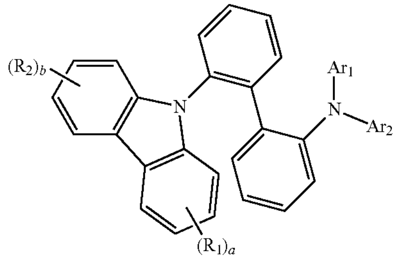

[Formula 1-2]

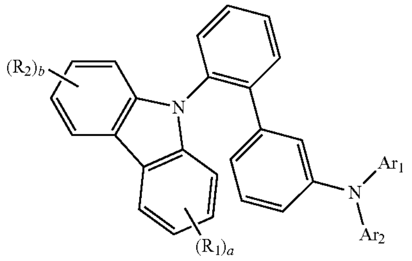

[Formula 1-3]

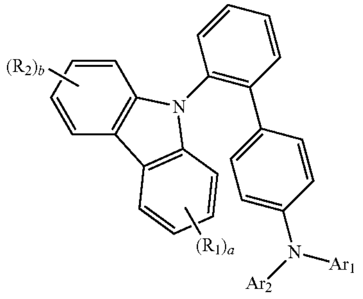

In Formula 1-1 to Formula 1-3, $R_1$, $R_2$, a, and b are the same as defined in Formula 1, and $Ar_1$ and $Ar_2$ are the same as defined in Formula 2.

In an embodiment, the group represented by Formula 2 may be represented by Formula 2-1 or Formula 2-2.

[Formula 2-1]

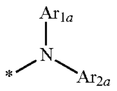

In Formula 2-1, $Ar_{1a}$ and $Ar_{2a}$ may each independently be a substituted or unsubstituted aryl group of 6 to 40 ring-forming carbon atoms, or a substituted or unsubstituted heteroaryl group of 5 to 40 ring-forming carbon atoms, or may be combined with an adjacent group to form a ring, and at least one hydrogen in $Ar_{1a}$ or $Ar_{2a}$ may be optionally substituted with deuterium.

[Formula 2-2]

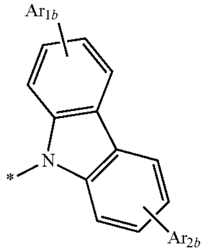

In Formula 2-2, $Ar_{1b}$ and $Ar_{2b}$, may each independently be a hydrogen atom, a deuterium atom, or a substituted or unsubstituted aryl group of 6 to 40 ring-forming carbon atoms.

In an embodiment, the polycyclic compound represented by Formula 1 may be represented by any one of Formula 3-1 to Formula 3-6.

[Formula 3-1]

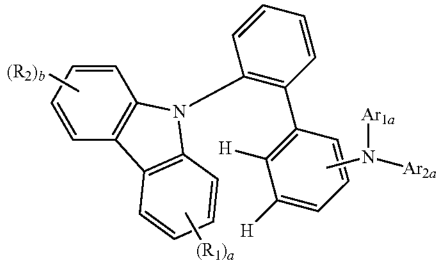

[Formula 3-2]

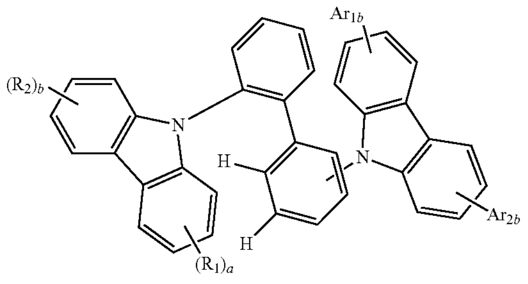

[Formula 3-3]

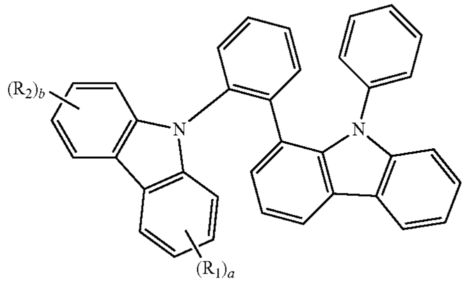

-continued

[Formula 3-4]

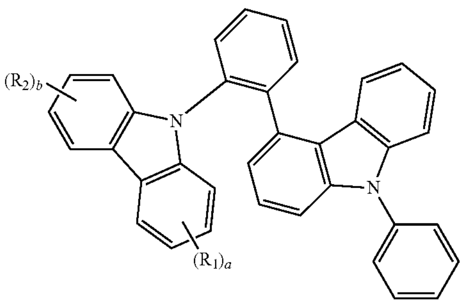

[Formula 3-5]

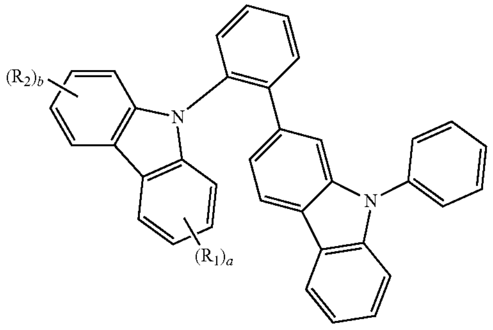

[Formula 3-6]

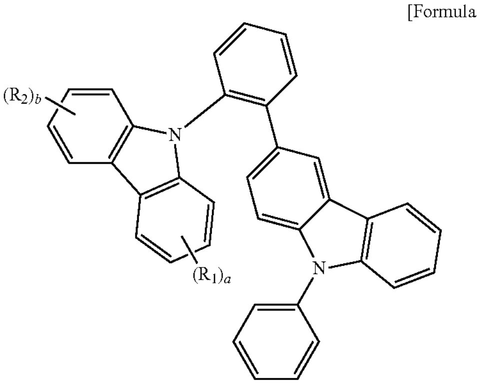

In Formula 3-1 to Formula 3-6, $R_1$, $R_2$, a, and b are the same as defined in Formula 1, $Ar_{1a}$ and $Ar_{1a}$ are the same as defined in Formula 2-1, and $Ar_{1b}$ and $Ar_{2b}$ are the same as defined in Formula 2-2.

In an embodiment, a may be equal to or greater than 1.

In an embodiment, $R_1$ and $R_2$ may each independently be a substituted or unsubstituted aryl group of 6 to 40 ring-forming carbon atoms, a substituted or unsubstituted heteroaryl group of 5 to 40 ring-forming carbon atoms, or a substituted or unsubstituted alkyl group of 1 to 20 carbon atoms.

In an embodiment, $Ar_1$ and $Ar_2$ may each independently be a substituted or unsubstituted aryl group of 6 to 40 ring-forming carbon atoms, or a substituted or unsubstituted heteroaryl group of 5 to 40 ring-forming carbon atoms, or may be combined with an adjacent group to form a ring, or $Ar_1$ and $Ar_2$ may be combined with each other to form a ring.

In an embodiment, the polycyclic compound represented by Formula 1 may be any one selected from Compound Group 1A to Compound Group 1J, which are explained below.

In an embodiment, a light emitting element may include a first electrode, a second electrode disposed on the first electrode, and at least one functional layer disposed between the first electrode and the second electrode and including the polycyclic compound of an embodiment.

In an embodiment, the at least one functional layer may include an emission layer, a hole transport region disposed between the first electrode and the emission layer, and an electron transport region disposed between the emission layer and the second electrode. The hole transport region may include the polycyclic compound.

In an embodiment, the hole transport region may include at least one of a hole injection layer, a hole transport layer, or an electron blocking layer, and at least one of the hole transport layer or the electron blocking layer may include the polycyclic compound.

In an embodiment, the emission layer may emit blue light or green light.

In an embodiment, the emission layer may include a compound represented by Formula E-1, which is explained below.

BRIEF DESCRIPTION OF THE DRAWINGS

The accompanying drawings are included to provide a further understanding of the embodiments, and are incorporated in and constitute a part of this specification. The drawings illustrate embodiments of the disclosure and principles thereof. The above and other aspects and features of the disclosure will become more apparent by describing in detail embodiments thereof with reference to the attached drawings, in which.

DETAILED DESCRIPTION OF THE EMBODIMENTS

Figure 1:
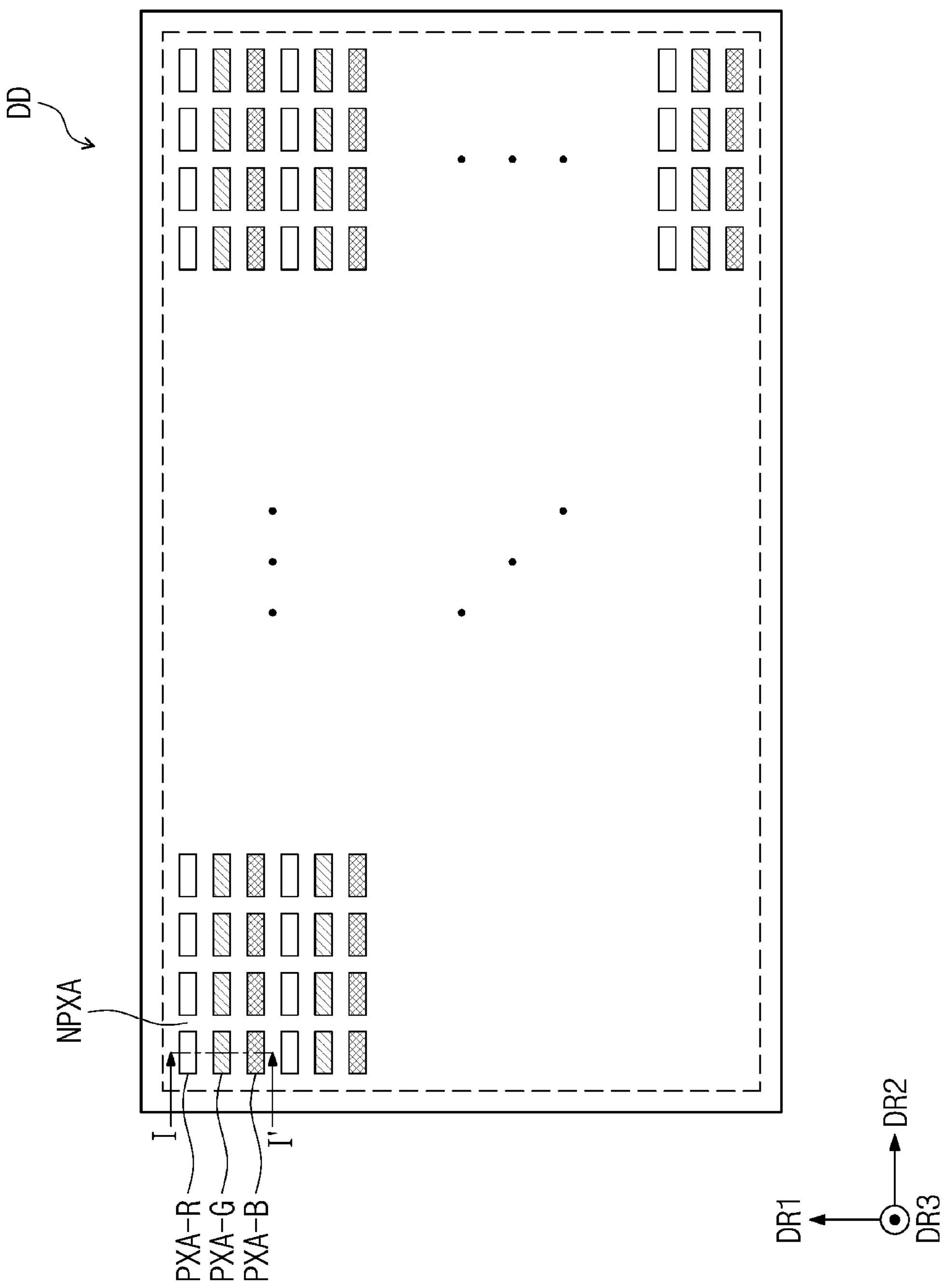
FIG. 1 is a plan view showing a display apparatus according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the specification, it will be understood that when an element (or region, layer, part, etc.) is referred to as being “on”, “connected to”, or “coupled to” another element, it can be directly on, connected to, or coupled to the other element, or one or more intervening elements may be present therebetween. In a similar sense, when an element (or region, layer, part, etc.) is described as “covering” another element, it can directly cover the other element, or one or more intervening elements may be present therebetween.

In the specification, when an element is “directly on,” “directly connected to,” or “directly coupled to” another element, there are no intervening elements present. For example, “directly on” may mean that two layers or two elements are disposed without an additional element such as an adhesion element therebetween.

As used herein, the expressions used in the singular such as “a,” “an,” and “the,” are intended to include the plural forms as well, unless the context clearly indicates otherwise.

As used herein, the term “and/or” includes any and all combinations of one or more of the associated listed items. For example, “A and/or B” may be understood to mean “A, B, or A and B.” The terms “and” and “or” may be used in the conjunctive or disjunctive sense and may be understood to be equivalent to “and/or”.

The term “at least one of” is intended to include the meaning of “at least one selected from the group of” for the purpose of its meaning and interpretation. For example, “at least one of A and B” may be understood to mean “A, B, or A and B.” When preceding a list of elements, the term, “at least one of,” modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms “below”, “beneath”, “lower”, “above”, “upper”, or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned “below” or “beneath” another device may be placed “above” another device. Accordingly, the illustrative term “below” may include both the lower and upper positions. The device may also be oriented in other directions and thus the spatially relative terms may be interpreted differently depending on the orientations.

The terms “about” or “approximately” as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, “about” may mean within one or more standard deviations, or within ±20%, ±10%, or ±5% of the stated value.

It should be understood that the terms “comprises,” “comprising,” “includes,” “including,” “have,” “having,” “contains,” “containing,” and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

In the specification, the term “substituted or unsubstituted” may mean a group that is substituted or unsubstituted with at least one substituent selected from the group consisting of a deuterium atom, a halogen atom, a cyano group, a nitro group, an amino group, a silyl group, an oxy group, a thio group, a sulfinyl group, a sulfonyl group, a carbonyl group, a boron group, a phosphine oxide group, a phosphine sulfide group, an alkyl group, an alkenyl group, an alkynyl group, an alkoxy group, a hydrocarbon ring group, an aryl group, and a heterocyclic group. Each of the substituents listed above may itself be substituted or unsubstituted. For example, a biphenyl group may be interpreted as an aryl group or may be interpreted as a phenyl group substituted with a phenyl group.

In the specification, the term “combined with an adjacent group to form a ring” may mean a group that is combined with an adjacent group to form a substituted or unsubstituted hydrocarbon ring or a substituted or unsubstituted heterocycle. The hydrocarbon ring may be an aliphatic hydrocarbon ring or an aromatic hydrocarbon ring. The heterocycle may be an aliphatic heterocycle or an aromatic heterocycle. The hydrocarbon ring and the heterocycle may each independently be monocyclic or polycyclic. A ring that is formed by the combination of adjacent groups may itself be combined with another ring to form a spiro structure.

In the specification, the term “adjacent group” may mean a substituent substituted for an atom which is directly combined with an atom substituted with a corresponding substituent, another substituent substituted for an atom which is substituted with a corresponding substituent, or a substituent sterically positioned at the nearest position to a corresponding substituent. For example, in 1,2-dimethylbenzene, two methyl groups may be interpreted as “adjacent groups” to each other, and in 1,1-diethylcyclopentene, two ethyl groups may be interpreted as “adjacent groups” to each other. For example, in 4,5-dimethylphenanthrene, two methyl groups may be interpreted as “adjacent groups” to each other.

In the specification, examples of a halogen atom may include a fluorine atom, a chlorine atom, a bromine atom, or an iodine atom.

In the specification, an alkyl group may be a linear, a branched, or a cyclic type. The number of carbon atoms in the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the specification, an alkenyl group may be a hydrocarbon group that includes one or more carbon-carbon double bonds in the middle or at a terminus of an alkyl group having 2 or more carbon atoms. The alkenyl group may be a linear chain or a branched chain. The number of carbon atoms in the alkenyl group is not specifically limited, but may be 2 to 30, 2 to 20, or 2 to 10. Examples of the alkenyl group may include a vinyl group, a 1-butenyl group, a 1-pentenyl group, a 1,3-butadienyl aryl group, a styrenyl group, a styrylvinyl group, etc., without limitation.

In the specification, an alkynyl group may be a hydrocarbon group that includes one or more carbon-carbon triple bonds in the middle or at a terminus of an alkyl group having 2 or more carbon atoms. The alkynyl group may be a linear chain or a branched chain. The number of carbon atoms in the alkynyl group is not specifically limited, but may be 2 to 30, 2 to 20, or 2 to 10. Examples of the alkynyl group may include an ethynyl group, a propynyl group, etc., without limitation.

In the specification, a hydrocarbon ring group may be a functional group or a substituent derived from an aliphatic hydrocarbon ring. For example, the hydrocarbon ring group may be a saturated hydrocarbon ring group of 5 to 20 ring-forming carbon atoms.

In the specification, an aryl group may be a functional group or a substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc., without limitation.

In the specification, a fluorenyl group may be substituted, and two substituents may be combined with each other to form a spiro structure. Examples of substituted fluorenyl groups may include the following groups, but embodiments are not limited thereto.

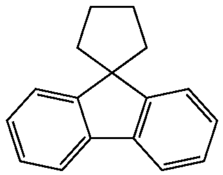
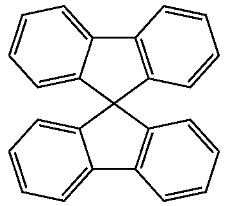
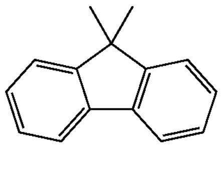
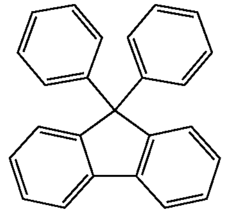

In the specification, a heterocyclic group may be a functional group or a substituent derived from a ring including one or more of B, O, N, P, Si, or S as heteroatoms. The heterocyclic group may be an aliphatic heterocyclic group or an aromatic heterocyclic group. The aromatic heterocyclic group may be a heteroaryl group. The aliphatic heterocyclic group and the aromatic heterocyclic group may each independently be monocyclic or polycyclic.

In the specification, the heterocyclic group may include one or more of B, O, N, P, Si, or S as heteroatoms. If the heterocyclic group includes two or more heteroatoms, the two or more heteroatoms may be the same as or different from each other. The heterocyclic group may be a monocyclic heterocyclic group or a polycyclic heterocyclic group, and the heterocyclic group may be a heteroaryl group. The number of ring-forming carbon atoms in the heterocyclic group may be 2 to 30, 2 to 20, or 2 to 10.

In the specification, an aliphatic heterocyclic group may include one or more of B, O, N, P, Si, or S as heteroatoms. The number of ring-forming carbon atoms of the aliphatic heterocyclic group may be 2 to 30, 2 to 20, or 2 to 10. Examples of the aliphatic heterocyclic group may include an oxirane group, a thiirane group, a pyrrolidine group, a piperidine group, a tetrahydrofuran group, a tetrahydrothiophene group, a thiane group, a tetrahydropyran group, a 1,4-dioxane group, etc., without limitation.

In the specification, a heteroaryl group may include one or more of B, O, N, P, Si, or S as heteroatoms. If the heteroaryl group includes two or more heteroatoms, the two or more heteroatoms may be the same as or different from each other. The heteroaryl group may be a monocyclic heterocyclic group or a polycyclic heterocyclic group. The number of ring-forming carbon atoms in the heteroaryl group may be 2 to 30, 2 to 20, or 2 to 10. Examples of the heteroaryl group may include thiophene, furan, pyrrole, imidazole, triazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuran, phenanthroline, thiazole, isooxazole, oxazole, oxadiazole, thiadiazole, phenothiazine, dibenzosilole, dibenzofuran, etc., without limitation.

In the specification, a silyl group may be an alkyl silyl group or an aryl silyl group. Examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc., without limitation.

In the specification, the number of carbon atoms in an amino group is not specifically limited, but may be 1 to 30. The amino group may be an alkyl amino group, an aryl amino group, or a heteroaryl amino group. Examples of the amino group may include a methylamino group, a dimethylamino group, a phenylamino group, a diphenylamino group, a naphthylamino group, a 9-methyl-anthracenylamino group, a triphenylamino group, etc., without limitation.

In the specification, the number of carbon atoms in a carbonyl group is not specifically limited, but may be 1 to 40, 1 to 30, or 1 to 20. For example, the carbonyl group may have one of the structures below, but is not limited thereto.

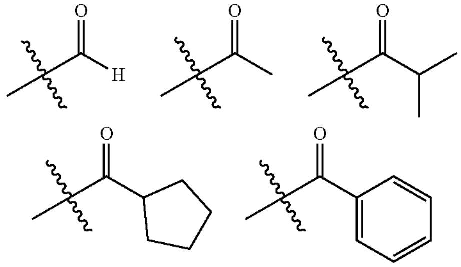

In the specification, the number of carbon atoms in a sulfinyl group or a sulfonyl group is not specifically limited, but may be 1 to 30. The sulfinyl group may be an alkyl sulfinyl group or an aryl sulfinyl group. The sulfonyl group may be an alkyl sulfonyl group or an aryl sulfonyl group.

In the specification, a thio group may be an alkyl thio group or an aryl thio group. The thio group may be a sulfur atom that is bonded to an alkyl group or an aryl group as defined above. Examples of the thio group may include a methylthio group, an ethylthio group, a propylthio group, a pentylthio group, a hexylthio group, an octylthio group, a dodecylthio group, a cyclopentylthio group, a cyclohexylthio group, a phenylthio group, a naphthylthio group, etc., without limitation.

In the specification, an oxy group may be an oxygen atom that is bonded to an alkyl group or an aryl group as defined above. The oxy group may be an alkoxy group or an aryl oxy group. The alkoxy group may be a linear, a branched, or a cyclic chain. The number of carbon atoms in the alkoxy group is not specifically limited but may be, for example, 1 to 20, or 1 to 10. Examples of the oxy group may include methoxy, ethoxy, n-propoxy, isopropoxy, butoxy, pentyloxy, hexyloxy, octyloxy, nonyloxy, decyloxy, benzyloxy, etc. However, embodiments are not limited thereto.

In the specification, the number of carbon atoms in an amine group is not specifically limited, but may be 1 to 30. The amine group may be an alkyl amine group or an aryl amine group. Examples of the amine group may include a methylamine group, a dimethylamine group, a phenylamine group, a diphenylamine group, a naphthylamine group, a 9-methyl-anthracenylamine group, etc., without limitation.

In the specification, the alkyl group in the alkylthio group, alkylsulfoxy group, alkylaryl group, alkylamino group, alkylboron group, alkyl silyl group, and alkyl amine group may be the same as the examples of the above-described alkyl group.

In the specification, the aryl group in the aryloxy group, arylthio group, arylsulfoxy group, aryl amino group, arylboron group, and aryl silyl group may be the same as the examples of the above-described aryl group.

In the specification, a direct linkage may be a single bond.

In the specification,

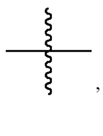

,

—*, and

each represent a bonding position to a neighboring atom.

Hereinafter, embodiments will be explained with reference to the drawings.

Figure 2:
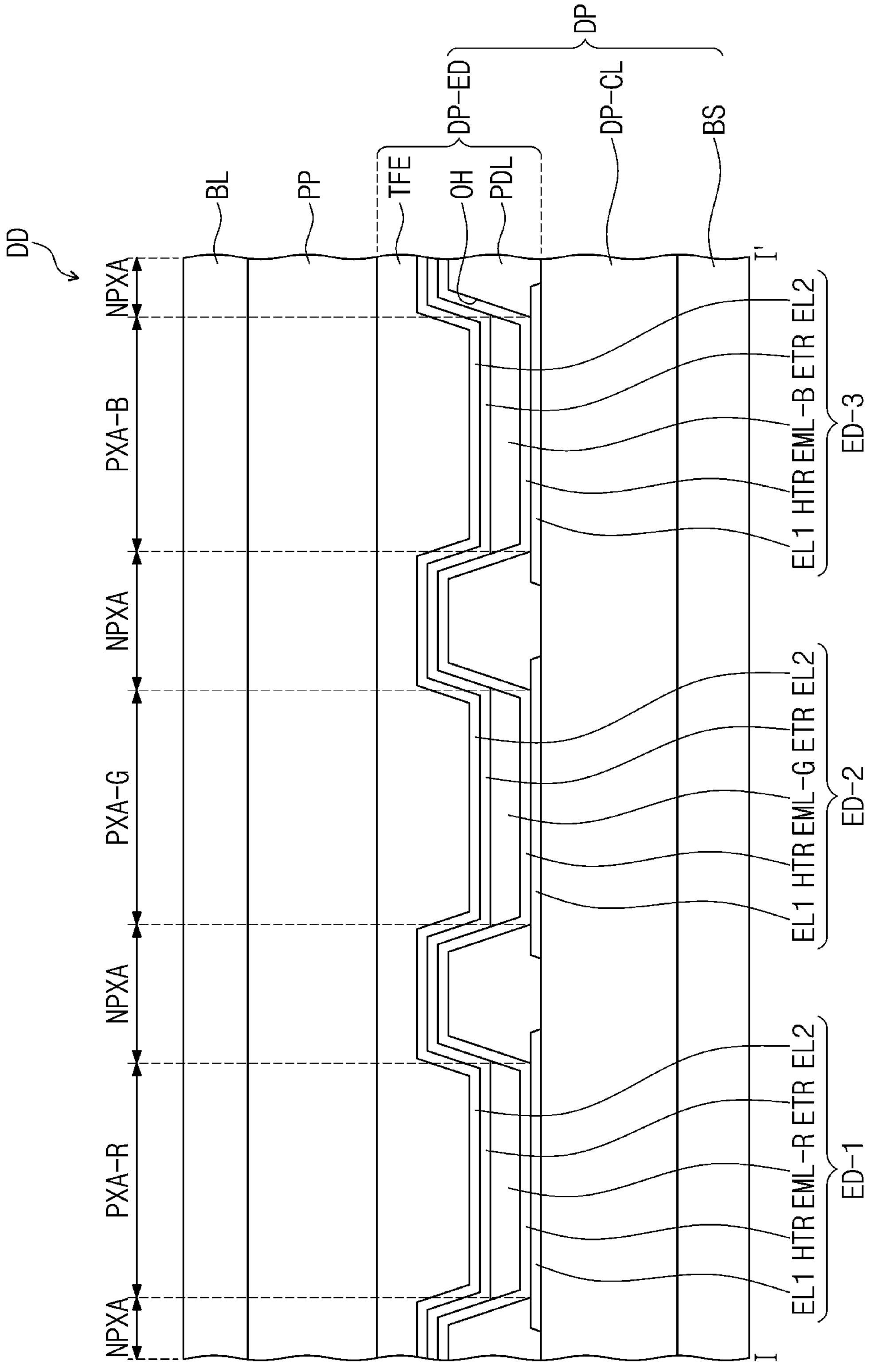
FIG. 2 is a schematic cross-sectional view showing a display apparatus according to an embodiment.

FIG. 1 is a plan view showing a display apparatus DD according to an embodiment. FIG. 2 is a schematic cross-sectional view showing a display apparatus DD according to an embodiment. FIG. 2 is a schematic cross-sectional view showing a portion corresponding to line I-I' of FIG. 1.

The display apparatus DD may include a display panel DP and an optical layer PP disposed on the display panel DP. The display panel DP includes light emitting elements ED-1, ED-2, and ED-3. The display apparatus DD may include multiples of each of the light emitting elements ED-1, ED-2, and ED-3. The optical layer PP may be disposed on the display panel DP to control light reflected at the display panel DP from an external light. The optical layer PP may include, for example, a polarization layer or a color filter layer. Although not shown in the drawings, in an embodiment, the optical layer PP may be omitted from the display apparatus DD.

A base substrate BL may be disposed on the optical layer PP. The base substrate BL may provide a base surface on which the optical layer PP is disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawings, in an embodiment, the base substrate BL may be omitted.

The display apparatus DD according to an embodiment may further include a plugging layer (not shown). The plugging layer (not shown) may be disposed between a display device layer DP-ED and a base substrate BL. The plugging layer (not shown) may be an organic layer. The plugging layer (not shown) may include at least one of an acrylic resin, a silicon-based resin, or an epoxy-based resin.

The display panel DP may include a base layer BS, a circuit layer DP-CL provided on the base layer BS, and a display device layer DP-ED. The display device layer DP-ED may include a pixel definition layer PDL, light emitting elements ED-1, ED-2, and ED-3 disposed in the pixel definition layer PDL, and an encapsulating layer TFE disposed on the light emitting elements ED-1, ED-2, and ED-3.

The base layer BS may provide a base surface on which the display device layer DP-ED is disposed. The base layer BS may be a glass substrate, a metal substrate, a plastic substrate, etc. However, embodiments are not limited thereto, and the base layer BS may include an inorganic layer, an organic layer, or a composite material layer.

In an embodiment, the circuit layer DP-CL is disposed on the base layer BS, and the circuit layer DP-CL may include transistors (not shown). Each of the transistors (not shown) may include a control electrode, an input electrode, and an output electrode. For example, the circuit layer DP-CL may include switching transistors and driving transistors for driving the light emitting elements ED-1, ED-2, and ED-3 of the display device layer DP-ED.

Each of the light emitting elements ED-1, ED-2, and ED-3 may have a structure of a light emitting element ED of an embodiment according to FIG. 3 to FIG. 6, which will be explained later. Each of the light emitting elements ED-1, ED-2, and ED-3 may include a first electrode EL1, a hole transport region HTR, emission layers EML-R, EML-G, and EML-B, an electron transport region ETR, and a second electrode EL2.

FIG. 2 shows an embodiment in which the emission layers EML-R, EML-G, and EML-B of light emitting elements ED-1, ED-2, and ED-3, are disposed in openings OH defined in a pixel definition layer PDL, and a hole transport region HTR, an electron transport region ETR, and a second electrode EL2 are each provided as a common layer for all of the light emitting elements ED-1, ED-2, and ED-3. However, embodiments are not limited thereto. Although not shown in FIG. 2, in an embodiment, the hole transport region HTR and the electron transport region ETR may each be patterned and provided in the openings OH defined in the pixel definition layer PDL. For example, in an embodiment, the hole transport region HTR, the emission layers EML-R, EML-G, and EML-B, and the electron transport region ETR of the light emitting elements ED-1, ED-2, and ED-3 may each be patterned and provided by an ink jet printing method.

An encapsulating layer TFE may cover the light emitting elements ED-1, ED-2, and ED-3. The encapsulating layer TFE may encapsulate the display device layer DP-ED. The encapsulating layer TFE may be a thin film encapsulating layer. The encapsulating layer TFE may be a single layer or a stack of multiple layers. The encapsulating layer TFE may include at least one insulating layer. The encapsulating layer TFE according to an embodiment may include at least one inorganic layer (hereinafter, an encapsulating inorganic layer). The encapsulating layer TFE according to an embodiment may include at least one organic layer (hereinafter, an encapsulating organic layer) and at least one encapsulating inorganic layer.

The encapsulating inorganic layer may protect the display device layer DP-ED from moisture and/or oxygen, and the encapsulating organic layer may protect the display device layer DP-ED from foreign materials such as dust particles. The encapsulating inorganic layer may include silicon nitride, silicon oxy nitride, silicon oxide, titanium oxide, or aluminum oxide, without limitation. The encapsulating organic layer may include an acrylic compound, an epoxy-based compound, etc. The encapsulating organic layer may include a photopolymerizable organic material, without limitation.

The encapsulating layer TFE may be disposed on the second electrode EL2 and may be disposed to fill the openings OH.

Referring to FIG. 1 and FIG. 2, the display apparatus DD may include non-luminous areas NPXA and luminous areas PXA-R, PXA-G, and PXA-B. The luminous areas PXA-R, PXA-G, and PXA-B may each be an area emitting light produced from the light emitting elements ED-1, ED-2, and ED-3, respectively. The luminous areas PXA-R, PXA-G, and PXA-B may be separated from each other in a plan view.

The luminous areas PXA-R, PXA-G, and PXA-B may be areas separated by the pixel definition layer PDL. The non-luminous areas NPXA may be areas between neighboring luminous areas PXA-R, PXA-G, and PXA-B and may correspond to the pixel definition layer PDL. For example, in an embodiment, each of the luminous areas PXA-R, PXA-G, and PXA-B may correspond to a pixel. The pixel definition layer PDL may separate the light emitting elements ED-1, ED-2, and ED-3. The emission layers EML-R, EML-G, and EML-B of the light emitting elements ED-1, ED-2, and ED-3 may be disposed in the openings OH defined in the pixel definition layer PDL and separated from each other.

The luminous areas PXA-R, PXA-G, and PXA-B may be divided into groups according to the color of light produced from the light emitting elements ED-1, ED-2, and ED-3. In the display apparatus DD of an embodiment, shown in FIG. 1 and FIG. 2, three luminous areas PXA-R, PXA-G, and PXA-B emitting red light, green light, and blue light are illustrated. For example, the display apparatus DD of an embodiment may include a red luminous area PXA-R, a green luminous area PXA-G, and a blue luminous area PXA-B, which are distinct from each other.

In the display apparatus DD according to an embodiment, the light emitting elements ED-1, ED-2, and ED-3 may emit light having different wavelength regions. For example, in an embodiment, the display apparatus DD may include a first light emitting element ED-1 emitting red light, a second light emitting element ED-2 emitting green light, and a third light emitting element ED-3 emitting blue light. For example, each of the red luminous area PXA-R, the green luminous area PXA-G, and the blue luminous area PXA-B of the display apparatus DD may respectively correspond to the first light emitting element ED-1, the second light emitting element ED-2, and the third light emitting element ED-3.

However, embodiments are not limited thereto, and the first to third light emitting elements ED-1, ED-2, and ED-3 may emit light in a same wavelength region, or at least one thereof may emit light in a different wavelength region. For example, all the first to third light emitting elements ED-1, ED-2, and ED-3 may emit blue light.

The luminous areas PXA-R, PXA-G and PXA-B in the display apparatus DD according to an embodiment may be arranged in a stripe configuration. Referring to FIG. 1, the red luminous areas PXA-R, the green luminous areas PXA-G, and the blue luminous areas PXA-B may be arranged along a second directional axis DR2. In another embodiment, the red luminous area PXA-R, the green luminous area PXA-G, and the blue luminous area PXA-B may be arranged by turns along a first directional axis DR1.

In FIG. 1 and FIG. 2, the areas of the luminous areas PXA-R, PXA-G, and PXA-B are shown as having a similar size, but embodiments are not limited thereto. The areas of the luminous areas PXA-R, PXA-G, and PXA-B may be different from each other according to a wavelength region of emitted light. The areas of the luminous areas PXA-R, PXA-G, and PXA-B may be areas in a plan view that are defined by the first directional axis DR1 and the second directional axis DR2.

The arrangement type of the luminous areas PXA-R, PXA-G, and PXA-B is not limited to the configuration shown in FIG. 1, and the arrangement of the red luminous areas PXA-R, the green luminous areas PXA-G, and the blue luminous areas PXA-B may be provided in various combinations according to the display quality properties which area required for the display apparatus DD. For example, the arrangement type of the luminous areas PXA-R, PXA-G, and PXA-B may be a PENTILE™ configuration or a diamond configuration.

In an embodiment, the areas of the luminous areas PXA-R, PXA-G, and PXA-B may be different in size from each other. For example, in an embodiment, an area of the green luminous area PXA-G may be smaller than an area of the blue luminous area PXA-B, but embodiments are not limited thereto.

Hereinafter, FIG. 3 to FIG. 6 are each a schematic cross-sectional view showing a light emitting element according to embodiments. The light emitting element ED according to an embodiment may include a first electrode EL1, a second electrode EL2 oppositely disposed to the first electrode EL1, and at least one functional layer disposed between the first electrode EL1 and the second electrode EL2. The light emitting element ED of an embodiment may include a polycyclic compound of an embodiment, which will be explained later, in at least one functional layer.

Figure 3:
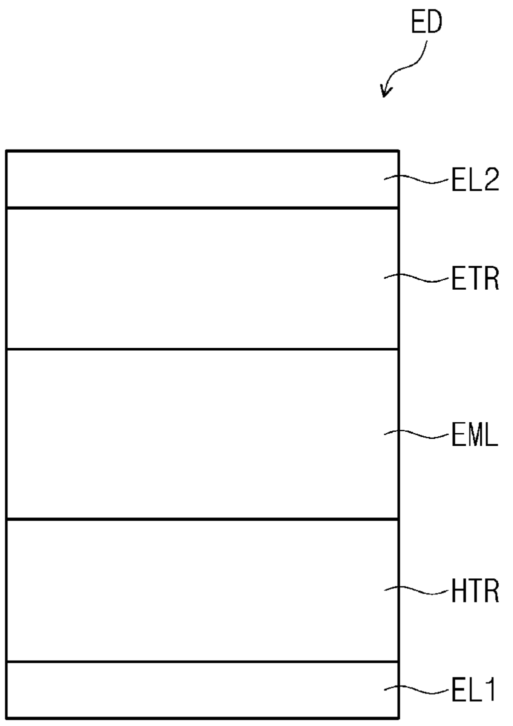
FIG. 3 is a schematic cross-sectional view showing a light emitting element according to an embodiment.

The light emitting element ED may include a hole transport region HTR, an emission layer EML, an electron transport region ETR, etc., stacked in order, as the at least one functional layer. Referring to FIG. 3, the light emitting element ED of an embodiment may include a first electrode EL1, a hole transport region HTR, an emission layer EML, an electron transport region ETR, and a second electrode EL2, stacked in that order.

Figure 4:
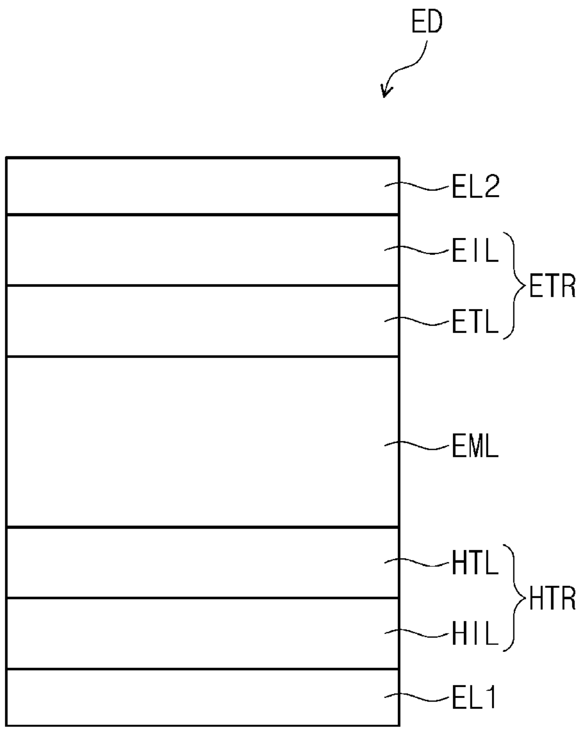
FIG. 4 is a schematic cross-sectional view showing a light emitting element according to an embodiment.
Figure 5:
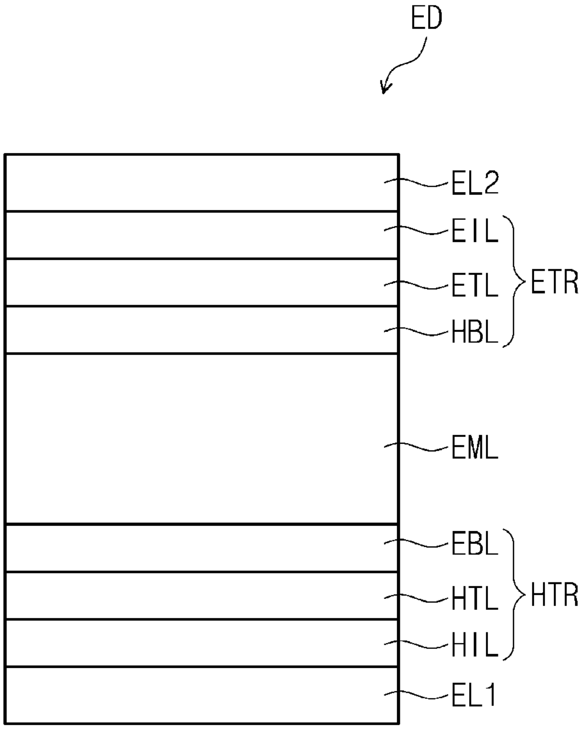
FIG. 5 is a schematic cross-sectional view showing a light emitting element according to an embodiment.
Figure 6:
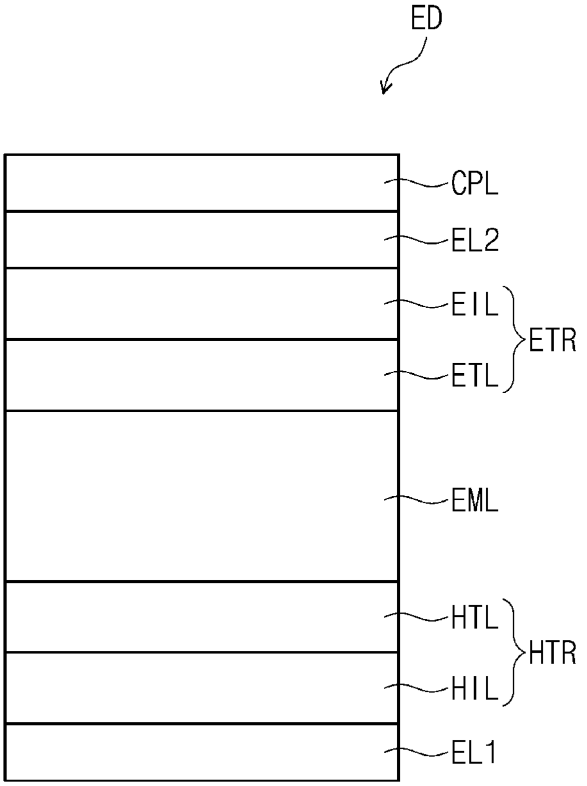
FIG. 6 is a schematic cross-sectional view showing a light emitting element according to an embodiment.

In comparison to FIG. 3, FIG. 4 shows a schematic cross-sectional view of a light emitting element ED of an embodiment, wherein a hole transport region HTR includes a hole injection layer HIL and a hole transport layer HTL, and an electron transport region ETR includes an electron injection layer EIL and an electron transport layer ETL. In comparison to FIG. 3, FIG. 5 shows a schematic cross-sectional view of a light emitting element ED of an embodiment, wherein a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. In comparison to FIG. 4, FIG. 6 shows a schematic cross-sectional view of a light emitting element ED of an embodiment that includes a capping layer CPL disposed on the second electrode EL2.

The light emitting element ED of an embodiment may include a polycyclic compound of an embodiment, which will be explained later, in a hole transport region HTR. In the light emitting element ED of an embodiment, at least one of the hole injection layer HIL, the hole transport layer HTL, or the electron blocking layer EBL of the hole transport region HTR, may include the polycyclic compound of an embodiment. For example, at least one of the hole transport layer HTL or the electron blocking layer EBL may include the polycyclic compound of an embodiment.

In the light emitting element ED according to an embodiment, the first electrode EL1 has conductivity. The first electrode EL1 may be formed of a metal material, a metal alloy, or a conductive compound. The first electrode EL1 may be an anode or a cathode. However, embodiments are not limited thereto. For example, the first electrode EL1 may be a pixel electrode. The first electrode EL1 may be a transmissive electrode, a transflective electrode, or a reflective electrode. The first electrode EL1 may include at least one of Ag, Mg, Cu, Al, Pt, Pd, Au, Ni, Nd, Ir, Cr, Li, Ca, LiF, Mo, Ti, W, In, Sn, Zn, oxides thereof, compounds thereof, or mixtures thereof.

If the first electrode EL1 is a transmissive electrode, the first electrode EL1 may include a transparent metal oxide such as indium tin oxide (ITO), indium zinc oxide (IZO), zinc oxide (ZnO), or indium tin zinc oxide (ITZO). If the first electrode EL1 is a transflective electrode or a reflective electrode, the first electrode EL1 may include Ag, Mg, Cu, Al, Pt, Pd, Au, Ni, Nd, Ir, Cr, Li, Ca, LiF/Ca (e.g., a stacked structure of LiF and Ca), LiF/Al (e.g., a stacked structure of LiF and Al), Mo, Ti, W, compounds thereof, or mixtures thereof (for example, a mixture of Ag and Mg). In another embodiment, the first electrode EL1 may have a structure including multiple layers including a reflective layer or a transflective layer formed of the above materials, and a transmissive conductive layer formed of ITO, IZO, ZnO, or ITZO. For example, the first electrode EL1 may have a three-layer structure of ITO/Ag/ITO. However, embodiments are not limited thereto. The first electrode EL1 may include the above-described metal materials, combinations of two or more metal materials selected from the above-described metal materials, or oxides of the above-described metal materials. A thickness of the first electrode EL1 may be in a range of about 700 Å to about 10,000 Å. For example, the thickness of the first electrode EL1 may be in a range of about 1,000 Å to about 3,000 Å.

The hole transport region HTR is provided on the first electrode EL1. The hole transport region HTR may be a layer formed of a single material, a layer formed of different materials, or a multilayer structure including layers formed of different materials.

The hole transport region HTR may include at least one of a hole injection layer HIL, a hole transport layer HTL, or an emission blocking layer EBL. In other embodiments, the hole transport region HTR may have a structure of a single layer of a hole injection layer HIL or a hole transport layer HTL, or may have a structure of a single layer formed of a hole injection material and a hole transport material. In an embodiment, the hole transport region HTR may have a structure of a single layer formed of different materials, or may have a structure in which a hole injection layer HIL/hole transport layer HTL, a hole injection layer HIL/hole transport layer HTL/buffer layer (not shown), a hole injection layer HIL/buffer layer (not shown), or a hole transport layer HTL/buffer layer (not shown) are stacked in its respective stated order from the first electrode EL1, but embodiments are not limited thereto.

A thickness of the hole transport region HTR may be in a range of about 50 Å to about 15,000 Å. The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The light emitting element ED of an embodiment may include a polycyclic compound of an embodiment, represented by Formula 1 in a hole transport region HTR. In the light emitting element ED of an embodiment, a hole transport layer HTL may include a polycyclic compound of an embodiment, represented by Formula 1. In the light emitting element ED of an embodiment, an electron blocking layer EBL may include a polycyclic compound of an embodiment, represented by Formula 1.

[Formula 1]

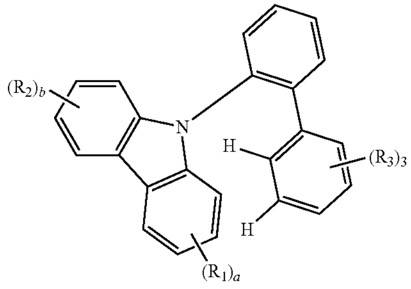

In Formula 1, $R_1$ and $R_2$ may each independently be a substituted or unsubstituted aryl group of 6 to 40 ring-forming carbon atoms, a substituted or unsubstituted heteroaryl group of 5 to 40 ring-forming carbon atoms, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted alkoxy group of 1 to 20 carbon atoms, a substituted or unsubstituted alkylthio group of 1 to 20 carbon atoms, a substituted or unsubstituted aryloxy group of 6 to 40 ring-forming carbon atoms, a substituted or unsubstituted arylthio group of 6 to 40 ring-forming carbon atoms, or a substituted or unsubstituted silyl group. For example, $R_1$ and $R_2$ may each independently be a methyl group, a substituted or unsubstituted phenyl group, a substituted or unsubstituted carbazole group, a substituted or unsubstituted naphthyl group, or a substituted or unsubstituted dibenzofuran group. However, embodiments are not limited thereto.

In Formula 1, one of $R_3$ may be a group represented by Formula 2 and may be bonded to a ring at an ortho position, a meta position, or a para position with respect to a phenyl group bonded to a nitrogen atom of a carbazole group. The remainder of $R_3$ may each independently be a hydrogen atom or a deuterium atom.

In Formula 1, a may be an integer from 0 to 4, and b may be an integer from 1 to 4. For example, a may be equal to or greater than 1, and the sum of a and b may be equal to or greater than 2. For example, a may be an integer from 1 to 4, and b may be an integer from 1 to 4.

[Formula 2]

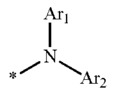

In Formula 2, $Ar_1$ and $Ar_2$ may each independently be a substituted or unsubstituted aryl group of 6 to 40 ring-forming carbon atoms, a substituted or unsubstituted heteroaryl group of 5 to 40 ring-forming carbon atoms, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted alkoxy group of 1 to 20 carbon atoms, a substituted or unsubstituted alkylthio group of 1 to 20 carbon atoms, a substituted or unsubstituted aryloxy group of 6 to 40 ring-forming carbon atoms, a substituted or unsubstituted arylthio group of 6 to 40 ring-forming carbon atoms, or a substituted or unsubstituted silyl group, or may be combined with an adjacent group to form a ring, or $Ar_1$ and $Ar_2$ may be combined with each other to form a ring. In an embodiment, a ring formed through the combination of $Ar_1$ or $Ar_2$ with an adjacent group may be a carbazole derivative, and a ring formed by the combination of $Ar_1$ and $Ar_2$ with each other may be a carbazole derivative. However, embodiments are not limited thereto.

In Formula 2, —* represents a bonding site to Formula 1. For example, —* may be a bonding site at an ortho position, a meta position, or a para position with respect to a phenyl group bonded to the nitrogen atom of the carbazole group of Formula 1.

In the polycyclic compound of an embodiment represented by Formula 1, at least one hydrogen in Formula 1 or Formula 2 may be optionally substituted with deuterium.

In Formula 1, in case that an $R_3$ group represented by Formula 2 is bonded to a ring at an ortho position with respect to the phenyl group bonded to the nitrogen atom of the carbazole group, and $Ar_1$ and $Ar_2$ are combined with each other to form a ring, then a may be equal to or greater than 1, and $R_1$ and $R_2$ may not include alkyl groups.

In Formula 1, in case that an $R_3$ group represented by Formula 2 is bonded to a ring at a para position with respect to the phenyl group bonded to the nitrogen atom of the carbazole group, and $Ar_1$ and $Ar_2$ are not combined with each other to form a ring, then a may be equal to or greater than 1. For example, in case that $Ar_1$ and $Ar_2$ are each independently a substituted or unsubstituted aryl group of 6 to 40 ring-forming carbon atoms, a substituted or unsubstituted heteroaryl group of 5 to 40 ring-forming carbon atoms, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted alkoxy group of 1 to 20 carbon atoms, a substituted or unsubstituted alkylthio group of 1 to 20 carbon atoms, a substituted or unsubstituted aryloxy group of 6 to 40 ring-forming carbon atoms, a substituted or unsubstituted arylthio group of 6 to 40 ring-forming carbon atoms, or a substituted or unsubstituted silyl group, or are combined with an adjacent group to form a ring, then a may be equal to or greater than 1 ($a \geq 1$). For example, a may be an integer from 1 to 4. In case that $Ar_1$ and $Ar_2$ are combined with each other to form a ring, then a may be equal to or greater than 0 ($a \geq 0$). For example, a may be an integer from 0 to 4.

In an embodiment, the polycyclic compound represented by Formula 1 may be represented by any one of Formula 1-1 to Formula 1-3. Formula 1-1 is an example of a case where one of $R_3$ is a group represented by Formula 2 and bonded to a ring at an ortho position with respect to the phenyl group bonded to the nitrogen atom of the carbazole group in Formula 1. Formula 1-2 is an example of a case where one of $R_3$ is a group represented by Formula 2 and bonded to a ring at a meta position with respect to the phenyl group bonded to the nitrogen atom of the carbazole group in Formula 1. Formula 1-3 is an example of a case where one of $R_3$ is a group represented by Formula 2 and bonded to a ring at a para position with respect to the phenyl group bonded to the nitrogen atom of the carbazole group in Formula 1. In Formula 1-1 to Formula 1-3, $R_1$, $R_2$, a, and b are the same as defined in Formula 1, and $Ar_1$ and $Ar_2$ are the same as defined in Formula 2.

[Formula 1-1]

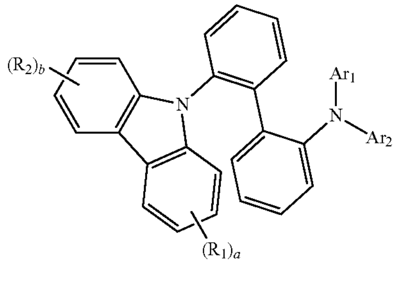

-continued

[Formula 1-2]

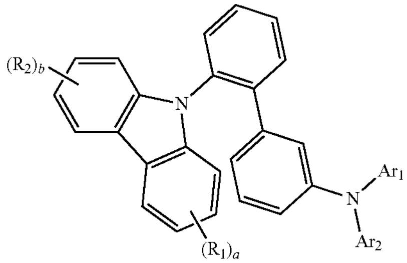

[Formula 1-3]

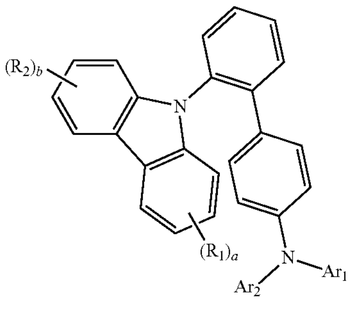

In an embodiment, the group represented by Formula 2 may be represented by Formula 2-1 or Formula 2-2.

[Formula 2-1]

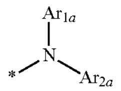

In Formula 2-1, $Ar_{1a}$ and $Ar_{2a}$ may each independently be a substituted or unsubstituted aryl group of 6 to 40 ring-forming carbon atoms, or a substituted or unsubstituted heteroaryl group of 5 to 40 ring-forming carbon atoms, or may be combined with an adjacent group to form a ring. For example, $Ar_{1a}$ and $Ar_{2a}$ may be combined with an adjacent group (for example, a phenyl group to which the nitrogen of Formula 2 is bonded) to form a carbazole ring. In another embodiment, $Ar_{1a}$ and $Ar_{2a}$ may be combined with each other to form a ring. However, embodiments are not limited thereto. In Formula 2-1, at least one hydrogen atom in $Ar_{1a}$ or $Ar_{2a}$ may optionally be substituted with deuterium.

[Formula 2-2]

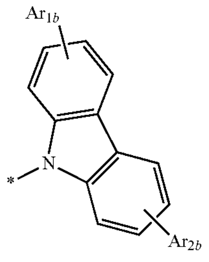

In Formula 2-2, $Ar_{1b}$ and $Ar_{2b}$ may each independently be a hydrogen atom, a deuterium atom, or a substituted or unsubstituted aryl group of 6 to 40 ring-forming carbon atoms. In Formula 2-2, at least one hydrogen atom in $Ar_{1b}$ and $Ar_{2b}$ may optionally be substituted with deuterium.

In an embodiment, the polycyclic compound represented by Formula 1 may be represented by any one of Formula 3-1 to Formula 3-6.

[Formula 3-1]

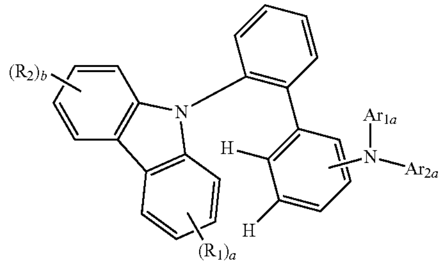

[Formula 3-2]

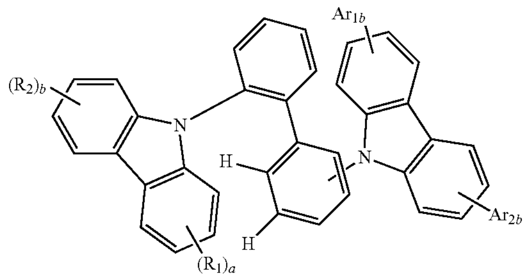

[Formula 3-3]

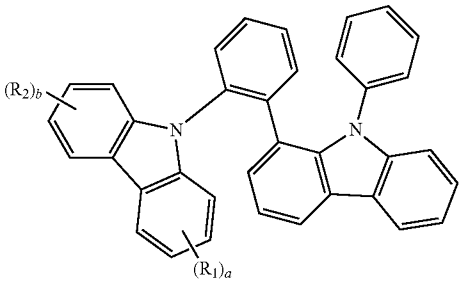

[Formula 3-4]

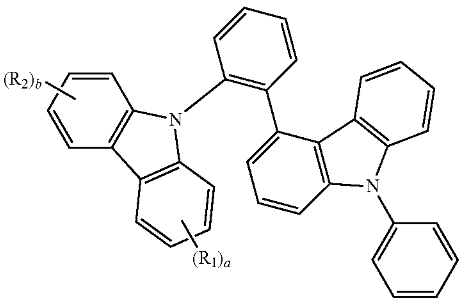

-continued

[Formula 3-5]

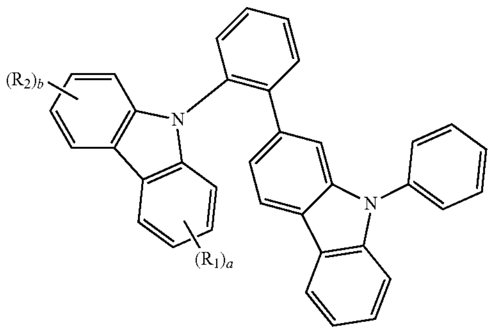

[Formula 3-6]

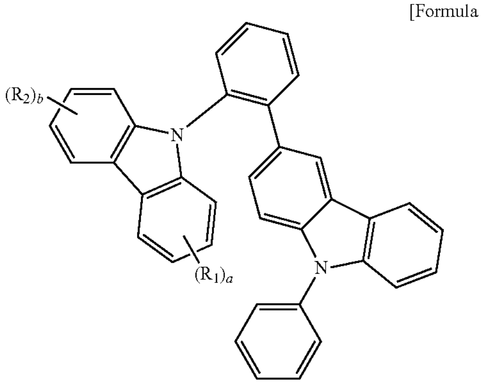

In Formula 3-1 to Formula 3-6, $R_1$, $R_2$, a, and "b" are the same as defined in Formula 1. In Formula 3-1, $Ar_{1a}$ and $Ar_{2a}$ are the same as defined in Formula 2-1, and in Formula 3-2, $Ar_{1b}$ and $Ar_{2b}$ are the same as defined in Formula 2-2.

In an embodiment, the polycyclic compound represented by Formula 1 may be any one selected from Compound Group 1 Å to Compound Group 1J. The hole transport region HTR of the light emitting element ED of an embodiment may include at least one of the polycyclic compounds in Compound Group 1 Å to Compound Group 1J. In Compound Groups 1 Å to 1J, D is a deuterium atom.

[Compound Group 1A]

A1

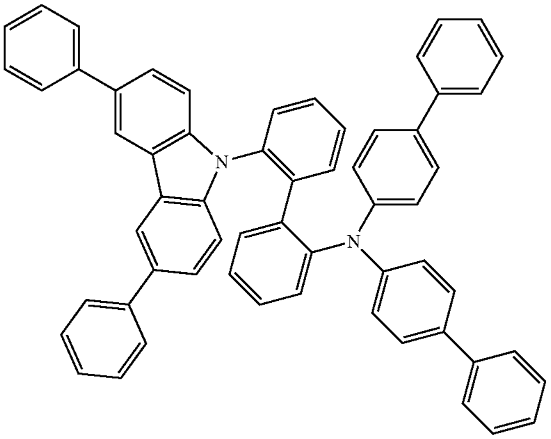

-continued

A2

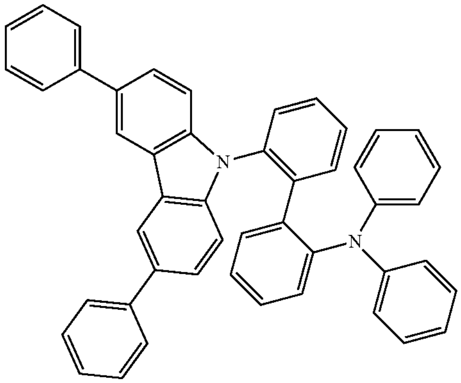

A3

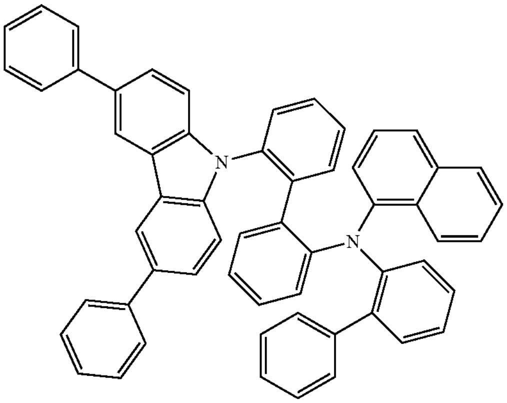

A4

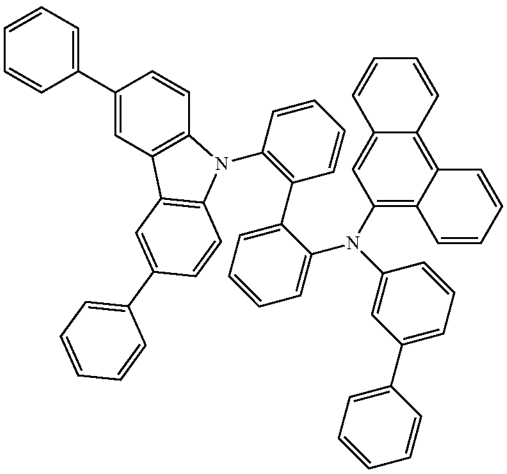

-continued
A5
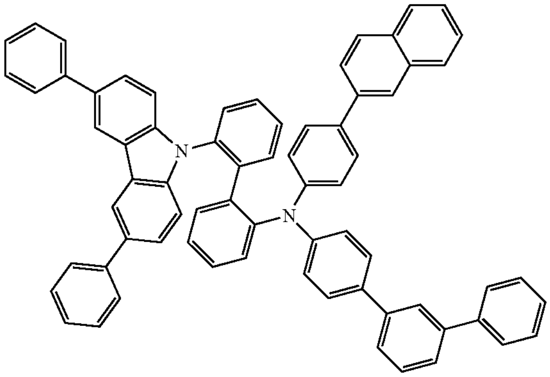
A6
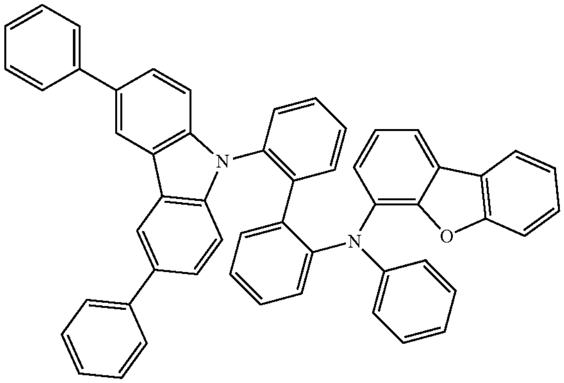
A7
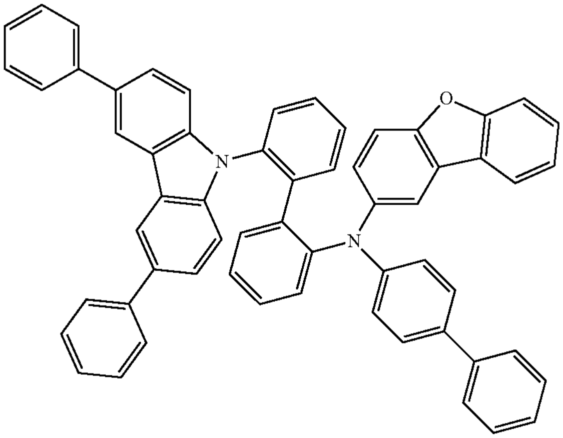
-continued
A8
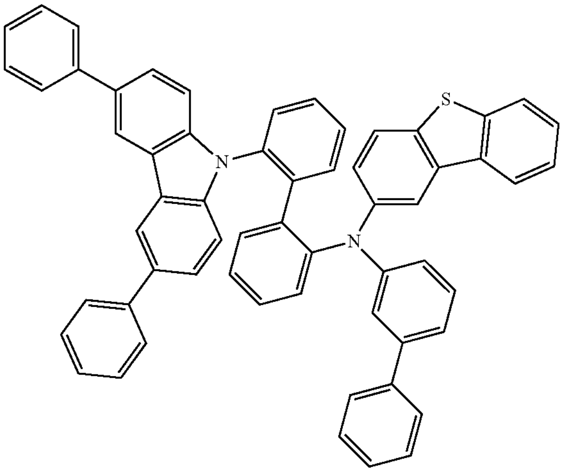
A9
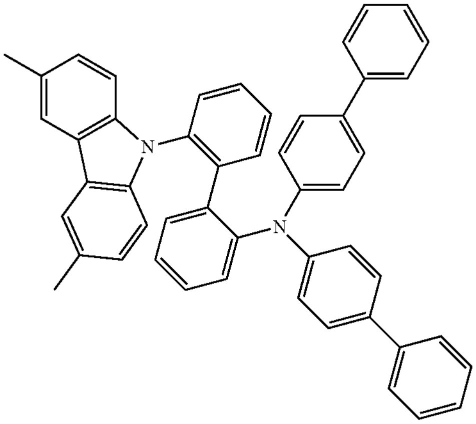
A10
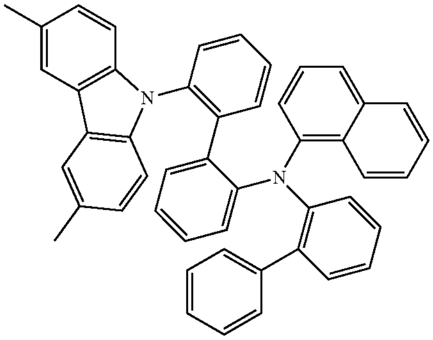
A11
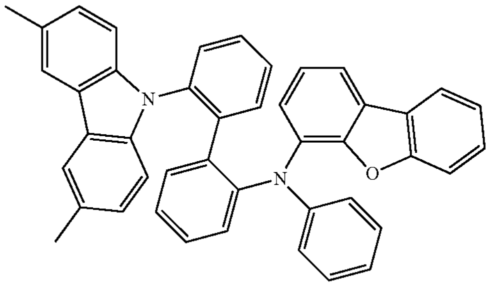

-continued
A12
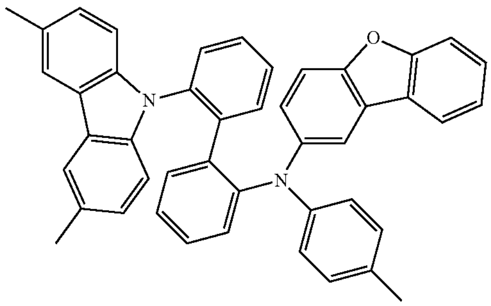
A13
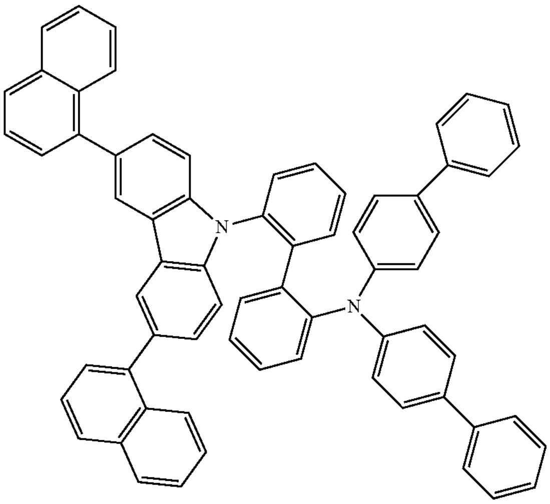
A14
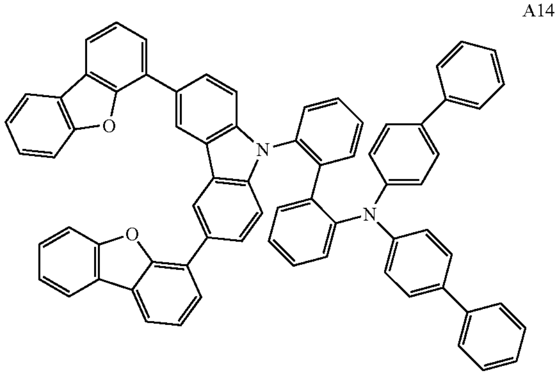
-continued
A15
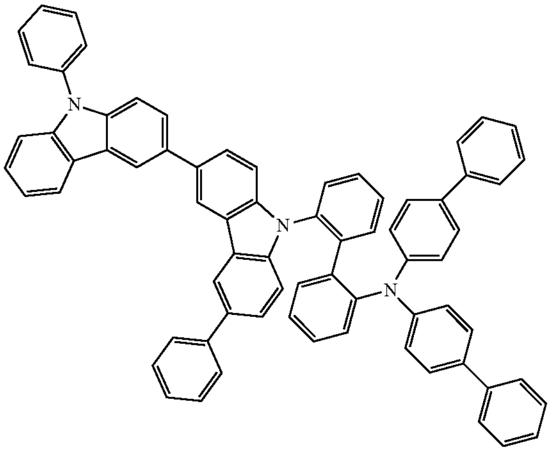
A16
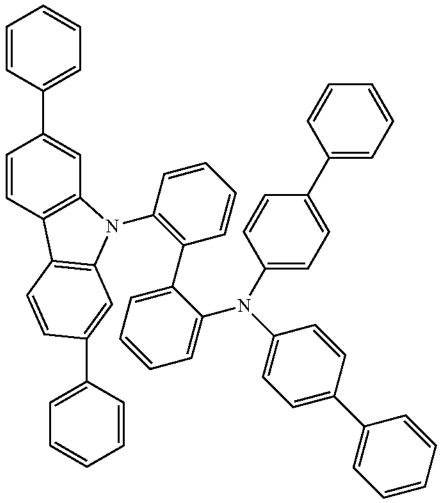
A17
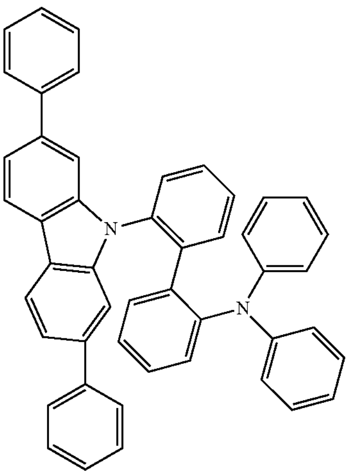

-continued
A18
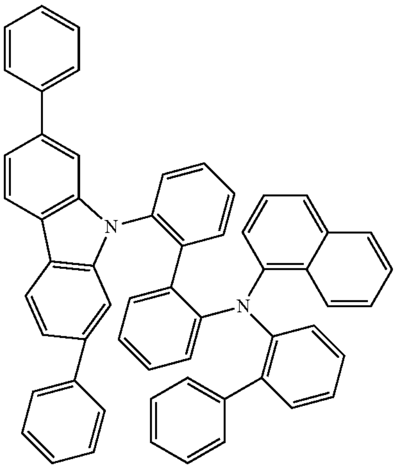
A19
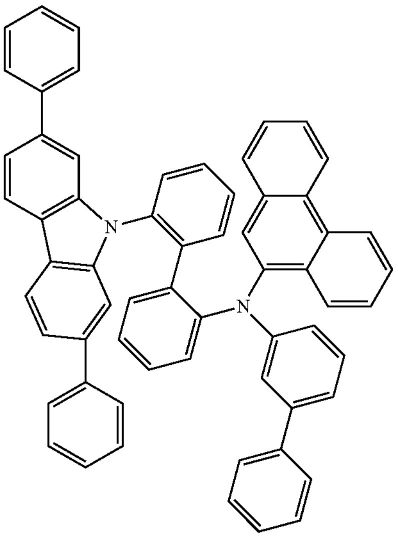
A20
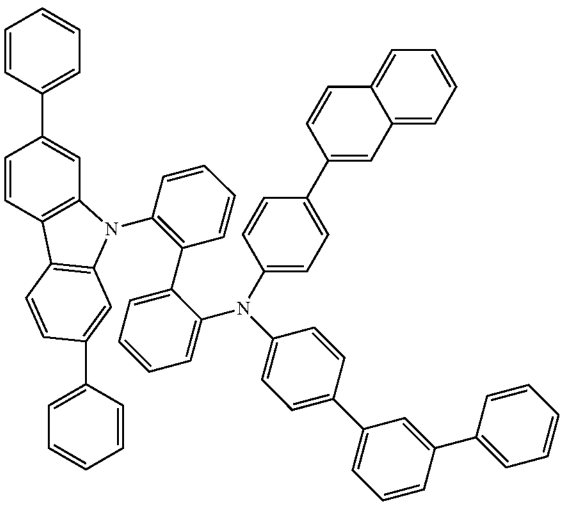
-continued
A21
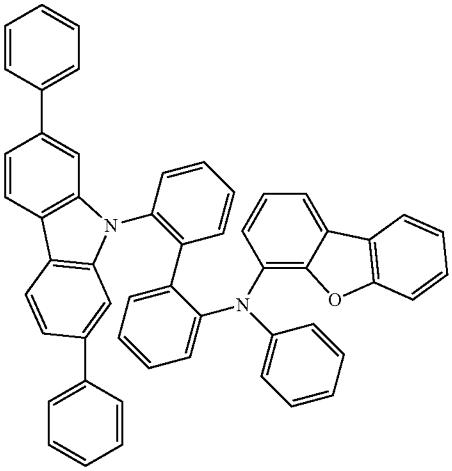
A22
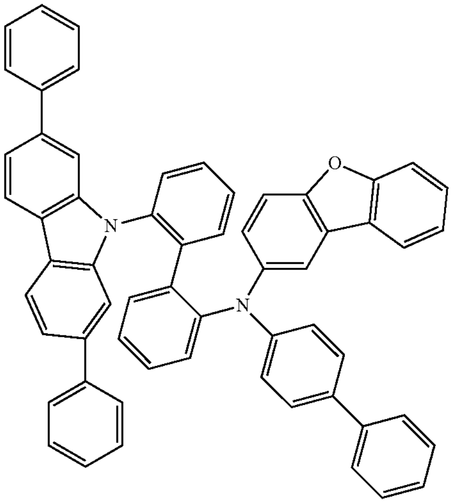
A23
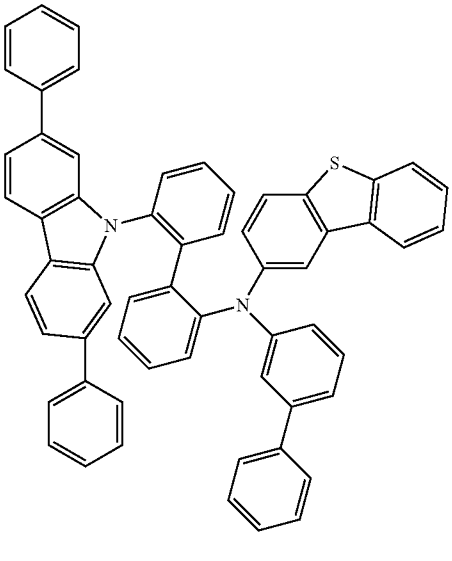

-continued
A24
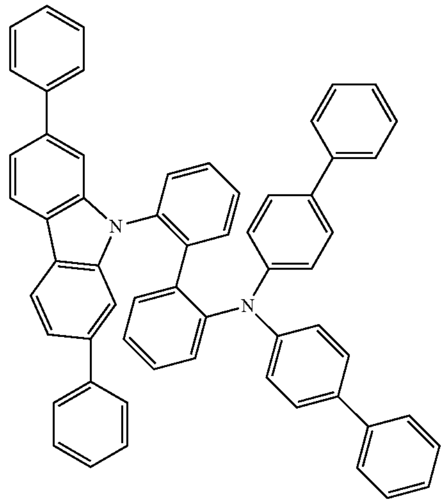
A25
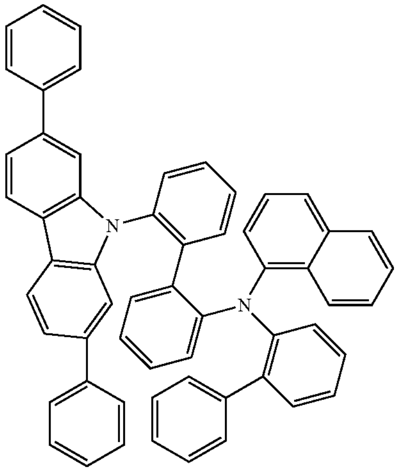
A26
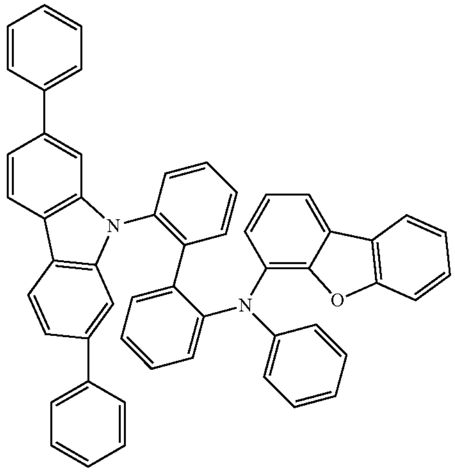
-continued
A27
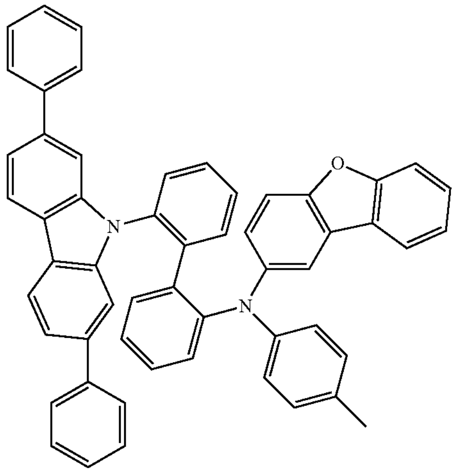
A28
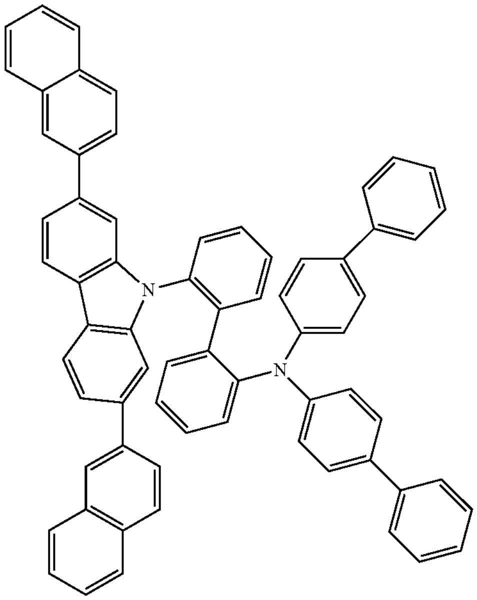
A29
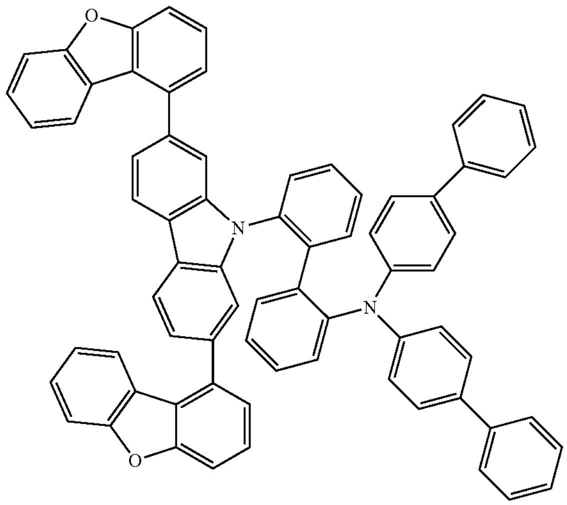

-continued
A30
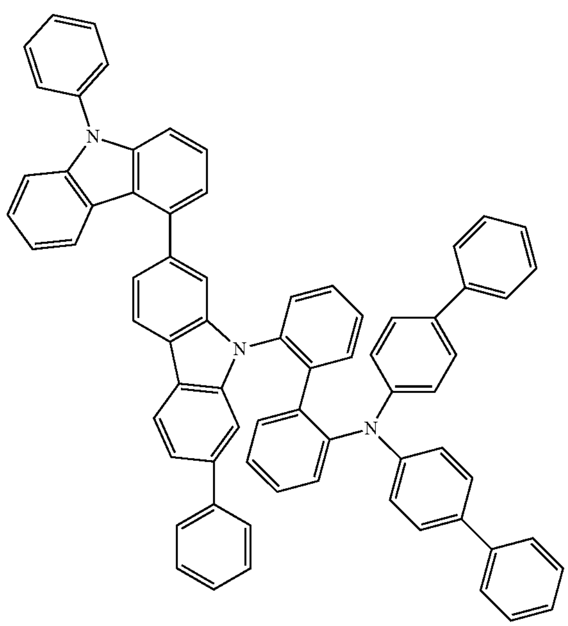
A31
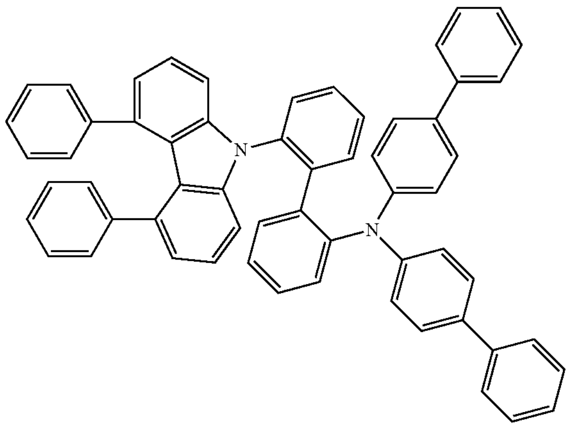
A32
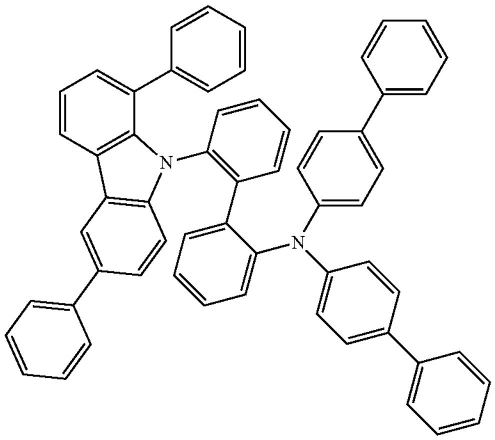
-continued
A33
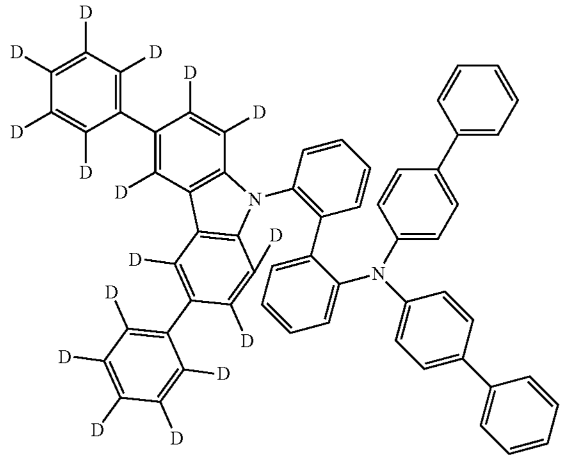
[Compound Group 1B]
B1
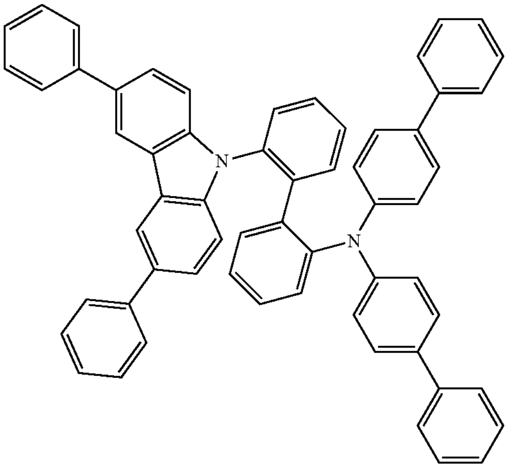
B2
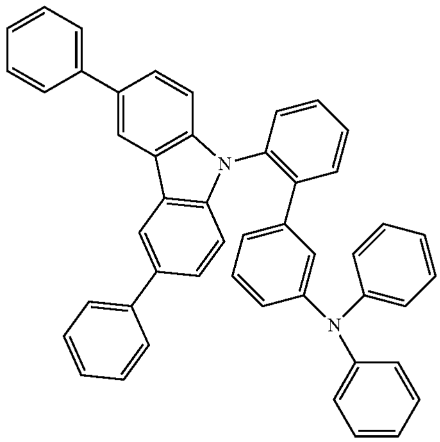

-continued
B3
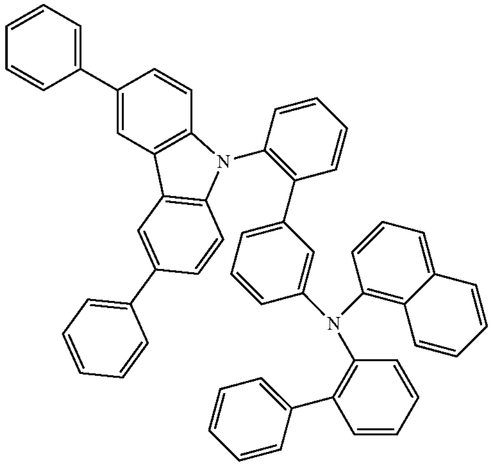
B4
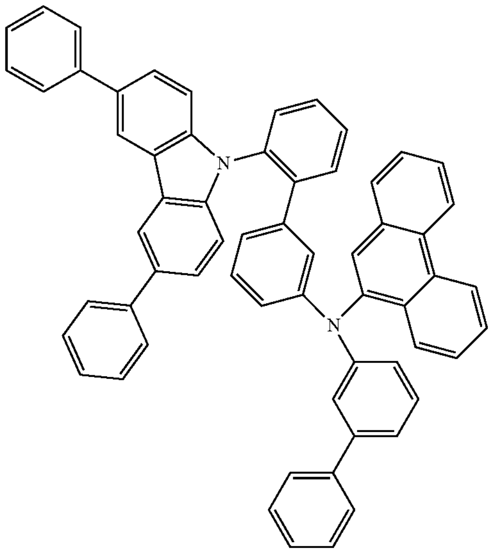
B5
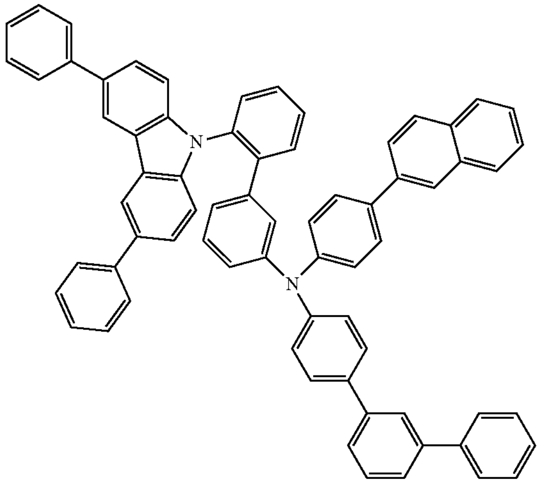
-continued
B6
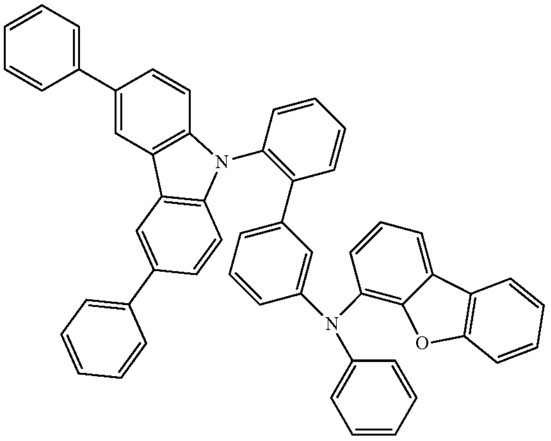
B7
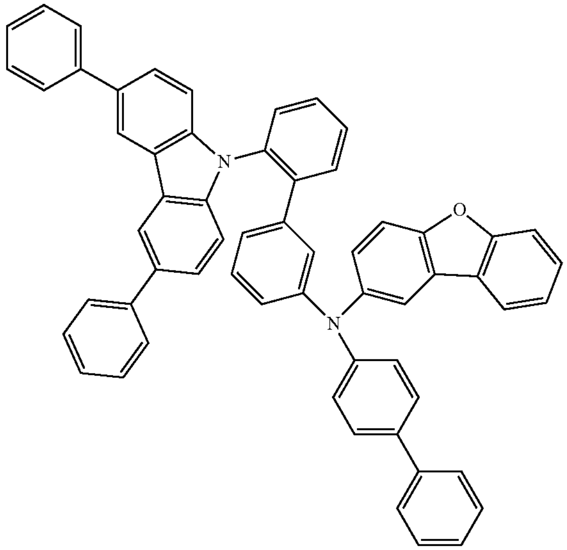
B8
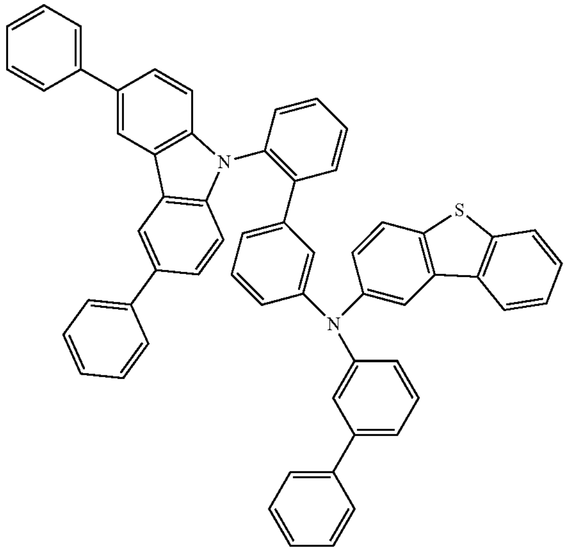

-continued
B9
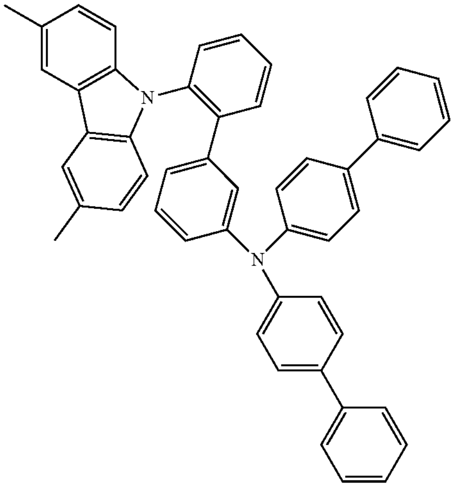
B10
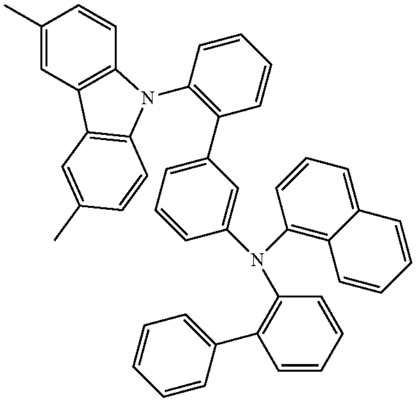
B11
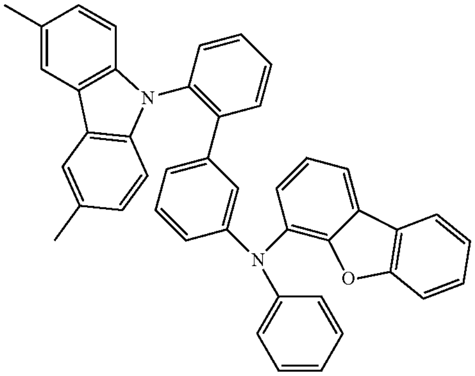
-continued
B12
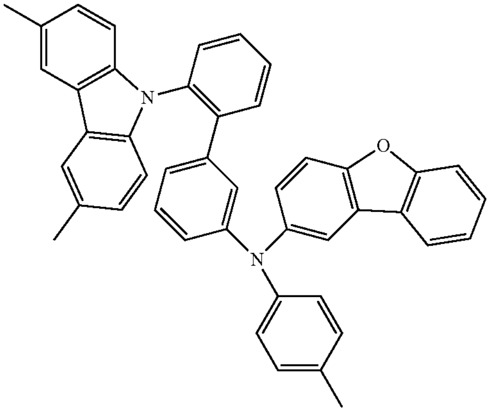
B13
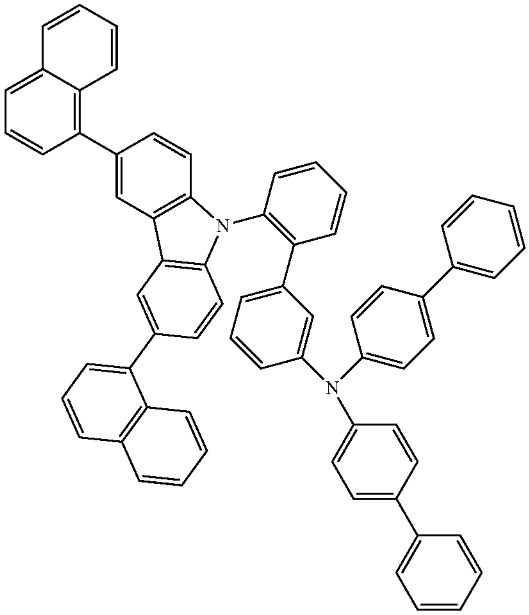
B14
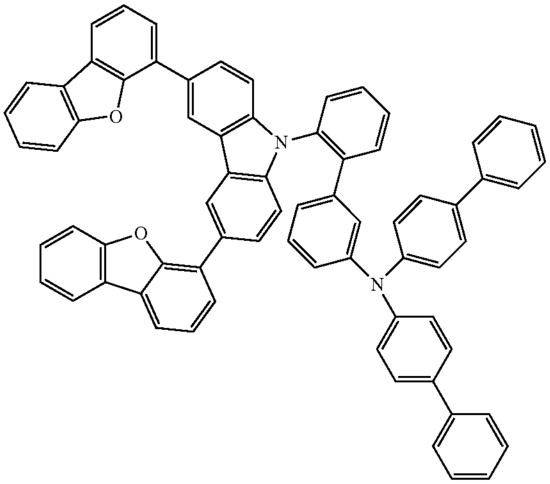

-continued
B15
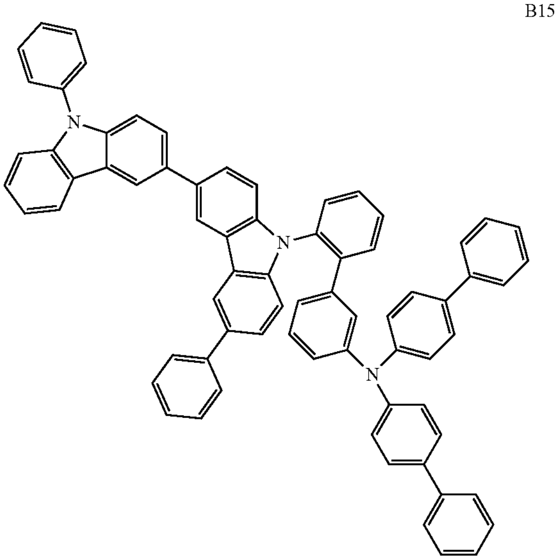
B16
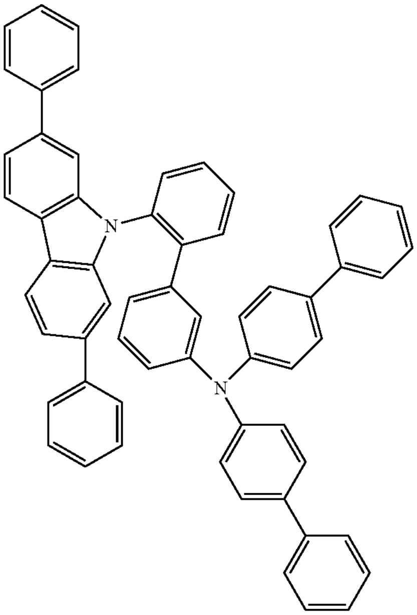
B17
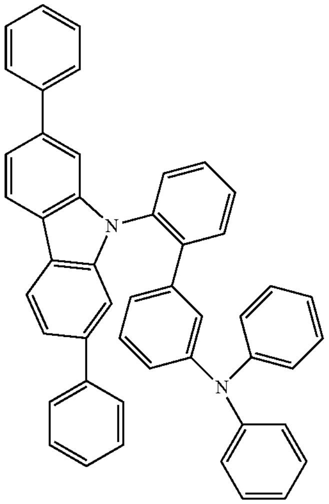
-continued
B18
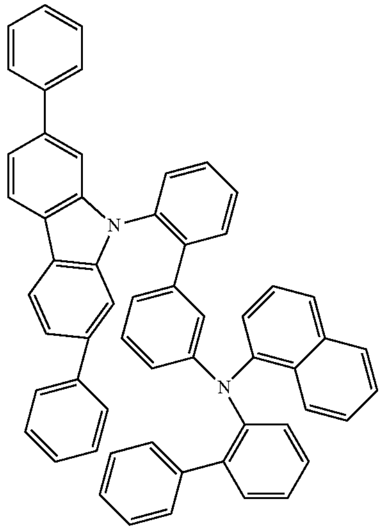
B19
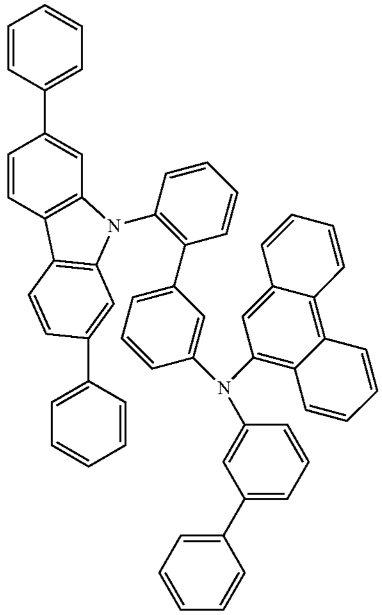

-continued
B20
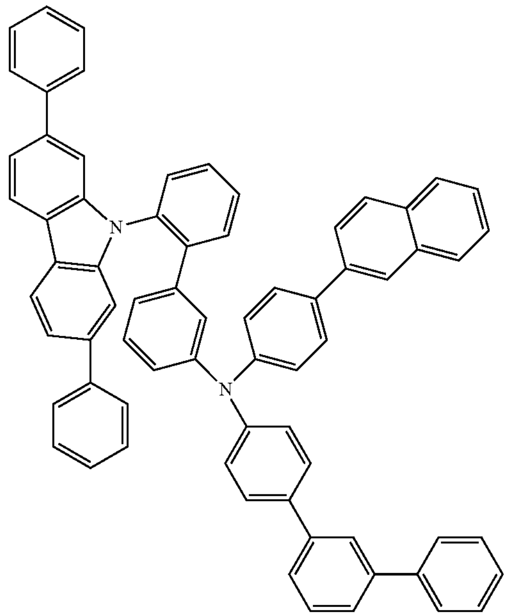
B21
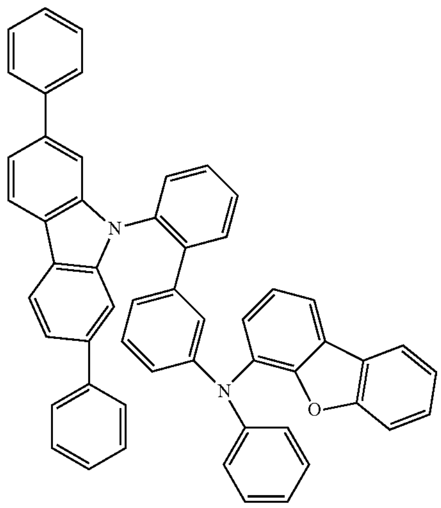
-continued
B22
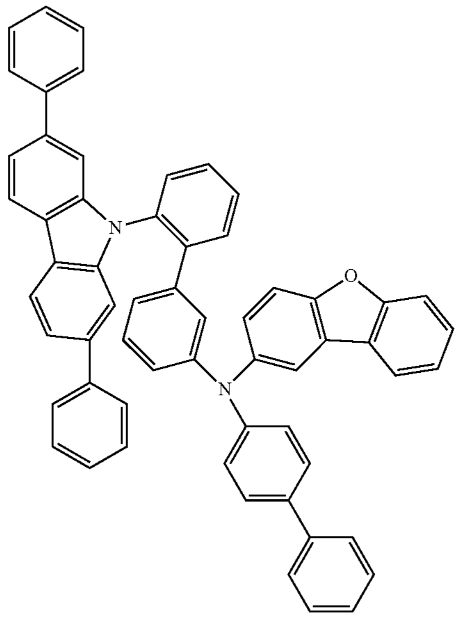
B23
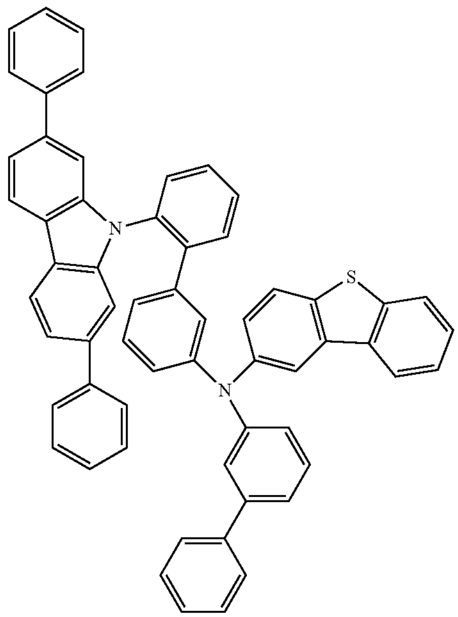

-continued
B24
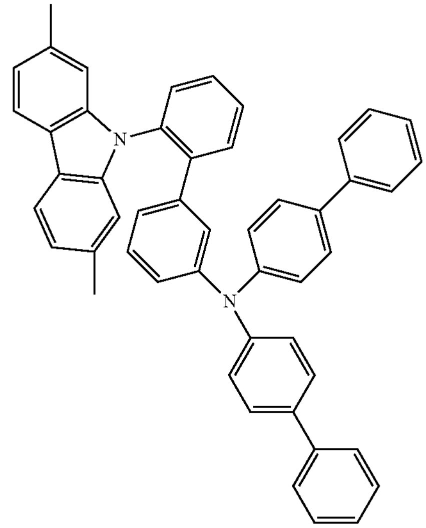
B25
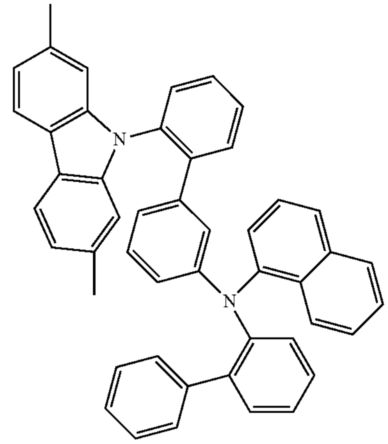
B26
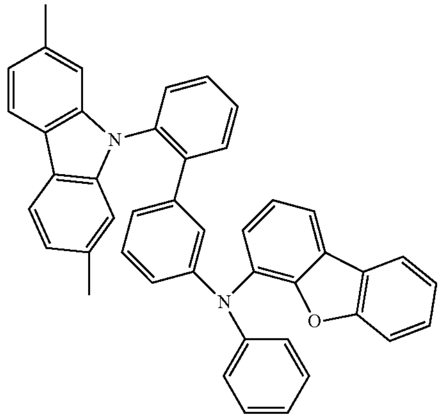
-continued
B27
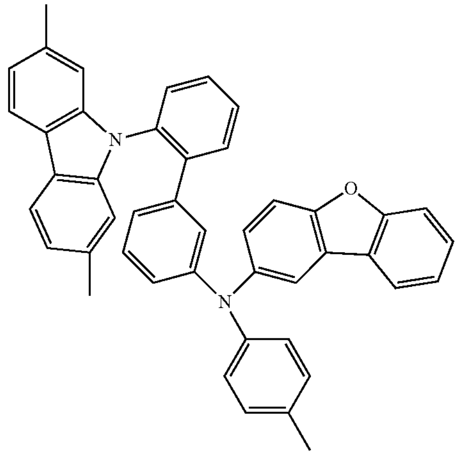
B28
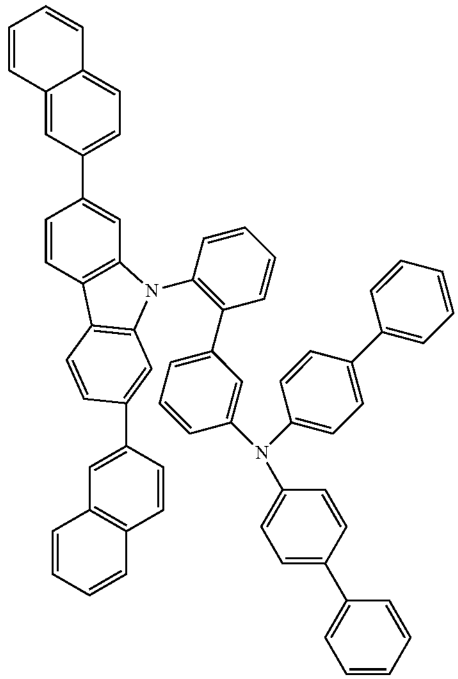

-continued
B29
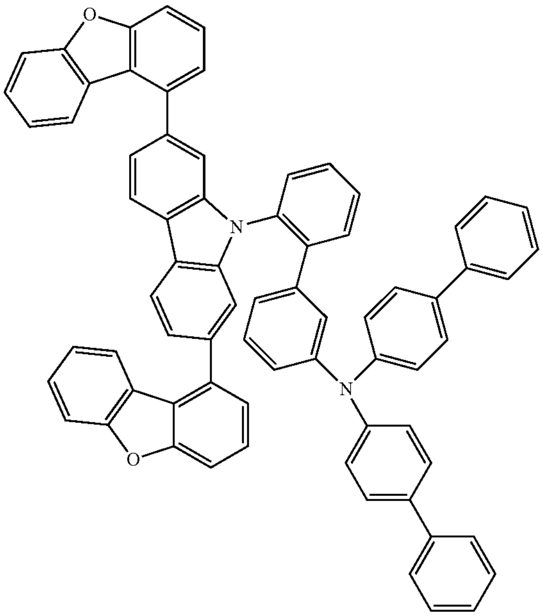
B30
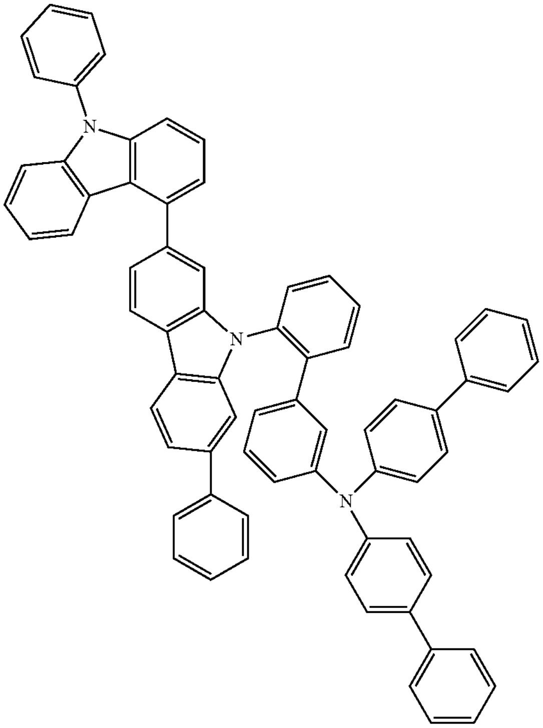
-continued
B31
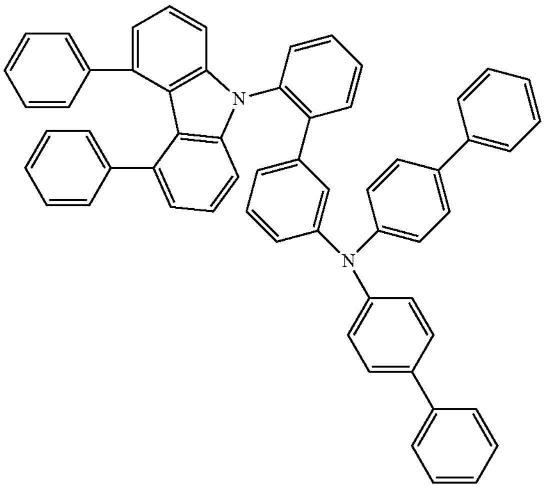
B32
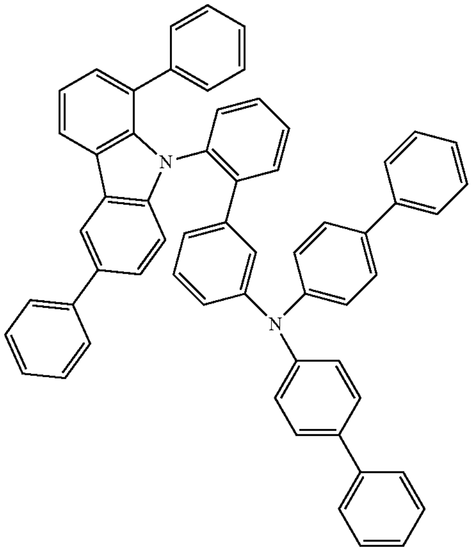
[Compound Group 1C]
C1
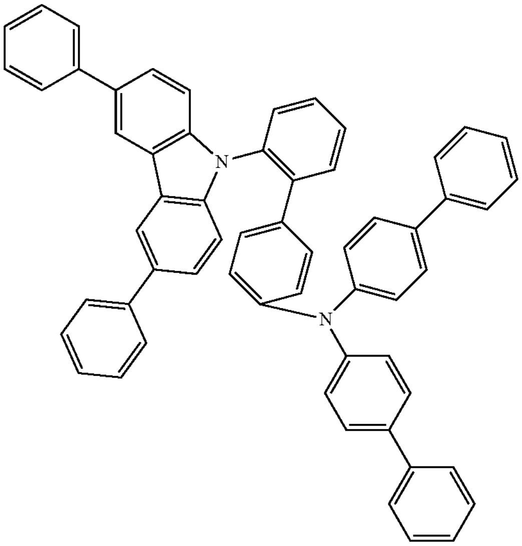

-continued
C2
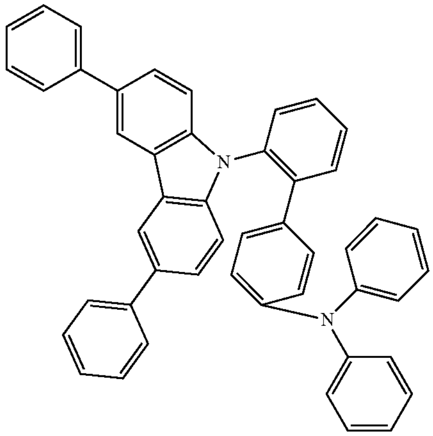
C3
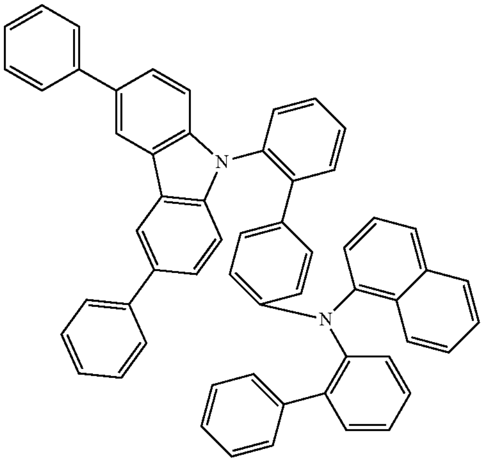
C4
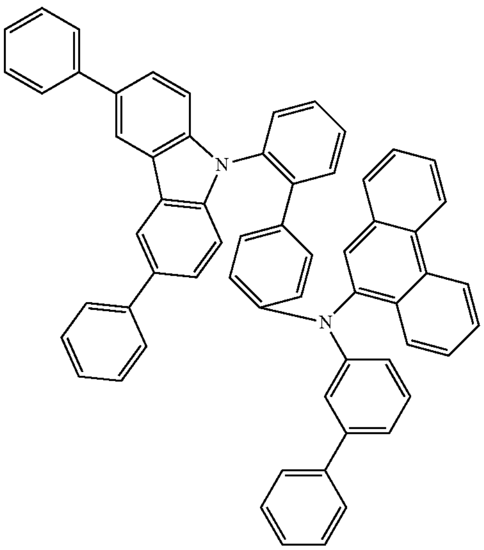
-continued
C5
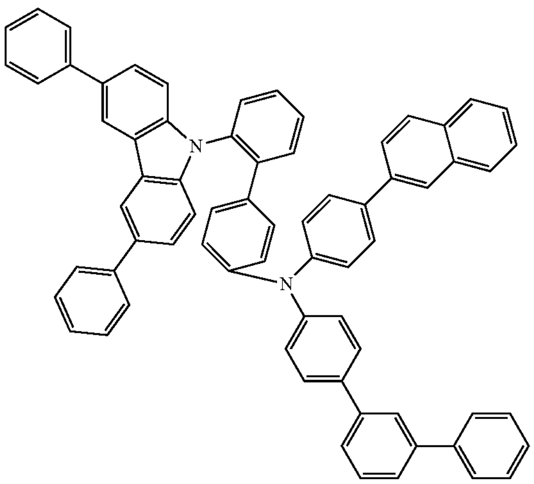
C6
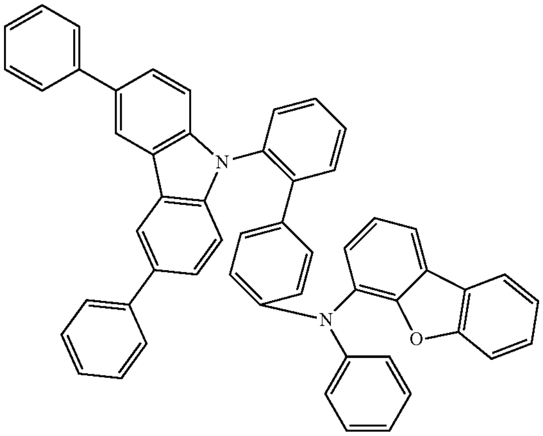
C7
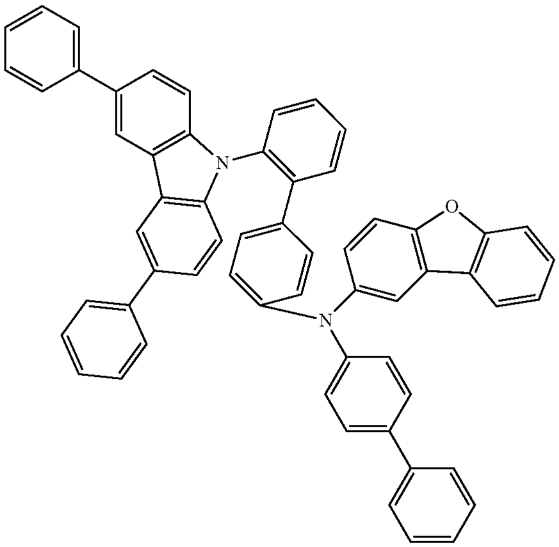

-continued
C8
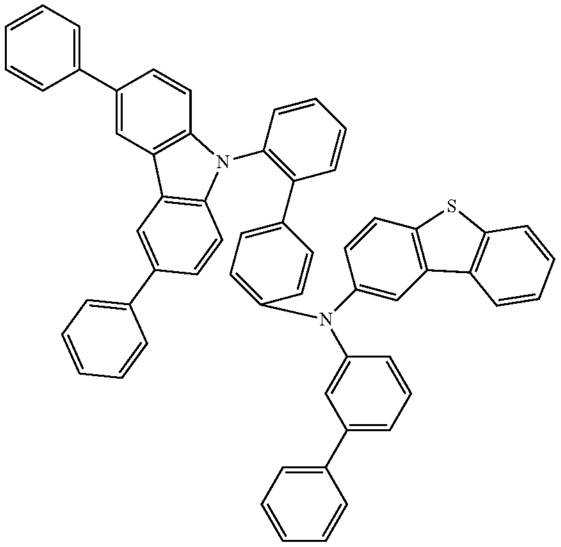
C9
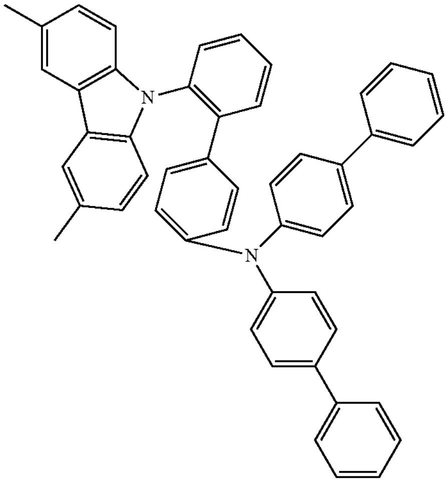
C10
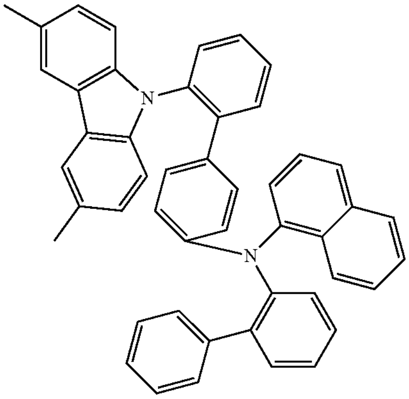
-continued
C11
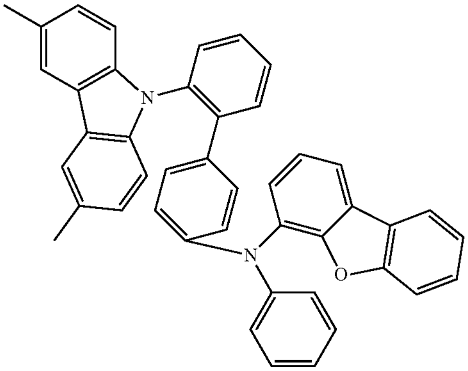
C12
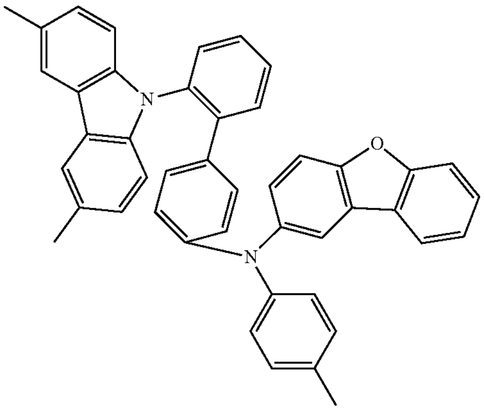
C13
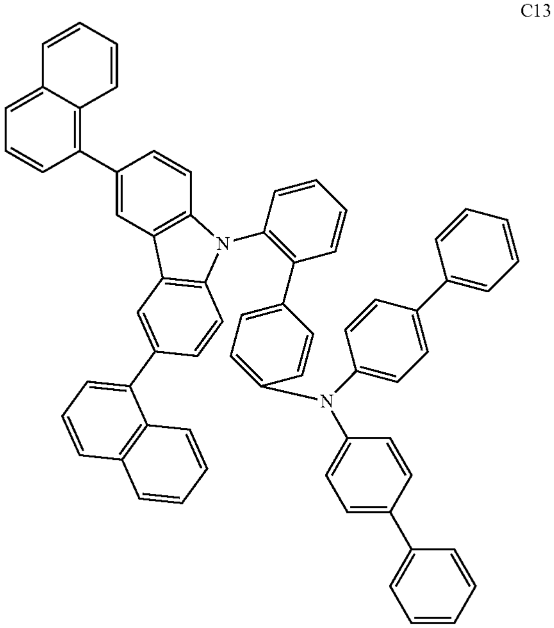

-continued
C14
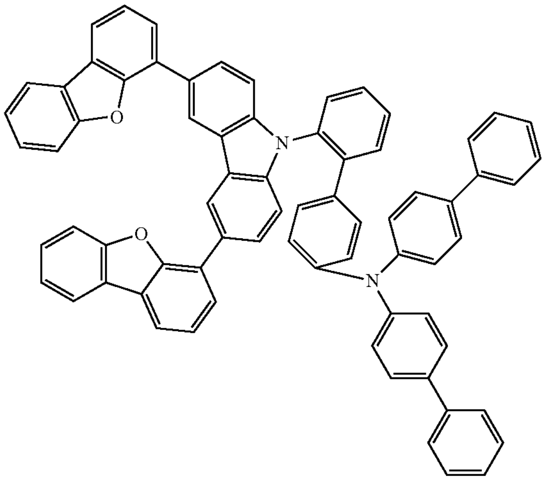
C15
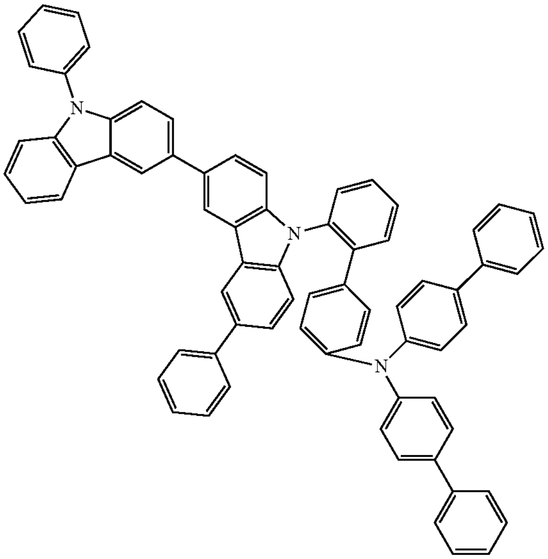
-continued
C16
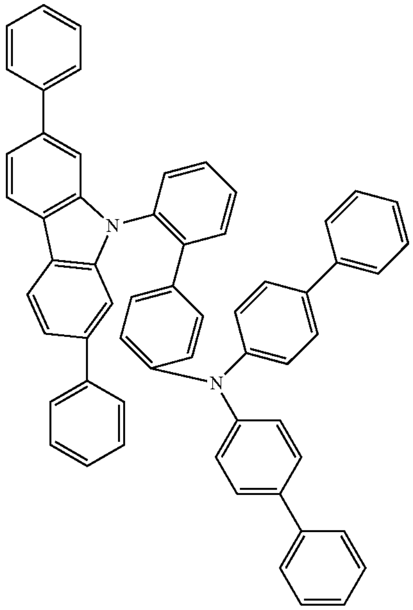
C17
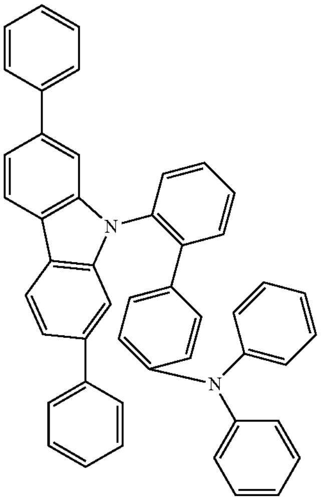
C18
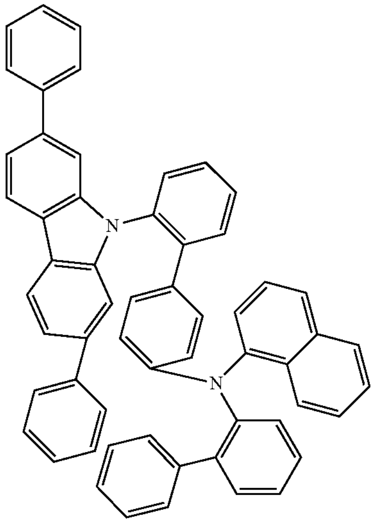

-continued
C19
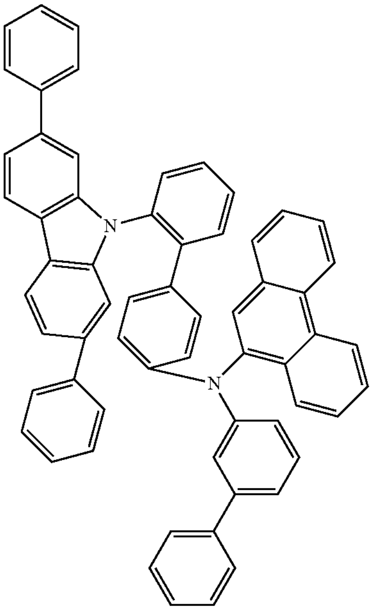
C20
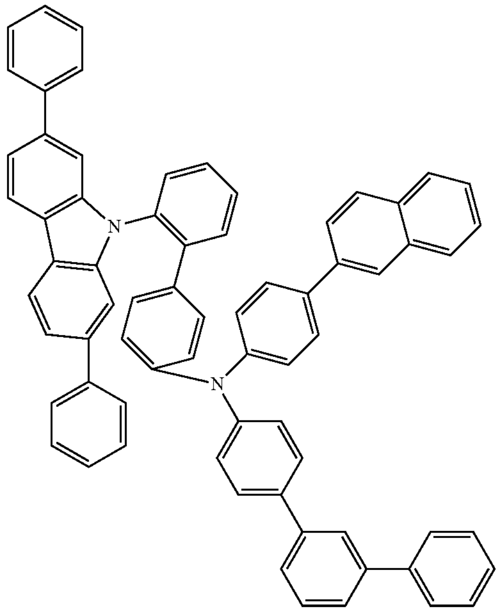
-continued
C21
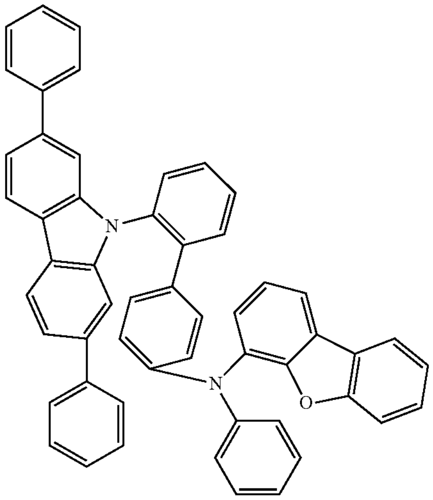
C22
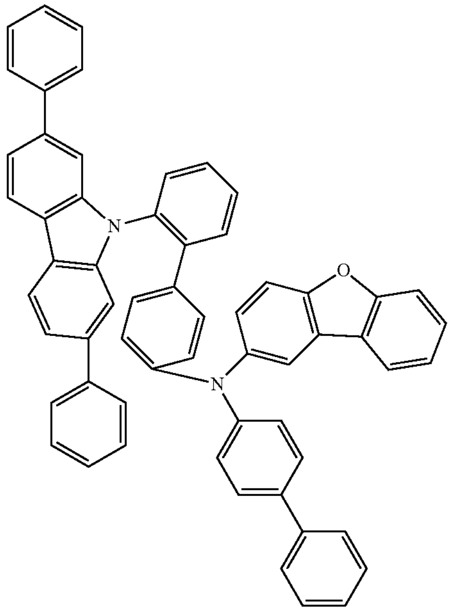

C23
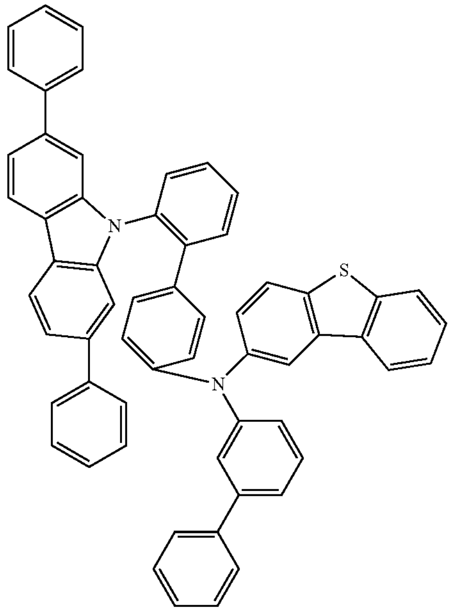
C24
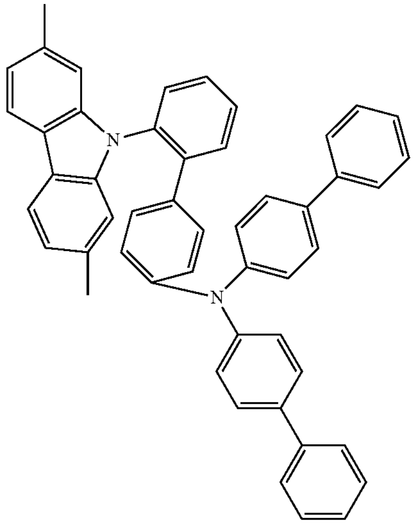
C25
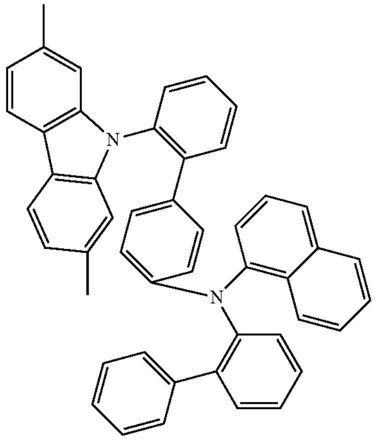
C26
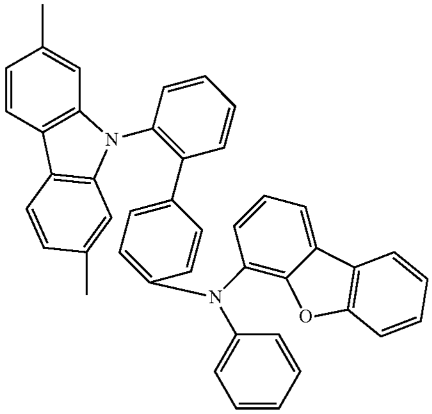
C27
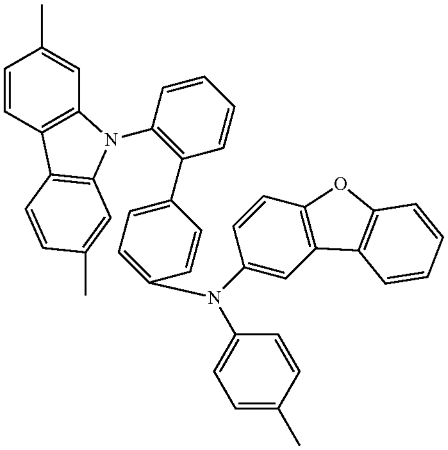
C28
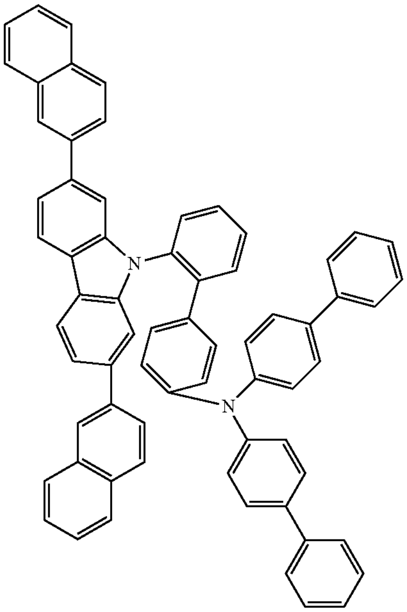

-continued
C29
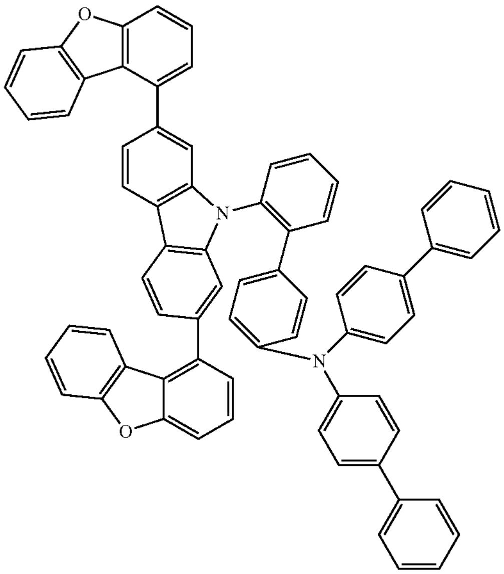
C30
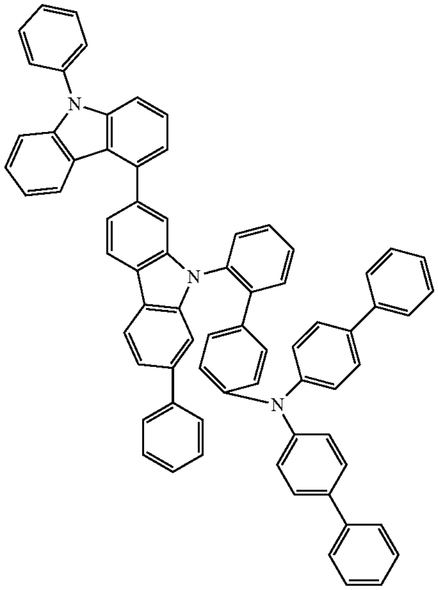
-continued
C31
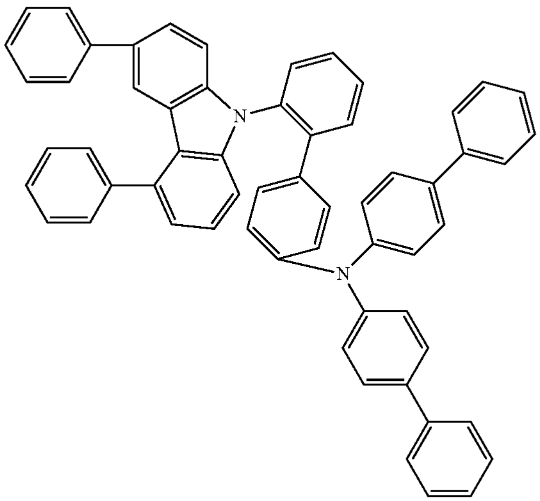
C32
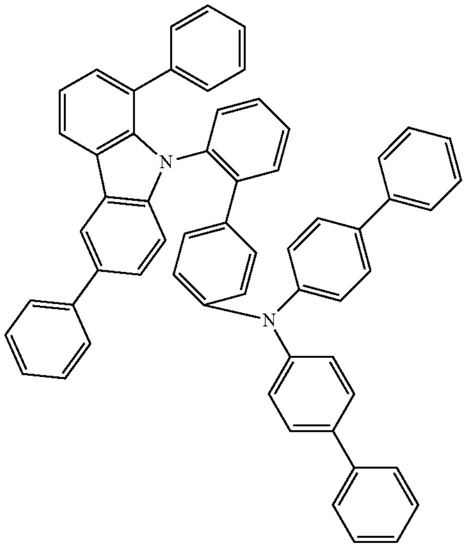
[Compound Group 1D]
D1
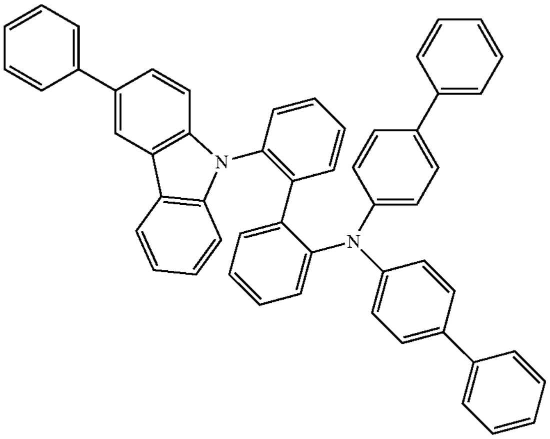

-continued
D2
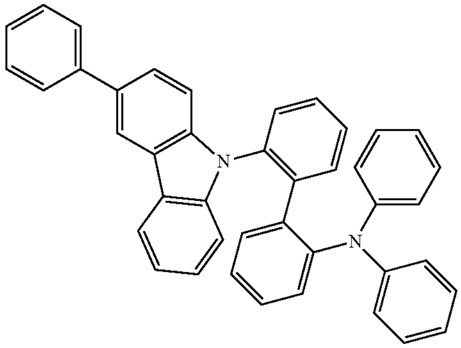
D3
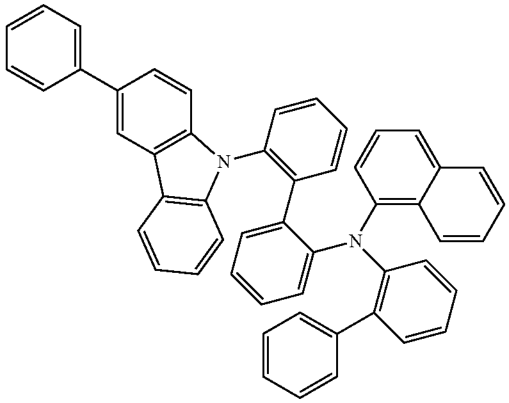
D4
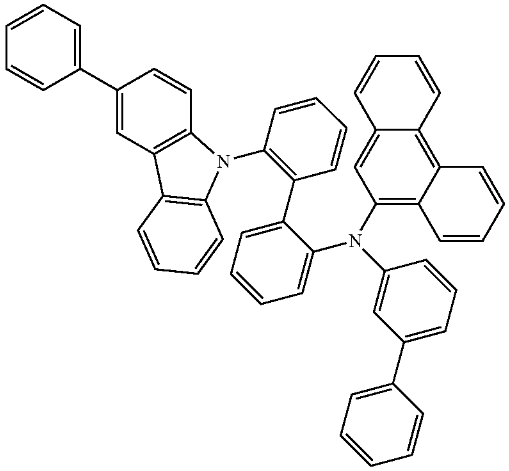
D5
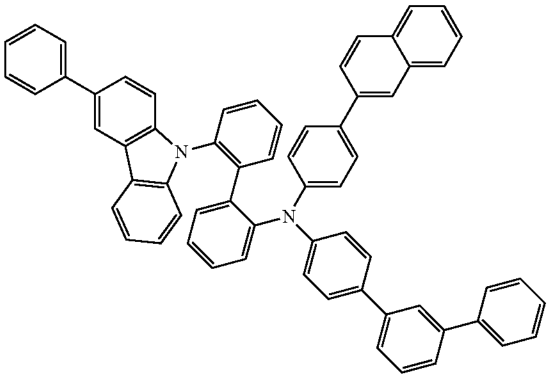
-continued
D6
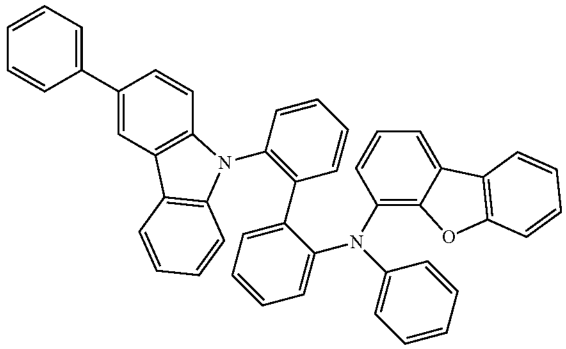
D7
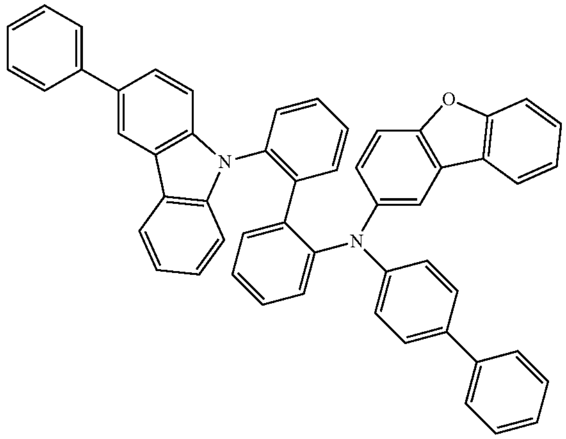
D8
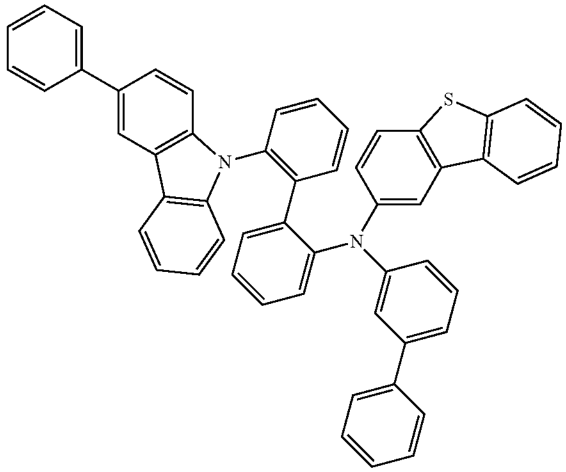

-continued
D9
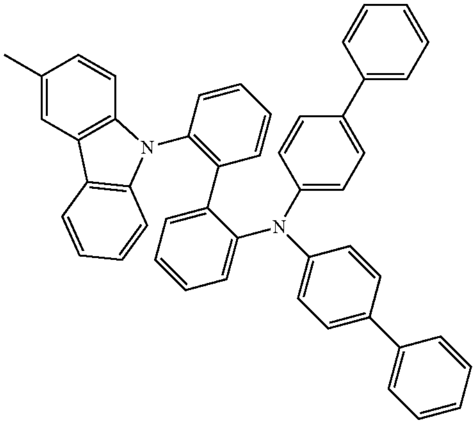
D10
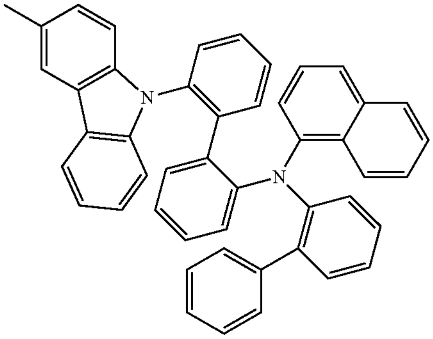
D11
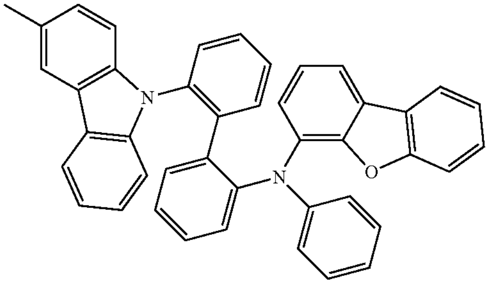
D12
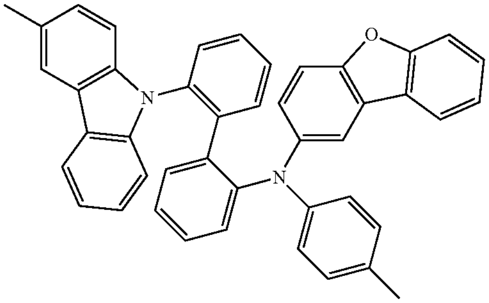
-continued
D13
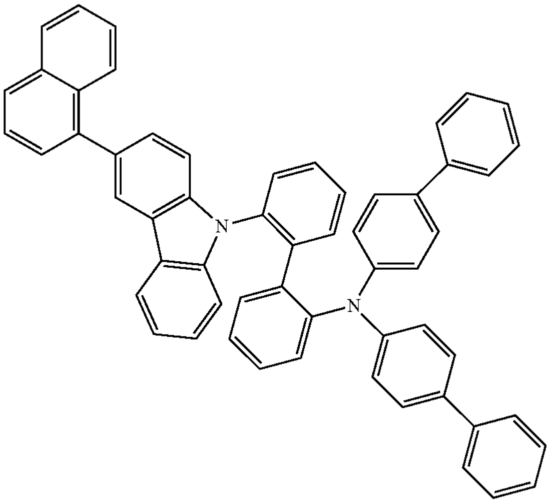
D14
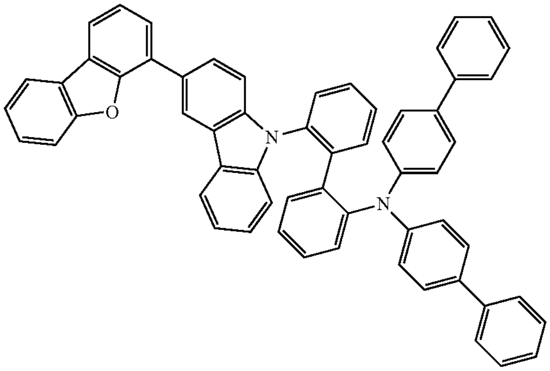
D15
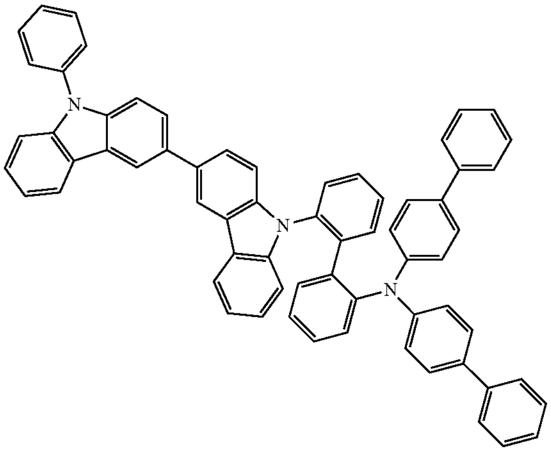

-continued
D16
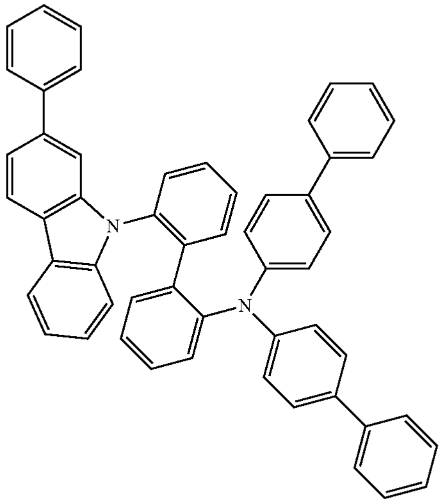
D17
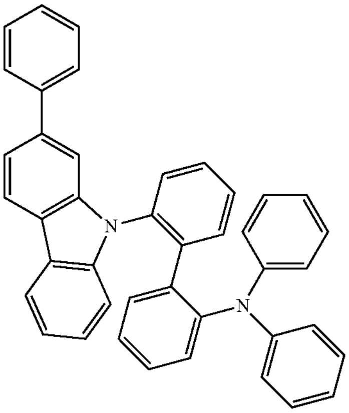
D18
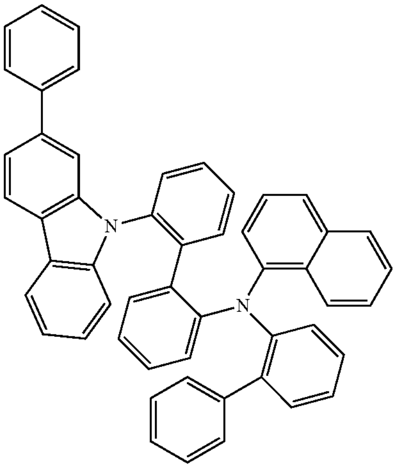
-continued
D19
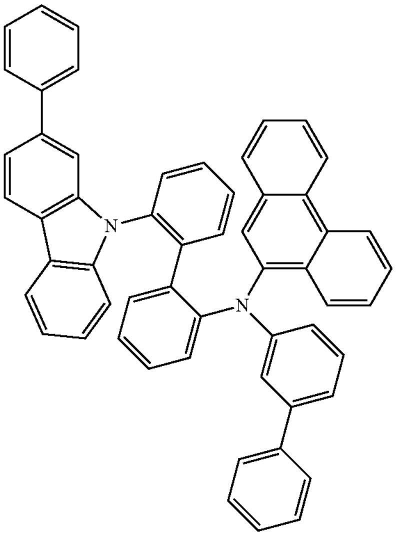
D20
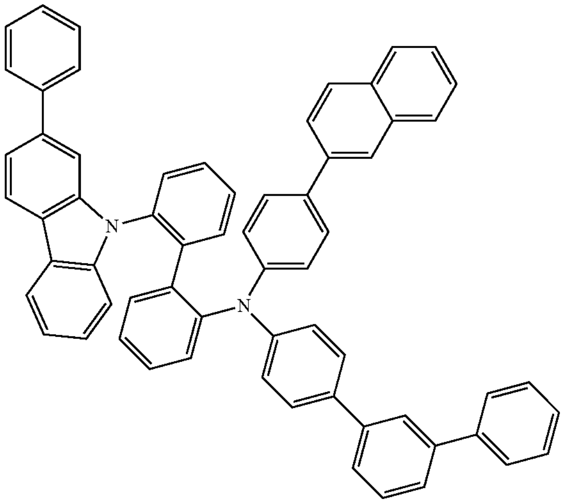
D21
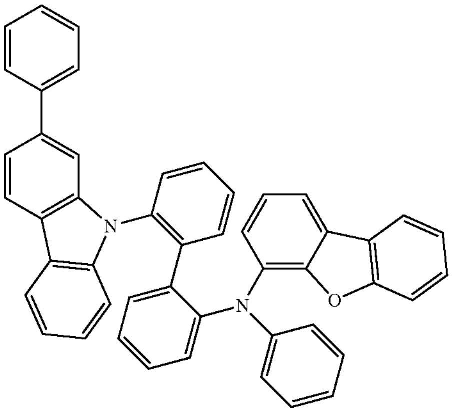

-continued
D22
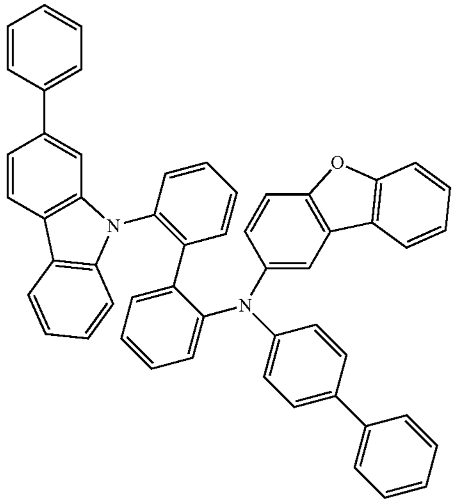
D23
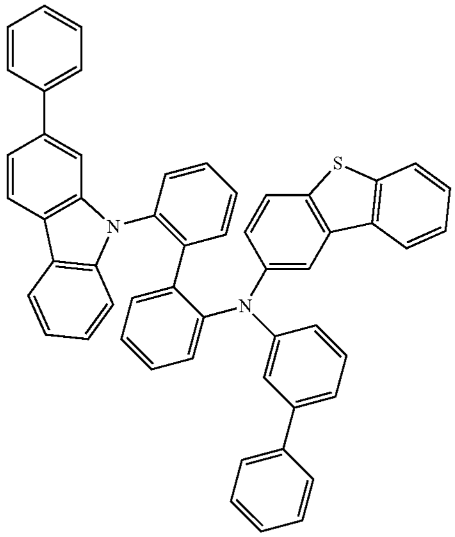
D24
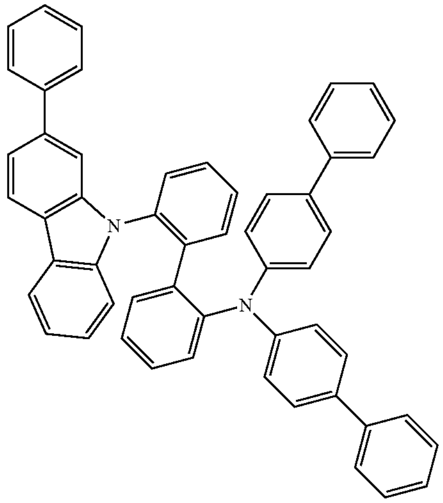
-continued
D25
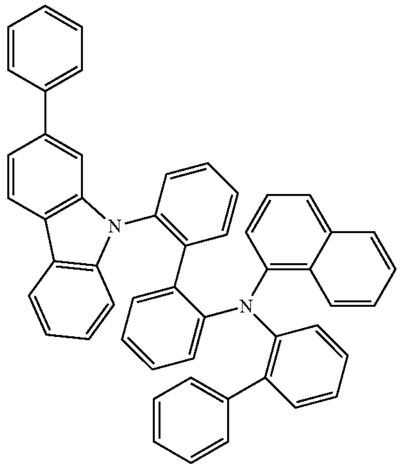
D26
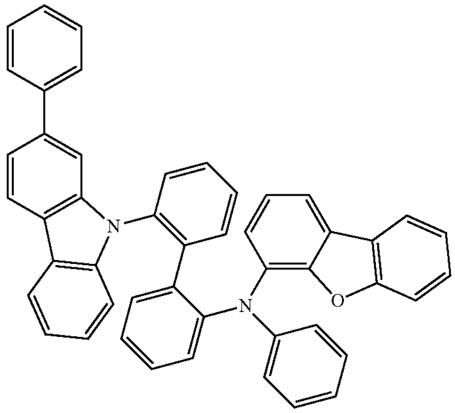
D27
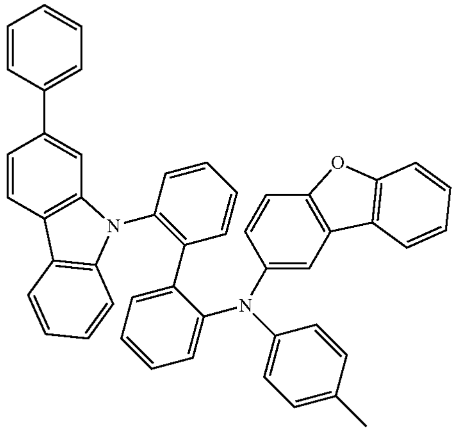

-continued
D28
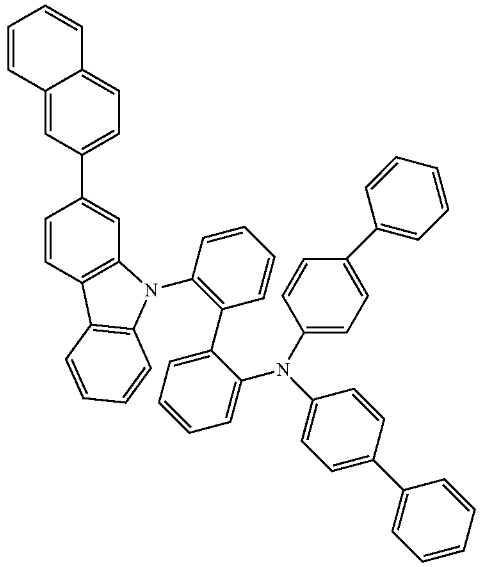
D29
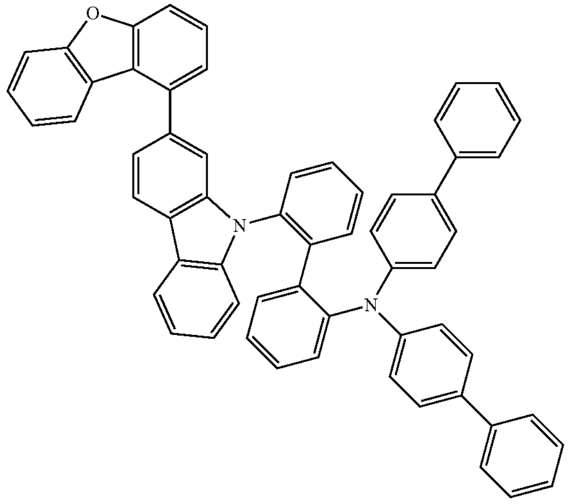
-continued
D30
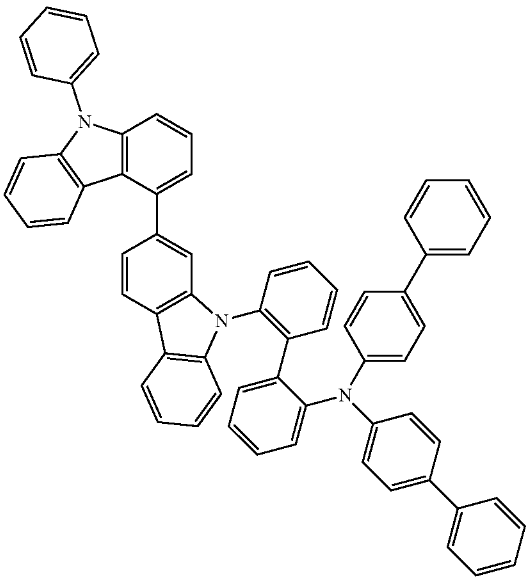
D31
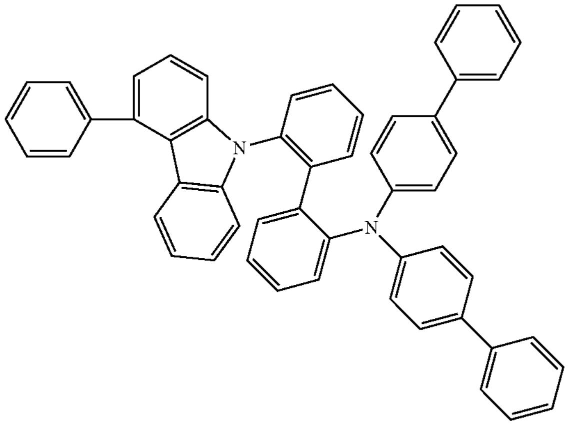
D32
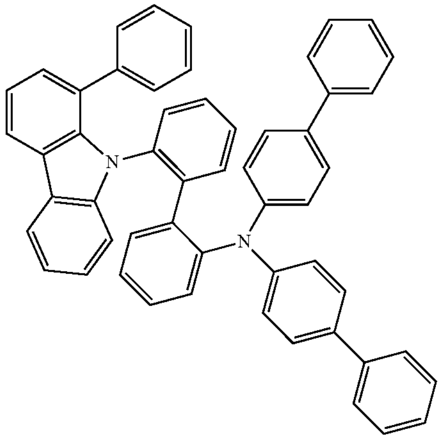

-continued
D33
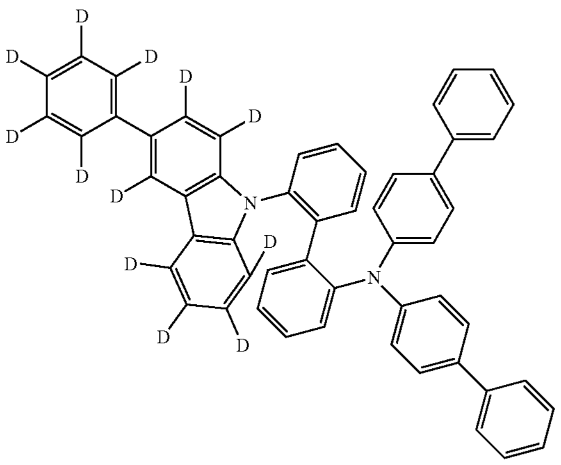
[Compound Group 1E]
E1
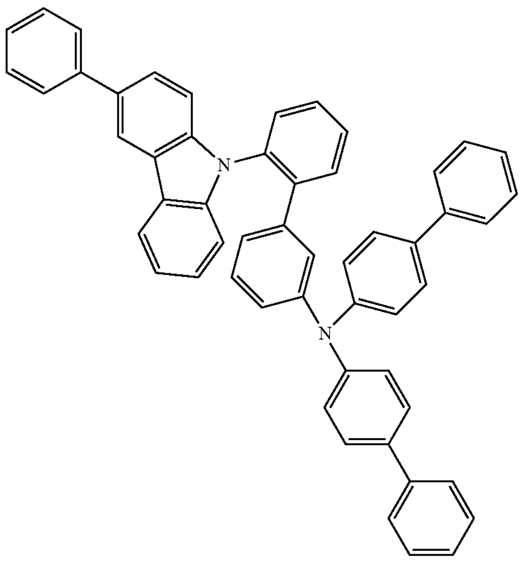
E2
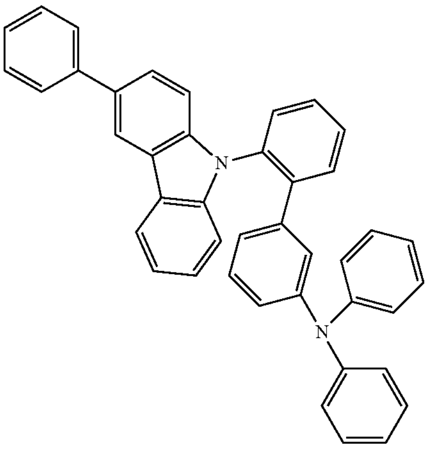
-continued
E3
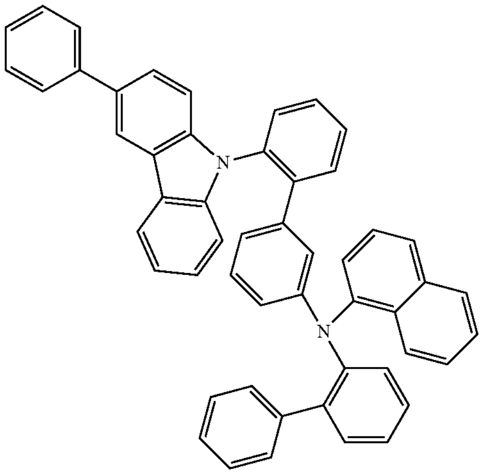
E4
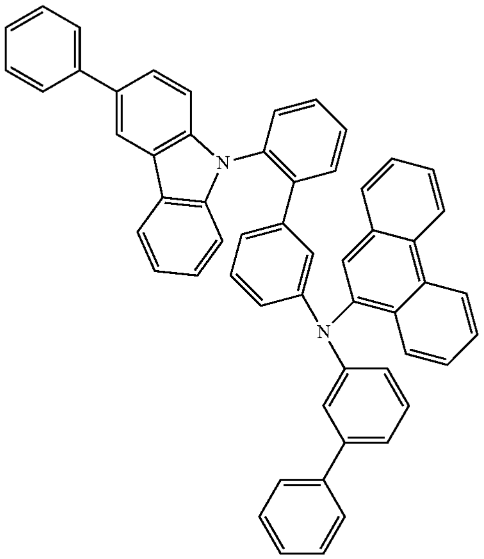
E5
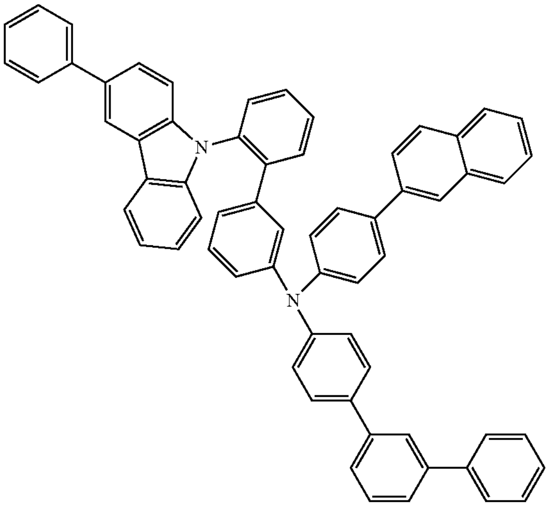

-continued
E6
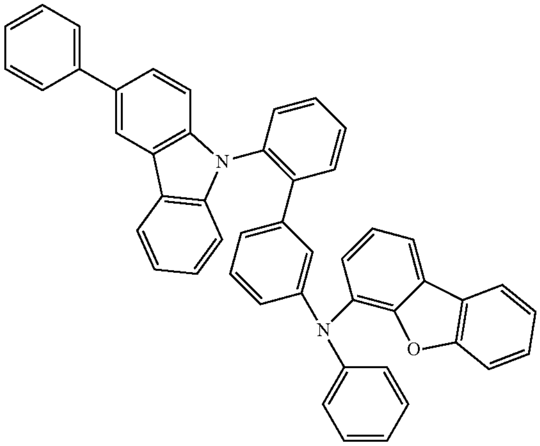
E7
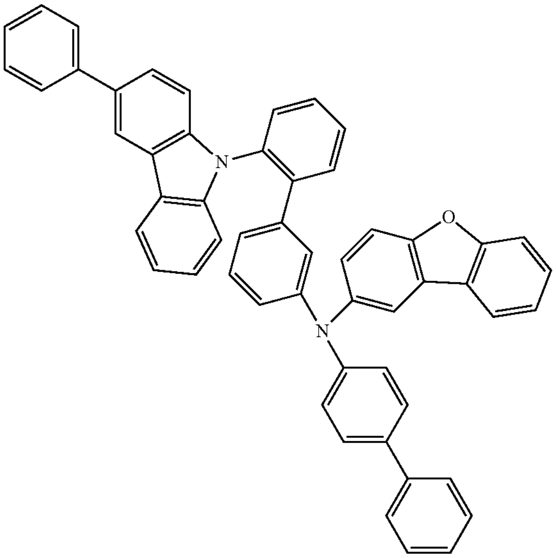
E8
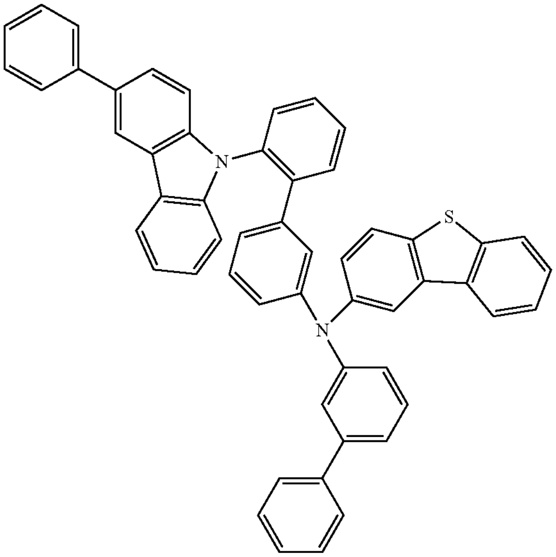
-continued
E9
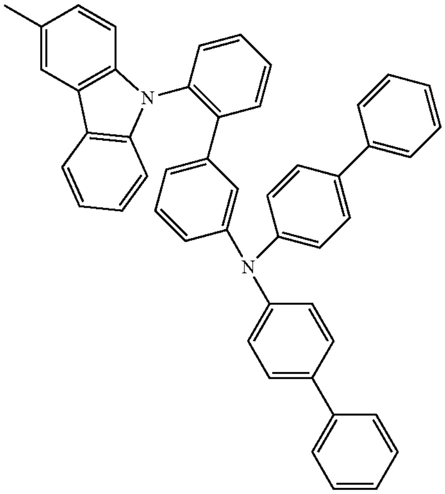
E10
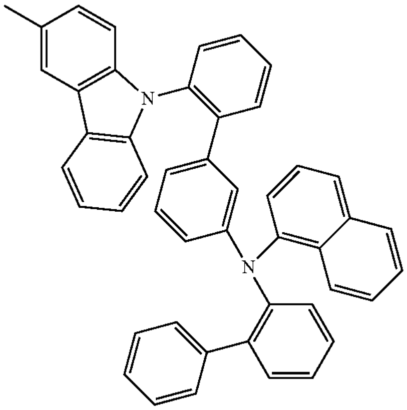
E11
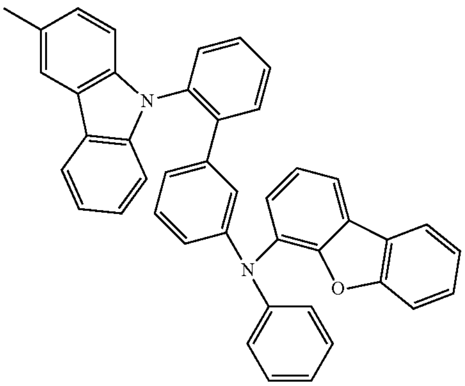

-continued
E12
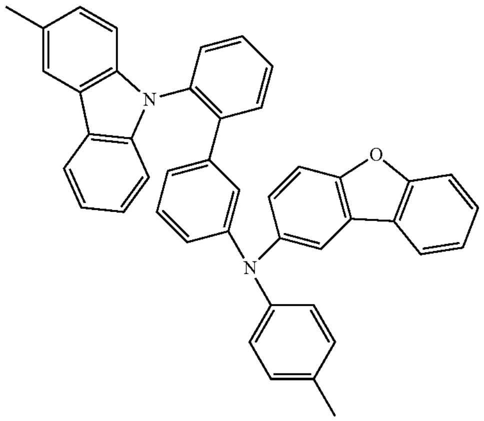
E13
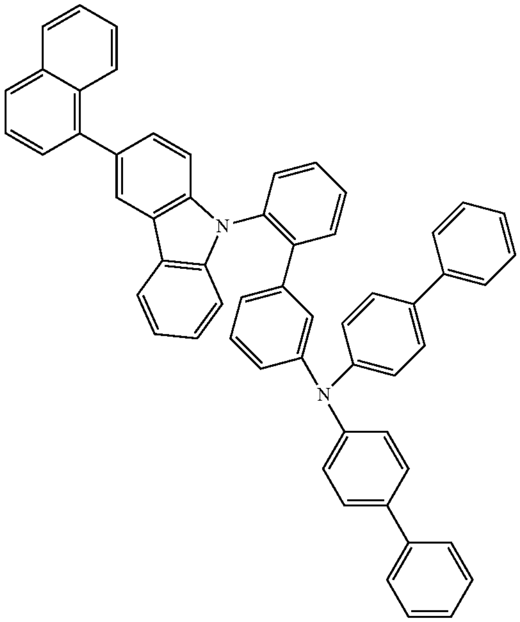
E14
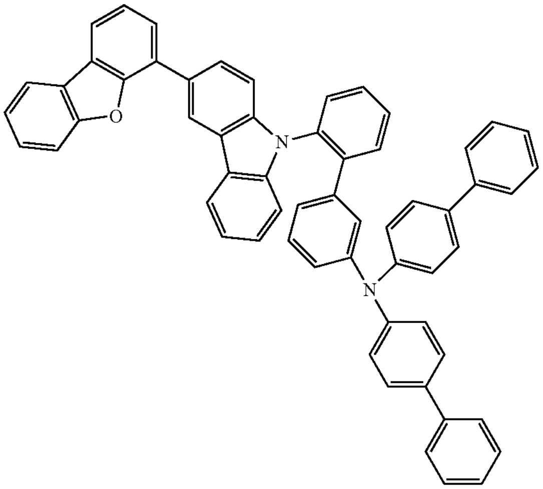
-continued
E15
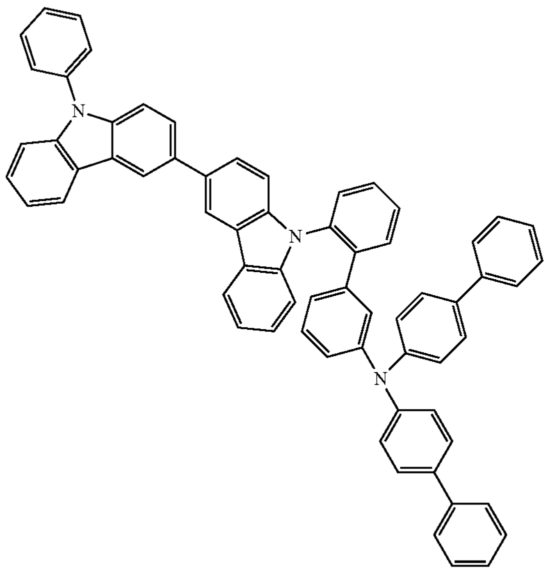
E16
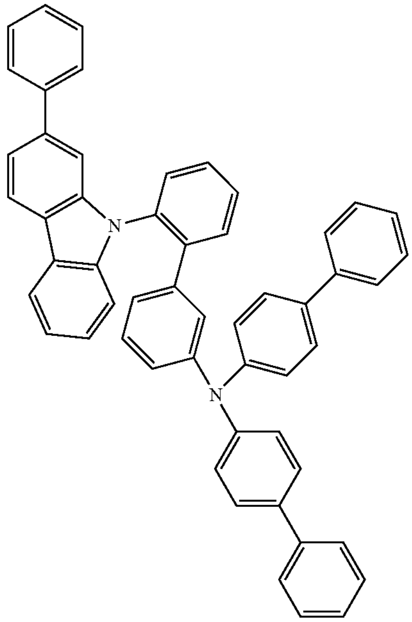

-continued
E17
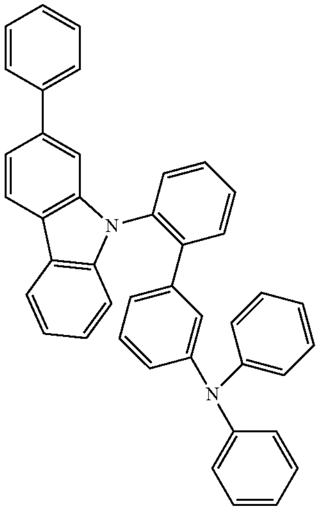
E18
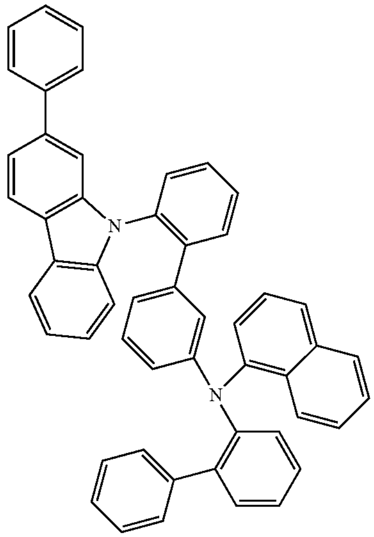
E19
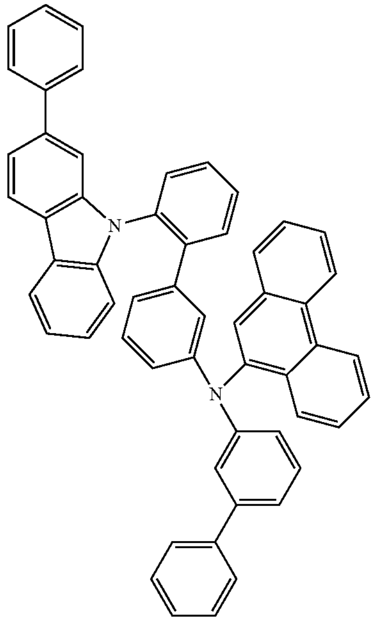
-continued
E20
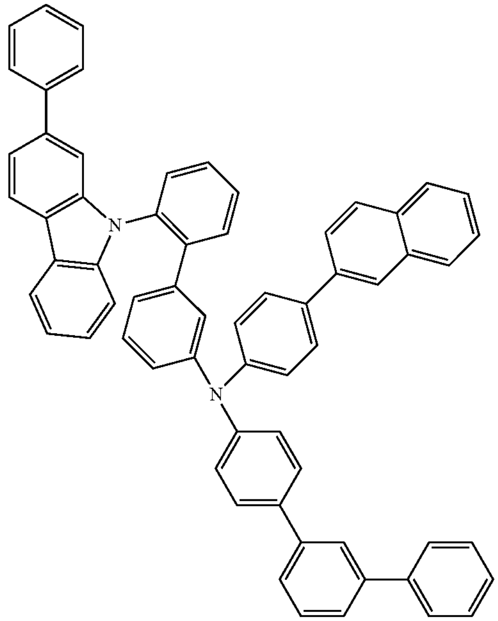
E21
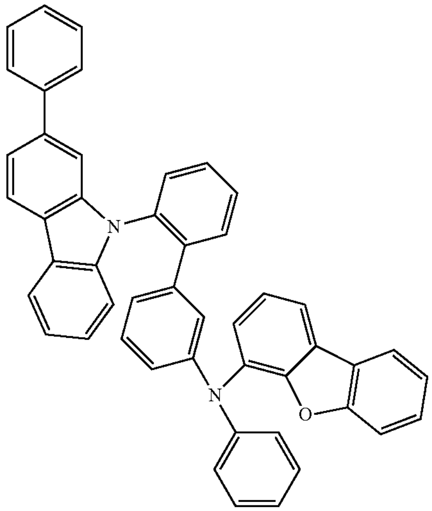

-continued
E22
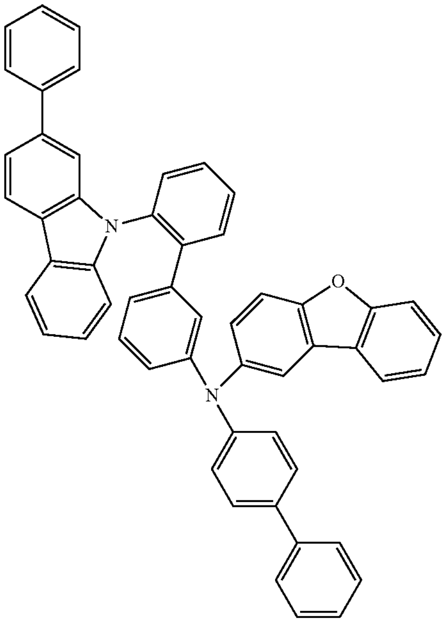
E23
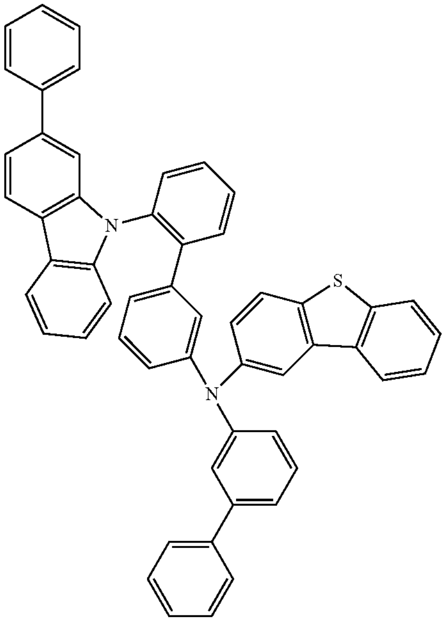
-continued
E24
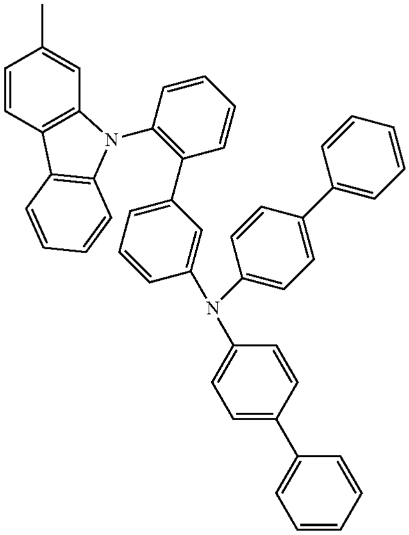
E25
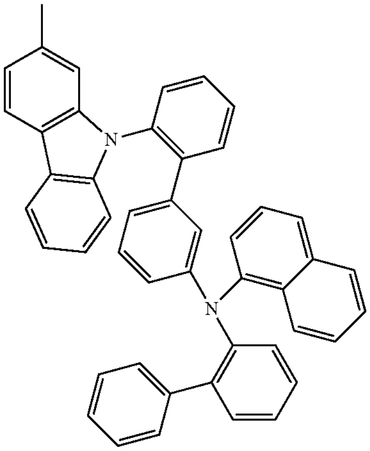
E26
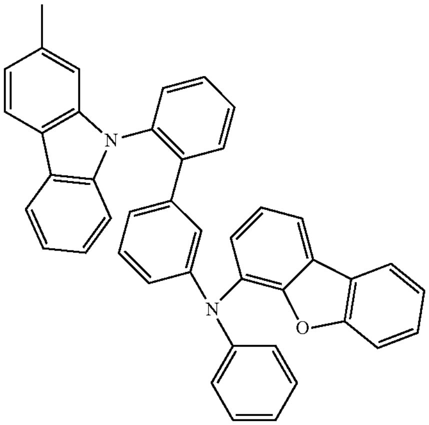

-continued
E27
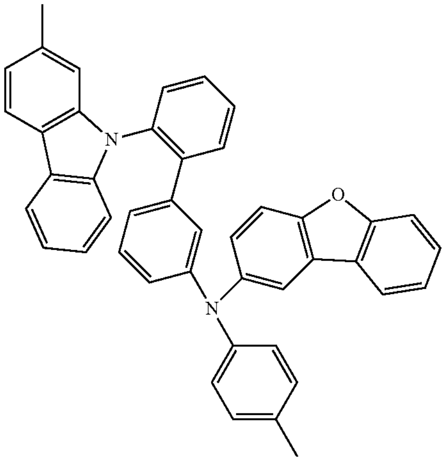
E28
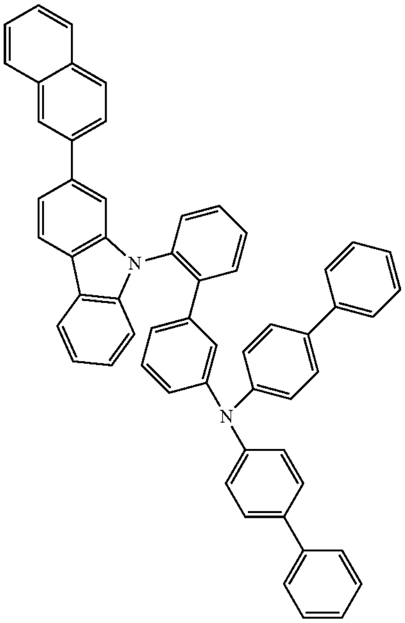
E29
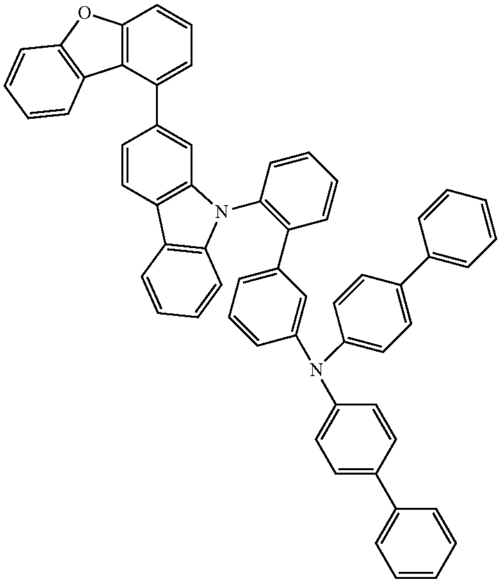
-continued
E30
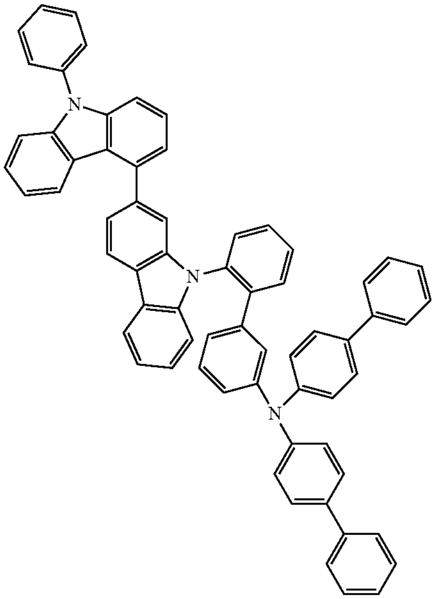
E31
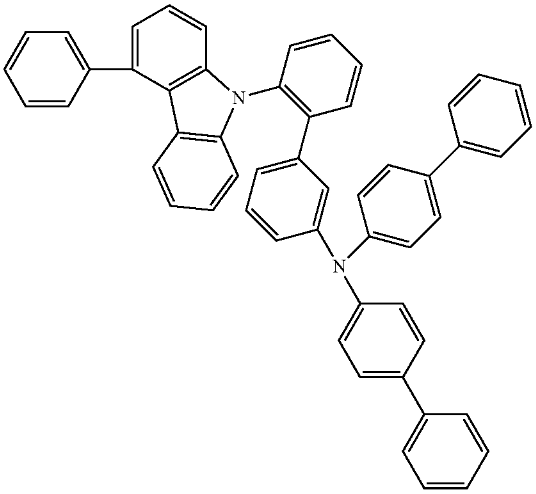
E32
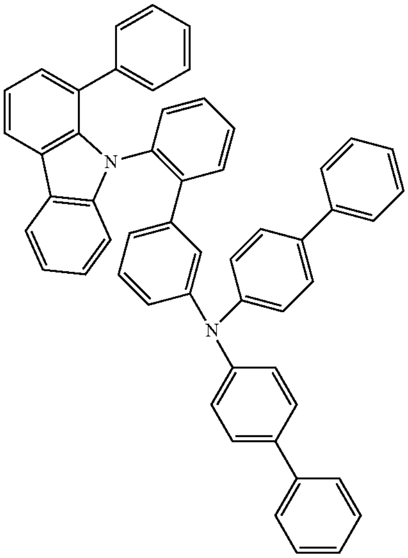

-continued
[Compound Group 1F]
F1
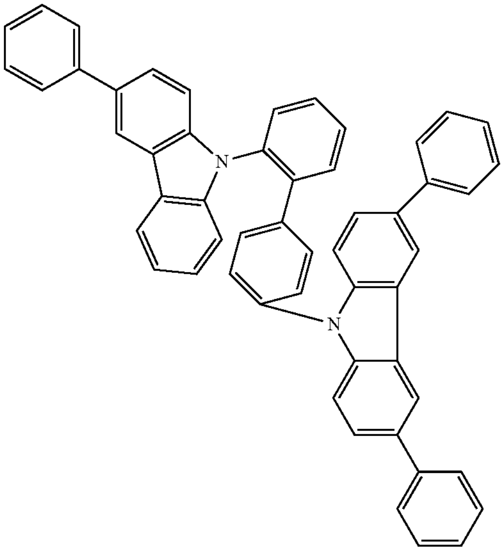
F2
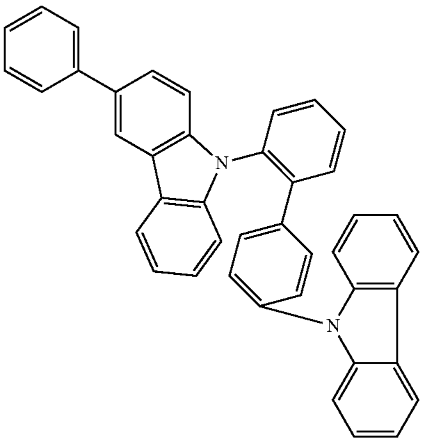
F3
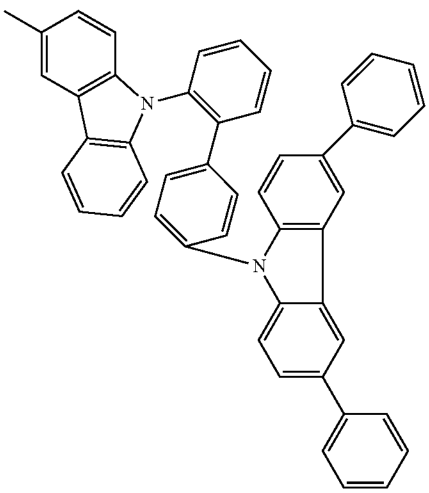
-continued
F4
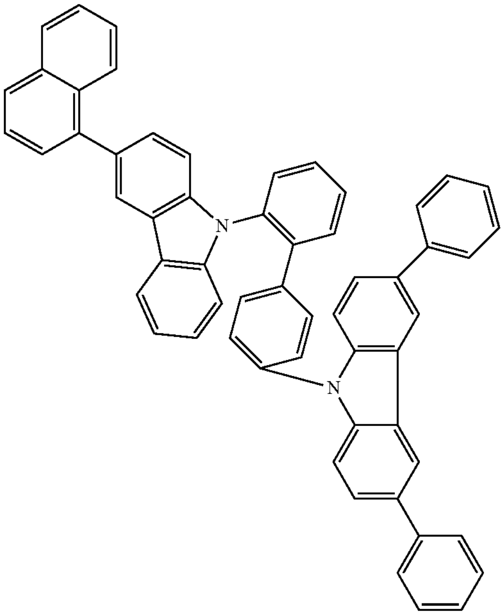
F5
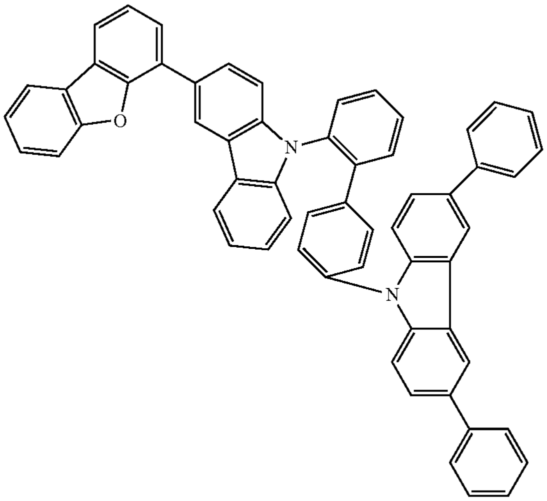

-continued
F6
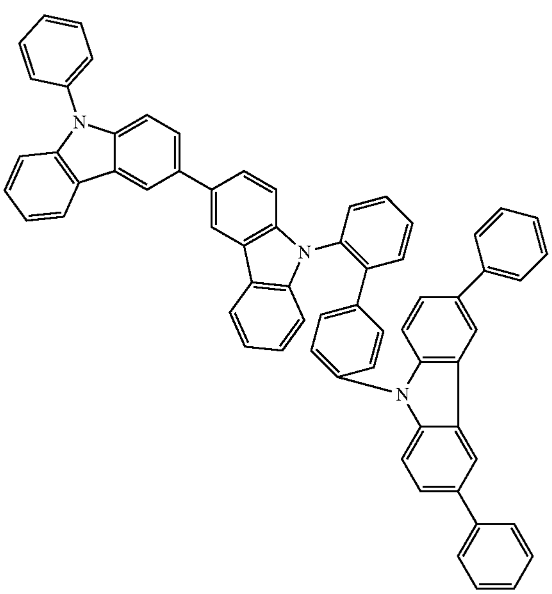
F7
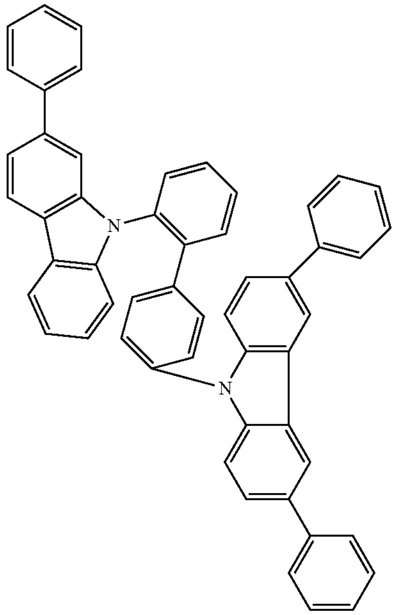
-continued
F8
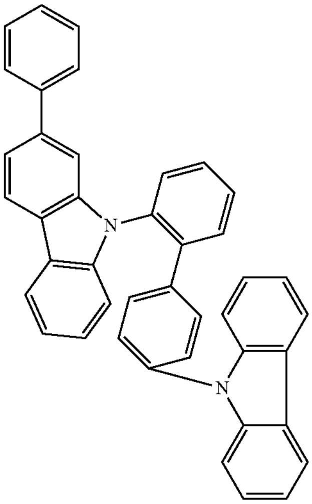
F9
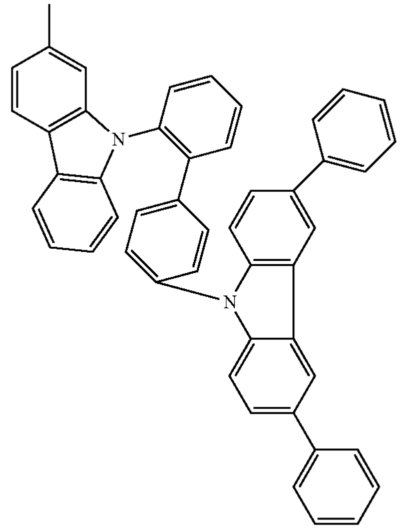
F10
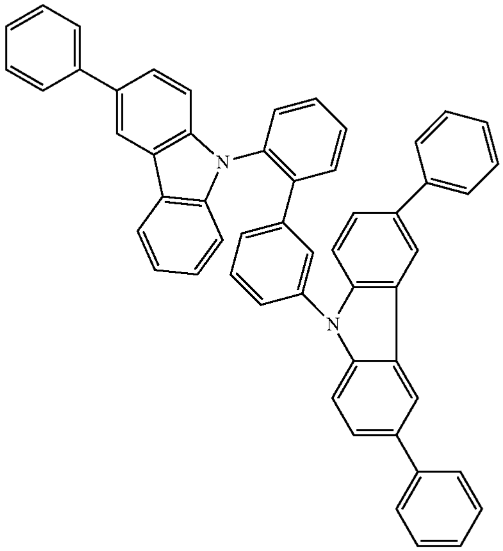

-continued
F11
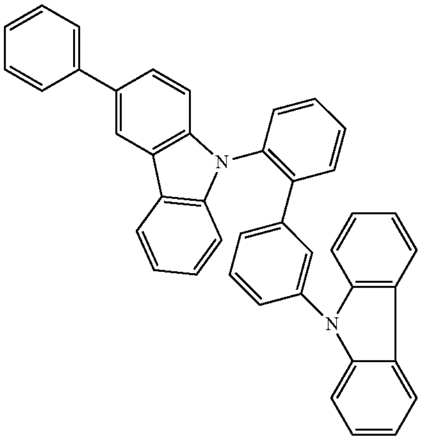
F12
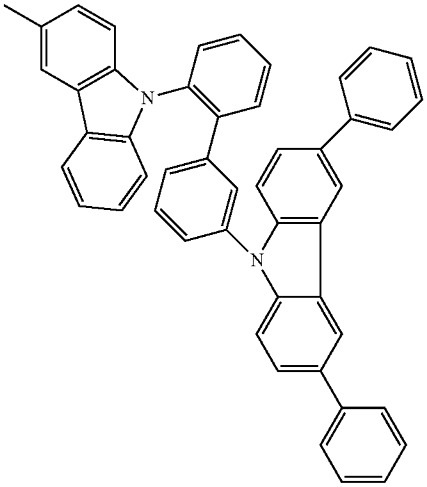
F13
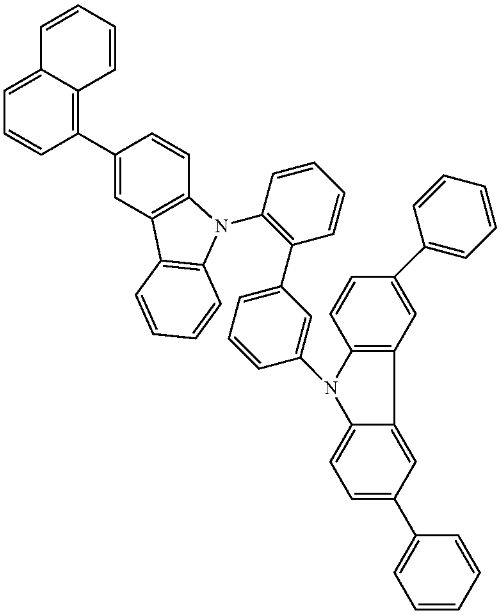
-continued
F14
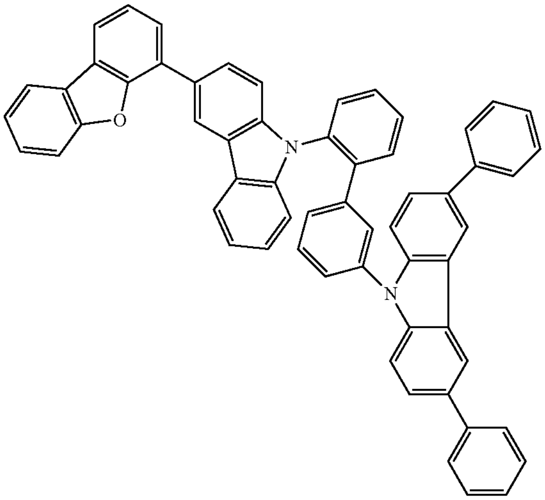
F15
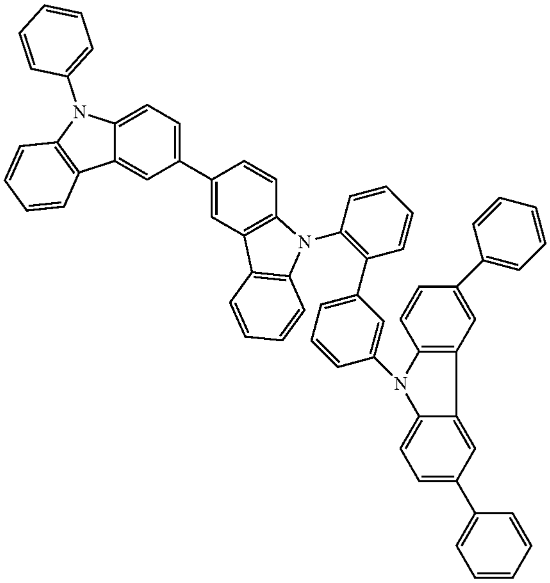

-continued
F16
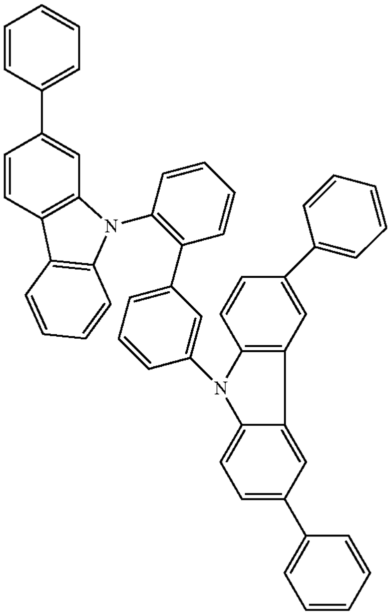
F17
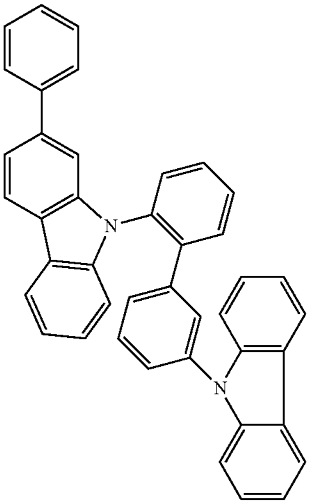
F18
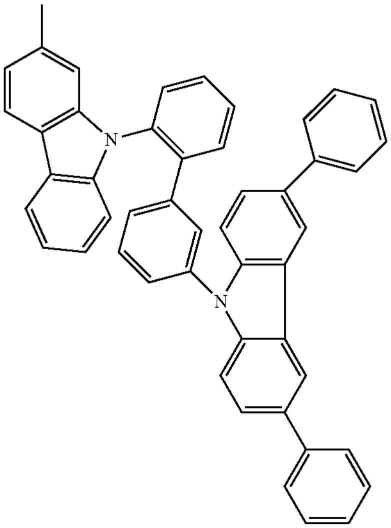
-continued
[Compound Group 1G]
G1
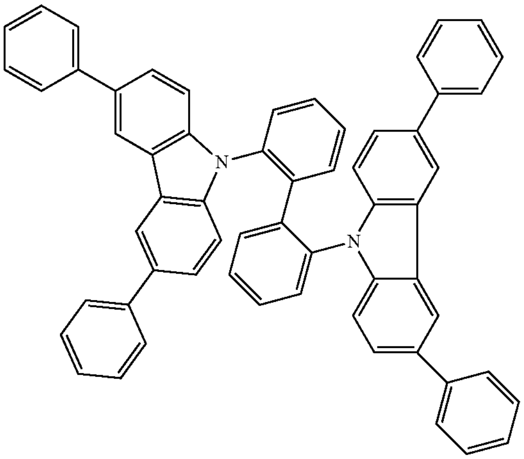
G2
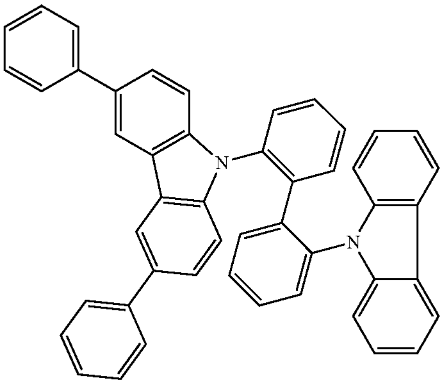
G3
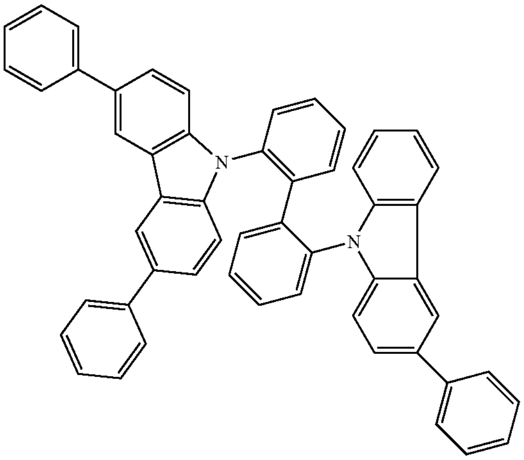

-continued
G4
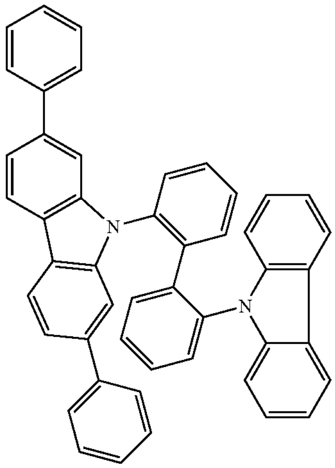
G5
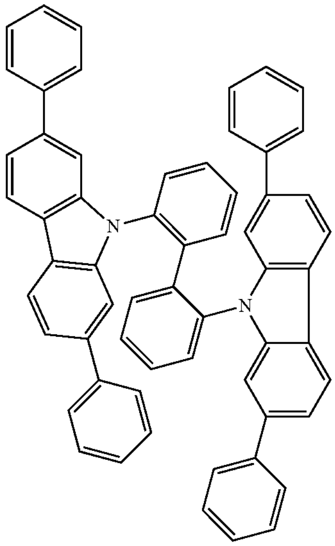
G6
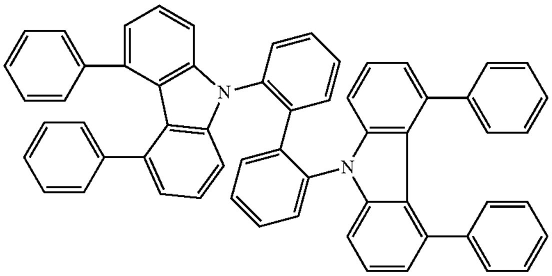
-continued
G7
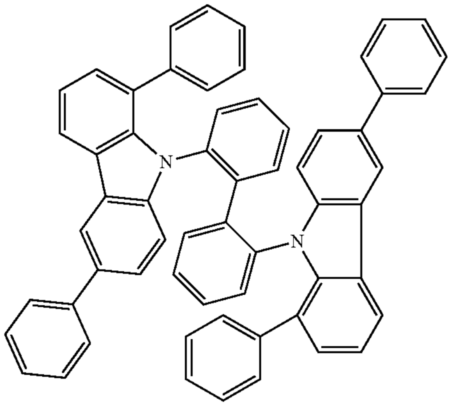
G8
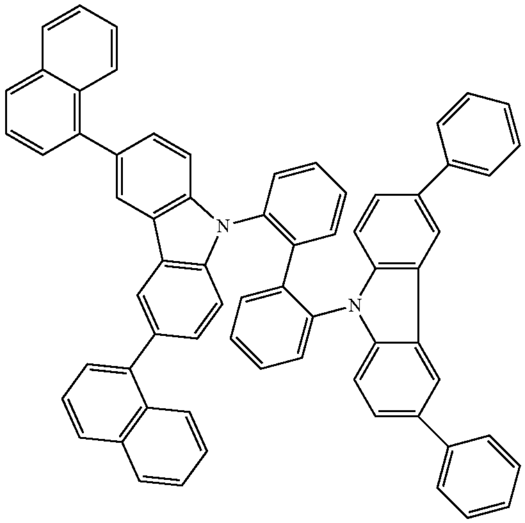
G9
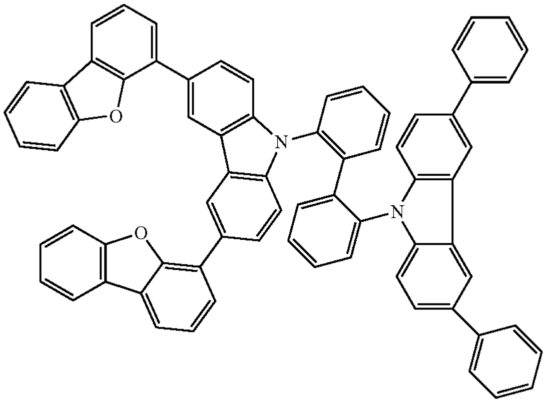

G10
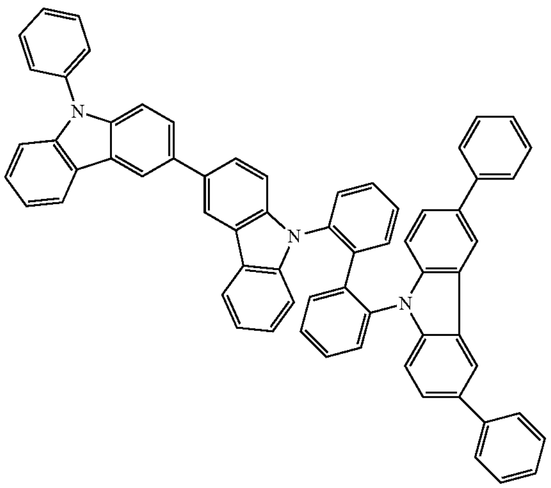
G11
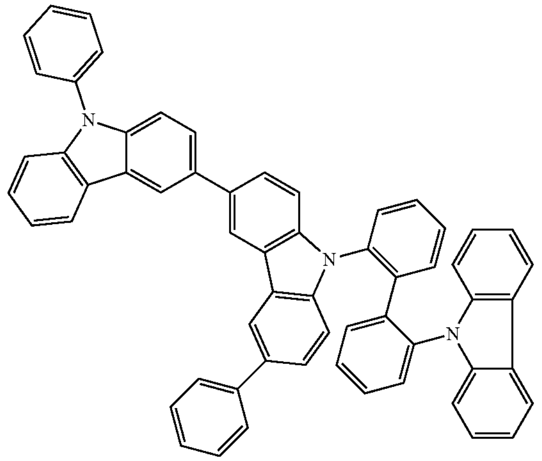
G12
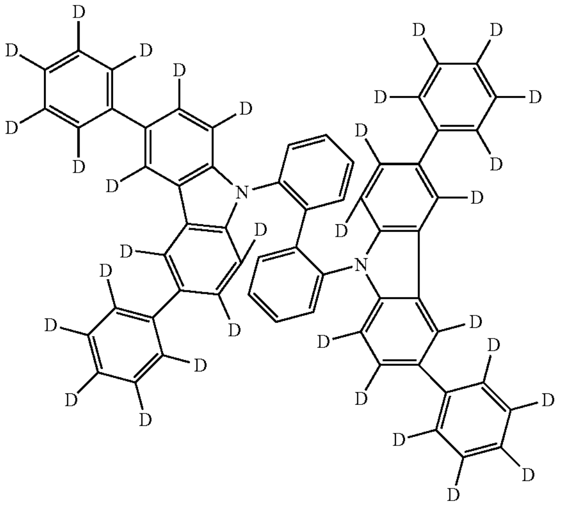
G13
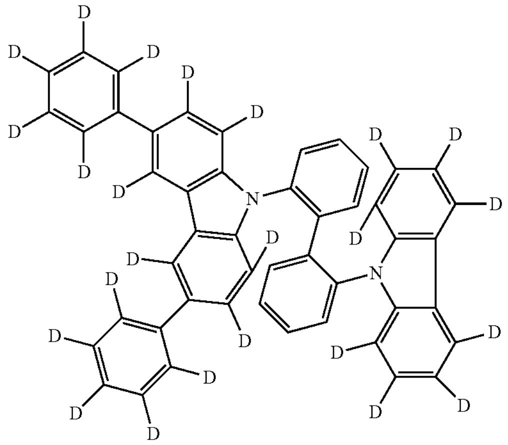
G14
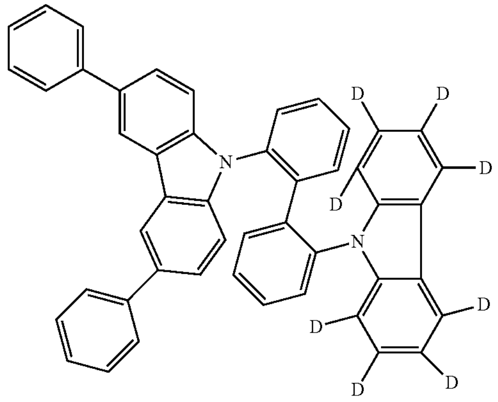
[Compound Group 1H]
H1
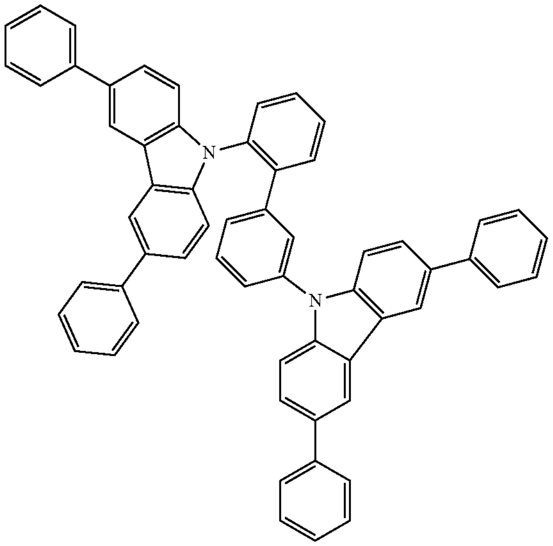

-continued
H2
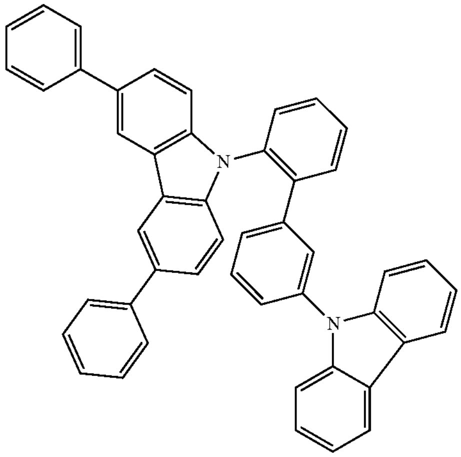
H3
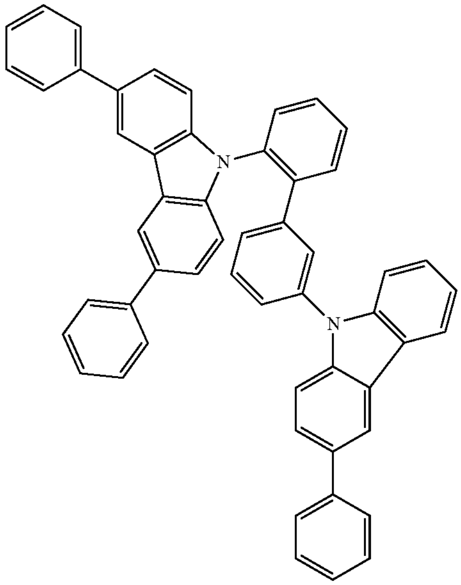
H4
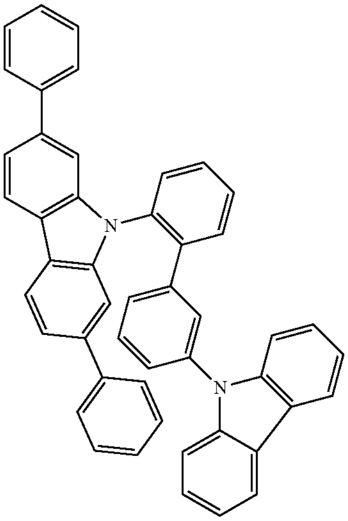
-continued
H5
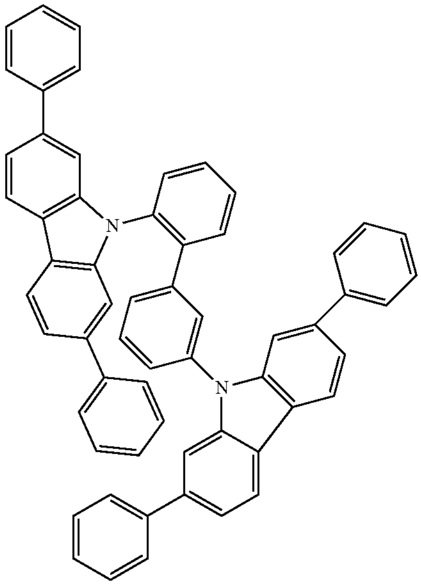
H6
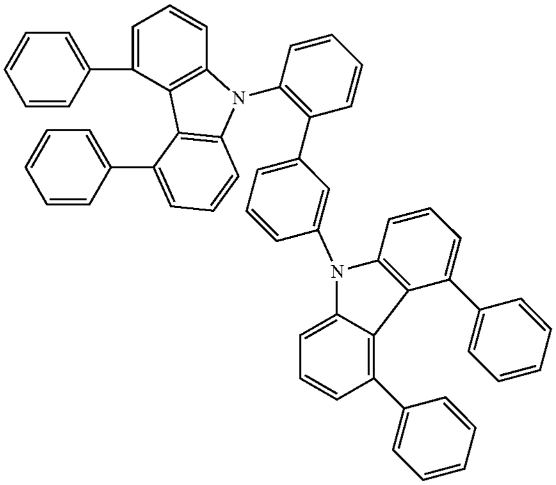
H7
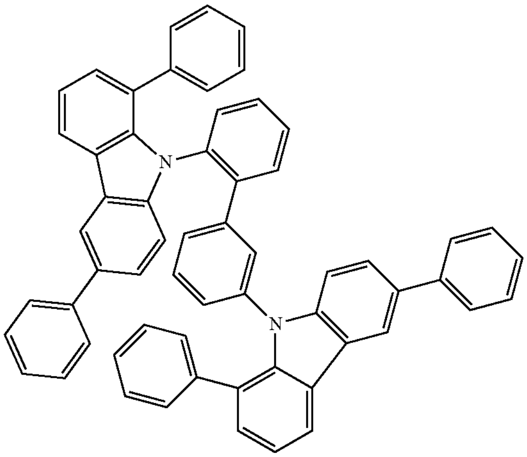

-continued
H8
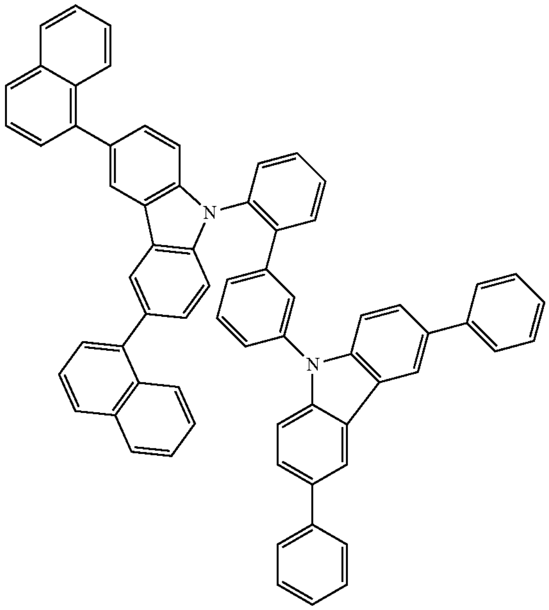
H9
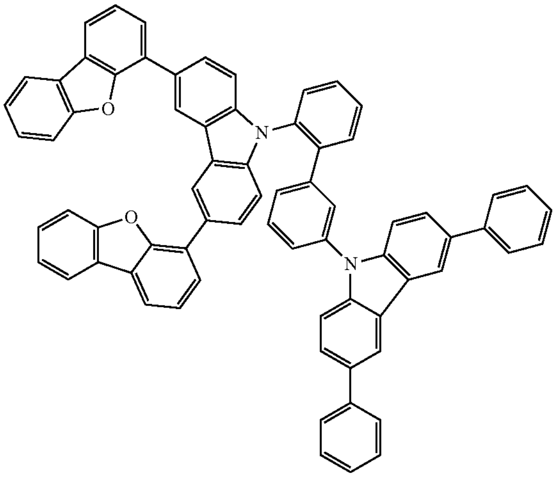
-continued
H10
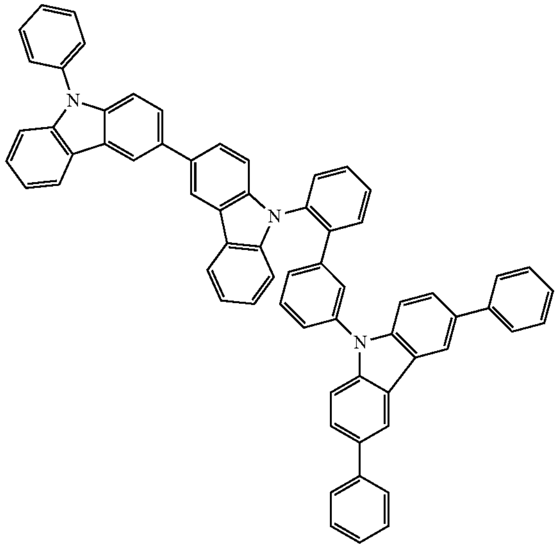
H11
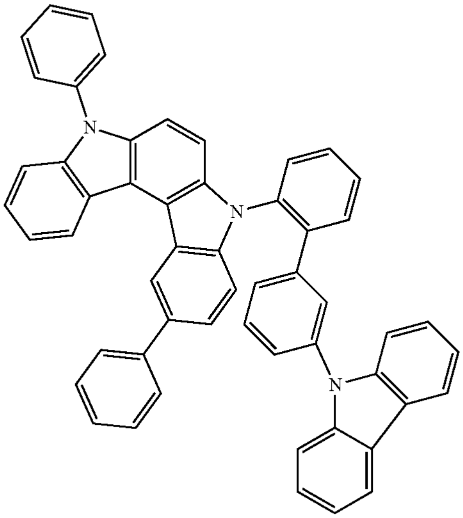
[Compound Group 1I]
I1
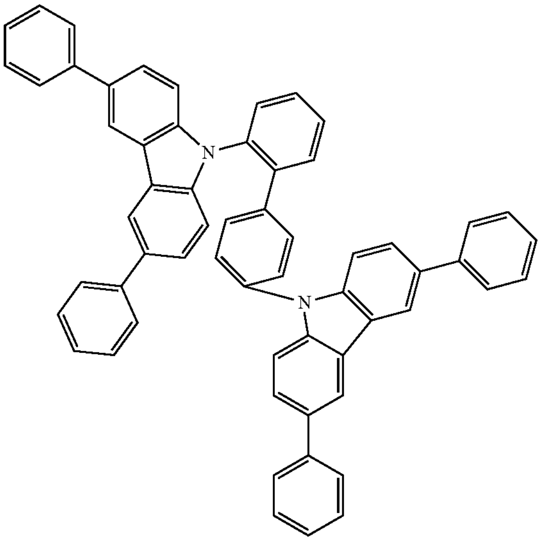

-continued
I2
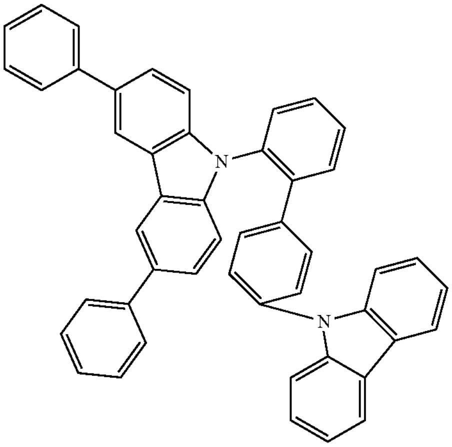
I3
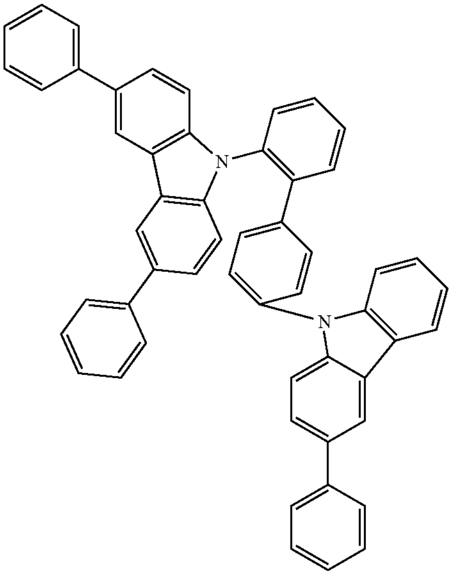
I4
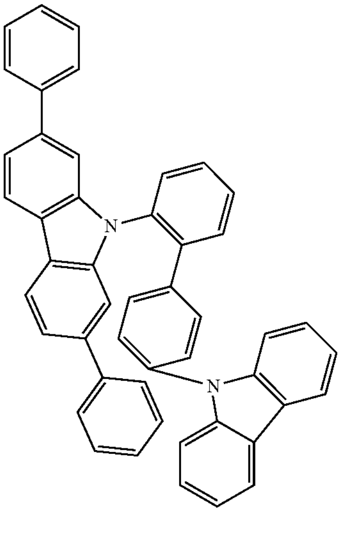
-continued
I5
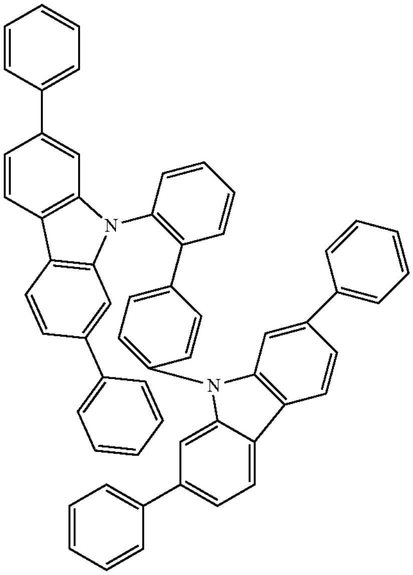
I6
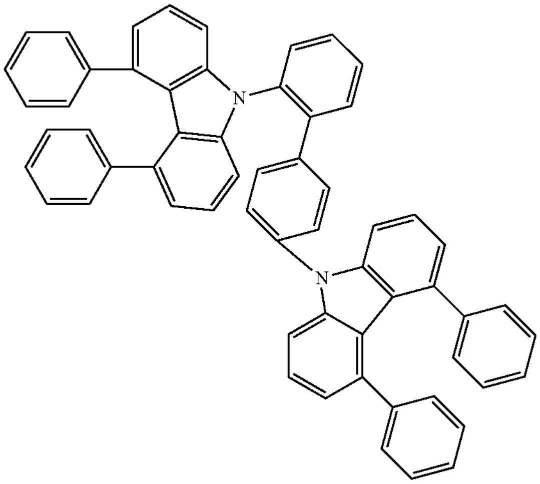
I7
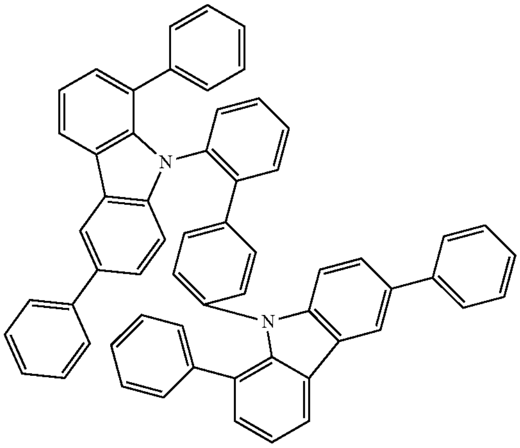

-continued
I8
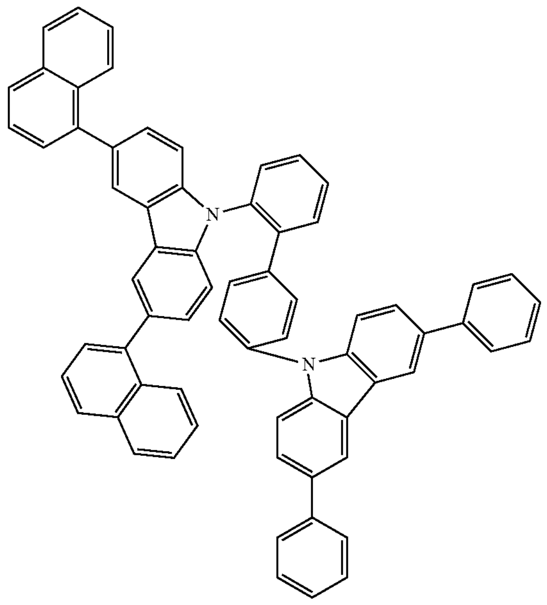
I9
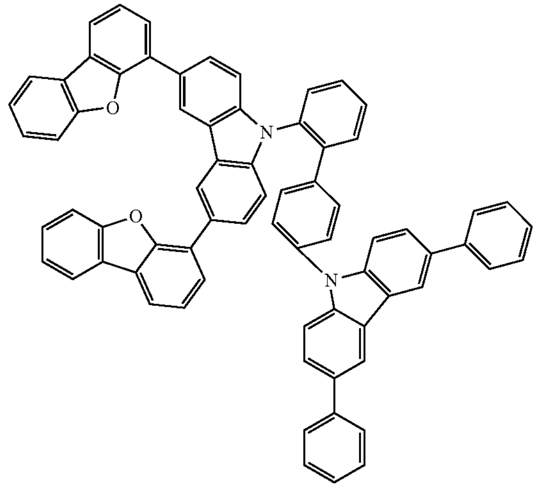
-continued
I10
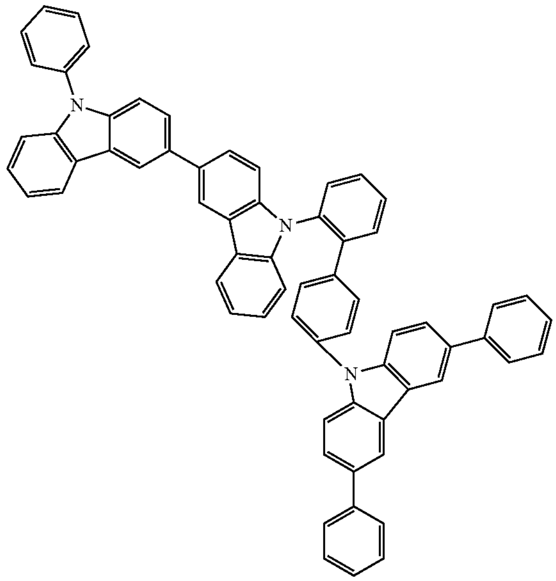
I11
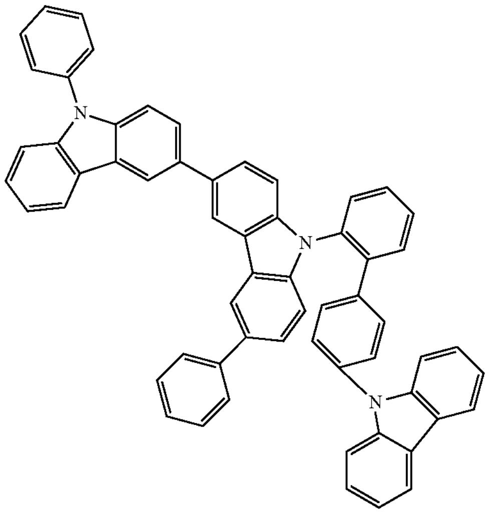
[Compound Group 1J]
J1
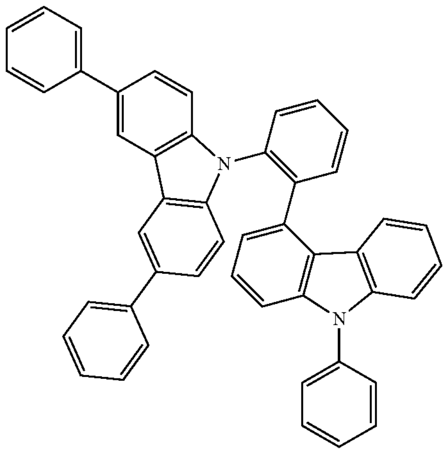

-continued
J2
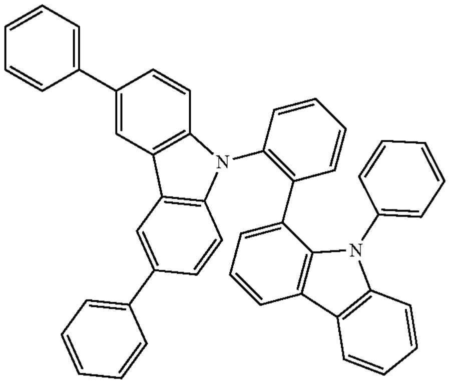
J3
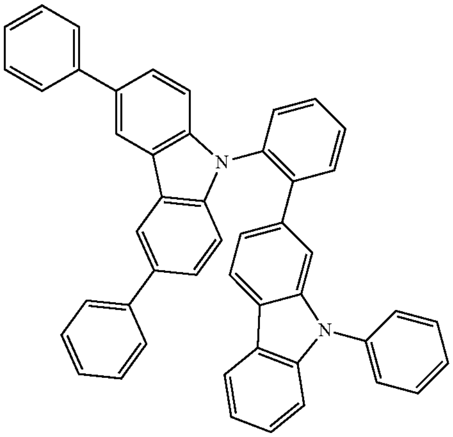
J4
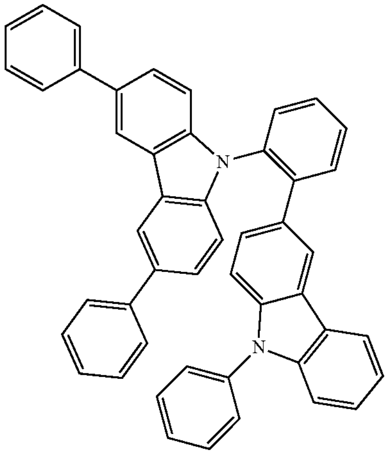
-continued
J5
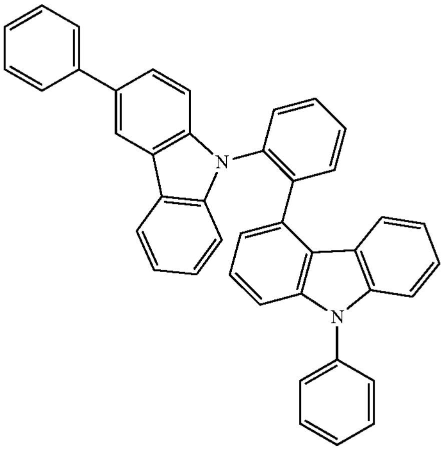
J6
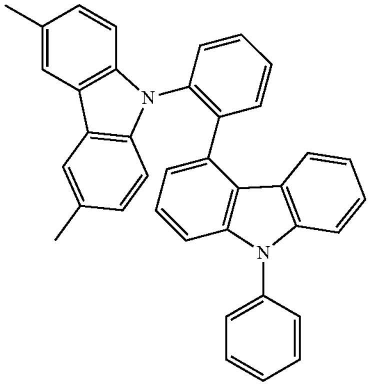
J7
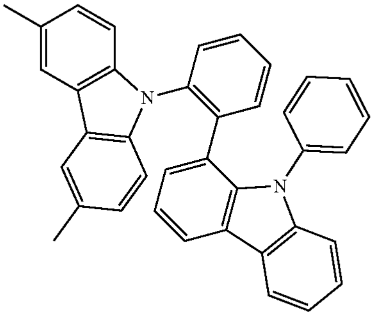
J8
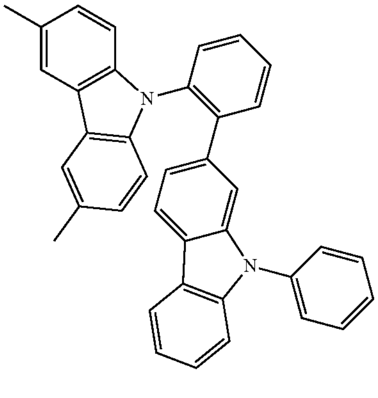

-continued
J9
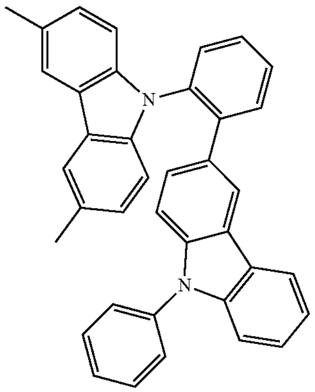
J10
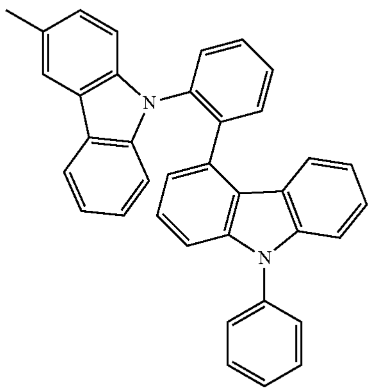
J11
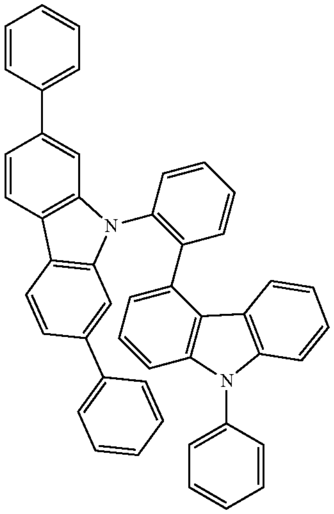
-continued
J12
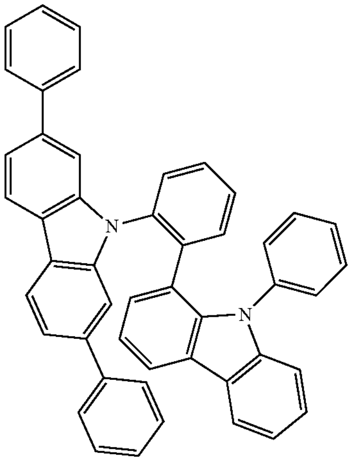
J13
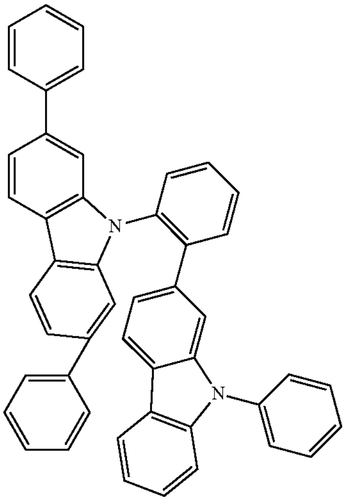
J14
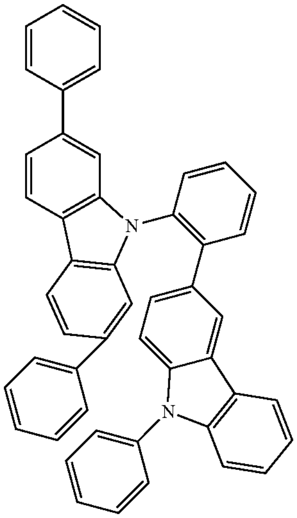

-continued
J15
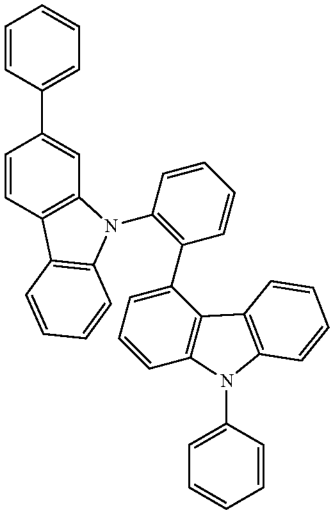
J16
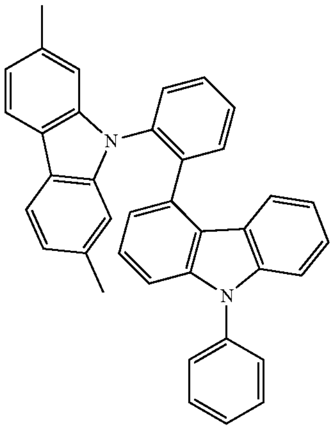
J17
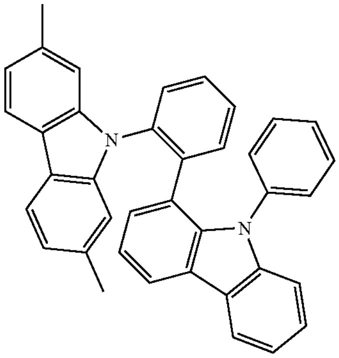
-continued
J18
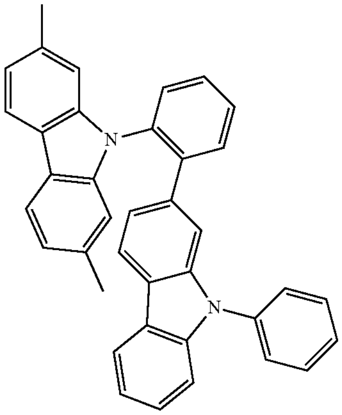
J19
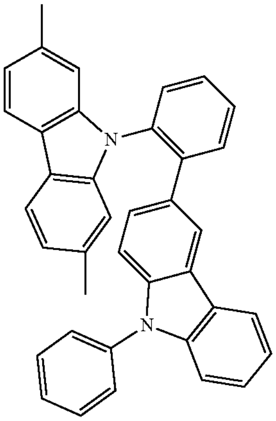
J20
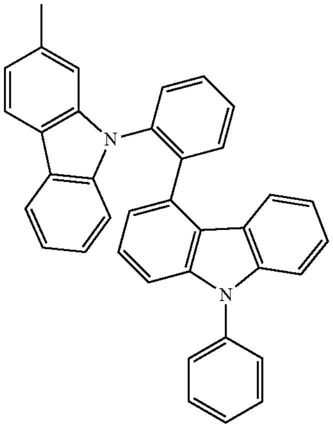

J21
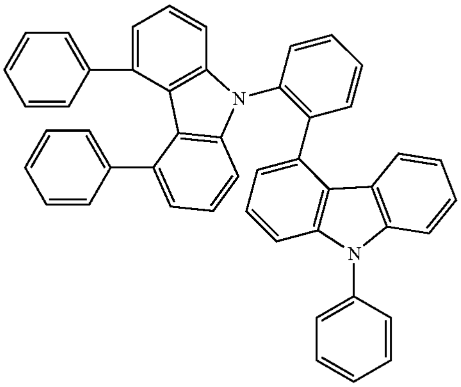
J22
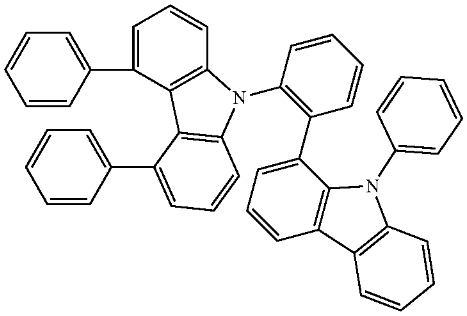
J23
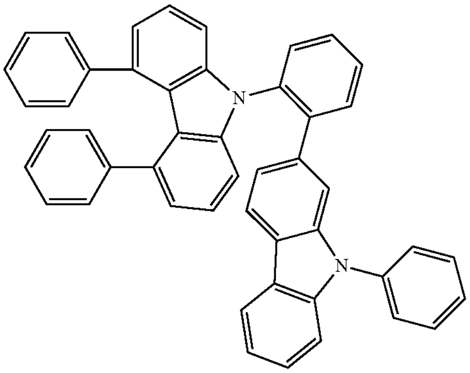
J24
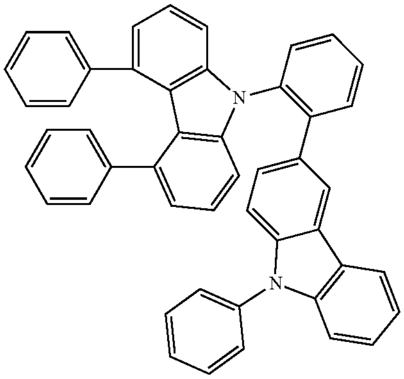
J25
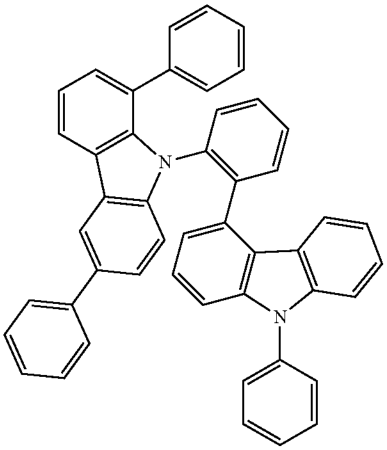
J26
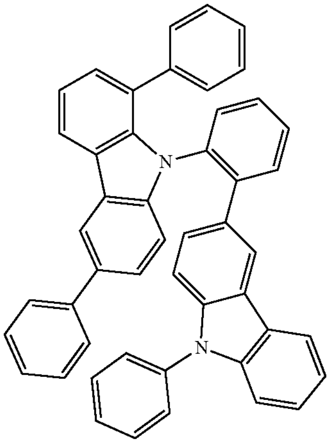
J27
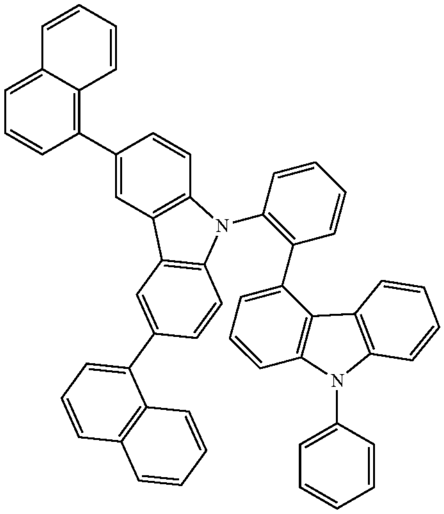

-continued

J28

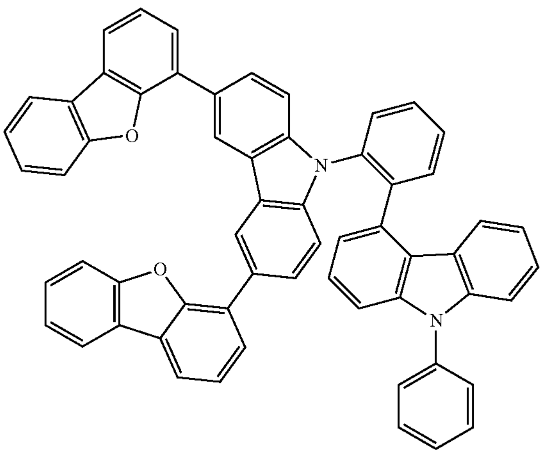

J29

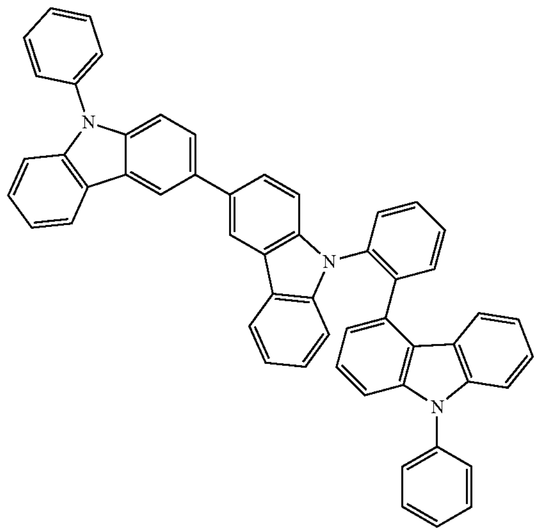

J30

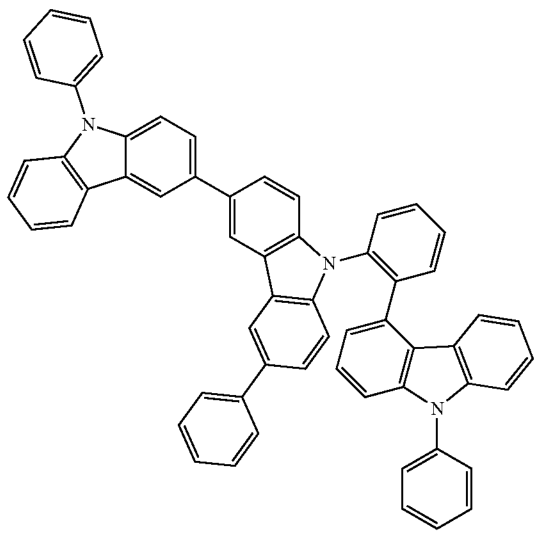

-continued

J31

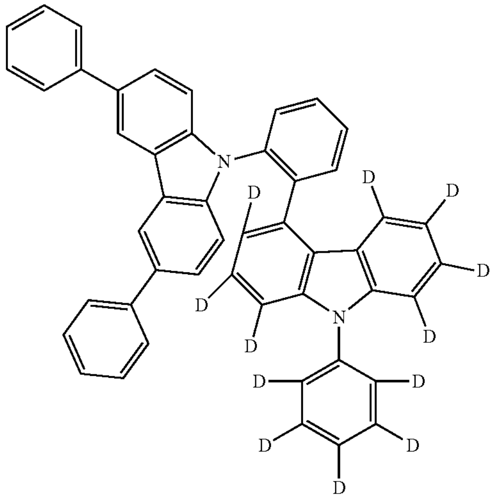

The polycyclic compound of an embodiment, represented by Formula 1, may include at least one substituent at a carbazole skeleton including a biphenyl linker. In the polycyclic compound of an embodiment, an amine compound is bonded to the biphenyl group which is used as the linker and which has a relatively low deposition temperature in contrast to a linker such as a naphthyl group and a fluorene group, thereby showing excellent thermal resistance. In the polycyclic compound of an embodiment, the carbazole skeleton includes at least one substituent as embodied in $R_1$ and $R_2$ to improve hole injection. Accordingly, the life of the polycyclic compound of an embodiment, represented by Formula 1 may increase. The emission efficiency and life of a light emitting element of an embodiment, including the polycyclic compound of an embodiment may be improved.

The light emitting element ED of an embodiment may further include a material for a hole transport region, explained below in addition to the polycyclic compound of an embodiment in the hole transport region HTR.

The hole transport region HTR may include a compound represented by Formula H-1.

[Formula H-1]

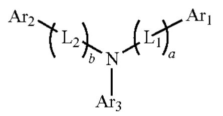

In Formula H-1, $L_1$ and $L_2$ may each independently be a direct linkage, a substituted or unsubstituted arylene group of 6 to 30 ring-forming carbon atoms, or a substituted or unsubstituted heteroarylene group of 2 to 30 ring-forming carbon atoms. In Formula H-1, a and b may each independently be an integer from 0 to 10. If a or b is 2 or more, multiple $L_1$ groups and multiple $L_2$ groups may each independently be a substituted or unsubstituted arylene group of 6 to 30 ring-forming carbon atoms, or a substituted or unsubstituted heteroarylene group of 2 to 30 ring-forming carbon atoms.

In Formula H-1, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. In Formula H-1, $Ar_3$ may be a substituted or unsubstituted aryl group of 6 to 30 ring-forming carbon atoms or a substituted or unsubstituted heteroaryl group of 2 to 30 ring-forming carbon atoms.

The compound represented by Formula H-1 may be a monoamine compound. In another embodiment, the compound represented by Formula H-1 may be a diamine compound in which at least one of $Ar_1$ to $Ar_3$ includes an amine group as a substituent. In still another embodiment, the compound represented by Formula H-1 may be a carbazole-based compound in which at least one of $Ar_1$ or $Ar_2$ includes a substituted or unsubstituted carbazole group, or a fluorene-based compound in which at least one of $Ar_1$ or $Ar_2$ includes a substituted or unsubstituted fluorene group.

The compound represented by Formula H-1 may be any one selected from Compound Group H. However, the compounds shown in Compound Group H are only presented as examples, and the compound represented by Formula H-1 is not limited to the compounds shown in Compound Group H.

[Compound Group H]

H-1-1

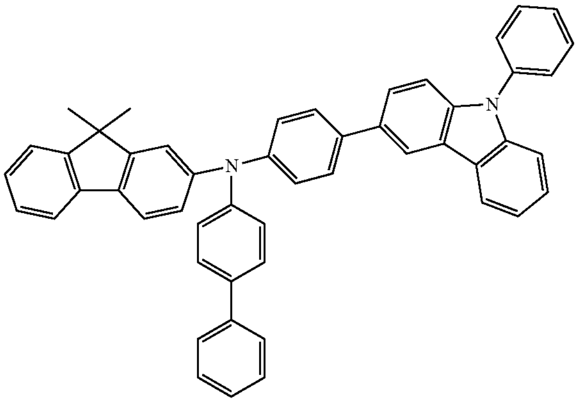

H-1-2

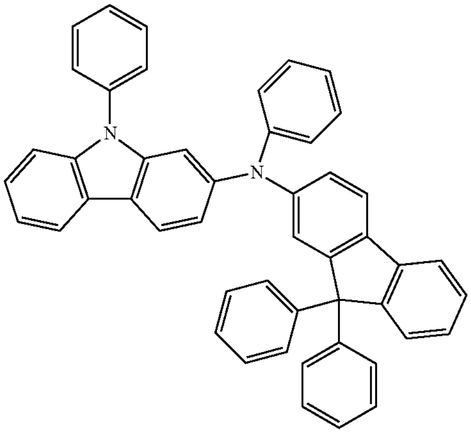

-continued

H-1-3

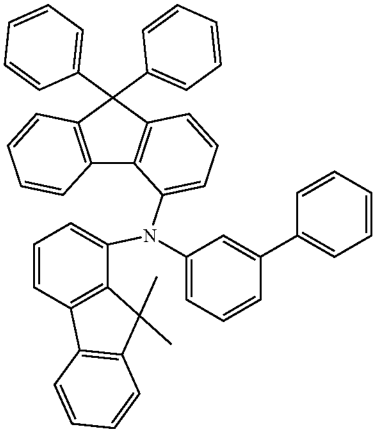

H-1-4

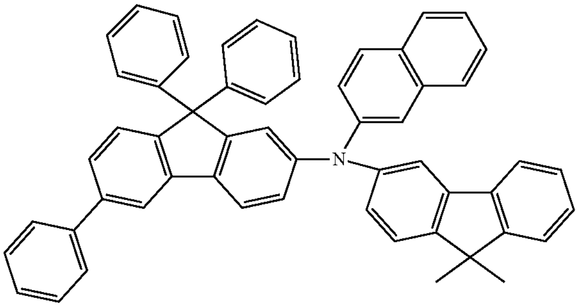

H-1-5

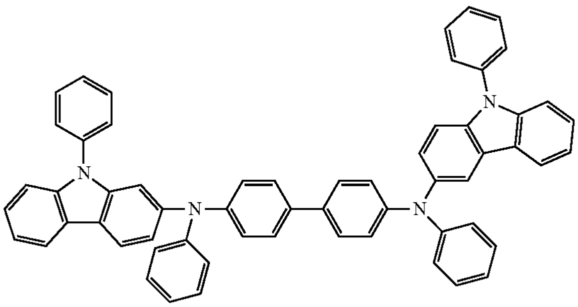

H-1-6

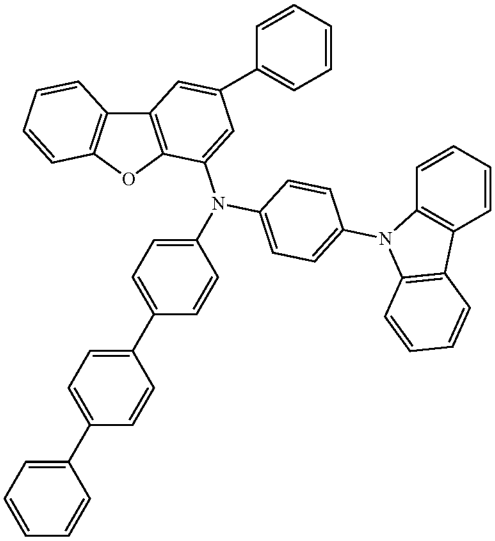

-continued
H-1-7
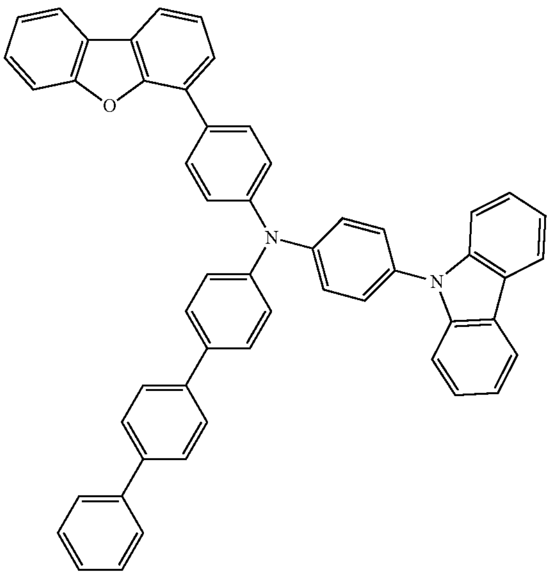
H-1-8
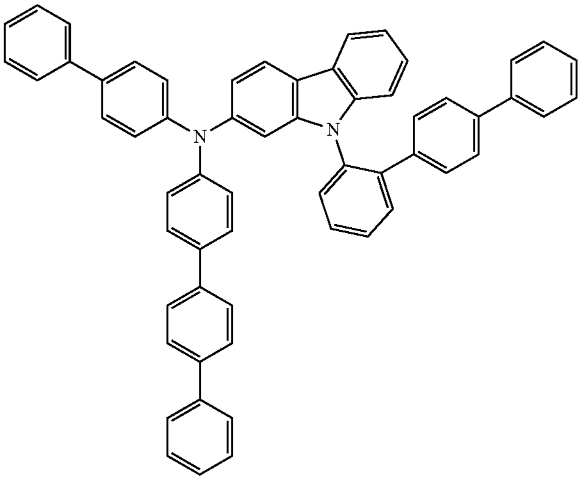
H-1-9
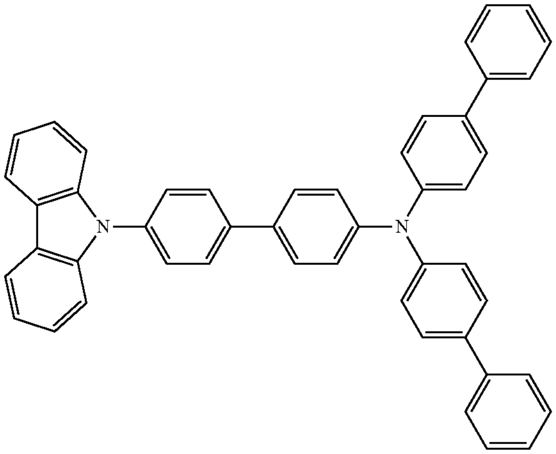
-continued
H-1-10
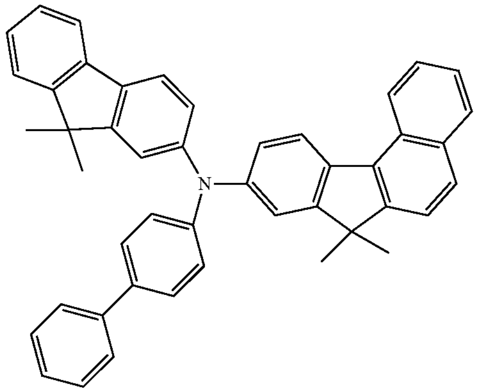
H-1-11
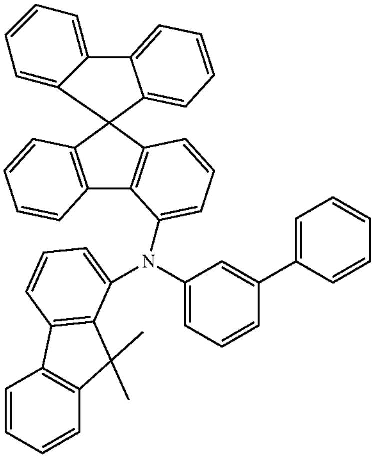
H-1-12
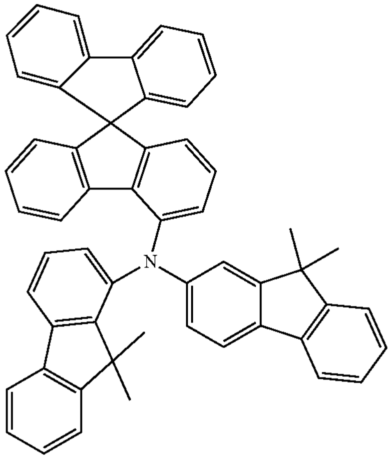

-continued
H-1-13
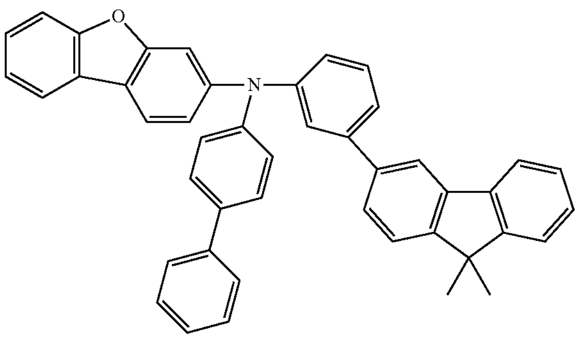
H-1-14
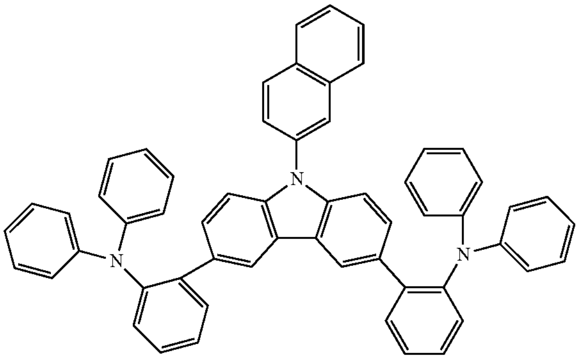
H-1-15
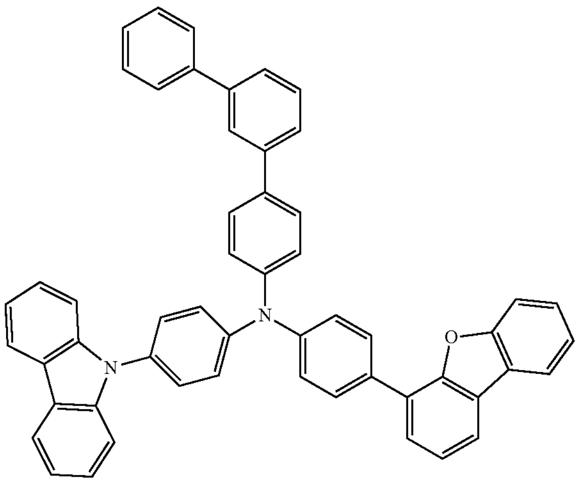
-continued
H-1-16
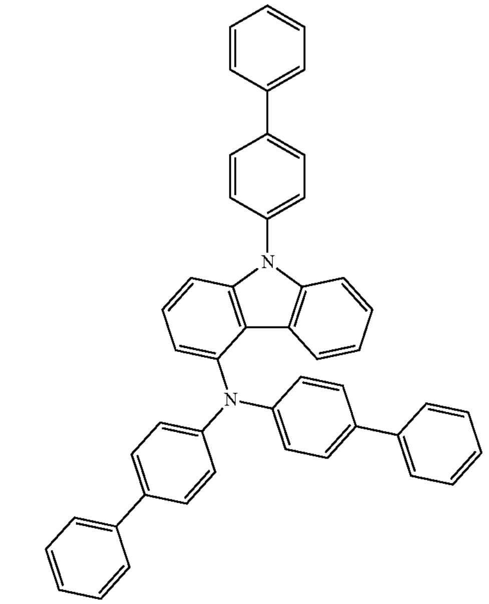
H-1-17
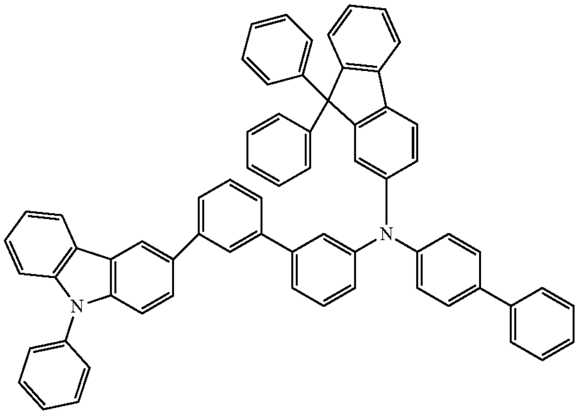
H-1-18
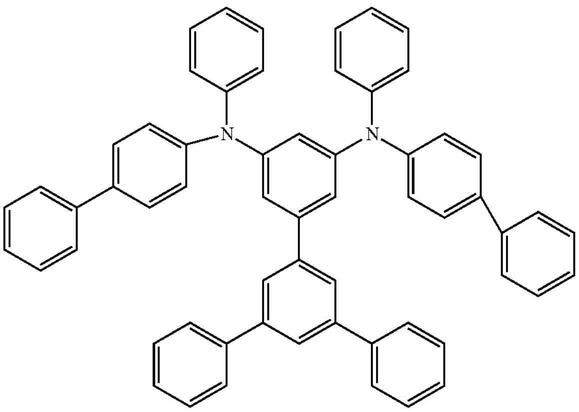

-continued

H-1-19

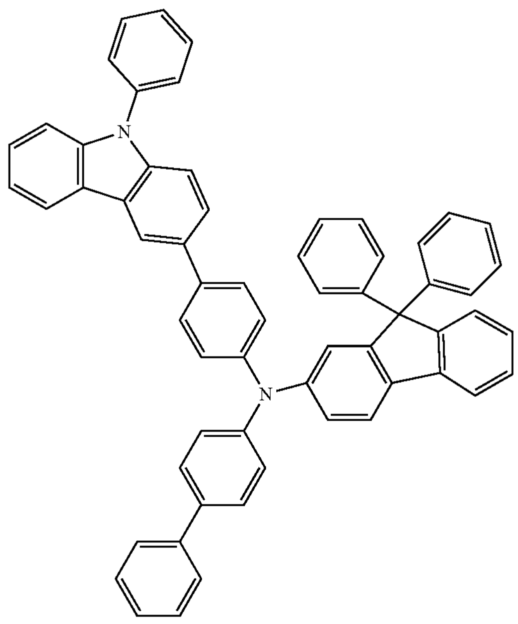

The hole transport region HTR may include a phthalocyanine compound such as copper phthalocyanine, $N^1,N^{1'}$-([1,1'-biphenyl]-4,4'-diyl)bis($N^1$-phenyl-$N^4,N^4$-di-m-tolyl-benzene-1,4-diamine) (DNTPD), 4,4',4"-[tris(3-methylphenyl)phenylamino] triphenylamine (m-MTDATA), 4,4',4"-tris(N,N-diphenylamino)triphenylamine (TDATA), 4,4',4"-tris[N(2-naphthyl)-N-phenylamino]-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB or NPD), triphenylamine-containing polyetherketone (TPAPEK), 4-isopropyl-4'-methyl diphenyliodonium [tetrakis(pentafluorophenyl)borate], and dipyrazino[2,3-f:2',3'-h] quinoxaline-2,3,6,7,10,11-hexacarbonitrile (HAT-CN).

The hole transport region HTR may include carbazole derivatives such as N-phenyl carbazole and polyvinyl carbazole, fluorene-based derivatives, N,N'-bis(3-methylphenyl)-N,N'-diphenyl-[1,1"-biphenyl]-4,4'-diamine (TPD), triphenylamine-based derivatives such as 4,4',4"-tris(N-carbazolyl)triphenylamine (TCTA), N,N'-di(1-naphthalene-1-yl)-N,N'-diphenyl-benzidine (NPB), 4,4'-cyclohexylidene bis[N,N-bis(4-methylphenyl)benzeneamine] (TAPC), 4,4'-bis[N,N'-(3-tolyl)amino]-3,3'-dimethylbiphenyl (HMTPD), 1,3-bis(N-carbazolyl)benzene (mCP), etc.

The hole transport region HTR may include 9-(4-tert-butylphenyl)-3,6-bis(triphenylsilyl)-9H-carbazole (CzSi), 9-phenyl-9H-3,9'-bicarbazole (CCP), 1,3-bis(1,8-dimethyl-9H-carbazol-9-yl)benzene (mDCP), etc.

The hole transport region HTR may include the compounds of the hole transport region in at least one of the hole injection layer HIL, the hole transport layer HTL, or the electron blocking layer EBL.

A thickness of the hole transport region HTR may be in a range of about 100 Å to about 10,000 Å. For example, the thickness of the hole transport region HTR may be in a range of about 100 Å to about 5,000 Å. In case that the hole transport region HTR includes a hole injection layer HIL, a thickness of the hole injection region HIL may be, for example, in a range of about 30 Å to about 1,000 Å. In case that the hole transport region HTR includes a hole transport layer HTL, a thickness of the hole transport layer HTL may be in a range of about 30 Å to about 1,000 Å. In case that the hole transport region HTR includes an electron blocking layer, a thickness of the electron blocking layer EBL may be in a range of about 10 Å to about 1,000 Å. If the thicknesses of the hole transport region HTR, the hole injection layer HIL, the hole transport layer HTL, and the electron blocking layer EBL satisfy the above-described ranges, satisfactory hole transport properties may be achieved without a substantial increase of driving voltage.

The hole transport region HTR may further include a charge generating material to increase conductivity, in addition to the above-described materials. The charge generating material may be dispersed uniformly or non-uniformly in the hole transport region HTR. The charge generating material may be, for example, a p-dopant. The p-dopant may include at least one of metal halide compounds, quinone derivatives, metal oxides, and cyano group-containing compounds, without limitation. For example, the p-dopant may include metal halide compounds such as CuI and RbI, quinone derivatives such as tetracyanoquinodimethane (TCNQ) and 2,3,5,6-tetrafluoro-7,7',8,8-tetracyanoquinodimethane (F4-TCNQ), metal oxides such as tungsten oxide and molybdenum oxide, cyano group-containing compounds such as dipyrazino[2,3-f: 2',3'-h] quinoxaline-2,3,6,7,10,11-hexacarbonitrile (HATCN) and 4-[[2,3-bis[cyano-(4-cyano-2,3,5,6-tetrafluorophenyl)methylidene]cyclopropylidene]-cyanomethyl]-2,3,5,6-tetrafluorobenzonitrile (NDP9), etc., without limitation.

As described above, the hole transport region HTR may further include at least one of a buffer layer (not shown) or an electron blocking layer EBL, in addition to the hole injection layer HIL and the hole transport layer HTL. The buffer layer (not shown) may compensate for a resonance distance according to a wavelength of light emitted from an emission layer EML and may increase emission efficiency. Materials which may be included in the hole transport region HTR may be used as materials included in the buffer layer (not shown). The electron blocking layer EBL may block the injection of electrons from the electron transport region ETR to the hole transport region HTR.

The emission layer EML is provided on the hole transport region HTR. The emission layer EML may have a thickness, for example, in a range of about 100 Å to about 1,000 Å. For example, the emission layer EML may have a thickness in a range of about 100 Å to about 300 Å. The emission layer EML may be a layer formed of a single material, a layer formed of different materials, or a multilayer structure having layers formed of different materials.

In the light emitting element ED of an embodiment, the emission layer EML may emit blue light or green light. The light emitting element ED of an embodiment may include the polycyclic compound of an embodiment in a hole transport region HTR and may show high efficiency and long-life characteristics in a blue emission region and/or a green emission region. However, embodiments are not limited thereto.

In the light emitting element ED of an embodiment, the emission layer EML may include anthracene derivatives, pyrene derivatives, fluoranthene derivatives, chrysene derivatives, dihydrobenzanthracene derivatives, or triphenylene derivatives. For example, the emission layer EML may include anthracene derivatives or pyrene derivatives.

In the light emitting elements ED of embodiments, shown in FIG. 3 to FIG. 6, the emission layer EML may include a host and a dopant, and the emission layer EML may include a compound represented by Formula E-1. The compound represented by Formula E-1 may be used as a fluorescence host material.

[Formula E-1]

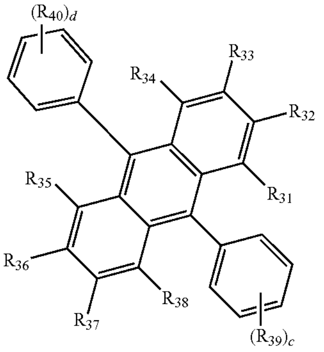

In Formula E-1, $R_{31}$ to $R_{40}$ may each independently be a hydrogen atom, a deuterium atom, a halogen atom, a substituted or unsubstituted silyl group, a substituted or unsubstituted thio group, a substituted or unsubstituted oxy group, a substituted or unsubstituted alkyl group of 1 to 10 carbon atoms, a substituted or unsubstituted alkenyl group of 2 to 10 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula E-1, $R_{31}$ to $R_{40}$ may be combined with an adjacent group to form a saturated hydrocarbon ring, an unsaturated hydrocarbon ring, a saturated heterocycle, or an unsaturated heterocycle.

In Formula E-1, c and d may each independently be an integer from 0 to 5.

The compound represented by Formula E-1 may be any one selected from Compound E1 to Compound E19.

E1

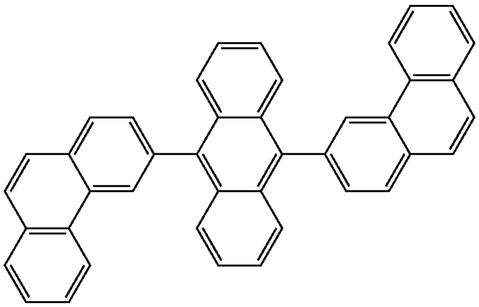

E2

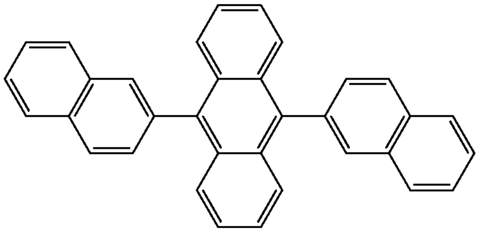

-continued

E3

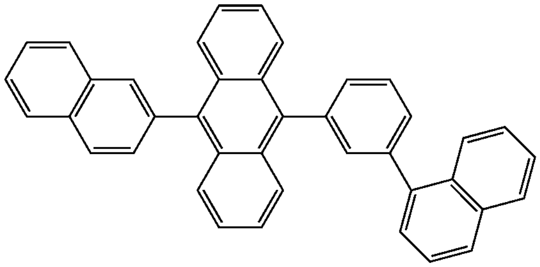

E4

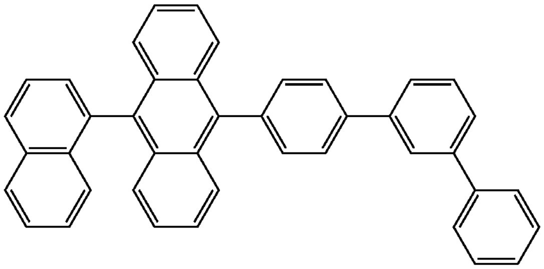

E5

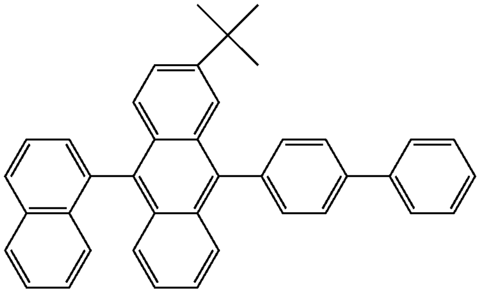

E6

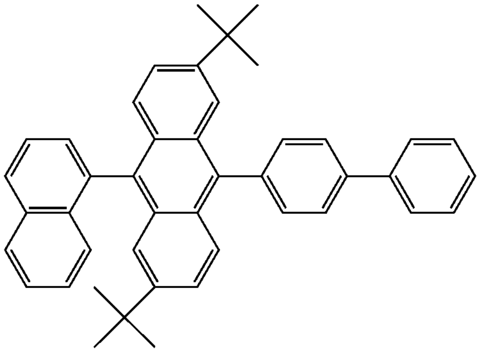

E7

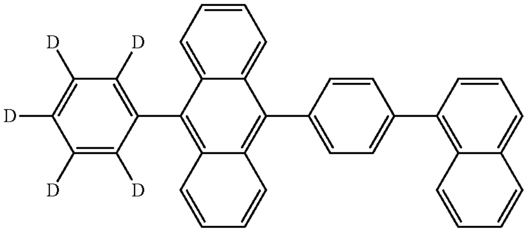

-continued
E8
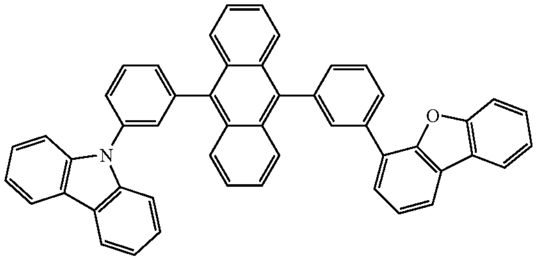
E9
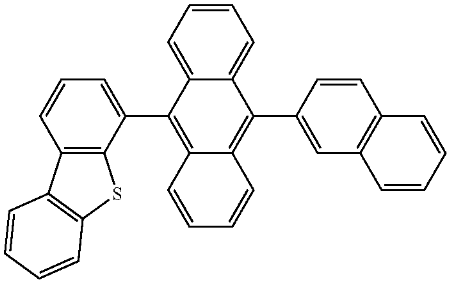
E10
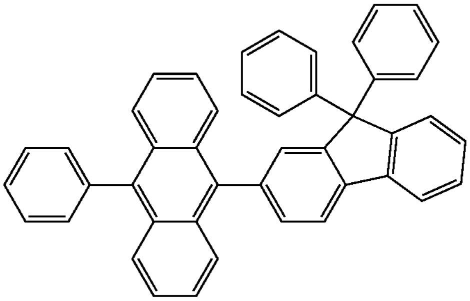
E11
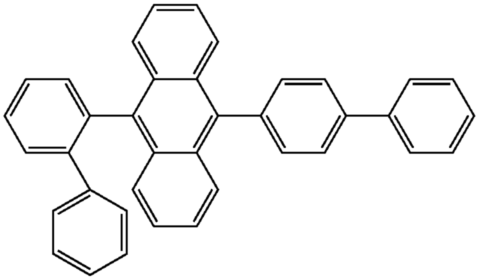
E12
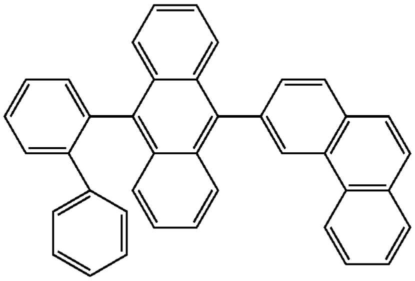
-continued
E13
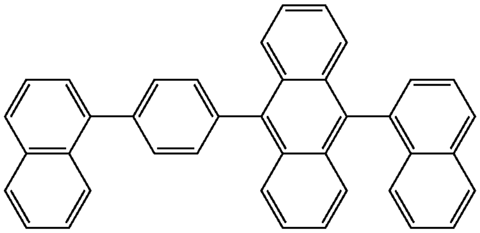
E14
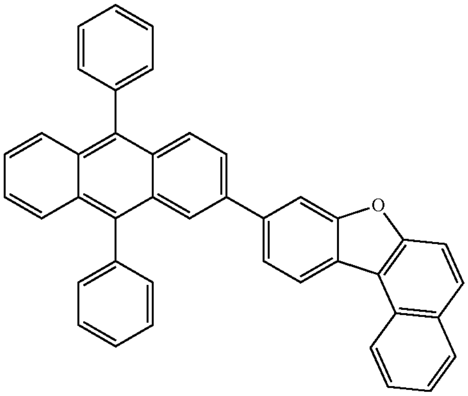
E15
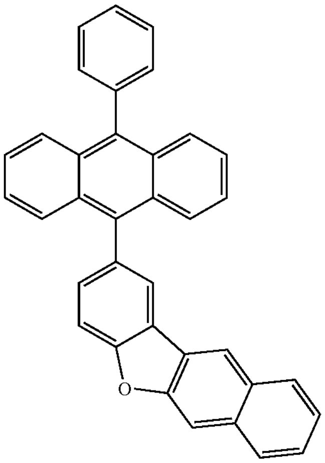
E16
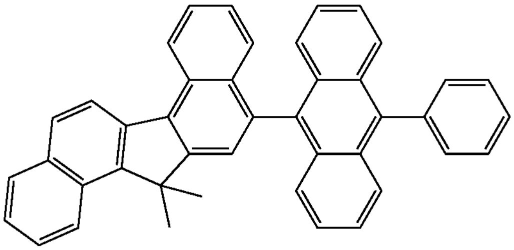

-continued

E17

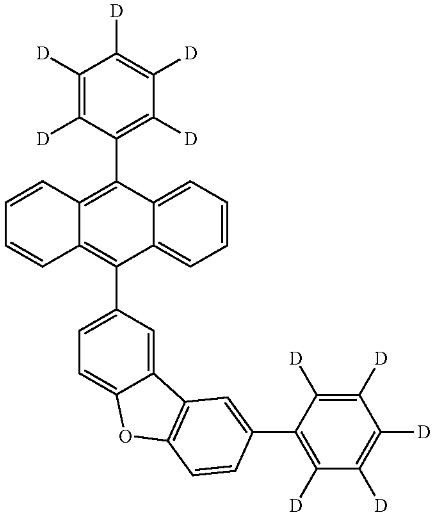

E18

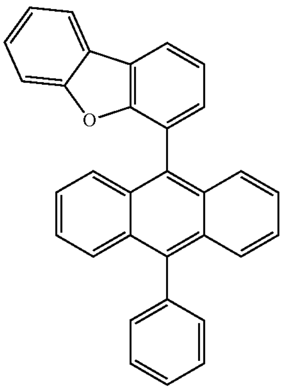

E19

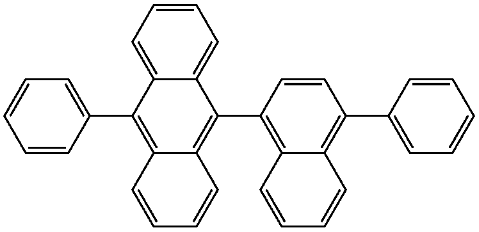

In an embodiment, the emission layer EML may include a compound represented by Formula E-2a or Formula E-2b. The compound represented by Formula E-2a or Formula E-2b may be used as a phosphorescence host material.

[Formula E-2a]

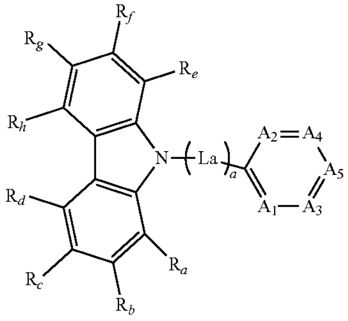

In Formula E-2a, a may be an integer from 0 to 10, $L_a$ may be a direct linkage, a substituted or unsubstituted arylene group of 6 to 30 ring-forming carbon atoms, or a substituted or unsubstituted heteroarylene group of 2 to 30 ring-forming carbon atoms. If a is 2 or more, multiple $L_a$ groups may each independently be a substituted or unsubstituted arylene group of 6 to 30 ring-forming carbon atoms, or a substituted or unsubstituted heteroarylene group of 2 to 30 ring-forming carbon atoms.

In Formula E-2a, $A_1$ to A5 may each independently be N or $C(R_i)$. $R_a$ to $R_i$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. $R_a$ to $R_i$ may be combined with an adjacent group to form a hydrocarbon ring or a heterocycle including N, O, S, etc. as a ring-forming atom.

In Formula E-2a, two or three of $A_1$ to A5 may be N, and the remainder of $A_1$ to A5 may be $C(R_i)$.

[Formula E-2b]

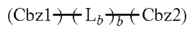

In Formula E-2b, Cbz1 and Cbz2 may each independently be an unsubstituted carbazole group, or a carbazole group substituted with an aryl group of 6 to 30 ring-forming carbon atoms. $L_b$ may be a direct linkage, a substituted or unsubstituted arylene group of 6 to 30 ring-forming carbon atoms, or a substituted or unsubstituted heteroarylene group of 2 to 30 ring-forming carbon atoms. In Formula E-2b, b is an integer from 0 to 10, and if b is 2 or more, multiple $L_b$ groups may each independently be a substituted or unsubstituted arylene group of 6 to 30 ring-forming carbon atoms, or a substituted or unsubstituted heteroarylene group of 2 to 30 ring-forming carbon atoms.

The compound represented by Formula E-2a or Formula E-2b may be any one selected from Compound Group E-2. However, the compounds shown in Compound Group E-2 are only presented as examples, and the compound represented by Formula E-2a or Formula E-2b is not limited to the compounds listed in Compound Group E-2.

[Compound Group E-2]
E-2-1
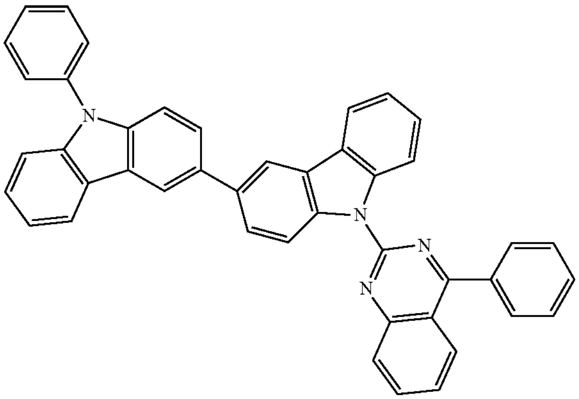
E-2-2
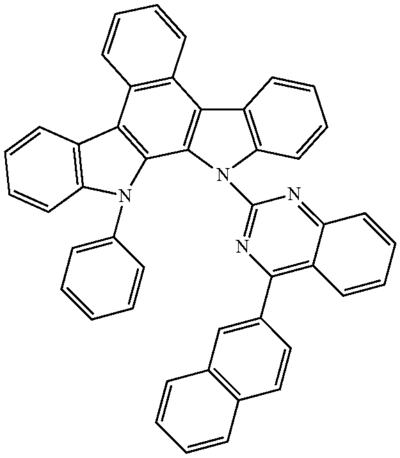
E-2-3
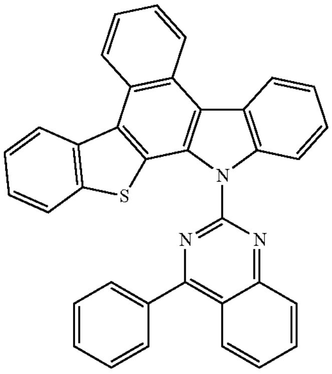
-continued
E-2-4
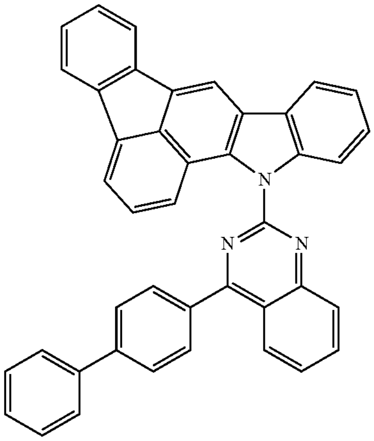
E-2-5
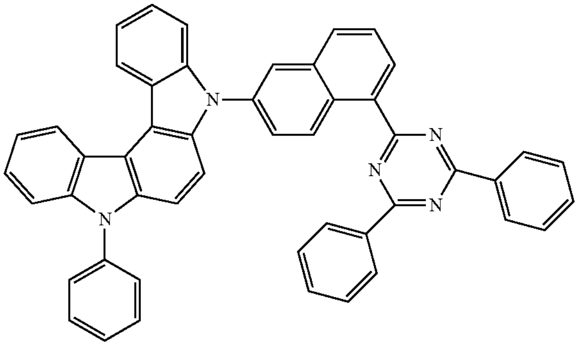
E-2-6
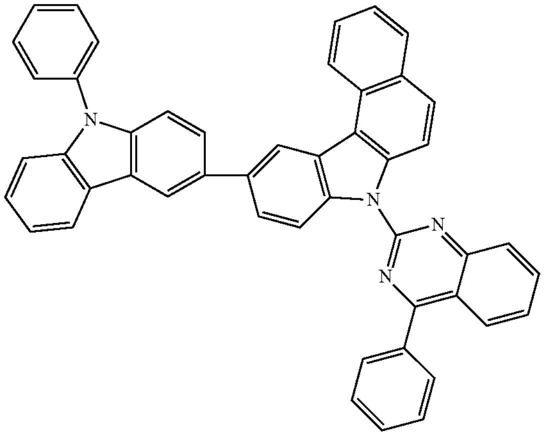

-continued
E-2-7
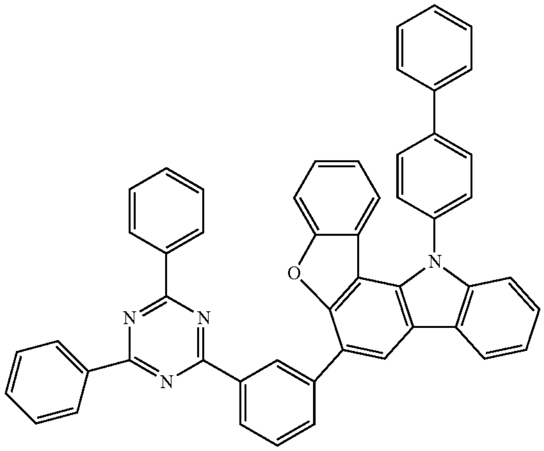
E-2-8
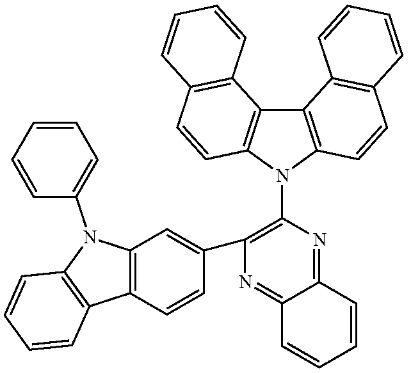
E-2-9
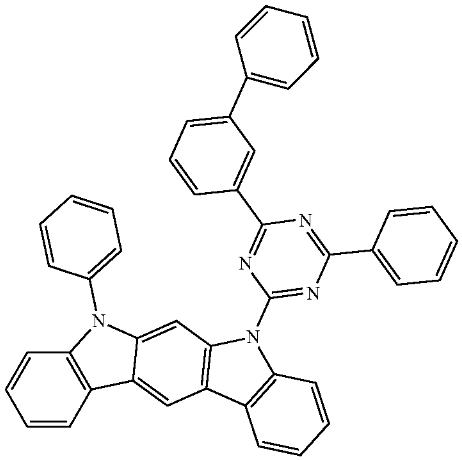
-continued
E-2-10
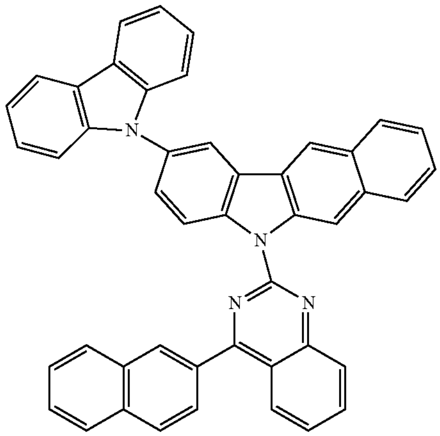
E-2-11
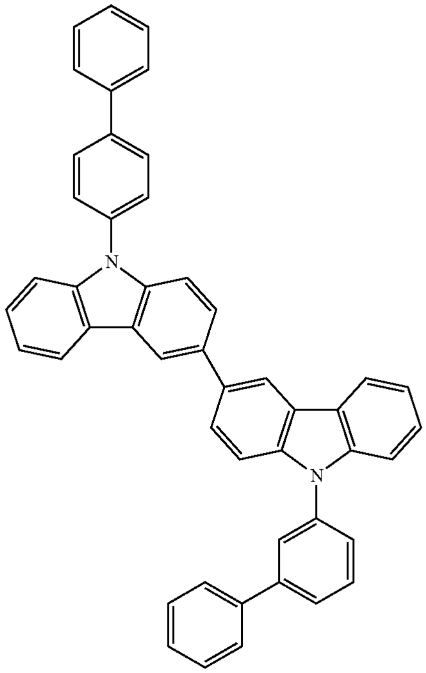
E-2-12
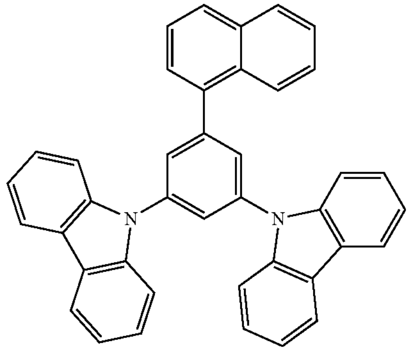

-continued
E-2-13
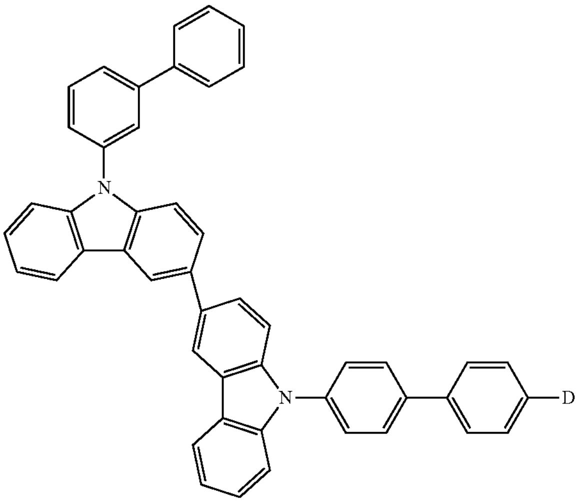
E-2-14
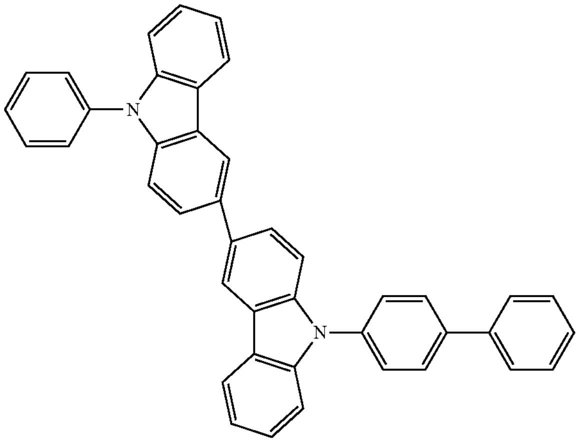
E-2-15
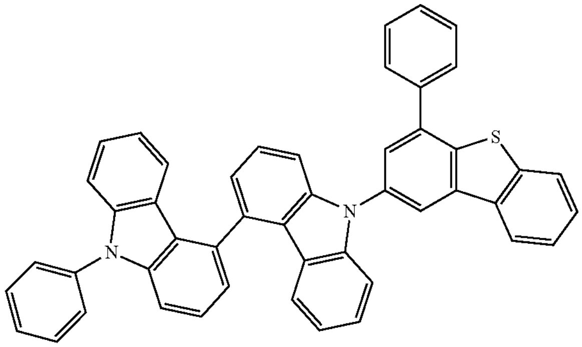
-continued
E-2-16
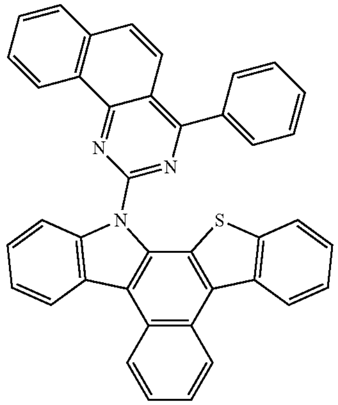
E-2-17
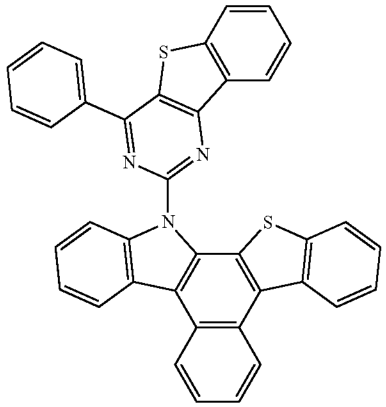
E-2-18
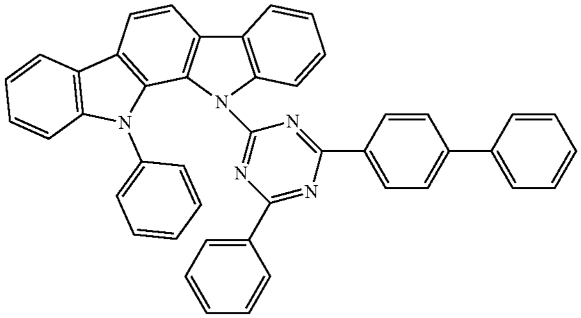
E-2-19
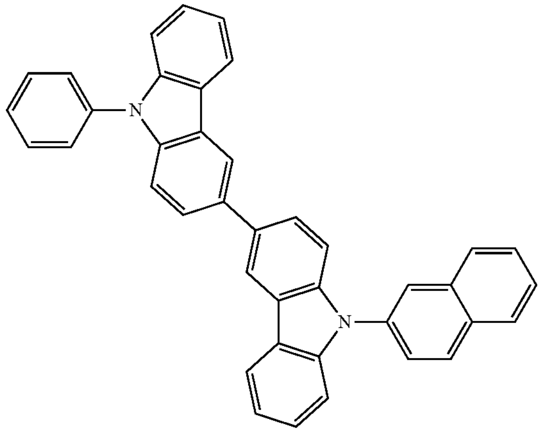

-continued

E-2-20

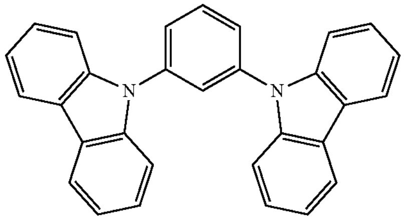

E-2-21

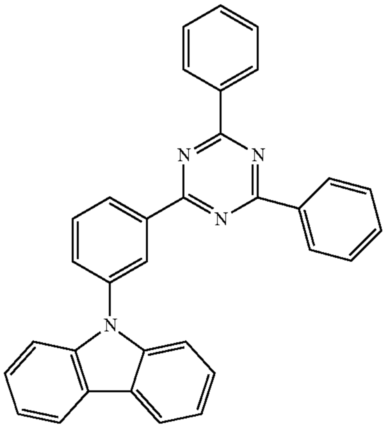

E-2-22

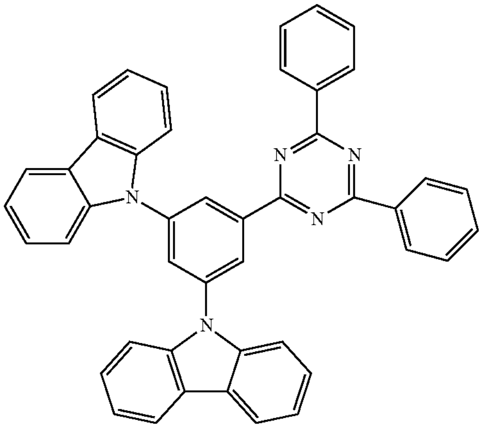

E-2-23

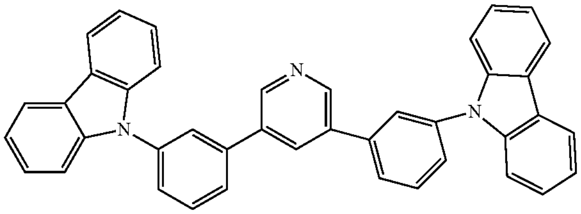

-continued

E-2-24

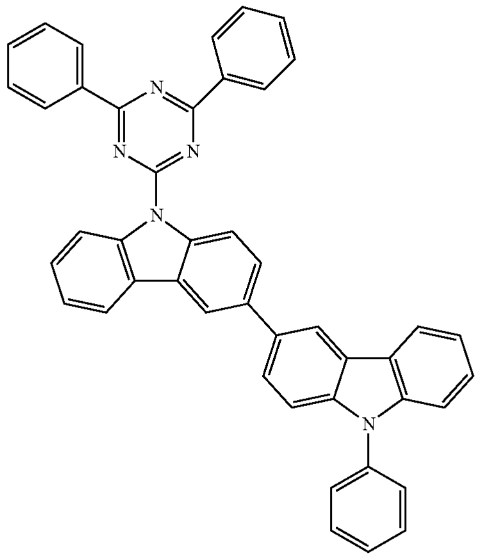

The emission layer EML may further include a material of the art as a host material. For example, the emission layer EML may include as a host material, at least one of bis (4-(9H-carbazol-9-yl) phenyl) diphenylsilane (BCPDS), (4-(1-(4-(diphenylamino) phenyl) cyclohexyl) phenyl) diphenyl-phosphine oxide (POPCPA), bis[2-(diphenylphosphino) phenyl] ether oxide (DPEPO), 4,4'-bis(carbazol-9-yl) biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TCTA), or 1,3,5-tris(1-phenyl-1H-benzo[d]imidazole-2-yl)benzene (TPBi). However, embodiments are not limited thereto. For example, tris(8-hydroxyquinolino)aluminum ($Alq_3$), 9,10-di (naphthalene-2-yl)anthracene (ADN), 2-tert-butyl-9,10-di (naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), etc. may be used as the host material.

The emission layer EML may include a compound represented by Formula M-a or Formula M-b. The compound represented by Formula M-a or Formula M-b may be used as a phosphorescence dopant material. In an embodiment, the compound represented by Formula M-a or Formula M-b may be used as an auxiliary dopant material.

[Formula M-a]

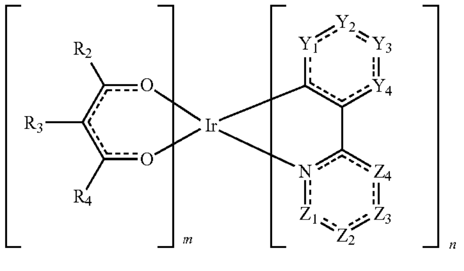

In Formula M-a, $Y_1$ to $Y_4$ and $Z_1$ to $Z_4$ may each independently be $C(R_1)$ or N, and $R_1$ to $R_4$ may each independently be a hydrogen atom, a deuterium atom, a substituted or unsubstituted amine group, a substituted or unsubstituted thio group, a substituted or unsubstituted oxy group, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula M-a, m may be 0 or 1, and n may be 2 or 3. In Formula M-a, if m is 0, n may be 3, and if m is 1, n may be 2.

The compound represented by Formula M-a may be used as a phosphorescence dopant.

The compound represented by Formula M-a may be any one selected from Compounds M-a1 to M-a25. However, Compounds M-a1 to M-a25 are only examples, and the compound represented by Formula M-a is not limited to Compounds M-a1 to M-a25.

M-a1

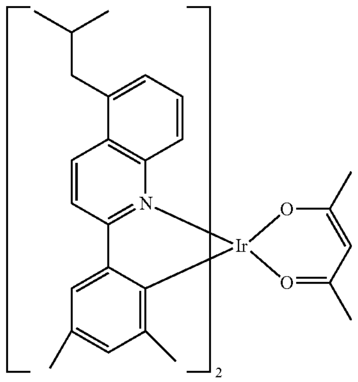

M-a2

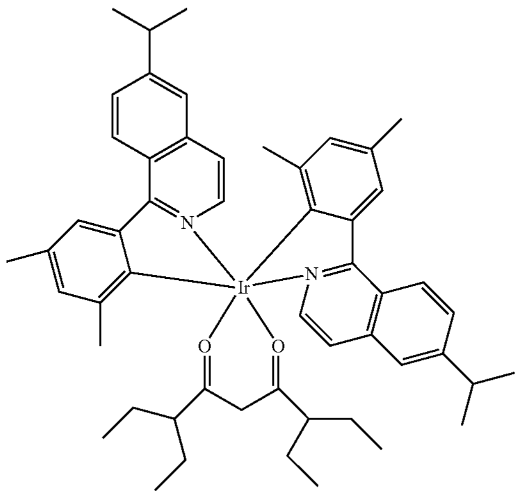

-continued

M-a3

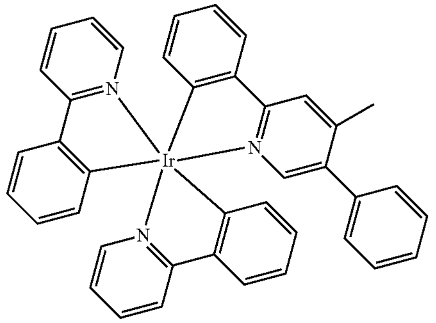

M-a4

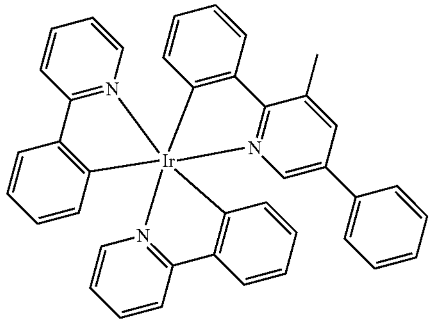

M-a5

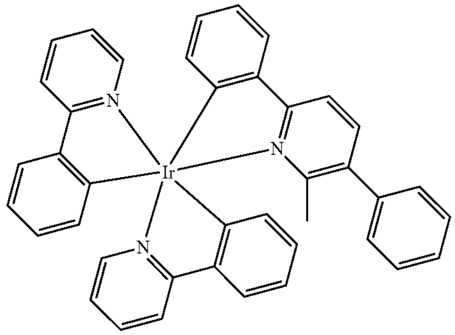

M-a6

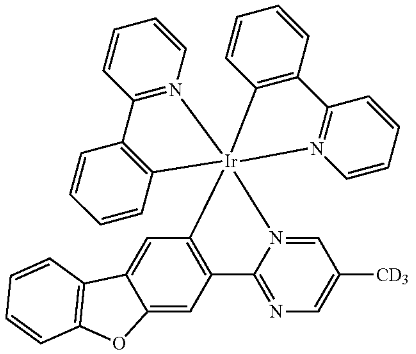

-continued
M-a7
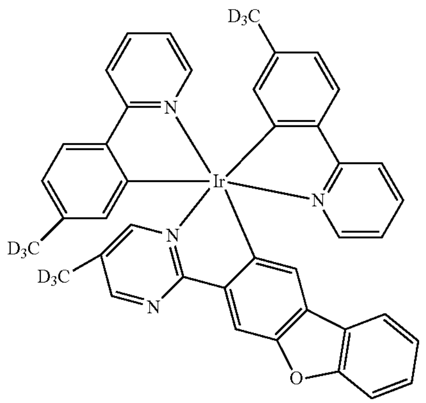
M-a8
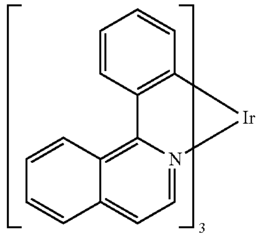
M-a9
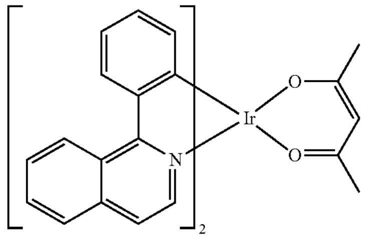
M-a10
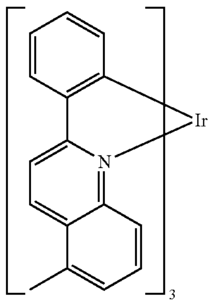
M-a11
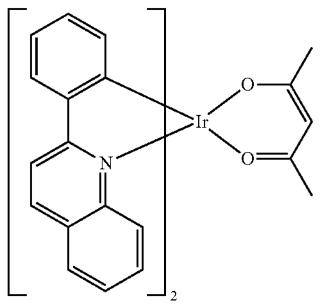
-continued
M-a12
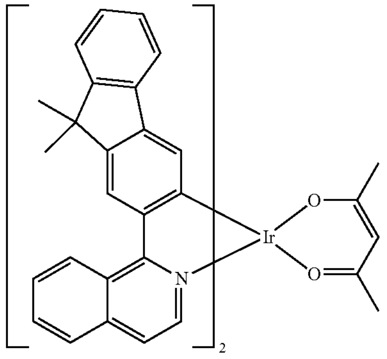
M-a13
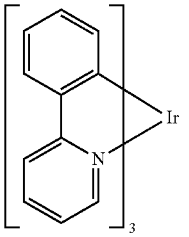
M-a14
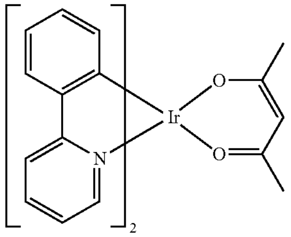
M-a15
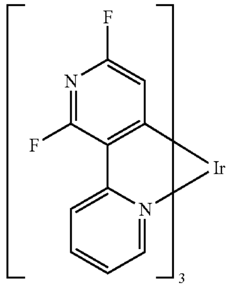
M-a16
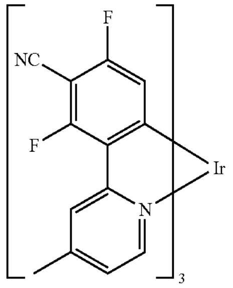

-continued
M-a17
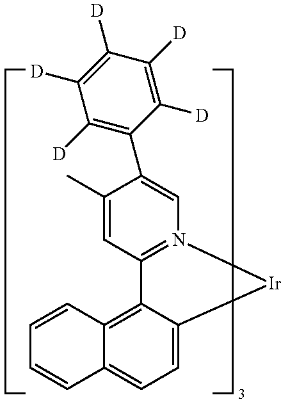
M-a18
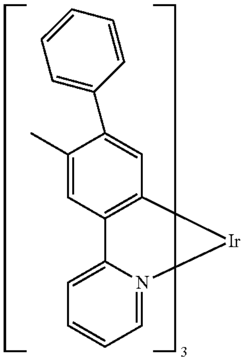
M-a19
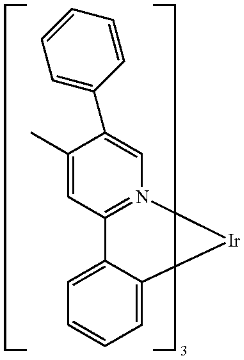
M-a20
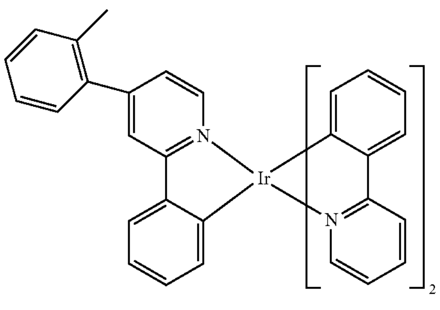
-continued
M-a21
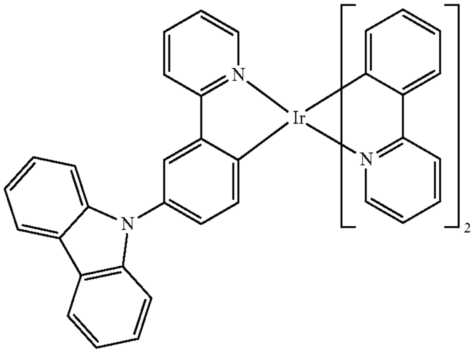
M-a22
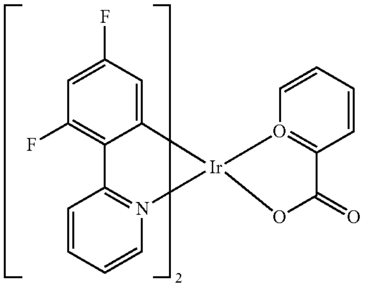
M-a23
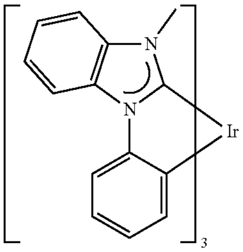
M-a24
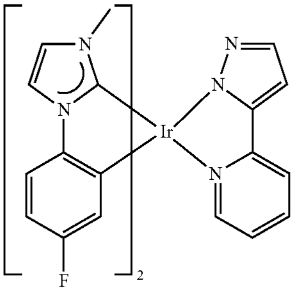
M-a25
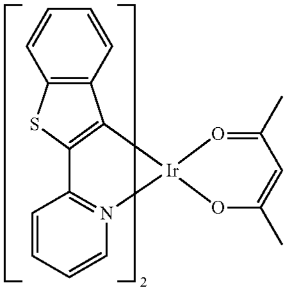
Compound M-a1 and Compound M-a2 may be used as red dopant materials, and Compound M-a3 to Compound M-a7 may be used as green dopant materials.

[Formula M-b]

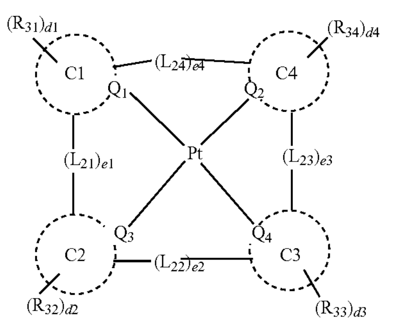

In Formula M-b, $Q_1$ to $Q_4$ may each independently be C or N, and C1 to C4 may each independently be a substituted or unsubstituted hydrocarbon ring of 5 to 30 ring-forming carbon atoms, or a substituted or unsubstituted heterocycle of 2 to 30 ring-forming carbon atoms. In Formula M-b, $L_{21}$ to $L_{24}$ may each independently be a direct linkage,

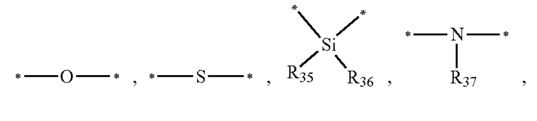

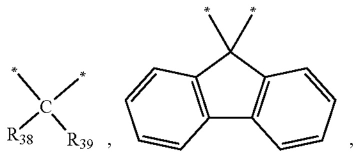

a substituted or unsubstituted divalent alkyl group of 1 to 20 carbon atoms, a substituted or unsubstituted arylene group of 6 to 30 ring-forming carbon atoms, or a substituted or unsubstituted heteroarylene group of 2 to 30 ring-forming carbon atoms, and e1 to e4 may each independently be 0 or 1. In Formula M-b, $R_{31}$ to $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring, and d1 to d4 may each independently be an integer from 0 to 4.

The compound represented by Formula M-b may be used as a blue phosphorescence dopant or as a green phosphorescence dopant. The compound represented by Formula M-b may be further included in an emission layer EML as an auxiliary dopant.

The compound represented by Formula M-b may be any one selected from Compounds M-b-1 to M-b-11. However, Compounds M-b-1 to M-b-11 are only examples, and the compound represented by Formula M-b is not limited to Compounds M-b-1 to M-b-11.

M-b-1

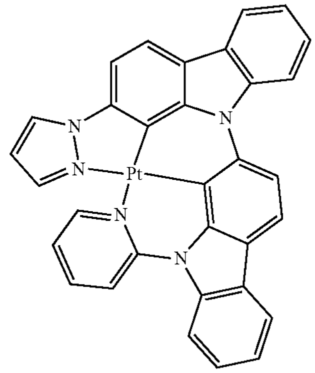

M-b-2

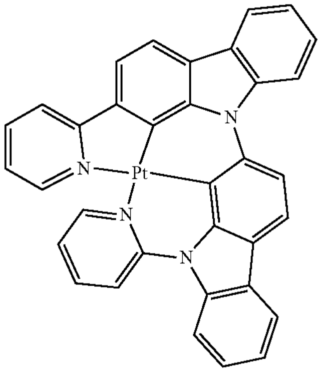

M-b-3

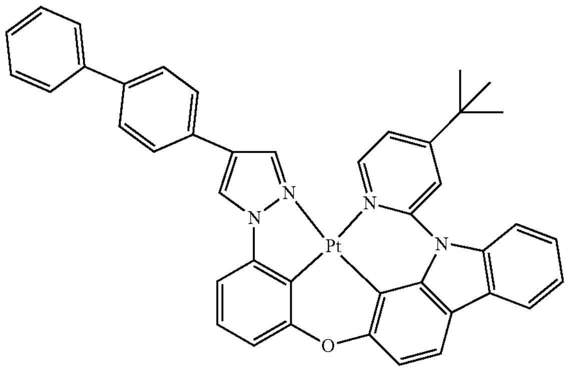

M-b-4

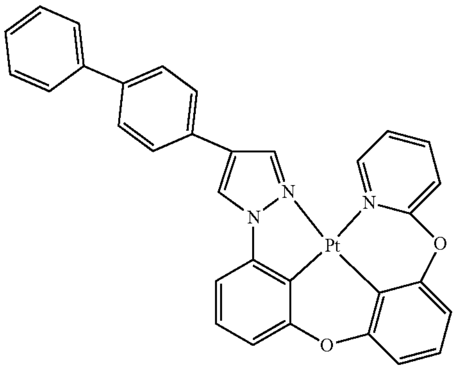

-continued

M-b-5

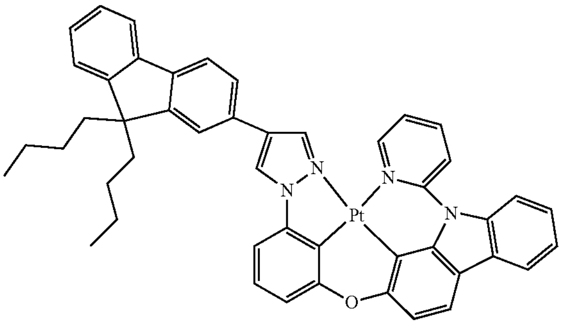

M-b-6

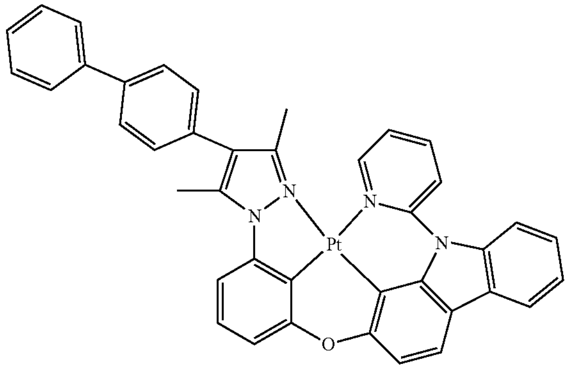

M-b-7

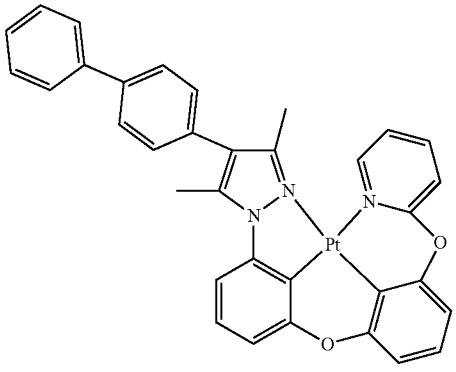

M-b-8

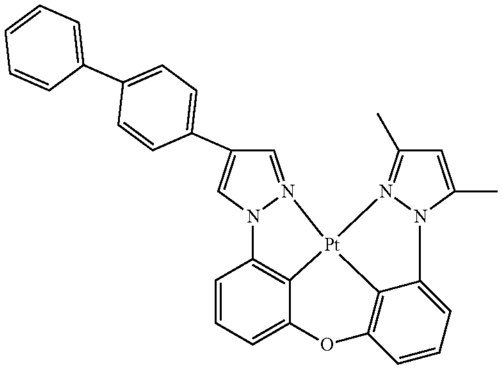

-continued

M-b-9

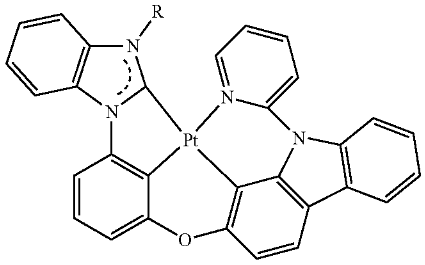

M-b-10

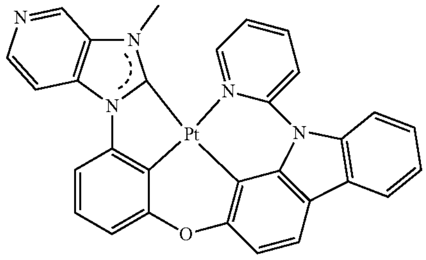

M-b-11

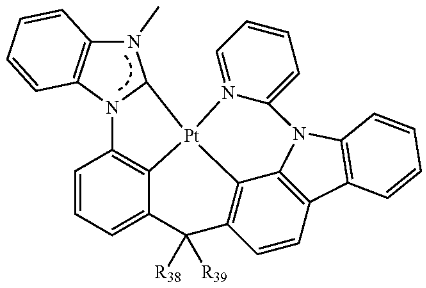

In Compounds M-b-1 to M-b-11, R, $R_{38}$, and $R_{39}$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

The emission layer EML may include a compound represented by any one of Formula F-a to Formula F-c. The compounds represented by Formula F-a to Formula F-c may be used as fluorescence dopant materials.

[Formula F-a]

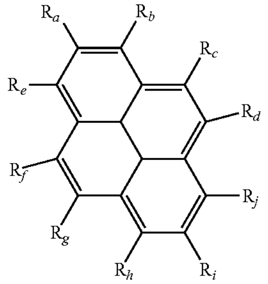

In Formula F-a, two of $R_a$ to may each independently be substituted with a group represented by *—$NAr_1Ar_2$. The remainder of $R_a$ to $R_j$ not substituted with the group represented by *—$NAr_1Ar_2$ may each independently be a hydrogen atom, a deuterium atom, a halogen atom, a cyano group, a substituted or unsubstituted amine group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In the group represented by *—$NAr_1Ar_2$, $Ar_1$ and $Ar_2$ may each independently be a substituted or unsubstituted aryl group of 6 to 30 ring-forming carbon atoms, or a substituted or unsubstituted heteroaryl group of 2 to 30 ring-forming carbon atoms. For example, at least one of $Ar_1$ or $Ar_2$ may each independently be a heteroaryl group including O or S as a ring-forming atom.

[Formula F-b]

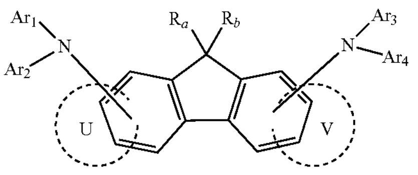

In Formula F-b, $R_a$ and $R_b$ may each independently be a hydrogen atom, a deuterium atom, a substituted or unsubstituted alkyl group of 1 to 20 carbon atoms, a substituted or unsubstituted alkenyl group of 2 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring. In Formula F-b, $Ar_1$ to $Ar_4$ may each independently be a substituted or unsubstituted aryl group of 6 to 30 ring-forming carbon atoms, or a substituted or unsubstituted heteroaryl group of 2 to 30 ring-forming carbon atoms.

In Formula F-b, U and V may each independently be a substituted or unsubstituted hydrocarbon ring of 5 to 30 ring-forming carbon atoms, or a substituted or unsubstituted heterocycle of 2 to 30 ring-forming carbon atoms.

In Formula F-b, the number of rings represented by U and V may each independently be 0 or 1. For example, in Formula F-b, if the number of U or V is 1, a fused ring may be present at the part designated by U or V, and if the number of U or V is 0, a fused ring may not be present at the part designated by U or V. If the number of U is 0 and the number of V is 1, or if the number of U is 1 and the number of V is 0, a fused ring having the fluorene core of Formula F-b may be a ring compound with four rings. If the number of both U and V is 0, a fused ring having the fluorene core of Formula F-b may be a ring compound with three rings. If the number of both U and V is 1, a fused ring having the fluorene core of Formula F-b may be a ring compound with five rings.

[Formula F-c]

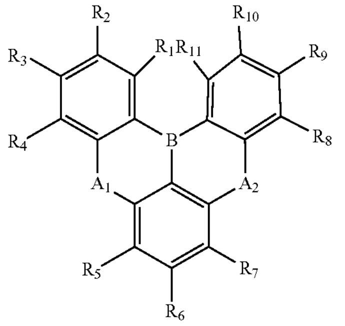

In Formula F-c, $A_1$ and $A_2$ may each independently be O, S, Se, or $N(R_m)$, and $R_m$ may be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In Formula F-c, $R_1$ to $R_{11}$ may each independently be a hydrogen atom, a deuterium atom, a halogen atom, a cyano group, a substituted or unsubstituted amine group, a substituted or unsubstituted boryl group, a substituted or unsubstituted oxy group, a substituted or unsubstituted thio group, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms, or may be combined with an adjacent group to form a ring.

In Formula F-c, $A_1$ and $A_2$ may each independently be combined with the substituents of an adjacent ring to form a fused ring. For example, if $A_1$ and $A_2$ are each independently $N(R_m)$, $A_1$ may be combined with $R_4$ or $R_5$ to form a ring. For example, A2 may be combined with $R_7$ or $R_8$ to form a ring.

In an embodiment, the emission layer EML may include as a dopant material, styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalen-2-yl)vinyl)phenyl)-N-phenylbenzenamine (N-BDAVBi), and 4,4'-bis[2-(4-(N,N-diphenylamino)phenyl)vinyl]biphenyl (DPAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, and 1,4-bis(N,N-diphenylamino)pyrene), etc.

In an embodiment, if multiple emission layers EML are included, at least one emission layer EML may include a phosphorescence dopant material. For example, the phosphorescence dopant may be a metal complex including iridium (Ir), platinum (Pt), osmium (Os), gold (Au), titanium (Ti), zirconium (Zr), hafnium (Hf), europium (Eu), terbium (Tb), or thulium (Tm). For example, iridium(III) bis(4,6-difluorophenylpyridinato-N, C2')picolinate (FIrpic), bis(2,4-difluorophenylpyridinato)-tetrakis(1-pyrazolyl)borate iridium(III) (Fir6), or platinum octaethyl porphyrin (PtOEP) may be used as the phosphorescence dopant. However, embodiments are not limited thereto.

In an embodiment, the emission layer EML may include a hole transport host and an electron transport host. In an embodiment, the emission layer EML may include an auxiliary dopant and a light-emitting dopant. A phosphorescence dopant material or a thermally activated delayed fluorescence dopant material may be included as the auxiliary dopant. For example, in an embodiment, the emission layer EML may include a hole transport host, an electron transport host, an auxiliary dopant, and a light-emitting dopant.

In the emission layer EML, an exciplex may be formed by the hole transport host and the electron transport host. The triplet energy of the exciplex formed by the hole transport host and the electron transport host may correspond to a T1 gap between the lowest unoccupied molecular orbital (LUMO) energy level of the electron transport host and the highest occupied molecular orbital (HOMO) energy level of the hole transport host.

In an embodiment, a triplet energy (T1) of the exciplex formed by the hole transport host and the electron transport host may be in a range of about 2.4 eV to about 3.0 eV. The triplet energy of the exciplex may be a value smaller than an energy gap of each host material. Accordingly, the exciplex may have a triplet energy equal to or less than about 3.0 eV, which is the energy gap of the hole transport host and the electron transport host.

In an embodiment, at least one emission layer EML may include a quantum dot. The quantum dot may be selected from a Group II-VI compound, a Group III-VI compound, a Group compound, a Group III-V compound, a Group III-II-V compound, a Group IV-VI compound, a Group IV element, a Group IV compound, and combinations thereof.

The Group II-VI compound may be selected from: a binary compound selected from the group consisting of CdSe, CdTe, CdS, ZnS, ZnSe, ZnTe, ZnO, HgS, HgSe, HgTe, MgSe, MgS, and mixtures thereof; a ternary compound selected from the group consisting of CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and mixtures thereof; a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and mixtures thereof; or any combination thereof.

The Group III-V compound may include a binary compound such as $In_2S_3$, and $In_2Se_3$; a ternary compound such as $InGaS_3$, and $InGaSe_3$; or any combination thereof.

The Group compound may be selected from: a ternary compound selected from the group consisting of AgInS, $AgInS_2$, CuInS, $CuInS_2$, $AgGaS_2$, $CuGaS_2$, $CuGaO_2$, $AgGaO_2$, $AgAlO_2$ and mixtures thereof; a quaternary compound such as $AgInGaS_2$, and $CuInGaS_2$; or any combination thereof.

The Group III-V compound may be selected from: a binary compound selected from the group consisting of GaN, GaP, GaAs, GaSb, AlN, AlP, AlAs, AlSb, InN, InP, InAs, InSb, and mixtures thereof; a ternary compound selected from the group consisting of GaNP, GaNAs, GaNSb, GaPAs, GaPSb, AlNP, AlNAs, AlNSb, AlPAs, AlPSb, InGaP, InAlP, InNP, InNAs, InNSb, InPAs, InPSb, and mixtures thereof; a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and mixtures thereof; or any combination thereof. The Group III-V compound may further include a Group II metal. For example, InZnP, etc. may be selected as a Group III-II-V compound.

The Group IV-VI compound may be selected from: a binary compound selected from the group consisting of SnS, SnSe, SnTe, PbS, PbSe, PbTe, and mixtures thereof; a ternary compound selected from the group consisting of SnSeS, SnSeTe, SnSTe, PbSeS, PbSeTe, PbSTe, SnPbS, SnPbSe, SnPbTe, and mixtures thereof; a quaternary compound selected from the group consisting of SnPbSSe, SnPbSeTe, SnPbSTe, and mixtures thereof; or any combination thereof. The Group IV element may be selected from the group consisting of Si, Ge, and a mixture thereof. The Group IV compound may be a binary compound selected from the group consisting of SiC, SiGe, and a mixture thereof.

A binary compound, a ternary compound, or a quaternary compound may be present in a particle at a uniform concentration or may be present in a particle at a partially different concentration distribution. In an embodiment, the quantum dot may have a core/shell structure in which a quantum dot surrounds another quantum dot. An interface between the core and the shell may have a concentration gradient in which the concentration of an element that is present in the shell decreases toward the center.

In embodiments, the quantum dot may have the above-described core-shell structure including a core including a nanocrystal and a shell surrounding the core. The shell of the quantum dot may function as a protection layer that prevents chemical deformation of the core to maintain semiconductor properties and/or may function as a charging layer that imparts the quantum dot with electrophoretic properties. The shell may have a single layer structure or a multilayer structure. Examples of the shell of the quantum dot may include a metal oxide, a non-metal oxide, a semiconductor compound, or combinations thereof.

For example, the metal oxide or the non-metal oxide may include a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$ and NiO, or a ternary compound such as $MgAl_2O_4$, $CoFe_2O_4$, $NiFe_2O_4$ and $CoMn_2O_4$, but embodiments are not limited thereto.

The semiconductor compound may include CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments are not limited thereto.

The quantum dot may have a full width of half maximum (FWHM) of an emission wavelength spectrum equal to or less than about 45 nm. For example, the quantum dot may have a FWHM of an emission wavelength spectrum equal to or less than about 40 nm. For example, the quantum dot may have a FWHM of an emission wavelength spectrum equal to or less than about 30 nm. Within these ranges, color purity or color reproducibility may be improved. Light emitted through the quantum dot may be emitted in all directions, so that light viewing angle properties may be improved.

The form of the quantum dot may be any which is used in the art, without specific limitation. For example, the quantum dot may have a spherical shape, a pyramidal shape, a multi-arm shape, or a cubic shape, or the quantum dot may be in the form of a nanoparticle, a nanotube, a nanowire, a nanofiber, a nanoplate particle, etc.

The quantum dot may control the color of light emitted according to a particle size thereof, and accordingly, the quantum dot may have various emission colors such as blue, red, or green.

In the light emitting element ED of an embodiment, as shown in FIG. 3 to FIG. 6, the electron transport region ETR is provided on the emission layer EML. The electron transport region ETR may include at least one of a hole blocking layer HBL, an electron transport layer ETL, or an electron injection layer EIL. However, embodiments are not limited thereto.

The electron transport region ETR may be a layer formed of a single material, a layer formed of different materials, or a multilayer structure having layers formed of different materials.

For example, the electron transport region ETR may have a single layer structure of an electron injection layer EIL or an electron transport layer ETL, or a single layer structure formed of an electron injection material and an electron transport material. In other embodiments, the electron transport region ETR may have a single layer structure formed of different materials, or may have a structure in which an electron transport layer ETL/electron injection layer EIL, a hole blocking layer HBL/electron transport layer ETL/electron injection layer EIL, or an electron transport layer ETL/buffer layer (not shown)/electron injection layer EIL, are stacked in its respective stated order stacked from the emission layer EML, but embodiments are not limited thereto. A thickness of the electron transport region ETR may be, for example, in a range of about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

The electron transport region ETR may include a compound represented by Formula ET-1.

[Formula ET-1]

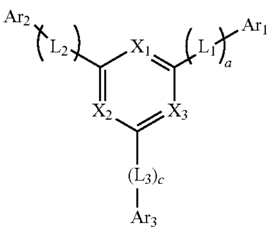

In Formula ET-1, at least one of $X_1$ to $X_3$ may be N, and the remainder of $X_1$ to $X_3$ may each independently be $C(R_a)$. $R_a$ may be a hydrogen atom, a deuterium atom, a substituted or unsubstituted alkyl of 1 to 20 carbon atoms, a substituted or unsubstituted aryl group of 6 to 30 ring-forming carbon atoms, or a substituted or unsubstituted heteroaryl group of 2 to 30 ring-forming carbon atoms. In Formula ET-1, $Ar_1$ to $Ar_3$ may each independently be a hydrogen atom, a deuterium atom, a substituted or unsubstituted alkyl group of 1 to 20 carbon atoms, a substituted or unsubstituted aryl group of 6 to 30 ring-forming carbon atoms, or a substituted or unsubstituted heteroaryl group of 2 to 30 ring-forming carbon atoms.

In Formula ET-1, a to c may each independently be an integer from 0 to 10. In Formula ET-1, $L_1$ to $L_3$ may be each independently a direct linkage, a substituted or unsubstituted arylene group of 6 to 30 ring-forming carbon atoms, or a substituted or unsubstituted heteroarylene group of 2 to 30 ring-forming carbon atoms. If a to c are 2 or more, $L_1$ to $L_3$ may each independently be a substituted or unsubstituted arylene group of 6 to 30 ring-forming carbon atoms, or a substituted or unsubstituted heteroarylene group of 2 to 30 ring-forming carbon atoms.

The electron transport region ETR may include an anthracene-based compound. However, embodiments are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1, O8)-(1,1'-biphenyl-4-olato)aluminum (BAlq), berylliumbis(benzoquinolin-10-olate ($Bebq_2$), 9,10-di(naphthalene-2-yl) anthracene (ADN), 1,3-bis[3,5-di(pyridin-3-yl)phenyl] benzene (BmPyPhB), diphenyl(4-(triphenylsilyl)phenyl) phosphine oxide (TSPO1), and mixtures thereof, without limitation.

The electron transport region ETR may include at least one of Compounds ET1 to ET36.

ET1

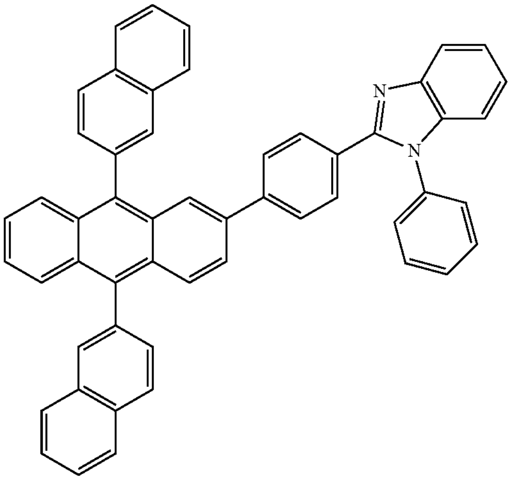

ET2

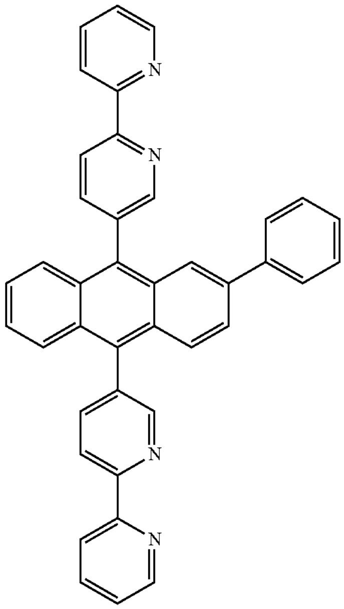

-continued
ET3
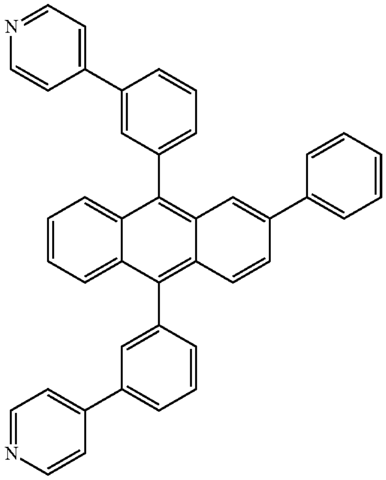
ET4
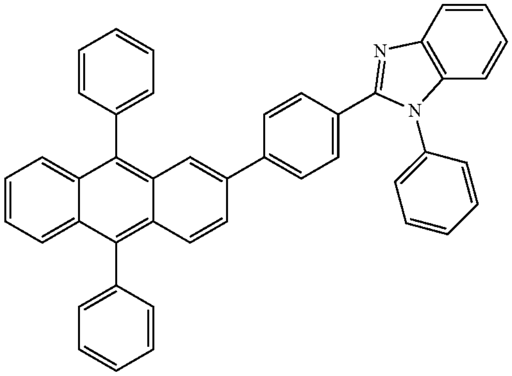
ET5
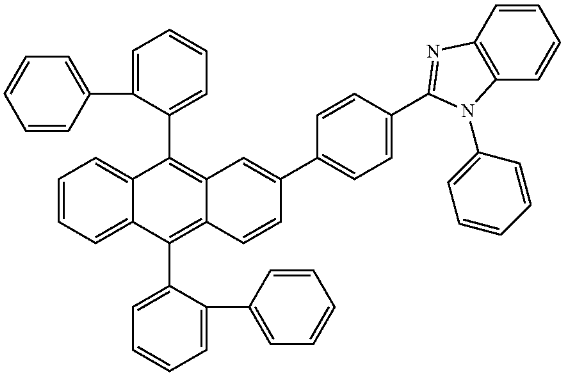
ET6
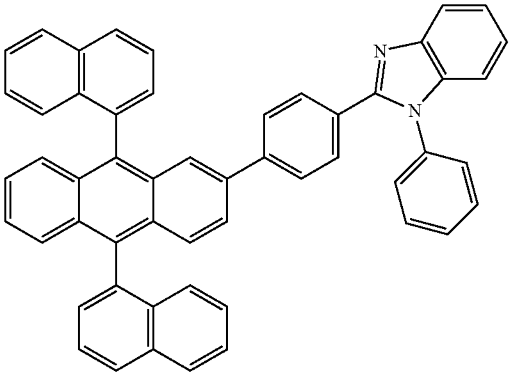
-continued
ET7
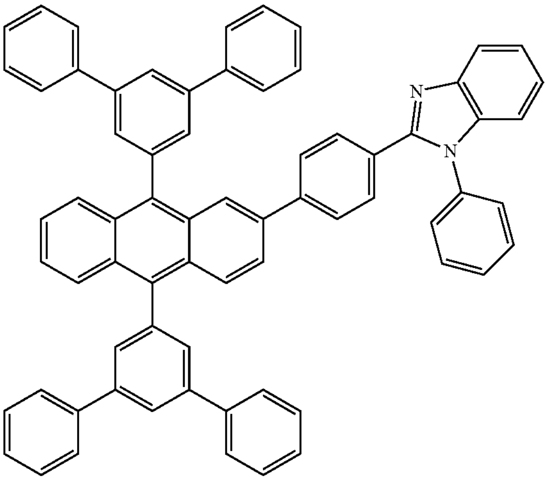
ET8
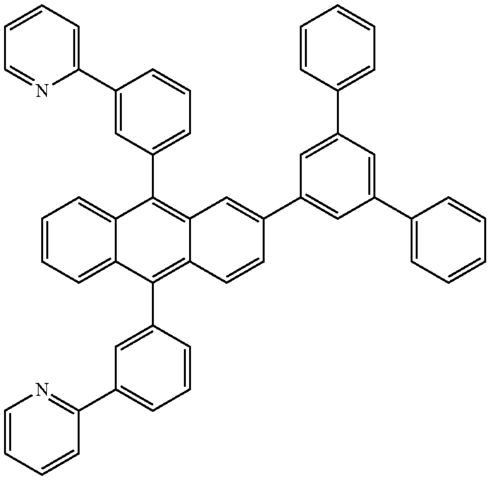
ET9
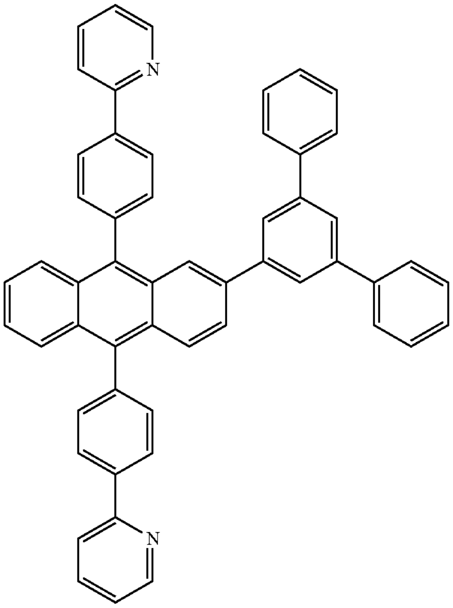

-continued
ET10
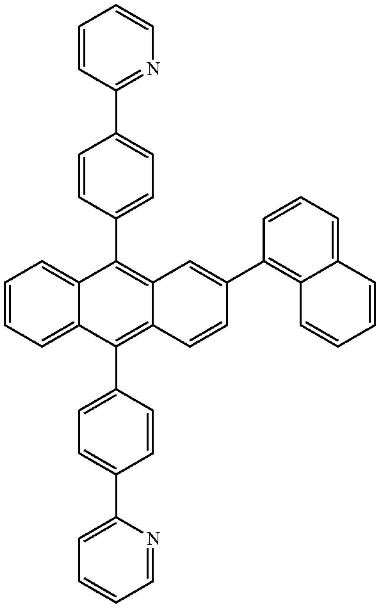
ET11
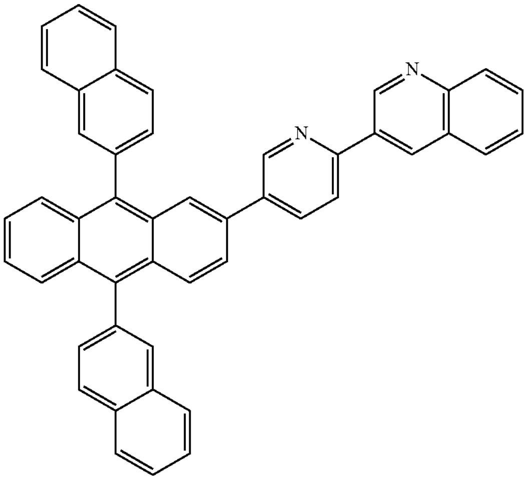
ET12
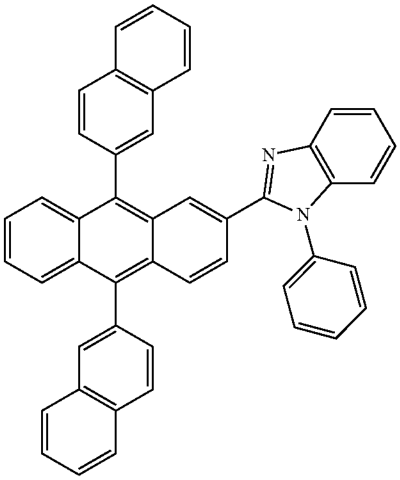
-continued
E13
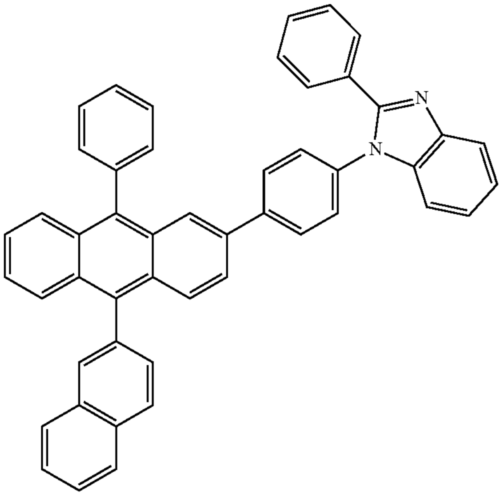
E14
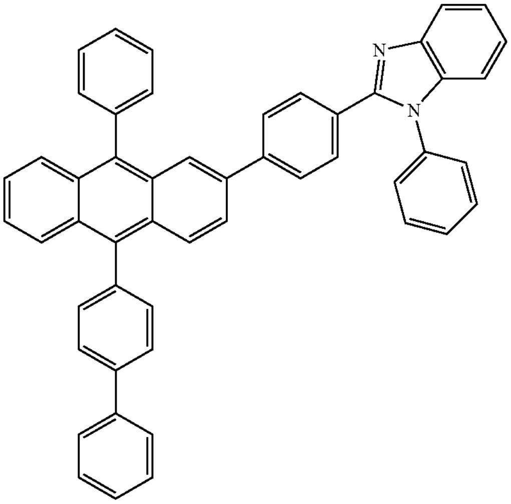
E15
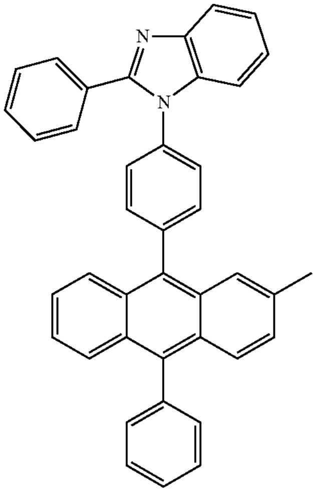

-continued
ET16
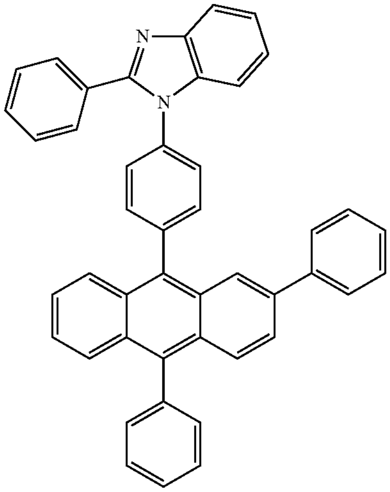
ET17
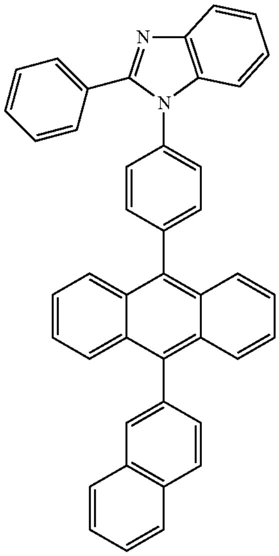
ET18
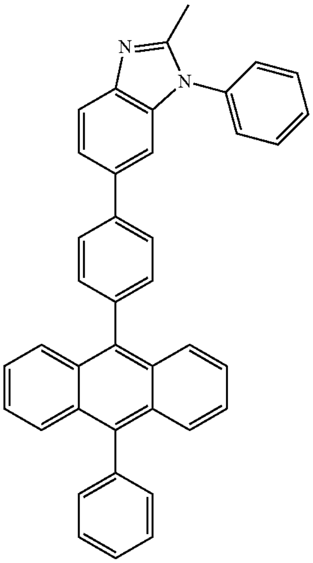
-continued
ET19
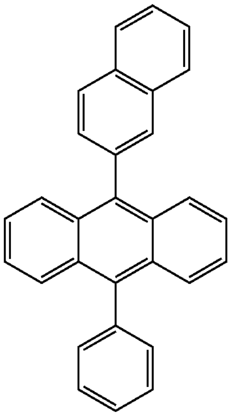
ET20
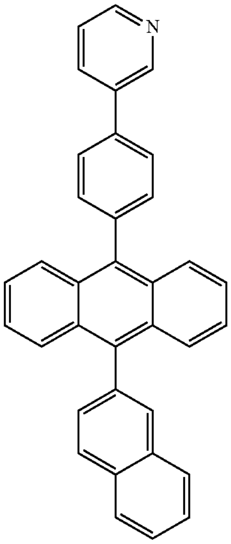
ET21
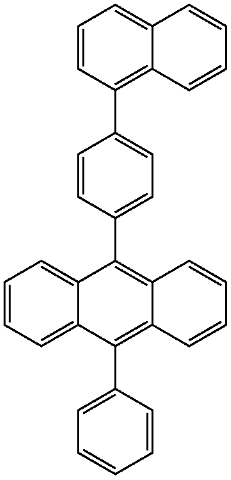

-continued
ET22
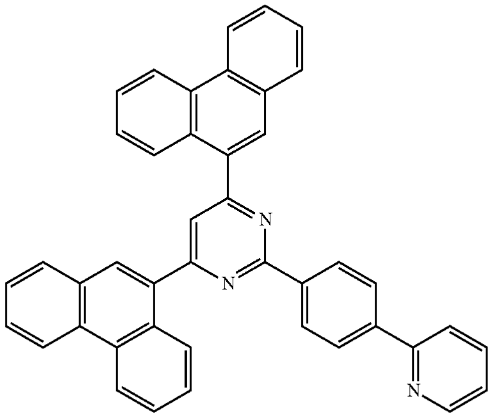
ET23
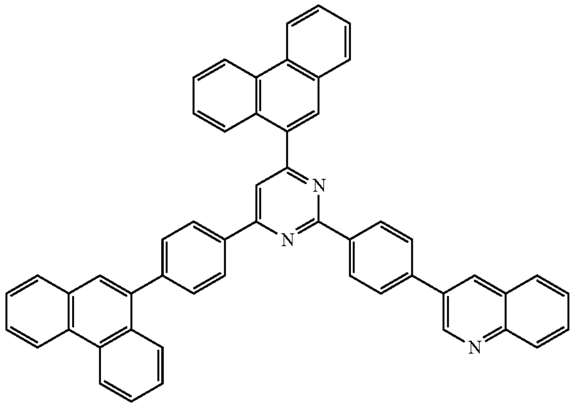
ET24
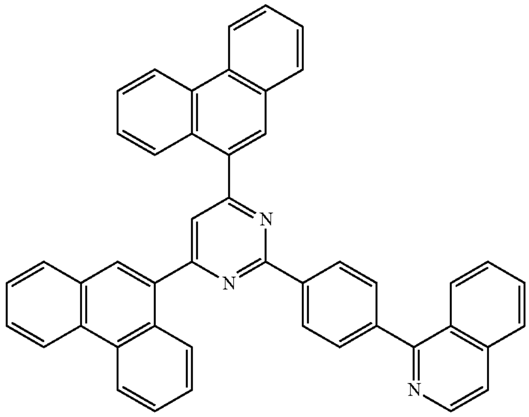
-continued
ET25
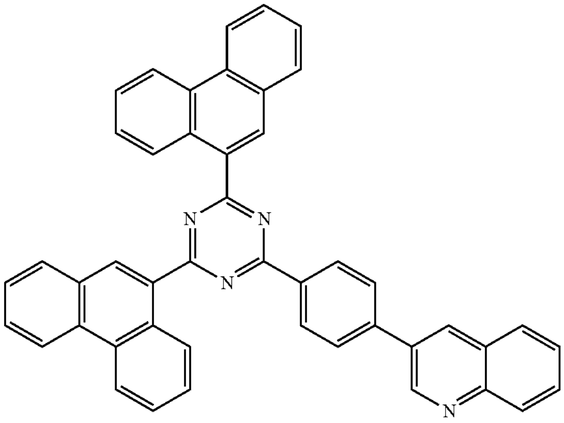
ET26
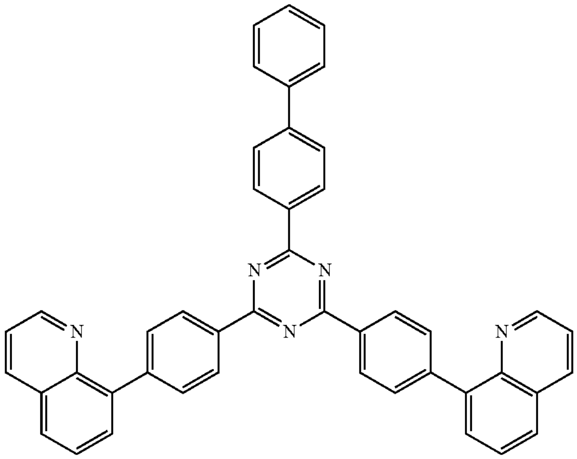
ET27
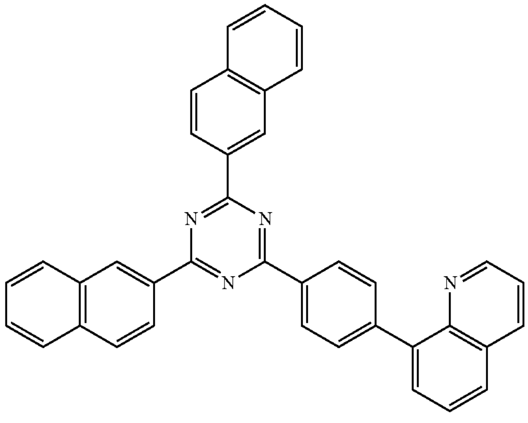

-continued
ET28
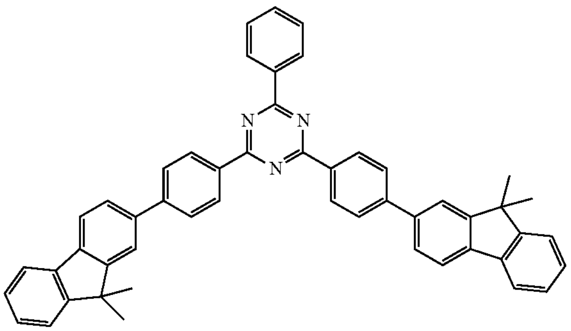
ET29
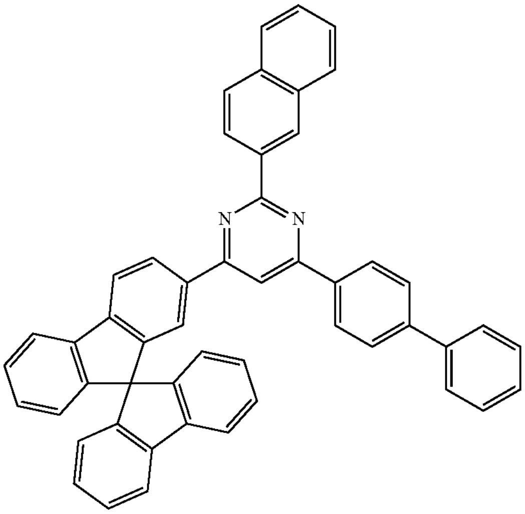
ET30
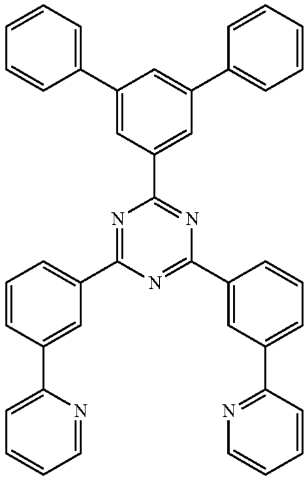
-continued
ET31
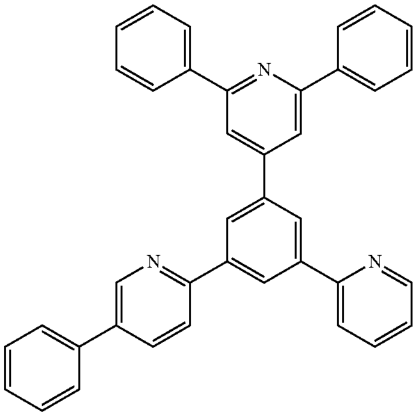
ET32
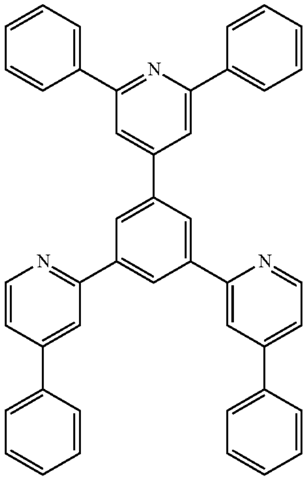
ET33
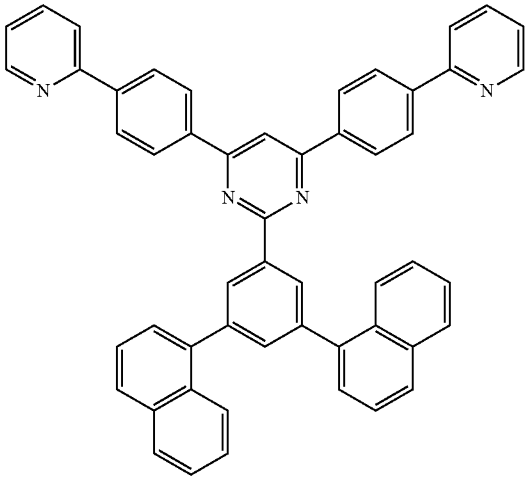

-continued

ET34

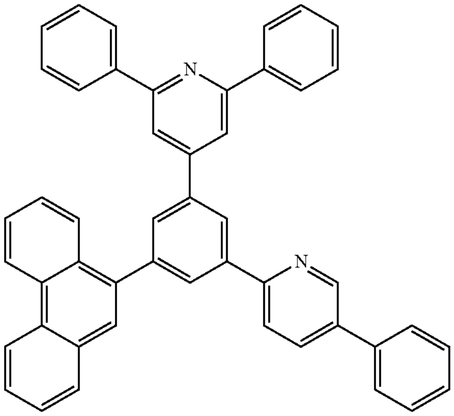

ET35

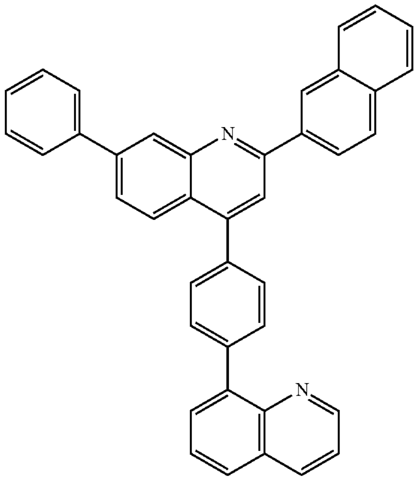

ET36

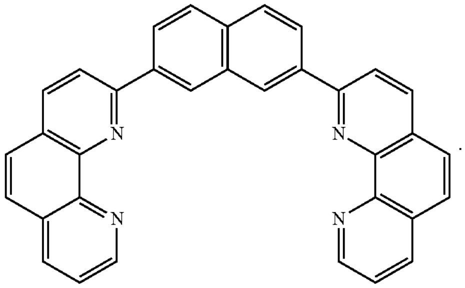

The electron transport region ETR may include a metal halide such as LiF, NaCl, CsF, RbCl, RbI, CuI, or KI, a lanthanide such as Yb, or a co-depositing material of the metal halide and the lanthanide. For example, the electron transport region ETR may include KI:Yb, RbI:Yb, LiF:Yb, etc., as the co-depositing material. The electron transport region ETR may include a metal oxide such as $Li_2O$ and BaO, or 8-hydroxy-lithium quinolate (Liq). However, embodiments are not limited thereto. The electron transport region ETR also may be formed of a mixture material of an electron transport material and an insulating organo metal salt. The organo metal salt may be a material having an energy band gap equal to or greater than about 4 eV. For example, the organo metal salt may include metal acetates, metal benzoates, metal acetoacetates, metal acetylacetonates, or metal stearates.

The electron transport region ETR may include at least one of 2,9-dimethyl-4,7-diphenyl-1,10-phenanthroline (BCP), diphenyl(4-(triphenylsilyl)phenyl)phosphine oxide (TSPO1) or 4,7-diphenyl-1,10-phenanthroline (Bphen) in addition to the aforementioned materials. However, embodiments are not limited thereto.

The electron transport region ETR may include the compounds of the electron transport region in at least one of an electron injection layer EIL, an electron transport layer ETL, or a hole blocking layer HBL.

If the electron transport region ETR includes an electron transport layer ETL, a thickness of the electron transport layer ETL may be in a range of about 100 Å to about 1,000 Å. For example, the thickness of the electron transport layer ETL may be in a range of about 150 Å to about 500 Å. If the thickness of the electron transport layer ETL satisfies the above-described range, satisfactory electron transport properties may be obtained without a substantial increase of driving voltage. If the electron transport region ETR includes an electron injection layer EIL, a thickness of the electron injection layer EIL may be in a range of about 1 Å to about 100 Å. For example, the thickness of the electron injection layer EIL may be in a range of about 3 Å to about 90 Å. If the thickness of the electron injection layer EIL satisfies the above described range, satisfactory electron injection properties may be obtained without inducing a substantial increase of driving voltage.

The second electrode EL2 is provided on the electron transport region ETR. The second electrode EL2 may be a common electrode. The second electrode EL2 may be a cathode or an anode, but embodiments are not limited thereto. For example, if the first electrode EL1 is an anode, then the second cathode EL2 may be a cathode, and if the first electrode EL1 is a cathode, then the second electrode EL2 may be an anode. The second electrode may include at least one of Ag, Mg, Cu, Al, Pt, Pd, Au, Ni, Nd, Ir, Cr, Li, Ca, LiF, Mo, Ti, W, In, Sn, Zn, oxides thereof, compounds thereof, or mixtures thereof.

The second electrode EL2 may be a transmissive electrode, a transflective electrode, or a reflective electrode. If the second electrode EL2 is a transmissive electrode, the second electrode EL2 may include a transparent metal oxide, for example, ITO, IZO, ZnO, ITZO, etc.

If the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca (e.g., a stacked structure of LiF and Ca), LiF/Al (e.g., a stacked structure of LiF and Al), Mo, Ti, Yb, W, compounds thereof, or mixtures thereof (for example, AgMg, AgYb, or MgYb). In another embodiment, the second electrode EL2 may have a multilayered structure including a reflective layer or a transflective layer formed of the above-described materials and a transparent conductive layer formed of ITO, IZO, ZnO, ITZO, etc. For example, the second electrode EL2 may include the aforementioned metal materials, combinations of two or more metal materials selected from the aforementioned metal materials, or oxides of the aforementioned metal materials.

Although not shown in the drawings, the second electrode EL2 may be electrically connected to an auxiliary electrode. If the second electrode EL2 is electrically connected to the auxiliary electrode, the resistance of the second electrode EL2 may decrease.

In an embodiment, the light emitting element ED may further include a capping layer CPL disposed on the second electrode EL2. The capping layer CPL may be a multilayer or a single layer.

In an embodiment, the capping layer CPL may include an organic layer or an inorganic layer. For example, if the capping layer CPL includes an inorganic material, the inorganic material may include an alkali metal compound such as LiF, an alkaline earth metal compound such as $MgF_2$, SiON, SiNx, SiOy, etc.

For example, if the capping layer CPL includes an organic material, the organic material may include α-NPD, NPB, TPD, m-MTDATA, $Alq_3$, CuPc, N4,N4,N4',N4'-tetra(biphenyl-4-yl) biphenyl-4,4'-diamine (TPD15), 4,4',4"-tris(carbazol sol-9-yl) triphenylamine (TCTA), etc., or may include an epoxy resin, or acrylate such as methacrylate. The capping layer CPL may include at least one of Compounds P1 to P5, but embodiments are not limited thereto.

P1

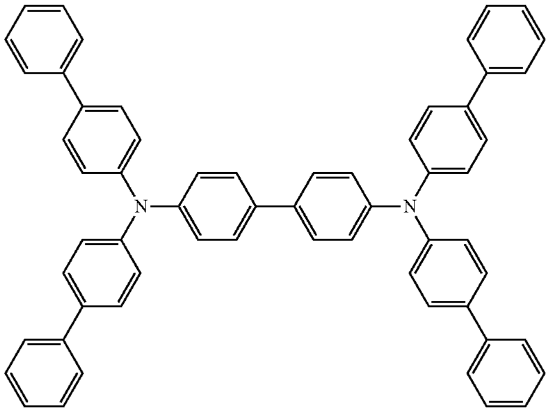

P2

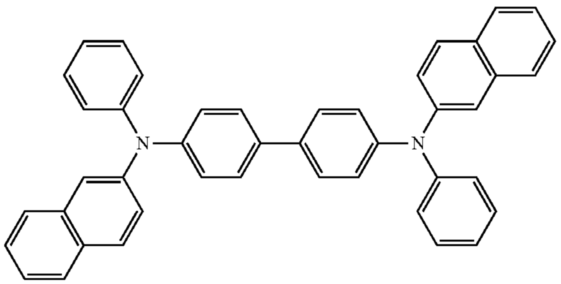

P3

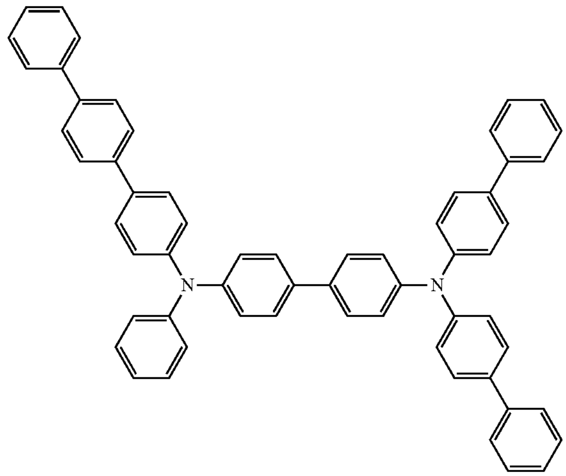

-continued

P4

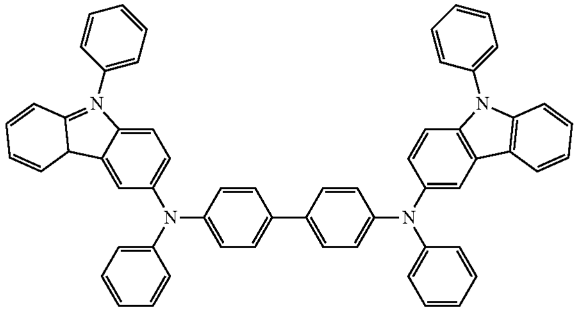

P5

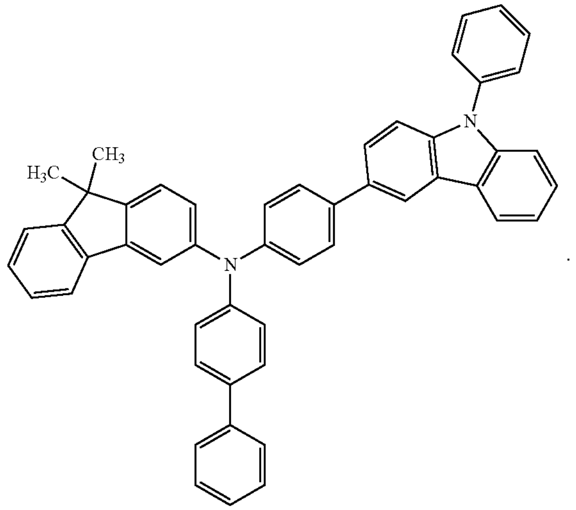

A refractive index of the capping layer CPL may be equal to or greater than about 1.6. For example, the refractive index of the capping layer CPL may be equal to or greater than about 1.6 with respect to light in a wavelength range of about 550 nm to about 660 nm.

FIG. 7 to FIG. 10 are each a schematic cross-sectional view of a display apparatus according to embodiments. In the explanation on the display apparatuses of embodiments, referring to FIG. 7 to FIG. 10, the parts which overlap with the explanation on FIG. 1 to FIG. 6 will not be explained again, and the different features will be explained.

Figure 7:
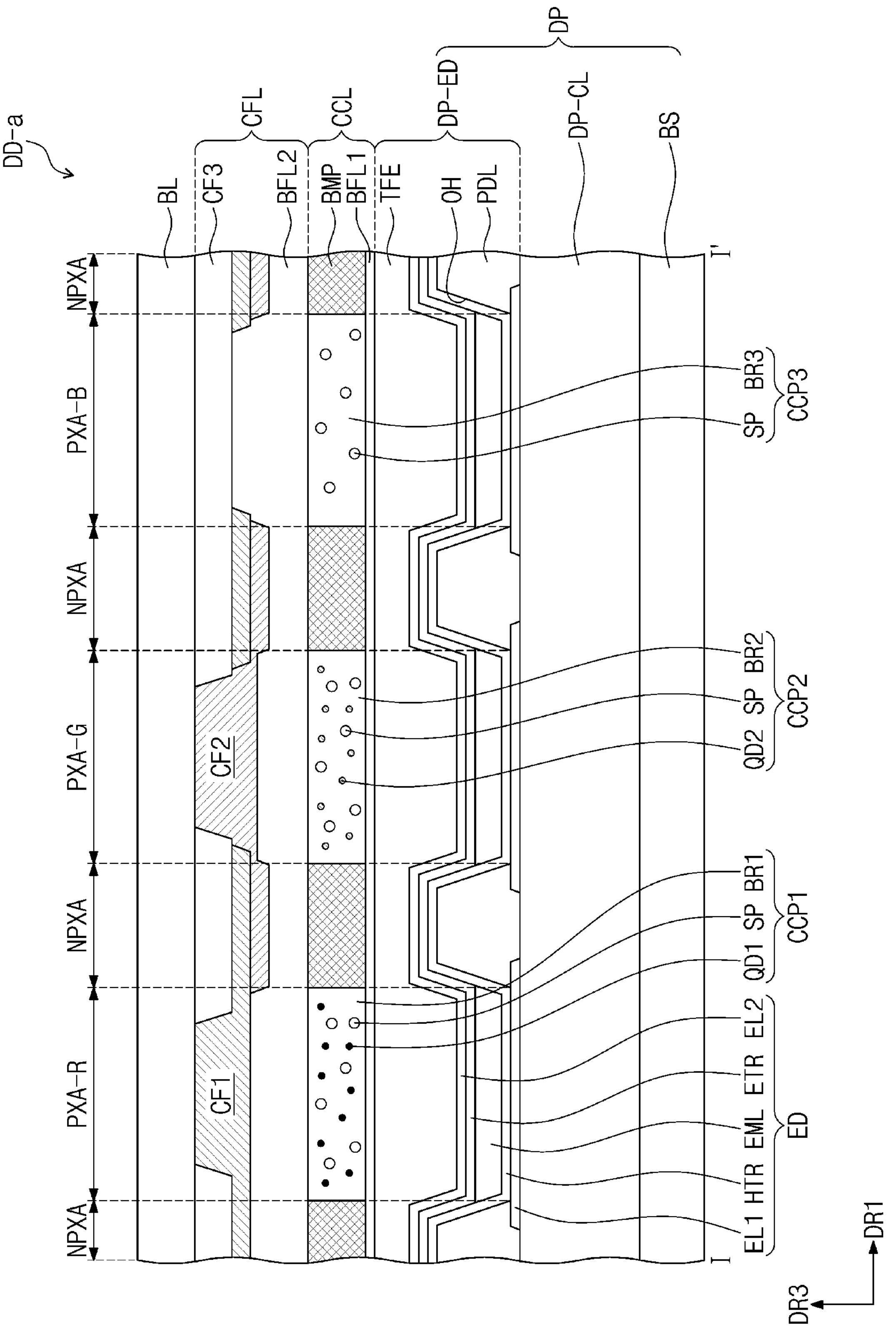
FIG. 7 is a schematic cross-sectional view showing a display apparatus according to an embodiment.

Referring to FIG. 7, a display apparatus DD-a according to an embodiment may include a display panel DP including a display device layer DP-ED, a light controlling layer CCL disposed on the display panel DP, and a color filter layer CFL.

In an embodiment shown in FIG. 7, the display panel DP includes a base layer BS, a circuit layer DP-CL provided on the base layer BS, and a display device layer DP-ED, and the display device layer DP-ED may include a light emitting element ED.

The light emitting element ED may include a first electrode EL1, a hole transport region HTR disposed on the first electrode EL1, an emission layer EML disposed on the hole transport region HTR, an electron transport region ETR disposed on the emission layer EML, and a second electrode EL2 disposed on the electron transport region ETR. The same structures of the light emitting elements of FIG. 3 to FIG. 6 may be applied to the structure of the light emitting element ED shown in FIG. 7.

The hole transport region HTR of the light emitting element ED, included in the display apparatus DD-a according to an embodiment, may include the polycyclic compound of an embodiment.

Referring to FIG. 7, the emission layer EML may be disposed in an opening OH defined in a pixel definition layer PDL. For example, the emission layer EML which is separated by the pixel definition layer PDL and correspondingly provided to each of luminous areas PXA-R, PXA-G, and PXA-B may emit light in a same wavelength region. In the display apparatus DD-a of an embodiment, the emission layer EML may emit blue light. Although not shown in the drawings, in an embodiment, the emission layer EML may be provided as a common layer for all luminous areas PXA-R, PXA-G, and PXA-B.

The light controlling layer CCL may be disposed on the display panel DP. The light controlling layer CCL may include a light converter. The light converter may be a quantum dot or a phosphor. The light converter may transform the wavelength of a provided light and may emit the transformed light. For example, the light controlling layer CCL may be a layer including a quantum dot or a layer including a phosphor.

The light controlling layer CCL may include light controlling parts CCP1, CCP2, and CCP3. The light controlling parts CCP1, CCP2, and CCP3 may be separated from one another.

Referring to FIG. 7, a partition pattern BMP may be disposed between the separated light controlling parts CCP1, CCP2, and CCP3, but embodiments are not limited thereto. In FIG. 7, the partition pattern BMP is shown so that it does not overlap the light controlling parts CCP1, CCP2, and CCP3, but at least a portion of the edge of the light controlling parts CCP1, CCP2, and CCP3 may overlap the partition pattern BMP.

The light controlling layer CCL may include a first light controlling part CCP1 including a first quantum dot QD1 that converts first color light provided from the light emitting element ED into second color light, a second light controlling part CCP2 including a second quantum dot QD2 that converts first color light provided from the light emitting element ED into third color light, and a third light controlling part CCP3 that transmits first color light provided from the light emitting element ED.

In an embodiment, the first light controlling part CCP1 may provide red light which is the second color light, and the second light controlling part CCP2 may provide green light which is the third color light. The third color controlling part CCP3 may transmit and provide blue light which is the first color light provided from the light emitting element ED. For example, the first quantum dot QD1 may be a red quantum dot, and the second quantum dot QD2 may be a green quantum dot. The same descriptions as provided above with respect to quantum dots may be applied to the quantum dots QD1 and QD2.

The light controlling layer CCL may further include a scatterer SP. The first light controlling part CCP1 may include the first quantum dot QD1 and the scatterer SP, the second light controlling part CCP2 may include the second quantum dot QD2 and the scatterer SP, and the third light controlling part CCP3 may not include a quantum dot but may include the scatterer SP.

The scatterer SP may be an inorganic particle. For example, the scatterer SP may include at least one of $TiO_2$, ZnO, $Al_2O_3$, $SiO_2$, or hollow silica. The scatterer SP may include at least one of $TiO_2$, ZnO, $Al_2O_3$, $SiO_2$, or hollow silica, or may be a mixture of two or more materials selected from $TiO_2$, ZnO, $Al_2O_3$, $SiO_2$, and hollow silica.

Each of the first light controlling part CCP1, the second light controlling part CCP2, and the third light controlling part CCP3 may include base resins BR1, BR2, and BR3 for dispersing the quantum dots QD1 and QD2 and the scatterer SP. In an embodiment, the first light controlling part CCP1 may include the first quantum dot QD1 and the scatterer SP dispersed in the first base resin BR1, the second light controlling part CCP2 may include the second quantum dot QD2 and the scatterer SP dispersed in the second base resin BR2, and the third light controlling part CCP3 may include the scatterer SP dispersed in the third base resin BR3. The base resins BR1, BR2, and BR3 may each be a medium in which the quantum dots QD1 and QD2 and the scatterer SP are dispersed, and may be composed of various resin compositions which may be generally referred to as a binder. For example, the base resins BR1, BR2, and BR3 may each independently be acrylic resins, urethane-based resins, silicone-based resins, epoxy-based resins, etc. The base resins BR1, BR2, and BR3 may each be a transparent resin. In an embodiment, the first base resin BR1, the second base resin BR2, and the third base resin BR3 may be the same as or different from each other.

The light controlling layer CCL may include a barrier layer BFL1. The barrier layer BFL1 may block the penetration of moisture and/or oxygen (hereinafter, will be referred to as "humidity/oxygen"). The barrier layer BFL1 may be disposed on the light controlling parts CCP1, CCP2, and CCP3 to block the exposure of the light controlling parts CCP1, CCP2, and CCP3 to humidity/oxygen. The barrier layer BFL1 may cover the light controlling parts CCP1, CCP2, and CCP3. The barrier layer BFL2 may be provided between the light controlling parts CCP1, CCP2, and CCP3 and a color filter layer CFL.

The barrier layers BFL1 and BFL2 may each include at least one inorganic layer. For example, the barrier layers BFL1 and BFL2 may each be formed of an inorganic material. For example, the barrier layers BFL1 and BFL2 may each independently include silicon nitride, aluminum nitride, zirconium nitride, titanium nitride, hafnium nitride, tantalum nitride, silicon oxide, aluminum oxide, titanium oxide, tin oxide, cerium oxide, silicon oxynitride, or a metal thin film securing light transmittance. The barrier layers BFL1 and BFL2 may each further include an organic layer. The barrier layers BFL1 and BFL2 may be composed of a single layer or of multiple layers.

In the display apparatus DD-a of an embodiment, the color filter layer CFL may be disposed on the light controlling layer CCL. In an embodiment, the color filter layer CFL may be disposed directly on the light controlling layer CCL. For example, the barrier layer BFL2 may be omitted.

The color filter layer CFL may include filters CF1, CF2, and CF3. The color filter layer CFL may include a first filter CF1 transmitting second color light, a second filter CF2 transmitting third color light, and a third filter CF3 transmitting first color light. For example, the first filter CF1 may be a red filter, the second filter CF2 may be a green filter, and the third filter CF3 may be a blue filter. Each of the filters CF1, CF2, and CF3 may include a polymer photosensitive resin and a pigment or dye. The first filter CF1 may include a red pigment or dye, the second filter CF2 may include a green pigment or dye, and the third filter CF3 may include a blue pigment or dye. However, embodiments are not limited thereto, and the third filter CF3 may not include a pigment or dye. The third filter CF3 may include a polymer photosensitive resin and may not include a pigment or dye.

The third filter CF3 may be transparent. The third filter CF3 may be formed of a transparent photosensitive resin.

In an embodiment, the first filter CF1 and the second filter CF2 may each be yellow filters. The first filter CF1 and the second filter CF2 may be provided in one body without distinction. Each of the first to third filters CF1, CF2, and CF3 may be disposed corresponding to a red luminous area PXA-R, green luminous area PXA-G, and blue luminous area PXA-B, respectively.

Although not shown in the drawings, the color filter layer CFL may include a light blocking part (not shown). The color filter layer CFL may include the light blocking part (not shown) disposed so as to overlap with the boundaries of the filters CF1, CF2, and CF3. The light blocking part (not shown) may be a black matrix. The light blocking part (not shown) may include an organic light blocking material or an inorganic light blocking material, such as a black pigment or black dye. The light blocking part (not shown) may distinguish the boundaries between adjacent filters CF1, CF2, and CF3. In an embodiment, the light blocking part (not shown) may be formed of a blue filter.

A base substrate BL may be disposed on the color filter layer CFL. The base substrate BL may provide a base surface on which the color filter layer CFL, the light controlling layer CCL, etc. are disposed. The base substrate BL may be a glass substrate, a metal substrate, a plastic substrate, etc. However, embodiments are not limited thereto, and the base substrate BL may include an inorganic layer, an organic layer, or a composite material layer. Although not shown in the drawing, in an embodiment, the base substrate BL may be omitted.

Figure 8:
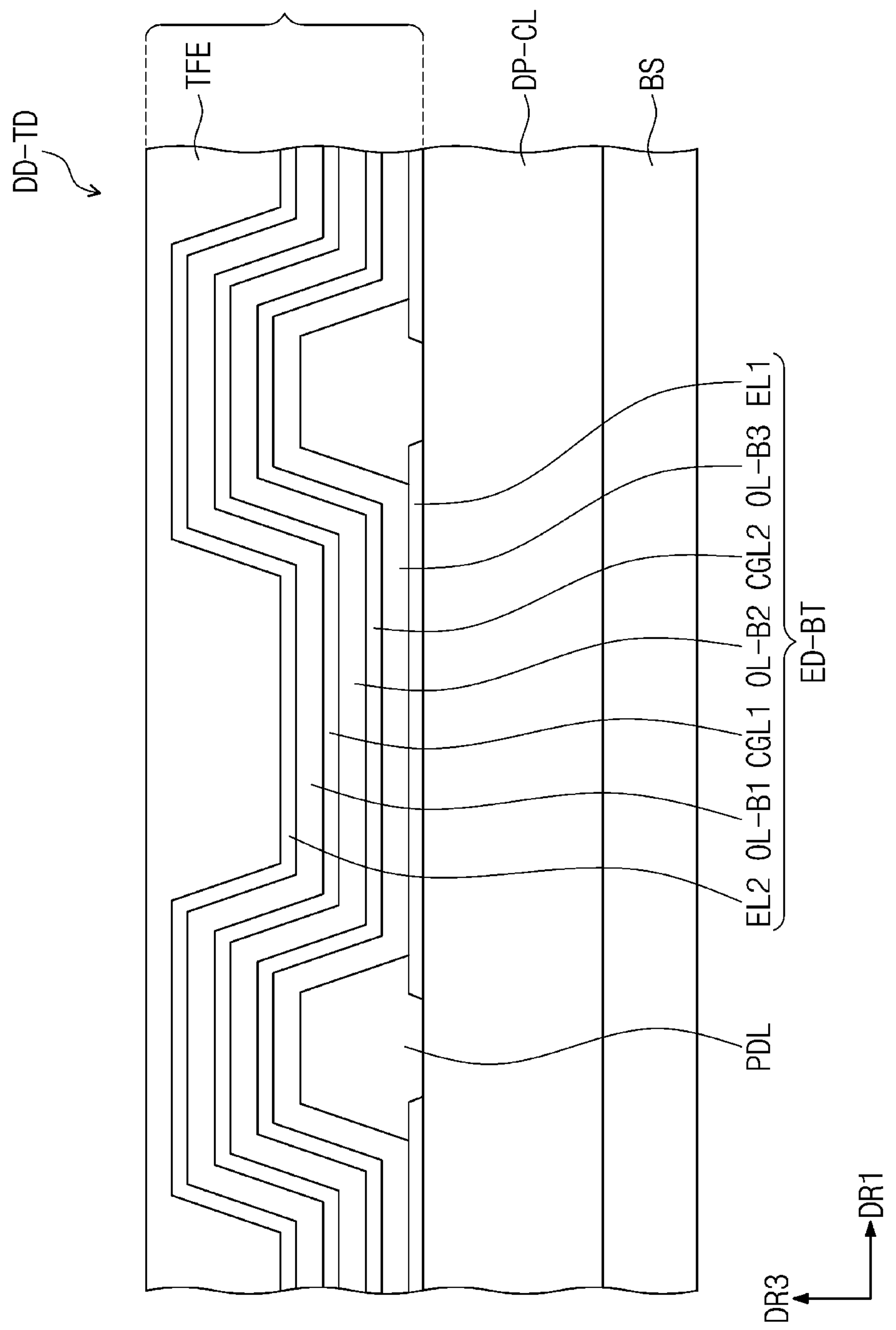
FIG. 8 is a schematic cross-sectional view showing a display apparatus according to an embodiment.

FIG. 8 is a schematic cross-sectional view showing a portion of the display apparatus according to an embodiment. In FIG. 8, a schematic cross-sectional view of a portion corresponding to the display panel DP in FIG. 7 is shown. In a display apparatus DD-TD of an embodiment, the light emitting element ED-BT may include light emitting structures OL-B1, OL-B2, and OL-B3. The light emitting element ED-BT may include a first electrode EL1 and an oppositely disposed second electrode EL2, and the light emitting structures OL-B1, OL-B2, and OL-B3 stacked in a thickness direction and provided between the first electrode EL1 and the second electrode EL2. Each of the light emitting structures OL-B1, OL-B2, and OL-B3 may include an emission layer EML (FIG. 7), and a hole transport region HTR and an electron transport region ETR disposed with the emission layer EML (FIG. 7) therebetween.

For example, the light emitting element ED-BT included in the display apparatus DD-TD of an embodiment may be a light emitting element having a tandem structure and including multiple emission layers.

In an embodiment shown in FIG. 8, light emitted from the light emitting structures OL-B1, OL-B2, and OL-B3 may be all blue light. However, embodiments are not limited thereto, and the wavelength regions of light emitted from each of the light emitting structures OL-B1, OL-B2, and OL-B3 may be different from each other. For example, the light emitting element ED-BT including the light emitting structures OL-B1, OL-B2, and OL-B3 emitting light in different wavelength regions may emit white light.

Charge generating layers CGL1 and CGL2 may be disposed between neighboring light emitting structures OL-B1, OL-B2, and OL-B3. The charge generating layers CGL1 and CGL2 may each independently include a p-type charge generating layer and/or an n-type charge generating layer.

The above-described polycyclic compound of an embodiment may be included in at least one of the light emitting structures OL-B1, OL-B2, and OL-B3 included in the display apparatus DD-TD of an embodiment.

Figure 9:
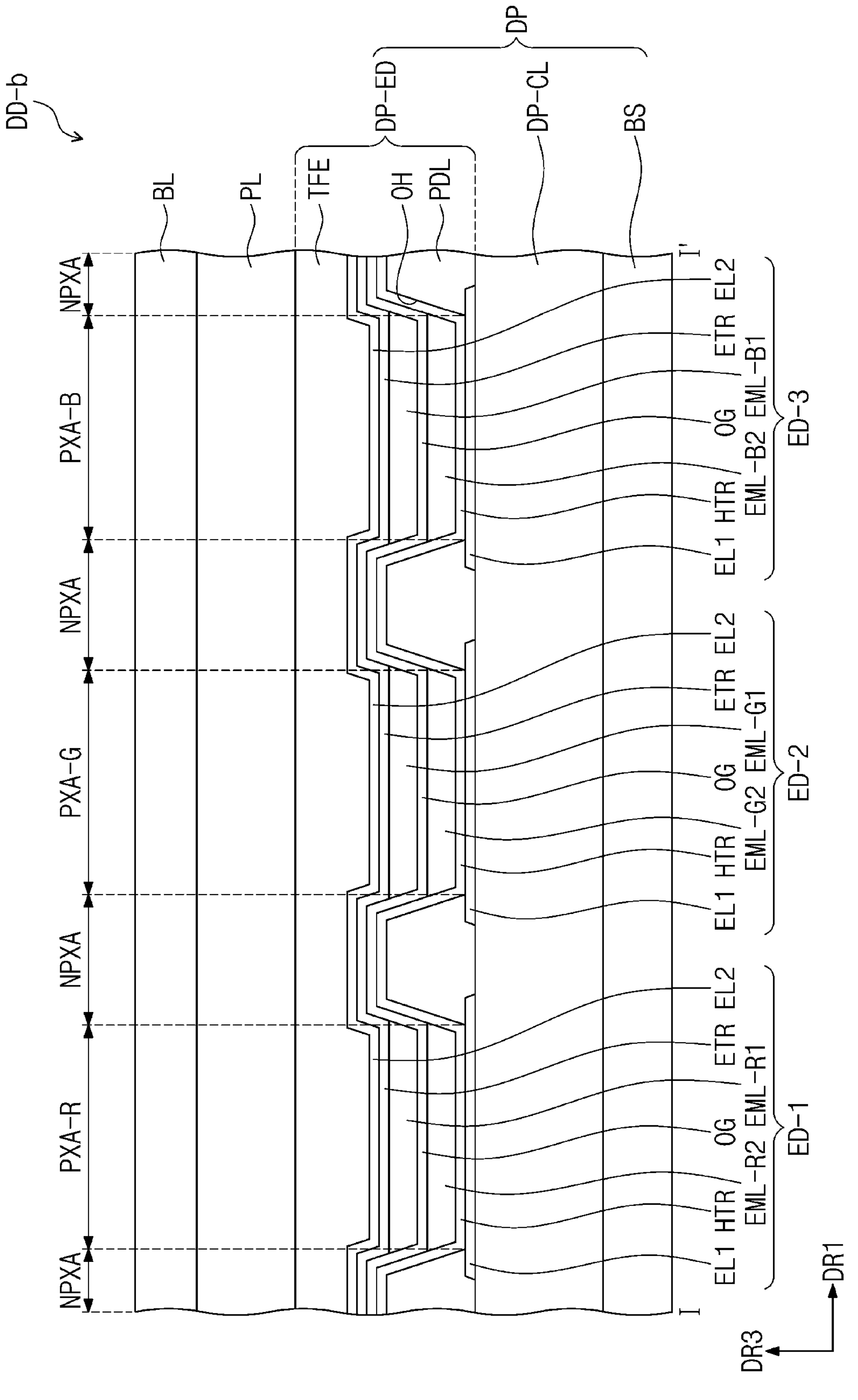
FIG. 9 is a schematic cross-sectional view showing a display apparatus according to an embodiment.

Referring to FIG. 9, a display apparatus DD-b according to an embodiment may include light emitting elements ED-1, ED-2, and ED-3, formed by stacking two emission layers. In comparison to the display apparatus DD of an embodiment shown in FIG. 2, an embodiment shown in FIG. 9 is different in that first to third light emitting elements ED-1, ED-2, and ED-3 each include two emission layers stacked in a thickness direction. In the first to third light emitting elements ED-1, ED-2, and ED-3, two emission layers may emit light in a same wavelength region.

The first light emitting element ED-1 may include a first red emission layer EML-R1 and a second red emission layer EML-R2. The second light emitting element ED-2 may include a first green emission layer EML-G1 and a second green emission layer EML-G2. The third light emitting element ED-3 may include a first blue emission layer EML-B1 and a second blue emission layer EML-B2. An emission auxiliary part OG may be disposed between the first red emission layer EML-R1 and the second red emission layer EML-R2, between the first green emission layer EML-G1 and the second green emission layer EML-G2, and between the first blue emission layer EML-B1 and the second blue emission layer EML-B2.

The emission auxiliary part OG may be a single layer or a multilayer. The emission auxiliary part OG may include a charge generating layer. For example, the emission auxiliary part OG may include an electron transport region, a charge generating layer, and a hole transport region, stacked in that order. The emission auxiliary part OG may be provided as a common layer for all of the first to third light emitting elements ED-1, ED-2, and ED-3. However, embodiments are not limited thereto, and the emission auxiliary part OG may be patterned and provided in an opening OH defined in a pixel definition layer PDL.

The first red emission layer EML-R1, the first green emission layer EML-G1, and the first blue emission layer EML-B1 may be disposed between the hole transport region HTR and the emission auxiliary part OG. The second red emission layer EML-R2, the second green emission layer EML-G2 and the second blue emission layer EML-B2 may be disposed between the emission auxiliary part OG and the electron transport region ETR.

For example, the first light emitting element ED-1 may include a first electrode EL1, a hole transport region HTR, a second red emission layer EML-R2, an emission auxiliary part OG, a first red emission layer EML-R1, an electron transport region ETR, and a second electrode EL2, stacked in that order. The second light emitting element ED-2 may include a first electrode EL1, a hole transport region HTR, a second green emission layer EML-G2, an emission auxiliary part OG, a first green emission layer EML-G1, an electron transport region ETR, and a second electrode EL2, stacked in that order. The third light emitting element ED-3 may include a first electrode EL1, a hole transport region HTR, a second blue emission layer EML-B2, an emission auxiliary part OG, a first blue emission layer EML-B1, an electron transport region ETR, and a second electrode EL2, stacked in that order.

An optical auxiliary layer PL may be disposed on a display device layer DP-ED. The optical auxiliary layer PL may include a polarization layer. The optical auxiliary layer PL may be disposed on a display panel DP and may control light reflected at the display panel DP from an external light.

Although not shown in the drawings, in an embodiment, the optical auxiliary layer PL may be omitted from the display apparatus DD-b.

Figure 10:
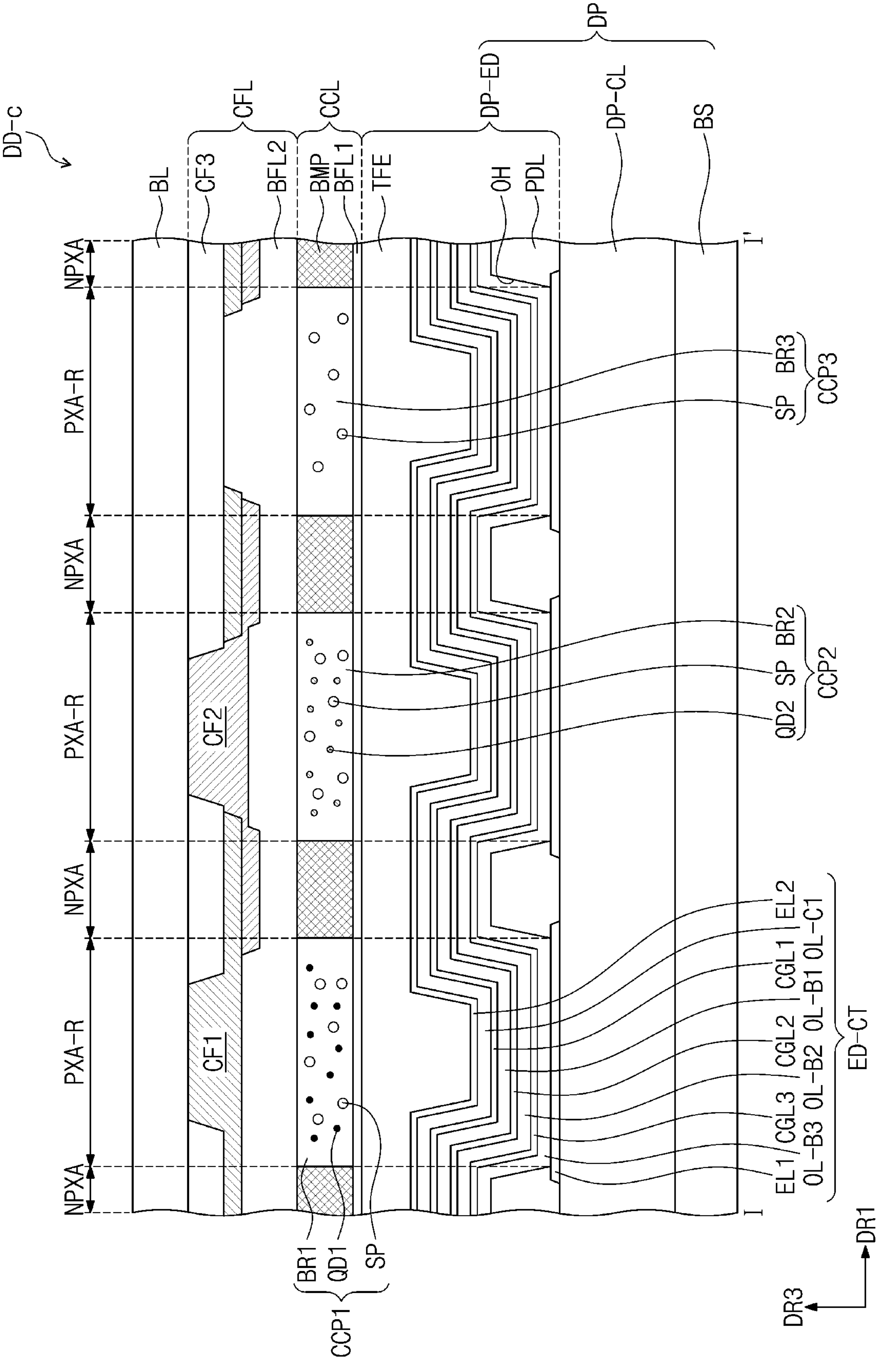
FIG. 10 is a schematic cross-sectional view showing a display apparatus according to an embodiment.

In comparison to FIG. 8 and FIG. 9, FIG. 10 shows a display apparatus DD-c that is different at least in that it includes four light emitting structures OL-B1, OL-B2, OL-B3, and OL-C1. A light emitting element ED-CT may include a first electrode EL1 and an oppositely disposed second electrode EL2, and first to fourth light emitting structures OL-B1, OL-B2, OL-B3, and OL-C1 stacked in order in a thickness direction between the first electrode EL1 and the second electrode EL2. Charge generating layers CGL1, CGL2, and CGL3 may be disposed between the first to fourth light emitting structures OL-B1, OL-B2, OL-B3, and OL-C1. Among the four light emitting structures, the first to third light emitting structures OL-B1, OL-B2, and OL-B3 may each emit blue light, and the fourth light emitting structure OL-C1 may emit green light. However, embodiments are not limited thereto, and the first to fourth light emitting structures OL-B1, OL-B2, OL-B3, and OL-C1 may all emit different wavelengths of light.

Charge generating layers CGL1, CGL2, and CGL3 may be disposed between neighboring light emitting structures OL-B1, OL-B2, OL-B3, and OL-C1. The charge generating layers CGL1, CGL2, and CGL3 may each independently include a p-type charge generating layer and/or an n-type charge generating layer.

The polycyclic compound of an embodiment may be included in at least one of the light emitting structures OL-B1, OL-B2, OL-B3, and OL-C1 that are included in the display apparatus DD-c.

The light emitting element ED according to an embodiment may include the polycyclic compound of an embodiment in at least one functional layer disposed between a first electrode EL1 and a second electrode EL2, and may show improved emission efficiency and improved life characteristics. The light emitting element ED according to an embodiment may include the polycyclic compound of an embodiment in at least one of a hole transport region HTR, an emission layer EML, or an electron transport region ETR, disposed between the first electrode EL1 and the second electrode EL2, or may include the polycyclic compound of an embodiment in a capping layer CPL.

For example, the polycyclic compound according to an embodiment may be included in the hole transport region HTR of the light emitting element ED of an embodiment, and the light emitting element of an embodiment may show excellent emission efficiency and long-life characteristics.

The polycyclic compound of an embodiment may include at least one substituent in a carbazole skeleton including a biphenyl group as a linker. In the polycyclic compound of an embodiment, in the biphenyl group used as the linker, an amine compound or a carbazole-based compound is bonded, and a deposition temperature is low to show excellent heat resistance. The carbazole skeleton in the polycyclic compound of an embodiment, at least one among the substituents explained referring to $R_1$ and $R_2$ may be included to improve hole injection. Accordingly, the life of the polycyclic compound of an embodiment, represented by Formula 1 may be improved. The emission efficiency and life of a light emitting element of an embodiment, including the polycyclic compound of an embodiment may be improved.

Hereinafter, the polycyclic compound according to an embodiment and the light emitting element of an embodiment including the polycyclic compound will be explained with reference to the Examples and the Comparative Examples. The Examples below are only provided as illustrations for understanding the disclosure, and the scope thereof is not limited thereto.

EXAMPLES

1. Synthesis of Polycyclic Compounds

A synthesis method of a polycyclic compound according to an embodiment will be explained by illustrating the synthesis methods of Compound A1, Compound A7, Compound A9, Compound A14, Compound A16, Compound B1, Compound C1, Compound D1, Compound G1, Compound G12, Compound H1, Compound J1, Compound J9 and Compound J29. The synthesis methods of the polycyclic compounds explained hereinafter are only examples, and the synthesis method of the polycyclic compound according to an embodiment is not limited to the examples below.

(1) Synthesis of Compound A1

Polycyclic Compound A1 according to an embodiment may be synthesized, for example, by the steps of the Reactions below.

[Reaction 1-1]

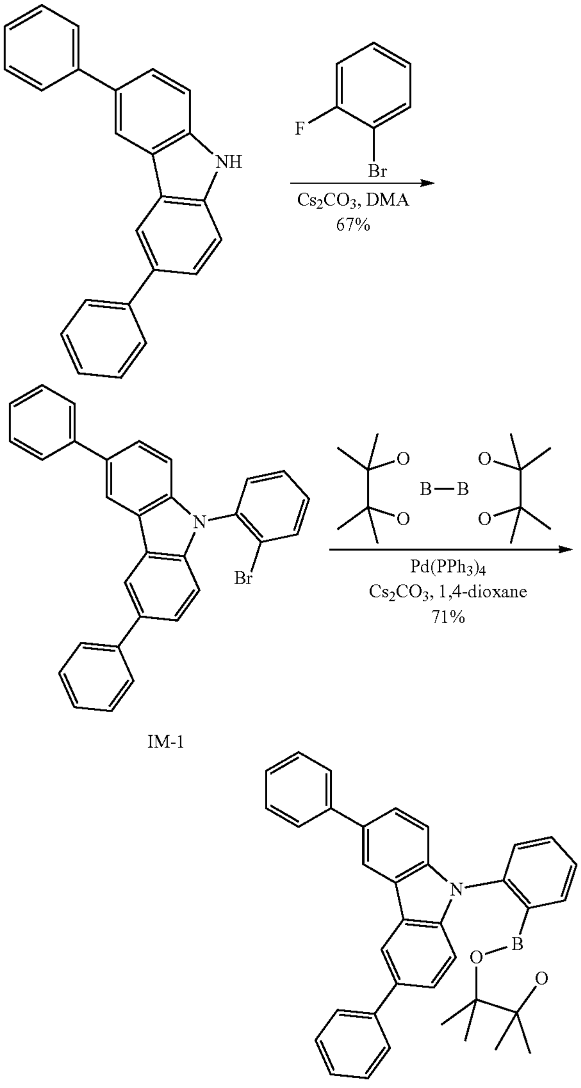

IM-1

IM-2

-continued

[Reaction 1-2]

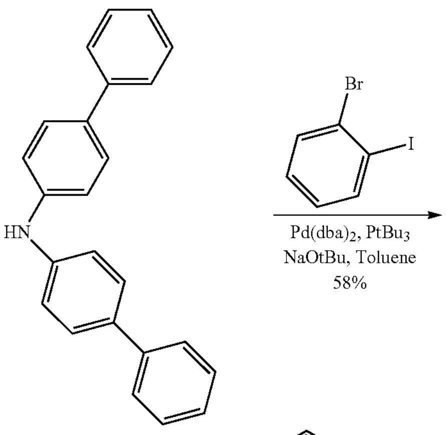

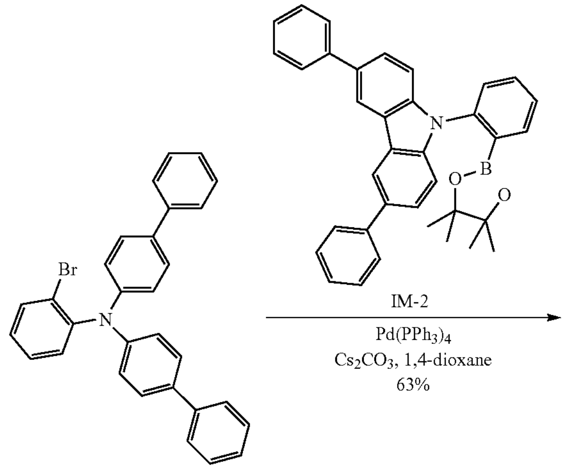

IM-3

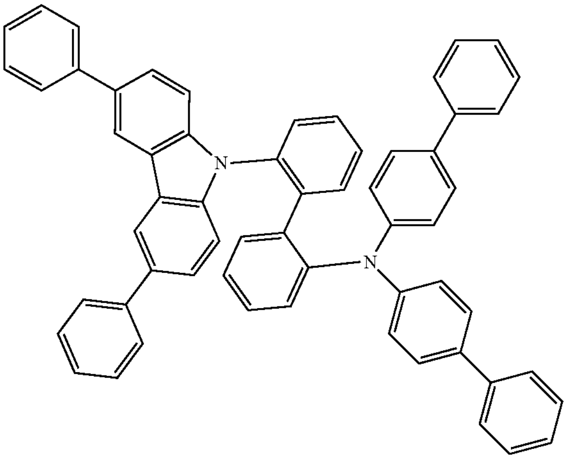

A1

1) Synthesis of Compound IM-1

Under an argon (Ar) atmosphere, to a 300 mL three-neck flask, 3,6-diphenyl-9H-carbazole (40.00 g, 125.2 mmol), $Cs_2CO_3$ (81.61 g, 2.0 equiv, 250.5 mmol), DMA (125 mL) and 1-bromo-2-fluorobenzene (43.83 g, 2.0 equiv, 250.5 mmol) were added in order, followed by heating to about 120° C. and stirring. After cooling to room temperature in the air, water and toluene were added to the reaction mixture, and an organic layer was separately taken. An organic layer extracted was washed with a saline solution and dried with $MgSO_4$. $MgSO_4$ was filtered, and an organic layer was concentrated. The crude product thus obtained was purified to obtain Compound IM-1 (39.82 g, yield 67%).

Through FAB-MS measurement, mass number of m/z=473 was observed as a molecular ion peak, and Compound IM-1 was confirmed.

2) Synthesis of Compound IM-2

Under an argon (Ar) atmosphere, to a 500 mL three-neck flask, Compound IM-1 (39.82 g, 83.94 mmol), $Pd(PPh_3)_4$ (19.40 g, 0.20 equiv, 16.79 mmol), $Cs_2CO_3$ (109.39 g, 4.0 equiv, 335.75 mmol), 1,4-dioxane (210 mL), and bis(pinacolato)diboron (85.26 g, 4.0 equiv, 335.8 mmol) were added in order, followed by heating, refluxing, and stirring. After cooling to room temperature in the air, water and toluene were added to the reaction mixture, and an organic layer was separately taken. An organic layer extracted was washed with a saline solution and dried with $MgSO_4$. $MgSO_4$ was filtered, and an organic layer was concentrated. The crude product thus obtained was purified to obtain Compound IM-2 (31.05 g, yield 71%).

Through FAB-MS measurement, mass number of m/z=521 was observed as a molecular ion peak, and Compound IM-2 was confirmed.

3) Synthesis of Compound IM-3

Under an argon (Ar) atmosphere, to a 2000 mL three-neck flask, di([1,1'-biphenyl]-4-yl)amine (30.00 g, 93.34 mmol), $Pd(dba)_2$ (2.68 g, 0.05 equiv, 4.67 mmol), $NaO^tBu$ (8.97 g, 1.0 equiv, 93.34 mmol), toluene (900 mL), 1-bromo-2-iodobenzene (52.81 g, 2.0 equiv, 186.7 mmol) and $P^tBu_3$ (3.78 g, 0.2 equiv, 18.7 mmol) were added in order, followed by heating, refluxing, and stirring. After cooling to room temperature in the air, water was added to the reaction mixture, and an organic layer was separately taken. Toluene was added to an aqueous layer, and an organic layer was extracted further. Extracted organic layers were collected, washed with a saline solution, and dried with $MgSO_4$. $MgSO_4$ was filtered, and an organic layer was concentrated. The crude product thus obtained was purified to obtain Compound IM-3 (25.81 g, yield 58%).

Through FAB-MS measurement, mass number of m/z=475 was observed as a molecular ion peak, and Compound IM-3 was confirmed.

4) Synthesis of Compound A1

Under an argon (Ar) atmosphere, to a 100 mL three-neck flask, Compound IM-3 (5.00 g, 10.5 mmol), $Pd(PPh_3)_4$ (2.43 g, 0.20 equiv, 2.10 mmol), $Cs_2CO_3$ (10.3 g, 3.0 equiv, 31.5 mmol), 1,4-dioxane (40 mL), and Compound IM-2 (5.47 g, 1.0 equiv, 10.5 mmol) were added in order, followed by heating, refluxing, and stirring. After cooling to room temperature in the air, water and toluene were added to the reaction mixture, and an organic layer was separated. An organic layer extracted was washed with a saline solution and dried with $MgSO_4$. $MgSO_4$ was filtered, and an organic layer was concentrated. The crude product thus obtained was purified to obtain Compound A1 (5.22 g, yield 63%).

Through FAB-MS measurement, mass number of m/z=790 was observed as a molecular ion peak, and Compound A1 was confirmed.

(2) Synthesis of Compound A7

Polycyclic Compound A7 according to an embodiment may be synthesized, for example, by the steps of Reaction 2 below.

[Reaction 2]

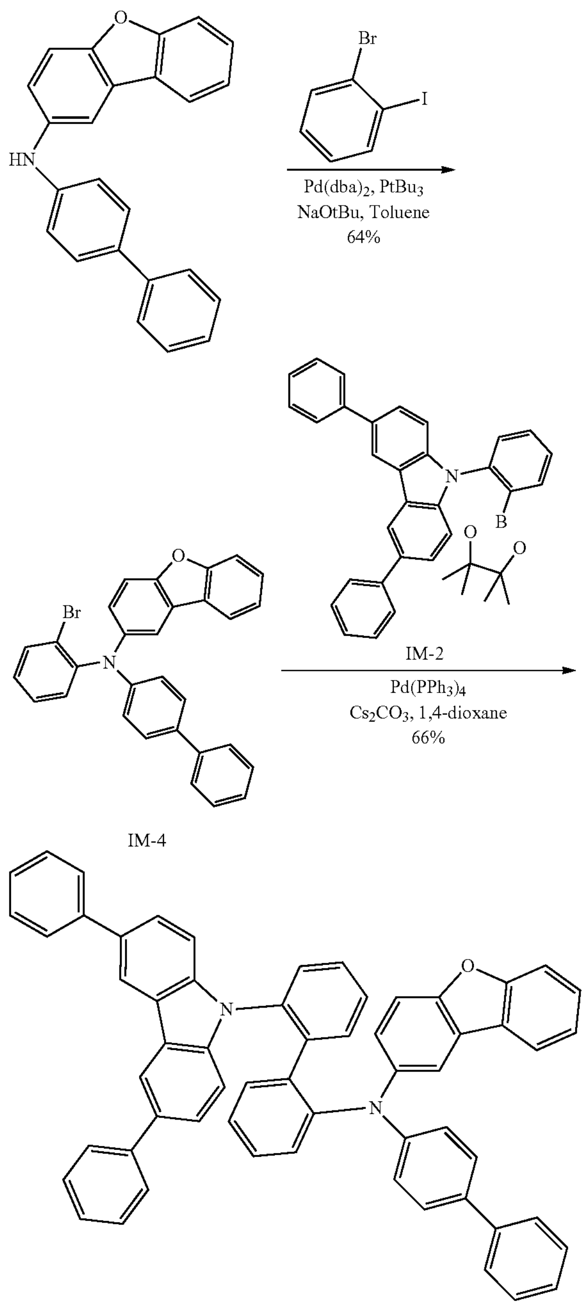

IM-4

A7

1) Synthesis of Compound IM-4

Under an argon (Ar) atmosphere, to a 1000 mL three-neck flask, N-([1,1'-biphenyl]-4-yl)dibenzo[b,d]furan-2-amine (15.00 g, 44.72 mmol), Pd(dba)$_2$ (1.29 g, 0.05 equiv, 2.24 mmol), NaO$^t$Bu (4.30 g, 1.0 equiv, 44.7 mmol), toluene (450 mL), 1-bromo-2-iodobenzene (25.30 g, 2.0 equiv, 89.44 mmol) and P$^t$Bu$_3$ (1.81 g, 0.2 equiv, 8.94 mmol) were added in order, followed by heating, refluxing, and stirring. After cooling to room temperature in the air, water was added to the reaction mixture, and an organic layer was separately taken. Toluene was added to an aqueous layer, and organic layers were extracted further. The extracted organic layers were collected, washed with a saline solution, and dried with $MgSO_4$. $MgSO_4$ was filtered, and an organic layer was concentrated. The crude product thus obtained was purified to obtain Compound IM-4 (13.98 g, yield 64%).

Through FAB-MS measurement, mass number of m/z=489 was observed as a molecular ion peak, and Compound IM-4 was confirmed.

2) Synthesis of Compound A7

Under an argon (Ar) atmosphere, to a 200 mL three-neck flask, Compound IM-2 (6.50 g, 13.3 mmol), Pd(PPh$_3$)$_4$ (3.06 g, 0.20 equiv, 2.65 mmol), $Cs_2CO_3$ (13.0 g, 3.0 equiv, 39.8 mmol), 1,4-dioxane (66 mL), and Compound IM-2 (6.91 g, 1.0 equiv, 13.3 mmol) were added in order, followed by heating, refluxing, and stirring. After cooling to room temperature in the air, water and toluene were added to the reaction mixture, and an organic layer was separately taken. An organic layer extracted was washed with a saline solution and dried with $MgSO_4$. $MgSO_4$ was filtered, and an organic layer was concentrated. The crude product thus obtained was purified to obtain Compound A7 (7.00 g, yield 66%).

Through FAB-MS measurement, mass number of m/z=804 was observed as a molecular ion peak, and Compound A7 was confirmed.

(3) Synthesis of Compound A9

Polycyclic Compound A9 according to an embodiment may be synthesized, for example, by the steps of the Reactions below.

[Reaction 3-1]

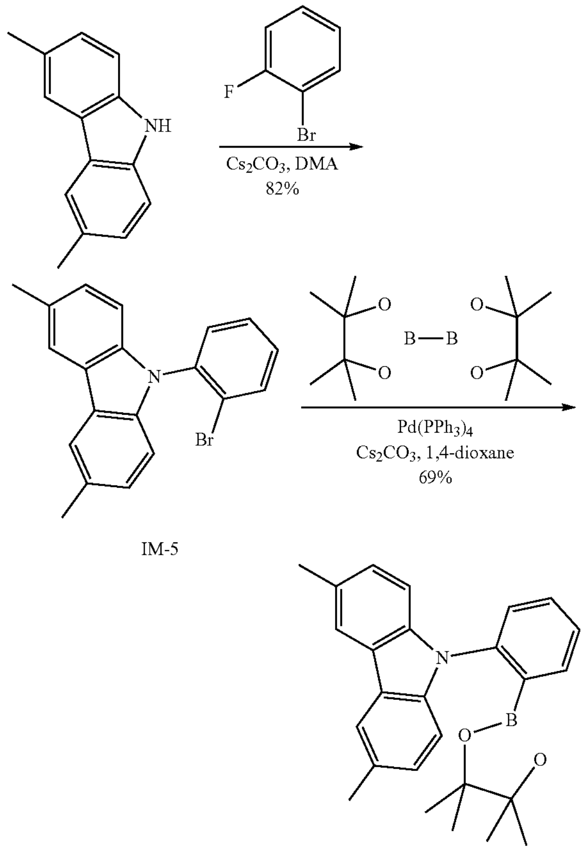

IM-5

IM-6

-continued

[Reaction 3-2]

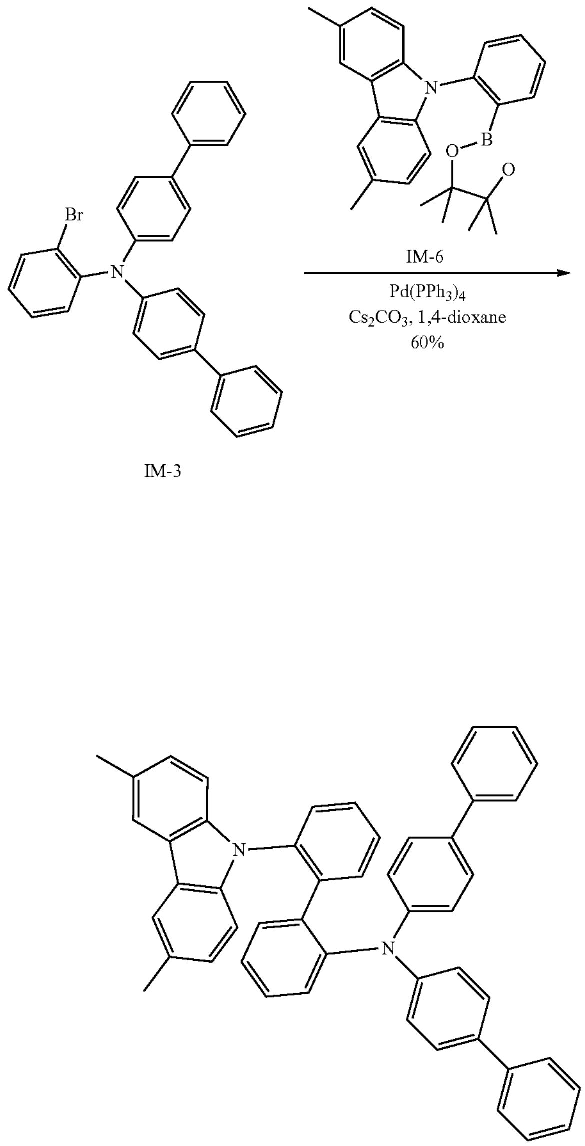

IM-3

IM-6

A9

1) Synthesis of Compound IM-5

Under an argon (Ar) atmosphere, to a 200 mL three-neck flask, 3,6-dimethyl-9H-carbazole (15.00 g, 76.82 mmol), $Cs_2CO_3$ (50.06 g, 2.0 equiv, 153.6 mmol), DMA (80 mL) and 1-bromo-2-fluorobenzene (26.89 g, 2.0 equiv, 153.6 mmol) were added in order, followed by heating to about 120° C. and stirring. After cooling to room temperature in the air, water and toluene were added to the reaction mixture, and an organic layer was separated. An organic layer extracted was washed with a saline solution and dried with $MgSO_4$. $MgSO_4$ was filtered, and an organic layer was concentrated. The crude product thus obtained was purified to obtain Compound IM-5 (22.02 g, yield 82%).

Through FAB-MS measurement, mass number of m/z=349 was observed as a molecular ion peak, and Compound IM-5 was confirmed.

2) Synthesis of Compound IM-6

Under an argon (Ar) atmosphere, to a 500 mL three-neck flask, Compound IM-5 (22.02 g, 62.87 mmol), $Pd(PPh_3)_4$ (14.53 g, 0.20 equiv, 12.57 mmol), $Cs_2CO_3$ (81.93 g, 4.0 equiv, 251.5 mmol), 1,4-dioxane (200 mL), and bis(pinacolato)diboron (63.86 g, 4.0 equiv, 251.5 mmol) were added in order, followed by heating, refluxing, and stirring. After cooling to room temperature in the air, water and toluene were added to the reaction mixture, and an organic layer was separated. An organic layer extracted was washed with a saline solution and dried with $MgSO_4$. $MgSO_4$ was filtered, and an organic layer was concentrated. The crude product thus obtained was purified to obtain Compound IM-6 (17.22 g, yield 69%).

Through FAB-MS measurement, mass number of m/z=397 was observed as a molecular ion peak, and Compound IM-6 was confirmed.

3) Synthesis of Compound A9

Under an argon (Ar) atmosphere, to a 200 mL three-neck flask, Compound IM-3 (5.00 g, 10.5 mmol), $Pd(PPh_3)_4$ (2.43 g, 0.20 equiv, 2.10 mmol), $Cs_2CO_3$ (10.3 g, 3.0 equiv, 31.5 mmol), 1,4-dioxane (50 mL), and Compound IM-6 (4.17 g, 1.0 equiv, 10.5 mmol) were added in order, followed by heating, refluxing, and stirring. After cooling to room temperature in the air, water and toluene were added to the reaction mixture, and an organic layer was separated. An extracted organic layer was washed with a saline solution and dried with $MgSO_4$. $MgSO_4$ was filtered, and an organic layer was concentrated. The crude product thus obtained was purified to obtain Compound A9 (4.22 g, yield 60%).

Through FAB-MS measurement, mass number of m/z=666 was observed as a molecular ion peak, and Compound A9 was confirmed.

(4) Synthesis of Compound A14

Polycyclic Compound A14 according to an embodiment may be synthesized, for example, by the steps of the Reactions below.

[Reaction 4-1]

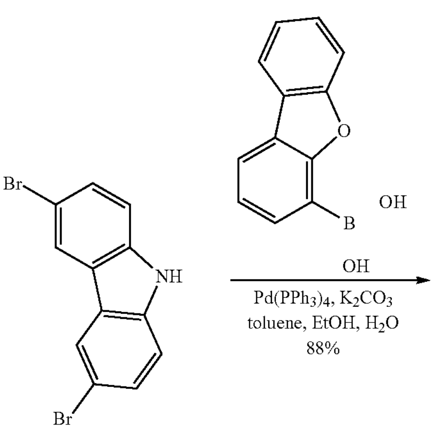

-continued
-continued
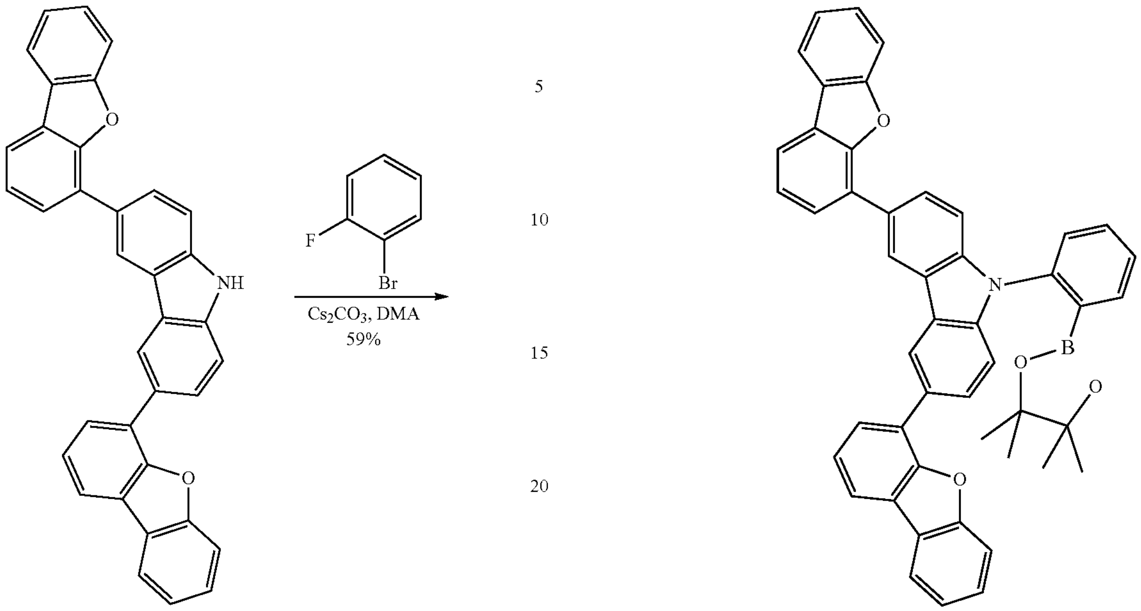
IM-7
IM-9
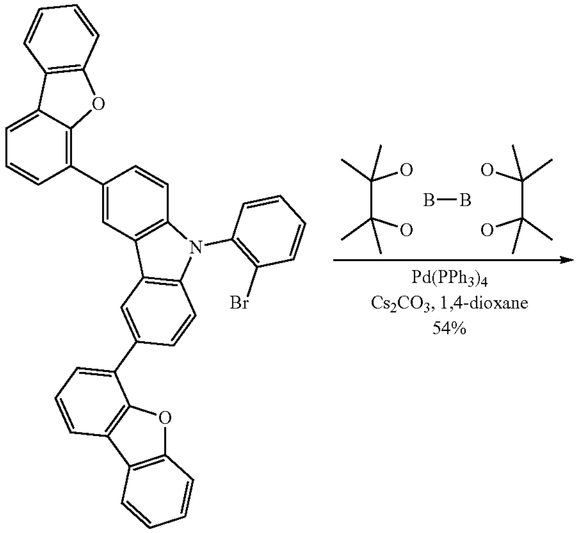
IM-8
[Reaction 4-2]
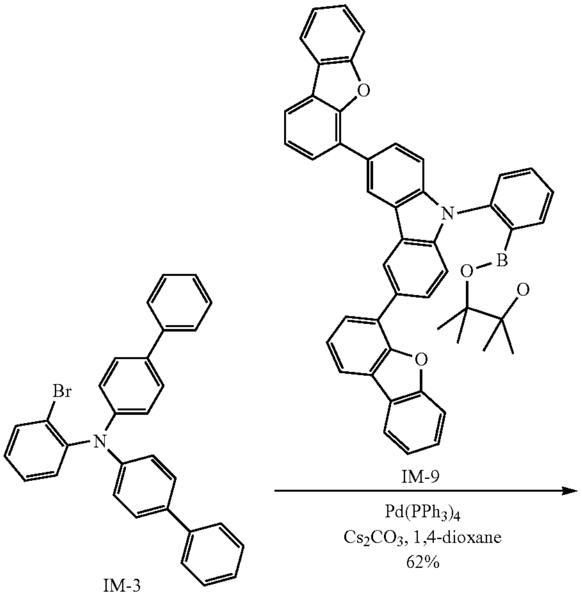
IM-9
IM-3

-continued

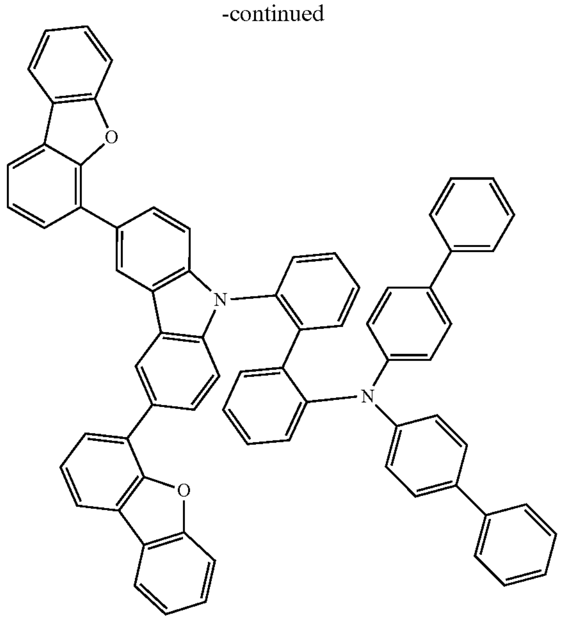

A14

1) Synthesis of Compound IM-7

Under an argon (Ar) atmosphere, to a 1000 mL three-neck flask, 3,6-dibromocarbazole (20.00 g, 61.54 mmol), dibenzo[b,d]furan-4-ylboronic acid (28.70 g, 2.2 equiv, 135.4 mmol), $Pd(PPh_3)_4$ (7.11 g, 0.10 equiv, 6.15 mmol), $K_2CO_3$ (18.71 g, 2.2 equiv, 135.4 mmol), toluene (250 mL), ethanol (EtOH, 120 mL), and $H_2O$ (60 mL) were added in order, followed by heating, refluxing, and stirring. After cooling to room temperature in the air, water and toluene were added to the reaction mixture, and an organic layer was separately taken. An organic layer extracted was washed with a saline solution and dried with $MgSO_4$. $MgSO_4$ was filtered, and an organic layer was concentrated. The crude product thus obtained was purified to obtain Compound IM-7 (27.03 g, yield 88%).

Through FAB-MS measurement, mass number of m/z=499 was observed as a molecular ion peak, and Compound IM-7 was confirmed.

2) Synthesis of Compound IM-8

Under an argon (Ar) atmosphere, to a 200 mL three-neck flask, Compound IM-7 (27.03 g, 54.11 mmol), $Cs_2CO_3$ (35.26 g, 2.0 equiv, 108.2 mmol), DMA (60 mL) and 1-bromo-2-fluorobenzene (18.94 g, 2.0 equiv, 108.2 mmol) were added in order, followed by heating to about 120° C. and stirring. After cooling to room temperature in the air, water and toluene were added to the reaction mixture, and an organic layer was separated. An organic layer extracted was washed with a saline solution and dried with $MgSO_4$. $MgSO_4$ was filtered, and an organic layer was concentrated. The crude product thus obtained was purified to obtain Compound IM-8 (20.89 g, yield 59%).

Through FAB-MS measurement, mass number of m/z=653 was observed as a molecular ion peak, and Compound IM-8 was confirmed.

3) Synthesis of Compound IM-9

Under an argon (Ar) atmosphere, to a 500 mL three-neck flask, Compound IM-8 (20.89 g, 31.91 mmol), $Pd(PPh_3)_4$ (7.38 g, 0.20 equiv, 6.38 mmol), $Cs_2CO_3$ (41.59 g, 4.0 equiv, 127.7 mmol), 1,4-dioxane (250 mL), and bis(pinacolato)diboron (32.42 g, 4.0 equiv, 127.7 mmol) were added in order, followed by heating, refluxing, and stirring. After cooling to room temperature in the air, water and toluene were added to the reaction mixture, and an organic layer was separated. An extracted organic layer was washed with a saline solution and dried with $MgSO_4$. $MgSO_4$ was filtered, and an organic layer was concentrated. The crude product thus obtained was purified to obtain Compound IM-9 (12.12 g, yield 54%).

Through FAB-MS measurement, mass number of m/z=701 was observed as a molecular ion peak, and Compound IM-9 was confirmed.

4) Synthesis of Compound A14

Under an argon (Ar) atmosphere, to a 200 mL three-neck flask, Compound IM-3 (5.48 g, 11.5 mmol), $Pd(PPh_3)_4$ (2.66 g, 0.20 equiv, 2.30 mmol), $Cs_2CO_3$ (11.2 g, 3.0 equiv, 34.5 mmol), 1,4-dioxane (60 mL), and IM-9 (8.07 g, 1.0 equiv, 11.5 mmol) were added in order, followed by heating, refluxing, and stirring. After cooling to room temperature in the air, water and toluene were added to the reaction mixture, and an organic layer was separately taken. An extracted organic layer was washed with a saline solution and dried with $MgSO_4$. $MgSO_4$ was filtered, and an organic layer was concentrated. The crude product thus obtained was purified to obtain Compound A14 (6.90 g, yield 62%).

Through FAB-MS measurement, mass number of m/z=970 was observed as a molecular ion peak, and Compound A14 was confirmed.

(5) Synthesis of Compound A16

Polycyclic Compound A16 according to an embodiment may be synthesized, for example, by the steps of the Reactions below.

[Reaction 5-1]

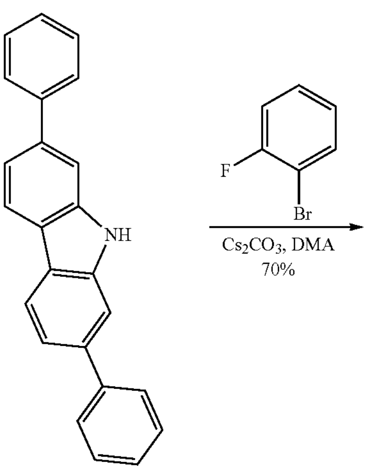

-continued

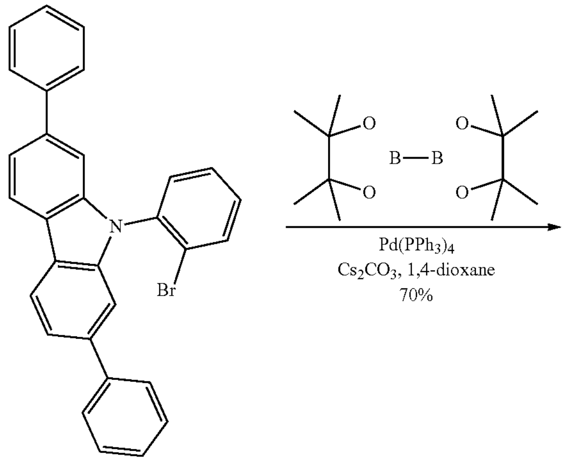

IM-10

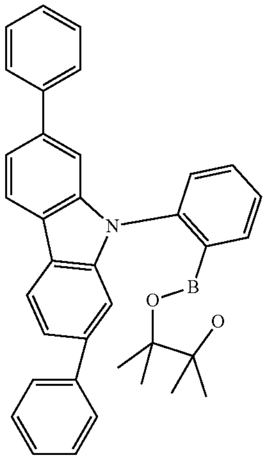

IM-11

[Reaction 5-2]

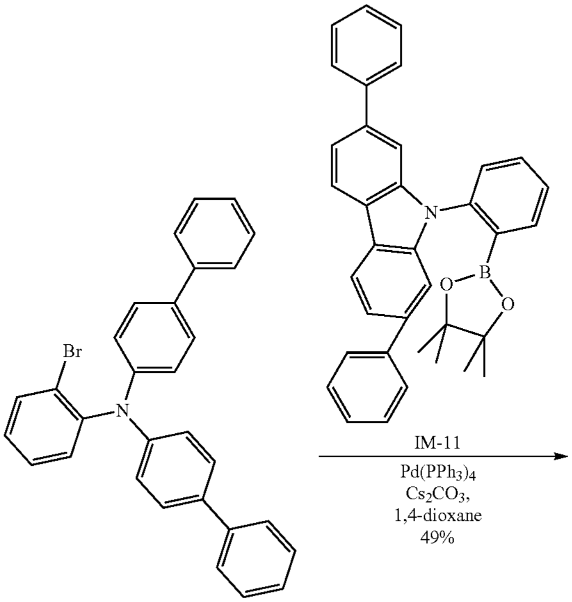

IM-3

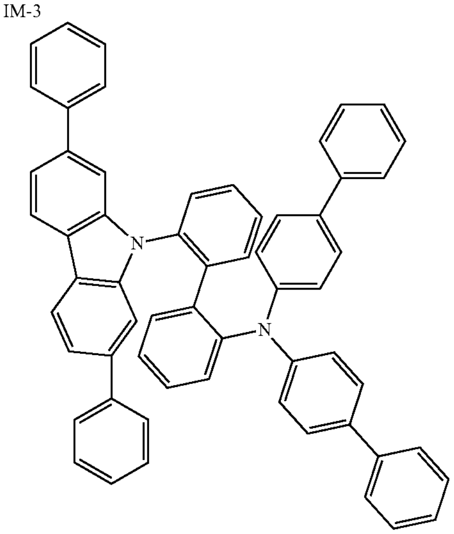

A16

1) Synthesis of Compound IM-10

Under an argon (Ar) atmosphere, to a 200 mL three-neck flask, 2,7-diphenyl-9H-carbazole (20.00 g, 62.62 mmol), $Cs_2CO_3$ (40.80 g, 2.0 equiv, 125.2 mmol), DMA (65 mL) and 1-bromo-2-fluorobenzene (21.92 g, 2.0 equiv, 125.2 mmol) were added in order, followed by heating to about 120° C. and stirring. After cooling to room temperature in the air, water and toluene were added to the reaction mixture, and an organic layer was separately taken. An organic layer extracted was washed with a saline solution and dried with $MgSO_4$. $MgSO_4$ was filtered, and an organic layer was concentrated. The crude product thus obtained was purified to obtain Compound IM-10 (20.70 g, yield 70%).

Through FAB-MS measurement, mass number of m/z=473 was observed as a molecular ion peak, and Compound IM-10 was confirmed.

2) Synthesis of Compound IM-11

Under an argon (Ar) atmosphere, to a 500 mL three-neck flask, Compound IM-10 (20.70 g, 43.63 mmol), $Pd(PPh_3)_4$ (10.08 g, 0.20 equiv, 8.73 mmol), $Cs_2CO_3$ (56.87 g, 4.0 equiv, 174.5 mmol), 1,4-dioxane (210 mL), and bis(pinacolato)diboron (44.32 g, 4.0 equiv, 174.5 mmol) were added in order, followed by heating, refluxing, and stirring. After cooling to room temperature in the air, water and toluene were added to the reaction mixture, and an organic layer was separately taken. An organic layer extracted was washed with a saline solution and dried with $MgSO_4$. $MgSO_4$ was filtered, and an organic layer was concentrated. The crude product thus obtained was purified to obtain Compound IM-11 (16.01 g, yield 70%).

Through FAB-MS measurement, mass number of m/z=521 was observed as a molecular ion peak, and Compound IM-11 was confirmed.

3) Synthesis of Compound A16

Under an argon (Ar) atmosphere, to a 200 mL three-neck flask, Compound IM-3 (7.31 g, 15.3 mmol), $Pd(PPh_3)_4$ (3.55 g, 0.20 equiv, 3.07 mmol), $Cs_2CO_3$ (15.0 g, 3.0 equiv, 46.0 mmol), 1,4-dioxane (80 mL), and Compound IM-11 (8.00 g, 1.0 equiv, 15.3 mmol) were added in order, followed by heating, refluxing, and stirring. After cooling to room temperature in the air, water and toluene were added to the reaction mixture, and an organic layer was separately taken. An extracted organic layer was washed with a saline solution and dried with $MgSO_4$. $MgSO_4$ was filtered, and an organic layer was concentrated. The crude product thus obtained was purified to obtain Compound A16 (5.96 g, yield 49%).

Through FAB-MS measurement, mass number of m/z=790 was observed as a molecular ion peak, and Compound A16 was confirmed.

(6) Synthesis of Compound B1

Polycyclic Compound B1 according to an embodiment may be synthesized, for example, by the steps of Reaction 6 below.

[Reaction 6]

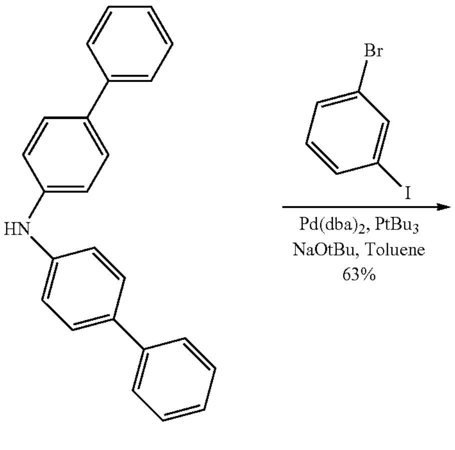

-continued

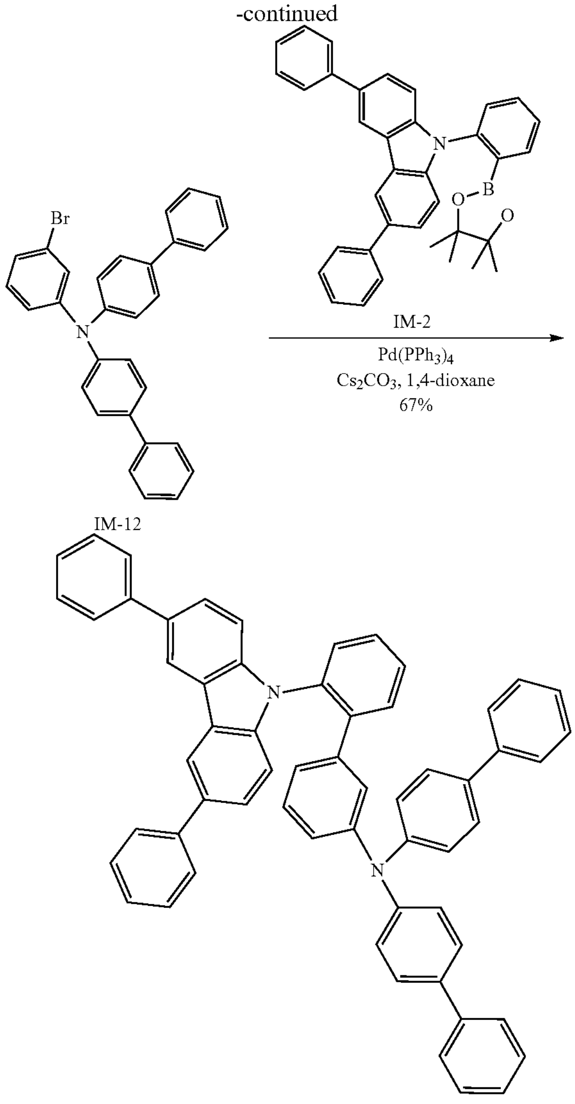

IM-12

IM-2

B1

1) Synthesis of Compound IM-12

Under an argon (Ar) atmosphere, to a 2000 mL three-neck flask, di([1,1'-biphenyl]-4-yl)amine (20.00 g, 62.22 mmol), $Pd(dba)_2$ (1.79 g, 0.05 equiv, 3.11 mmol), $NaO^tBu$ (5.98 g, 1.0 equiv, 62.22 mmol), toluene (600 mL), 1-bromo-3-iodobenzene (35.21 g, 2.0 equiv, 124.5 mmol) and $P^tBu_3$ (2.52 g, 0.2 equiv, 12.4 mmol) were added in order, followed by heating, refluxing, and stirring. After cooling to room temperature in the air, water was added to the reaction mixture, and an organic layer was separately taken. Toluene was added to an aqueous layer, and organic layers were extracted further. The extracted organic layers were collected, washed with a saline solution, and dried with $MgSO_4$. $MgSO_4$ was filtered, and an organic layer was concentrated. The crude product thus obtained was purified to obtain Compound IM-12 (18.72 g, yield 63%).

Through FAB-MS measurement, mass number of m/z=475 was observed as a molecular ion peak, and Compound IM-12 was confirmed.

2) Synthesis of Compound B1

Under an argon (Ar) atmosphere, to a 100 mL three-neck flask, Compound IM-12 (5.00 g, 10.5 mmol), $Pd(PPh_3)_4$ (2.43 g, 0.20 equiv, 2.10 mmol), $Cs_2CO_3$ (10.3 g, 3.0 equiv, 31.5 mmol), 1,4-dioxane (40 mL), and Compound IM-2 (5.47 g, 1.0 equiv, 10.5 mmol) were added in order, followed by heating, refluxing, and stirring. After cooling to room temperature in the air, water and toluene were added to the reaction mixture, and an organic layer was separated. An extracted organic layer was washed with a saline solution and dried with $MgSO_4$. $MgSO_4$ was filtered, and an organic layer was concentrated. The crude product thus obtained was purified to obtain Compound B1 (5.61 g, yield 67%).

Through FAB-MS measurement, mass number of m/z=790 was observed as a molecular ion peak, and Compound B1 was confirmed.

(7) Synthesis of Compound C1

Polycyclic Compound C1 according to an embodiment may be synthesized, for example, by the steps of Reaction 7 below.

[Reaction 7]

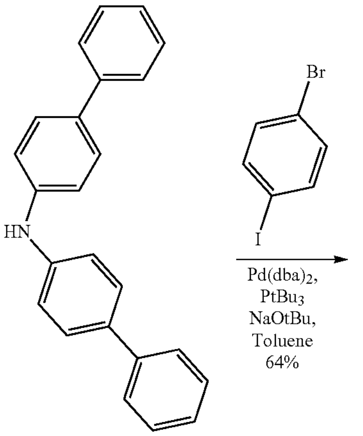

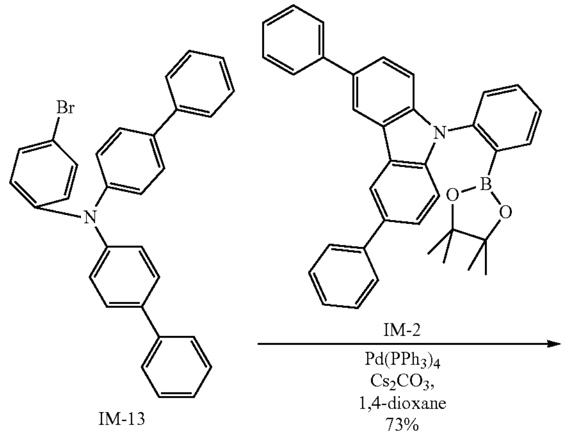

IM-13

-continued

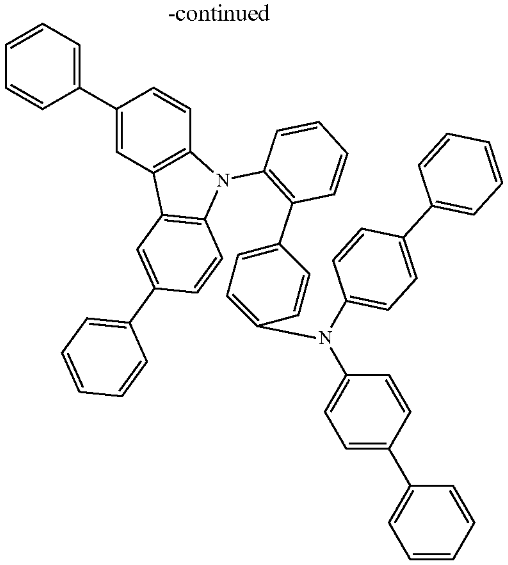

C1

1) Synthesis of Compound IM-13

Under an argon (Ar) atmosphere, to a 2000 mL three-neck flask, di([1,1'-biphenyl]-4-yl)amine (20.00 g, 62.22 mmol), $Pd(dba)_2$ (1.79 g, 0.05 equiv, 3.11 mmol), $NaO^tBu$ (5.98 g, 1.0 equiv, 62.22 mmol), toluene (600 mL), 1-bromo-3-iodobenzene (35.21 g, 2.0 equiv, 124.5 mmol) and $P^tBu_3$ (2.52 g, 0.2 equiv, 12.4 mmol) were added in order, followed by heating, refluxing, and stirring. After cooling to room temperature in the air, water was added to the reaction mixture, and an organic layer was separately taken. Toluene was added to an aqueous layer, and organic layers were extracted further. The extracted organic layers were collected, washed with a saline solution, and dried with $MgSO_4$. $MgSO_4$ was filtered, and an organic layer was concentrated. The crude product thus obtained was purified to obtain Compound IM-13 (18.90 g, yield 64%).

Through FAB-MS measurement, mass number of m/z=475 was observed as a molecular ion peak, and Compound IM-13 was confirmed.

2) Synthesis of Compound C1

Under an argon (Ar) atmosphere, to a 100 mL three-neck flask, Compound IM-13 (5.00 g, 10.5 mmol), $Pd(PPh_3)_4$ (2.43 g, 0.20 equiv, 2.10 mmol), $Cs_2CO_3$ (10.3 g, 3.0 equiv, 31.5 mmol), 1,4-dioxane (40 mL), and Compound IM-2 (5.47 g, 1.0 equiv, 10.5 mmol) were added in order, followed by heating, refluxing, and stirring. After cooling to room temperature in the air, water and toluene were added to the reaction mixture, and an organic layer was separately taken. An extracted organic layer was washed with a saline solution and dried with $MgSO_4$. $MgSO_4$ was filtered, and an organic layer was concentrated. The crude product thus obtained was purified to obtain Compound C1 (6.11 g, yield 73%).

Through FAB-MS measurement, mass number of m/z=790 was observed as a molecular ion peak, and Compound C1 was confirmed.

(8) Synthesis of Compound D1

Polycyclic Compound D1 according to an embodiment may be synthesized, for example, by the steps of the Reactions below.

[Reaction 8-1]

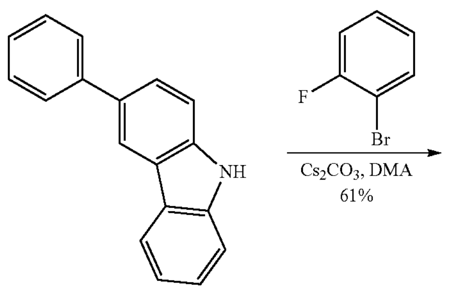

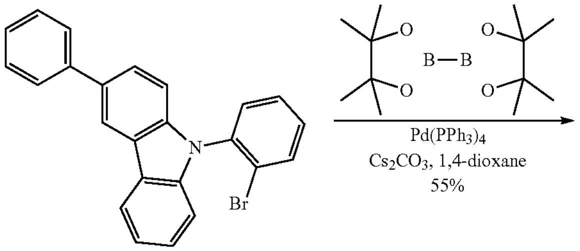

IM-14

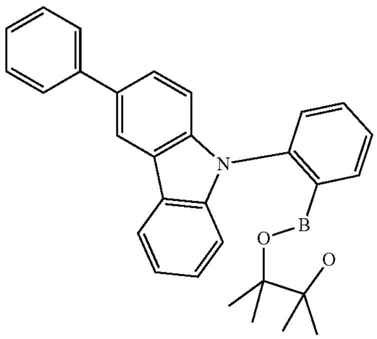

IM-15

[Reaction 8-2]

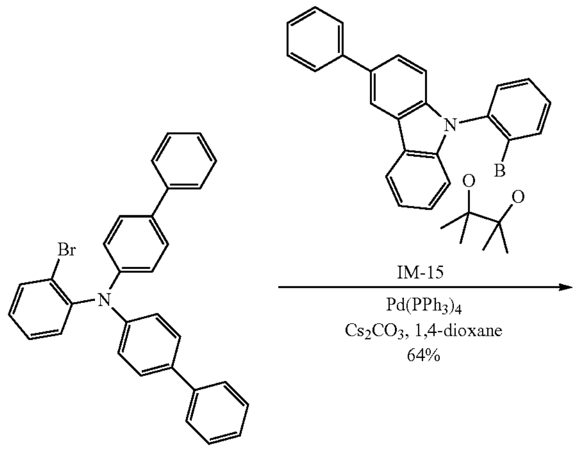

IM-3

-continued

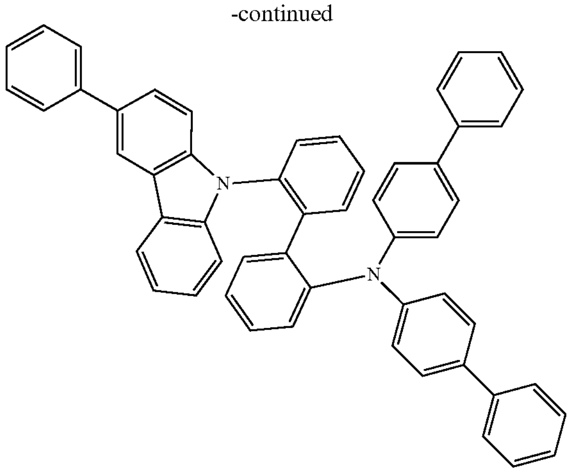

D1

1) Synthesis of Compound IM-14

Under an argon (Ar) atmosphere, to a 300 mL three-neck flask, 3-phenyl-9H-carbazole (18.00 g, 73.98 mmol), $Cs_2CO_3$ (48.21 g, 2.0 equiv, 148.0 mmol), DMA (75 mL) and 1-bromo-2-fluorobenzene (25.89 g, 2.0 equiv, 148.0 mmol) were added in order, followed by heating to about 120° C. and stirring. After cooling to room temperature in the air, water and toluene were added to the reaction mixture, and an organic layer was separately taken. An organic layer extracted was washed with a saline solution and dried with $MgSO_4$. $MgSO_4$ was filtered, and an organic layer was concentrated. The crude product thus obtained was purified to obtain Compound IM-14 (18.11 g, yield 61%).

Through FAB-MS measurement, mass number of m/z=397 was observed as a molecular ion peak, and Compound IM-14 was confirmed.

2) Synthesis of Compound IM-15

Under an argon (Ar) atmosphere, to a 500 mL three-neck flask, IM-14 (18.11 g, 45.47 mmol), $Pd(PPh_3)_4$ (10.5 g, 0.20 equiv, 9.09 mmol), $Cs_2CO_3$ (59.26 g, 4.0 equiv, 181.9 mmol), 1,4-dioxane (220 mL), and bis(pinacolato)diboron (46.18 g, 4.0 equiv, 181.9 mmol) were added in order, followed by heating, refluxing, and stirring. After cooling to room temperature in the air, water and toluene were added to the reaction mixture, and an organic layer was separated. The extracted organic layer was washed with a saline solution and dried with $MgSO_4$. $MgSO_4$ was filtered, and an organic layer was concentrated. The crude product thus obtained was purified to obtain Compound IM-15 (11.09 g, yield 55%).

Through FAB-MS measurement, mass number of m/z=445 was observed as a molecular ion peak, and Compound IM-15 was confirmed.

3) Synthesis of Compound D1

Under an argon (Ar) atmosphere, to a 200 mL three-neck flask, Compound IM-3 (5.00 g, 10.5 mmol), $Pd(PPh_3)_4$ (2.43 g, 0.20 equiv, 2.10 mmol), $Cs_2CO_3$ (10.3 g, 3.0 equiv, 31.5 mmol), 1,4-dioxane (50 mL), and Compound IM-15 (4.67 g, 1.0 equiv, 10.5 mmol) were added in order, followed by heating, refluxing, and stirring. After cooling to room temperature in the air, water and toluene were added to the reaction mixture, and an organic layer was separately taken. An extracted organic layer was washed with a saline solution and dried with $MgSO_4$. $MgSO_4$ was filtered, and an organic layer was concentrated. The crude product thus obtained was purified to obtain Compound D1 (4.82 g, yield 64%).

Through FAB-MS measurement, mass number of m/z=714 was observed as a molecular ion peak, and Compound D1 was confirmed.

(9) Synthesis of Compound G1

Polycyclic Compound G1 according to an embodiment may be synthesized, for example, by the step of Reaction 9 below.

[Reaction 9]

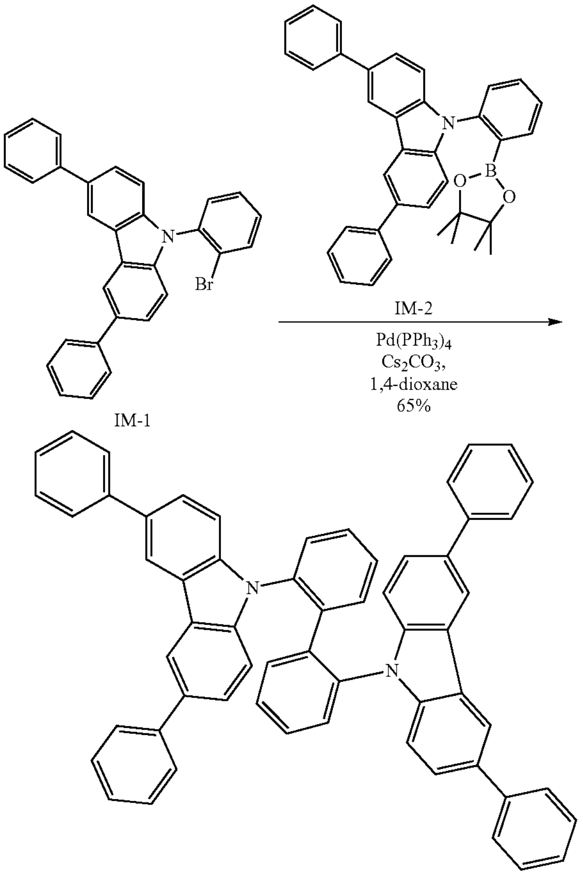

G1

1) Synthesis of Compound G1

Under an argon (Ar) atmosphere, to a 200 mL three-neck flask, Compound IM-1 (4.20 g, 8.85 mmol), $Pd(PPh_3)_4$ (2.05 g, 0.20 equiv, 1.77 mmol), $Cs_2CO_3$ (8.65 g, 3.0 equiv, 26.6 mmol), 1,4-dioxane (40 mL), and Compound IM-2 (4.62 g, 1.0 equiv, 8.85 mmol) were added in order, followed by heating, refluxing, and stirring. After cooling to room temperature in the air, water and toluene were added to the reaction mixture, and an organic layer was separately taken. An extracted organic layer was washed with a saline solution and dried with $MgSO_4$. $MgSO_4$ was filtered, and an organic layer was concentrated. The crude product thus obtained was purified to obtain Compound G1 (4.55 g, yield 65%).

Through FAB-MS measurement, mass number of m/z=788 was observed as a molecular ion peak, and Compound G1 was confirmed.

(10) Synthesis of Compound H1

Polycyclic Compound H1 according to an embodiment may be synthesized, for example, by the steps of Reaction 10 below.

[Reaction 10]

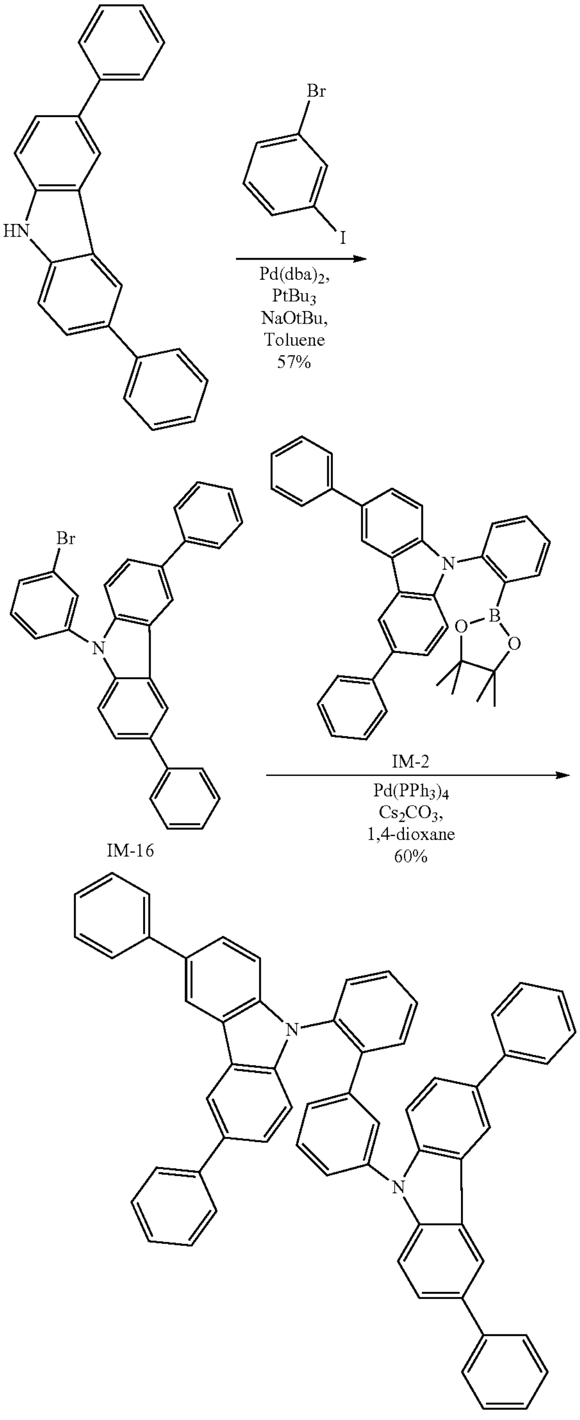

H1

1) Synthesis of Compound IM-16

Under an argon (Ar) atmosphere, to a 2000 mL three-neck flask, 3,6-diphenyl-9H-carbazole (15.00 g, 46.96 mmol), $Pd(dba)_2$ (1.35 g, 0.05 equiv, 2.35 mmol), $NaO^tBu$ (4.51 g, 1.0 equiv, 47.0 mmol), toluene (500 mL), 1-bromo-3-iodobenzene (26.57 g, 2.0 equiv, 93.92 mmol) and $P^tBu_3$ (1.90 g, 0.2 equiv, 9.39 mmol) were added in order, followed by heating, refluxing, and stirring. After cooling to room temperature in the air, water was added to the reaction mixture, and an organic layer was separately taken. Toluene was added to an aqueous layer, and organic layers were extracted further. The extracted organic layers were collected, washed with a saline solution, and dried with $MgSO_4$. $MgSO_4$ was filtered, and an organic layer was concentrated. The crude product thus obtained was purified to obtain Compound IM-16 (12.82 g, yield 57%).

Through FAB-MS measurement, mass number of m/z=473 was observed as a molecular ion peak, and Compound IM-16 was confirmed.

2) Synthesis of Compound H1

Under an argon (Ar) atmosphere, to a 200 mL three-neck flask, Compound IM-16 (5.50 g, 11.6 mmol), $Pd(PPh_3)_4$ (2.68 g, 0.20 equiv, 2.32 mmol), $Cs_2CO_3$ (11.33 g, 3.0 equiv, 34.78 mmol), 1,4-dioxane (60 mL), and Compound IM-2 (6.05 g, 1.0 equiv, 11.6 mmol) were added in order, followed by heating, refluxing, and stirring. After cooling to room temperature in the air, water and toluene were added to the reaction mixture, and an organic layer was separately taken. An extracted organic layer was washed with a saline solution and dried with $MgSO_4$. $MgSO_4$ was filtered, and an organic layer was concentrated. The crude product thus obtained was purified to obtain Compound H1 (5.51 g, yield 60%).

Through FAB-MS measurement, mass number of m/z=788 was observed as a molecular ion peak, and Compound H1 was confirmed.

(11) Synthesis of Compound J1

Polycyclic Compound J1 according to an embodiment may be synthesized, for example, by the step of Reaction 11 below.

[Reaction 11]

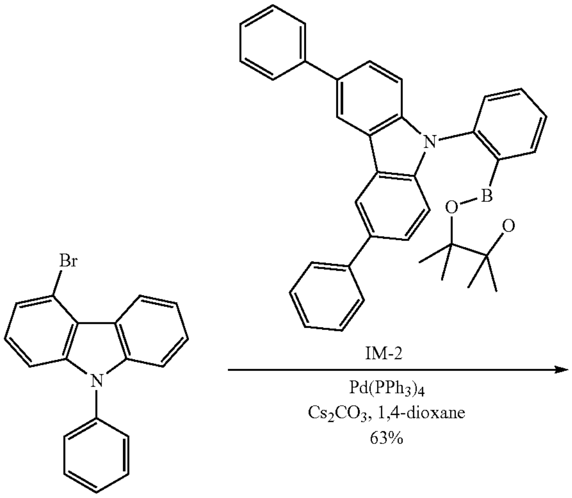

-continued

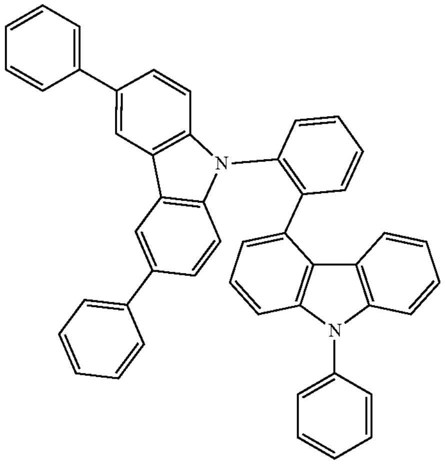

J1

1) Synthesis of Compound J1

Under an argon (Ar) atmosphere, to a 200 mL three-neck flask, 4-bromo-9-phenyl-9H-carbazole (4.30 g, 13.35 mmol), $Pd(PPh_3)_4$ (3.08 g, 0.20 equiv, 2.67 mmol), $Cs_2CO_3$ (13.04 g, 3.0 equiv, 40.04 mmol), 1,4-dioxane (70 mL), and Compound IM-2 (6.96 g, 1.0 equiv, 13.35 mmol) were added in order, followed by heating, refluxing, and stirring. After cooling to room temperature in the air, water and toluene were added to the reaction mixture, and an organic layer was separated. An extracted organic layer was washed with a saline solution and dried with $MgSO_4$. $MgSO_4$ was filtered, and an organic layer was concentrated. The crude product thus obtained was purified to obtain Compound J1 (5.38 g, yield 63%).

Through FAB-MS measurement, mass number of m/z=636 was observed as a molecular ion peak, and Compound J1 was confirmed.

(12) Synthesis of Compound J9

Polycyclic Compound J9 according to an embodiment may be synthesized, for example, by the step of Reaction 12 below.

[Reaction 12]

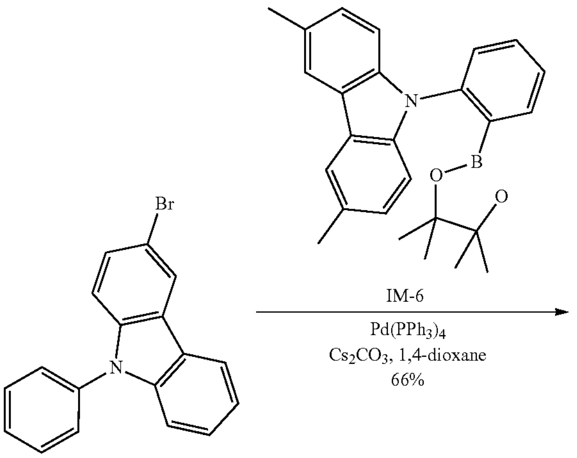

-continued

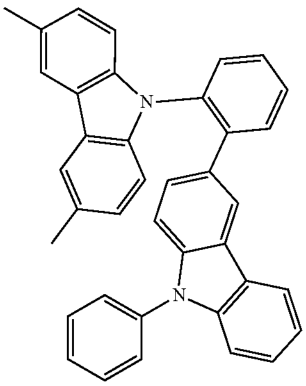

J9

1) Synthesis of Compound J9

Under an argon (Ar) atmosphere, to a 200 mL three-neck flask, 3-bromo-9-phenyl-9H-carbazole (5.00 g, 15.5 mmol), $Pd(PPh_3)_4$ (3.59 g, 0.20 equiv, 3.10 mmol), $Cs_2CO_3$ (15.2 g, 3.0 equiv, 46.6 mmol), 1,4-dioxane (75 mL), and Compound IM-6 (6.17 g, 1.0 equiv, 15.5 mmol) were added in order, followed by heating, refluxing, and stirring. After cooling to room temperature in the air, water and toluene were added to the reaction mixture, and an organic layer was separately taken. An extracted organic layer was washed with a saline solution and dried with $MgSO_4$. $MgSO_4$ was filtered, and an organic layer was concentrated. The crude product thus obtained was purified to obtain Compound J9 (5.22 g, yield 66%).

Through FAB-MS measurement, mass number of m/z=512 was observed as a molecular ion peak, and Compound J9 was confirmed.

(13) Synthesis of Compound J29

Polycyclic Compound J29 according to an embodiment may be synthesized, for example, by the steps of the Reactions below.

[Reaction 13-1]

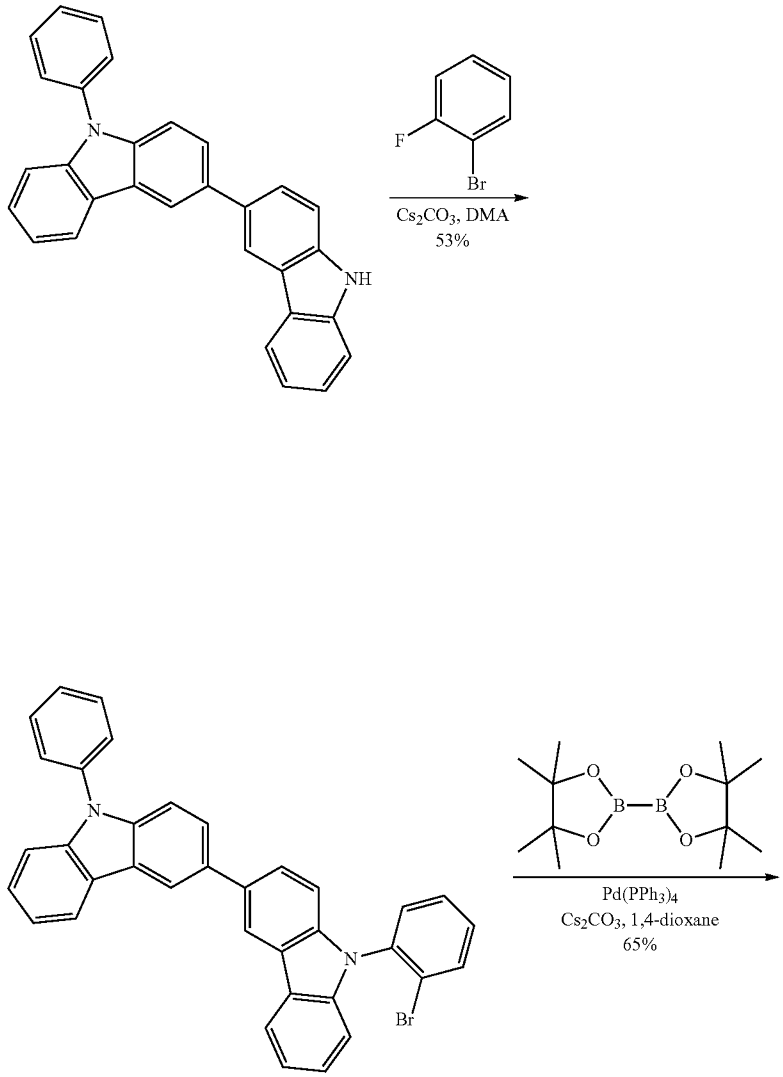

IM-17

-continued
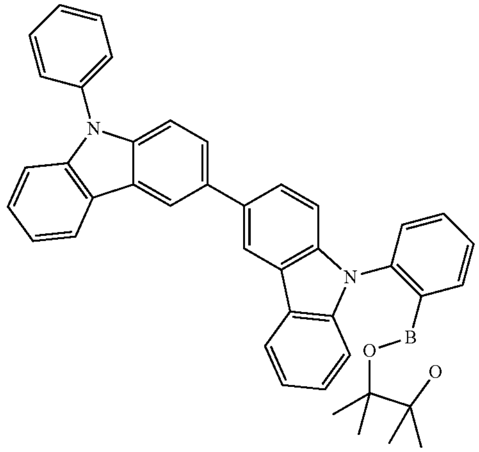
IM-18
[Reaction 13-2]
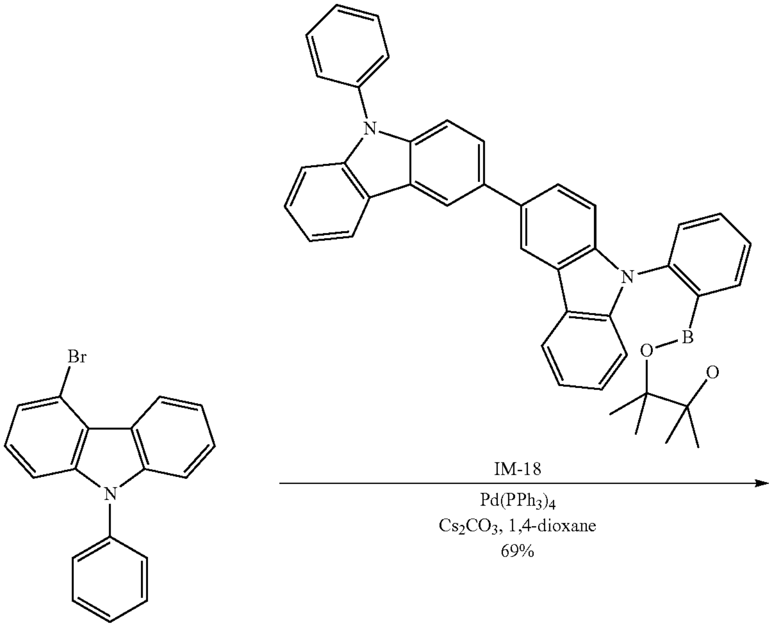

-continued

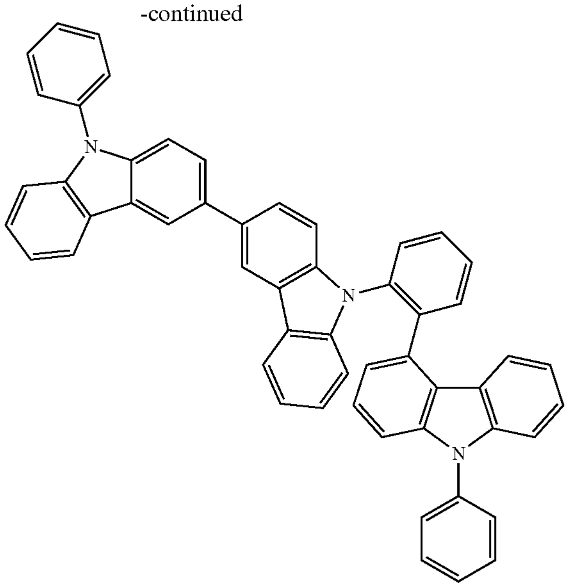

J29

1) Synthesis of Compound IM-17

Under an argon (Ar) atmosphere, to a 100 mL three-neck flask, 9-phenyl-9H,9'H-3,3'-bicarbazole (7.50 g, 18.36 mmol), $Cs_2CO_3$ (11.96 g, 2.0 equiv, 36.72 mmol), DMA (35 mL) and 1-bromo-2-fluorobenzene (6.43 g, 2.0 equiv, 36.7 mmol) were added in order, followed by heating to about 120° C. and stirring. After cooling to room temperature in the air, water and toluene were added to the reaction mixture, and an organic layer was separately taken. An organic layer extracted was washed with a saline solution and dried with $MgSO_4$. $MgSO_4$ was filtered, and an organic layer was concentrated. The crude product thus obtained was purified to obtain Compound IM-17 (5.51 g, yield 53%).

Through FAB-MS measurement, mass number of m/z=562 was observed as a molecular ion peak, and Compound IM-17 was confirmed.

2) Synthesis of Compound IM-18

Under an argon (Ar) atmosphere, to a 200 mL three-neck flask, Compound IM-17 (5.51 g, 9.78 mmol), $Pd(PPh_3)_4$ (2.26 g, 0.20 equiv, 1.96 mmol), $Cs_2CO_3$ (12.74 g, 4.0 equiv, 39.11 mmol), 1,4-dioxane (50 mL), and bis(pinacolato) diboron (9.93 g, 4.0 equiv, 39.11 mmol) were added in order, followed by heating, refluxing, and stirring. After cooling to room temperature in the air, water and toluene were added to the reaction mixture, and an organic layer was separately taken. The extracted organic layer was washed with a saline solution and dried with $MgSO_4$. $MgSO_4$ was filtered, and an organic layer was concentrated. The crude product thus obtained was purified to obtain Compound IM-18 (3.90 g, yield 65%).

Through FAB-MS measurement, mass number of m/z=610 was observed as a molecular ion peak, and Compound IM-18 was confirmed.

3) Synthesis of Compound J29

Under an argon (Ar) atmosphere, to a 100 mL three-neck flask, 4-bromo-9-phenyl-9H-carbazole (2.06 g, 6.39 mmol), $Pd(PPh_3)_4$ (1.48 g, 0.20 equiv, 1.28 mmol), $Cs_2CO_3$ (6.25 g, 3.0 equiv, 19.2 mmol), 1,4-dioxane (33 mL), and Compound IM-18 (3.90 g, 1.0 equiv, 6.39 mmol) were added in order, followed by heating, refluxing, and stirring. After cooling to room temperature in the air, water and toluene were added to the reaction mixture, and an organic layer was separately taken. An extracted organic layer was washed with a saline solution and dried with $MgSO_4$. $MgSO_4$ was filtered, and an organic layer was concentrated. The crude product thus obtained was purified to obtain Compound J29 (3.19 g, yield 69%).

Through FAB-MS measurement, mass number of m/z=725 was observed as a molecular ion peak, and Compound J29 was confirmed.

(14) Synthesis of Compound G12

Polycyclic Compound G12 according to an embodiment may be synthesized, for example, by the steps of the Reactions below.

[Reaction 14-1]

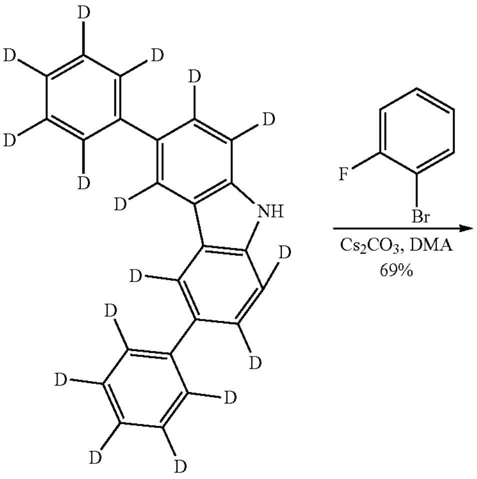

IM-20

-continued

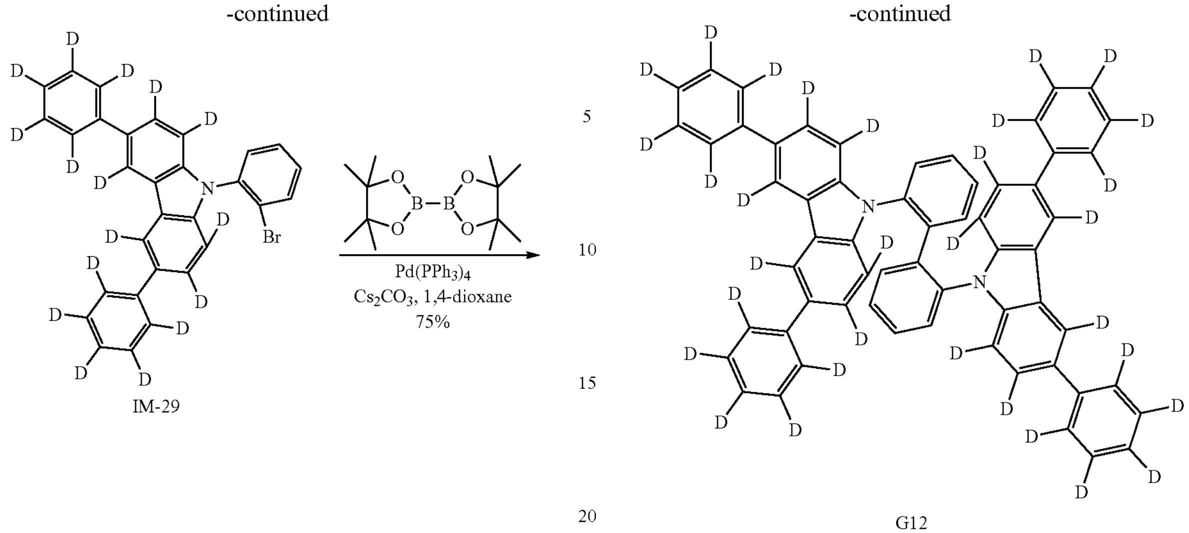

IM-29

G12

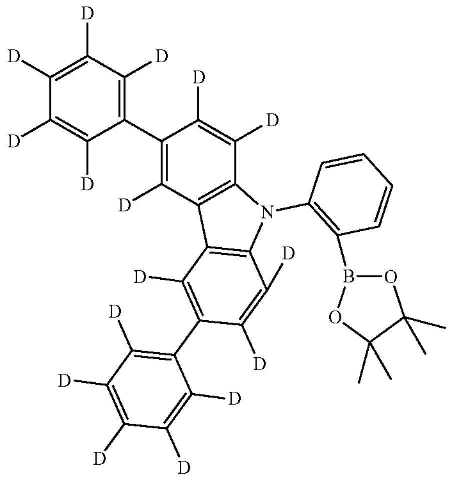

IM-20

[Reaction 14-2]

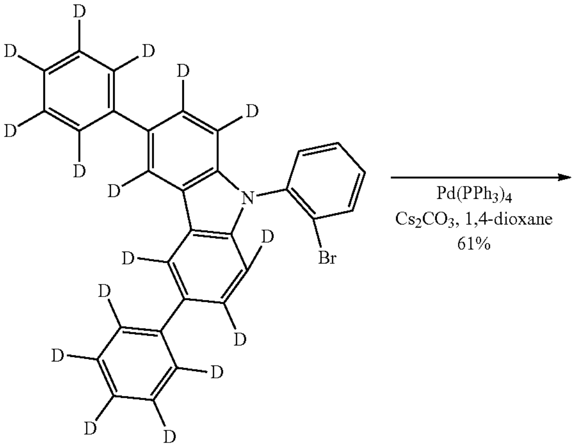

IM-19

1) Synthesis of Compound IM-19

Under an argon (Ar) atmosphere, to a 100 mL three-neck flask, 3,6-bis(phenyl-d5)-9H-carbazole-1,2,4,5,7,8-d6 (10.00 g, 29.81 mmol), $Cs_2CO_3$ (19.42 g, 2.0 equiv, 59.61 mmol), DMA (30 mL) and 1-bromo-2-fluorobenzene (10.43 g, 2.0 equiv, 59.61 mmol) were added in order, followed by heating to about 120° C. and stirring. After cooling to room temperature in the air, water and toluene were added to the reaction mixture, and an organic layer was separately taken. An organic layer extracted was washed with a saline solution and dried with $MgSO_4$. $MgSO_4$ was filtered, and an organic layer was concentrated. The crude product thus obtained was purified to obtain Compound IM-19 (10.08 g, yield 69%).

Through FAB-MS measurement, mass number of m/z=489 was observed as a molecular ion peak, and Compound IM-19 was confirmed.

2) Synthesis of Compound IM-20

Under an argon (Ar) atmosphere, to a 200 mL three-neck flask, Compound IM-19 (6.00 g, 12.2 mmol), $Pd(PPh_3)_4$ (2.83 g, 0.20 equiv, 2.45 mmol), $Cs_2CO_3$ (15.94 g, 4.0 equiv, 48.93 mmol), 1,4-dioxane (60 mL), and bis(pinacolato) diboron (12.43 g, 4.0 equiv, 48.93 mmol) were added in order, followed by heating, refluxing, and stirring. After cooling to room temperature in the air, water and toluene were added to the reaction mixture, and an organic layer was separately taken. The extracted organic layer was washed with a saline solution and dried with $MgSO_4$. $MgSO_4$ was filtered, and an organic layer was concentrated. The crude product thus obtained was purified to obtain Compound IM-20 (4.93 g, yield 75%).

Through FAB-MS measurement, mass number of m/z=537 was observed as a molecular ion peak, and Compound IM-20 was confirmed.

3) Synthesis of Compound G12

Under an argon (Ar) atmosphere, to a 200 mL three-neck flask, Compound IM-20 (4.12 g, 7.66 mmol), $Pd(PPh_3)_4$ (1.77 g, 0.20 equiv, 1.53 mmol), $Cs_2CO_3$ (7.49 g, 3.0 equiv, 23.0 mmol), 1,4-dioxane (40 mL), and Compound IM-19

(3.76 g, 1.0 equiv, 7.66 mmol) were added in order, followed by heating, refluxing, and stirring. After cooling to room temperature in the air, water and toluene were added to the reaction mixture, and an organic layer was separately taken. An extracted organic layer was washed with a saline solution and dried with $MgSO_4$. $MgSO_4$ was filtered, and an organic layer was concentrated. The crude product thus obtained was purified to obtain Compound G12 (3.83 g, yield 61%).

Through FAB-MS measurement, mass number of m/z=821 was observed as a molecular ion peak, and Compound G12 was confirmed.

2. Manufacture and Evaluation of Light Emitting Elements

The evaluation of light emitting elements including the compounds of the Examples and Comparative Examples was performed by a method below. The methods of manufacturing light emitting elements for element evaluation are described below.

(1) Manufacture of Light Emitting Element 1 and Light Emitting Element 2

1) Manufacture of Light Emitting Element 1 (Fluorescence Element)

On a glass substrate, ITO with a thickness of about 1500 Å was patterned, washed with ultrapure water, and treated with UV ozone for about 10 minutes to form a first electrode. 2-TNATA was deposited to a thickness of about 600 Å to form a hole injection layer. The Example Compound or Comparative Compound was deposited to a thickness of about 300 Å to form a hole transport layer.

An emission layer was formed of ADN doped 3% TBP to a thickness of about 250 Å. $Alq_3$ was deposited to a thickness of about 250 Å to form an electron transport layer, and LiF was deposited to a thickness of about 10 Å to form an electron injection layer.

Aluminum (Al) was deposited to a thickness of about 1000 Å to form a second electrode.

In an embodiment, the hole injection layer, the hole transport layer, the emission layer, the electron transport layer, the electron injection layer, and the second electrode were formed using a vacuum deposition apparatus.

2) Manufacture of Light Emitting Element 2 (Phosphorescence Element)

On a glass substrate, ITO with a thickness of about 1500 Å was patterned, washed with ultrapure water, and treated with UV ozone for about 10 minutes to form a first electrode. HAT-CN was deposited to a thickness of about 10 nm, and TAPC was deposited to a thickness of about 80 nm. The Example Compound or Comparative Compound was deposited to a thickness of about 5 nm to form a hole transport layer. An emission layer was formed of mCBP doped with 5% FIrpic to a thickness of about 20 nm. TmPyPb was deposited to a thickness of about 30 nm on the emission layer, and LiF was deposited to a thickness of about 0.5 nm to form an electron transport region. A second electrode of a thickness of about 100 nm was formed of aluminum (Al). All layers were formed using a vacuum deposition apparatus.

The Example Compounds and Comparative Compounds used for the manufacture of light emitting element 1 and light emitting element 2 are as follows.

<Example Compounds>

A16

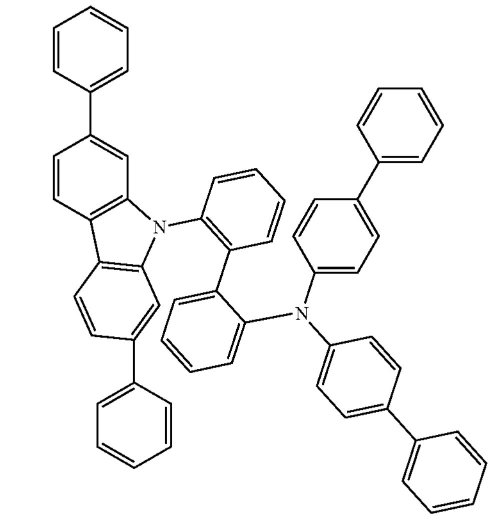

A14

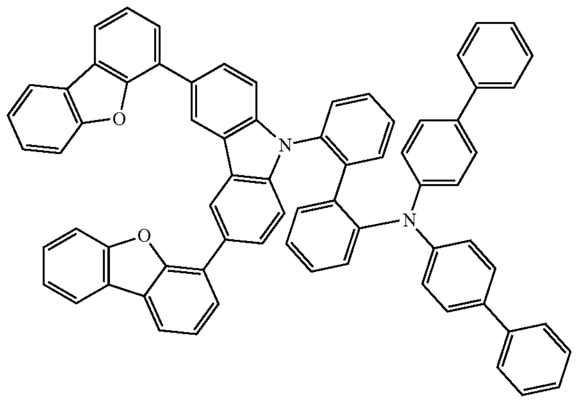

B1

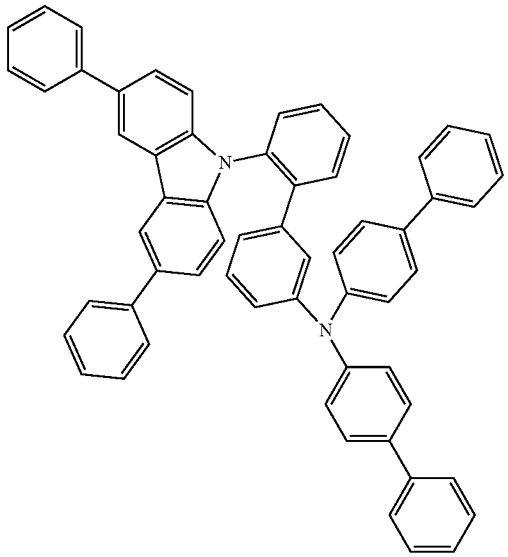

-continued
C1
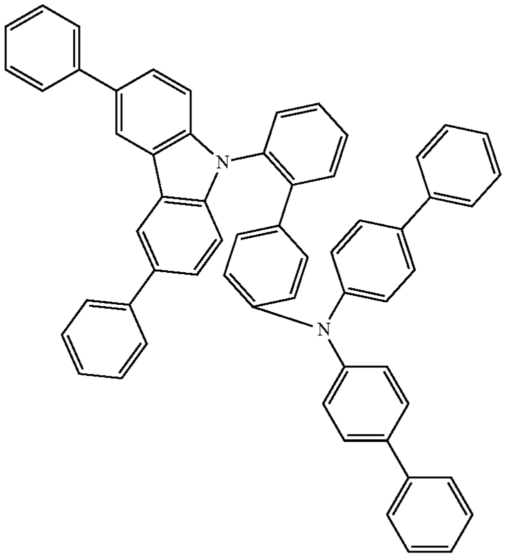
D1
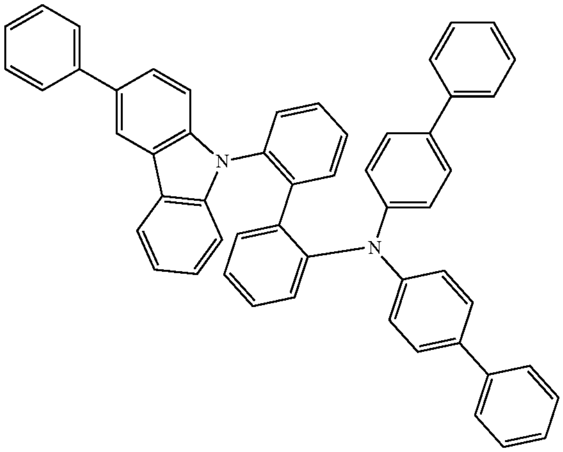
G1
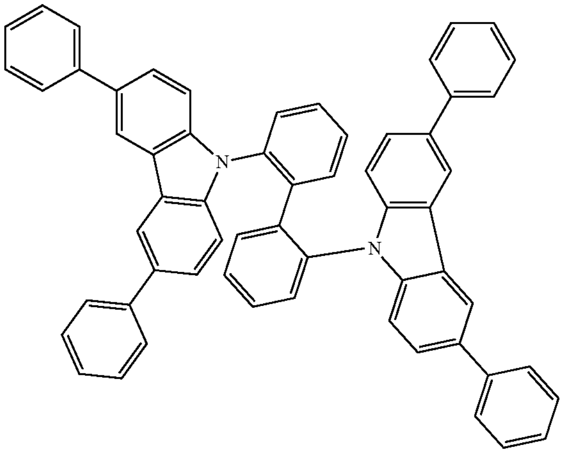
-continued
G12
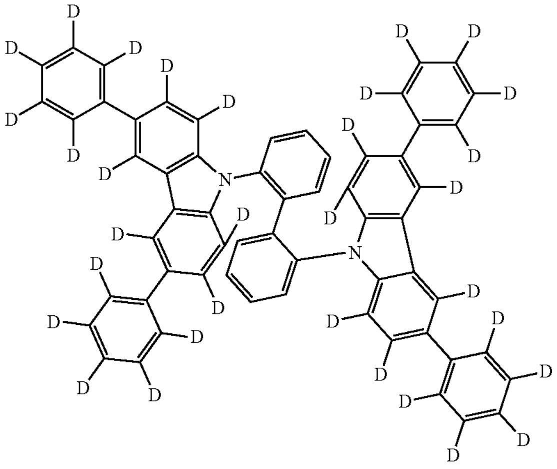
H1
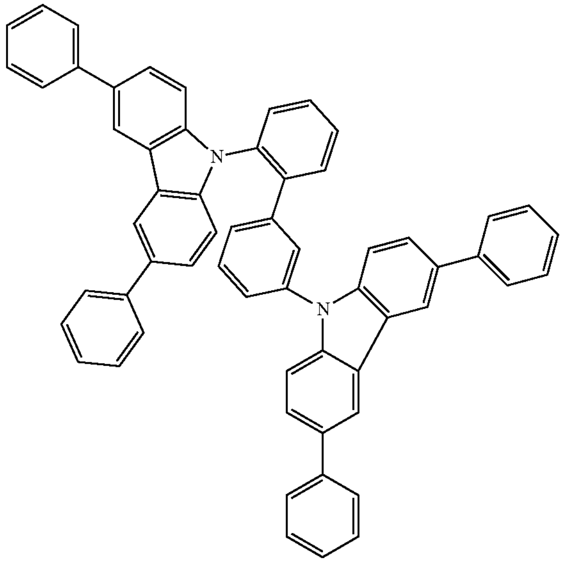
J1
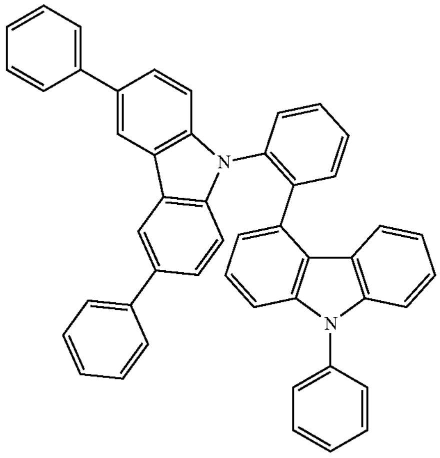

-continued
J9
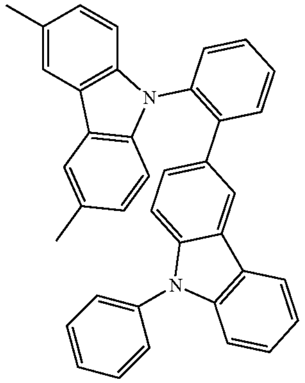
J29
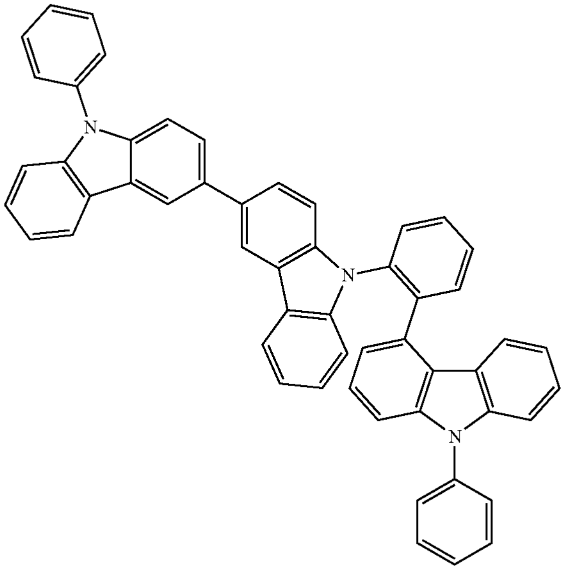
<Comparative Compounds>
R1
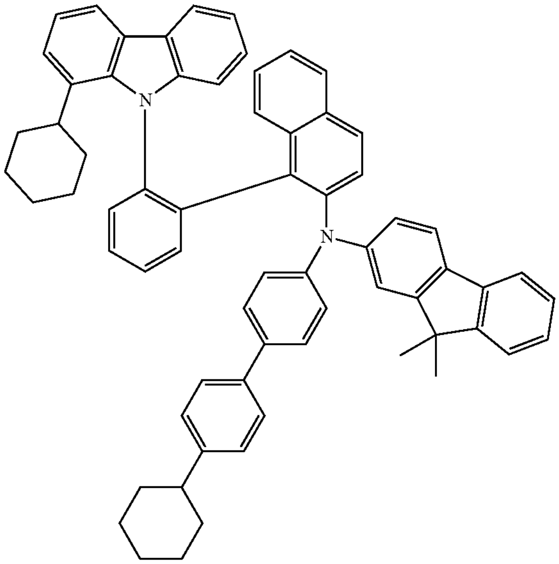
R2
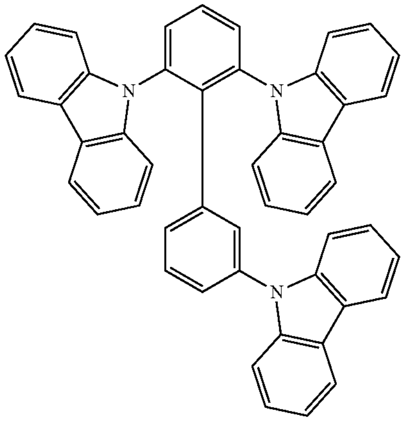

-continued
R3
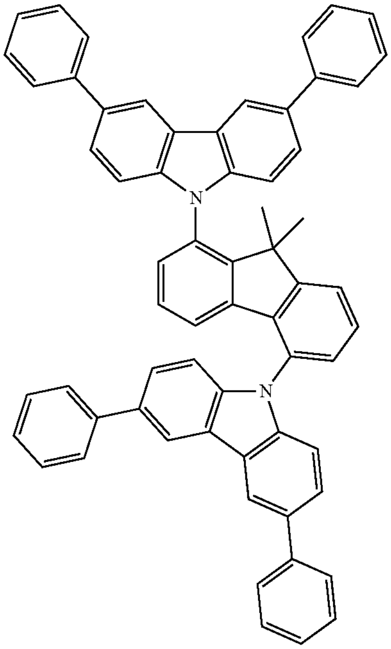
R4
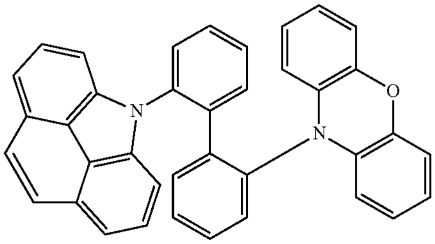
R5
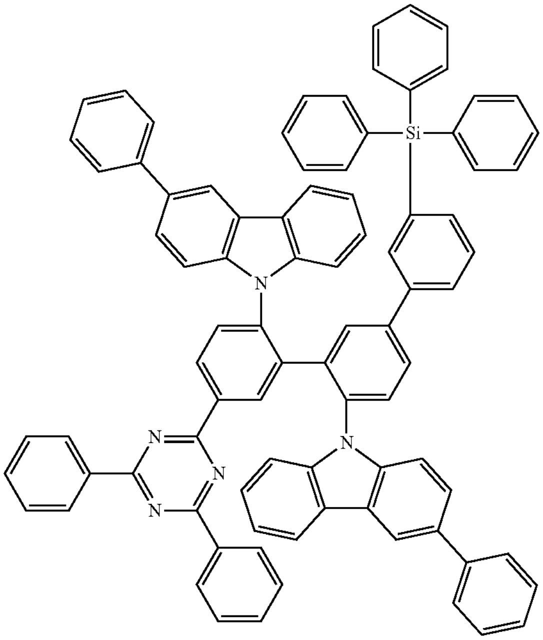
-continued
R6
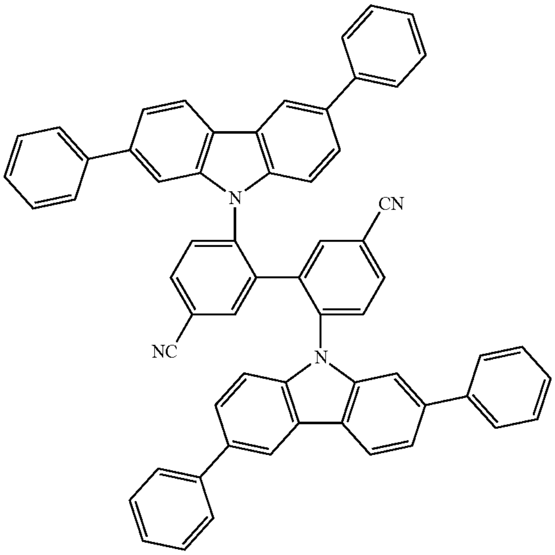
R7
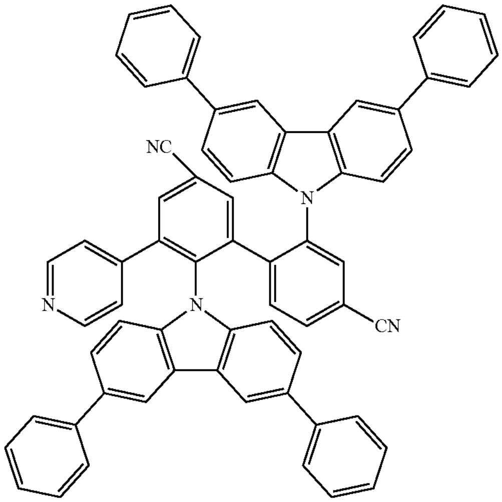

R8
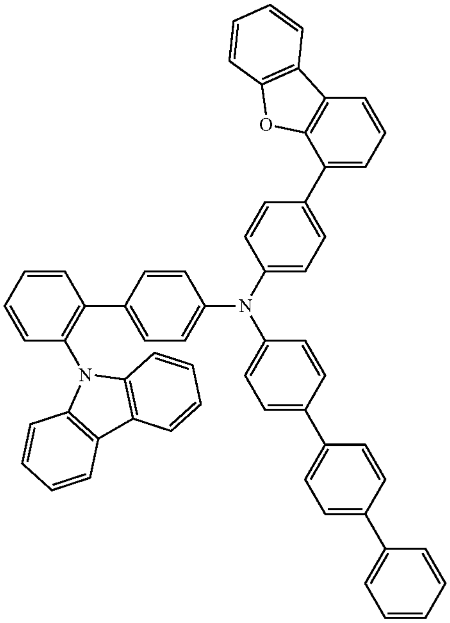
R9
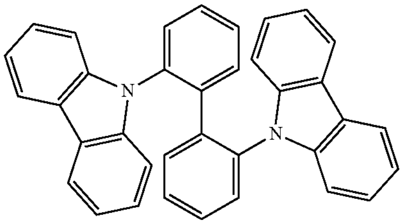
R10
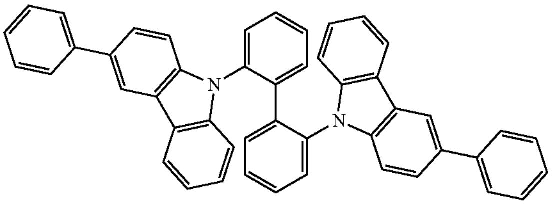
R11
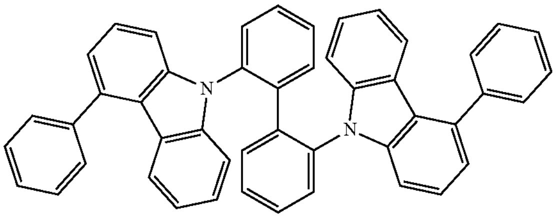
R12
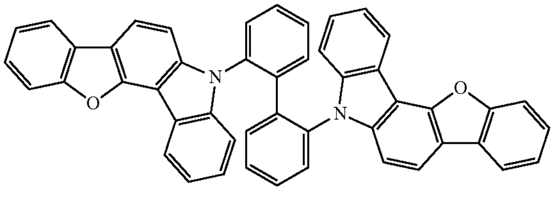
R13
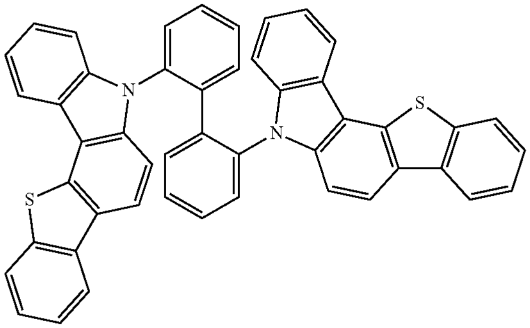
R14
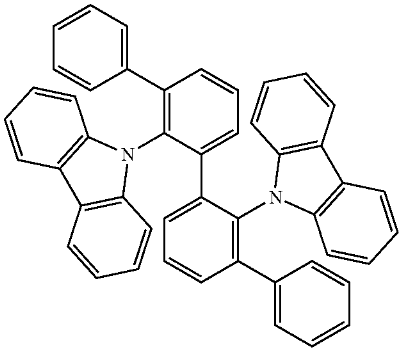
R15
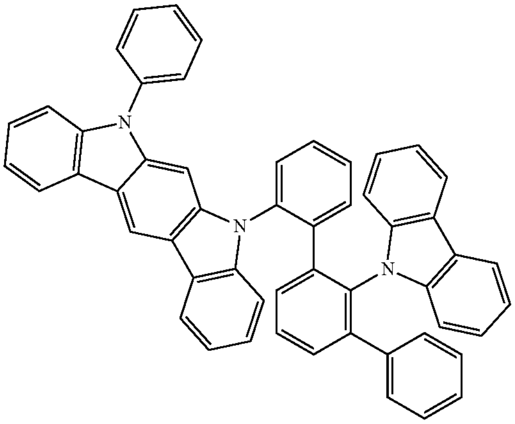
R16
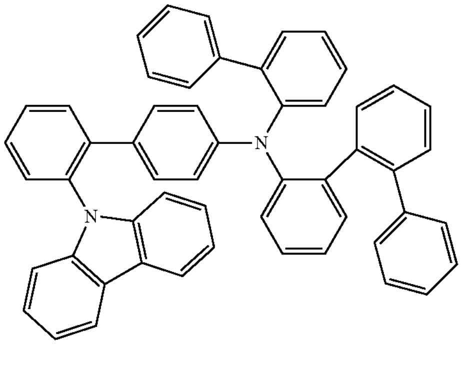

-continued
R17
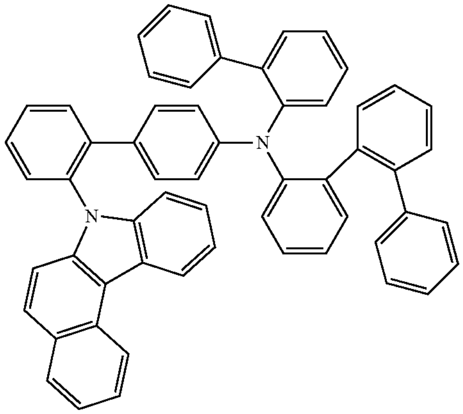
R18
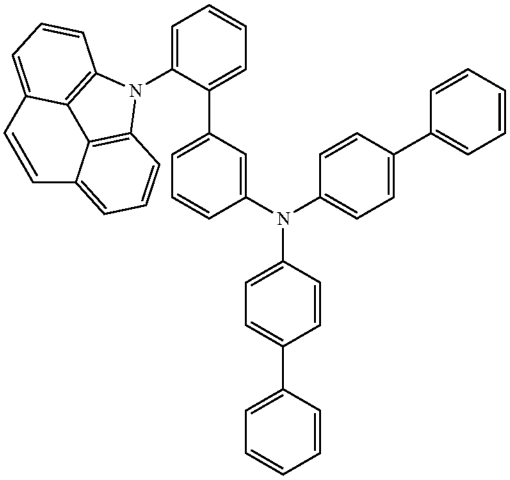
R19
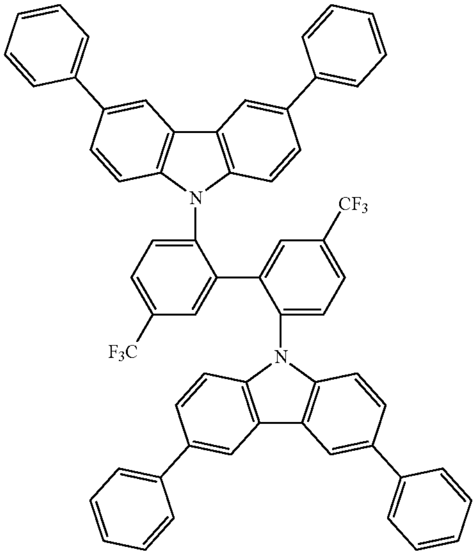
-continued
R20
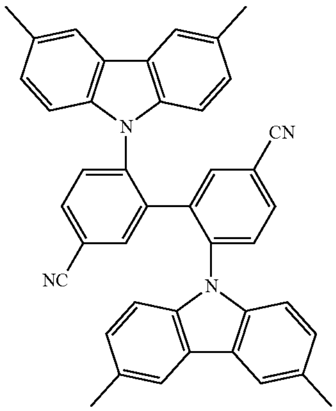
R21
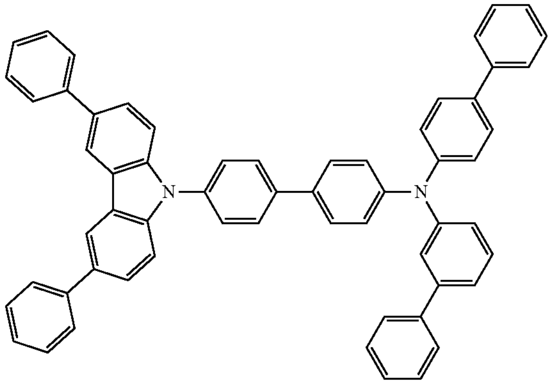
R22
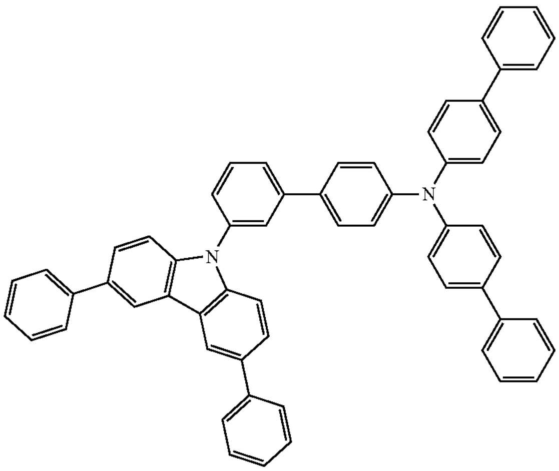
R23
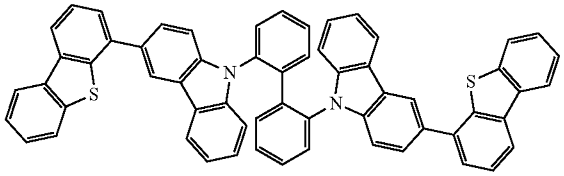

R24
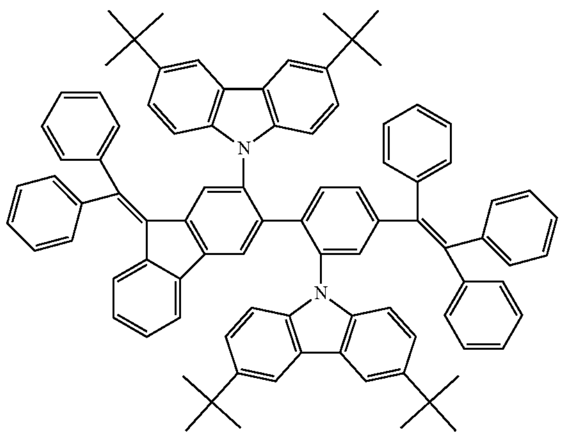
R25
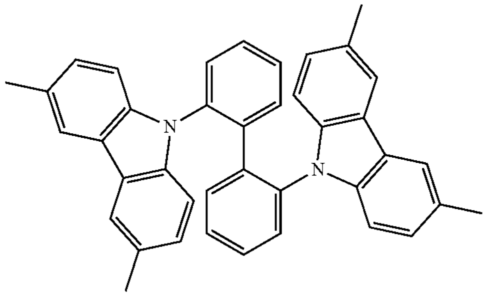
R26
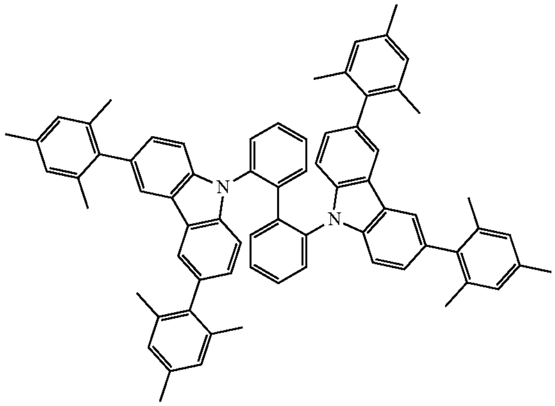
R27
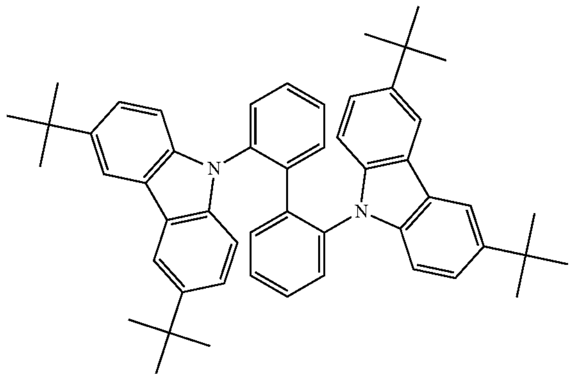
R28
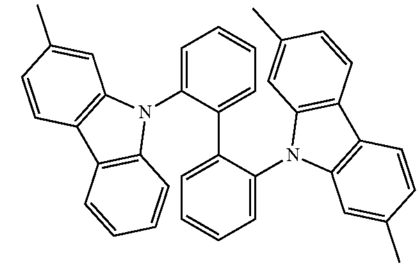
R29
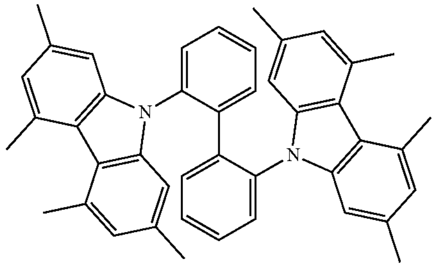
R30
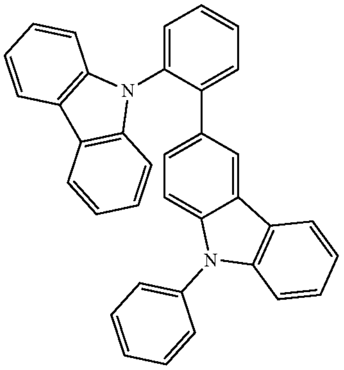
R31
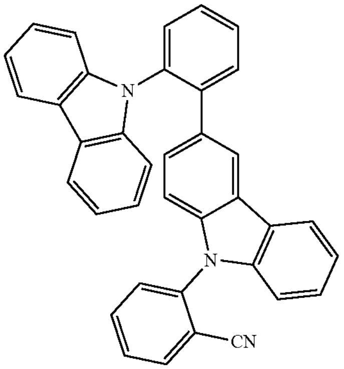

-continued

R32

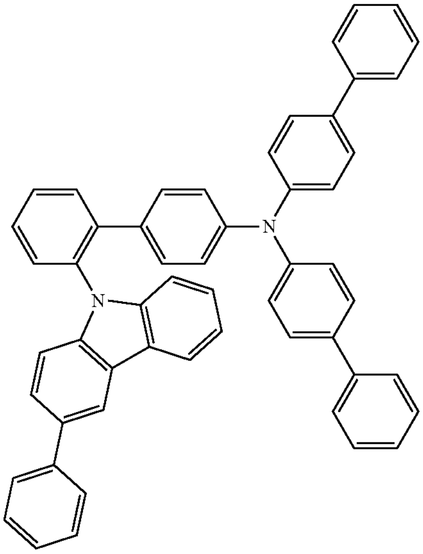

(2) Evaluation of Light Emitting Element 1 and Light Emitting Element 2

1) Evaluation of Light Emitting Element 1

In Table 1, the evaluation results of the light emitting elements 1 of Example 1-1 to Example 1-14 are shown, and in Table 2, the evaluation results of the light emitting elements 1 of Comparative Example 1-1 to Comparative Example 1-32 are shown. In Tables 1 and 2, the maximum emission efficiency and half-life of light emitting elements 1 manufactured are compared and shown. In the evaluation results on the properties of the Examples and Comparative Examples, the maximum emission efficiency represents the efficiency value at a current density of about 10 mA/$cm^2$, and the half-life represents luminance half-life from an initial luminance of about 100 cd/$m^2$ in a test at about 1.0 mA/$cm^2$.

In Tables 1 and 2, the maximum emission efficiency and half-life properties are relative values with the emission efficiency and life of Comparative Example 1-9 as 100%.

TABLE 1

| Division | Hole transport layer material | Maximum emission efficiency | Half-life |
|---|---|---|---|
| Example 1-1 | Example Compound A1 | 132% | 165% |
| Example 1-2 | Example Compound A7 | 135% | 158% |
| Example 1-3 | Example Compound A9 | 125% | 125% |
| Example 1-4 | Example Compound A14 | 137% | 136% |
| Example 1-5 | Example Compound A16 | 129% | 171% |
| Example 1-6 | Example Compound B1 | 131% | 170% |
| Example 1-7 | Example Compound C1 | 136% | 175% |
| Example 1-8 | Example Compound D1 | 120% | 134% |
| Example 1-9 | Example Compound G1 | 129% | 177% |
| Example 1-10 | Example Compound H1 | 124% | 169% |
| Example 1-11 | Example Compound J1 | 121% | 155% |
| Example 1-12 | Example Compound J9 | 118% | 129% |
| Example 1-13 | Example Compound J29 | 127% | 142% |
| Example 1-14 | Example Compound G12 | 134% | 187% |

TABLE 2

| Division | Hole transport layer material | Maximum emission efficiency | Half life |
|---|---|---|---|
| Comparative Example 1-1 | Comparative Compound R1 | 105% | 48% |
| Comparative Example 1-2 | Comparative Compound R2 | 107% | 92% |
| Comparative Example 1-3 | Comparative Compound R3 | 109% | 65% |
| Comparative Example 1-4 | Comparative Compound R4 | 103% | 82% |
| Comparative Example 1-5 | Comparative Compound R5 | 92% | 8% |
| Comparative Example 1-6 | Comparative Compound R6 | 99% | 33% |
| Comparative Example 1-7 | Comparative Compound R7 | 84% | 5% |
| Comparative Example 1-8 | Comparative Compound R8 | 109% | 101% |
| Comparative Example 1-9 | Comparative Compound R9 | 100% | 100% |
| Comparative Example 1-10 | Comparative Compound R10 | 108% | 110% |
| Comparative Example 1-11 | Comparative Compound R11 | 105% | 107% |
| Comparative Example 1-12 | Comparative Compound R12 | 108% | 87% |
| Comparative Example 1-13 | Comparative Compound R13 | 102% | 76% |
| Comparative Example 1-14 | Comparative Compound R14 | 98% | 105% |
| Comparative Example 1-15 | Comparative Compound R15 | 107% | 90% |
| Comparative Example 1-16 | Comparative Compound R16 | 105% | 92% |
| Comparative Example 1-17 | Comparative Compound R17 | 108% | 88% |
| Comparative Example 1-18 | Comparative Compound R18 | 103% | 84% |
| Comparative Example 1-19 | Comparative Compound R19 | 101% | 45% |
| Comparative Example 1-20 | Comparative Compound R20 | 100% | 23% |
| Comparative Example 1-21 | Comparative Compound R21 | 111% | 86% |
| Comparative Example 1-22 | Comparative Compound R22 | 112% | 88% |
| Comparative Example 1-23 | Comparative Compound R23 | 106% | 75% |
| Comparative Example 1-24 | Comparative Compound R24 | 74% | 17% |
| Comparative Example 1-25 | Comparative Compound R25 | 110% | 92% |
| Comparative Example 1-26 | Comparative Compound R26 | 106% | 66% |
| Comparative Example 1-27 | Comparative Compound R27 | 110% | 74% |
| Comparative Example 1-28 | Comparative Compound R28 | 104% | 85% |
| Comparative Example 1-29 | Comparative Compound R29 | 105% | 70% |

TABLE 2-continued

| Division | Hole transport layer material | Maximum emission efficiency | Half life |
|---|---|---|---|
| Comparative Example 1-30 | Comparative Compound R30 | 98% | 97% |
| Comparative Example 1-31 | Comparative Compound R31 | 94% | 26% |
| Comparative Example 1-32 | Comparative Compound R32 | 115% | 109% |

Referring to the results of Table 1 and Table 2, it could be found that the light emitting element 1 (fluorescence element) using the polycyclic compound of an embodiment as a hole transport layer material showed excellent emission efficiency and element life characteristics.

[Reference Formula K]

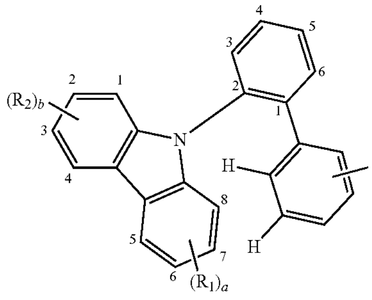

The polycyclic compounds of embodiments used in Example 1-1 to Example 1-14 include a substituent in any one of position 1 to position 8 of carbazole (referring to Reference Formula K), and an amine compound or a carbazole-based compound is substituted with a linker therebetween, thereby showing increased life and efficiency. In the polycyclic compounds used in the Examples, carbazole having a substituent such as an alkyl group and an aromatic ring group has shallow HOMO, hole injection from a layer adjacent to the first electrode is improved, and as a result, it is thought that hole transport from a hole transport region to an emission layer is accelerated, and emission efficiency is improved. In the polycyclic compound used in the Examples, it is thought that since a biphenyl moiety is bonded to the nitrogen of carbazole having a substituent at position 2, partial structures including nitrogen approach, even greater hole transport capacity is shown due to interaction, and high emission efficiency is shown. In the polycyclic compound used in the Examples, positions 3 and 6 of carbazole have high reactivity with an electrophilic part, and low oxidation resistance is shown. However, it is thought that stability is improved by introducing substituents at positions 3 and 6, and the increase of life could be achieved. It is thought that such effects are confirmed even in case of introducing a substituent at position 2, and protecting effects of position 3 by a sterically large volume could be obtained. Carbazole has high planarity, and a deposition temperature is readily elevated. There are cases where decomposed materials produced at a high temperature degrades element life, but in the polycyclic compound used in the Examples, carbazole has a twisted skeleton by the interposition of a linker, planarity is decreased, and a deposition temperature is lowered. Accordingly, it is thought that if the polycyclic compound used in the Examples is applied in the light emitting element 1, high element life is shown.

The Comparative Compounds used in Comparative Examples 1-1 and 1-3 showed degraded results of element life and efficiency when compared to the Compounds used in Examples 1-1 to 1-14. It is thought that if a fused structure is included around a linker part, a deposition temperature is liable to increase, and decomposed materials produced during deposition deteriorate the performance of the elements.

The Comparative Compounds used in Comparative Examples 1-2, 1-8, 1-9, 1-14, 1-16, and 1-30 showed degraded results of element life and efficiency when compared to the Compounds used in Examples 1-1 to 1-14. It is thought that in Examples 1-1 to 1-14, carbazole has a substituent as described above, and efficiency and life were improved.

The Comparative Compounds used in Comparative Examples 1-4, 1-12, 1-13, 1-15, 1-17, and 1-18 showed degraded results of element life and efficiency when compared to the Compounds used in Examples 1-1 to 1-14. In the Comparative Compounds used in Comparative Examples 1-4, 1-12, 1-13, 1-15, 1-17, and 1-18, benzocarbazole, benzothienocarbazole, benzofuraocarbazole, and indolocarbazole skeletons have fused skeletons, high planarity, and an increased deposition temperature. It is thought that decomposed materials produced during deposition deteriorated element performance.

The Comparative Compounds used in Comparative Examples 1-5, 1-6, 1-7, 1-19, 1-20, and 1-31 showed results of largely reduced element life when compared to the Compounds used in Examples 1-1 to 1-14. It is thought that structures of electron withdrawing groups like triazine, nitrile, pyridine, and trifluoromethyl are bonded in the Comparative Compounds used in Comparative Examples 1-5, 1-6, 1-7, 1-19, 1-20, and 1-31, and it is thought that degraded tolerance of holes was shown when compared to the compounds used in the Examples.

The Comparative Compounds used in Comparative Examples 1-10, 1-11, and 1-23 showed degraded results of element life and efficiency when compared to the Compounds used in Examples 1-1 to 1-14. From the results of Examples 1-9 and 1-10, it is thought that two or more substituents were included in the same carbazole, efficiency and life were improved even further, and the substituent group effects of carbazole having the above-described substituent group showed excellent performance. In the case of an amine compound bonded at position 2 with respect to a biphenyl moiety, like the compound used in Example 1-8, though the substituent on the carbazole was one, sufficiently excellent performance was shown. The amine compound has higher hole transport capacity when compared to the carbazole, and it is thought that such an amine compound moiety and carbazole interposing a linker interact sterically closely, even there was one substituent on the carbazole, sufficiently high hole transport properties were shown, and high efficiency was shown. The compound used in Comparative Example 1-23 showed degraded life when compared to the compounds used in Comparative Examples 1-10 and 1-11. Dibenzothiophene has high planarity like carbazole, and is a skeleton having a high deposition temperature with the addition of interaction using a lone pair electron and an unoccupied orbital between sulfur atoms, and it is thought that element performance was degraded by the decomposition during deposition.

The Comparative Compounds used in Comparative Examples 1-21, and 1-22 showed degraded results of element life and efficiency when compared to the Compounds used in Examples 1-1 to 1-14. The compounds used in Examples 1-1 to 1-14 have a twisted skeleton, and it is thought that the decomposition temperature was lowered, the decomposition during decomposition was restrained, and the degradation of efficiency and life by decomposed materials were restrained.

The Comparative Compound used in Comparative Example 1-24 showed largely degraded results of element life when compared to the Compounds used in Examples 1-1 to 1-14. It is thought that styrene has low tolerance to heat and light and was degraded during deposition or driving an element to degrade performance.

The Comparative Compounds used in Comparative Examples 1-25, 1-26, 1-27, 1-28, and 1-29 showed largely degraded results of element life when compared to the Compounds used in Examples 1-1 to 1-14. An alkyl group bonded to an aromatic ring generally includes a benzyl position having high activity. Accordingly, it is thought that the compounds used in Examples 1-1, 1-2, 1-4, 1-5, 1-6, 1-7, 1-8, 1-9, 1-10, 1-11, and 1-13, which are composed of only aromatic rings, were difficult to deteriorate during deposition, and showed excellent properties. The compounds used in Examples 1-3 and 1-12 showed excellent performance though including an alkyl group. The compound used in Example 1-3 includes an amine compound having low planarity and a low deposition temperature when compared to carbazole, and the compound used in Example 1-12 has a low molecular weight when compared to the compound used in Comparative Example 1-25 and has a reduced deposition temperature. It is thought that by combining with such a skeleton degrading a deposition temperature, excellent performance was shown by using an alkyl group as a substituent.

The Comparative Compound used in Comparative Example 1-32 showed degraded results of element life and efficiency when compared to the Compounds used in Examples 1-1 to 1-14. In the compound used in Comparative Example 1-32, only one substituent is substituted on position 1 to position 8 of the same carbazole. The compound used in Example 1-7 includes two or more substituents at position 1 to position 8 of the same carbazole, and it is thought that efficiency and life were improved even further, and excellent performance was shown. Referring to the results of Example 1-8, in case of having an amine compound bonded at position 2 with respect to biphenyl, sufficiently excellent performance was shown even with one substituent on the carbazole. Like the compound used in Example 1-8, in the case where an amine moiety is bonded to the biphenyl moiety at position 2, due to the steric interaction with carbazole bonded with a biphenyl linker therebetween, it is thought that even better hole transport capacity was shown when compared to a case of bonding an amine moiety at position 4 with respect to a biphenyl linker like in the compound used in Comparative Example 1-32.

2) Evaluation of Light Emitting Elements 2

In Table 3, the evaluation results of the light emitting elements 2 of Example 2-1 to Example 2-7 are shown, and in Table 4, the evaluation results of the light emitting elements 2 of Comparative Example 2-1 to Comparative Example 2-32 are shown. In Tables 3 and 4, the maximum emission efficiency and half-life of light emitting elements 2 manufactured are compared and shown. In the evaluation results on the properties of the Examples and Comparative Examples, shown in Table 3 and Table 4, the maximum emission efficiency represents the efficiency value at a current density of about 10 mA/$cm^2$, and the half-life represents luminance half-life from an initial luminance of about 100 cd/$m^2$ in a test at about 1.0 mA/$cm^2$. In Table 3 and Table 4, the maximum emission efficiency and half-life properties are relative values with the emission efficiency and life of Comparative Example 2-9 as 100%.

TABLE 3

| Division | Hole transport layer material | Maximum emission efficiency | Half-life |
|---|---|---|---|
| Example 2-1 | Example Compound A1 | 136% | 144% |
| Example 2-2 | Example Compound A7 | 137% | 136% |
| Example 2-3 | Example Compound D1 | 125% | 128% |
| Example 2-4 | Example Compound G1 | 132% | 165% |
| Example 2-5 | Example Compound H1 | 129% | 155% |
| Example 2-6 | Example Compound J1 | 127% | 131% |
| Example 2-7 | Example Compound G12 | 138% | 177% |

TABLE 4

| Division | Hole transport layer material | Maximum emission efficiency | Half life |
|---|---|---|---|
| Comparative Example 2-1 | Comparative Compound R1 | 95% | 28% |
| Comparative Example 2-2 | Comparative Compound R2 | 110% | 88% |
| Comparative Example 2-3 | Comparative Compound R3 | 112% | 76% |
| Comparative Example 2-4 | Comparative Compound R4 | 105% | 85% |
| Comparative Example 2-5 | Comparative Compound R5 | 90% | 25% |
| Comparative Example 2-6 | Comparative Compound R6 | 98% | 63% |
| Comparative Example 2-7 | Comparative Compound R7 | 88% | 35% |
| Comparative Example 2-8 | Comparative Compound R8 | 97% | 93% |
| Comparative Example 2-9 | Comparative Compound R9 | 100% | 100% |
| Comparative Example 2-10 | Comparative Compound R10 | 111% | 108% |
| Comparative Example 2-11 | Comparative Compound R11 | 106% | 107% |
| Comparative Example 2-12 | Comparative Compound R12 | 104% | 80% |
| Comparative Example 2-13 | Comparative Compound R13 | 101% | 66% |
| Comparative Example 2-14 | Comparative Compound R14 | 103% | 89% |
| Comparative Example 2-15 | Comparative Compound R15 | 103% | 75% |
| Comparative Example 2-16 | Comparative Compound R16 | 107% | 72% |
| Comparative Example 2-17 | Comparative Compound R17 | 102% | 68% |
| Comparative Example 2-18 | Comparative Compound R18 | 100% | 74% |
| Comparative Example 2-19 | Comparative Compound R19 | 103% | 57% |
| Comparative Example 2-20 | Comparative Compound R20 | 102% | 48% |
| Comparative Example 2-21 | Comparative Compound R21 | 103% | 79% |
| Comparative Example 2-22 | Comparative Compound R22 | 110% | 78% |
| Comparative Example 2-23 | Comparative Compound R23 | 103% | 65% |

TABLE 4-continued

| Division | Hole transport layer material | Maximum emission efficiency | Half life |
|---|---|---|---|
| Comparative Example 2-24 | Comparative Compound R24 | 84% | 22% |
| Comparative Example 2-25 | Comparative Compound R25 | 103% | 94% |
| Comparative Example 2-26 | Comparative Compound R26 | 106% | 82% |
| Comparative Example 2-27 | Comparative Compound R27 | 105% | 77% |
| Comparative Example 2-28 | Comparative Compound R28 | 103% | 95% |
| Comparative Example 2-29 | Comparative Compound R29 | 104% | 91% |
| Comparative Example 2-30 | Comparative Compound R30 | 102% | 105% |
| Comparative Example 2-31 | Comparative Compound R31 | 92% | 66% |
| Comparative Example 2-32 | Comparative Compound R32 | 111% | 112% |

Referring to the results of Table 3 and Table 4, in the light emitting elements 2 (phosphorescence elements) using the polycyclic compounds according to embodiments as hole transport layer materials, Examples 2-1 to 2-7 showed long life and high efficiency when compared to Comparative Examples 2-1 to 2-32.

In the phosphorescence elements of Examples 2-1 to 2-7, like the fluorescence elements of Examples 1-1 to 1-14, explained referring to the results of Table 1 and Table 2, it is thought that the polycyclic compounds of embodiments use materials having a substituent at any one among position 1 to position 8 of carbazole (refer to Formula K) and amine or carbazole with a linker therebetween, and thus, hole transport capacity was improved, stability was improved, and the increase of life and efficiency were achieved according to the suppress of decomposition due to the deterioration of a decomposition temperature.

Comparative Examples 2-25, 2-26, 2-27, 2-28, and 2-29 showed degraded results of element life when compared to Examples 2-1 to 2-7. The results are the same as for the fluorescence elements, and it is thought that element degradation was induced during deposition due to a benzyl position having high activity. In order to avoid such element degradation, designs such as reducing the deposition temperature by including carbazole as amine as in Examples 2-1 to 2-3, excluding an alkyl group in a molecule including multiple carbazole having high planarity and high deposition temperature as in Examples 2-4 and 2-5, or reducing a molecular weight of a linker part as in Example 2-6, are thought effective.

In a phosphorescence element, it is important that a layer adjacent to an emission region sufficiently confines high triplet energy of the light emitting dopant of an emission region, but it is thought that the polycyclic compound according to an embodiment has a high T1 energy level by a twisted skeleton to suppress energy loss. It is thought that excellent results were shown in the phosphorescence element by having high hole transport capacity.

As described above, the compounds used in the Examples may improve emission efficiency and emission life at the same time when compared to the compounds used in the Comparative Examples. The light emitting elements (fluorescence element and phosphorescence element) according to embodiments use polycyclic compounds having a substituent at any one among position 1 to position 8 of carbazole, and an amine compound or a carbazole-based compound with a linker therebetween, and may improve element efficiency and element life at the same time.

The light emitting element of an embodiment includes the polycyclic compound of an embodiment in a hole transport region and may show improved emission efficiency and long-life characteristics.

The polycyclic compound according to an embodiment may be used as a material for a hole transport region of a light emitting element, and through this, the emission efficiency and element life of a light emitting element may be improved.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the following claims.

What is claimed is:

1. A light emitting element, comprising:

a first electrode;

a second electrode disposed on the first electrode; and at least one functional layer disposed between the first electrode and the second electrode, and comprising a polycyclic compound represented by the following Formula 1:

[Formula 1]

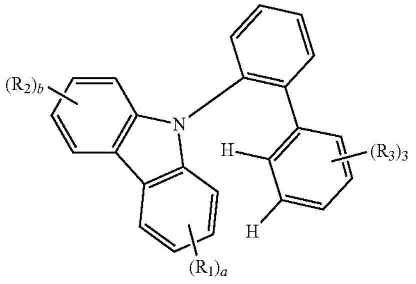

wherein in Formula 1, $R_1$ and $R_2$ are each independently a substituted or unsubstituted aryl group of 6 to 40 ring-forming carbon atoms, a substituted or unsubstituted heteroaryl group of 5 to 40 ring-forming carbon atoms, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted alkoxy group of 1 to 20 carbon atoms, a substituted or unsubstituted alkylthio group of 1 to 20 carbon atoms, a substituted or unsubstituted aryloxy group of 6 to 40 ring-forming carbon atoms, a substituted or unsubstituted arylthio group of 6 to 40 ring-forming carbon atoms, or a substituted or unsubstituted silyl group, a is an integer from 0 to 4, b is an integer from 1 to 4, one of $R_3$ is a group represented by Formula 2 and is bonded to a ring at an ortho position, a meta position, or a para position with respect to a phenyl group bonded to a nitrogen atom of a carbazole group, and the remainder of $R_3$ are each independently a hydrogen atom or a deuterium atom:

[Formula 2]

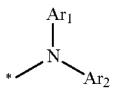

wherein in Formula 2, $Ar_1$ and $Ar_2$ are each independently a substituted or unsubstituted aryl group of 6 to 40 ring-forming carbon atoms, a substituted or unsubstituted heteroaryl group of 5 to 40 ring-forming carbon atoms, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted alkoxy group of 1 to 20 carbon atoms, a substituted or unsubstituted alkylthio group of 1 to 20 carbon atoms, a substituted or unsubstituted aryloxy group of 6 to 40 ring-forming carbon atoms, a substituted or unsubstituted arylthio group of 6 to 40 ring-forming carbon atoms, or a substituted or unsubstituted silyl group, or are combined with an adjacent group to form a ring, or $Ar_1$ and $Ar_2$ are combined with each other to form a ring, and —* is a bonding site to Formula 1, in case that an $R_3$ group represented by Formula 2 is bonded to a ring at an ortho position with respect to the phenyl group bonded to the nitrogen atom of the carbazole group, and $Ar_1$ and $Ar_2$ are combined with each other to form a ring, then a is equal to or greater than 1, and $R_1$ and $R_2$ do not include alkyl groups, in case that an $R_3$ group represented by Formula 2 is bonded to a ring at a para position with respect to the phenyl group bonded to the nitrogen atom of the carbazole group, and $Ar_1$ and $Ar_2$ are not combined with each other to form a ring, then a is equal to or greater than 1, and at least one hydrogen in Formula 1 or Formula 2 is optionally substituted with deuterium.

2. The light emitting element of claim 1, wherein the at least one functional layer comprises:

an emission layer;

a hole transport region disposed between the first electrode and the emission layer; and an electron transport region disposed between the emission layer and the second electrode, and the hole transport region comprises the polycyclic compound.

3. The light emitting element of claim 2, wherein the hole transport region comprises at least one of a hole injection layer, a hole transport layer, or an electron blocking layer, and at least one of the hole transport layer or the electron blocking layer comprises the polycyclic compound.

4. The light emitting element of claim 2, wherein the emission layer emits blue light or green light.

5. The light emitting element of claim 1, wherein the polycyclic compound represented by Formula 1 is represented by one of Formula 1-1 to Formula 1-3:

[Formula 1-1]

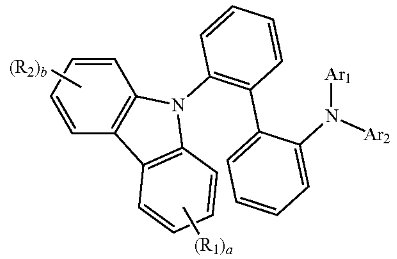

[Formula 1-2]

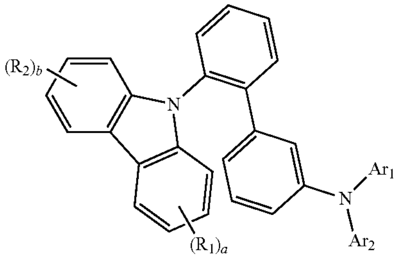

[Formula 1-3]

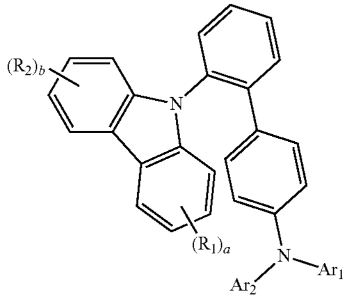

wherein in Formula 1-1 to Formula 1-3, $R_1$, $R_2$, a, and b are the same as defined in Formula 1, and $Ar_1$ and $Ar_2$ are the same as defined in Formula 2.

6. The light emitting element of claim 1, wherein the group represented by Formula 2 is represented by Formula 2-1 or Formula 2-2:

[Formula 2-1]

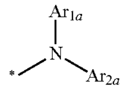

wherein in Formula 2-1, $Ar_{1a}$ and $Ar_{2a}$ are each independently a substituted or unsubstituted aryl group of 6 to 40 ring-forming carbon atoms, or a substituted or unsubstituted heteroaryl group of 5 to 40 ring-forming carbon atoms, or are combined with an adjacent group to form a ring, and at least one hydrogen atom in $Ar_{1a}$ or $Ar_{2a}$ is optionally substituted with deuterium,

[Formula 2-2]

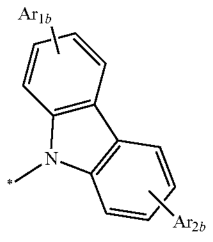

wherein in Formula 2-2, $Ar_{1b}$ and $Ar_{2b}$ are each independently a hydrogen atom, a deuterium atom, or a substituted or unsubstituted aryl group of 6 to 40 ring-forming carbon atoms.

7. The light emitting element of claim 6, wherein the polycyclic compound represented by Formula 1 is represented by one of Formula 3-1 to Formula 3-6:

[Formula 3-1]

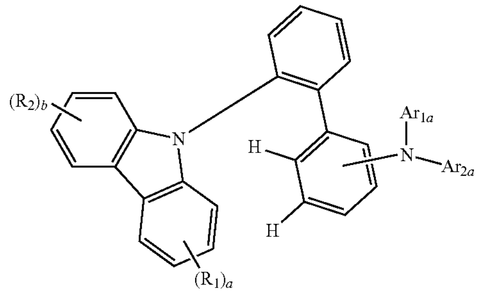

[Formula 3-2]

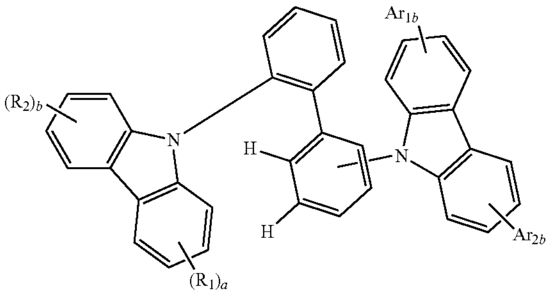

[Formula 3-3]

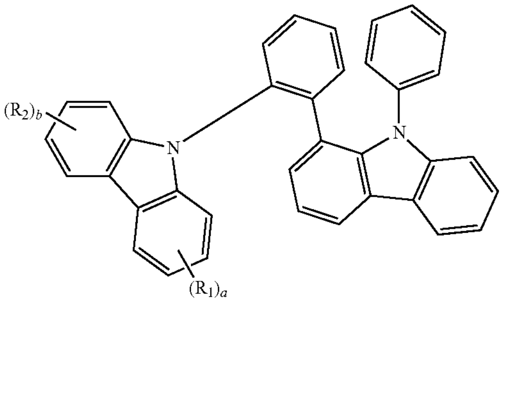

-continued

[Formula 3-4]

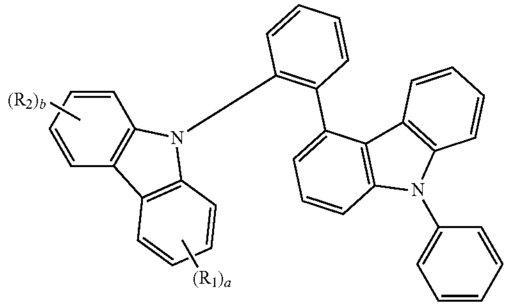

[Formula 3-5]

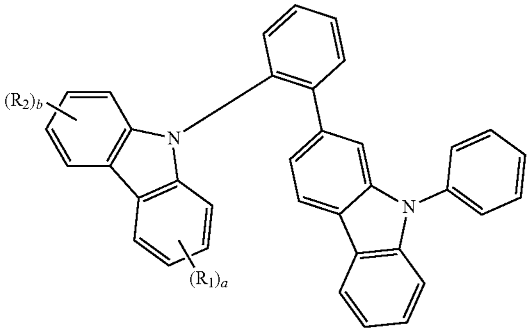

[Formula 3-6]

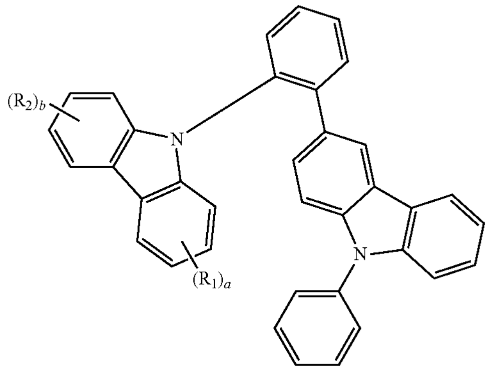

wherein in Formula 3-1 to Formula 3-6, $R_1$, $R_2$, a, and b are the same as defined in Formula 1, $Ar_{1a}$ and $Ar_{2a}$ are the same as defined in Formula 2-1, and $Ar_{1b}$ and $Ar_{2b}$ are the same as defined in Formula 2-2.

8. The light emitting element of claim 1, wherein a is equal to or greater than 1.

9. The light emitting element of claim 1, wherein $R_1$ and $R_2$ are each independently a substituted or unsubstituted aryl group of 6 to 40 ring-forming carbon atoms, a substituted or unsubstituted heteroaryl group of 5 to 40 ring-forming carbon atoms, or a substituted or unsubstituted alkyl group of 1 to 20 carbon atoms.

10. The light emitting element of claim 1, wherein $Ar_1$ and $Ar_2$ are each independently a substituted or unsubstituted aryl group of 6 to 40 ring-forming carbon atoms, or a substituted or unsubstituted heteroaryl group of 5 to 40 ring-forming carbon atoms, or are combined with an adjacent group to form a ring, or $Ar_1$ and $Ar_2$ are combined with each other to form a ring.

11. The light emitting element of claim 1, wherein the polycyclic compound represented by Formula 1 is one selected from Compound Group 1A to Compound Group 1J:

[Compound Group 1A]
A1
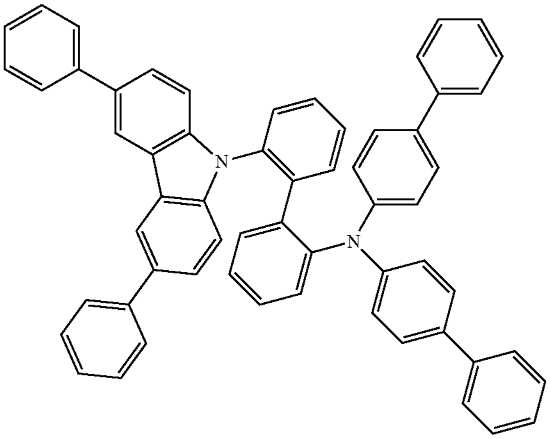
A2
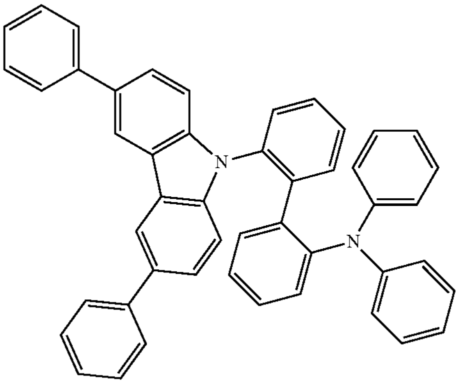
A3
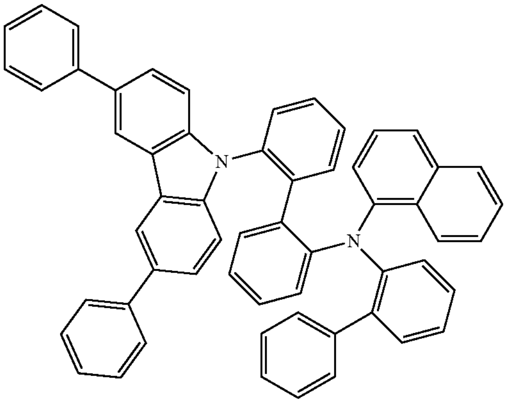
-continued
A4
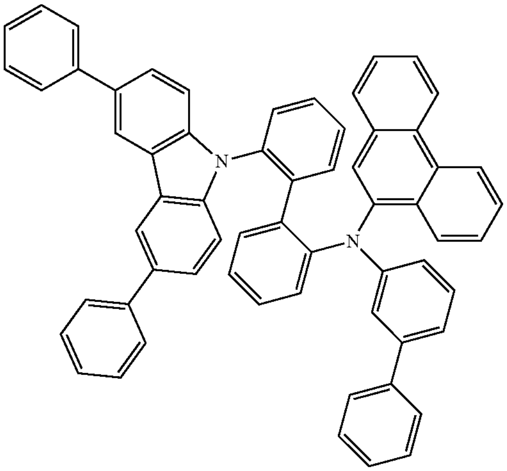
A5
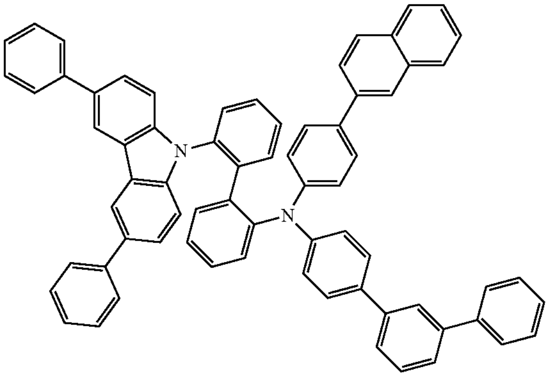
A6
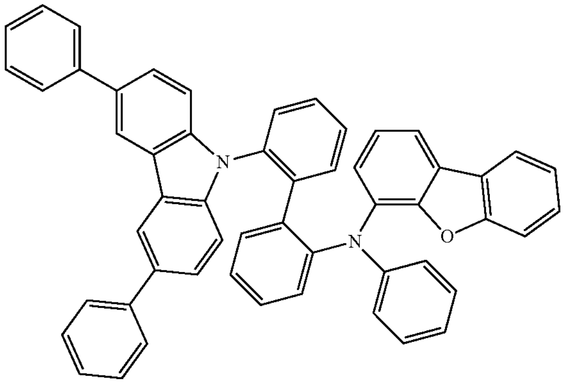

-continued
A7
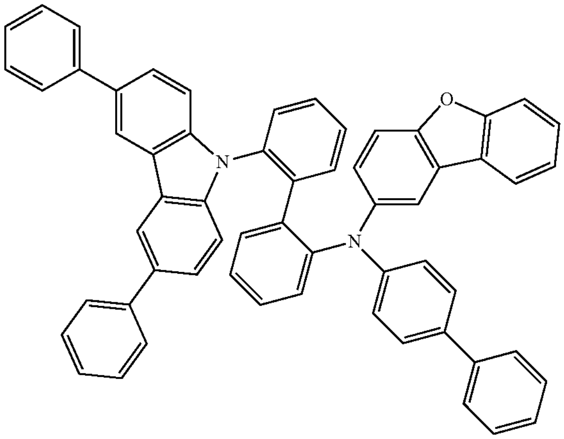
A8
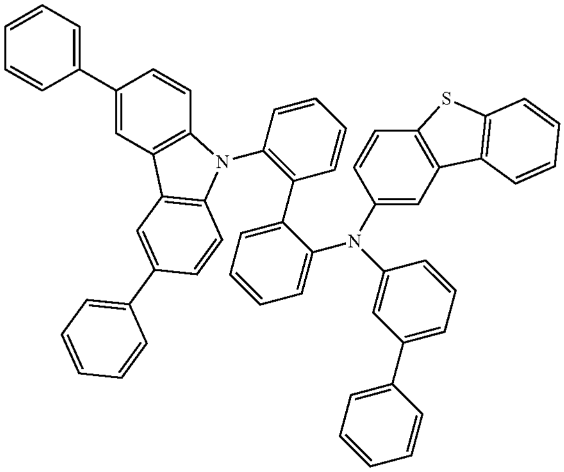
A9
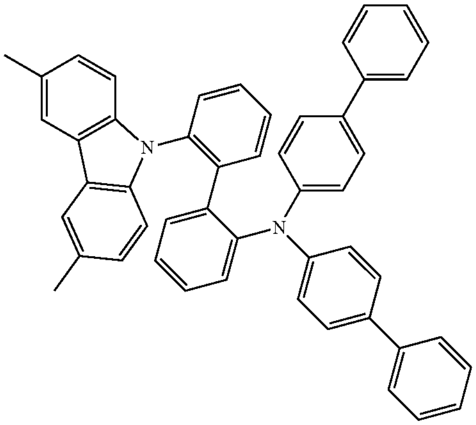
-continued
A10
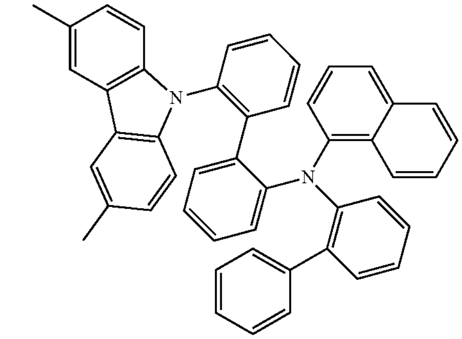
A11
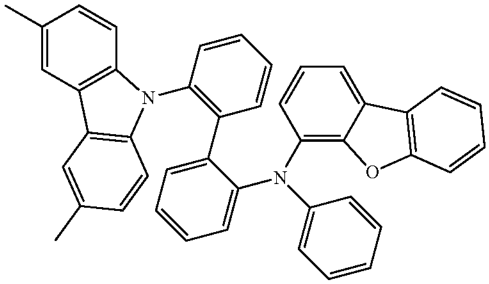
A12
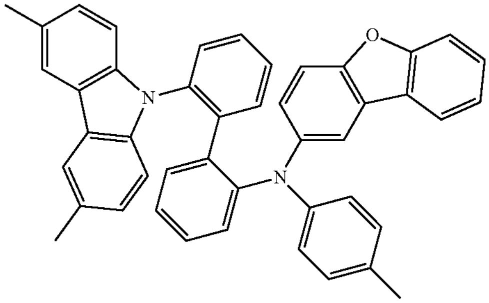
A13
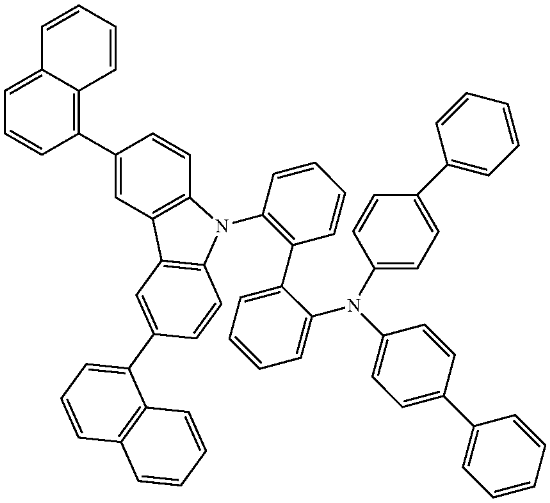

-continued
A14
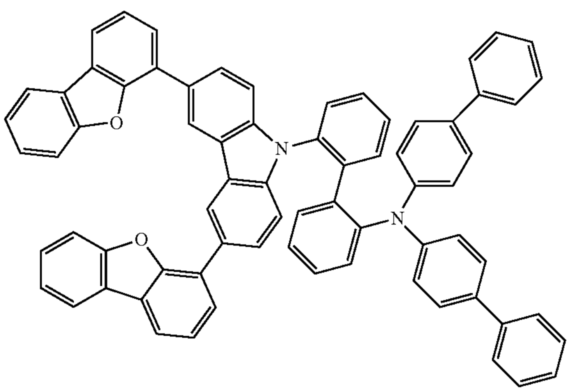
A15
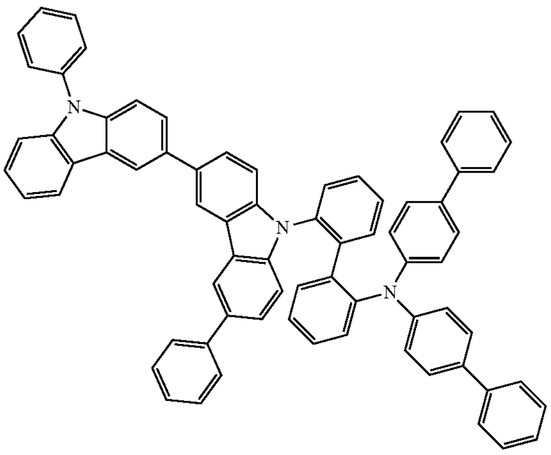
A16
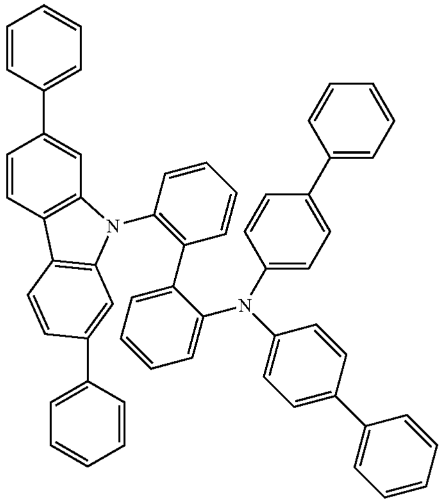
-continued
A17
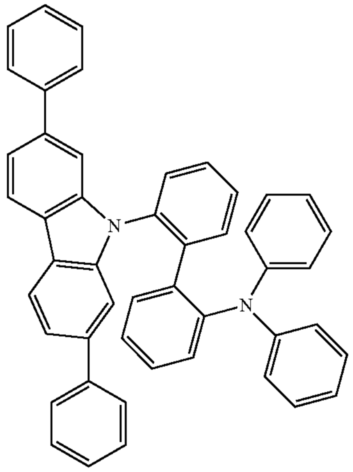
A18
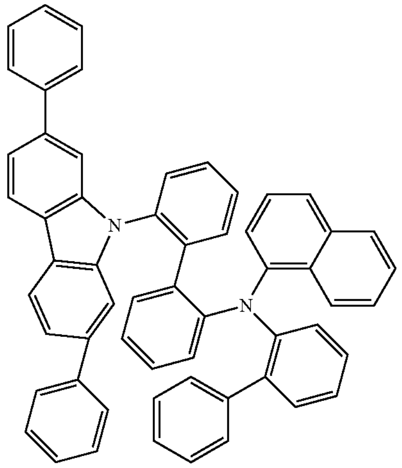
A19
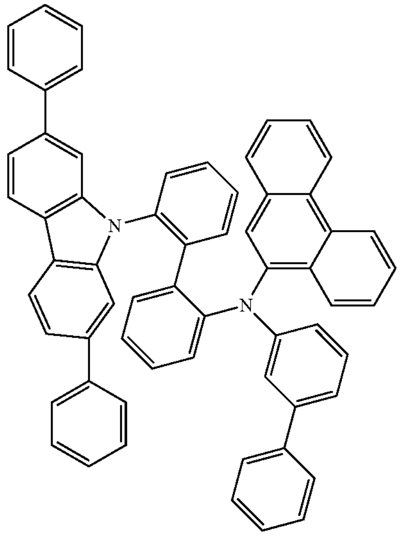

-continued
A20
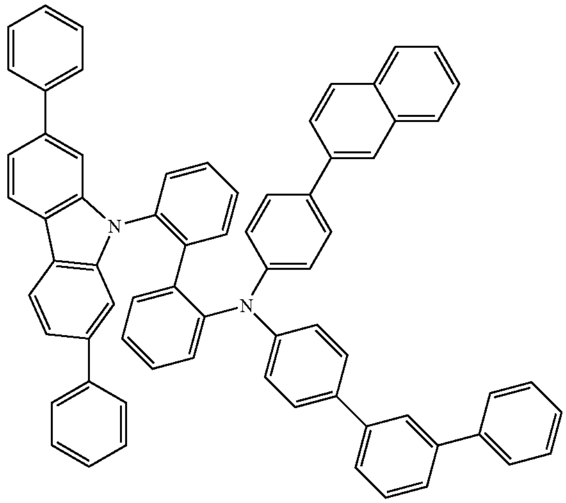
A21
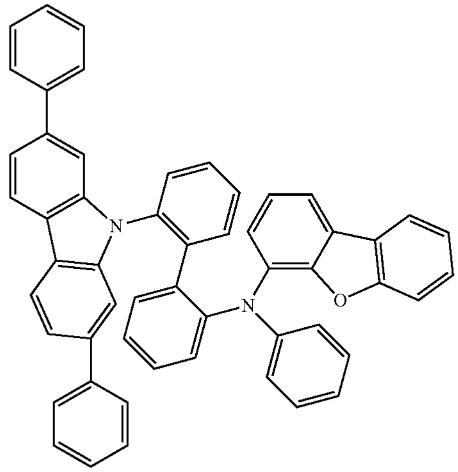
A22
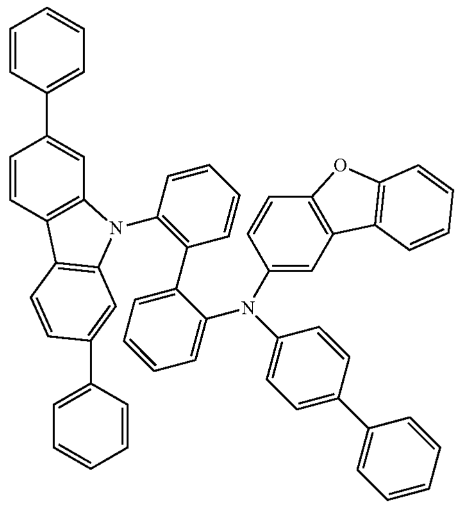
-continued
A23
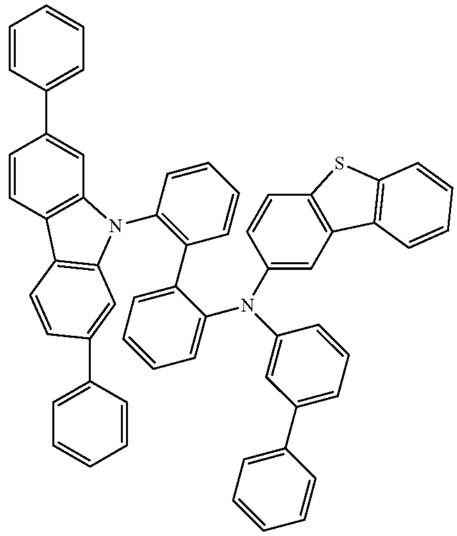
A24
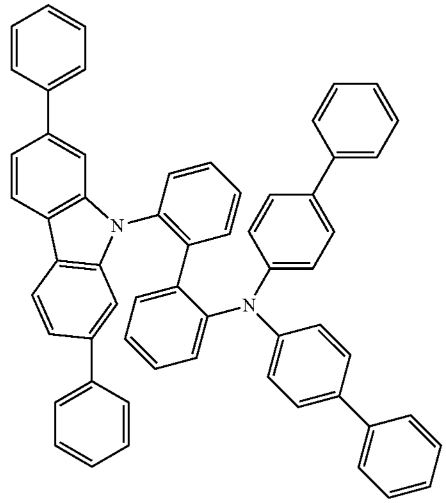
A25
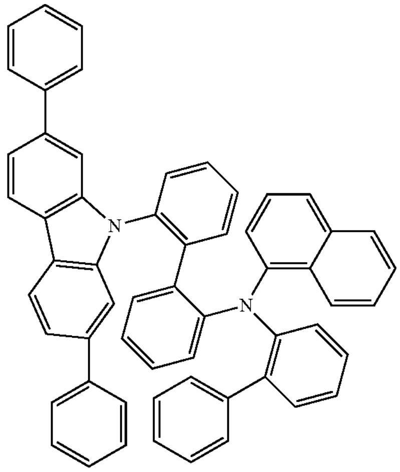

-continued
A26
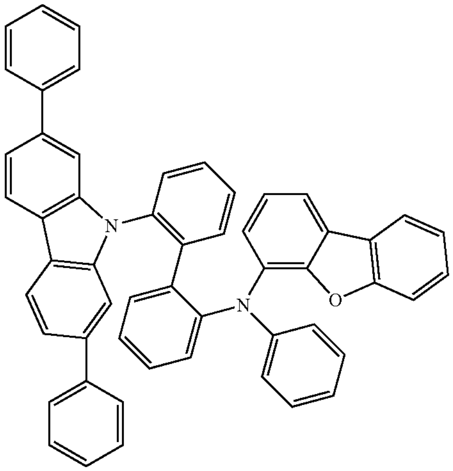
A27
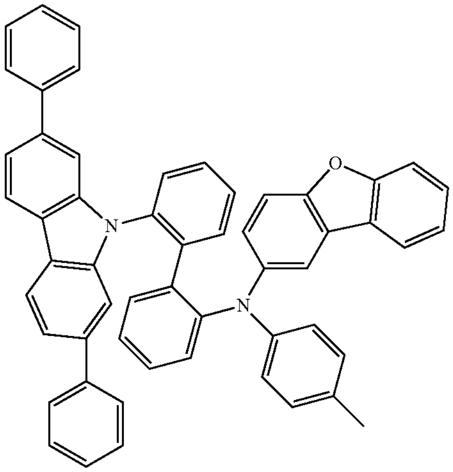
A28
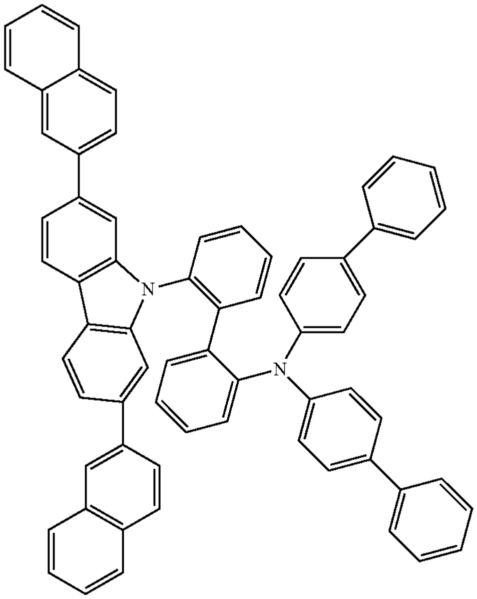
-continued
A29
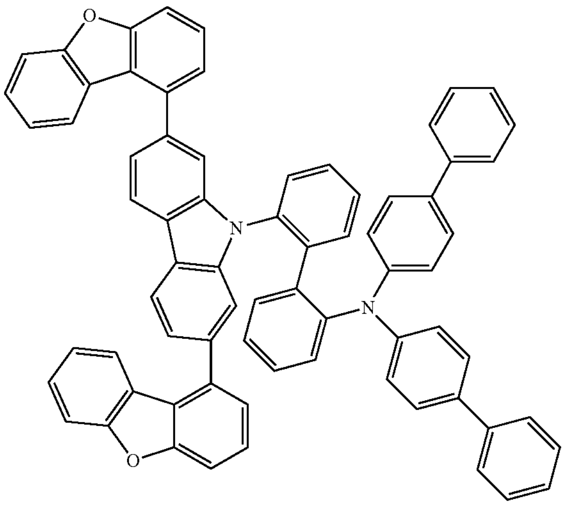
A30
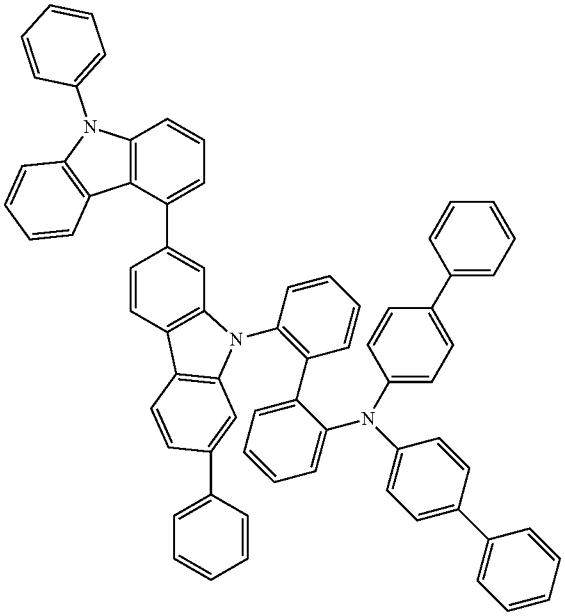
A31
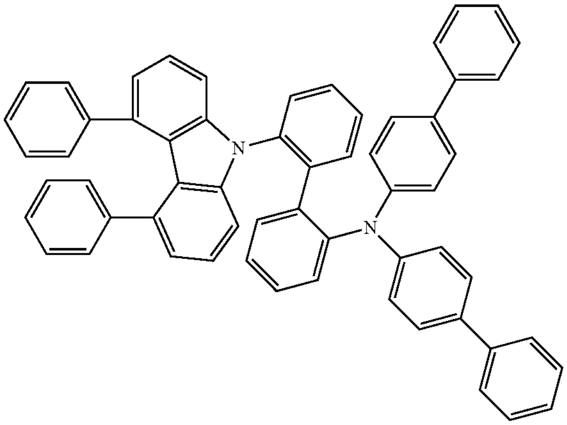

-continued
A32
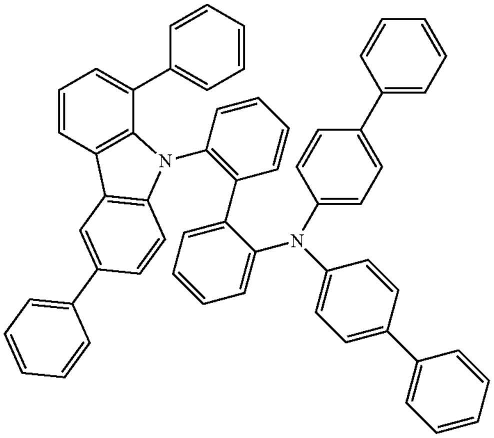
A33
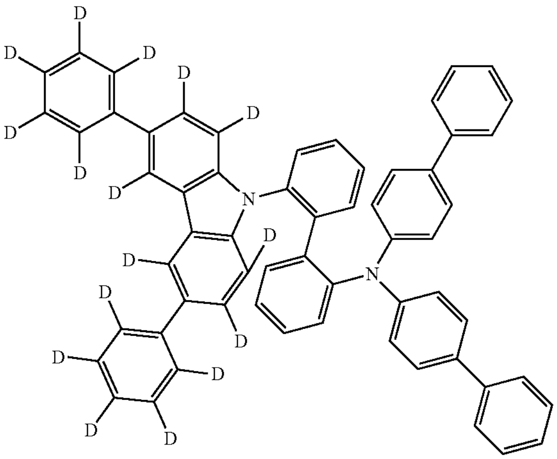
[Compound Group 1B]
B1
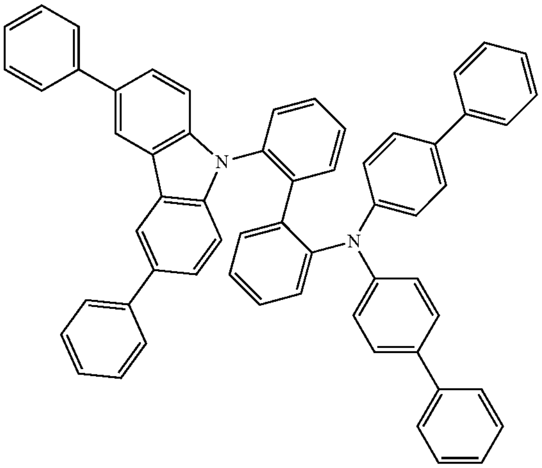
-continued
B2
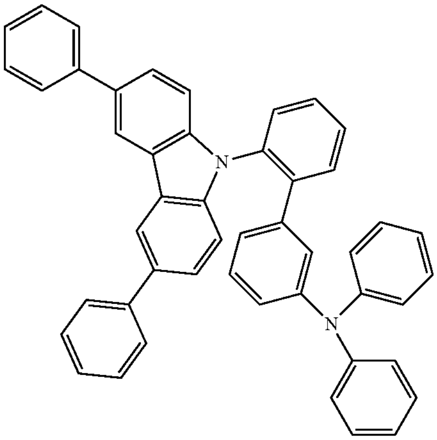
B3
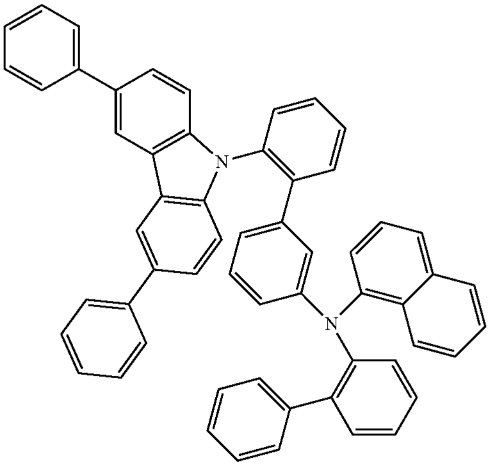
B4
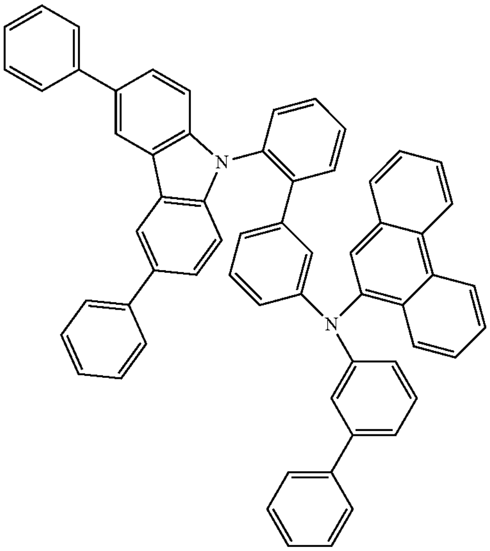

-continued
B5
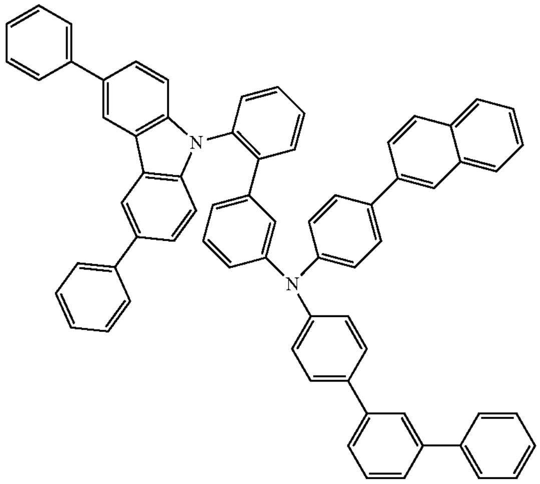
B6
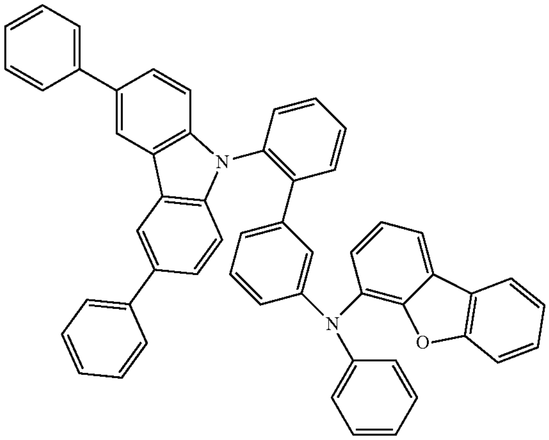
B7
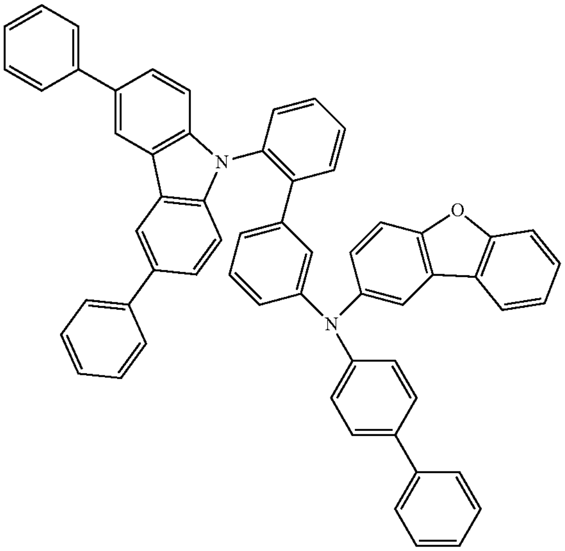
-continued
B8
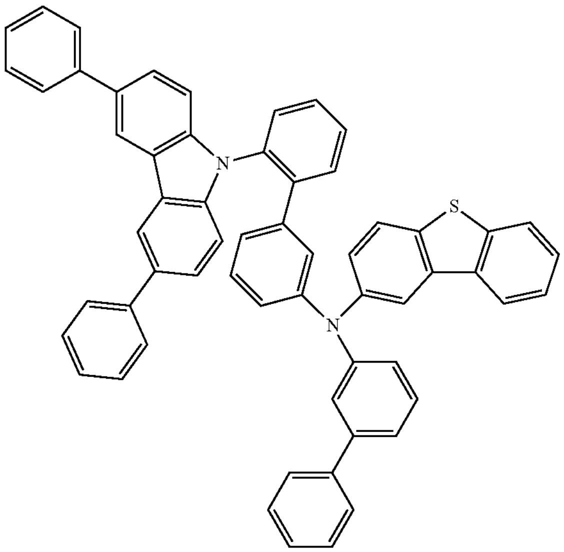
B9
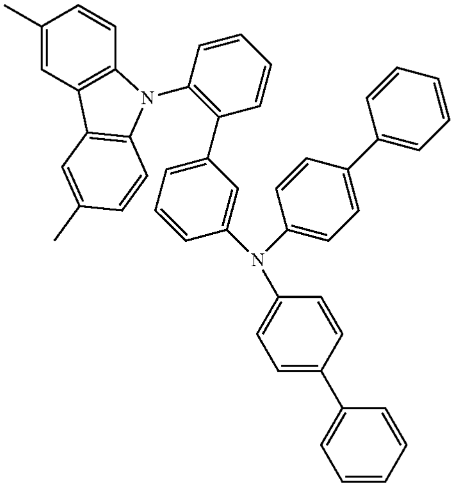
B10
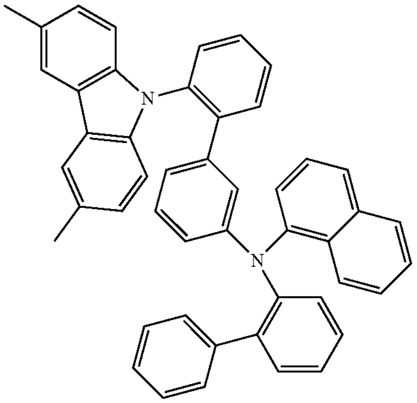

-continued
B11
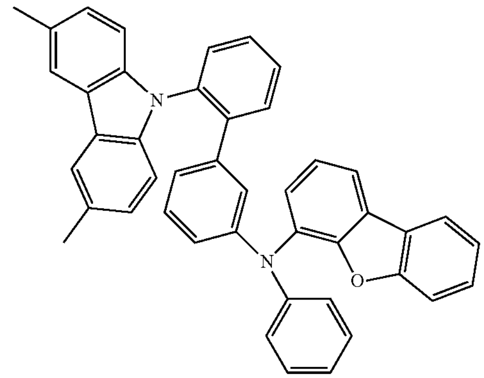
B12
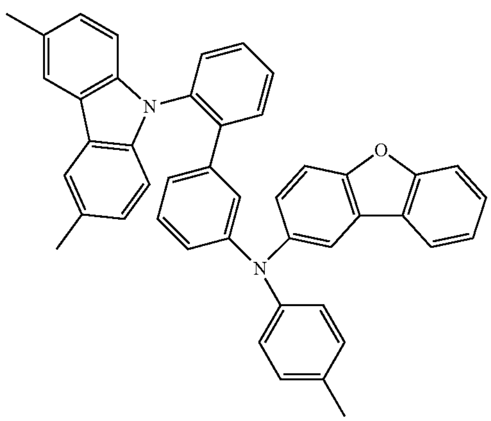
B13
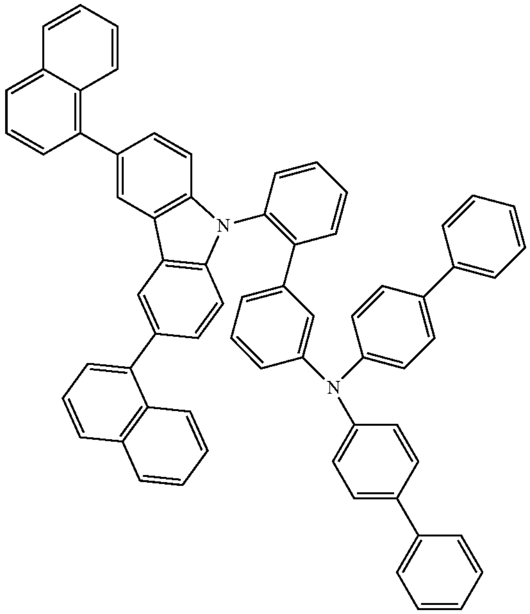
-continued
B14
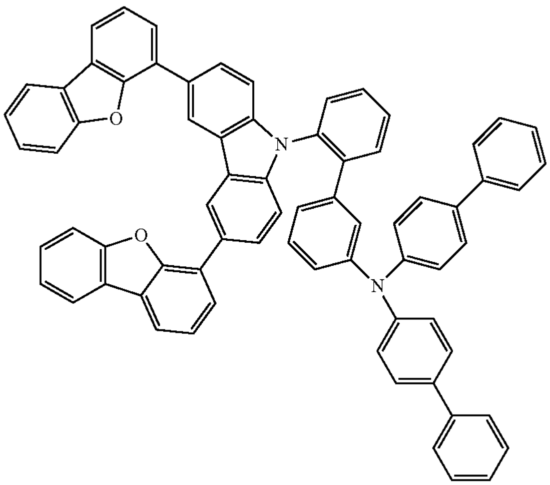
B15
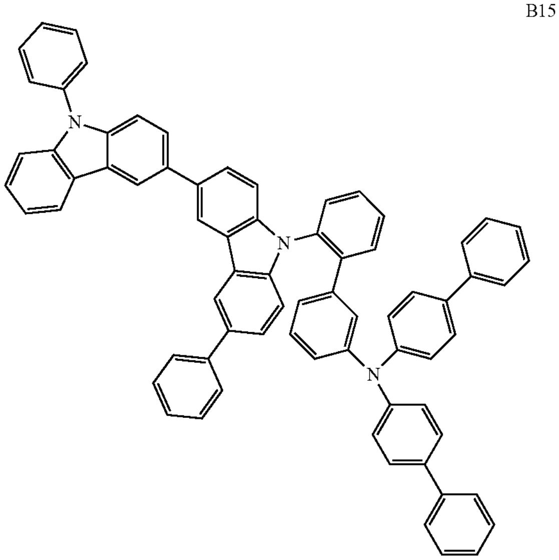
B16
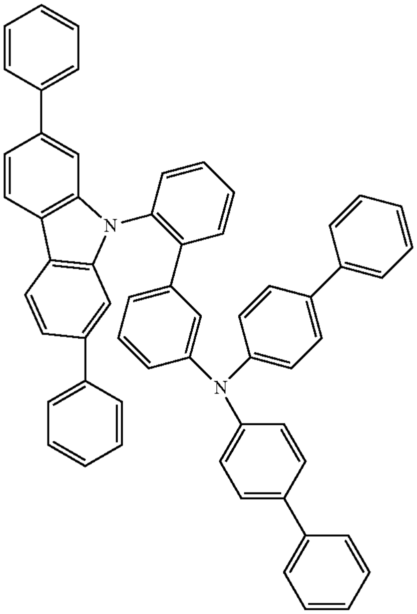

-continued
B17
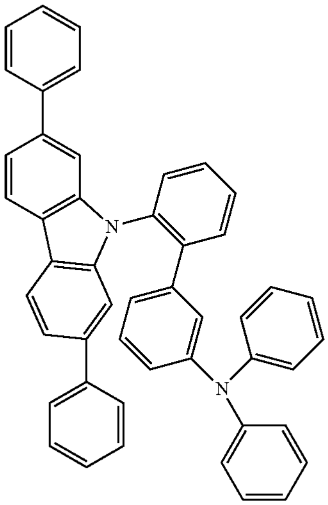
B18
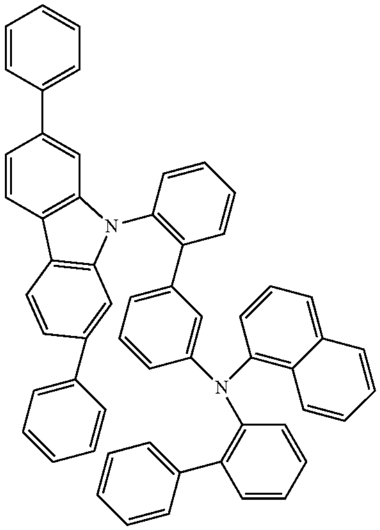
B19
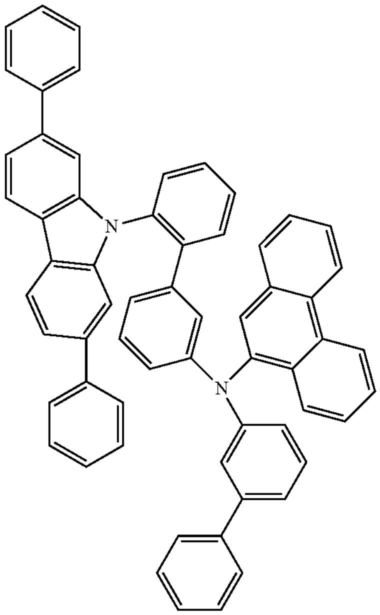
-continued
B20
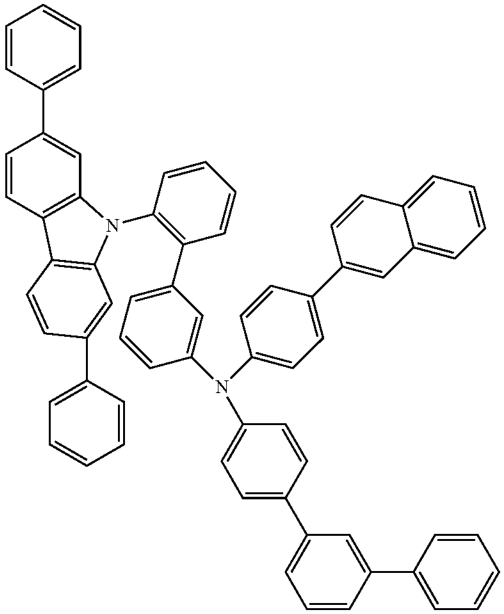
B21
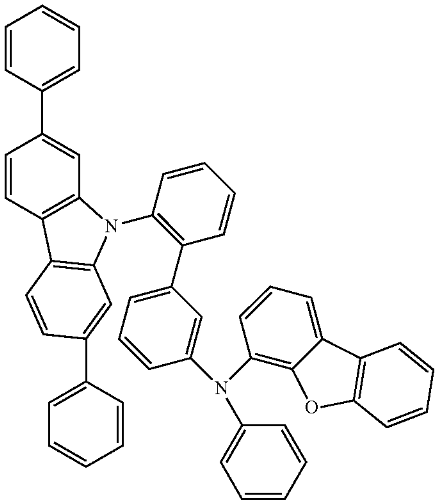

-continued
B22
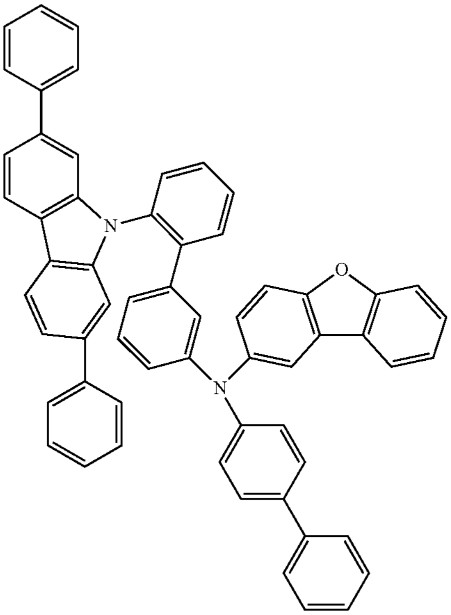
B23
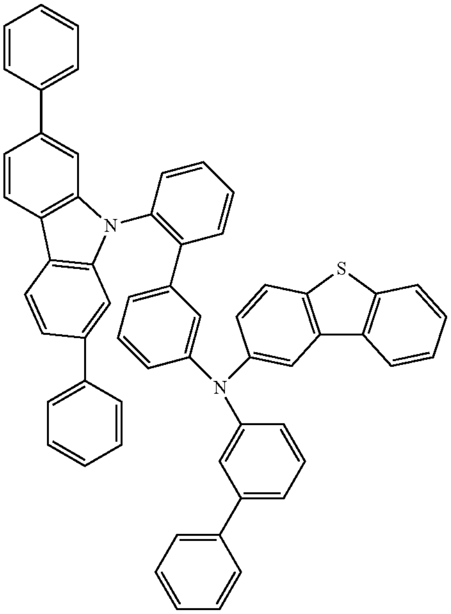
-continued
B24
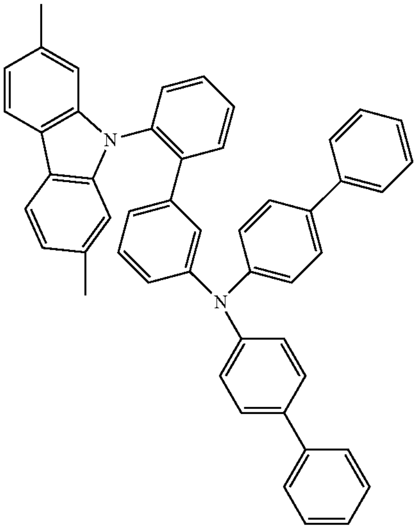
B25
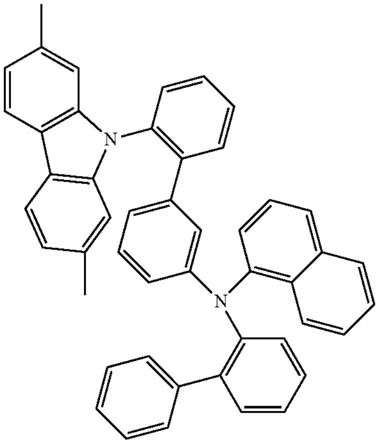
B26
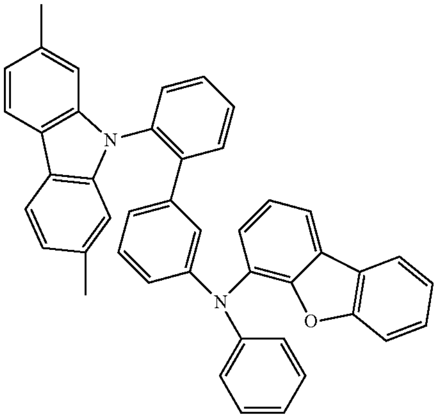

-continued
B27
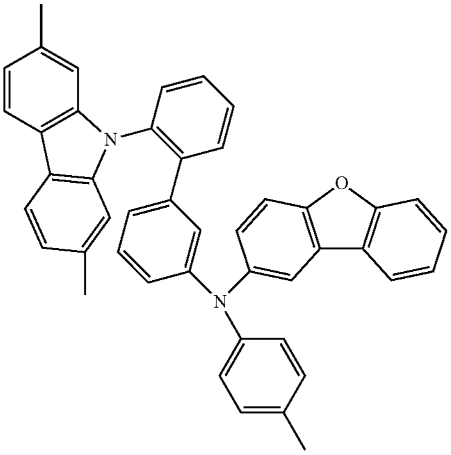
B28
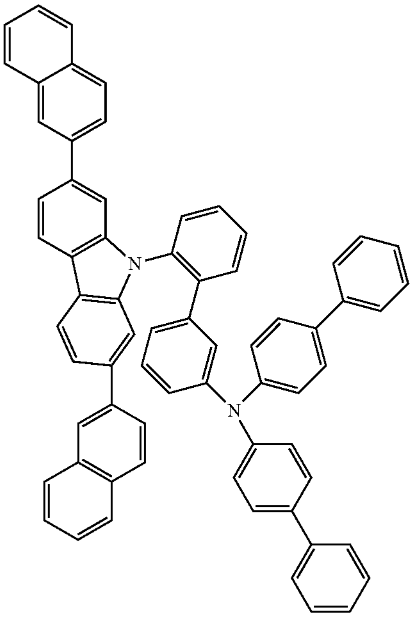
-continued
B29
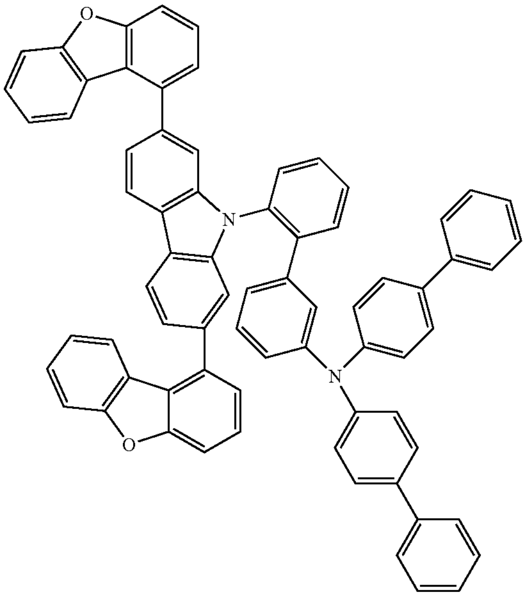
B30
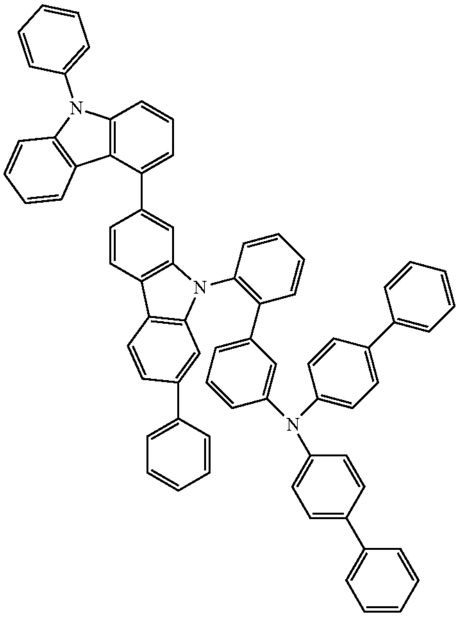

-continued
B31
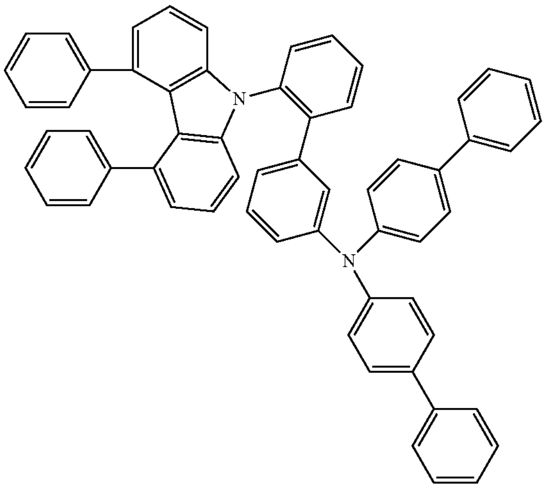
B32
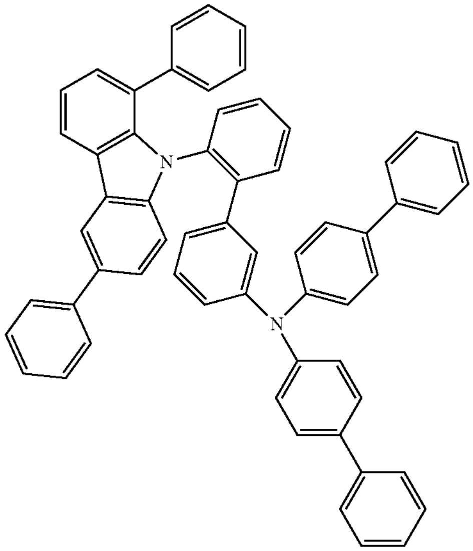
[Compound Group 1C]
C1
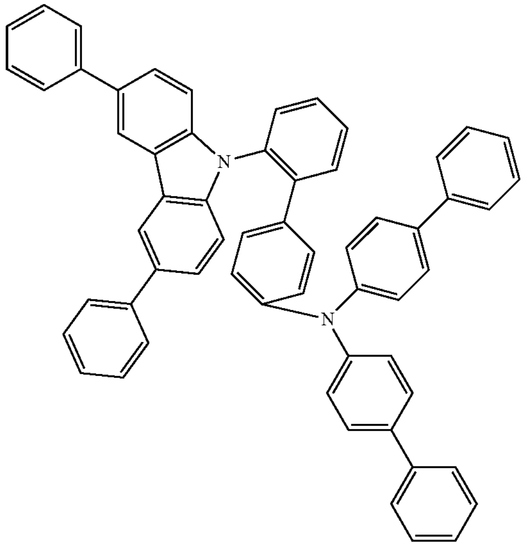
-continued
C2
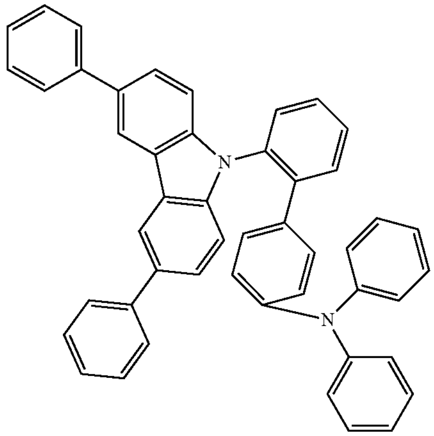
C3
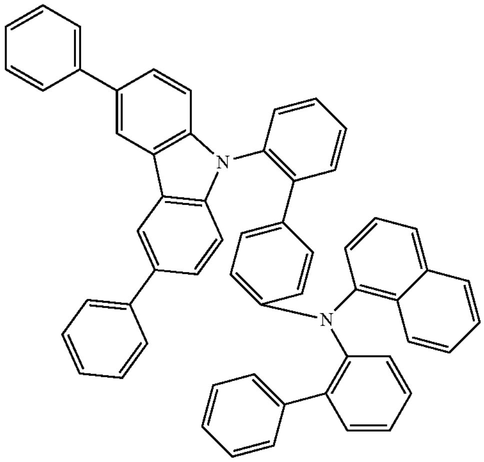
C4
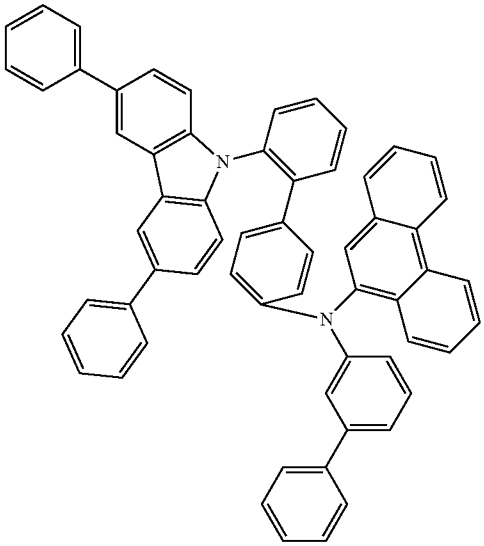

-continued
C5
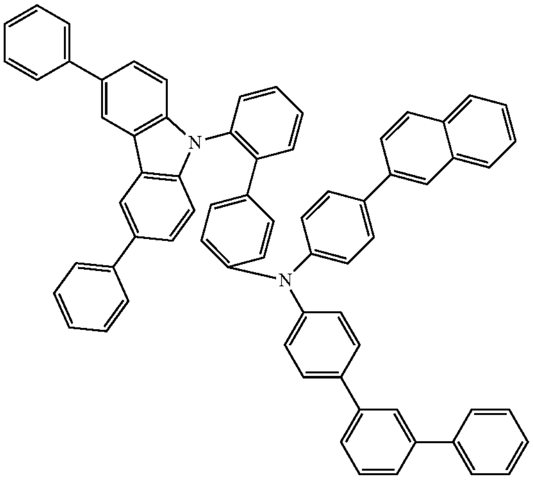
C6
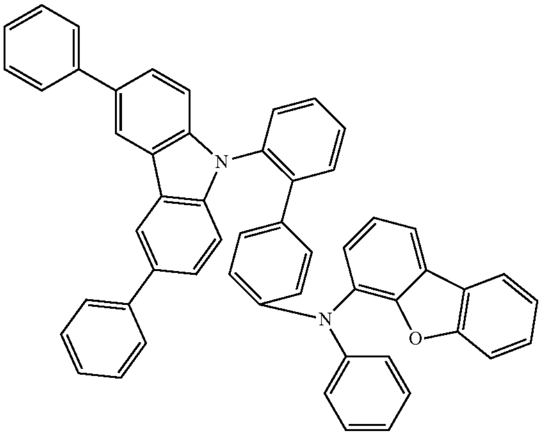
C7
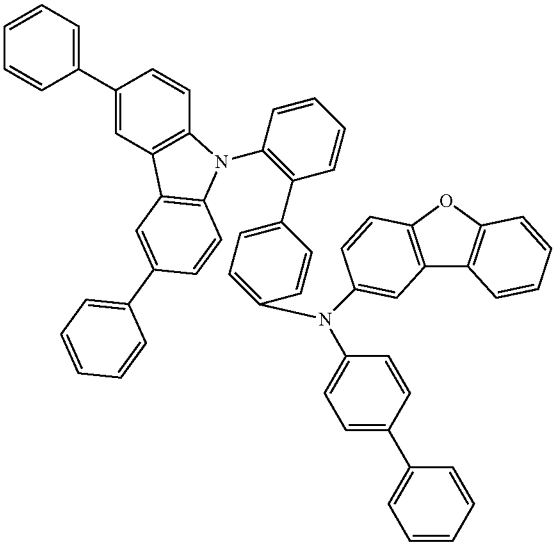
-continued
C8
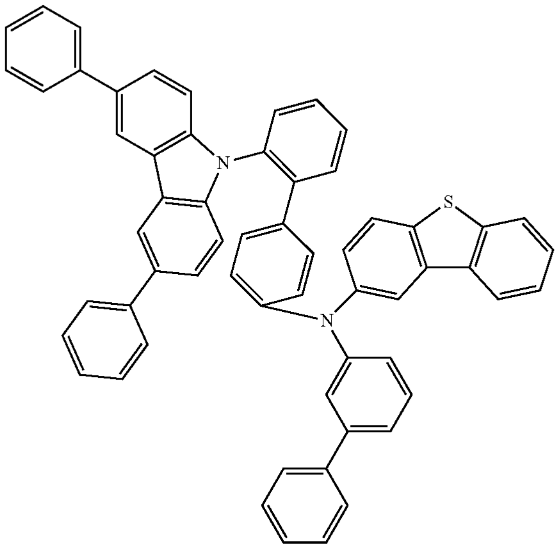
C9
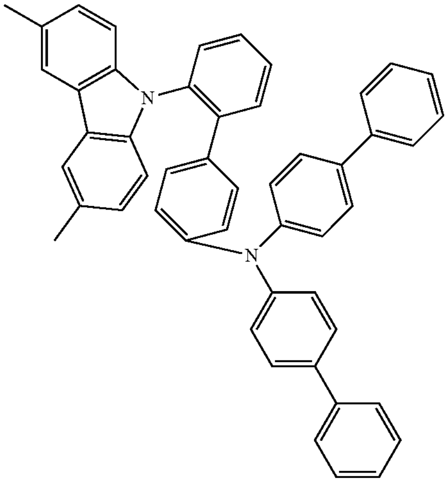
C10
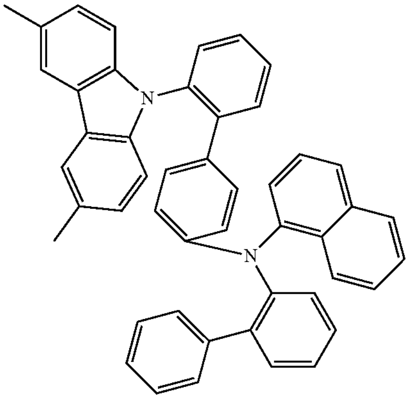

C11
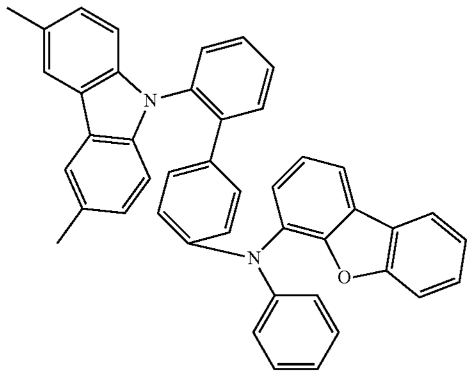
C12
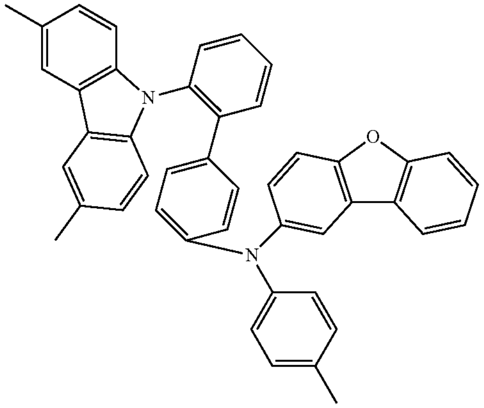
C13
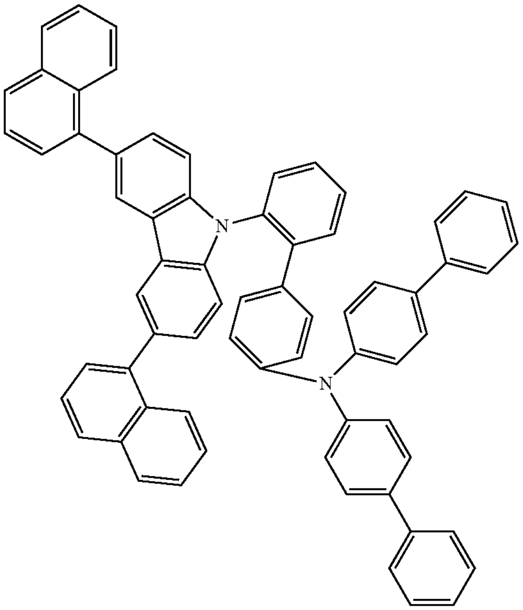
C14
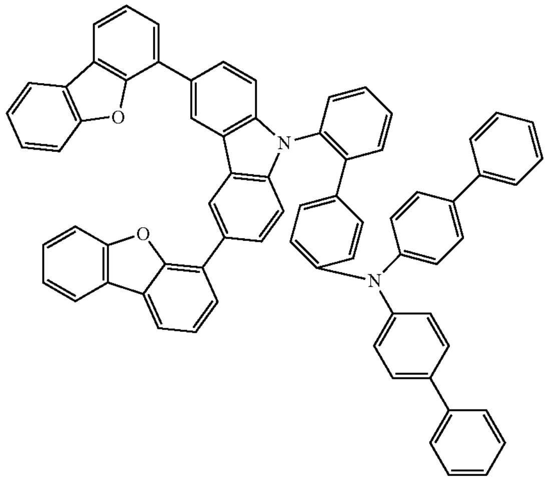
C15
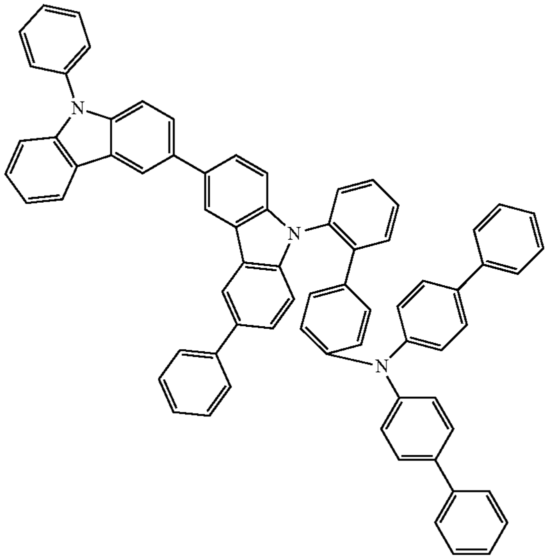

-continued
C16
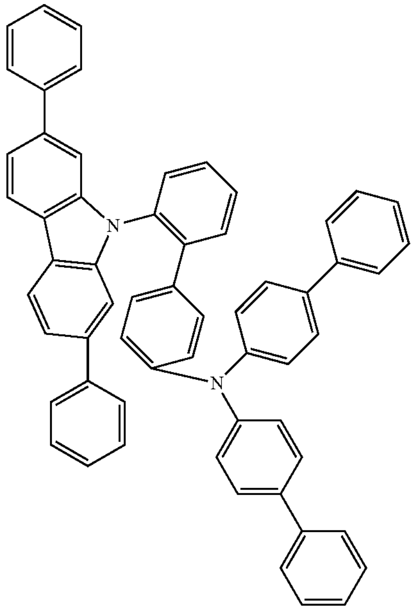
C17
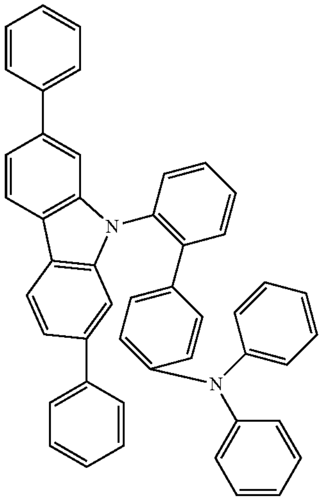
C18
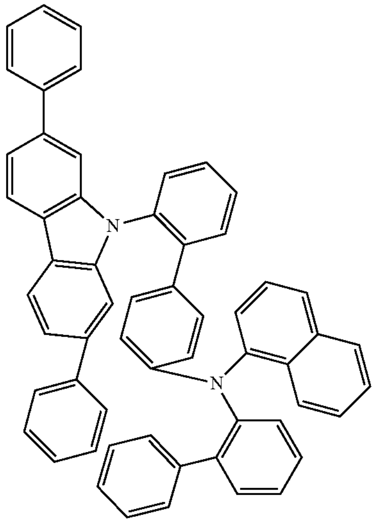
-continued
C19
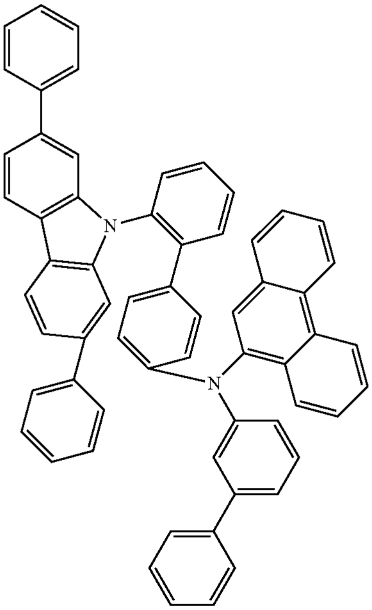
C20
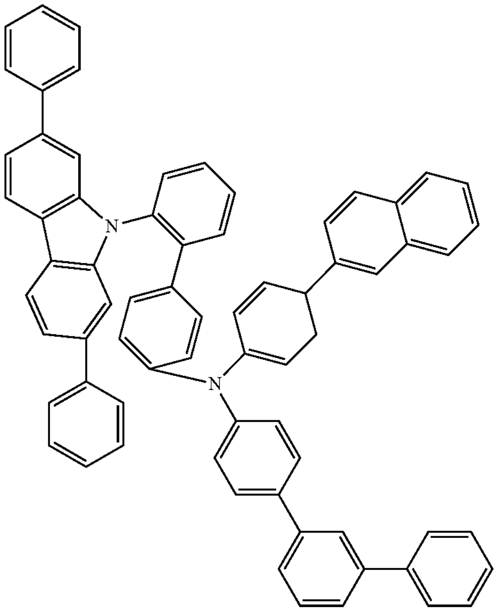

-continued
C21
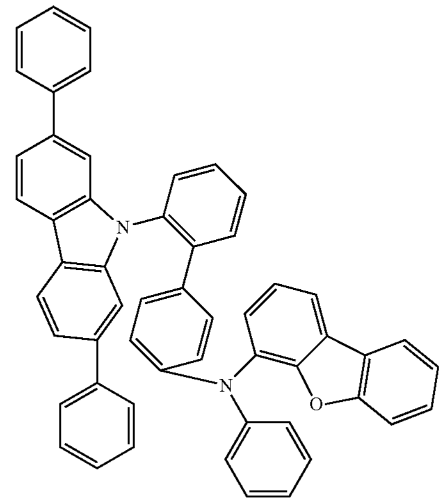
C22
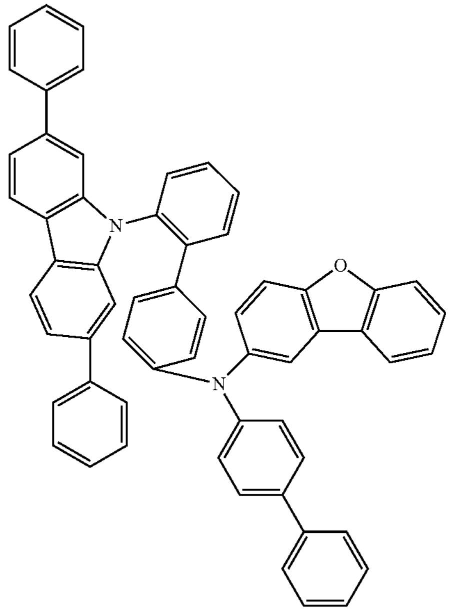
-continued
C23
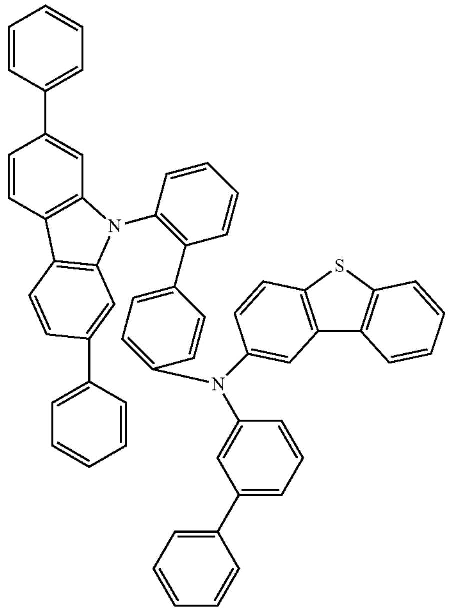
C24
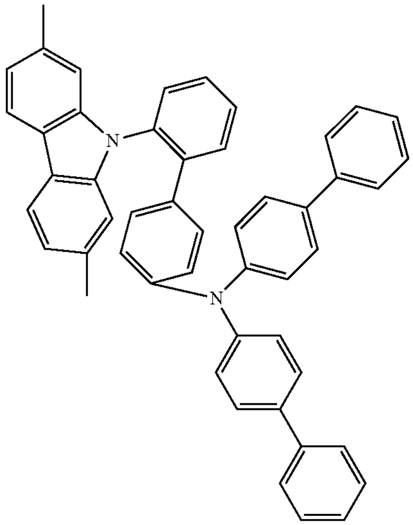
C25
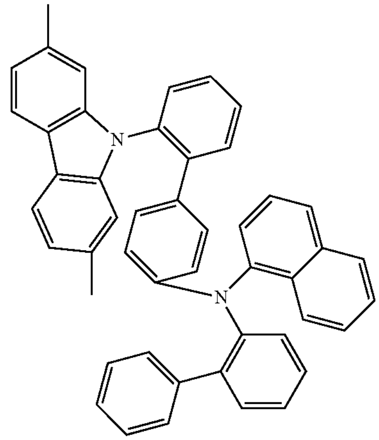

-continued
C26
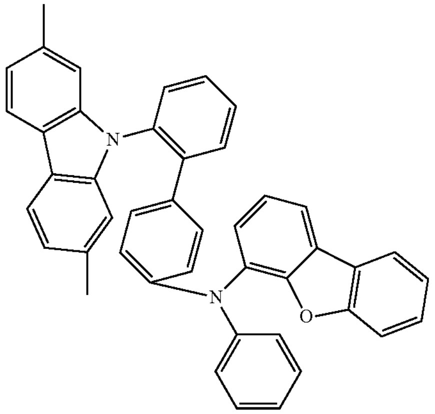
C27
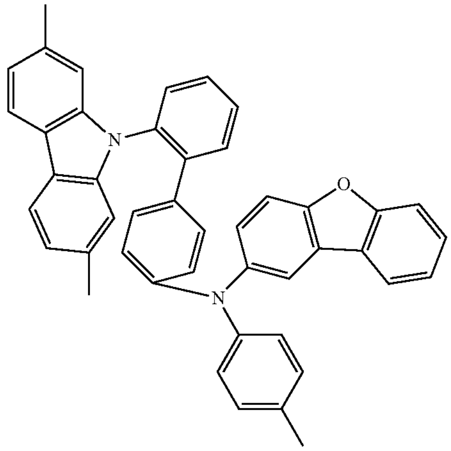
C28
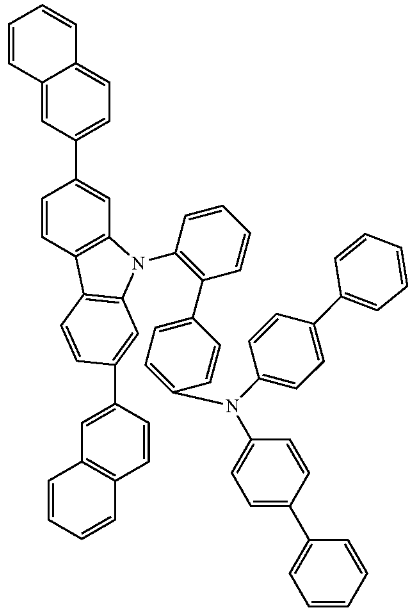
-continued
C29
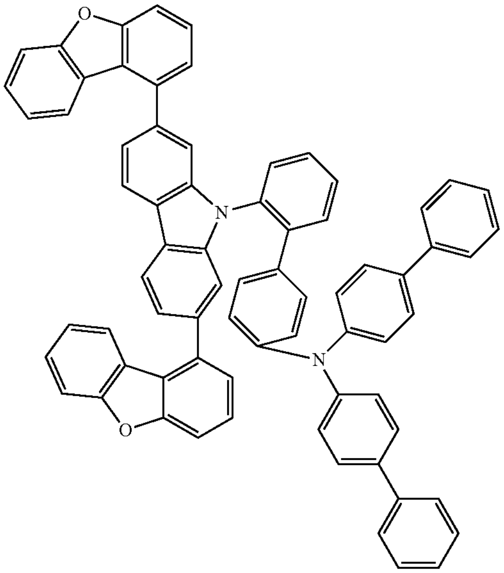
C30
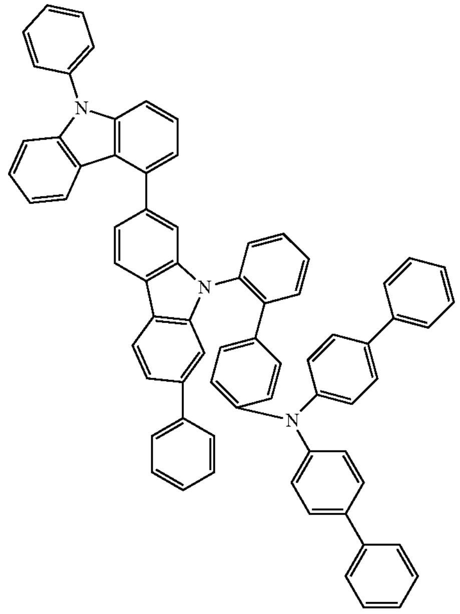

-continued
C31
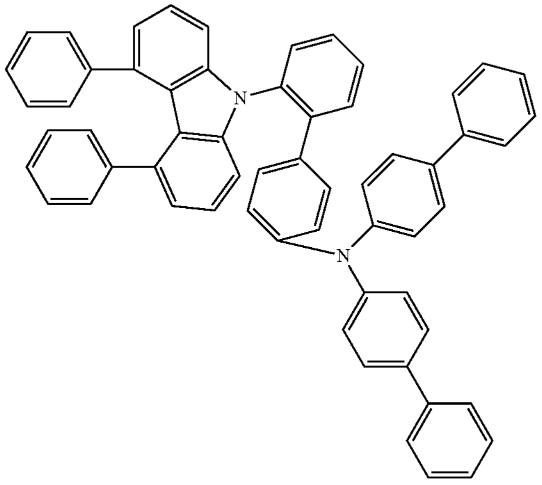
C32
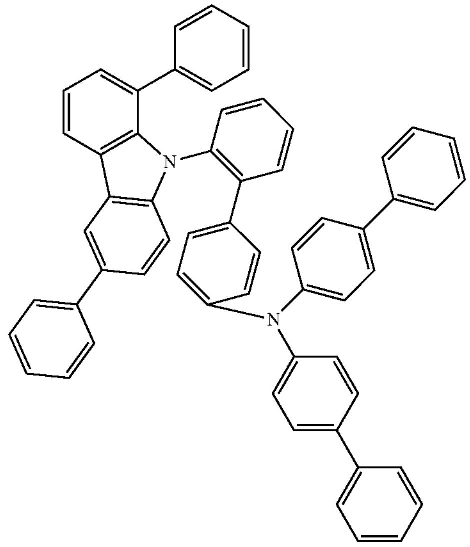
[Compound Group 1D]
D1
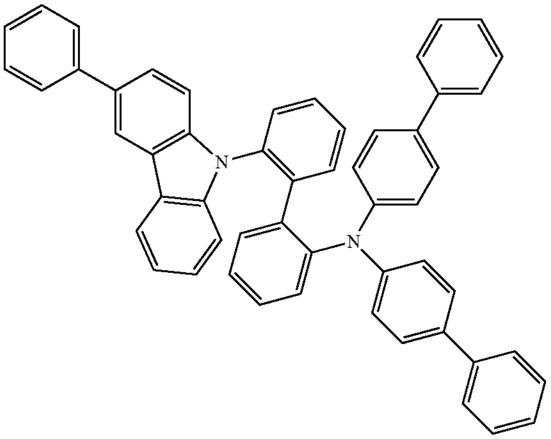
-continued
D2
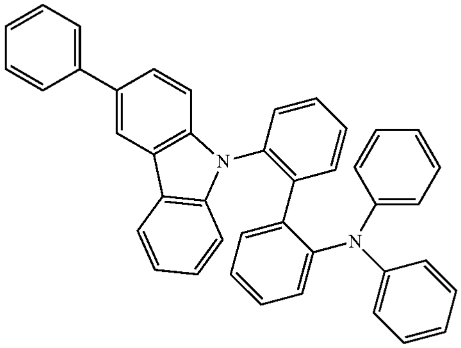
D3
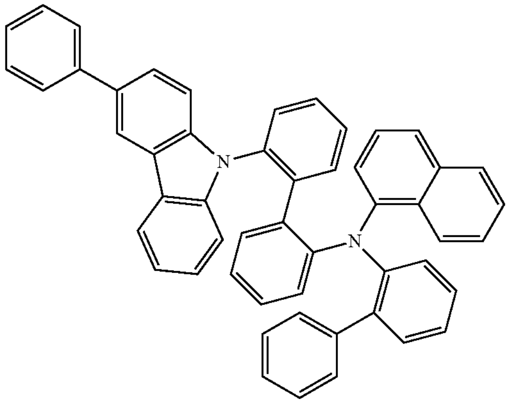
D4
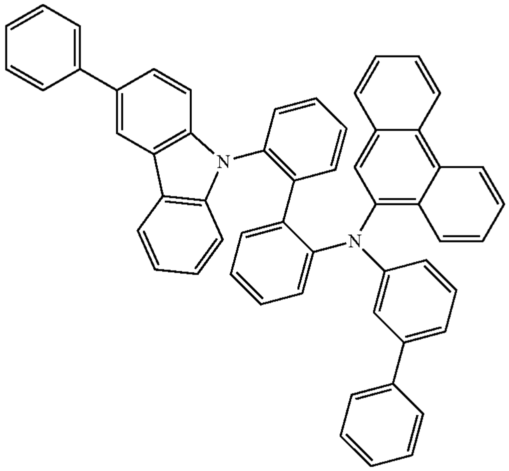
D5
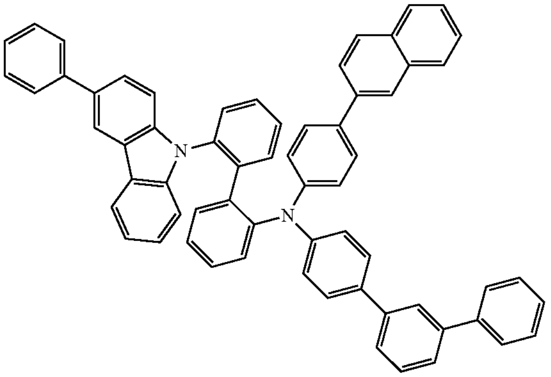

-continued
D6
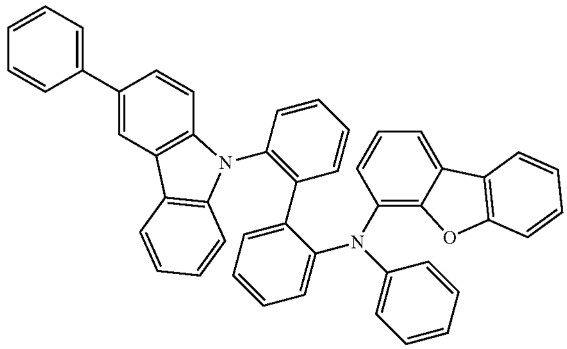
D7
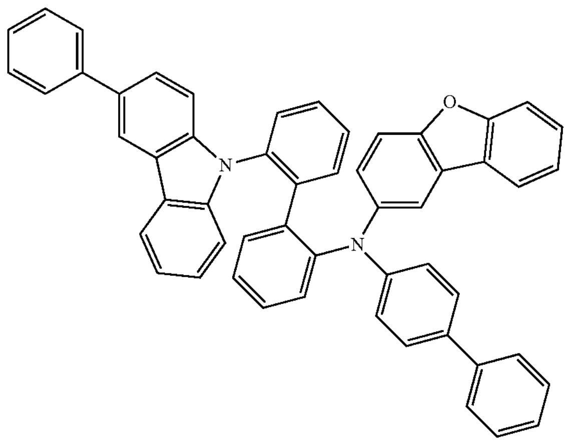
D8
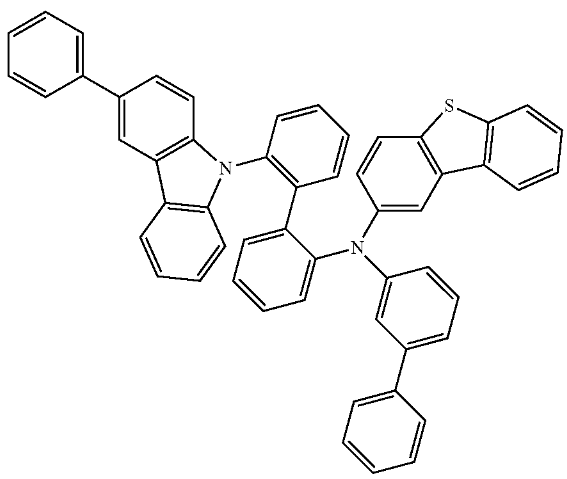
-continued
D9
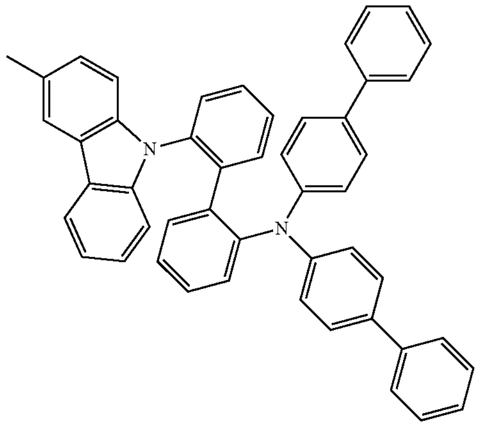
D10
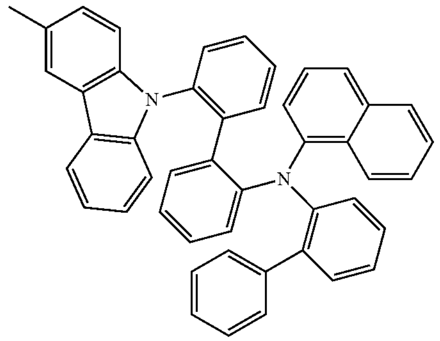
D11
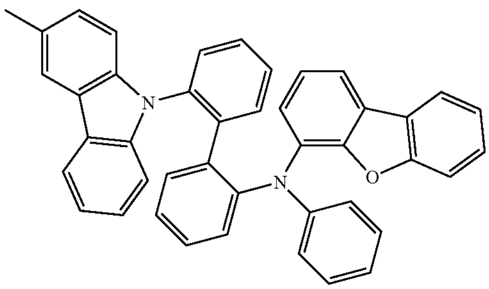
D12
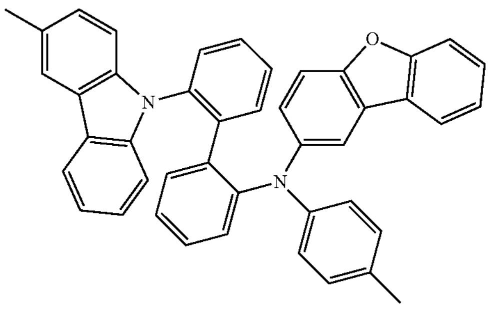

-continued
D13
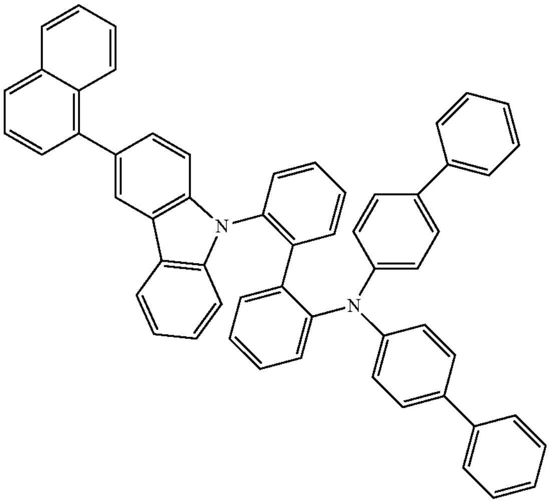
D14
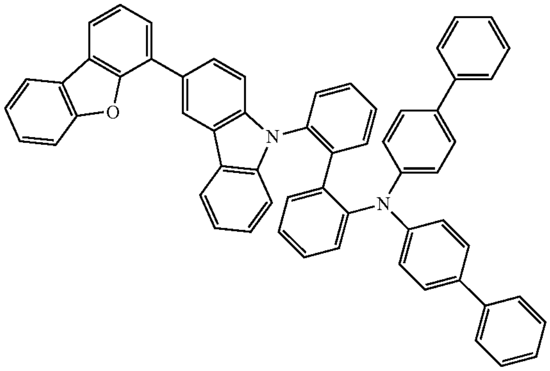
D15
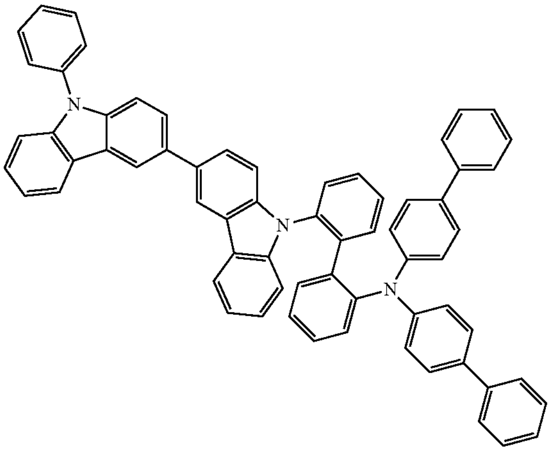
-continued
D16
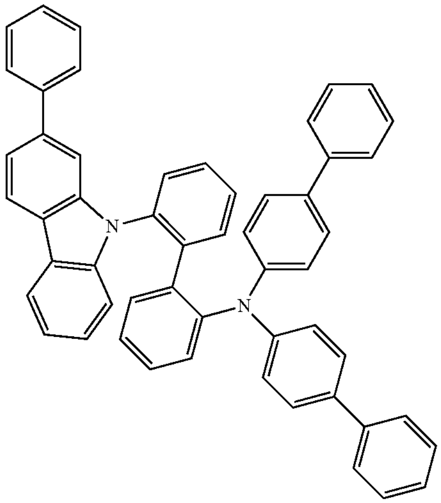
D17
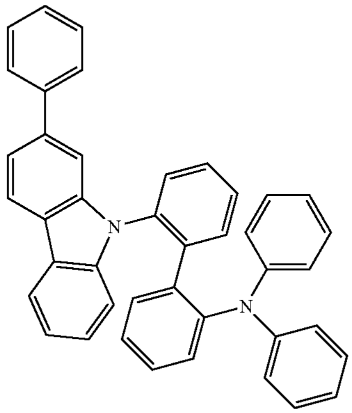
D18
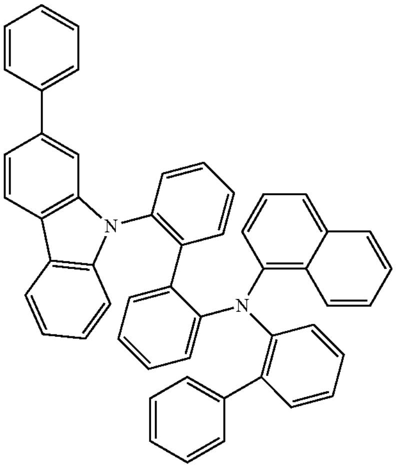

-continued
D19
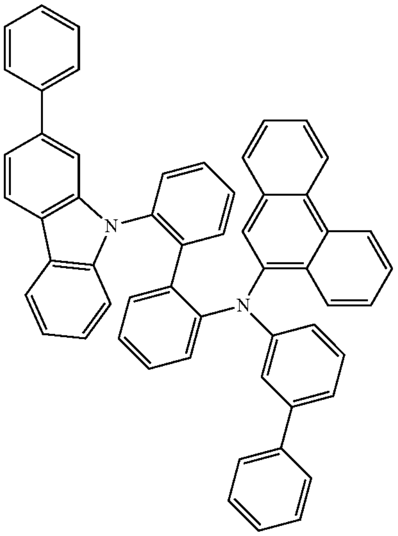
D20
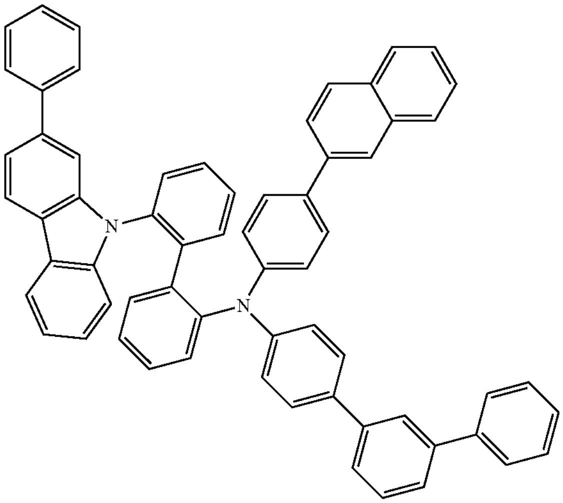
D21
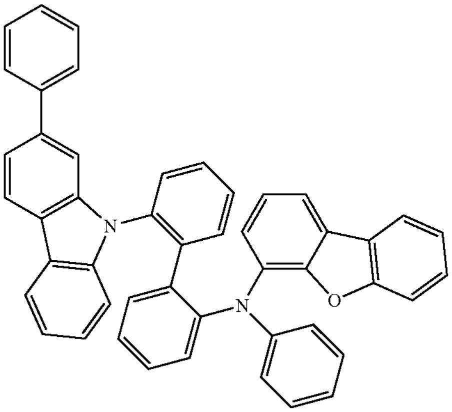
-continued
D22
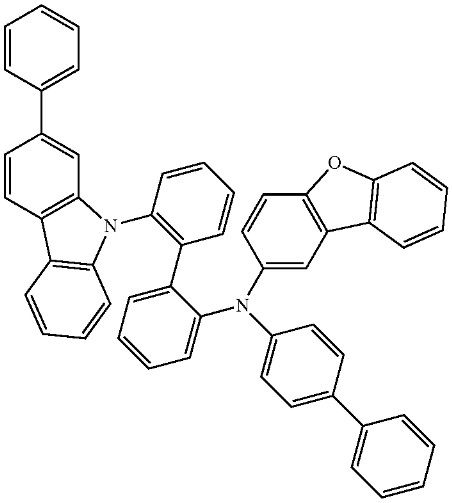
D23
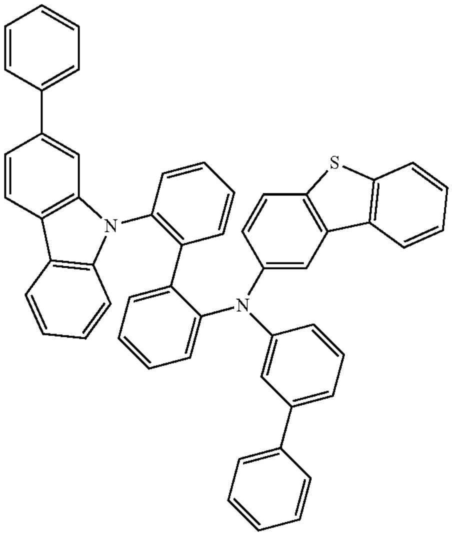
D24
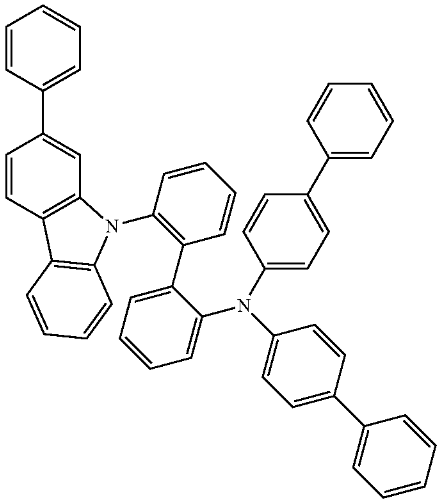

-continued
D25
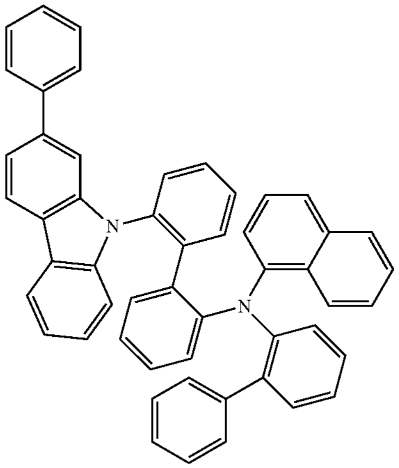
D26
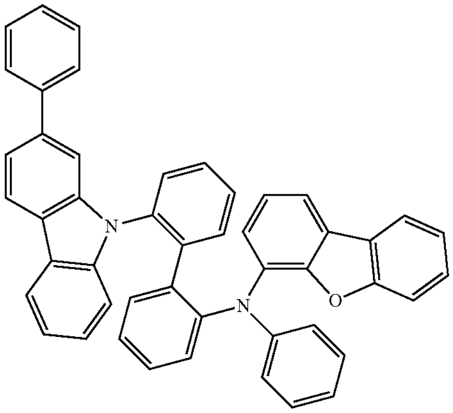
D27
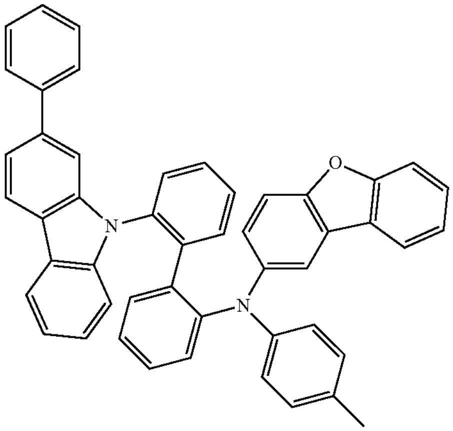
-continued
D28
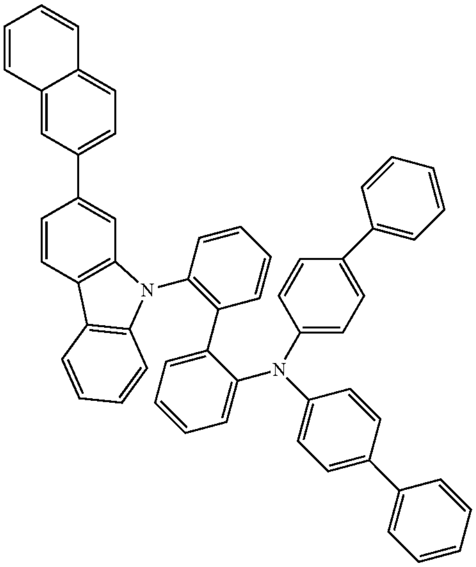
D29
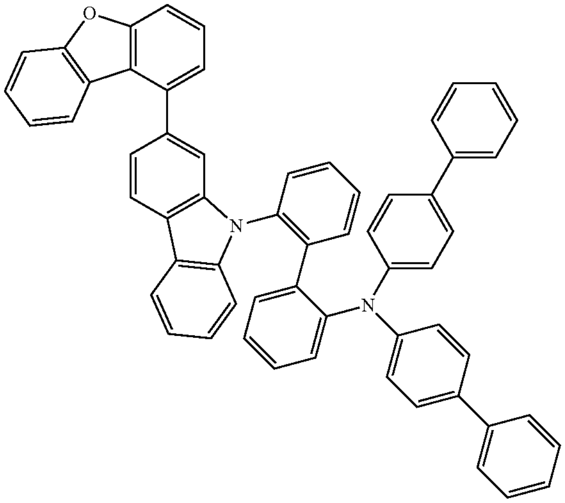

-continued
D30
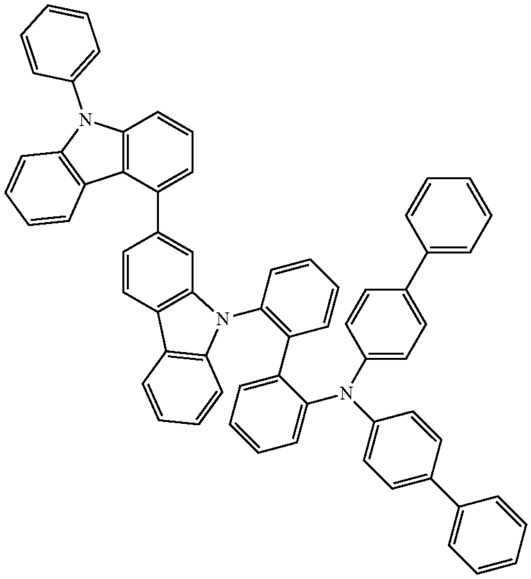
D31
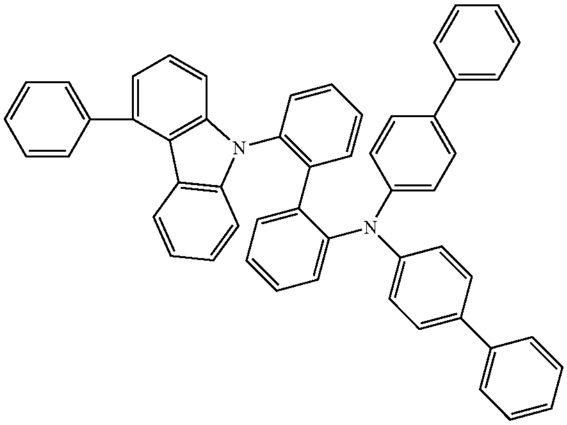
D32
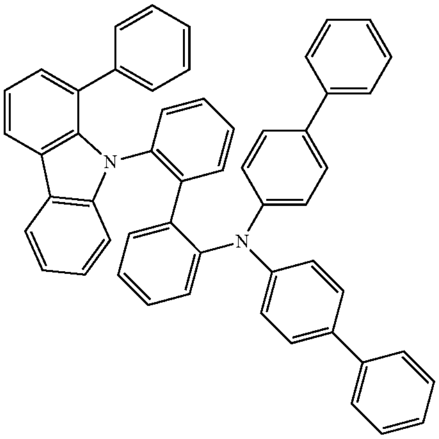
-continued
D33
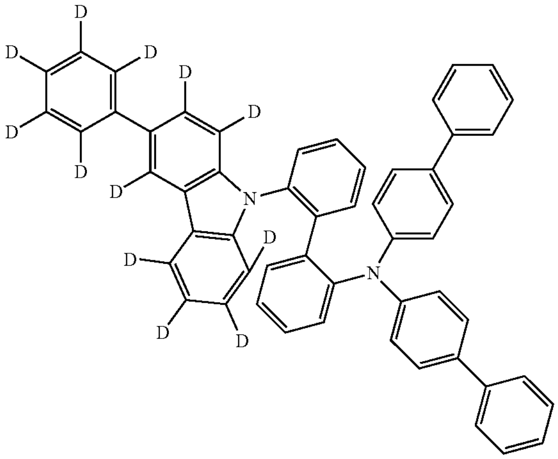
[Compound Group 1E]
E1
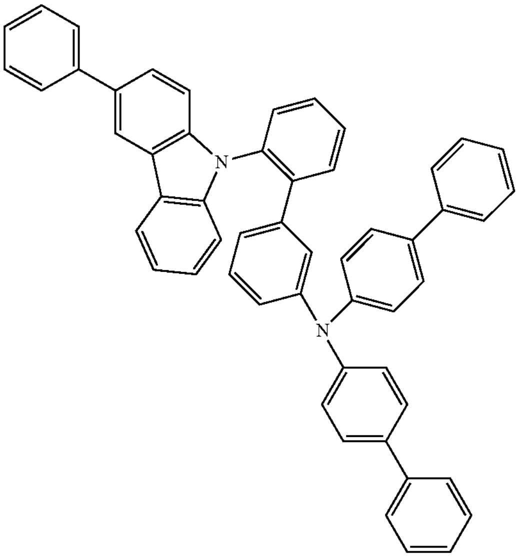
E2
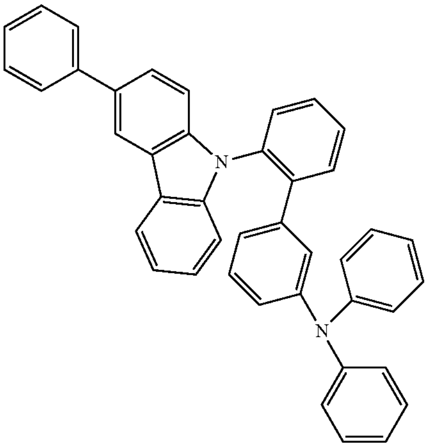

-continued
E3
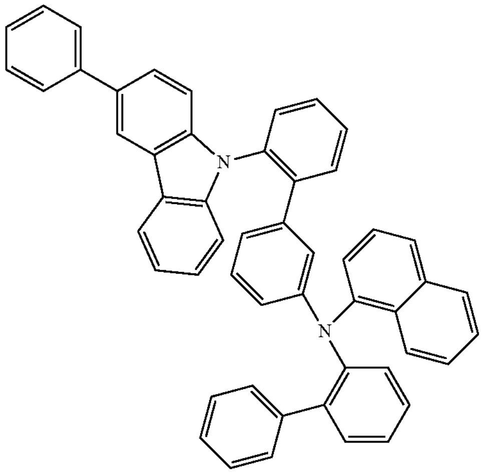
E4
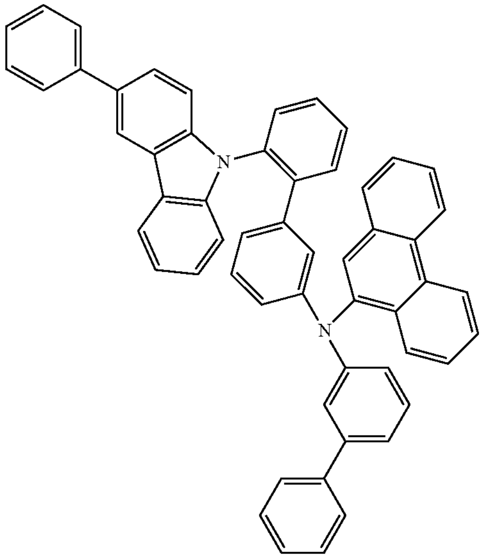
E5
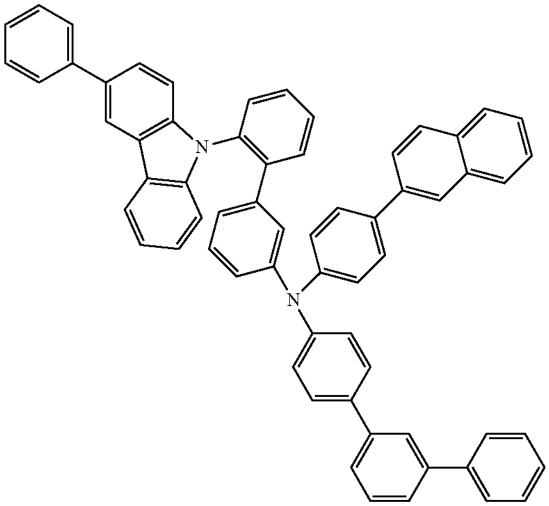
-continued
E6
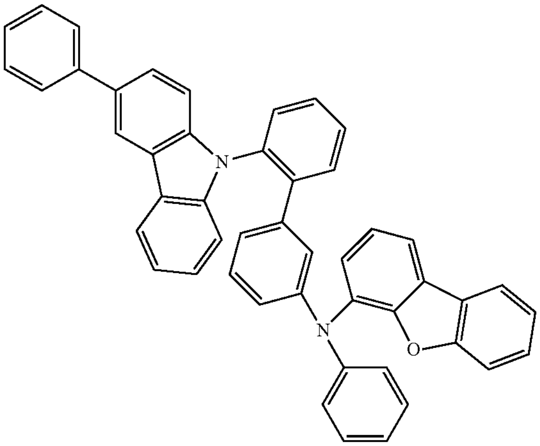
E7
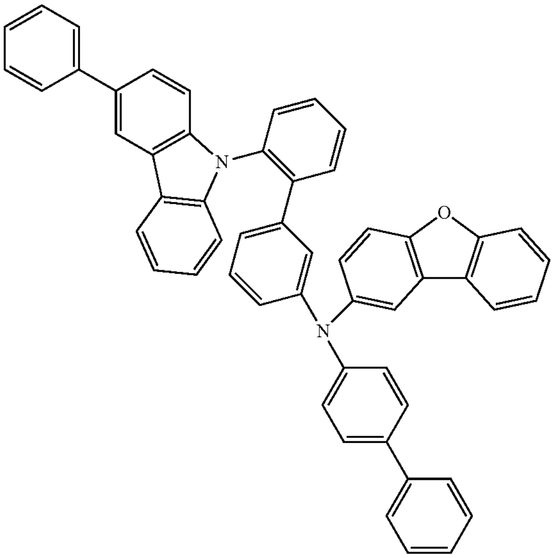
E8
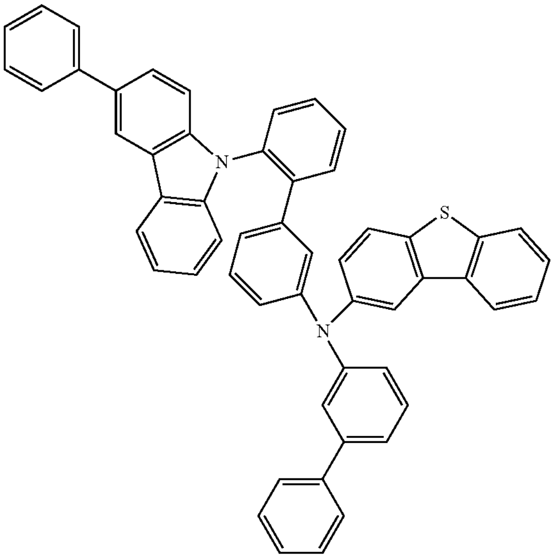

-continued
E9
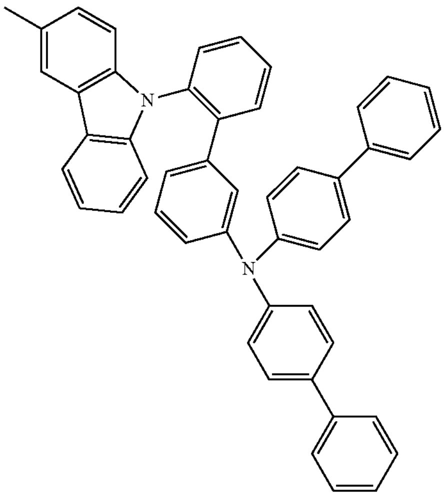
E10
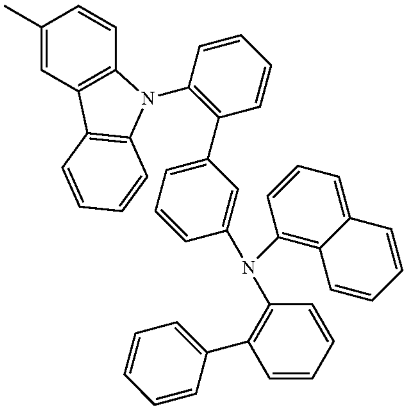
E11
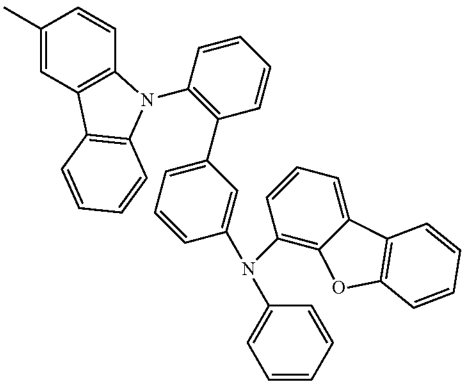
-continued
E12
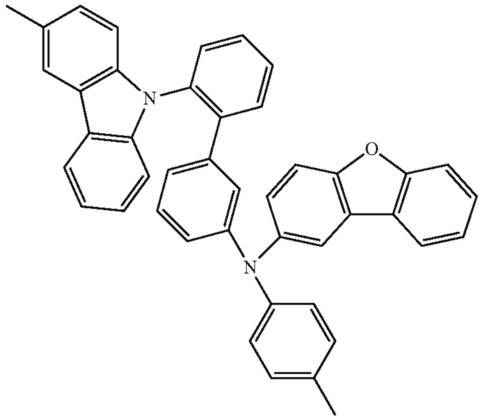
E13
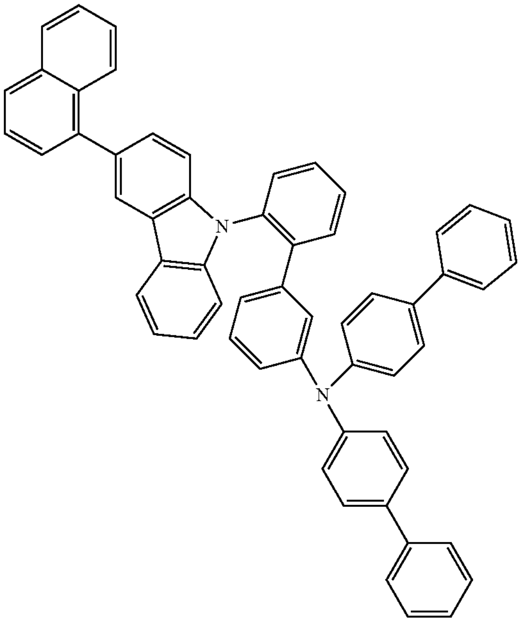
E14
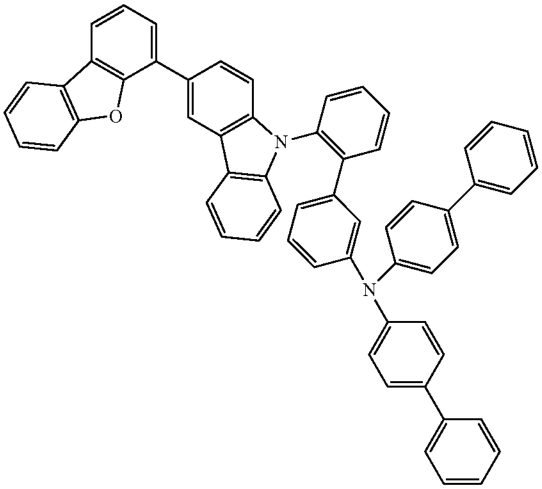

-continued
E15
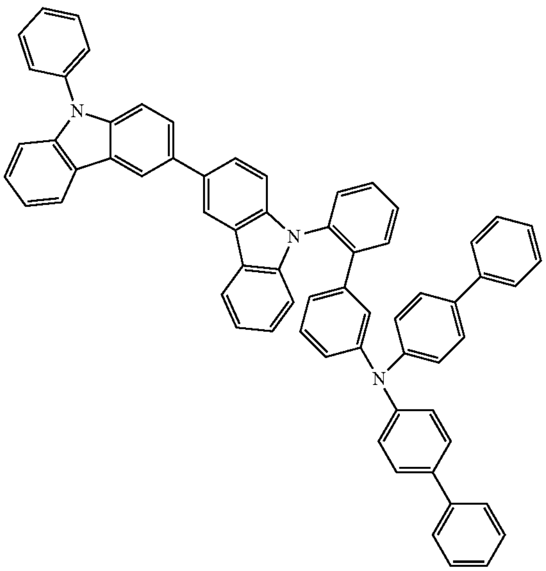
E16
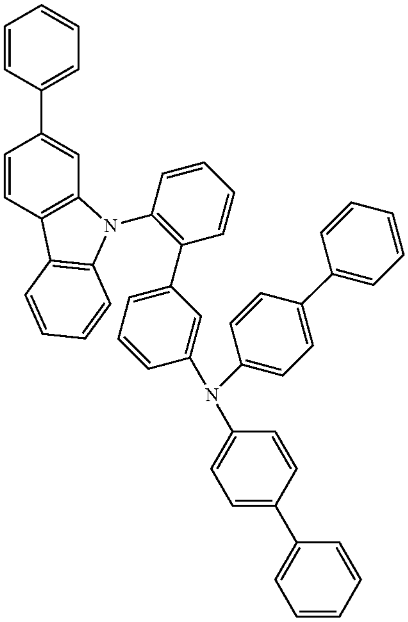
-continued
E17
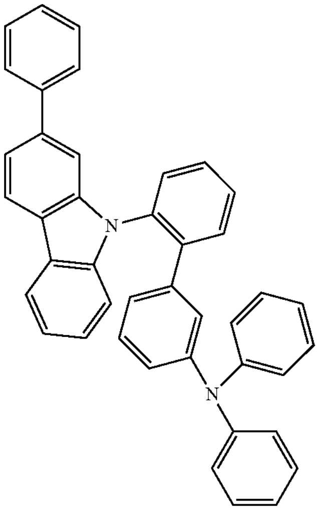
E18
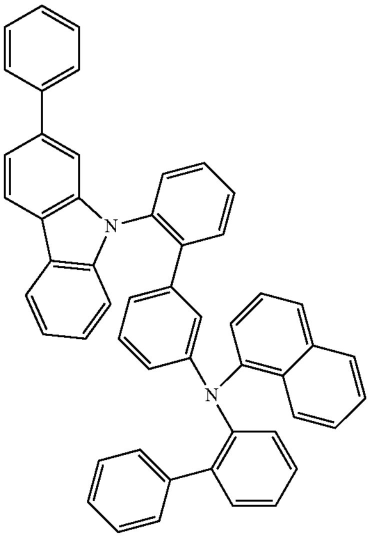
E19
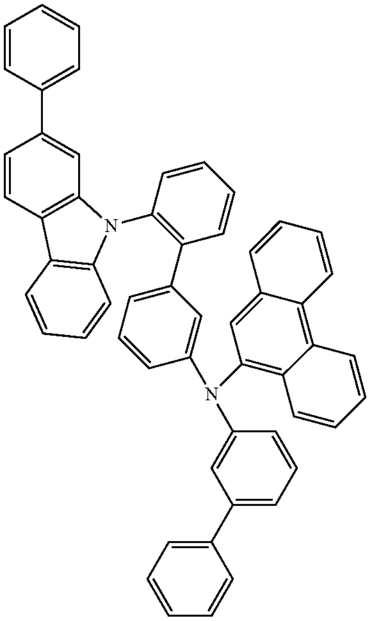

-continued
E20
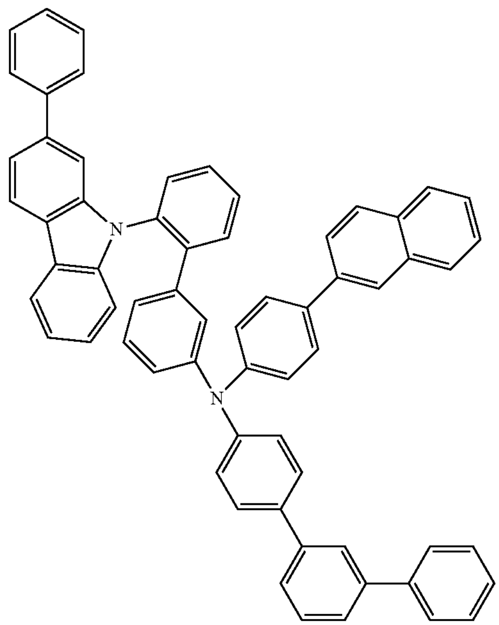
E21
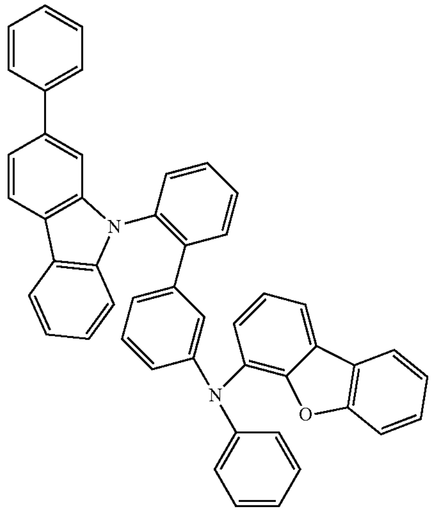
-continued
E22
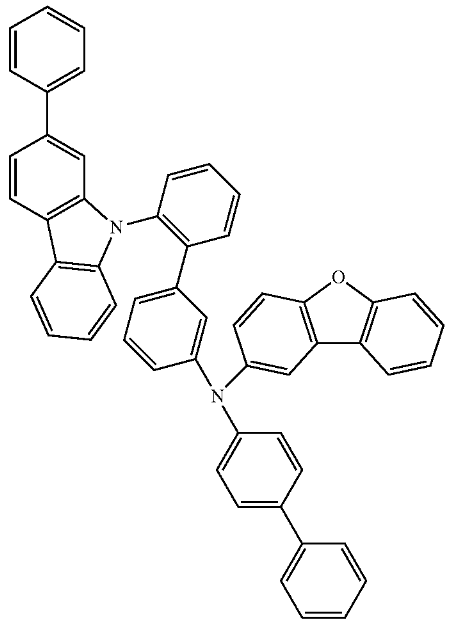
E23
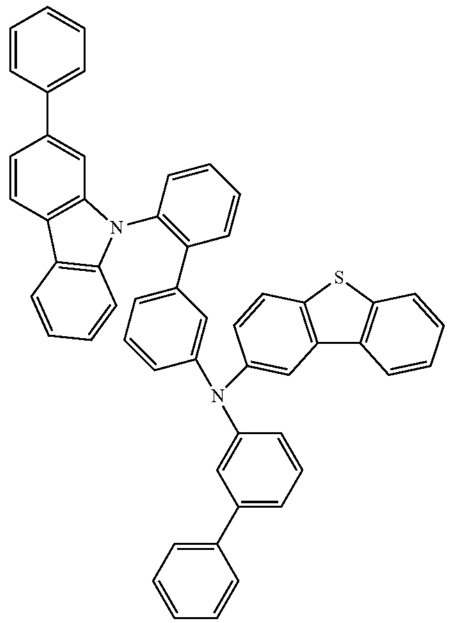

-continued
E24
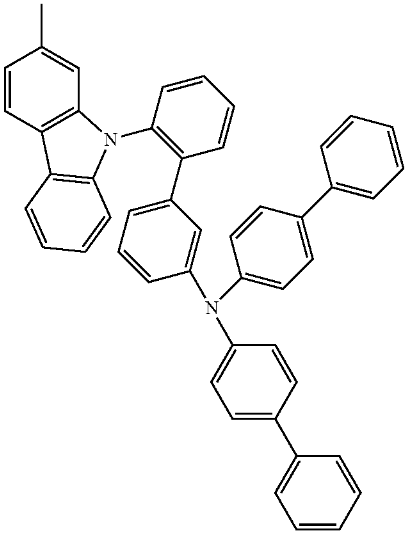
E25
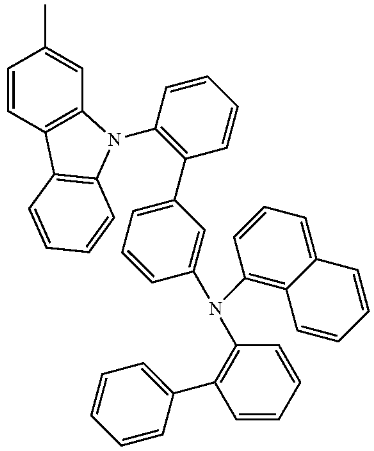
E26
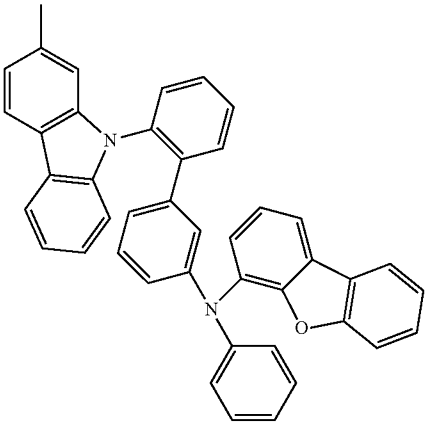
-continued
E27
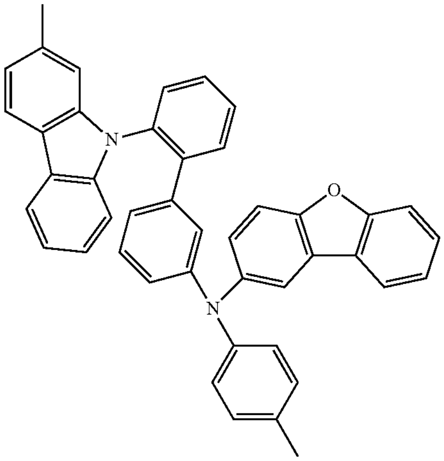
E28
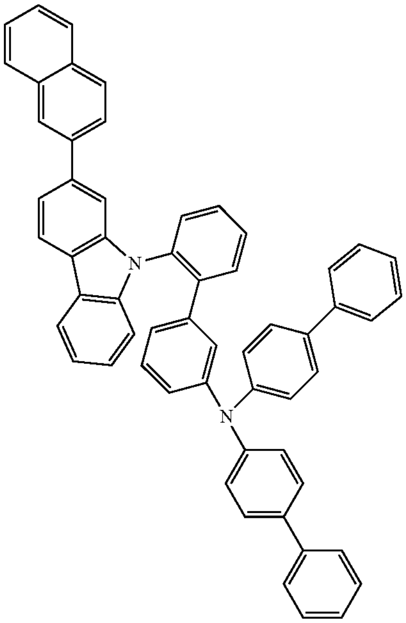
E29
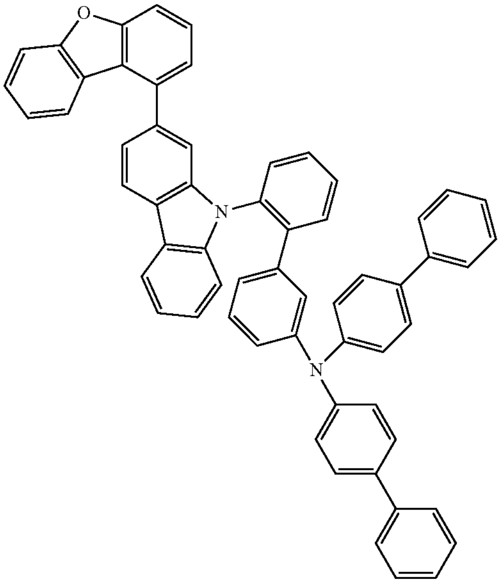

-continued
E30
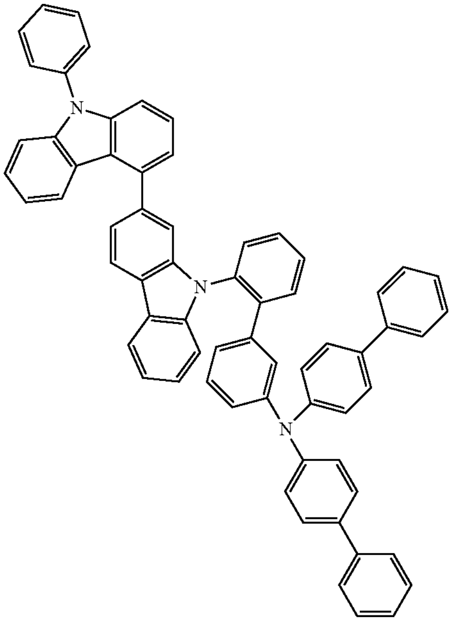
E31
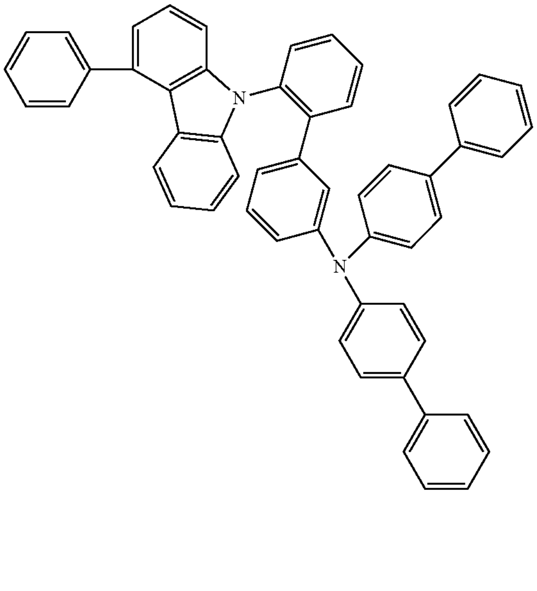
-continued
E32
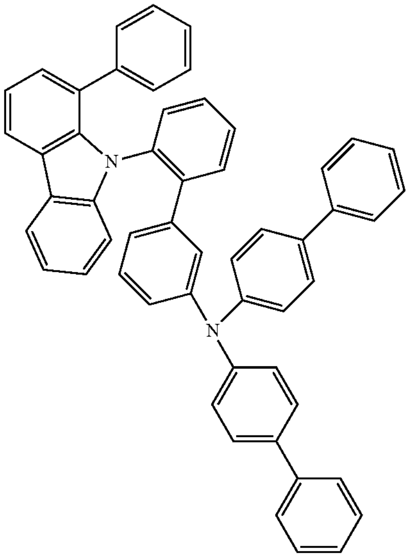
[Compound Group 1F]
F1
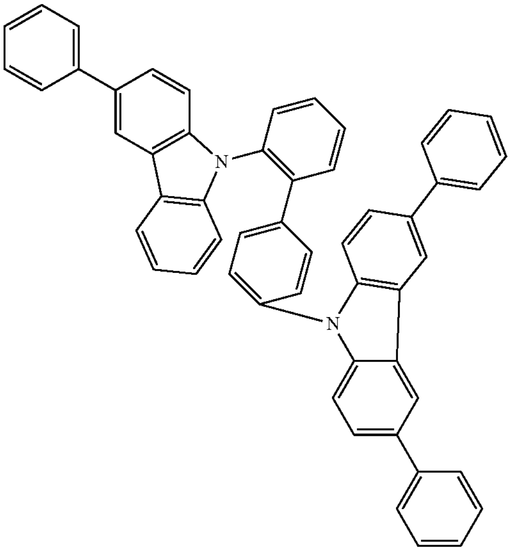
F2
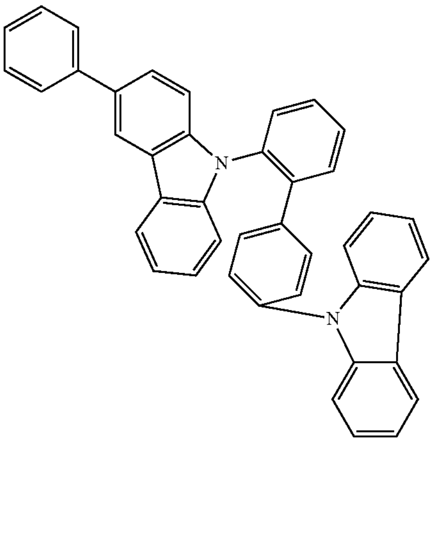

-continued
F3
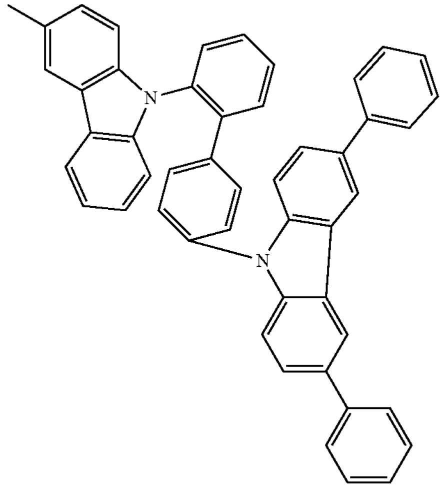
F4
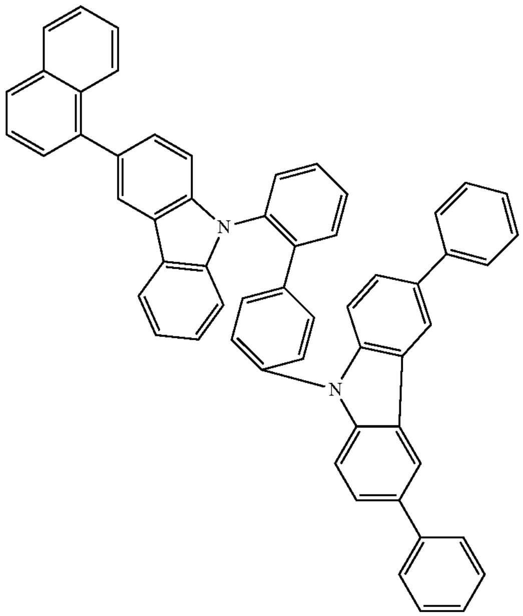
F5
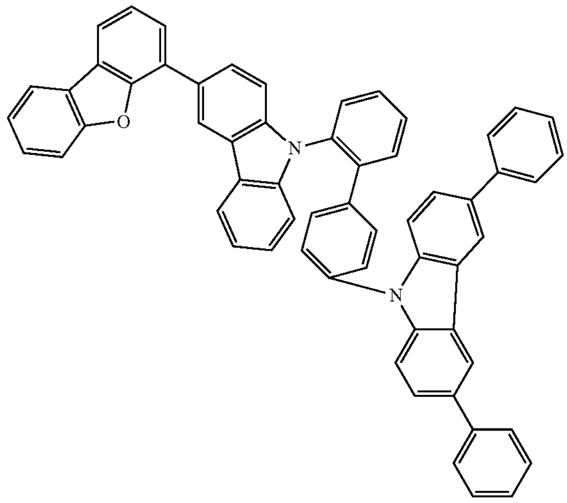
-continued
F6
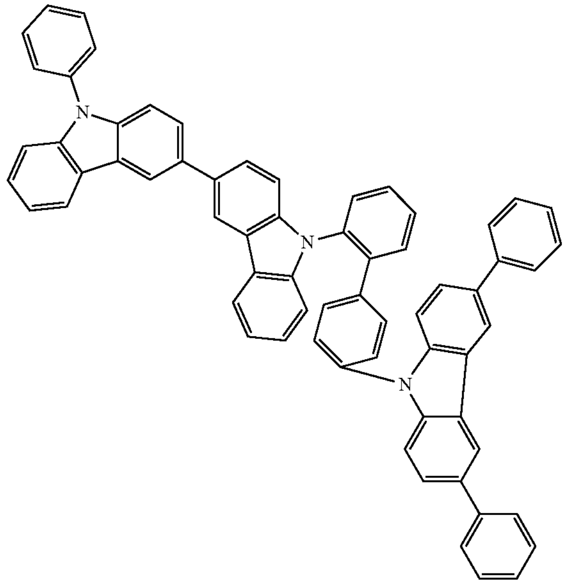
F7
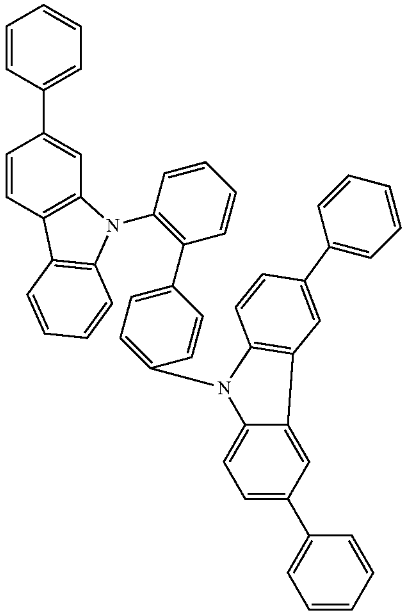

-continued
F8
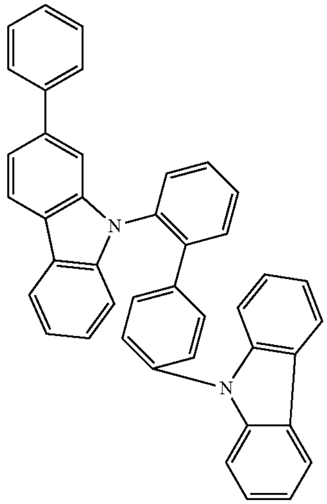
F9
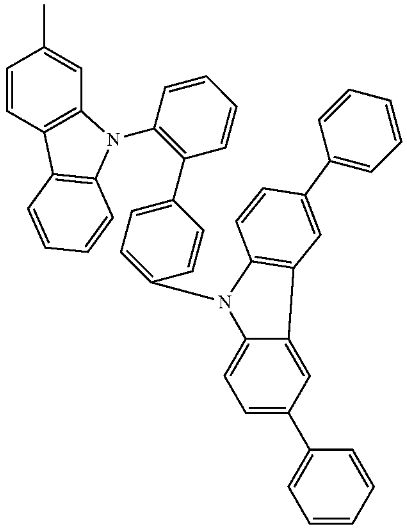
F10
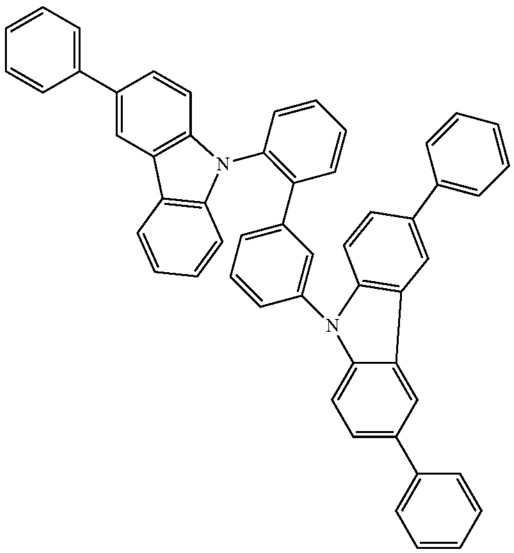
-continued
F11
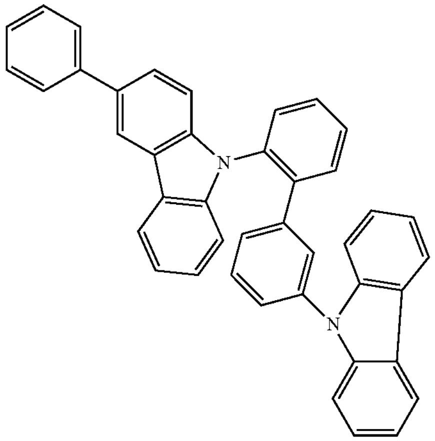
F12
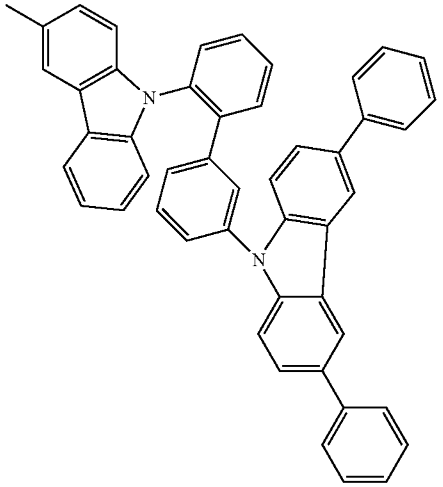
F13
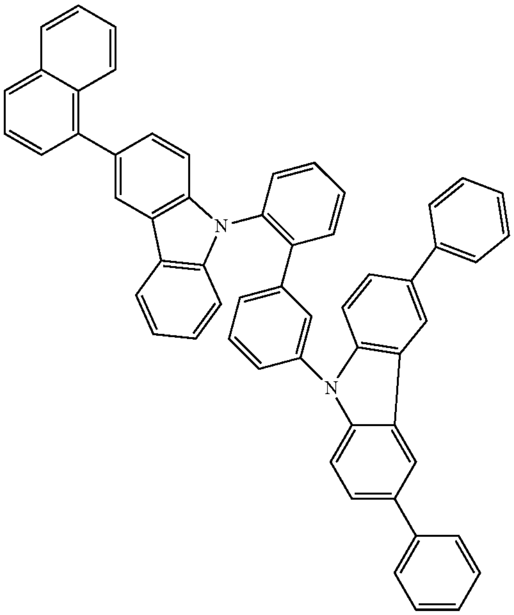

F14
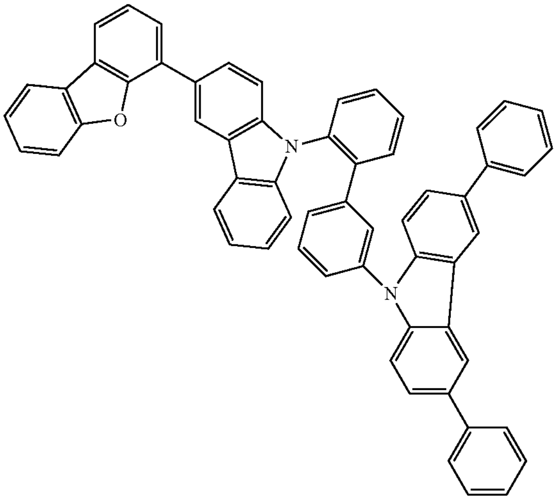
F15
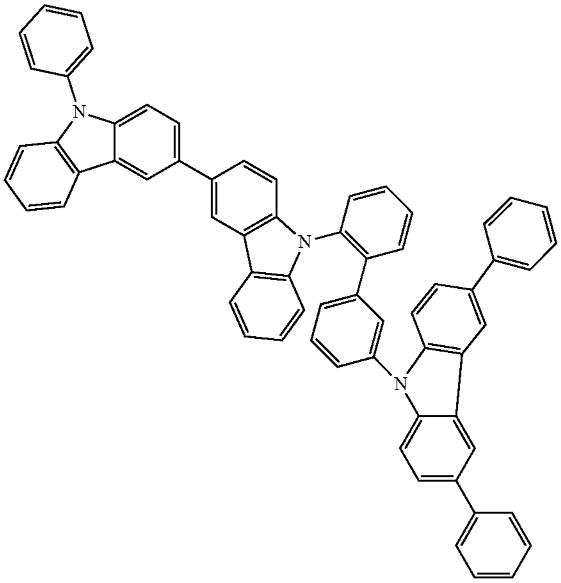
F16
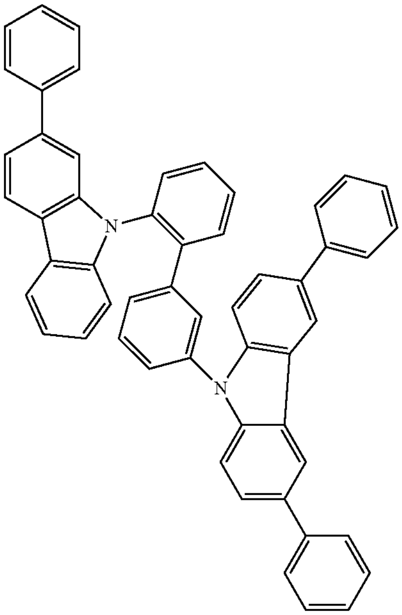
F17
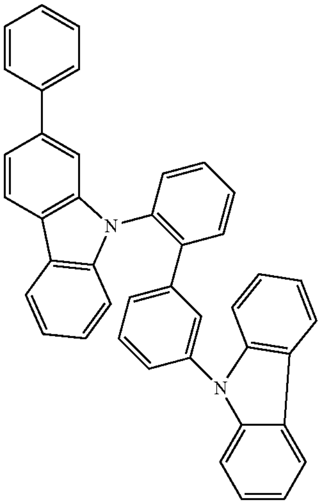
F18
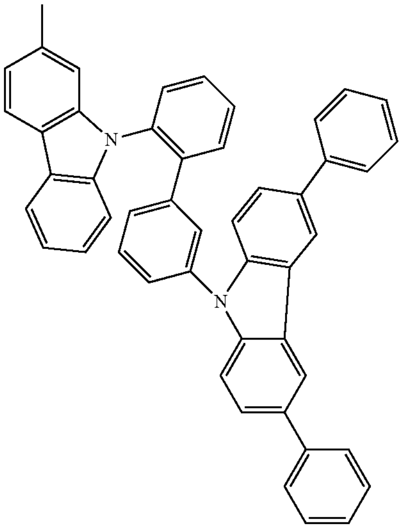

[Compound Group 1G]
G1
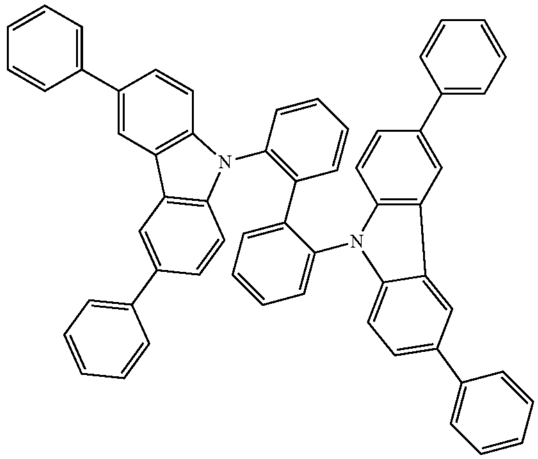
G2
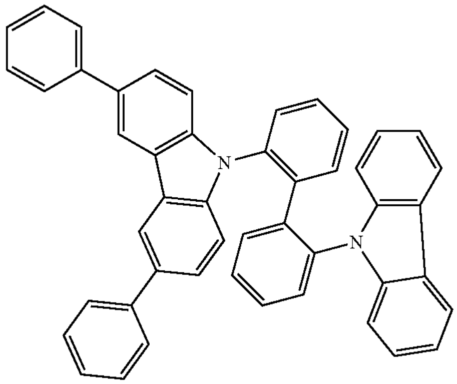
G3
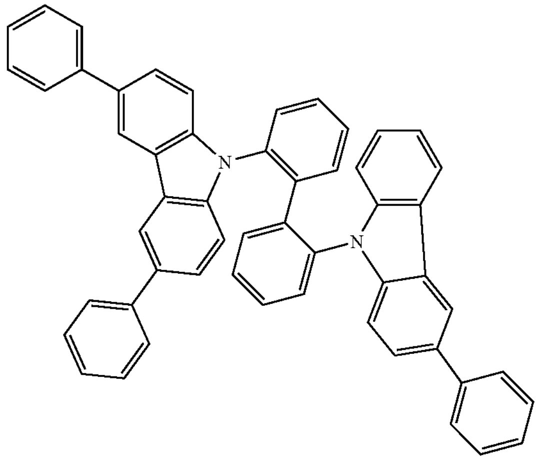
G4
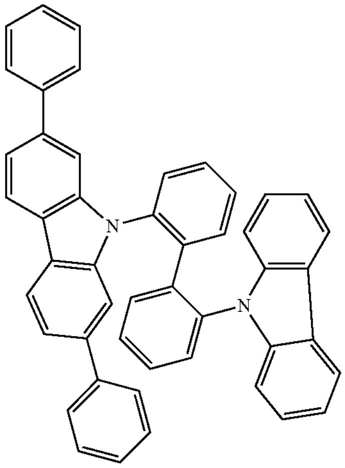
G5
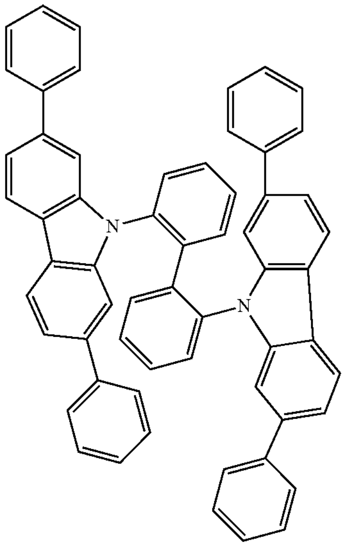
G6
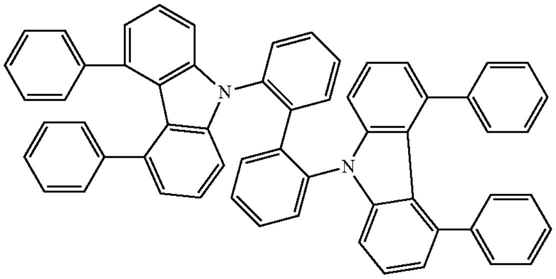

-continued
G7
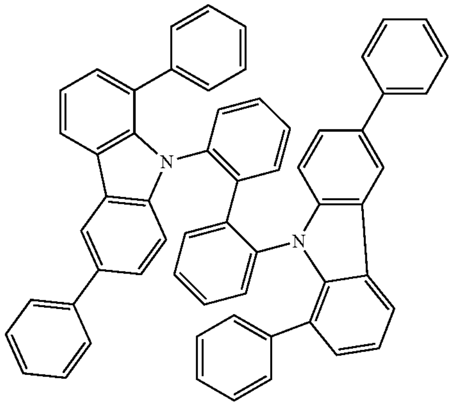
G8
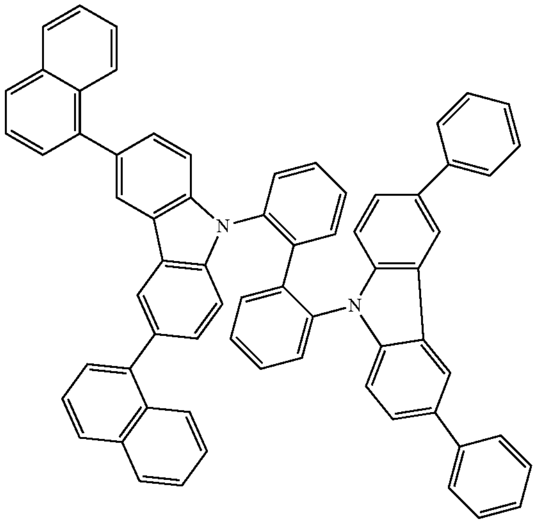
G9
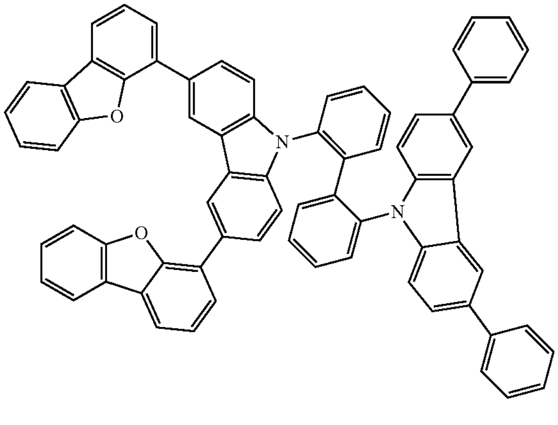
-continued
G10
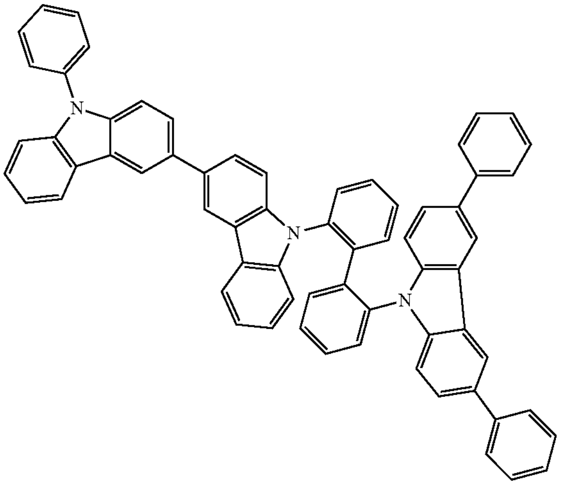
G11
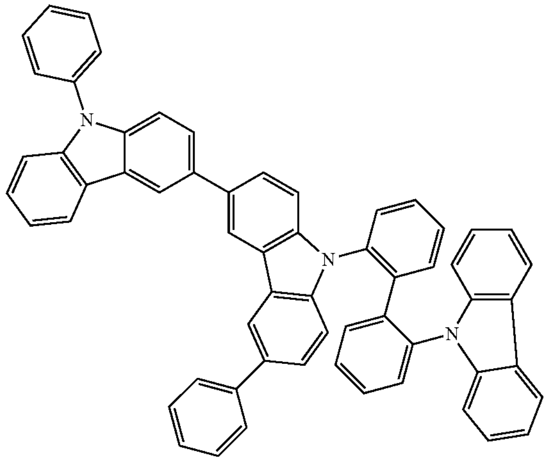
G12
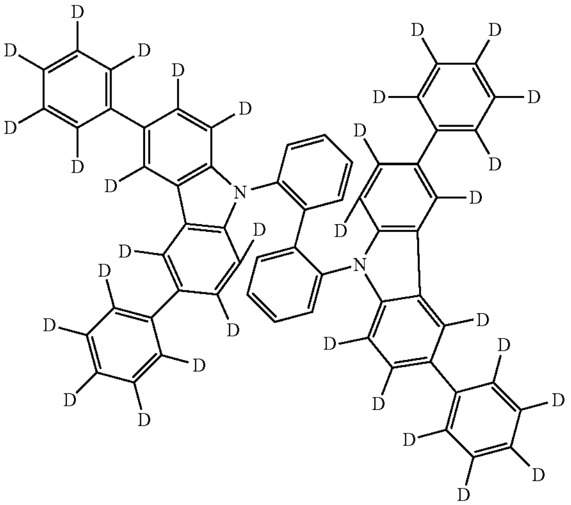

-continued
G13
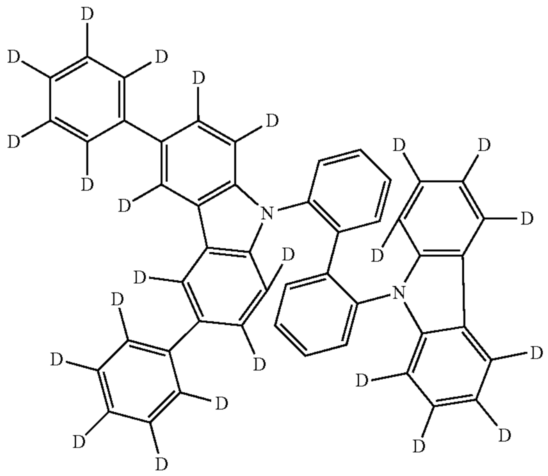
G14
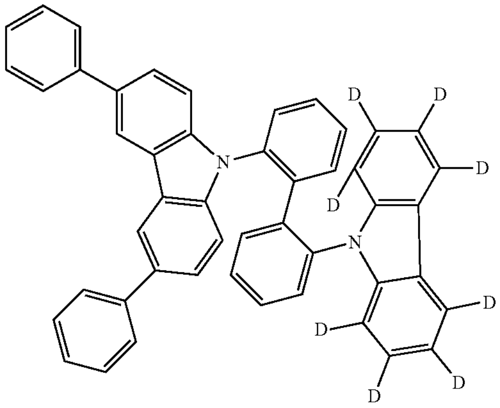
[Compound Group 1H]
H1
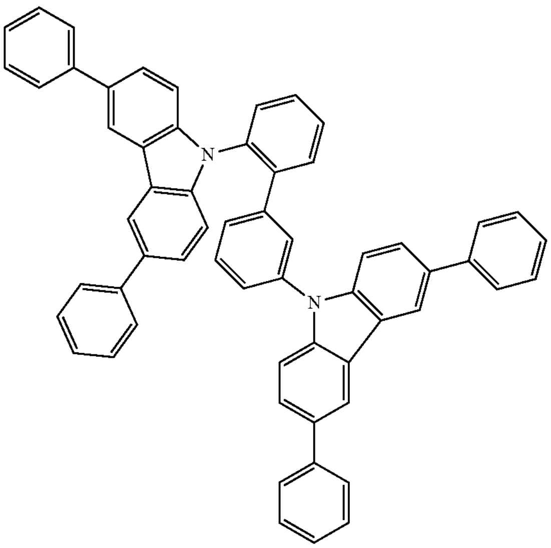
-continued
H2
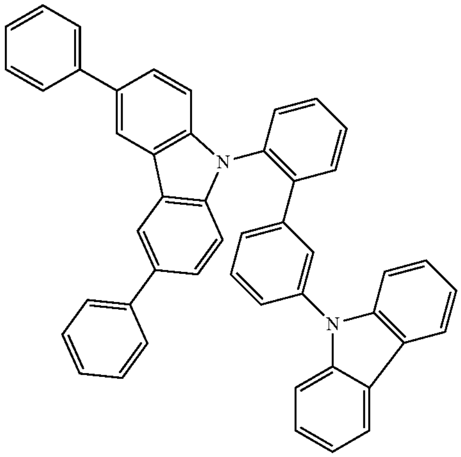
H3
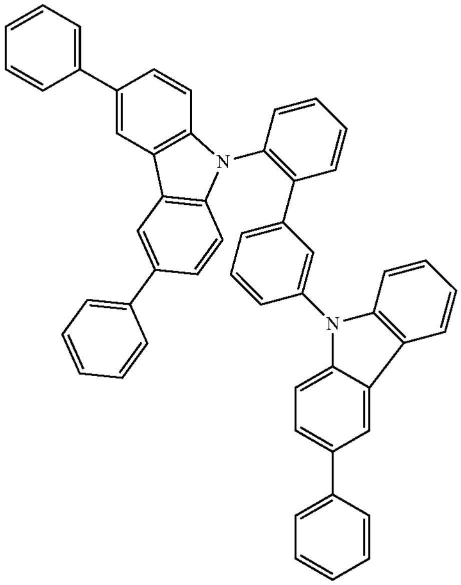
H4
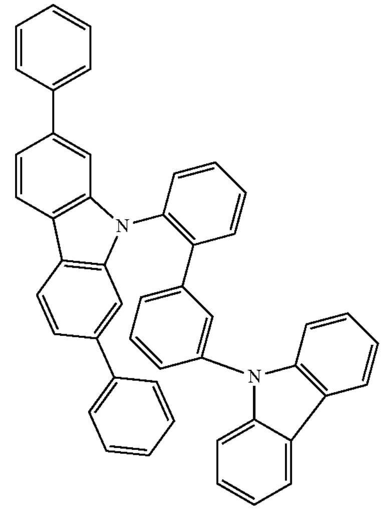

-continued
H5
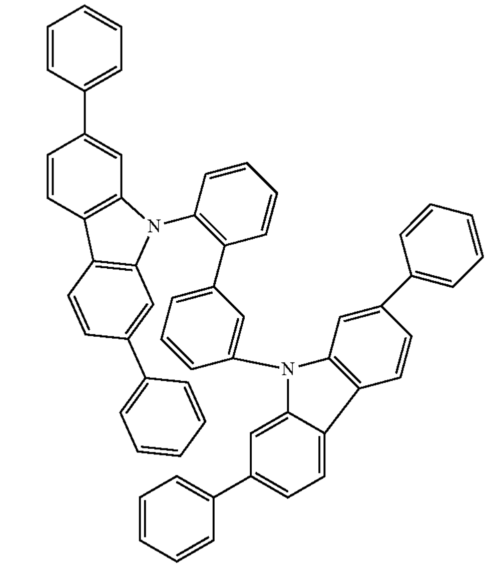
H6
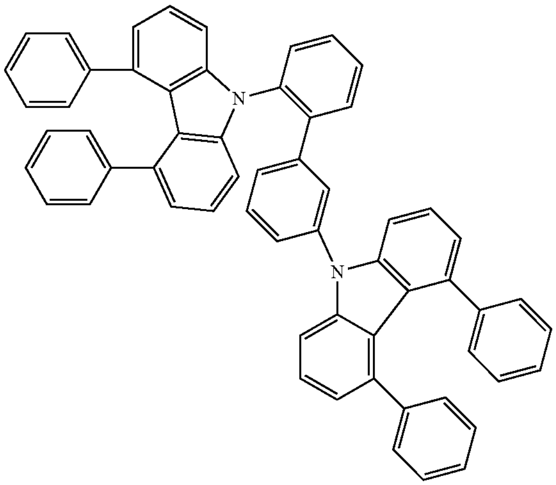
H7
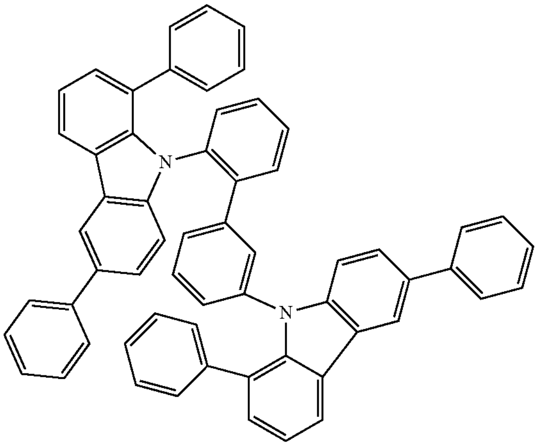
-continued
H8
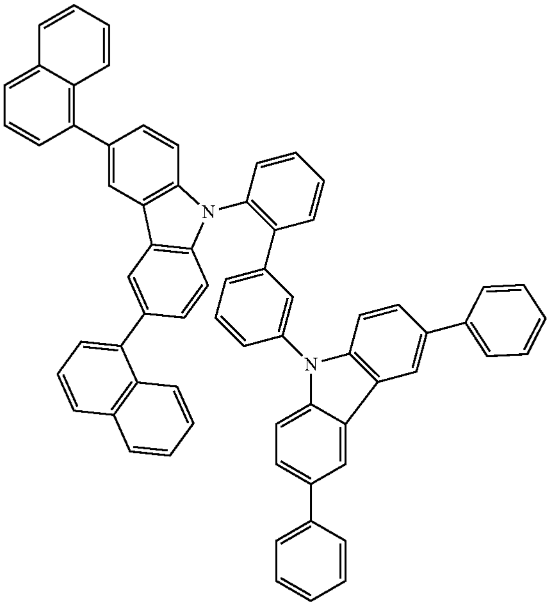
H9
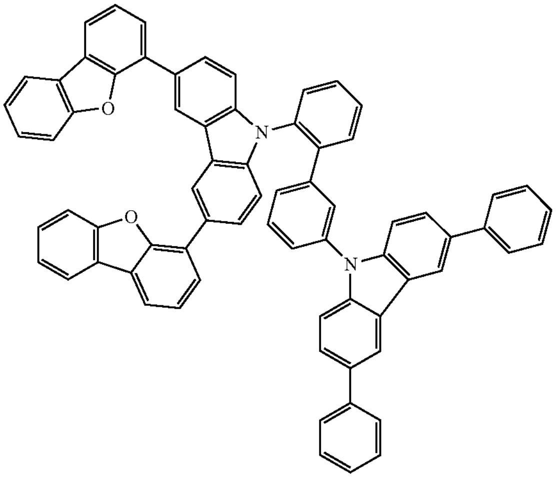

-continued
H10
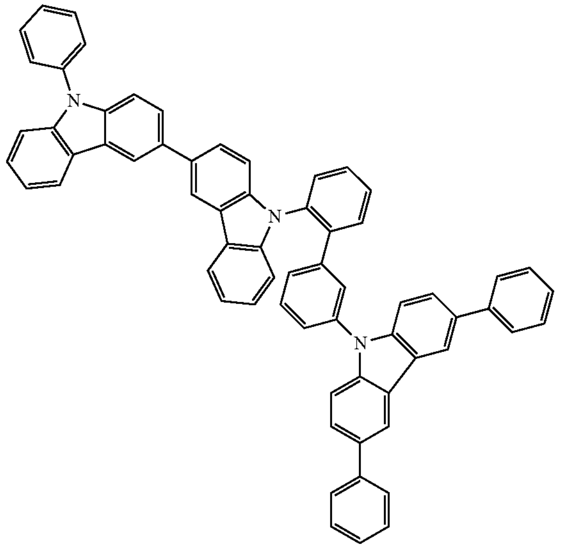
H11
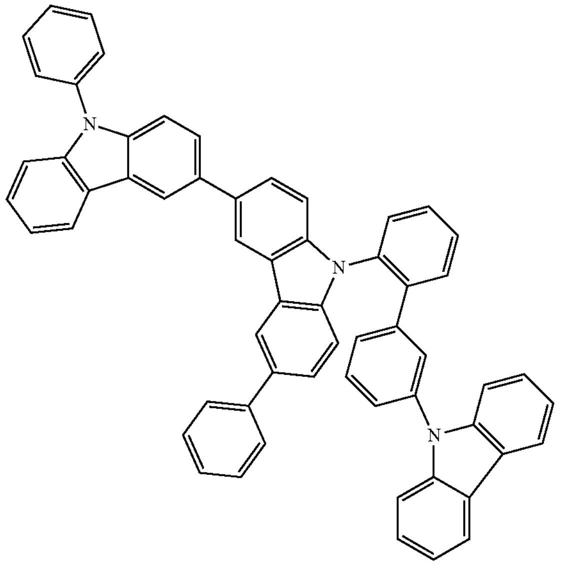
-continued
[Compound Group 1I]
I1
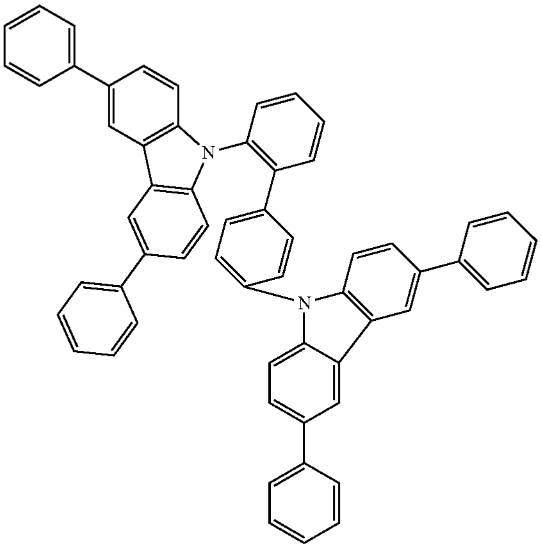
I2
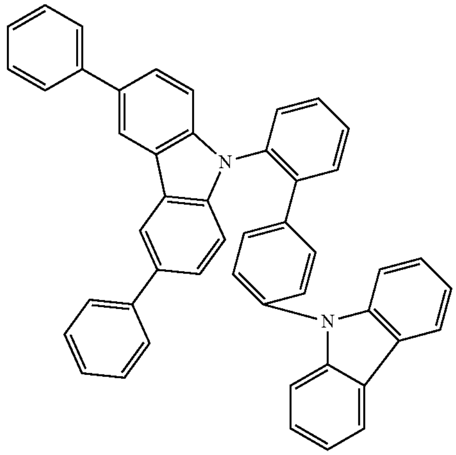
I3
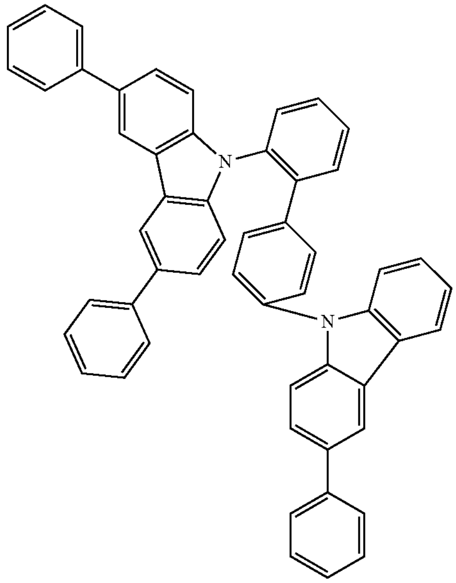

-continued
I4
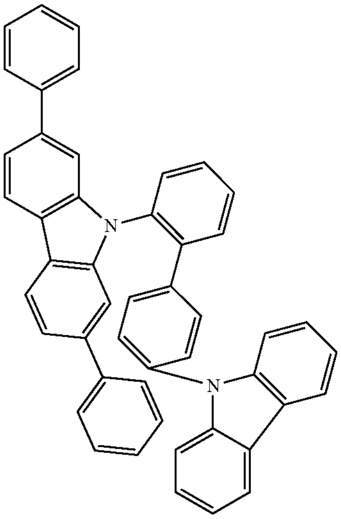
I5
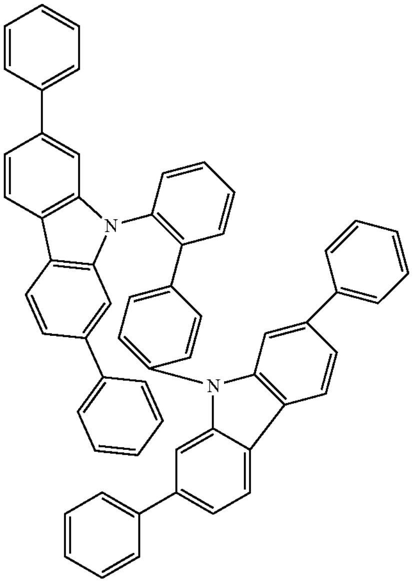
I6
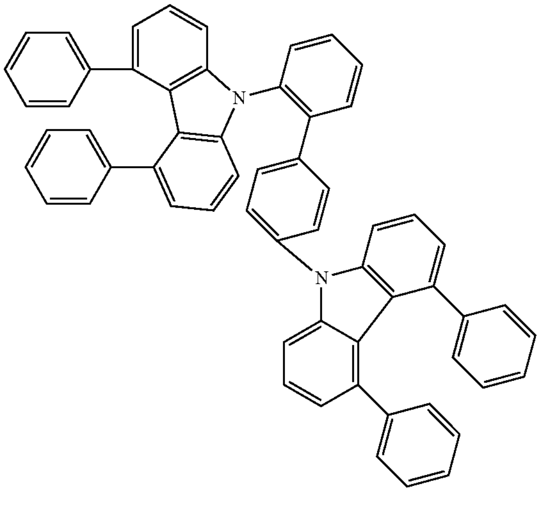
-continued
I7
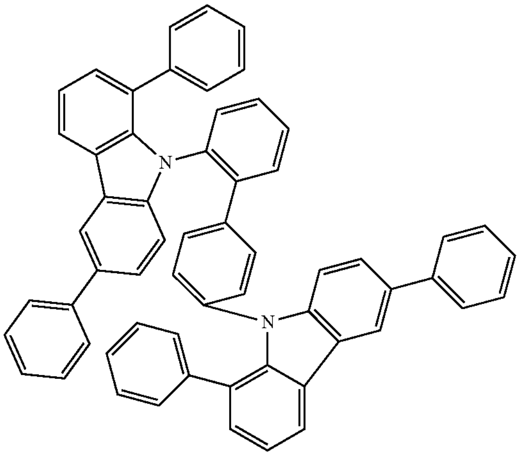
I8
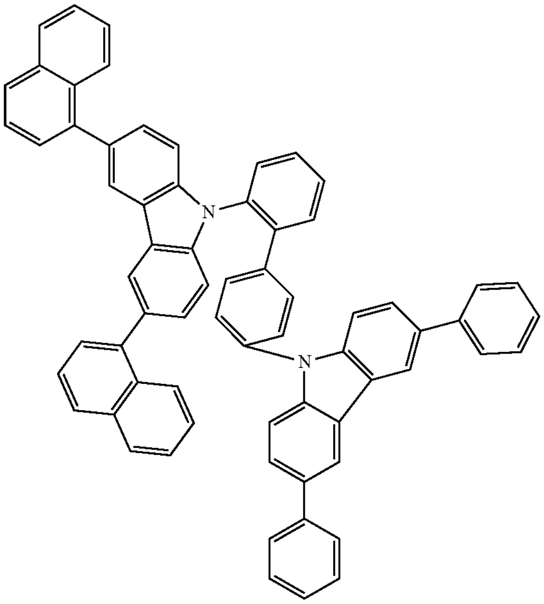
I9
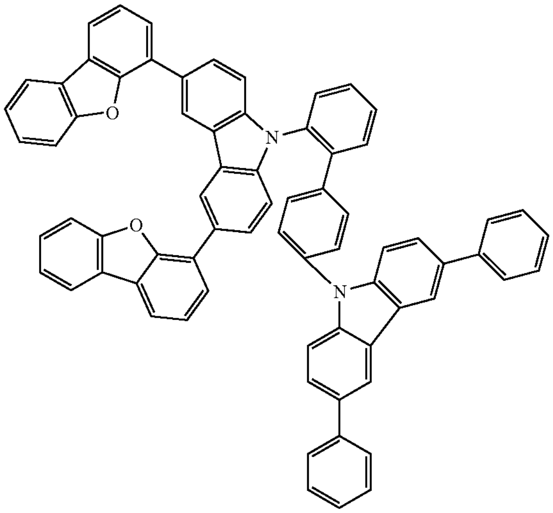

-continued
I10
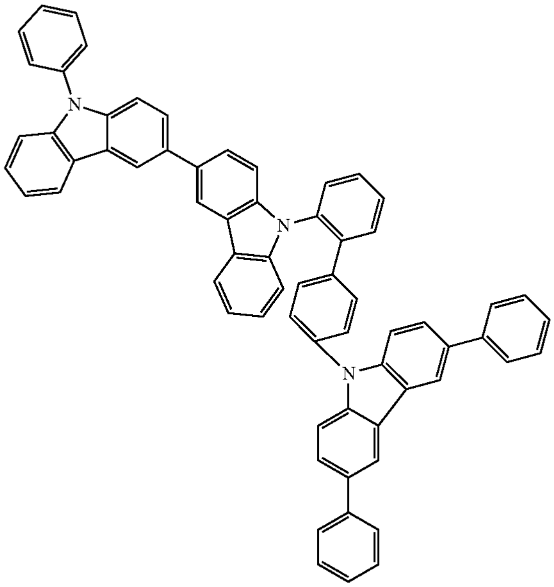
I11
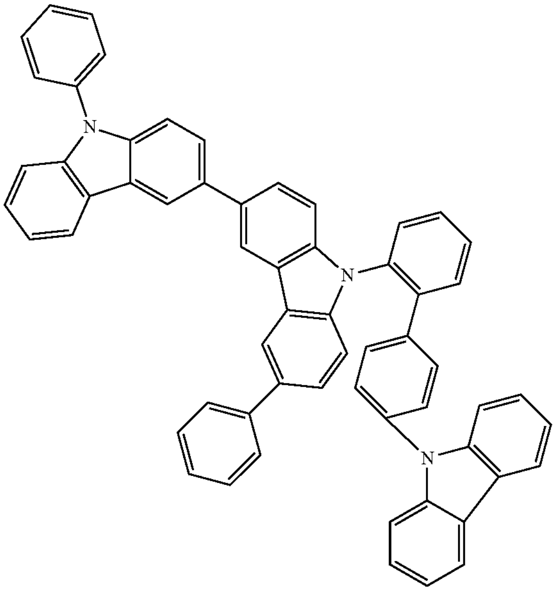
-continued
[Compound Group 1J]
J1
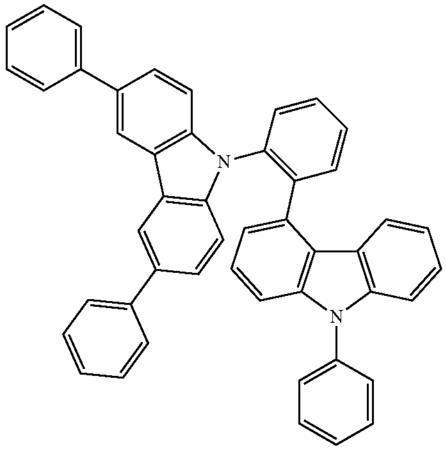
J2
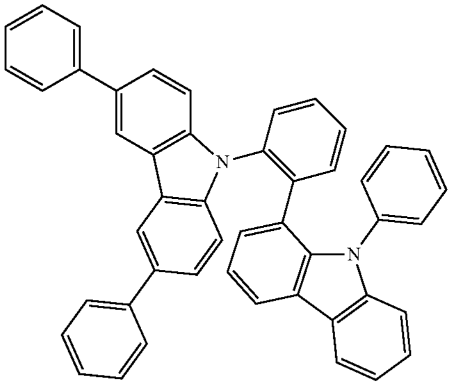
J3
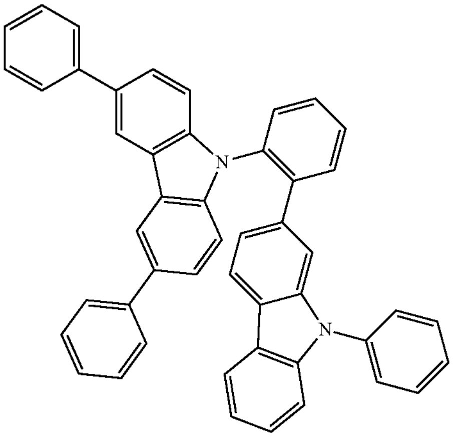

-continued
J4
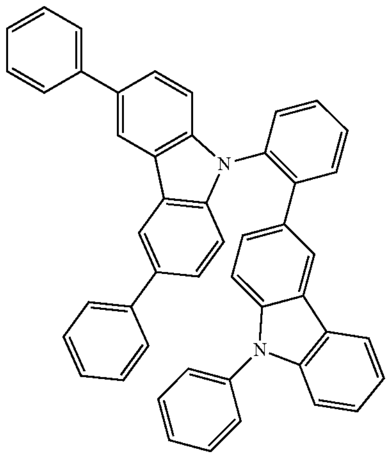
J5
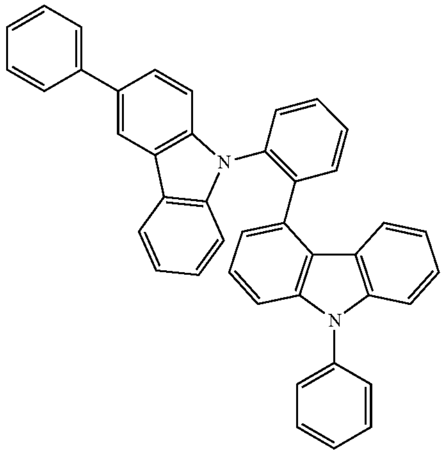
J6
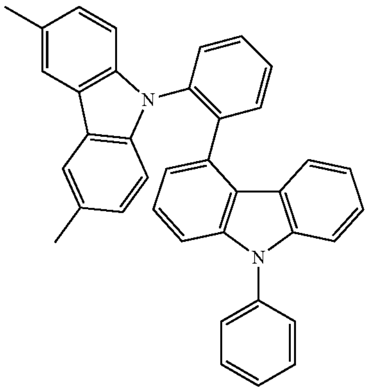
J7
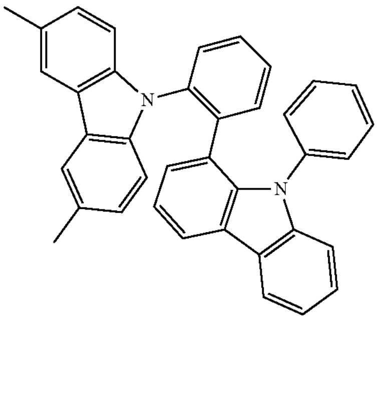
-continued
J8
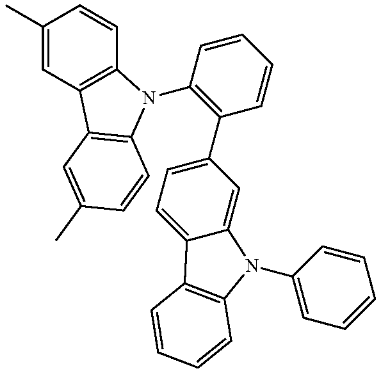
J9
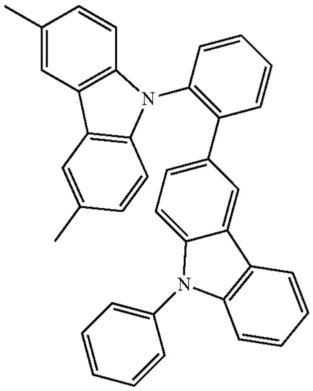
J10
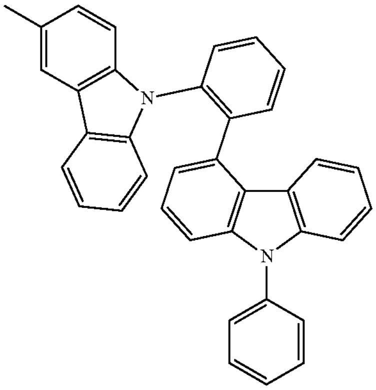

J11
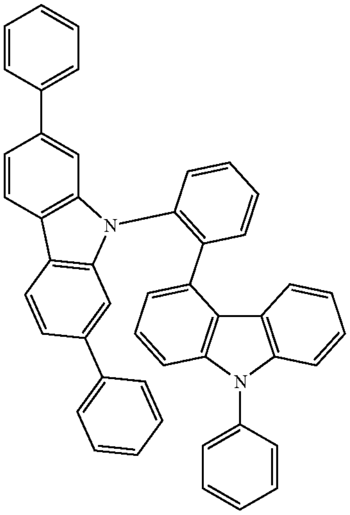
J12
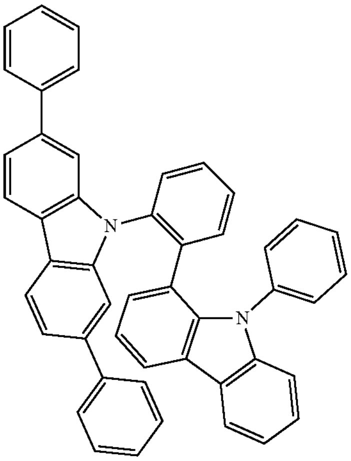
J13
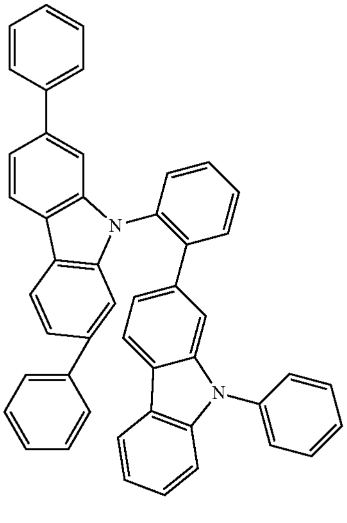
J14
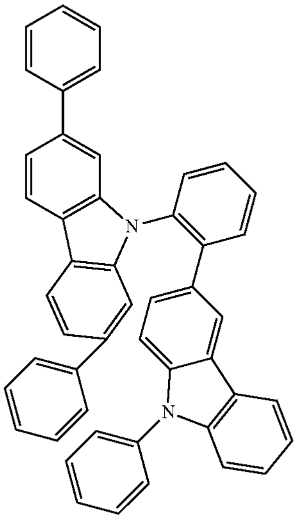
J15
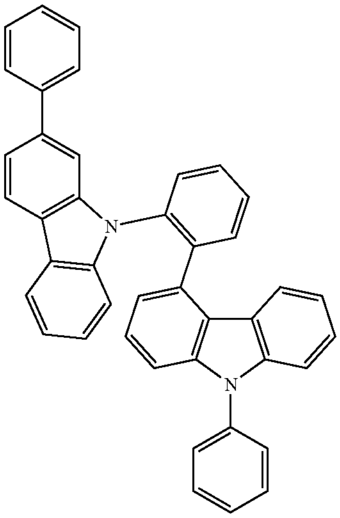
J16
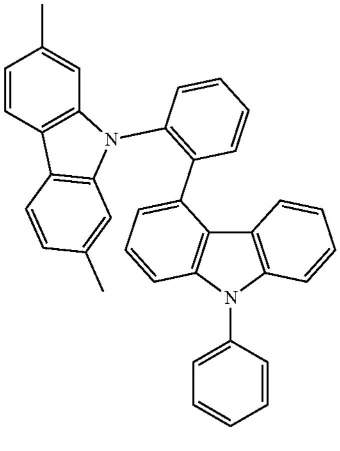

-continued
J17
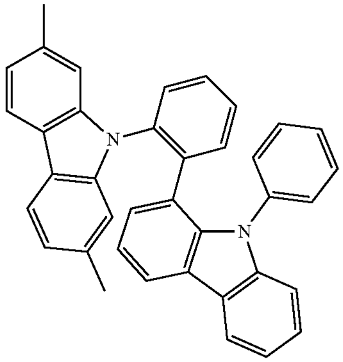
J18
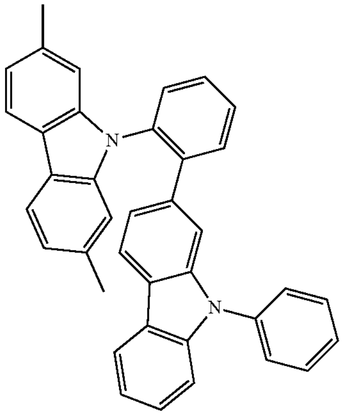
J19
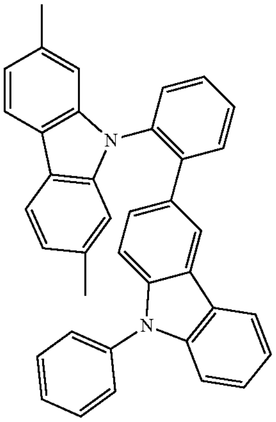
J20
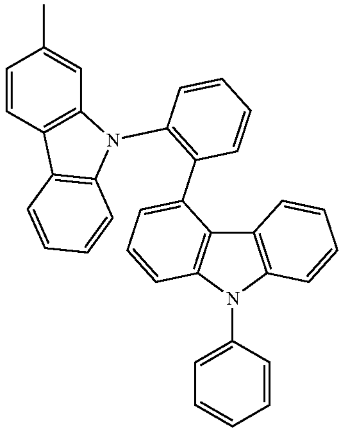
-continued
J21
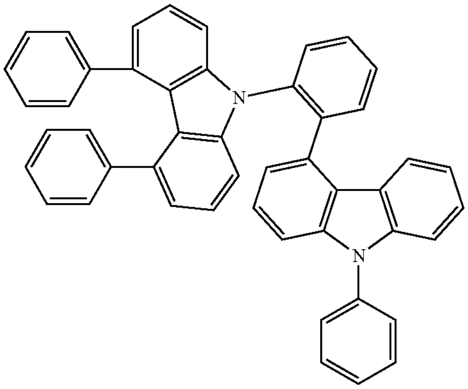
J22
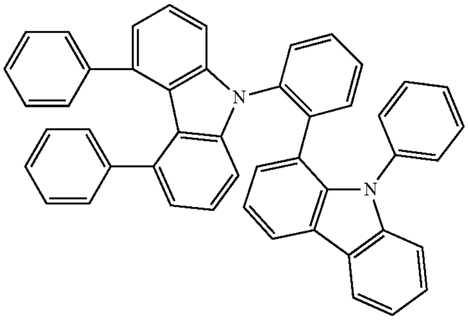
J23
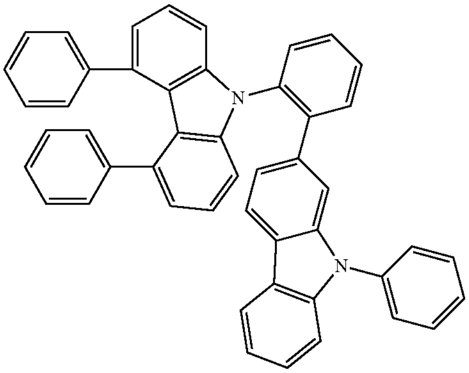
J24
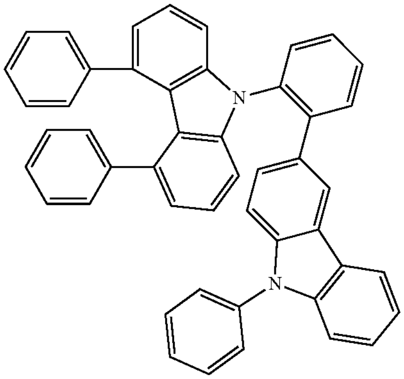

-continued
J25
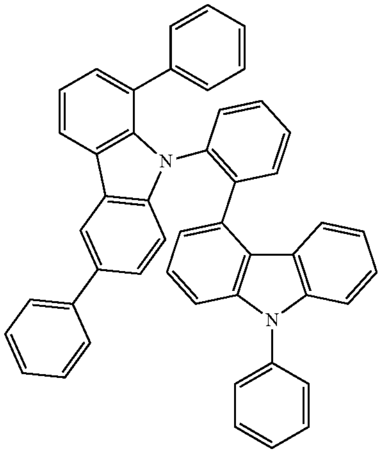
J26
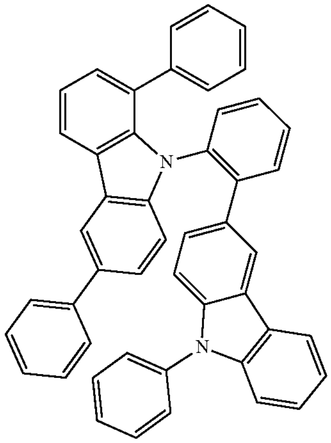
J27
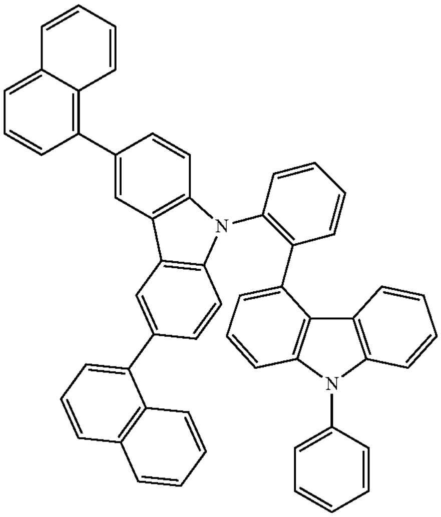
-continued
J28
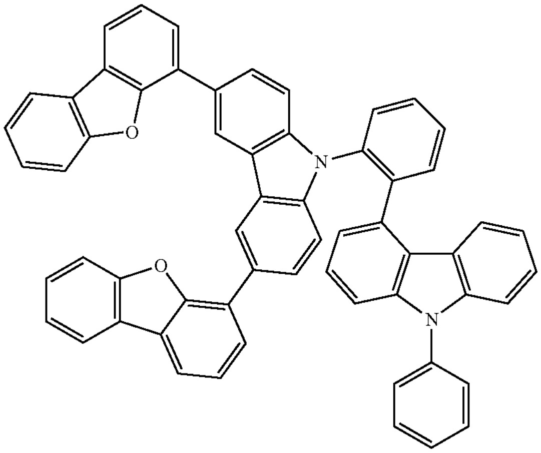
J29
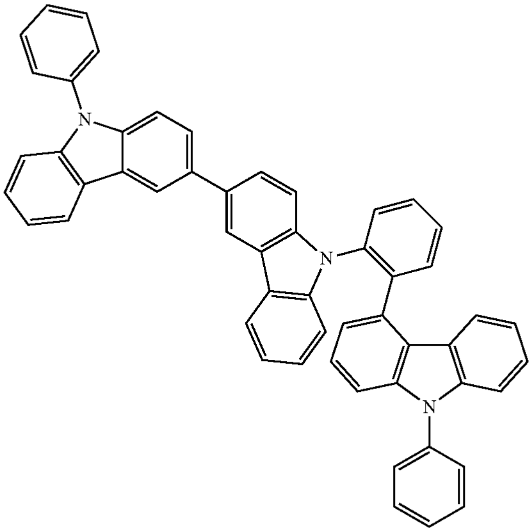
J30
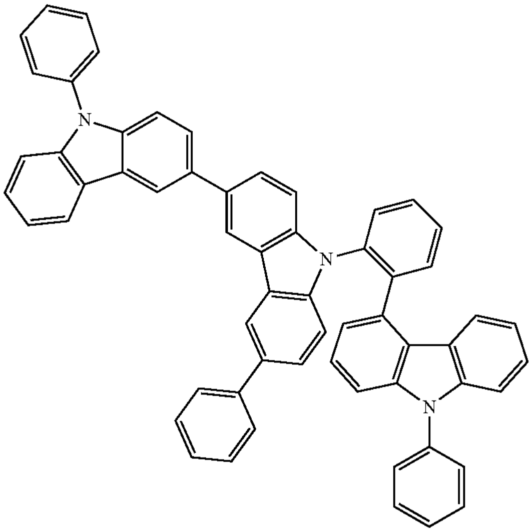

-continued

J31

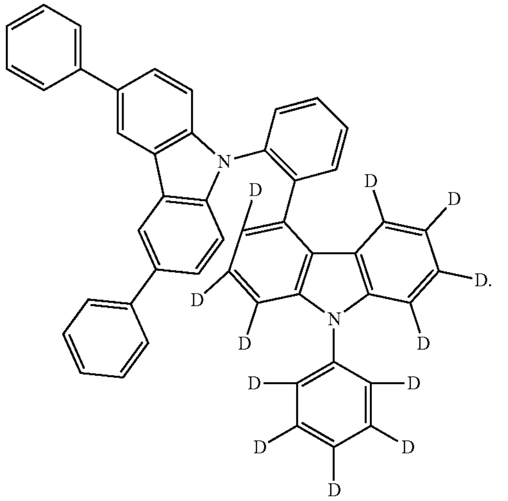

12. The light emitting element of claim 2, wherein the emission layer comprises a compound represented by Formula E-1:

[Formula E-1]

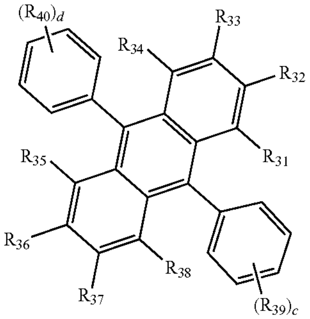

wherein in Formula E-1, c and d are each independently an integer from 0 to 5, $R_{31}$ to $R_{40}$ are each independently a hydrogen atom, a deuterium atom, a halogen atom, a substituted or unsubstituted silyl group, a substituted or unsubstituted alkyl group of 1 to 20 carbon atoms, a substituted or unsubstituted alkenyl group of 2 to 20 carbon atoms, a substituted or unsubstituted oxy group, a substituted or unsubstituted thiol group, a substituted or unsubstituted aryl group of 6 to 30 ring-forming carbon atoms, or a substituted or unsubstituted heteroaryl group of 2 to 30 ring-forming carbon atoms, or are combined with an adjacent group to form a ring.

13. A polycyclic compound represented by Formula 1:

[Formula 1]

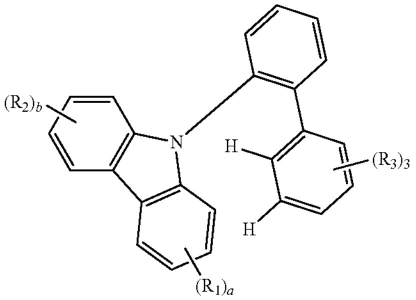

wherein in Formula 1, $R_1$ and $R_2$ are each independently a substituted or unsubstituted aryl group of 6 to 40 ring-forming carbon atoms, a substituted or unsubstituted heteroaryl group of 5 to 40 ring-forming carbon atoms, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted alkoxy group of 1 to 20 carbon atoms, a substituted or unsubstituted alkylthio group of 1 to 20 carbon atoms, a substituted or unsubstituted aryloxy group of 6 to 40 ring-forming carbon atoms, a substituted or unsubstituted arylthio group of 6 to 40 ring-forming carbon atoms, or a substituted or unsubstituted silyl group of 3 to 40 carbon atoms, a is an integer from 0 to 4, b is an integer from 1 to 4, one of $R_3$ is a group represented by Formula 2 and is bonded to a ring at an ortho position, a meta position, or a para position with respect to a phenyl group bonded to a nitrogen atom of a carbazole group, and the remainder $R_3$ are each independently a hydrogen atom or a deuterium atom:

[Formula 2]

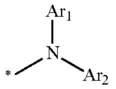

wherein in Formula 2, $Ar_1$ and $Ar_2$ are each independently a substituted or unsubstituted aryl group of 6 to 40 ring-forming carbon atoms, a substituted or unsubstituted heteroaryl group of 5 to 40 ring-forming carbon atoms, a substituted or unsubstituted alkyl group of 1 to 20 carbon atoms, a substituted or unsubstituted alkenyl group of 2 to 20 carbon atoms, a substituted or unsubstituted alkynyl group of 2 to 20 carbon atoms, a substituted or unsubstituted alkoxy group of 1 to 20 carbon atoms, a substituted or unsubstituted alkylthio group of 1 to 20 carbon atoms, a substituted or unsubstituted aryloxy group of 6 to 40 ring-forming carbon atoms, a substituted or unsubstituted arylthio group of 6 to 40 ring-forming carbon atoms, or a substituted or unsubstituted silyl group, or are combined with an adjacent group to form a ring, or $Ar_1$ and $Ar_2$ are combined with each other to form a ring, and —* is a bonding site to Formula 1, in case that an $R_3$ group represented by Formula 2 is bonded to a ring at an ortho position with respect to the phenyl group bonded to the nitrogen atom of the carbazole group, and $Ar_1$ and $Ar_2$ are combined with each other to form a ring, then a is equal to or greater than 1, and $R_1$ and $R_2$ do not include alkyl groups, and in case that an $R_3$ group represented by Formula 2 is bonded to a ring at a para position with respect to the phenyl group bonded to the nitrogen atom of the carbazole group, and $Ar_1$ and $Ar_2$ are not combined with each other to form a ring, then a is equal to or greater than 1, and at least one hydrogen in Formula 1 or Formula 2 is optionally substituted with deuterium.

14. The polycyclic compound of claim 13, wherein the polycyclic compound represented by Formula 1 is represented by one of Formula 1-1 to Formula 1-3:

[Formula 1-1]

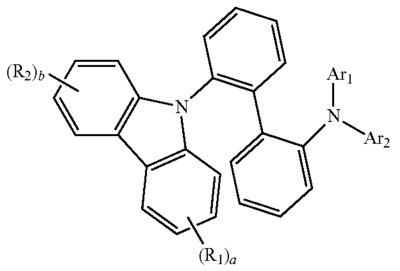

[Formula 1-2]

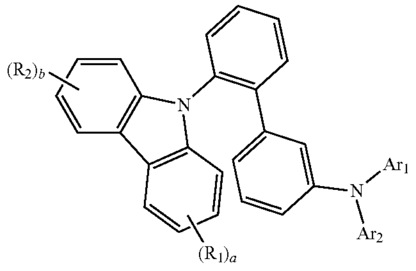

[Formula 1-3]

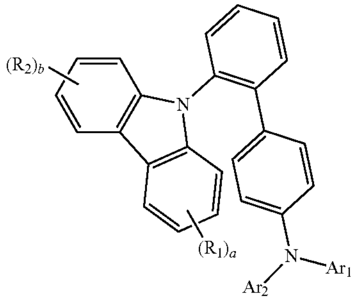

wherein in Formula 1-1 to Formula 1-3, $R_1$, $R_2$, a, and b are the same as defined in Formula 1, and $Ar_1$ and $Ar_2$ are the same as defined in Formula 2.

15. The polycyclic compound of claim 13, wherein the group represented by Formula 2 is represented by Formula 2-1 or Formula 2-2:

[Formula 2-1]

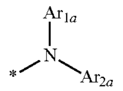

wherein in Formula 2-1, $Ar_{1a}$ and $Ar_{2a}$ are each independently a substituted or unsubstituted aryl group of 6 to 40 ring-forming carbon atoms, or a substituted or unsubstituted heteroaryl group of 5 to 40 ring-forming carbon atoms, or are combined with an adjacent group to form a ring, and at least one hydrogen in $Ar_{1a}$ or $Ar_{2a}$ is optionally substituted with deuterium,

[Formula 2-2]

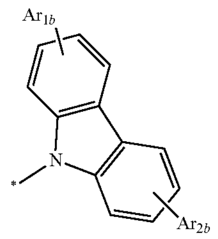

wherein in Formula 2-2, $Ar_{1b}$ and $Ar_{2b}$ are each independently a hydrogen atom, a deuterium atom, or a substituted or unsubstituted aryl group of 6 to 40 ring-forming carbon atoms.

16. The polycyclic compound of claim 15, wherein the polycyclic compound represented by Formula 1 is represented by one of Formula 3-1 to Formula 3-6:

[Formula 3-1]

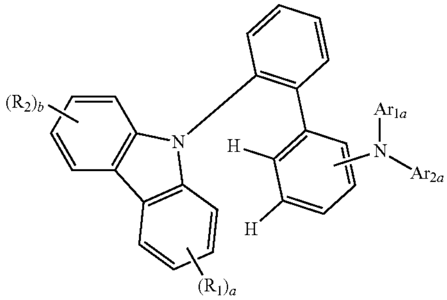

[Formula 3-2]

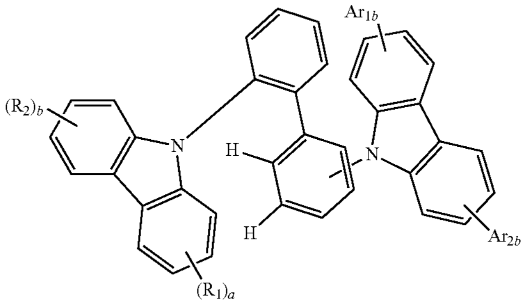

-continued

[Formula 3-3]

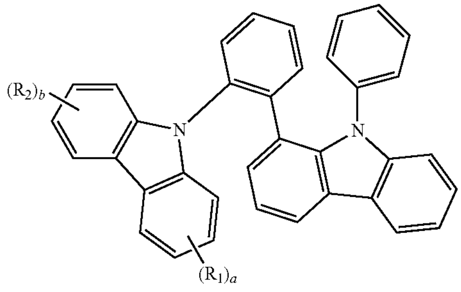

[Formula 3-4]

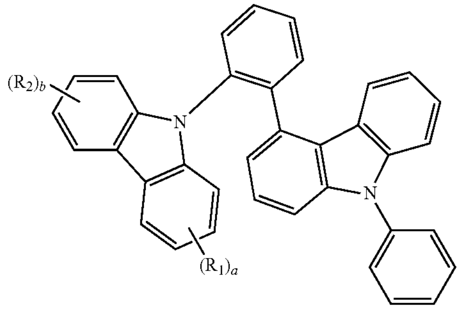

[Formula 3-5]

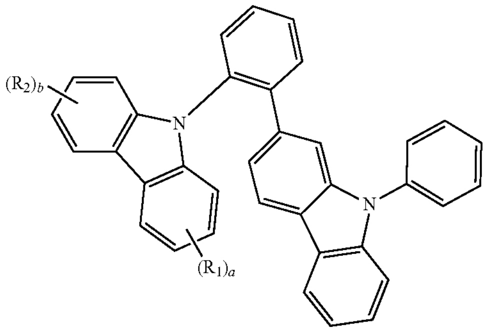

[Formula 3-6]

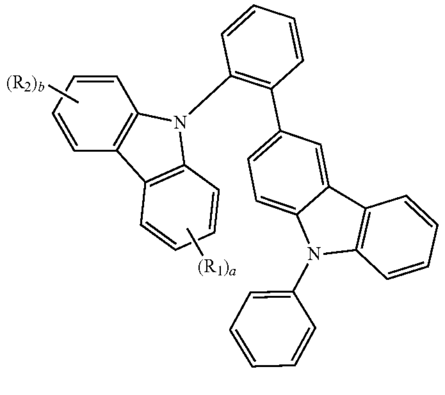

wherein in Formula 3-1 to Formula 3-6, $R_1$, $R_2$, a, and b are the same as defined in Formula 1, $Ar_{1a}$ and $Ar_{2a}$ are the same as defined in Formula 2-1, and $Ar_{1b}$ and $Ar_{2b}$ are the same as defined in Formula 2-2.

17. The polycyclic compound of claim 13, wherein a is equal to or greater than 1.

18. The polycyclic compound of claim 13, wherein $R_1$ and $R_2$ are each independently a substituted or unsubstituted aryl group of 6 to 40 ring-forming carbon atoms, a substituted or unsubstituted heteroaryl group of 5 to 40 ring-forming carbon atoms, or a substituted or unsubstituted alkyl group of 1 to 20 carbon atoms.

19. The polycyclic compound of claim 13, wherein $Ar_1$ and $Ar_2$ are each independently a substituted or unsubstituted aryl group of 6 to 40 ring-forming carbon atoms, or a substituted or unsubstituted heteroaryl group of 5 to 40 ring-forming carbon atoms, or are combined with an adjacent group to form a ring, or $Ar_1$ and $Ar_2$ are combined with each other to form a ring.

20. The polycyclic compound of claim 13, wherein the polycyclic compound represented by Formula 1 is one selected from Compound Group 1A to Compound Group 1J:

[Compound Group 1A]

A1

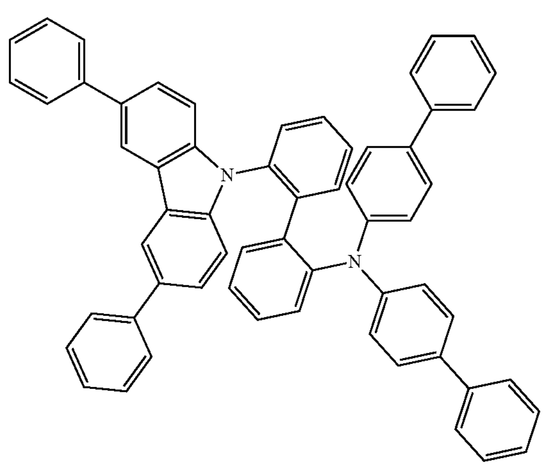

A2

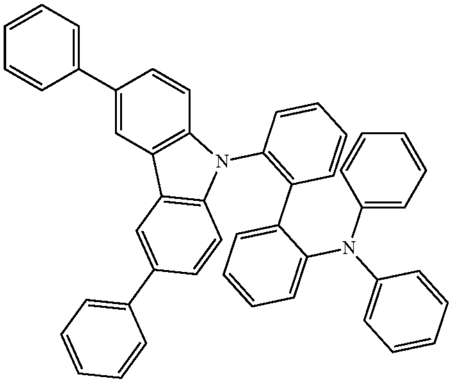

A3

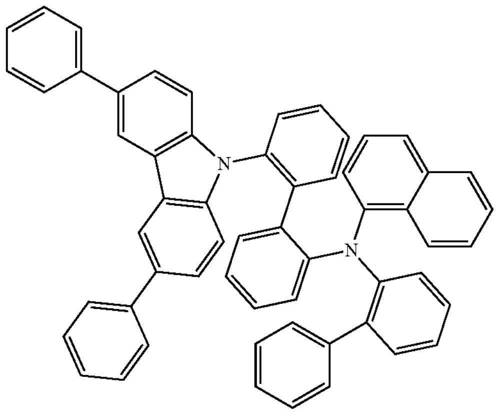

-continued
A4
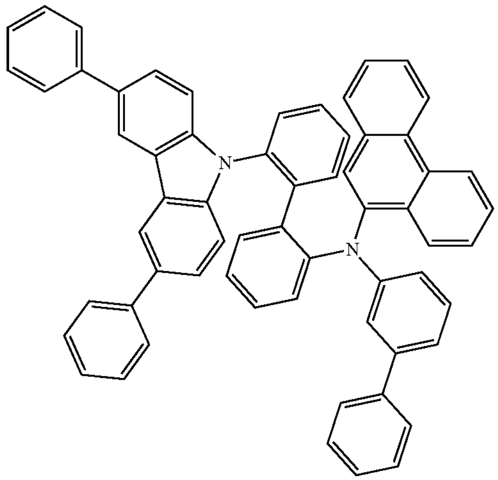
A5
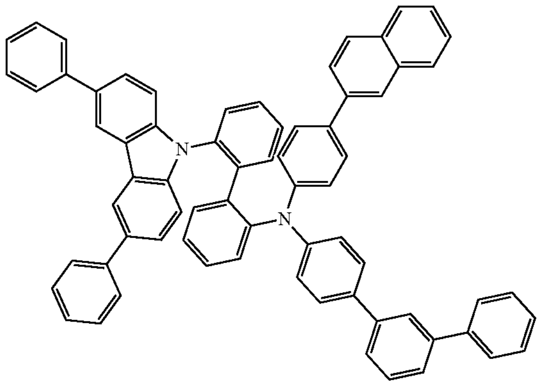
A6
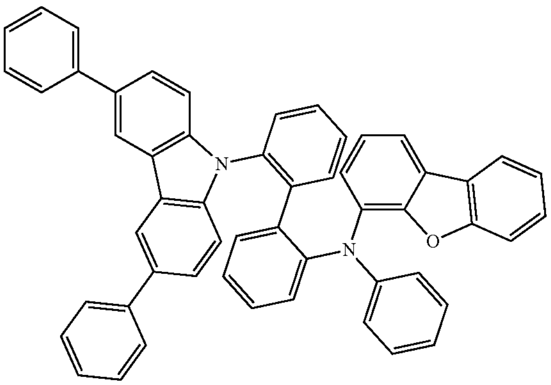
-continued
A7
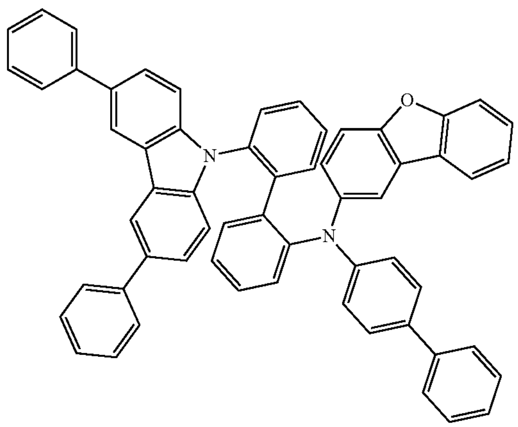
A8
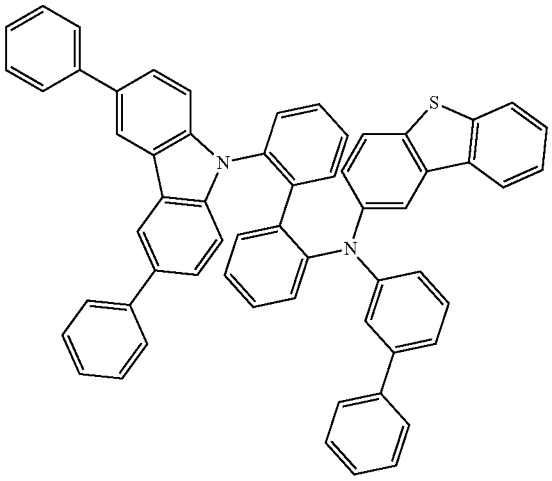
A9
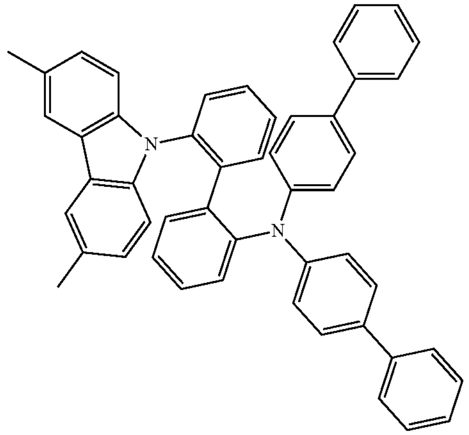

-continued
A10
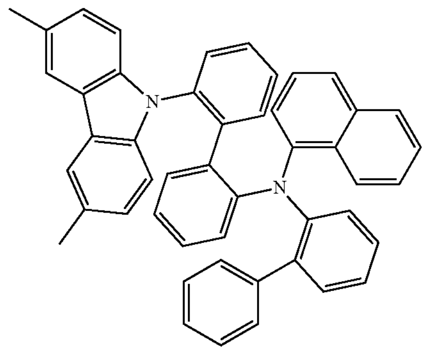
A11
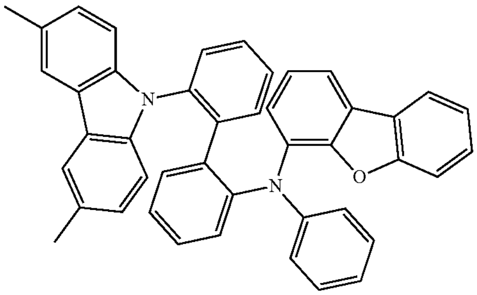
A12
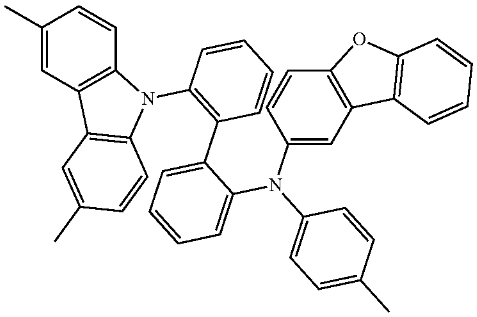
A13
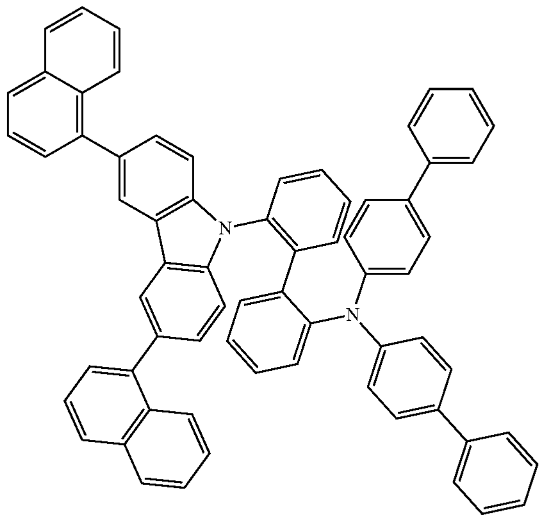
-continued
A14
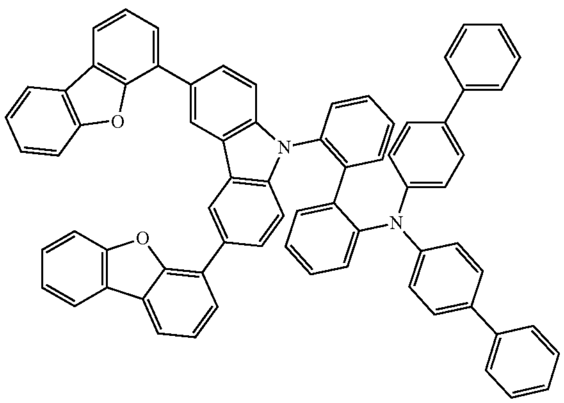
A15
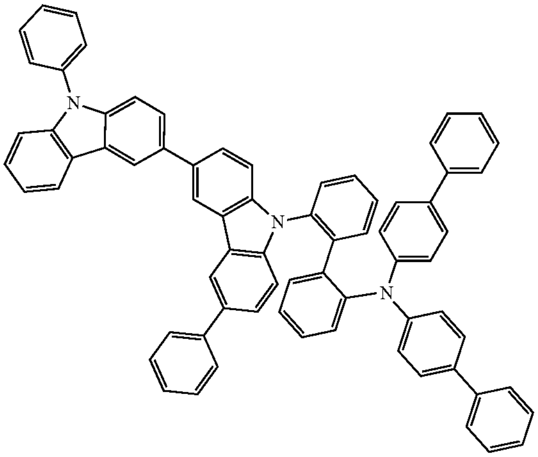
A16
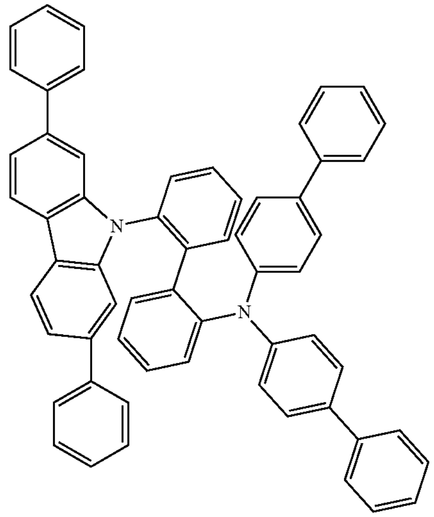

-continued
A17
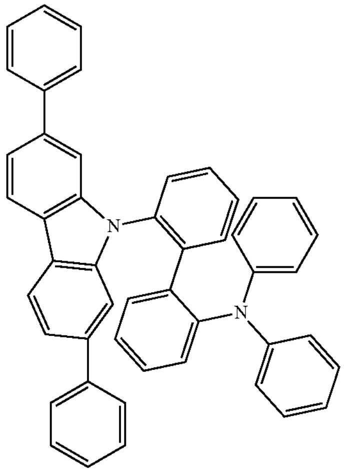
A18
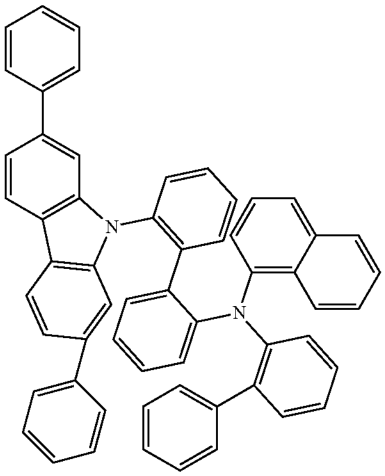
A19
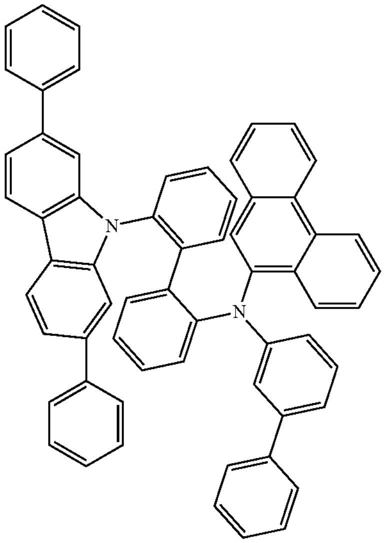
-continued
A20
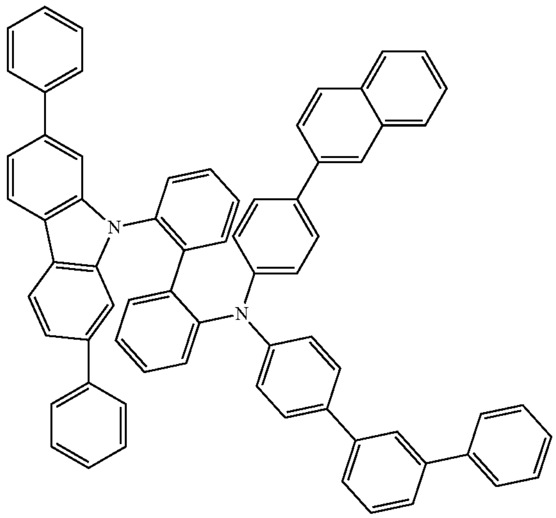
A21
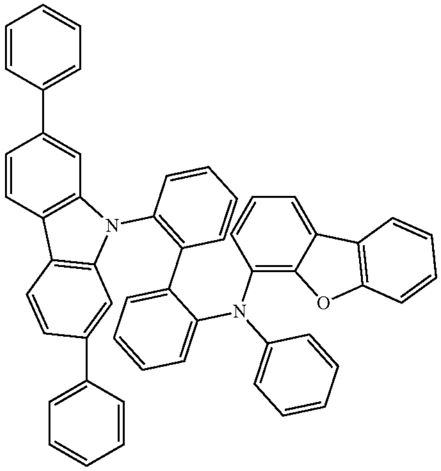
A22
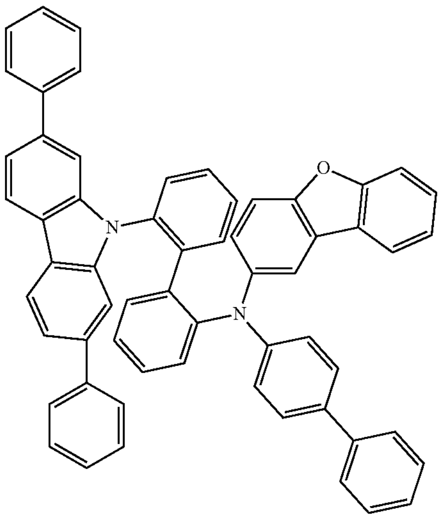

-continued
A23
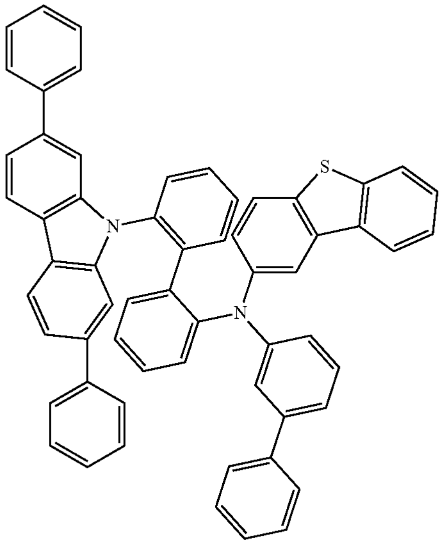
A24
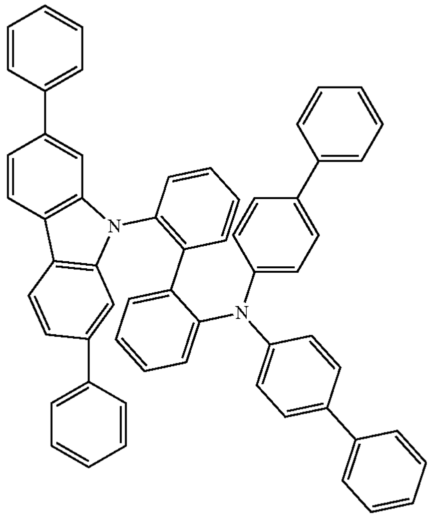
A25
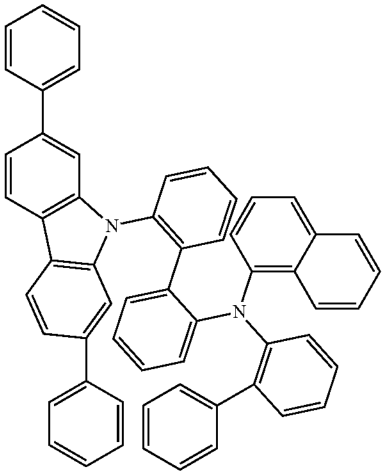
-continued
A26
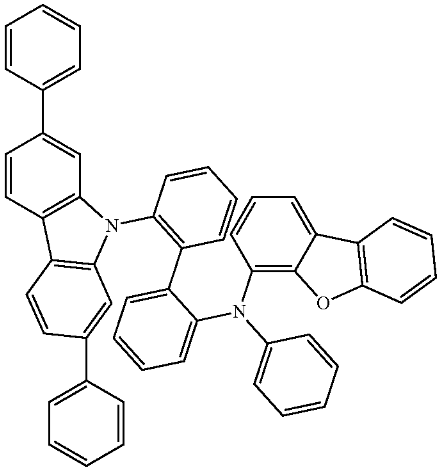
A27
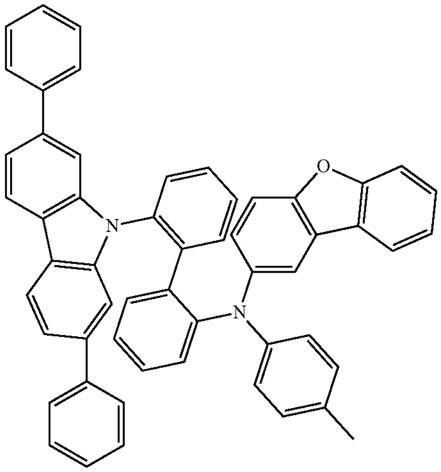
A28
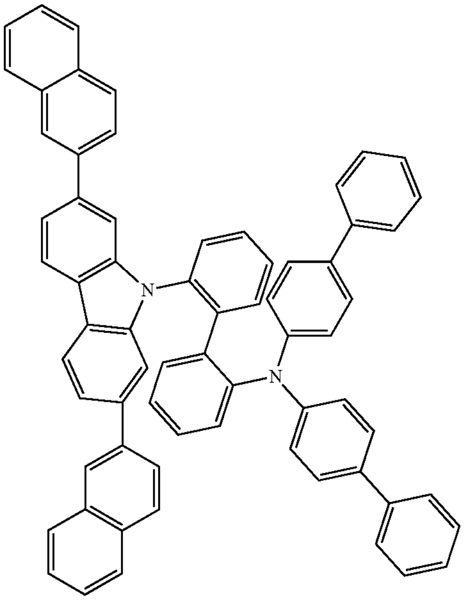

-continued
A29
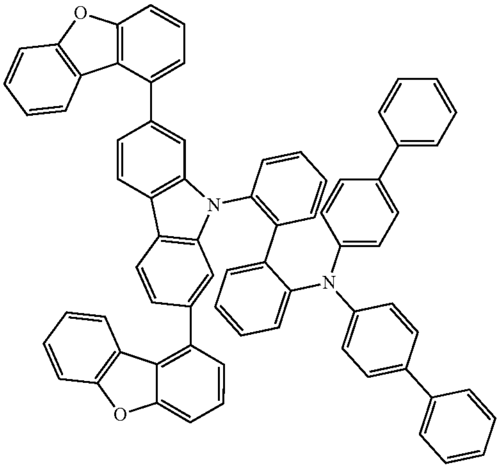
A30
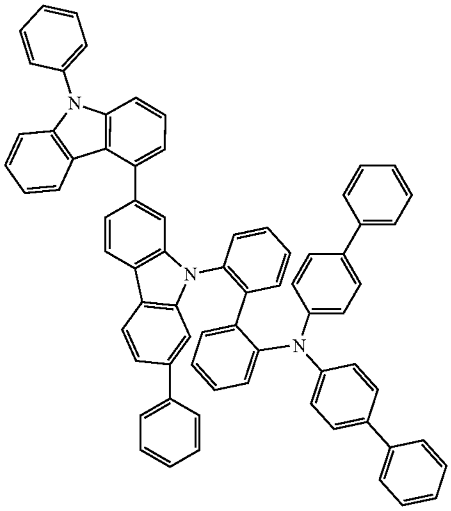
A31
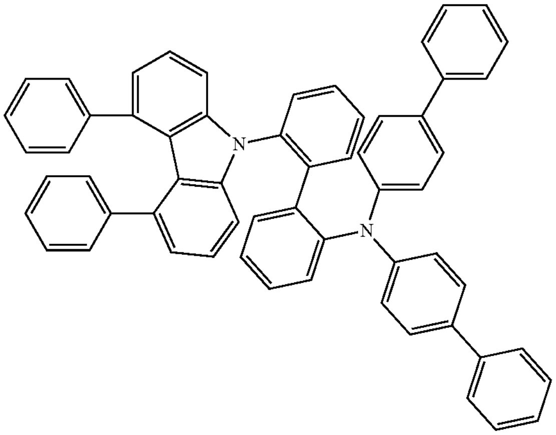
-continued
A32
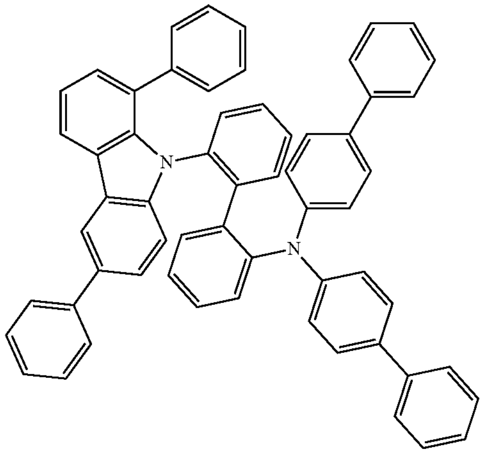
A33
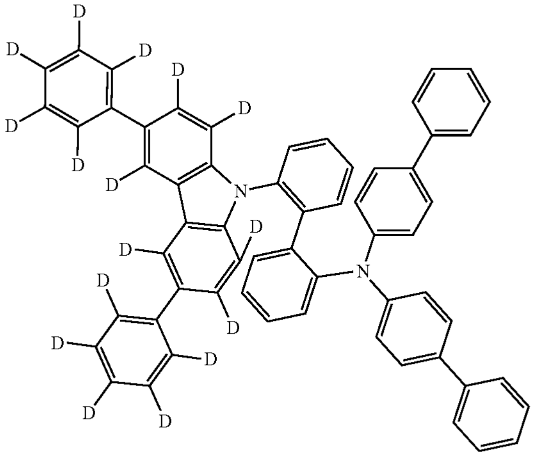
[Compound Group 1B]
B1
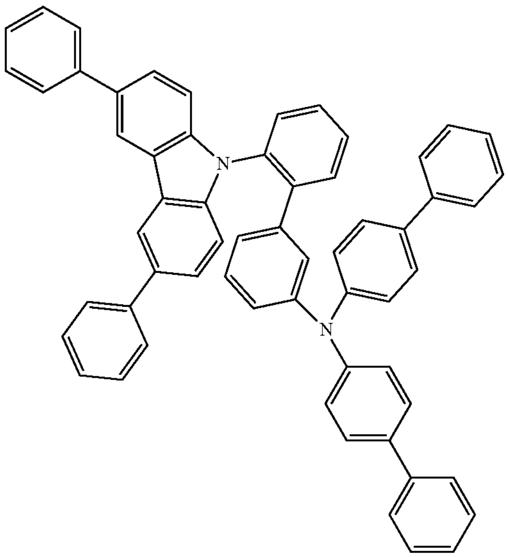

-continued
B2
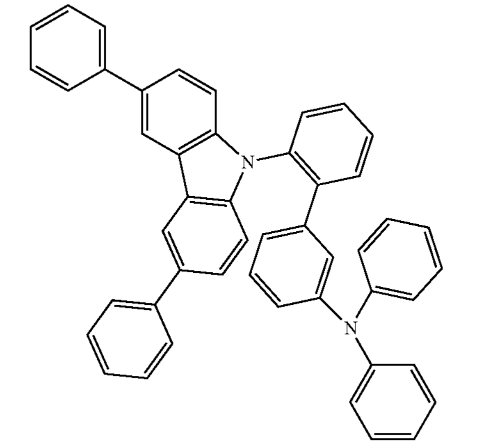
B3
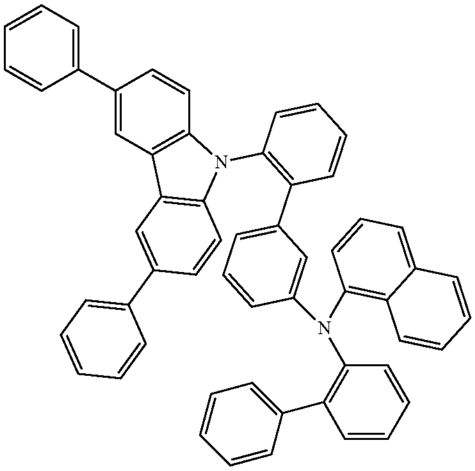
B4
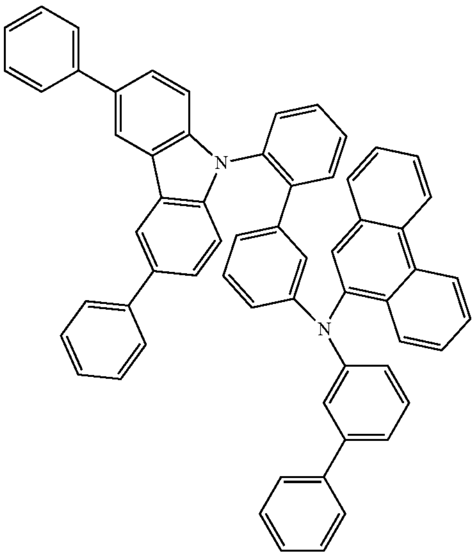
-continued
B5
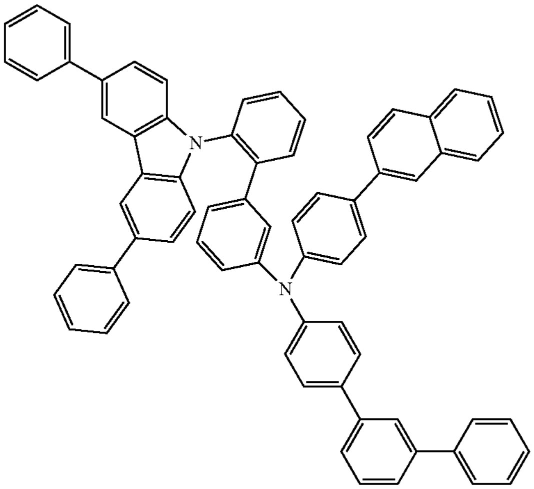
B6
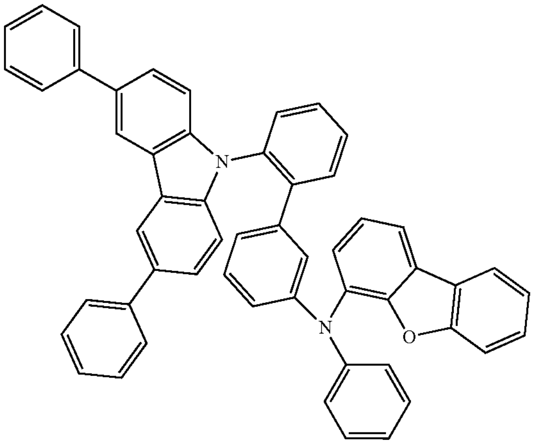
B7
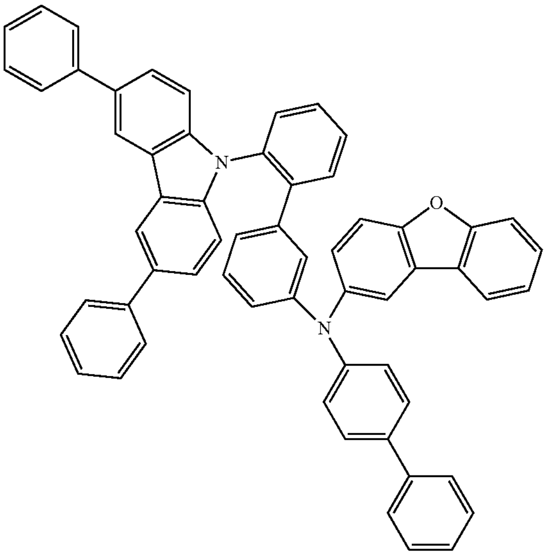

-continued
B8
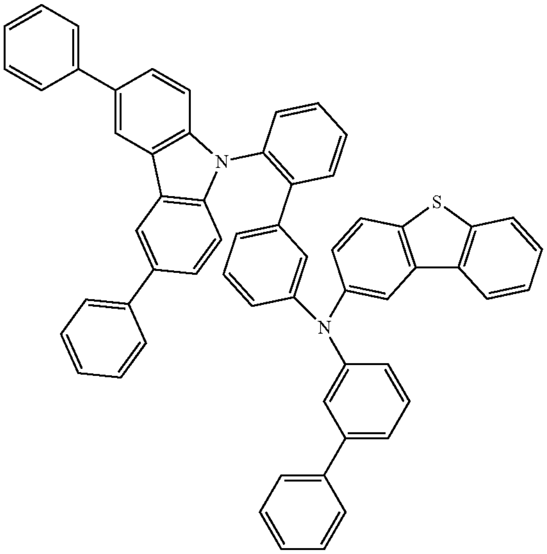
B9
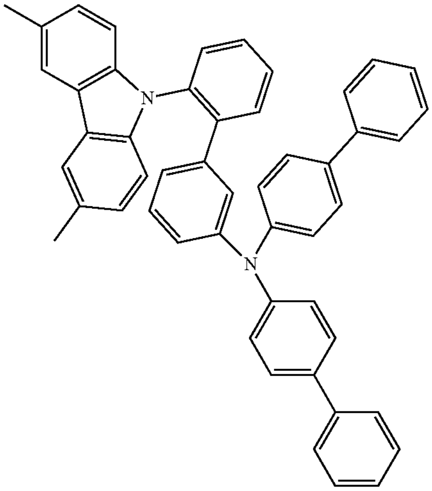
B10
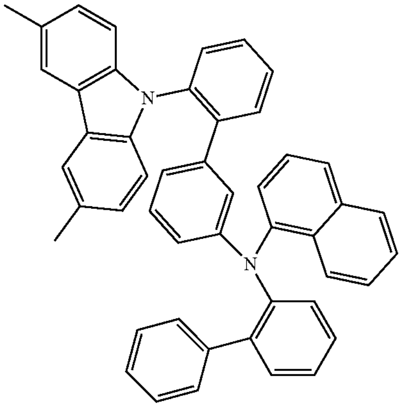
-continued
B11
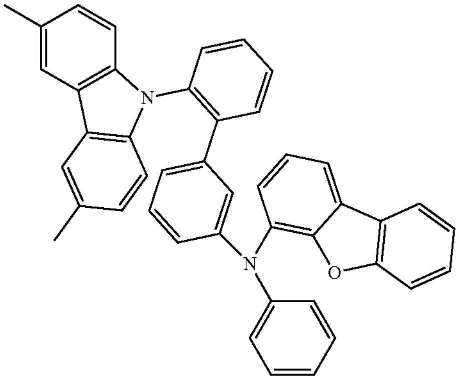
B12
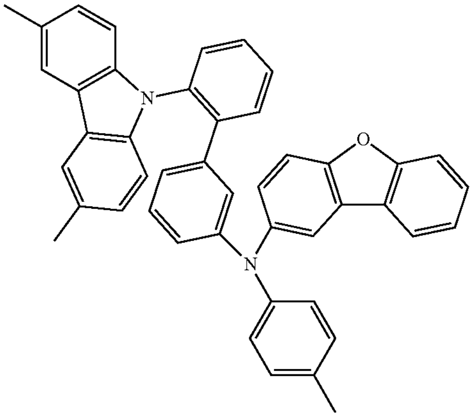
B13
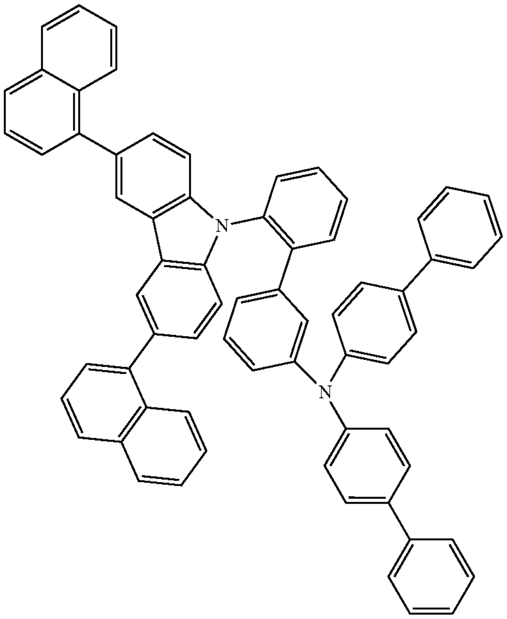

B14
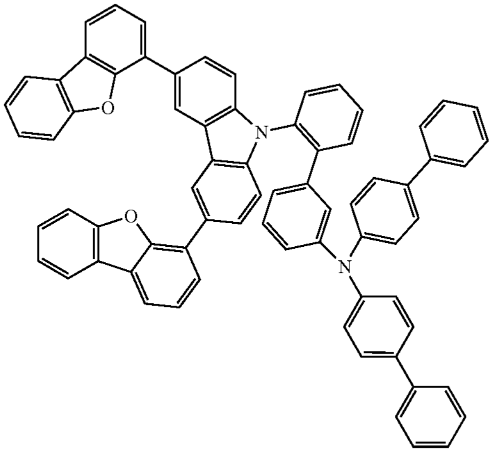
B15
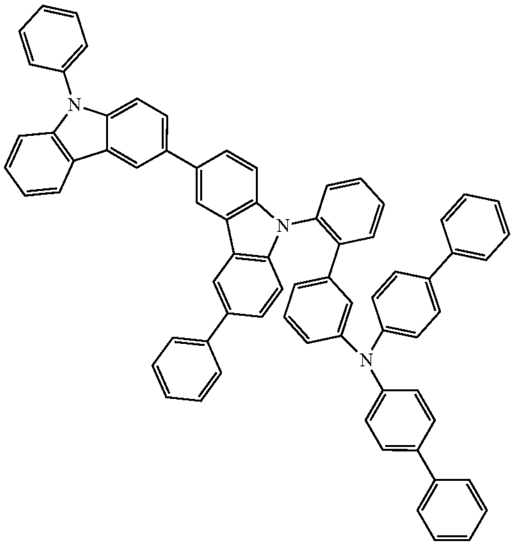
B16
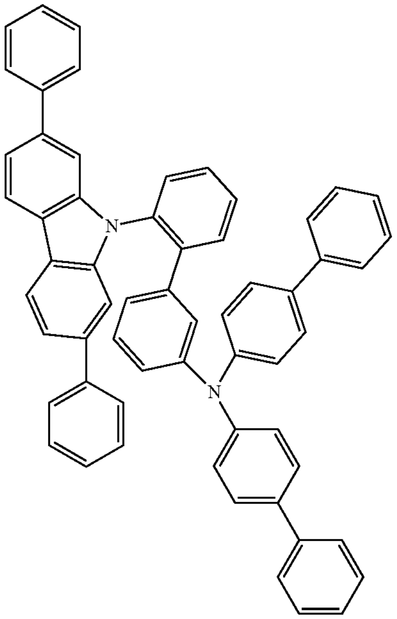
B17
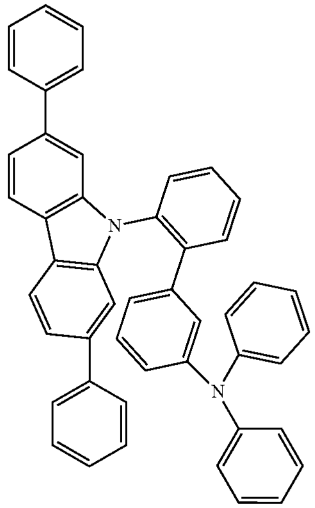
B18
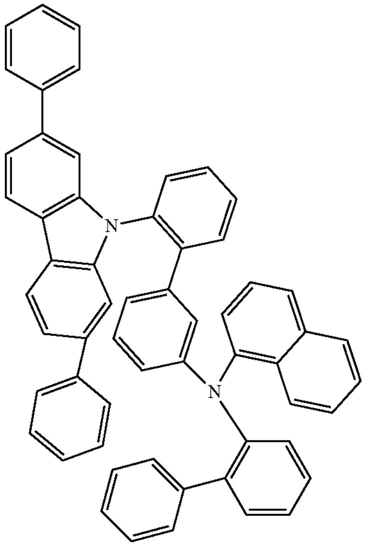

-continued
B19
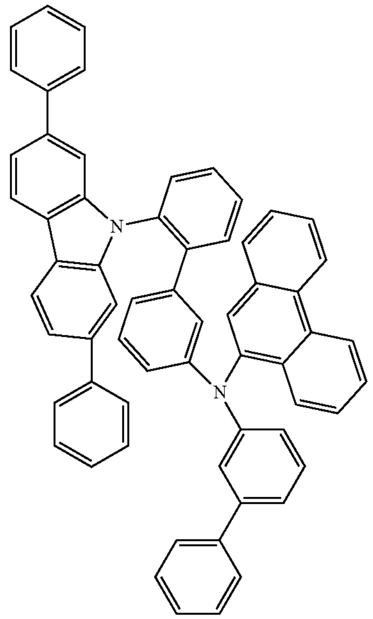
-continued
B21
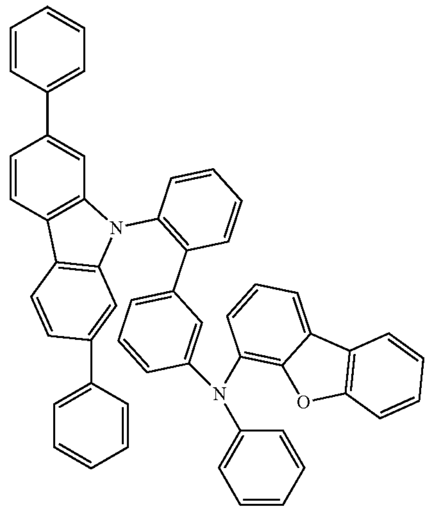
B20
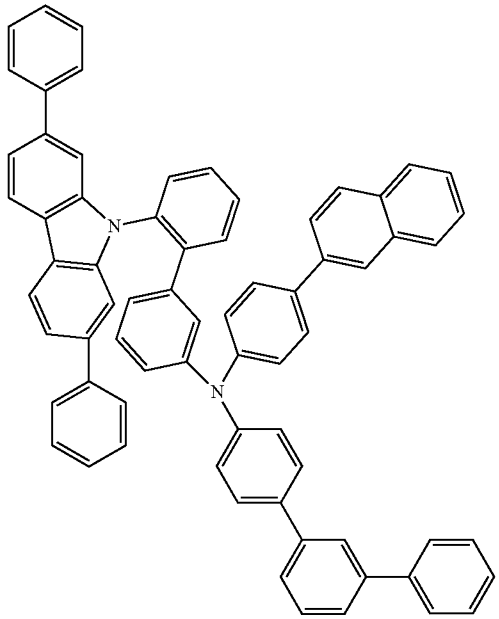
B22
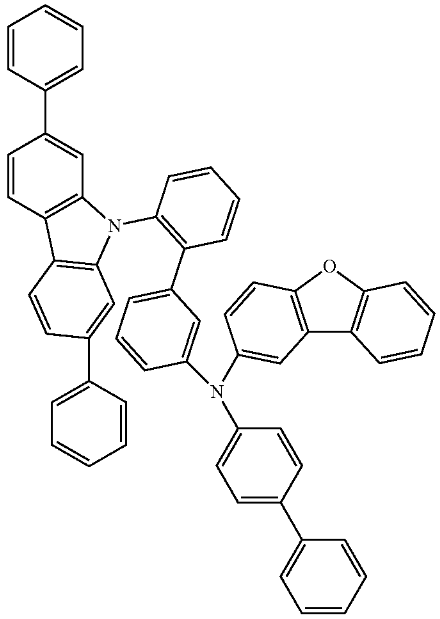

-continued
B23
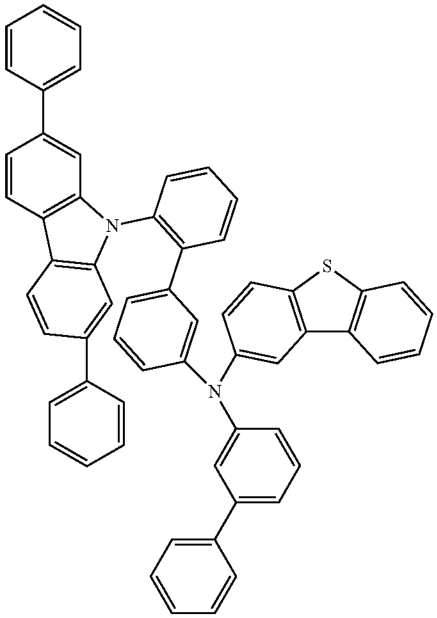
B24
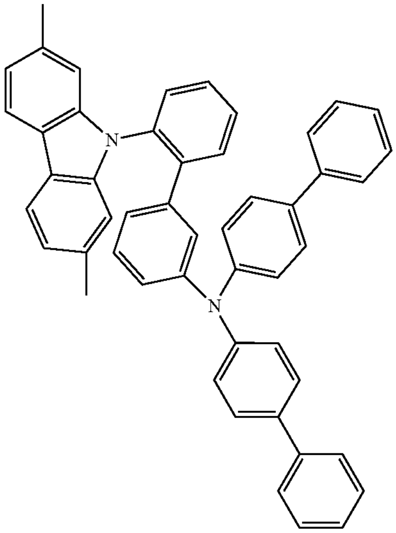
B25
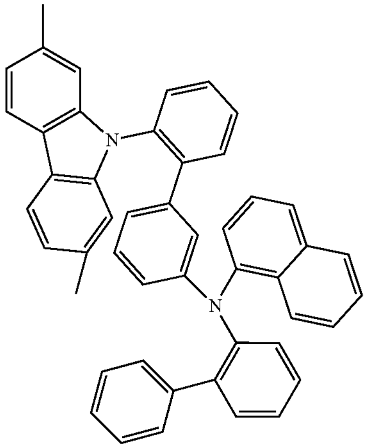
-continued
B26
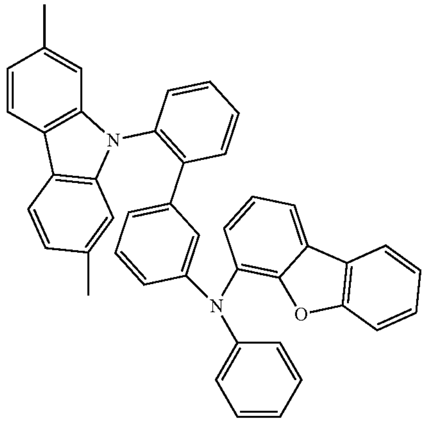
B27
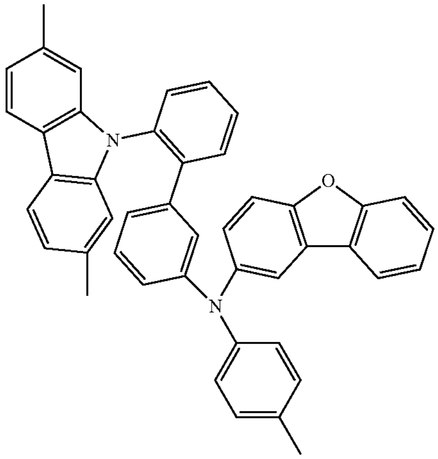
B28
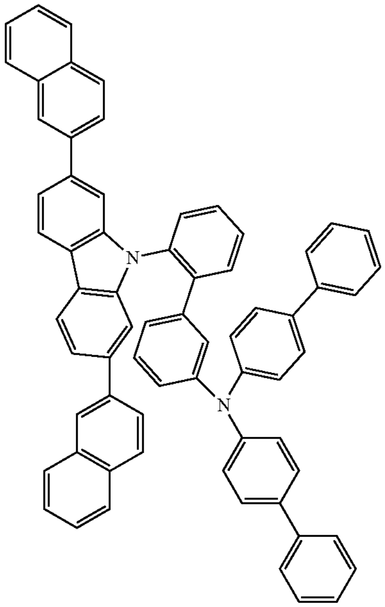

-continued
B29
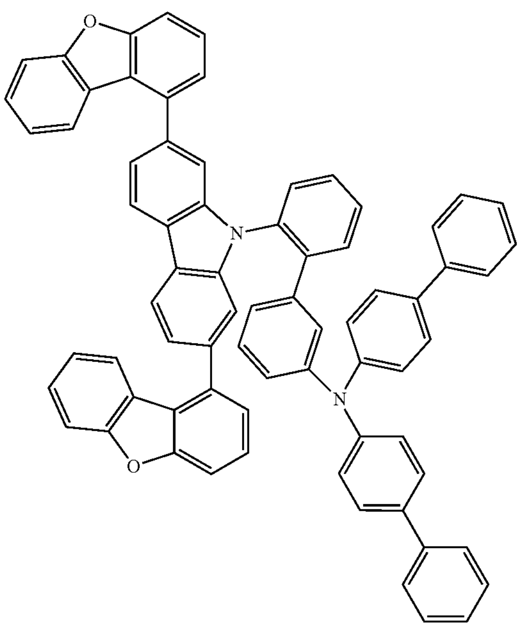
B30
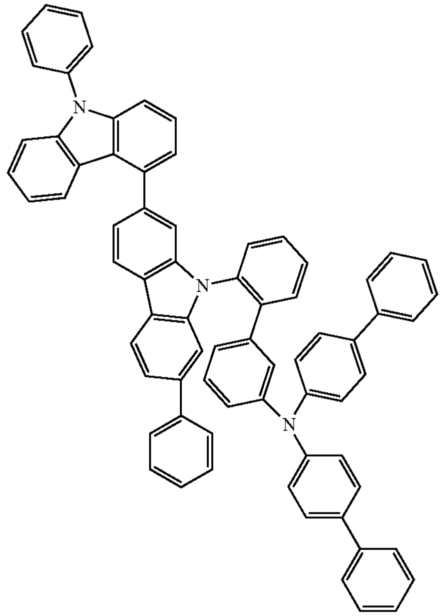
-continued
B31
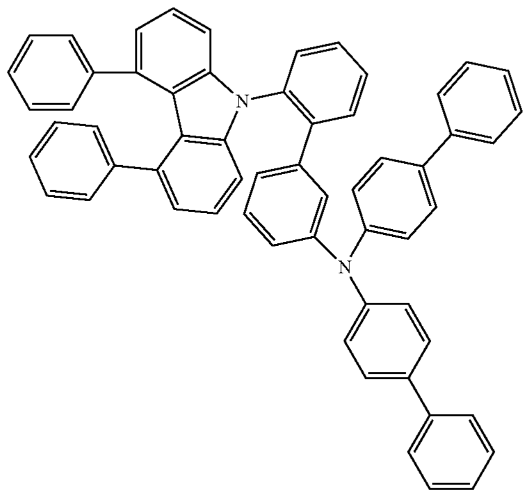
B32
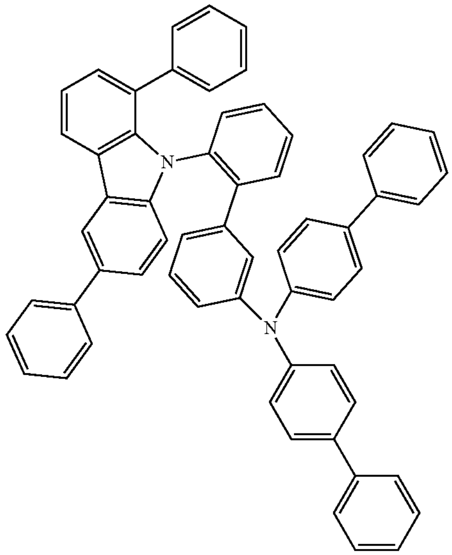
[Compound Group 1C]
C1
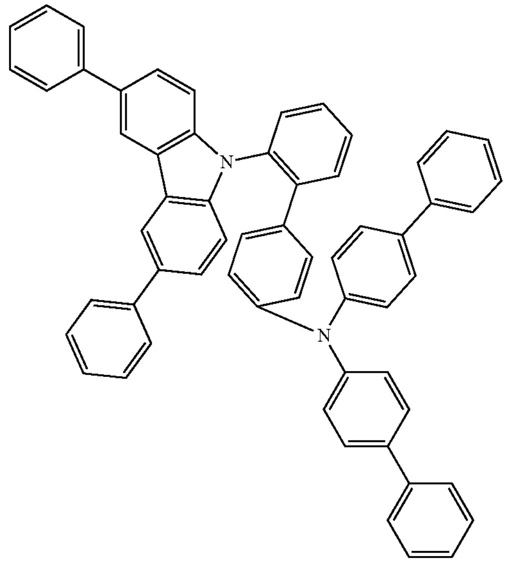

-continued
C2
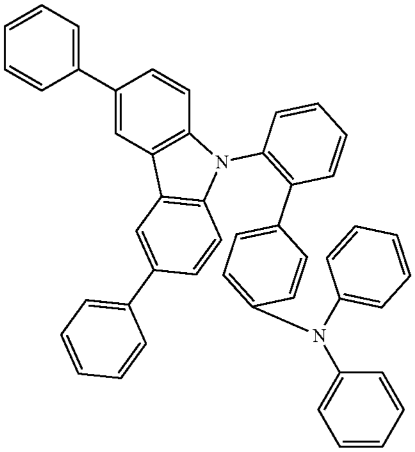
C3
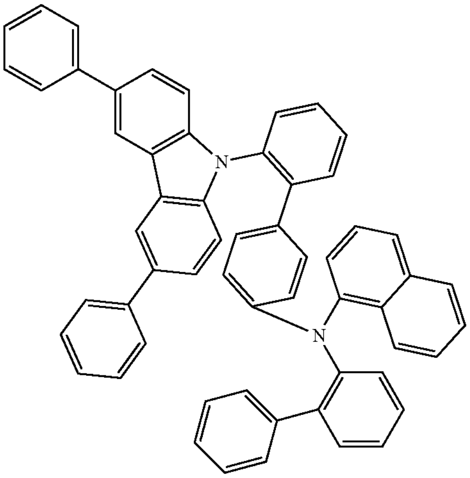
C4
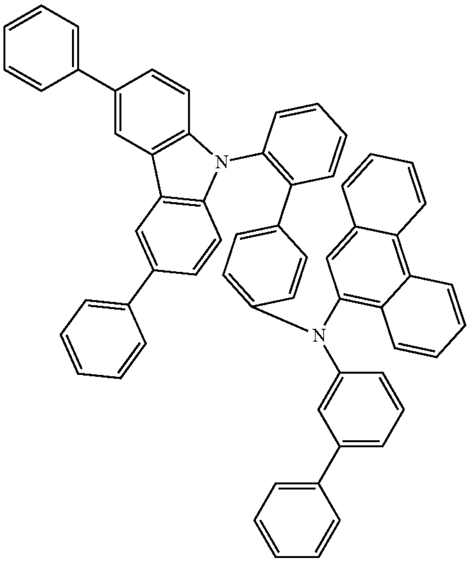
-continued
C5
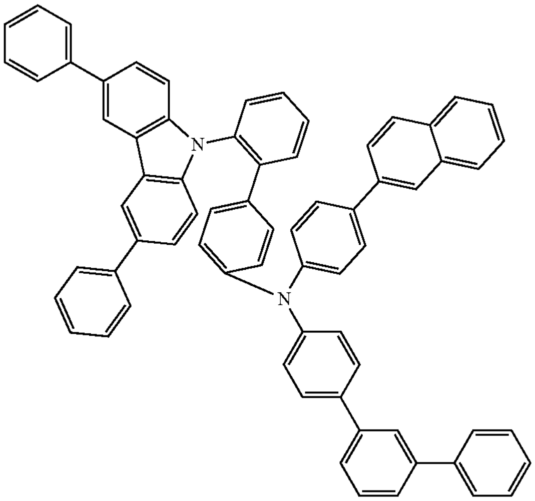
C6
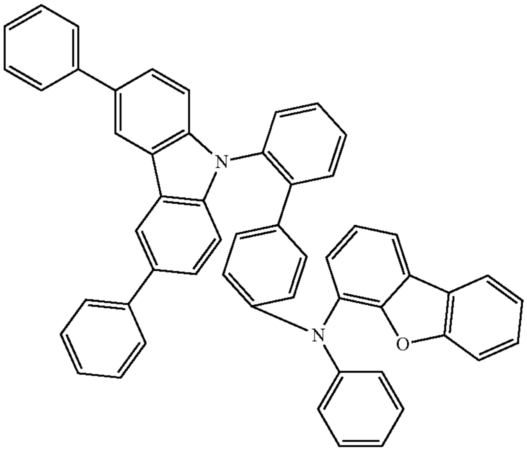
C7
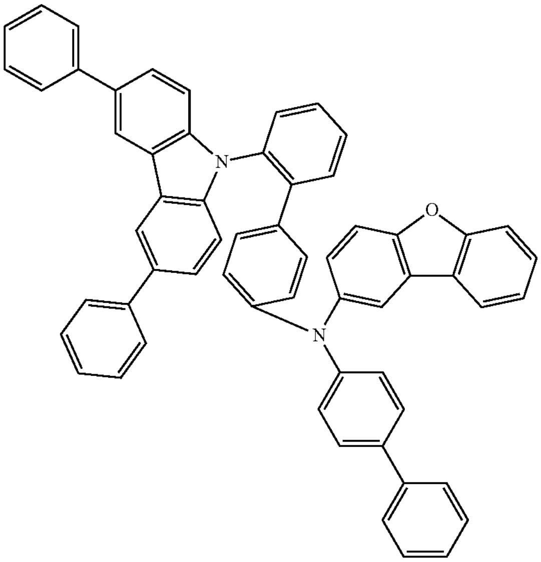

-continued
C8
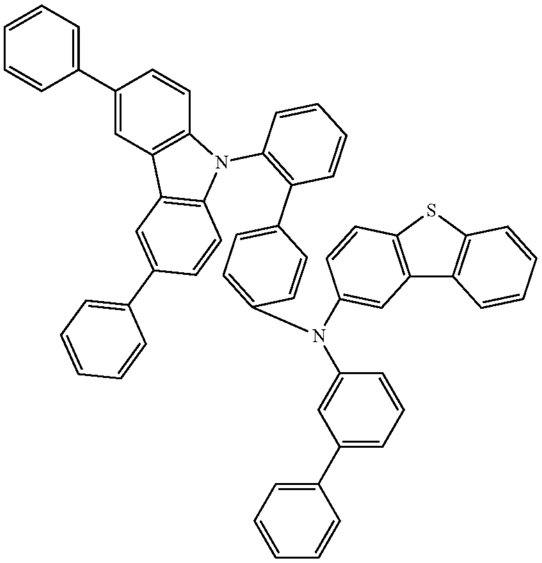
C9
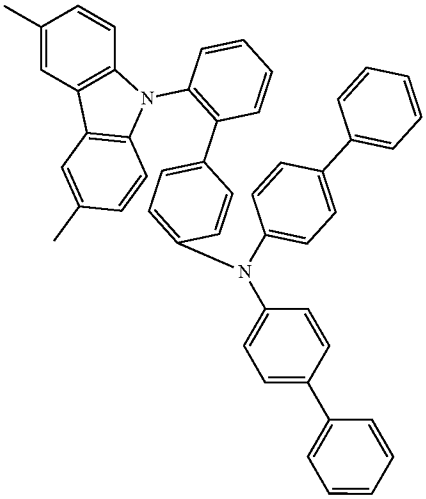
C10
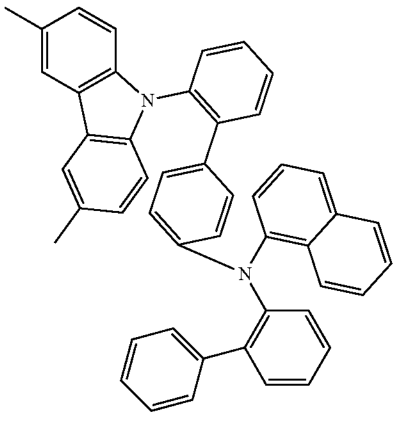
-continued
C11
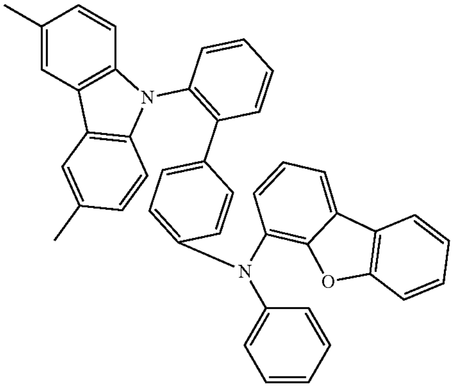
C12
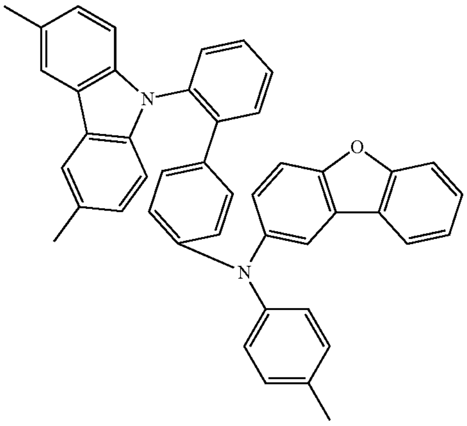
C13
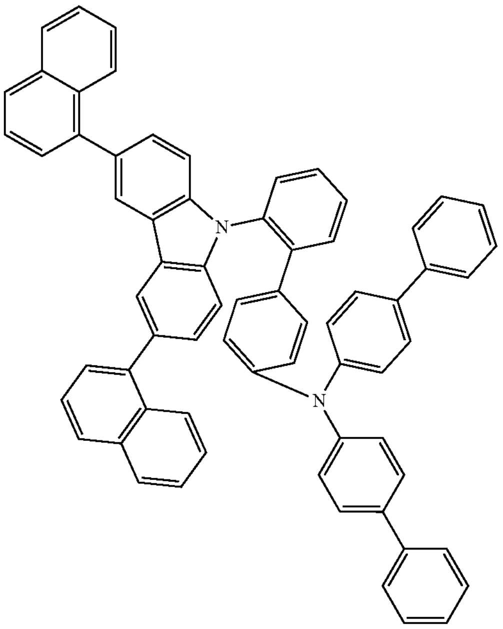

-continued
C14
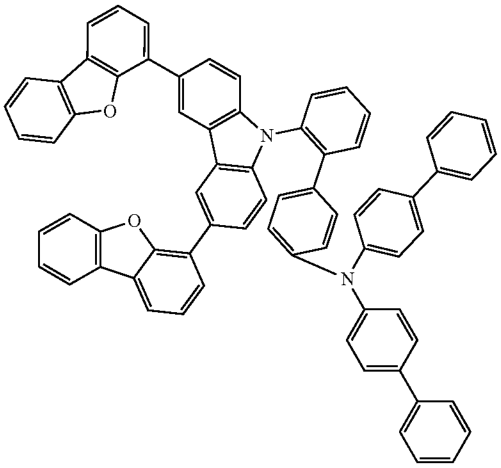
C15
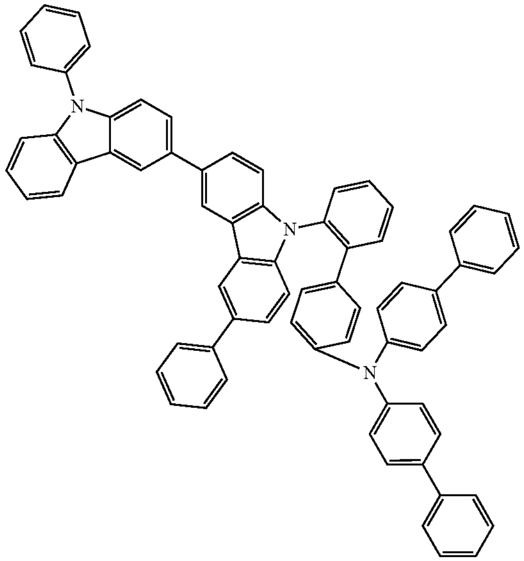
-continued
C16
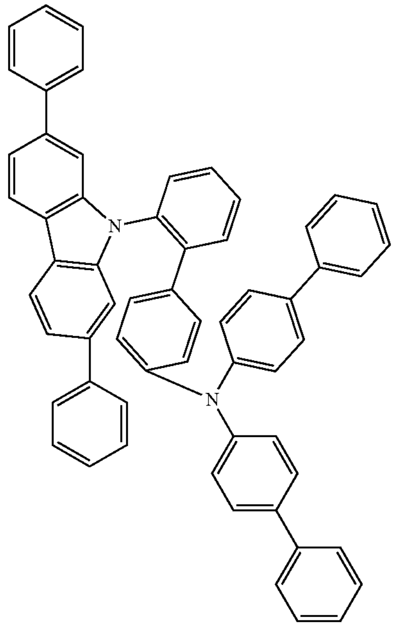
C17
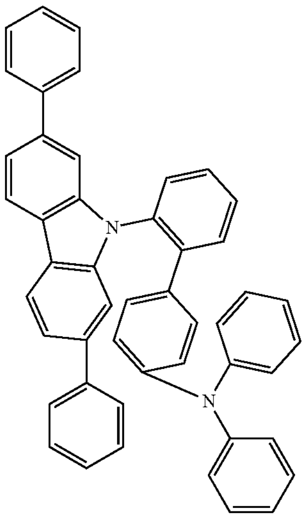

-continued
C18
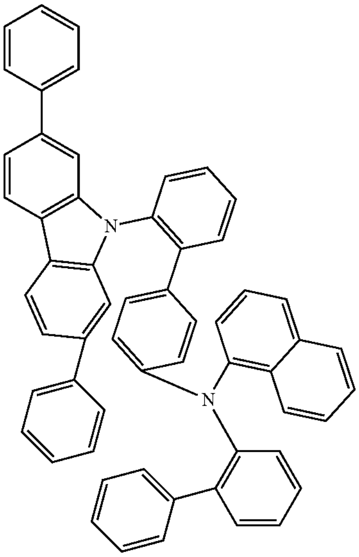
C19
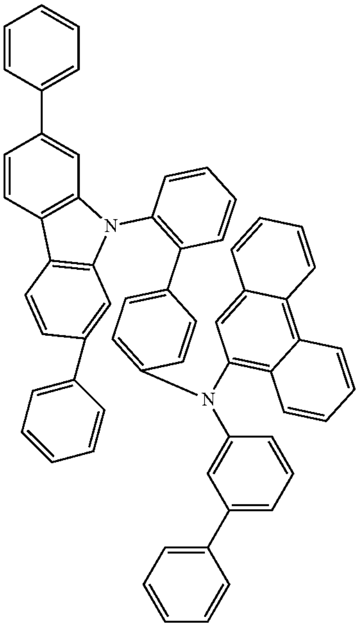
-continued
C20
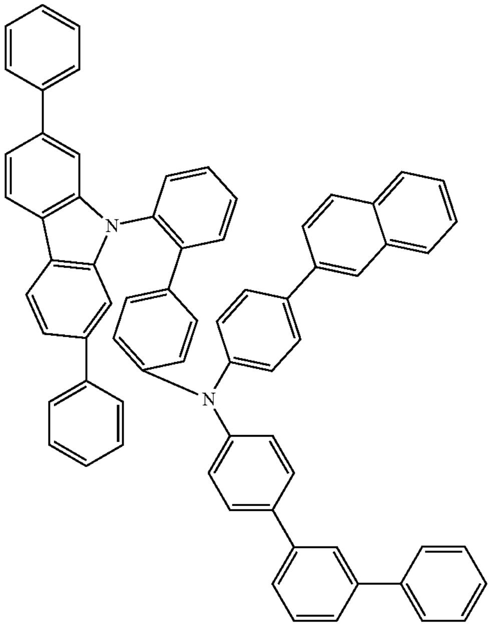
C21
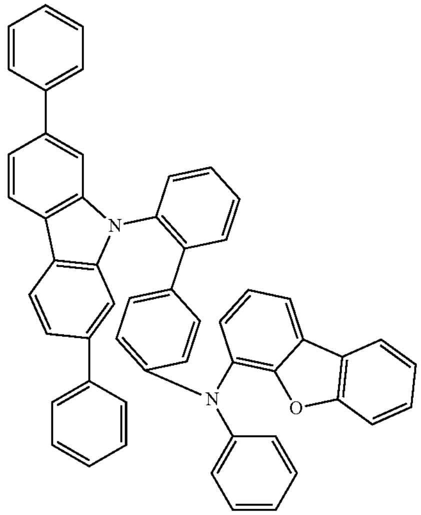

C22
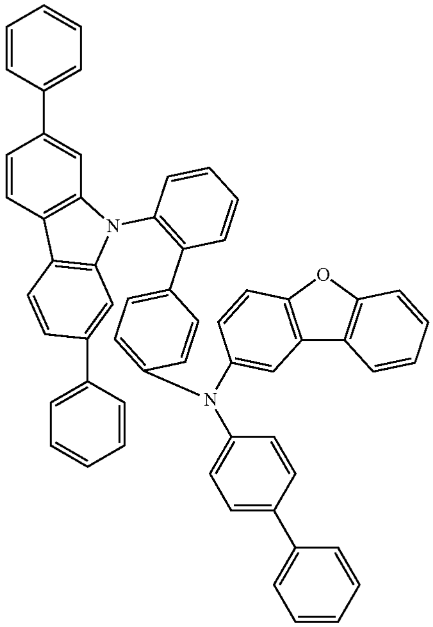
C23
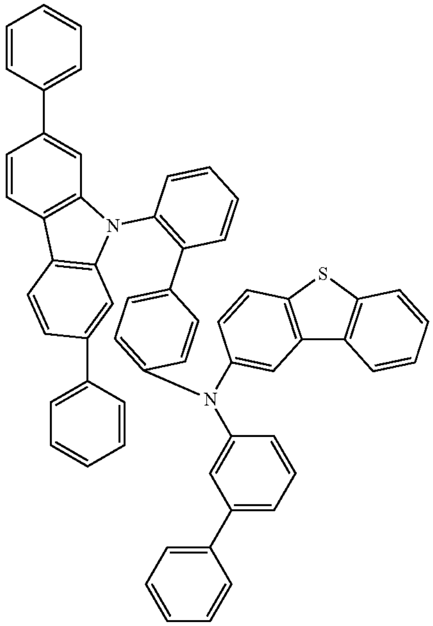
C24
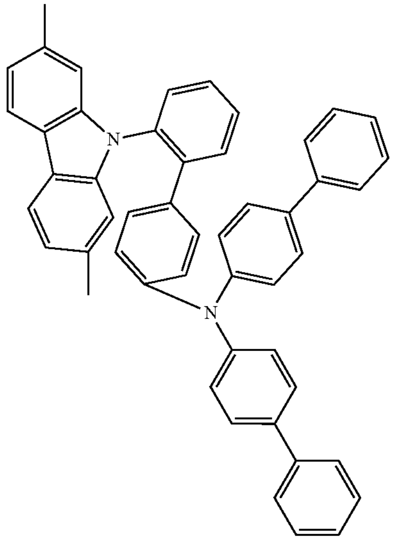
C25
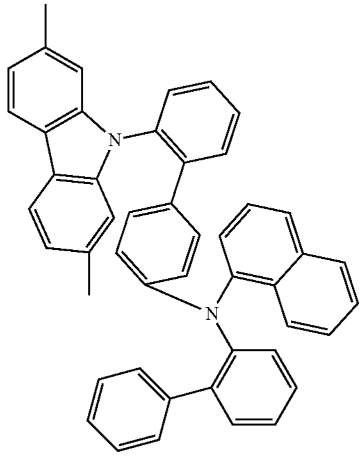
C26
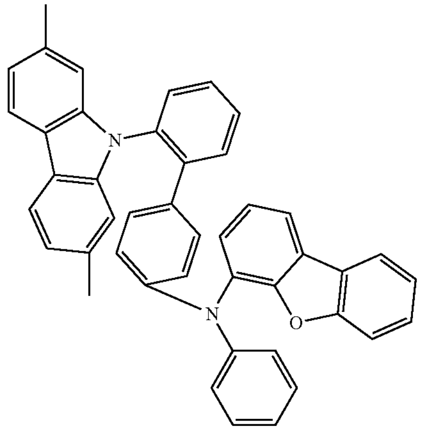

-continued
C27
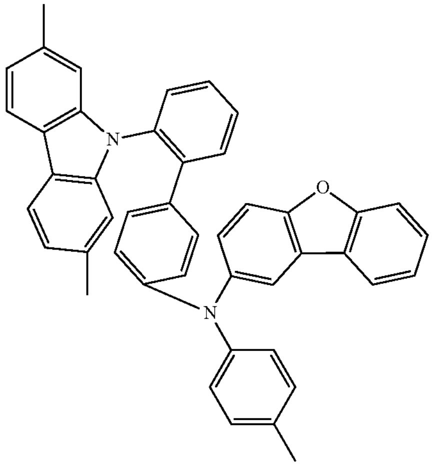
C28
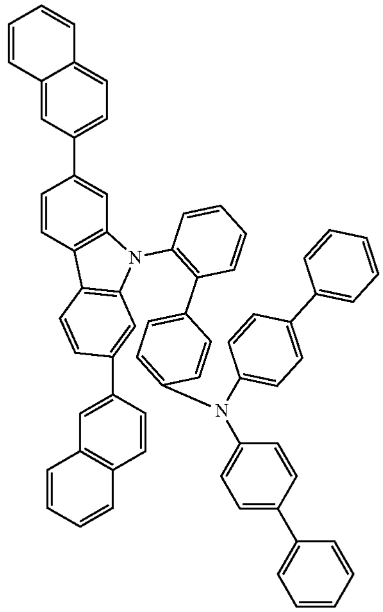
-continued
C29
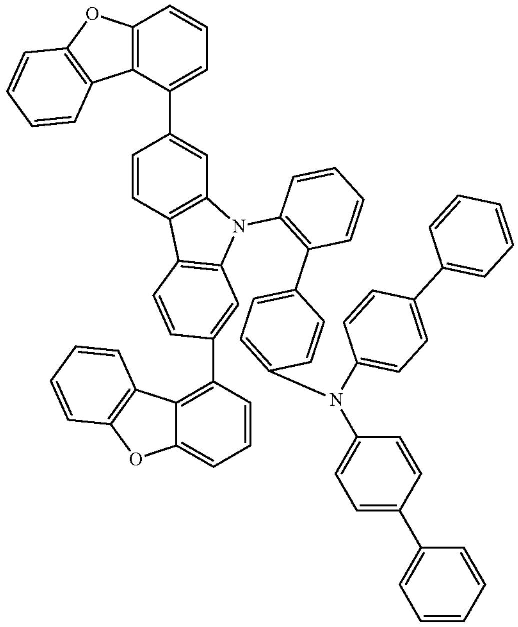
C30
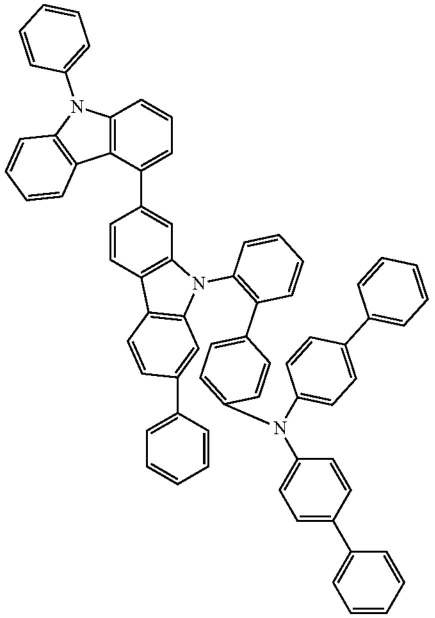

-continued
C31
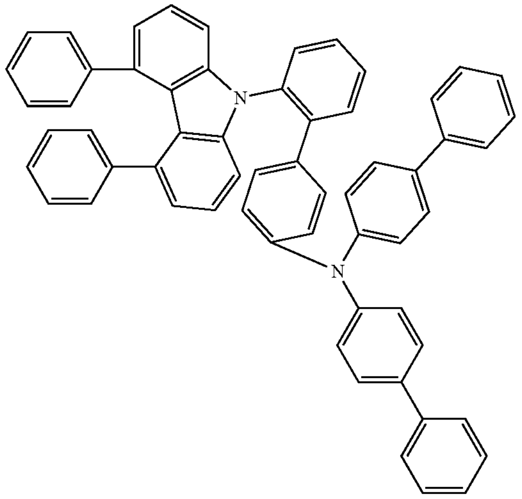
C32
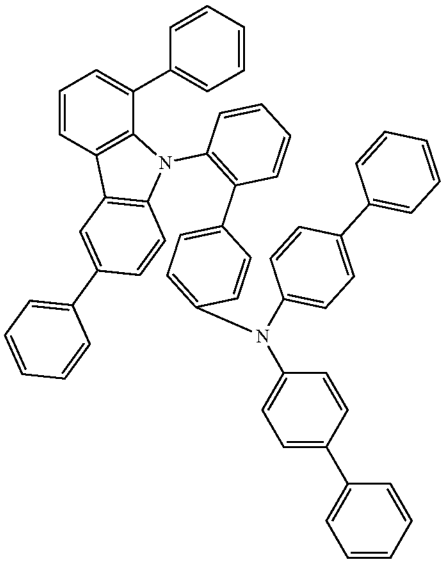
[Compound Group 1D]
D1
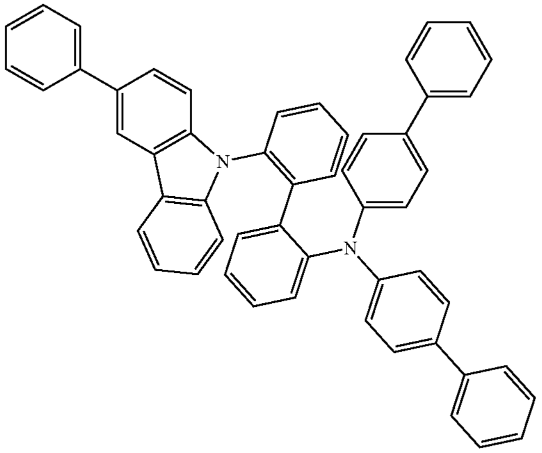
-continued
D2
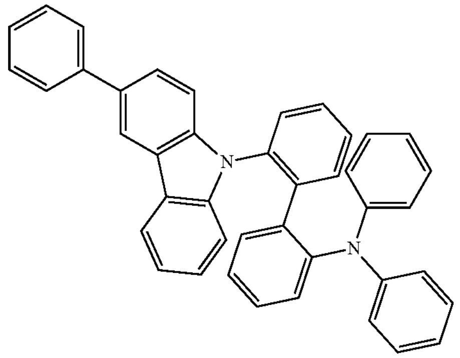
D3
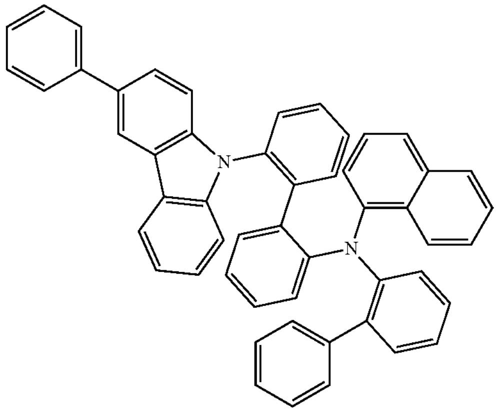
D4
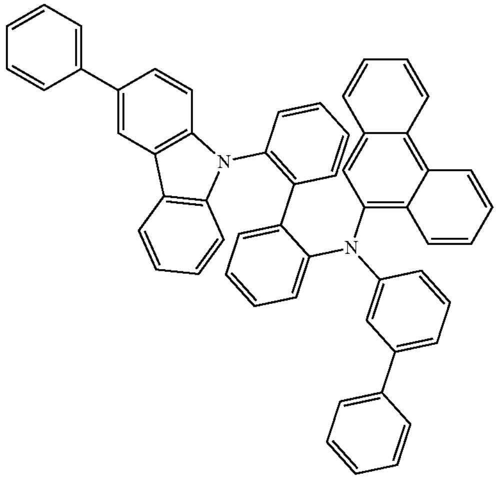

-continued
D5
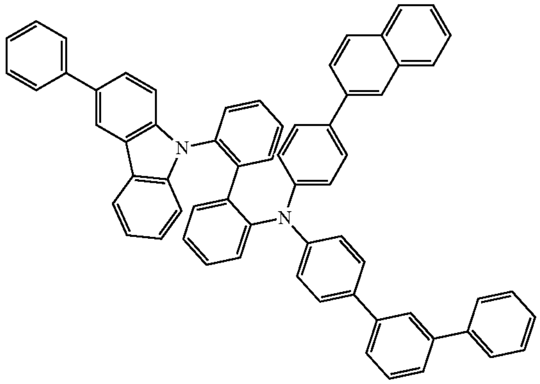
D6
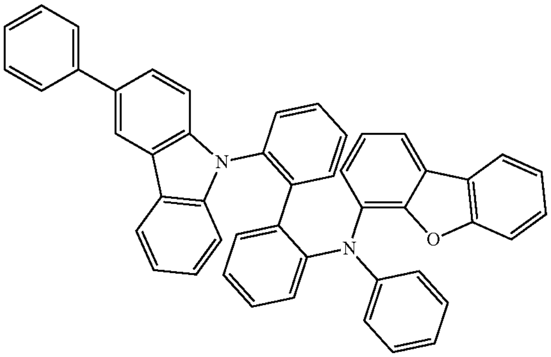
D7
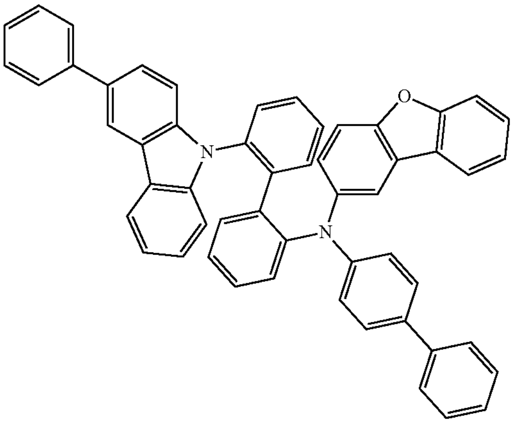
-continued
D8
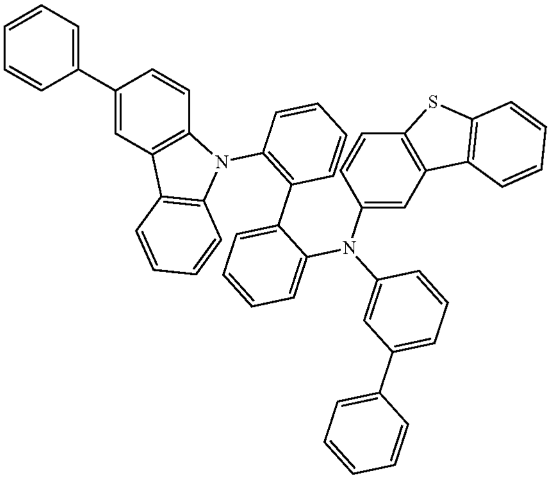
D9
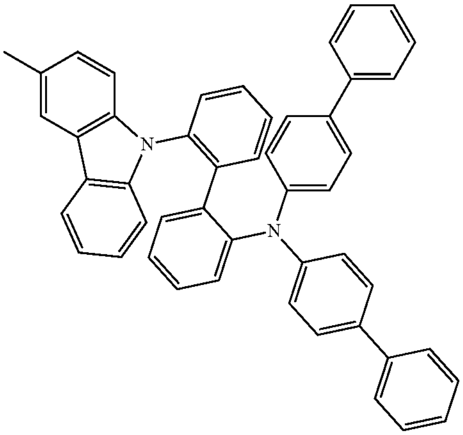
D10
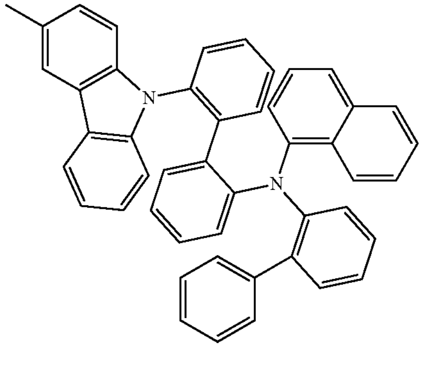
D11
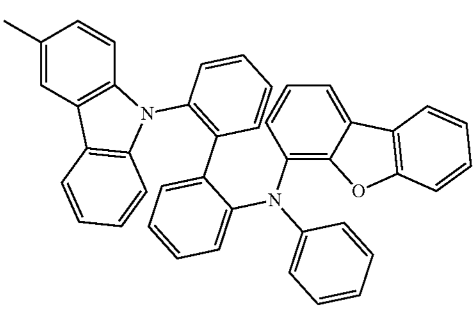

-continued
D12
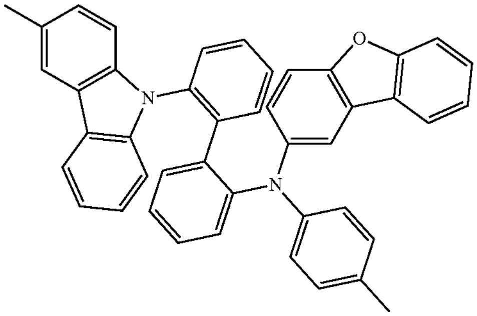
D13
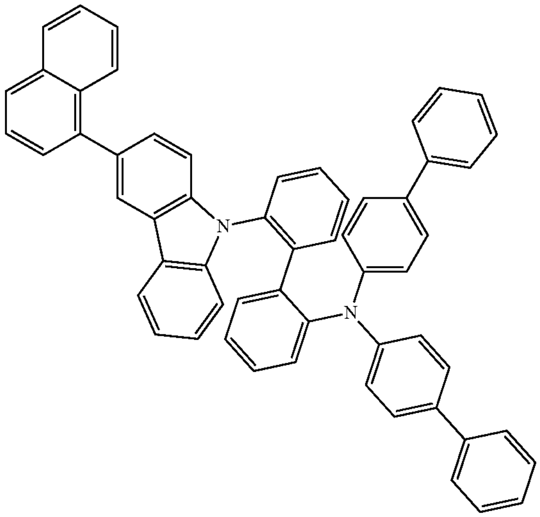
D14
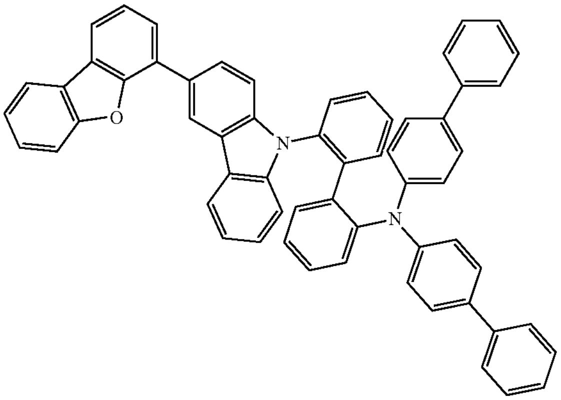
-continued
D15
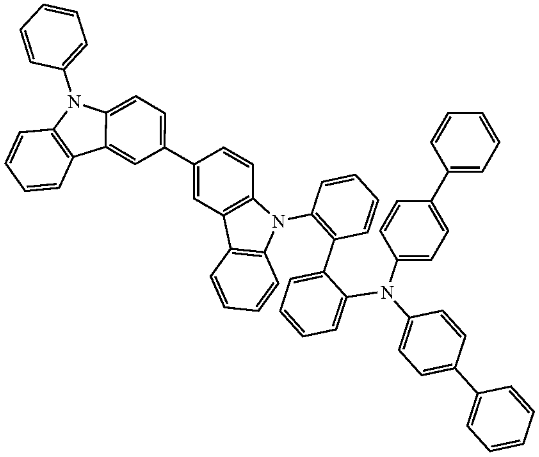
D16
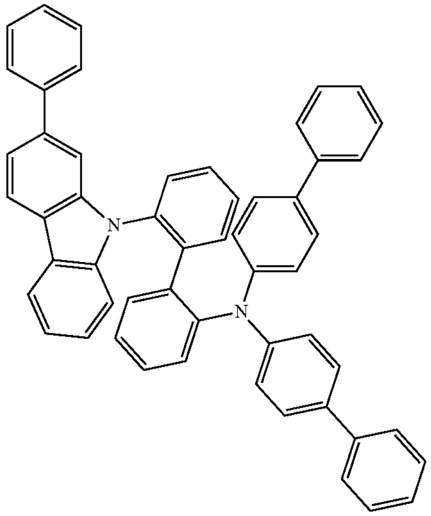
D17
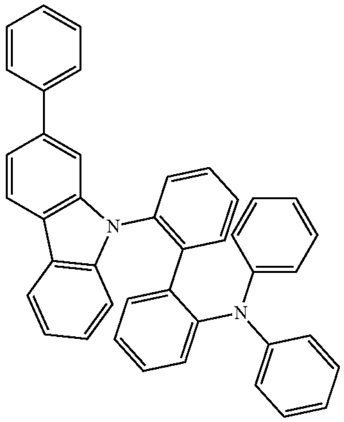

-continued
D18
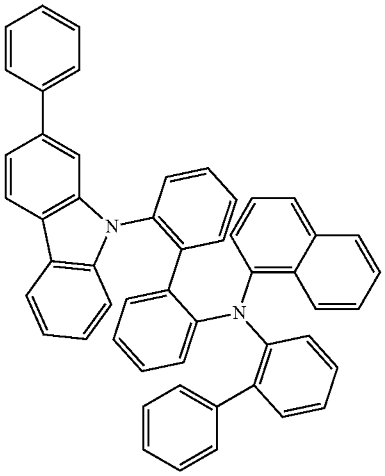
D19
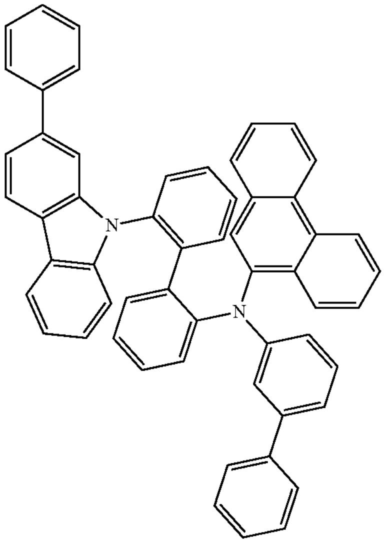
D20
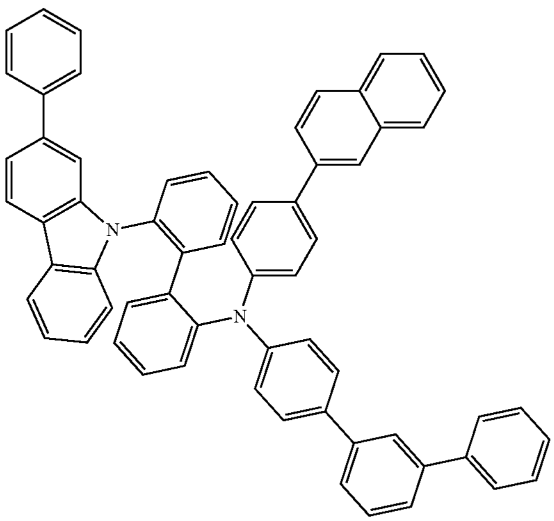
-continued
D21
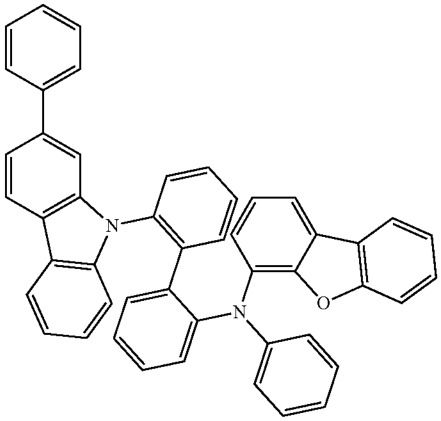
D22
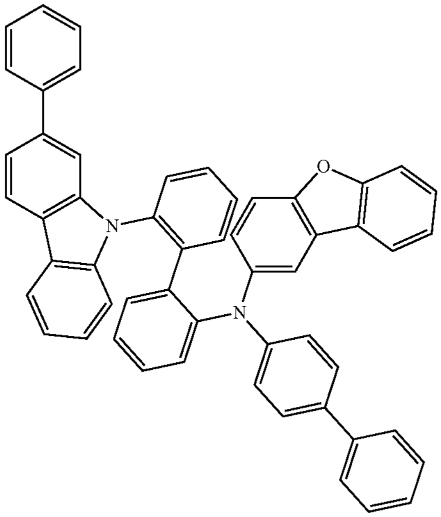
D23
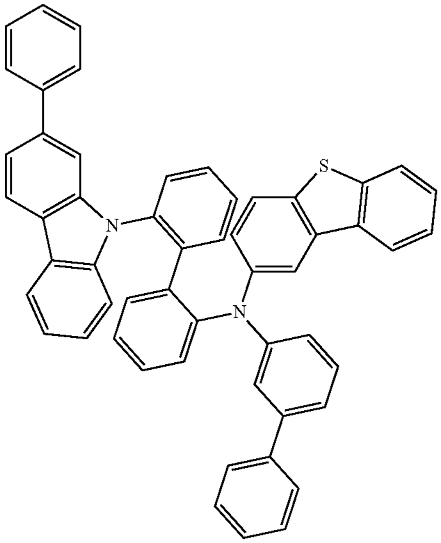

-continued
D24
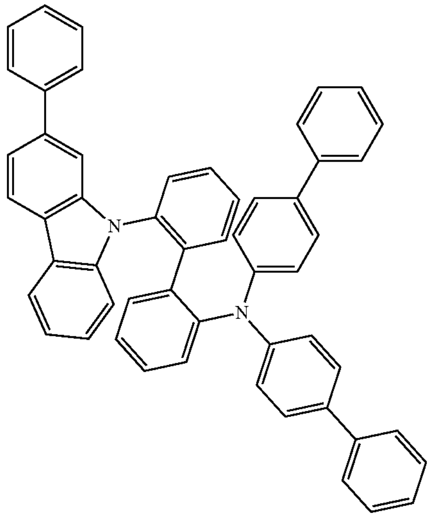
D25
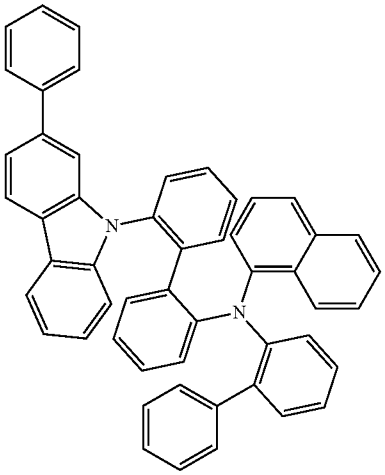
D26
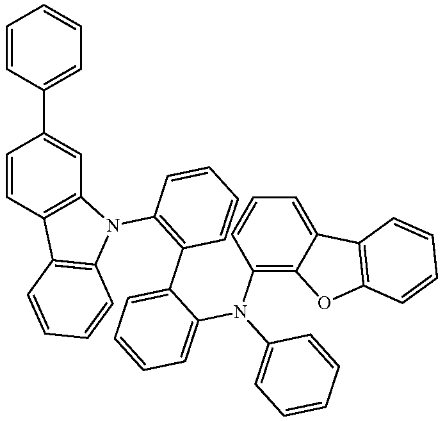
-continued
D27
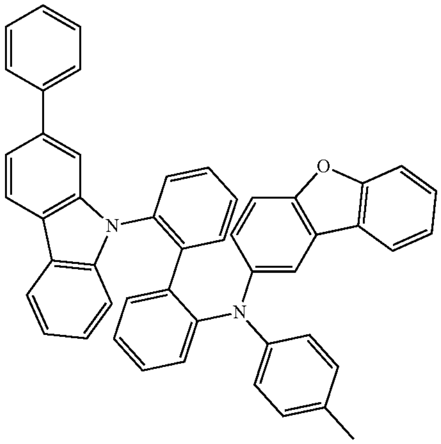
D28
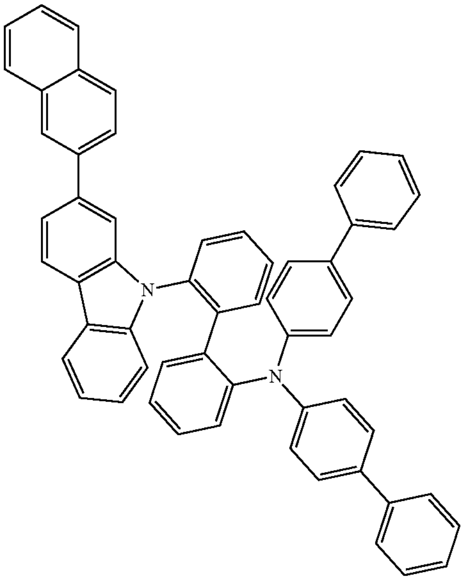
D29
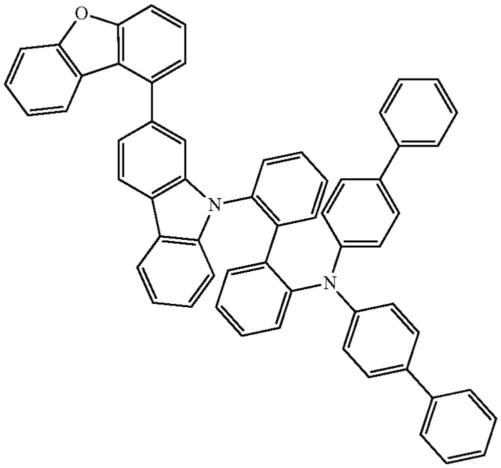

-continued
D30
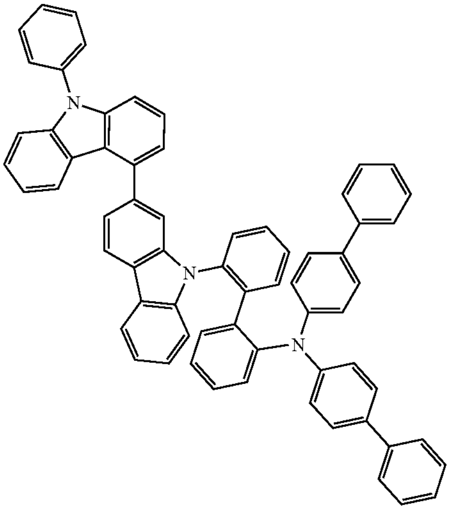
D31
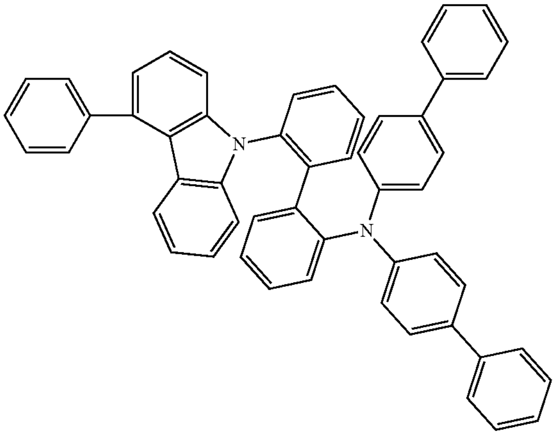
D32
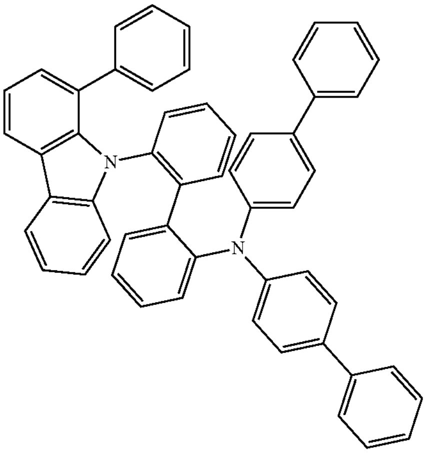
-continued
D33
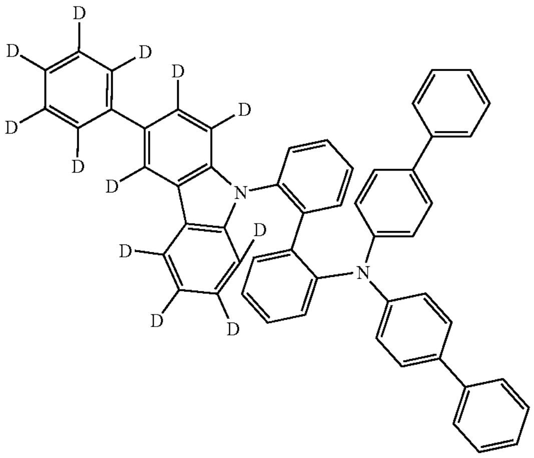
[Compound Group 1E]
E1
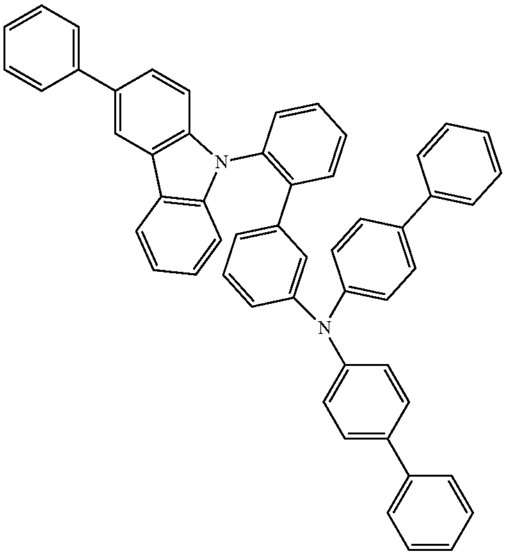
E2
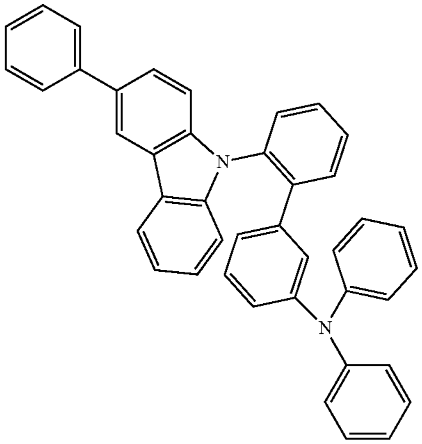

-continued
E3
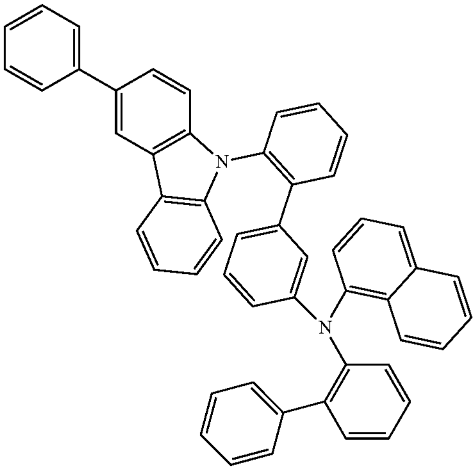
E4
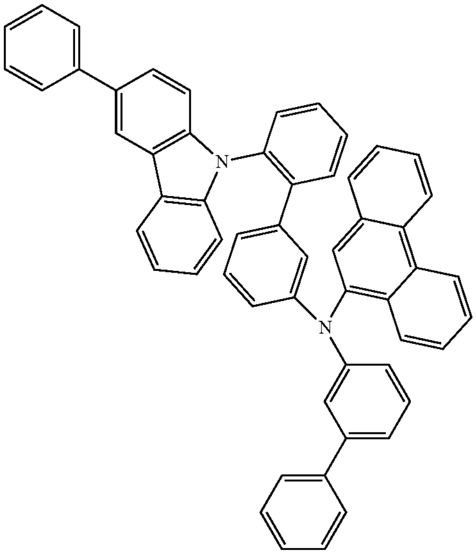
E5
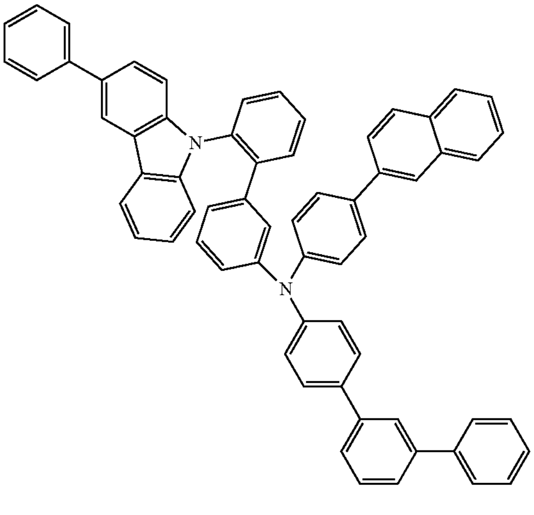
-continued
E6
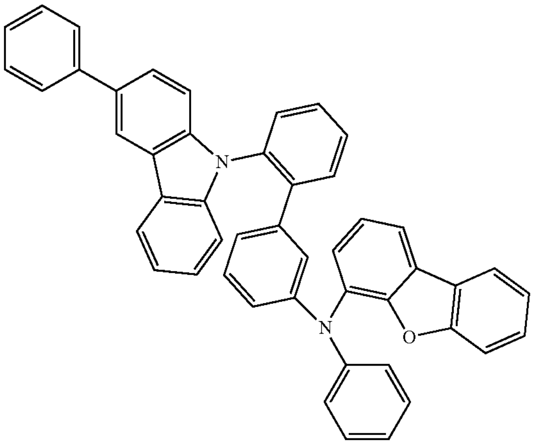
E7
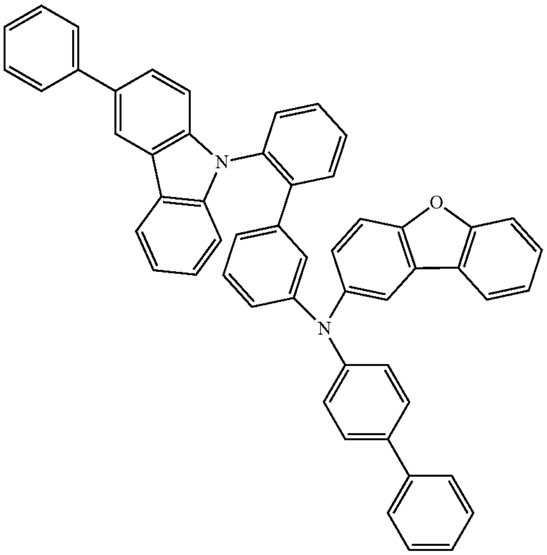
E8
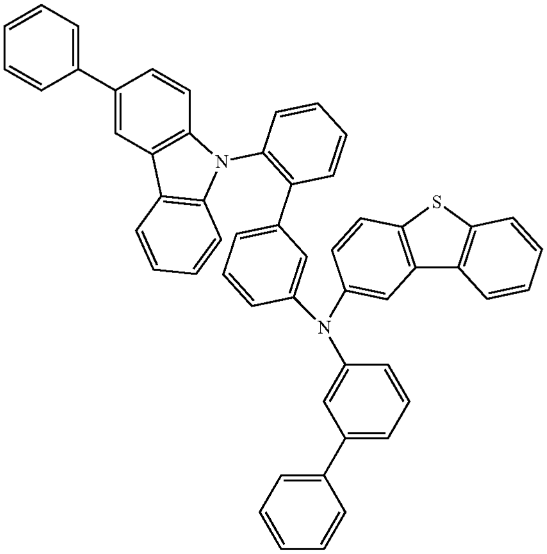

E9
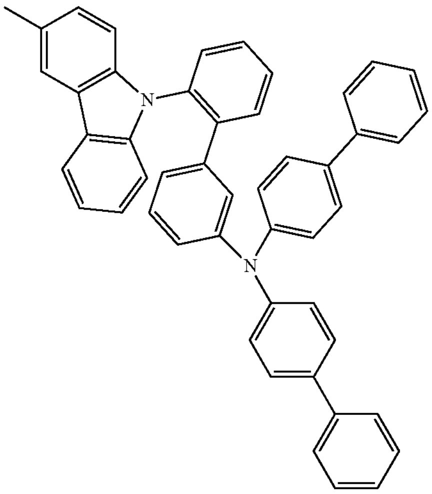
E10
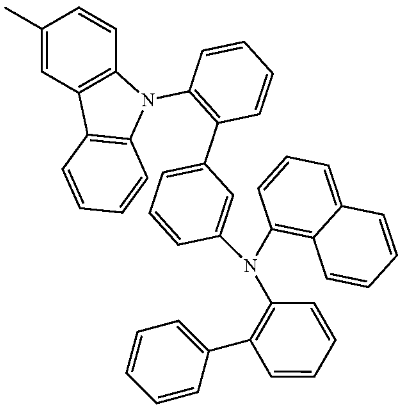
E11
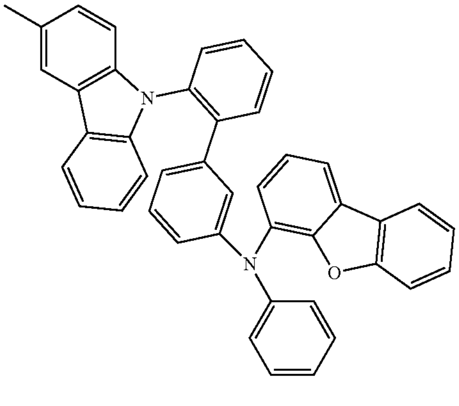
E12
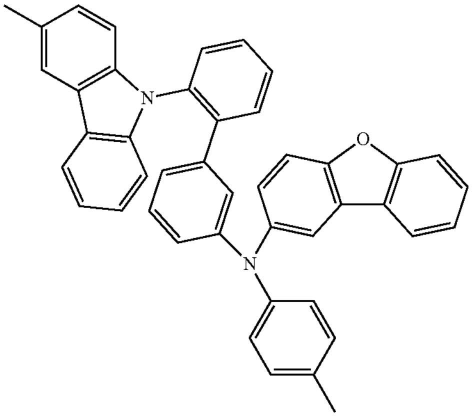
E13
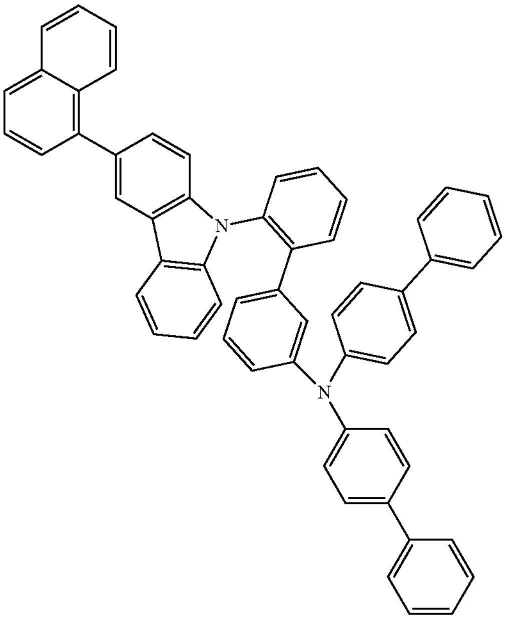
E14
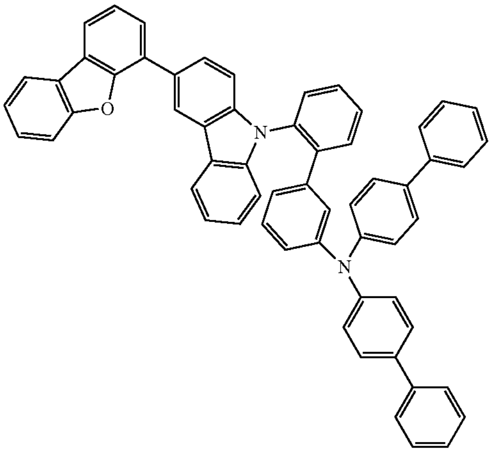

-continued
E15
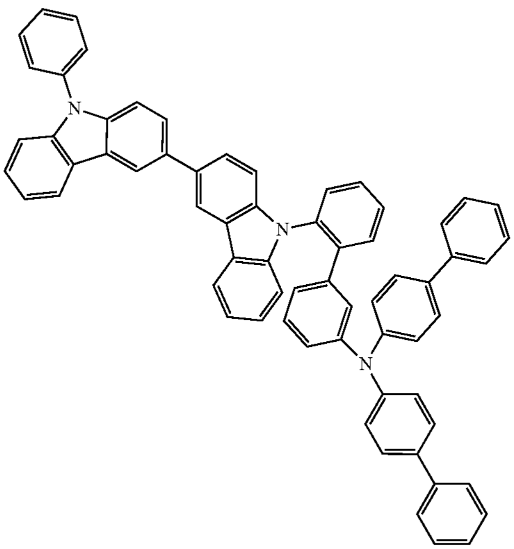
-continued
E17
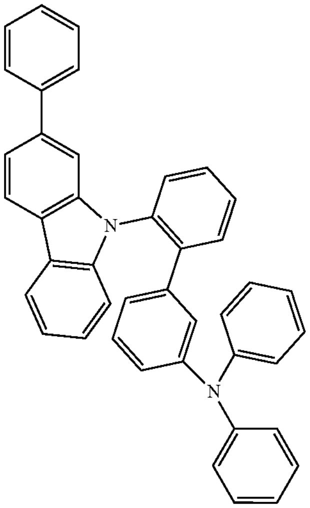
E16
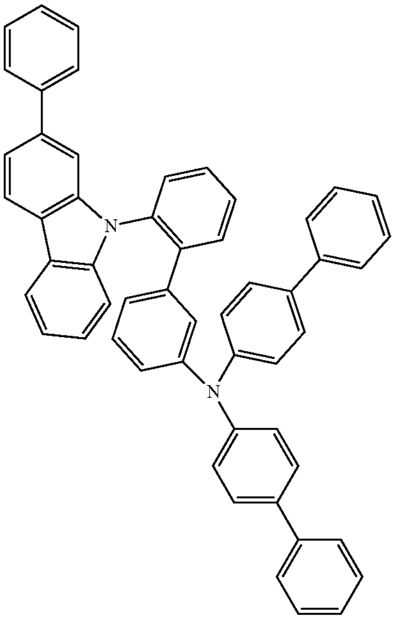
E18
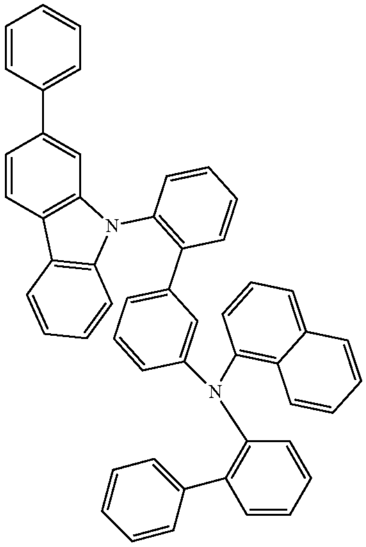

-continued
E19
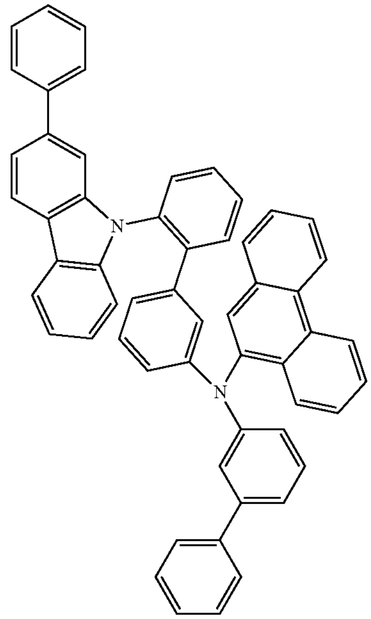
E20
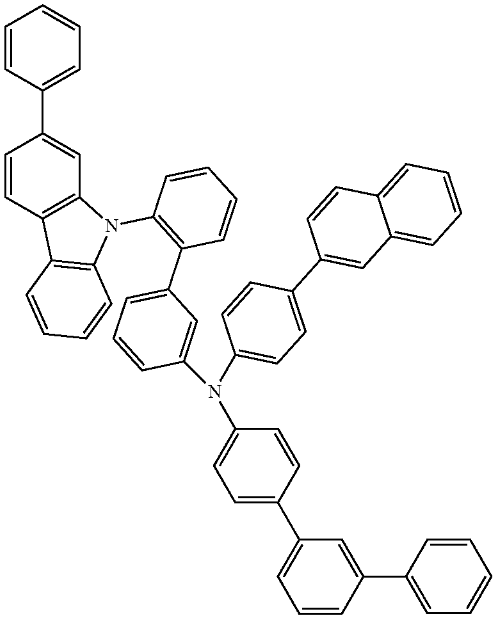
-continued
E21
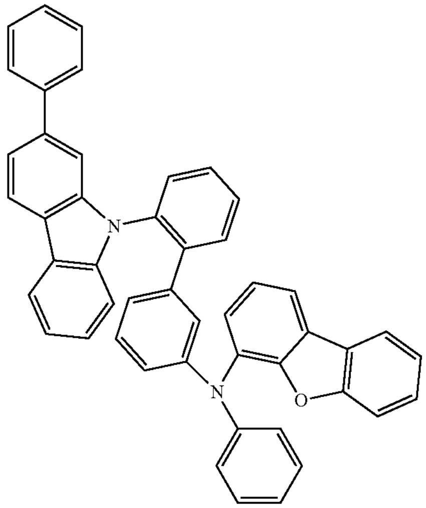
E22
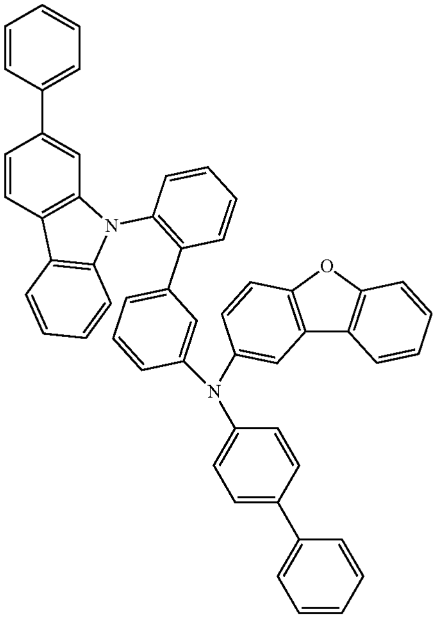

-continued
E23
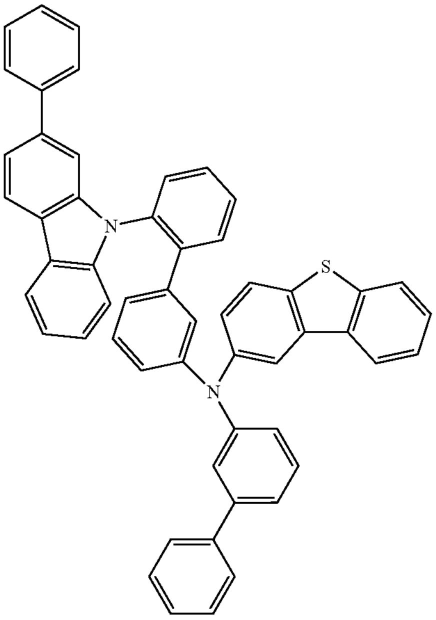
E24
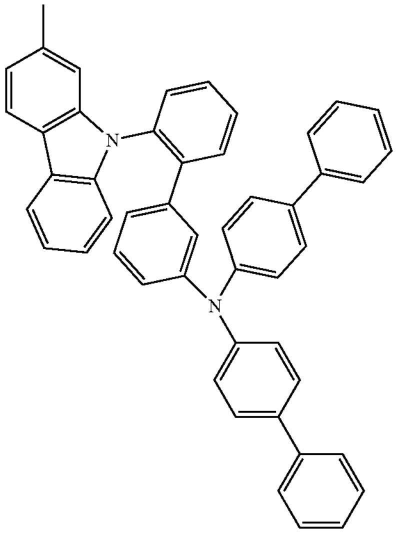
E25
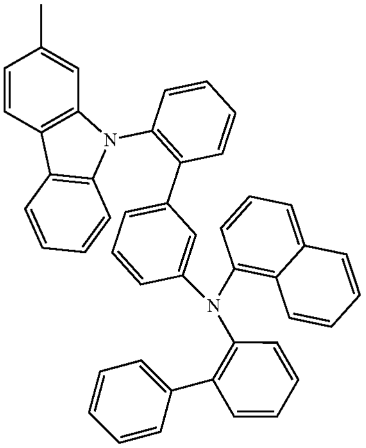
-continued
E26
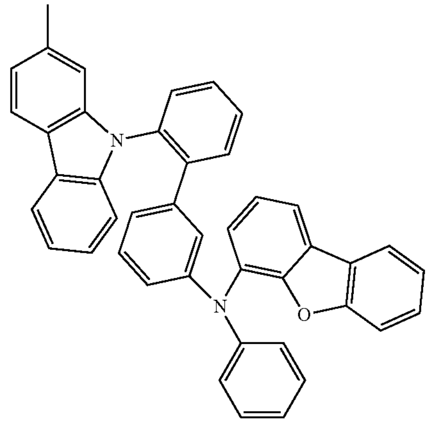
E27
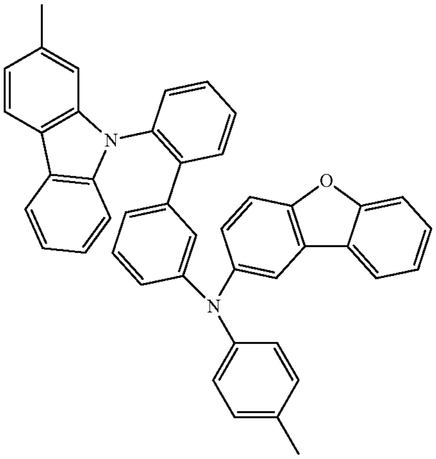
E28
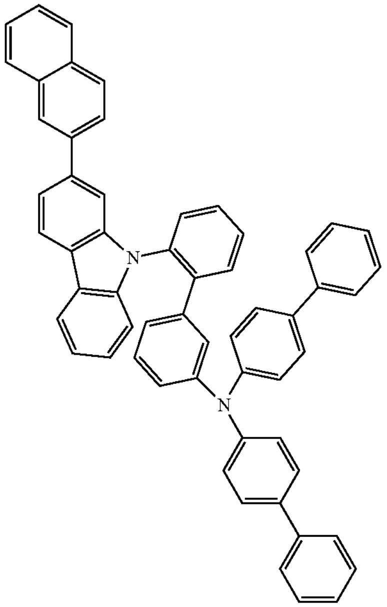

-continued
E29
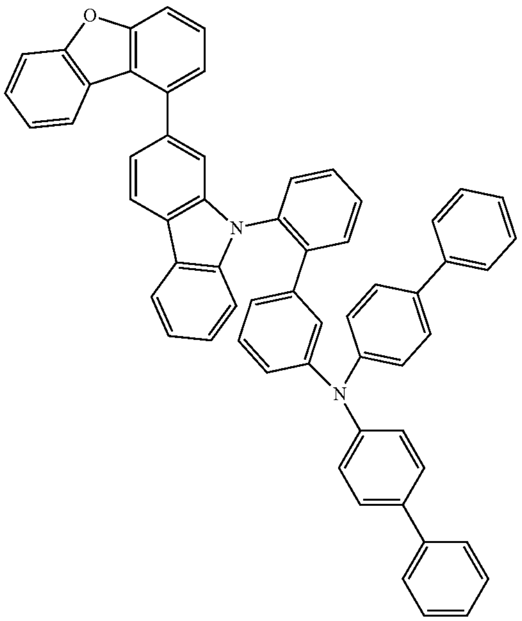
E30
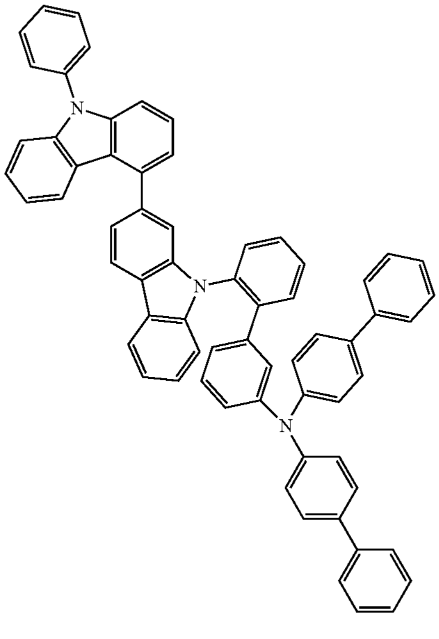
-continued
E31
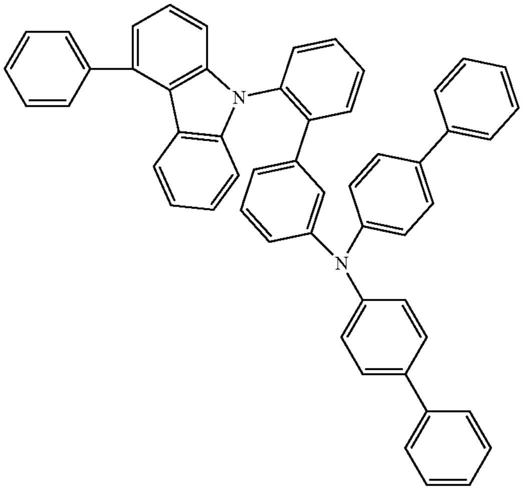
E32
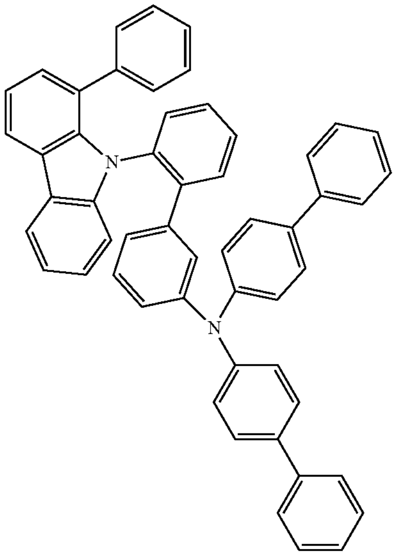
[Compound Group 1F]
F1
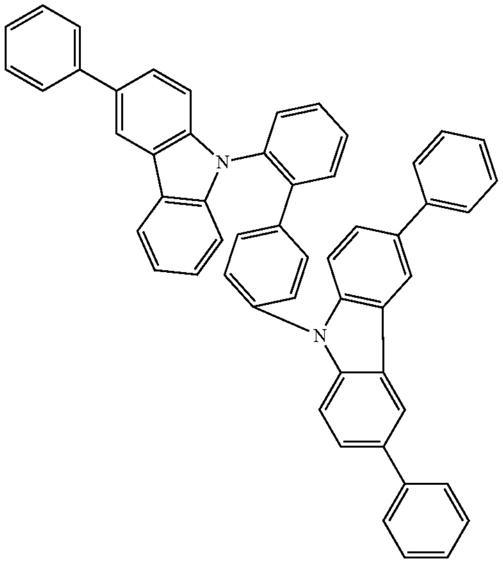

-continued
F2
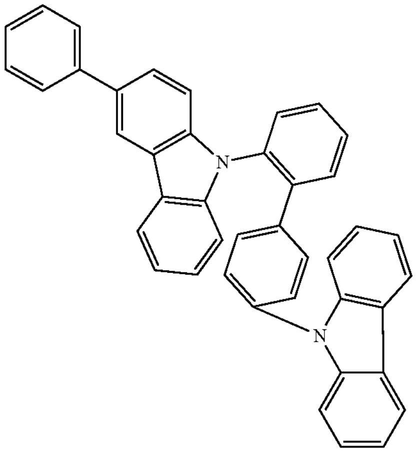
F3
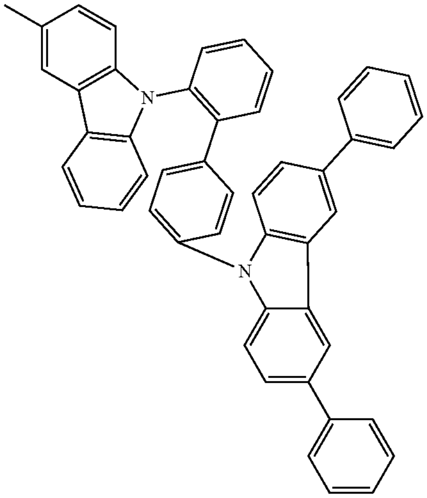
F4
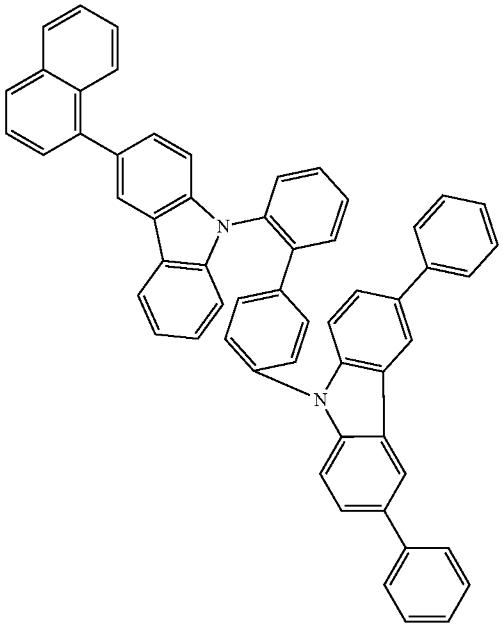
-continued
F5
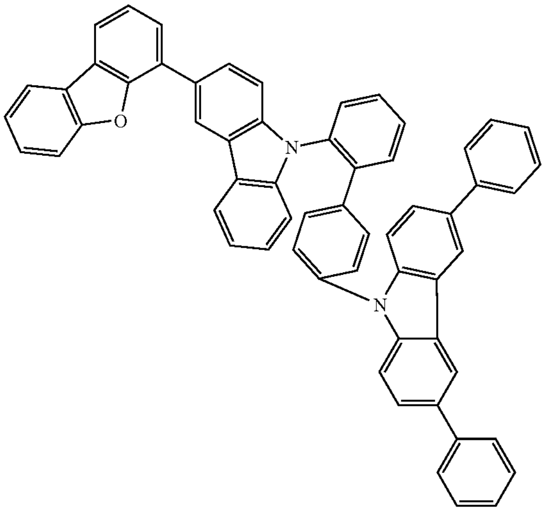
F6
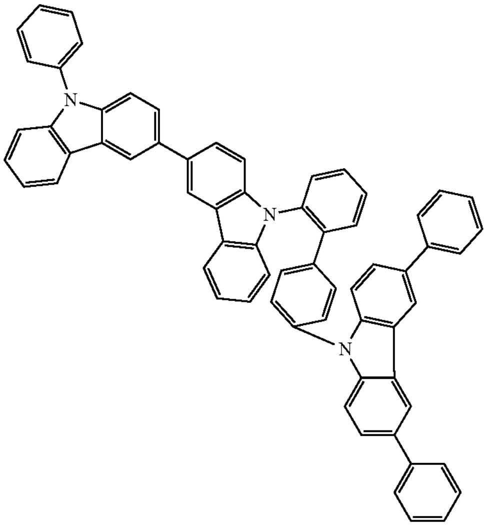

-continued
F7
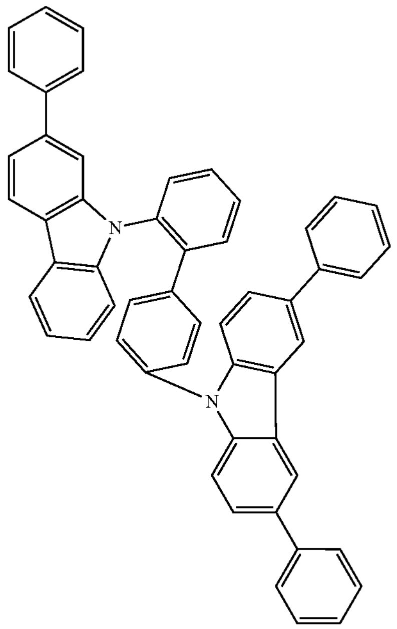
F8
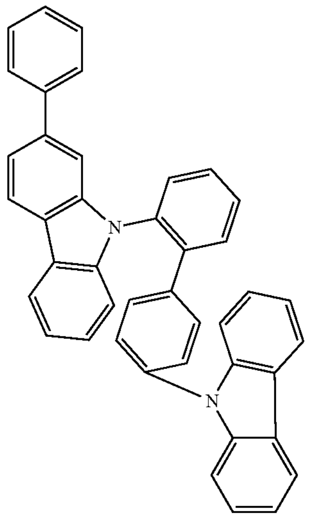
-continued
F9
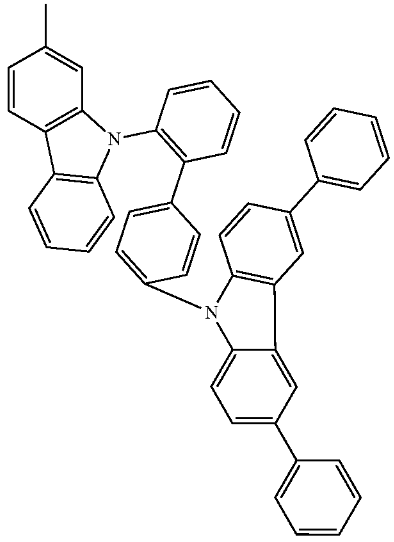
F10
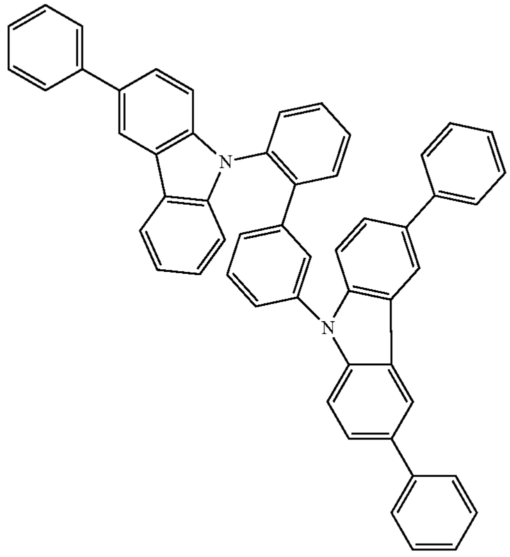
F11
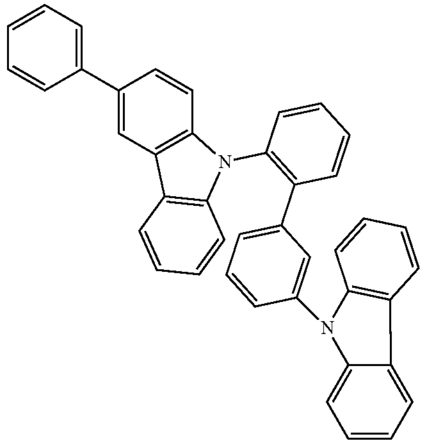

-continued
F12
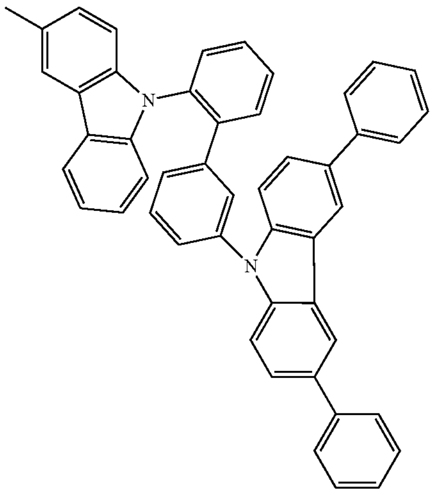
F13
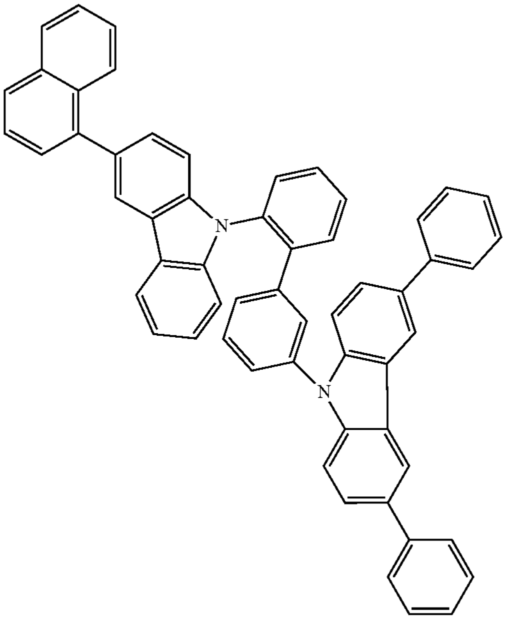
F14
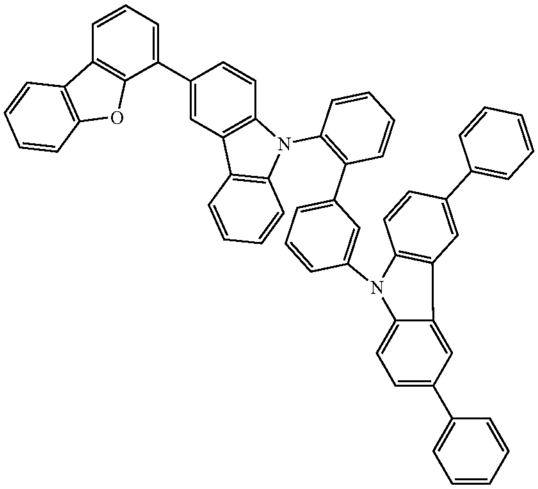
-continued
F15
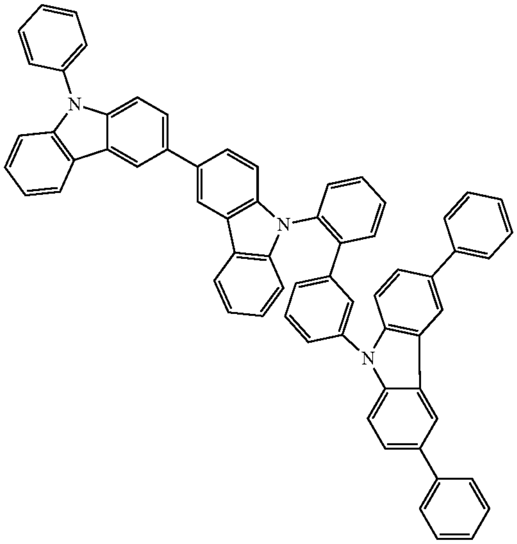
F16
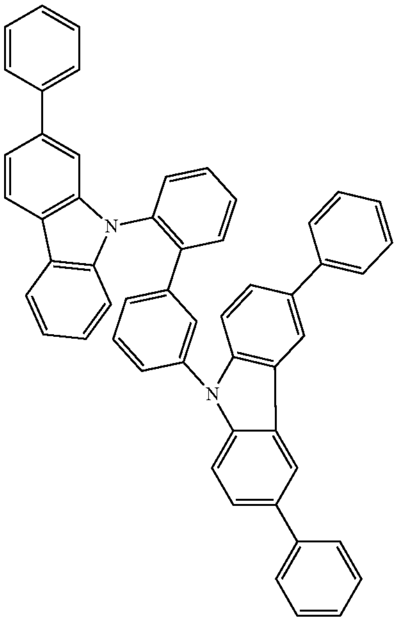

-continued
F17
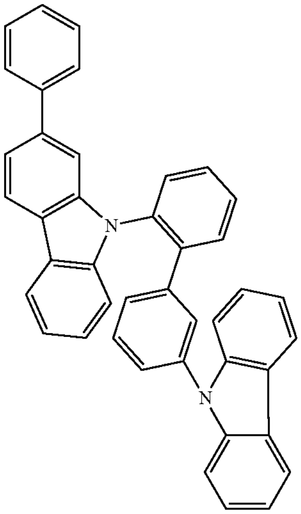
F18
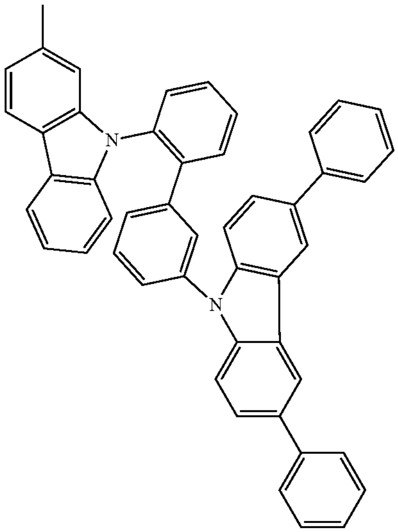
[Compound Group 1G]
G1
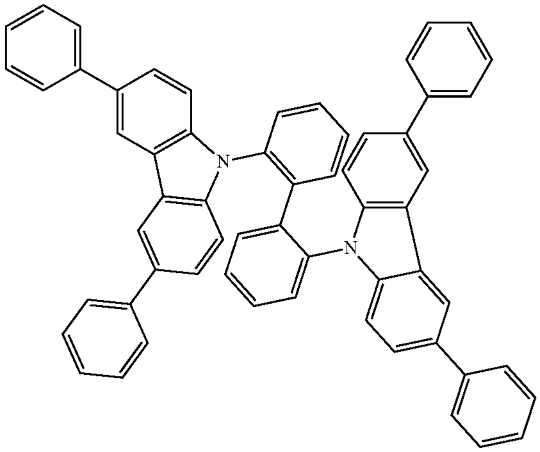
-continued
G2
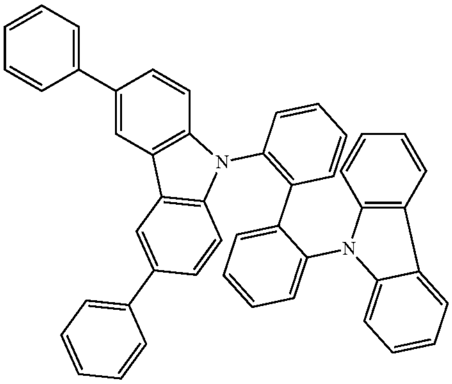
G3
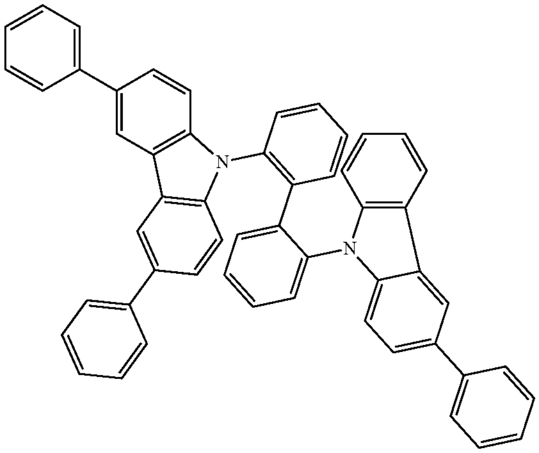
G4
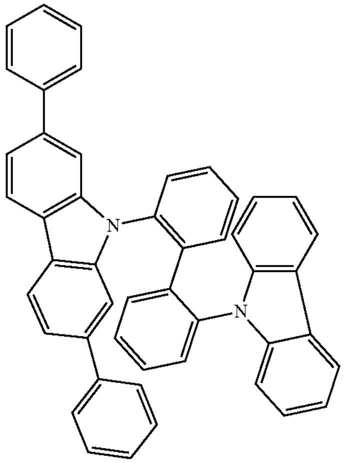

-continued
G5
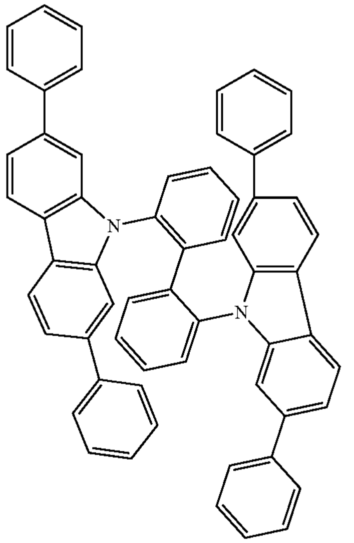
G6
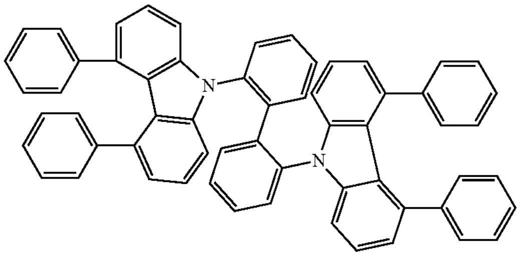
G7
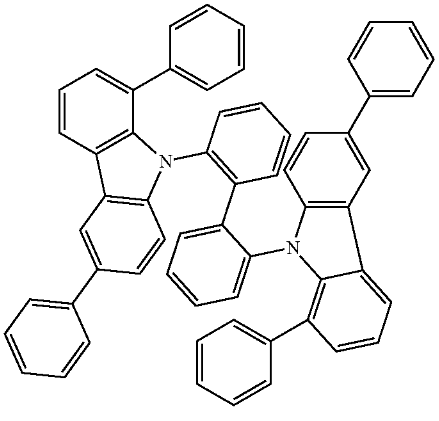
-continued
G8
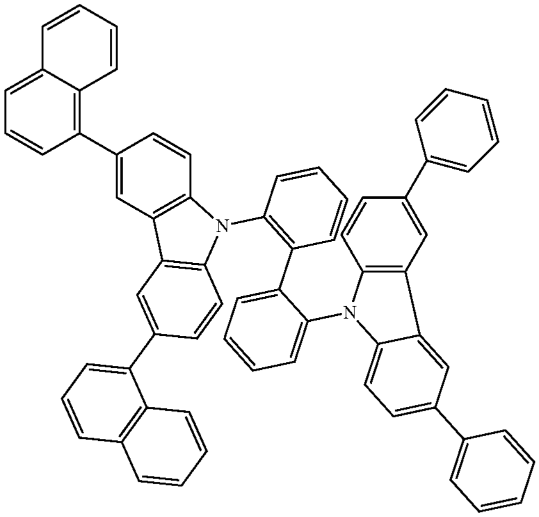
G9
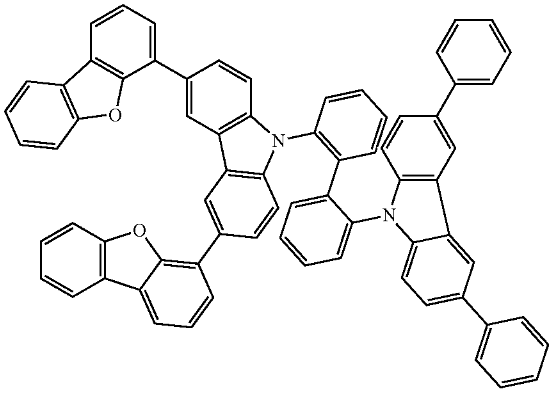
G10
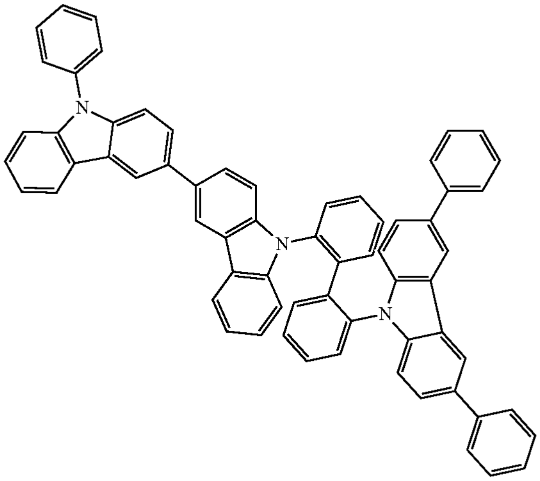

-continued
G11
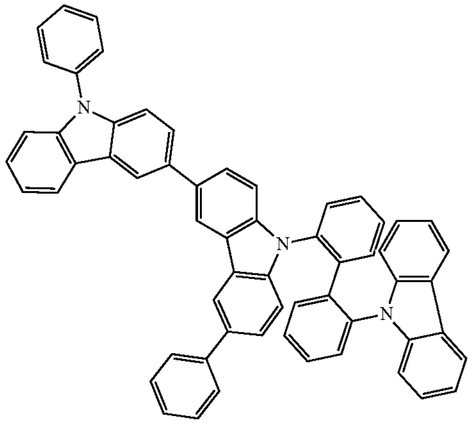
G12
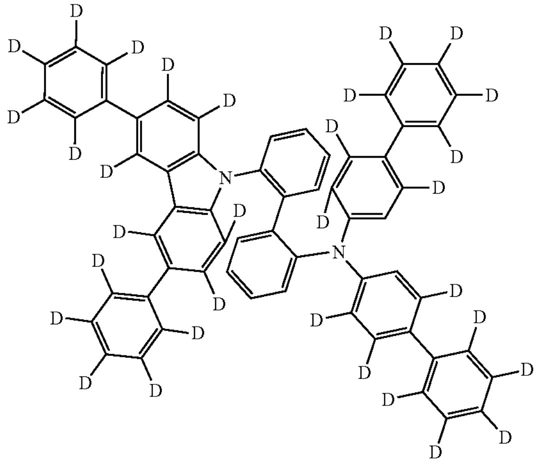
G13
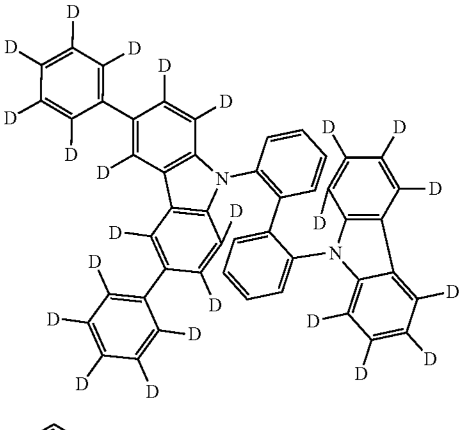
G14
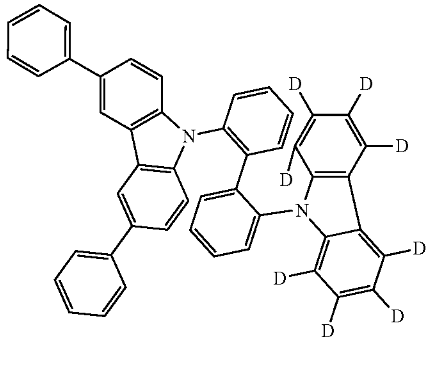
-continued
[Compound Group 1H]
H1
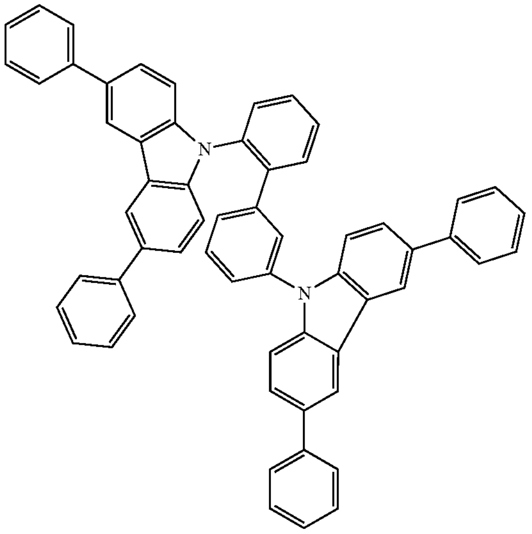
H2
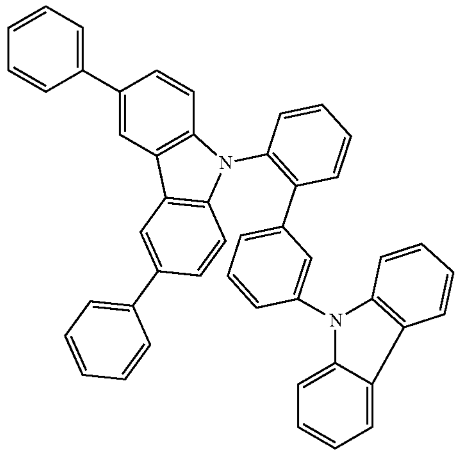
H3
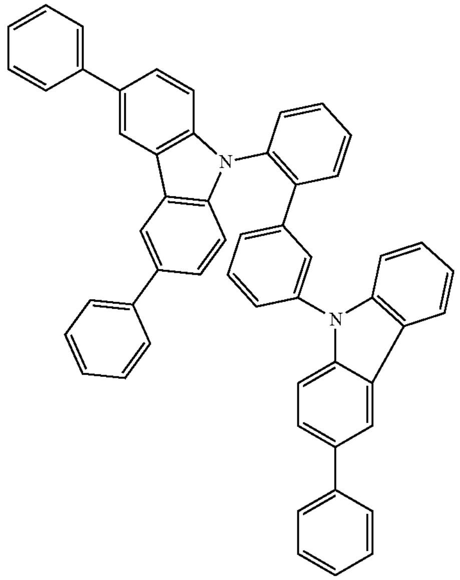

-continued
H4
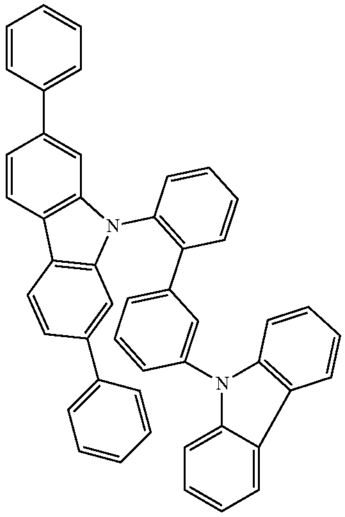
H5
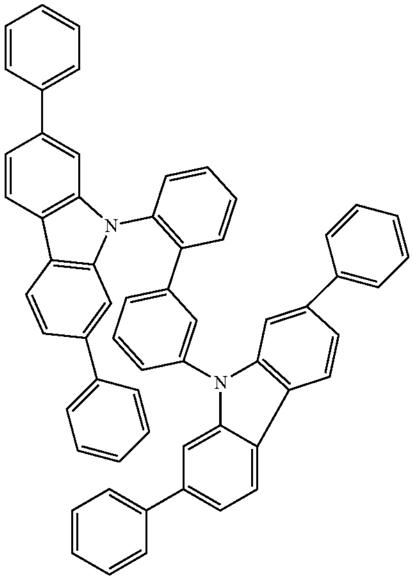
H6
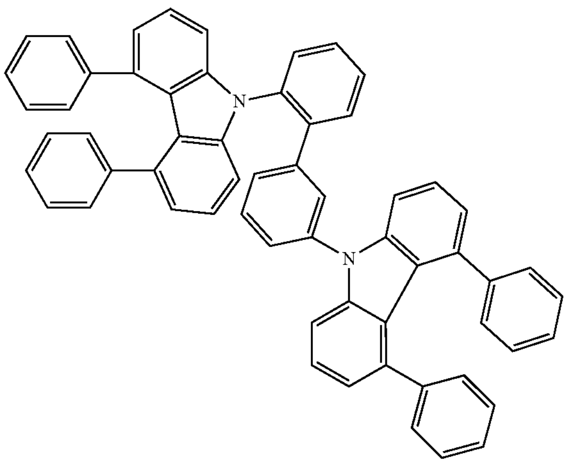
-continued
H7
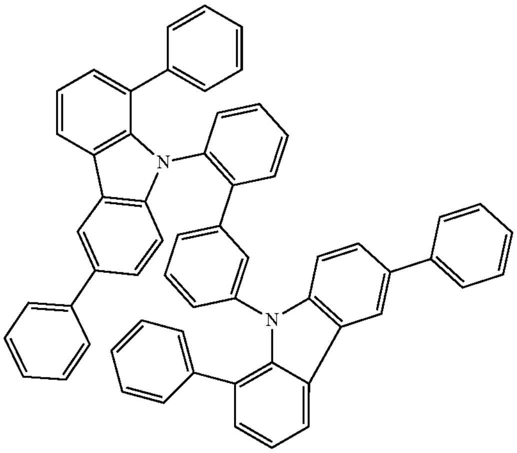
H8
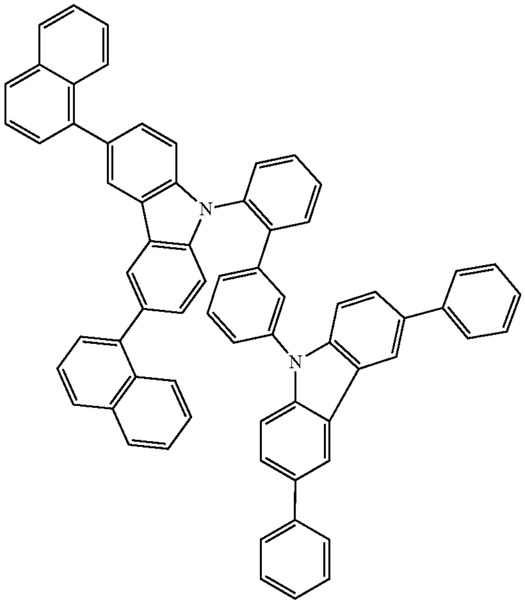
H9
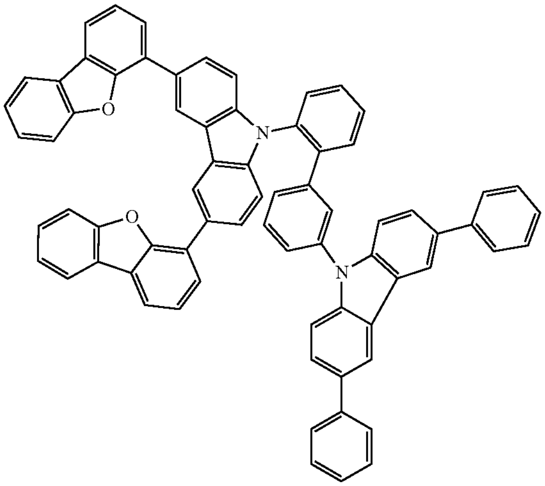

-continued
H10
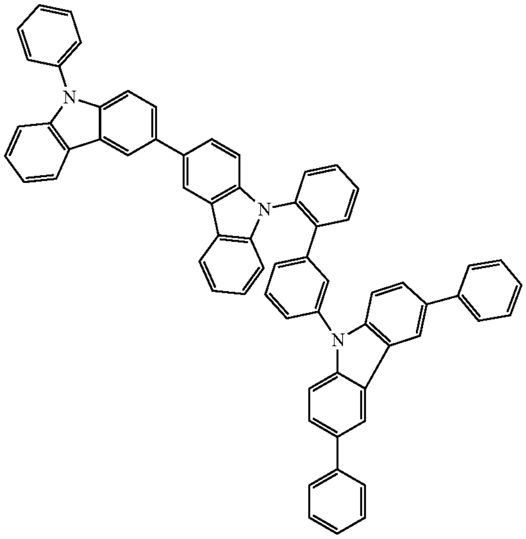
H11
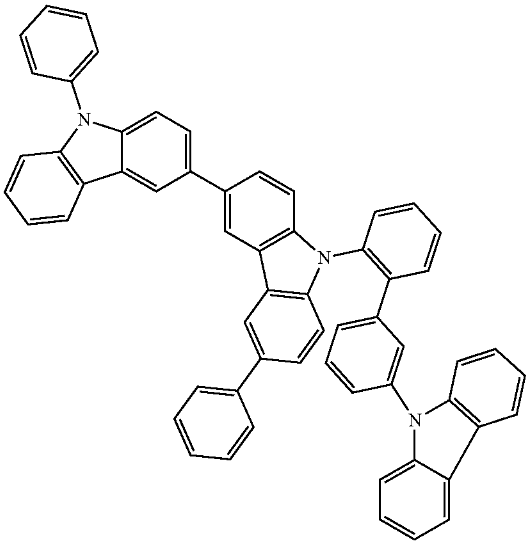
-continued
[Compound Group 1I]
I1
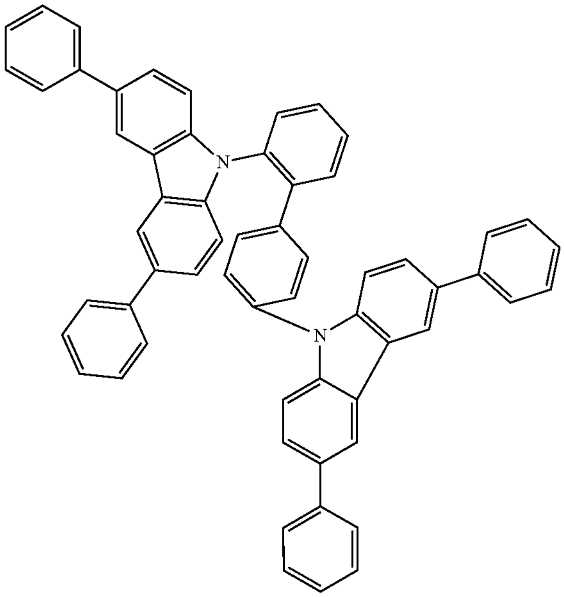
I2
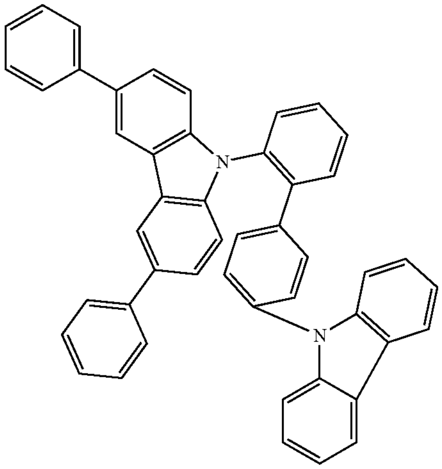

-continued
I3
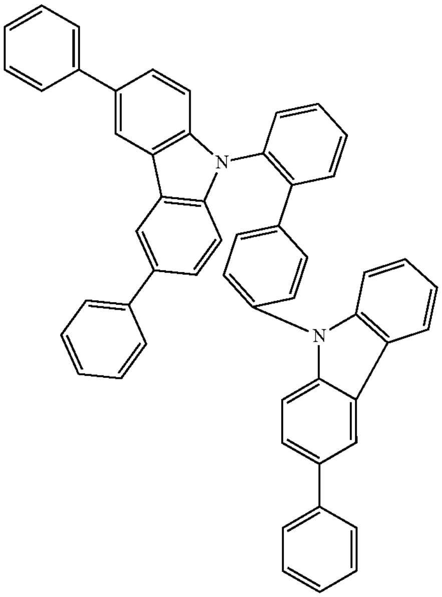
I4
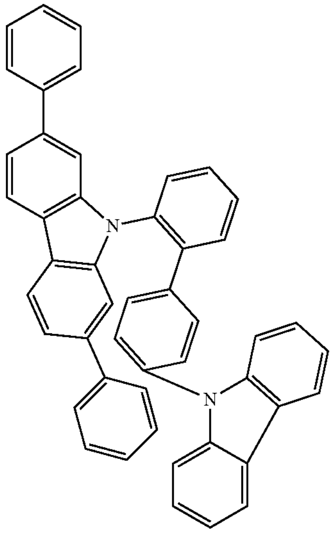
-continued
I5
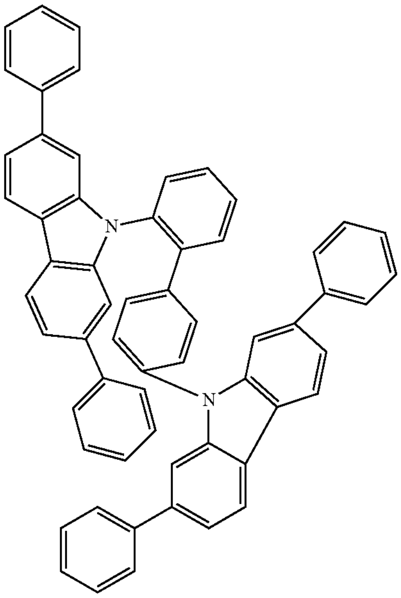
I6
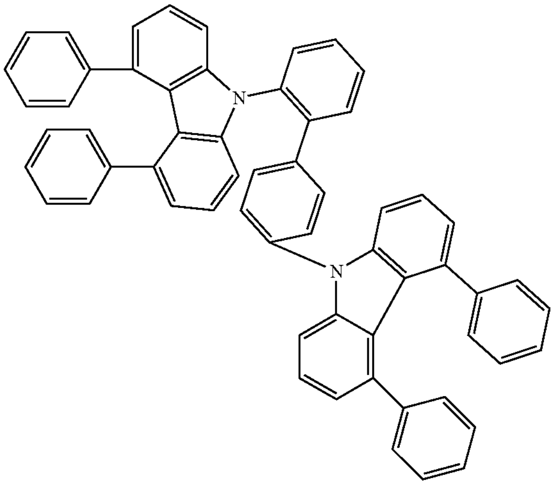
I7
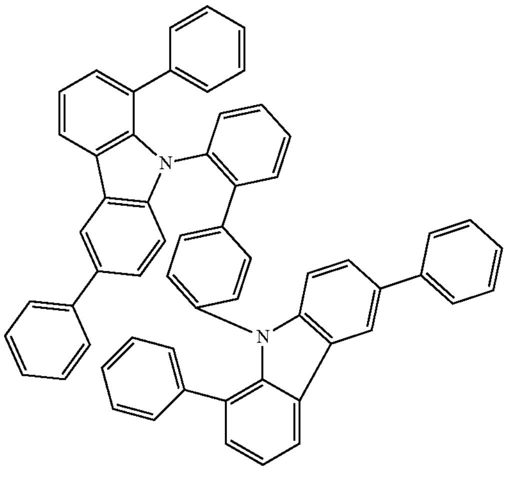

-continued
I8
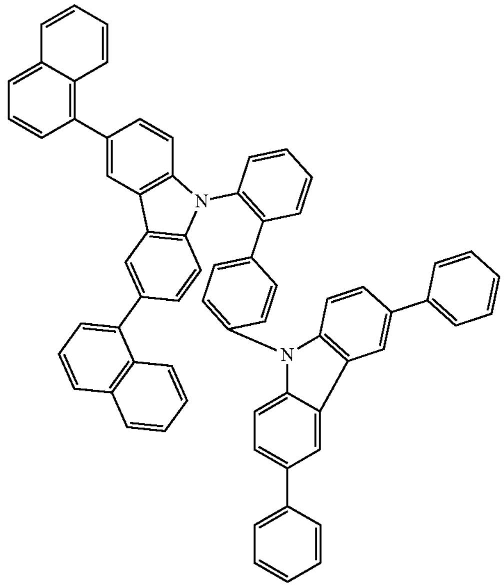
I9
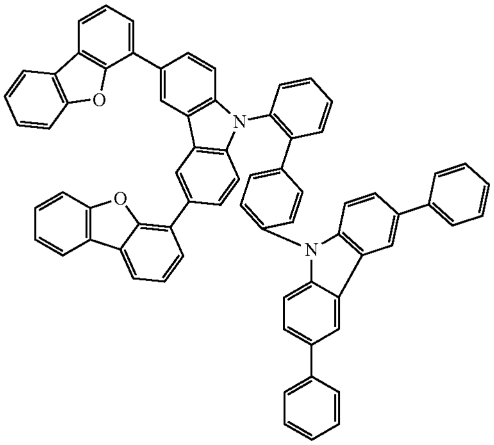
I10
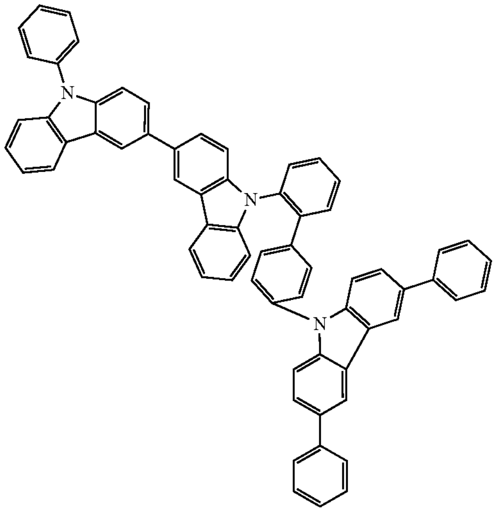
-continued
I11
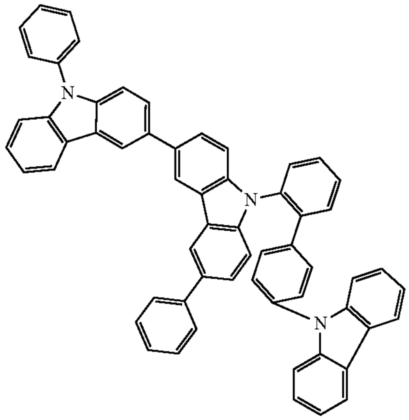
[Compound Group 1J]
J1
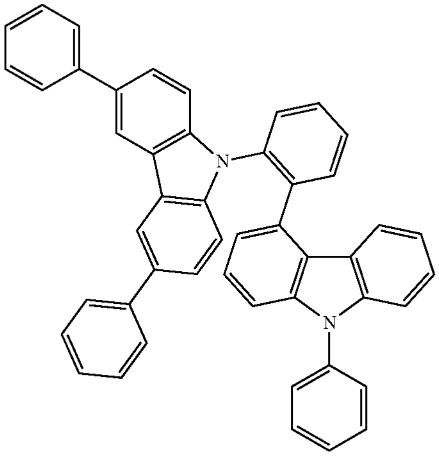
J2
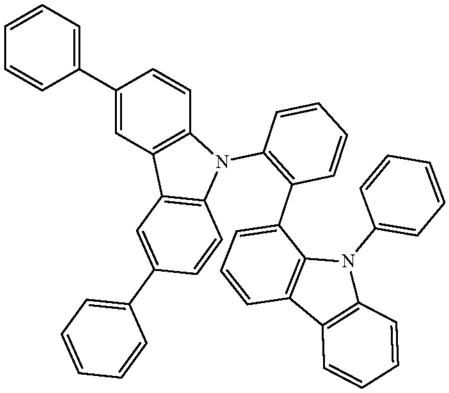

-continued
J3
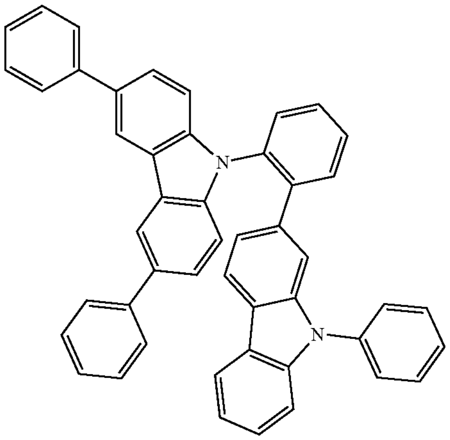
J4
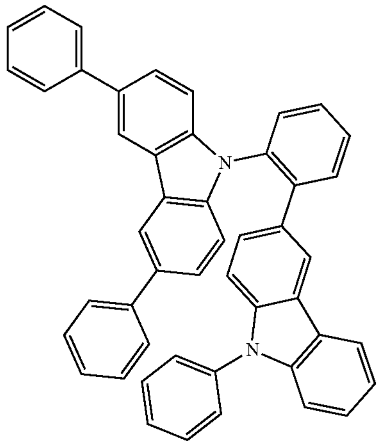
J5
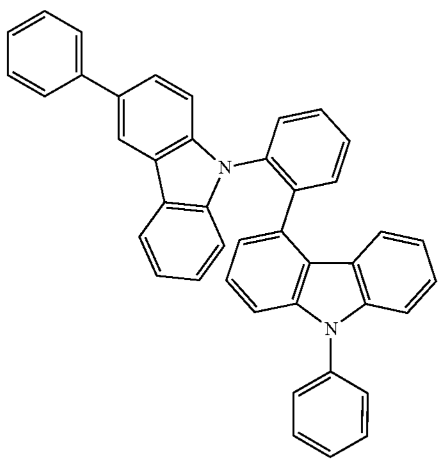
-continued
J6
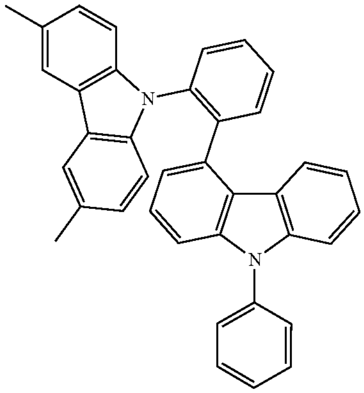
J7
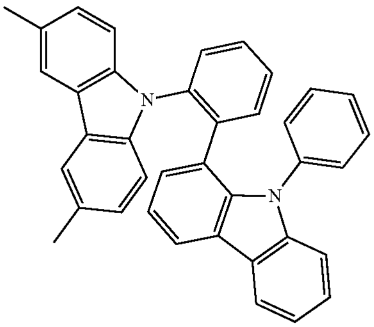
J8
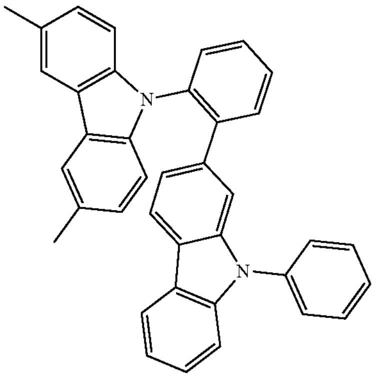
J9
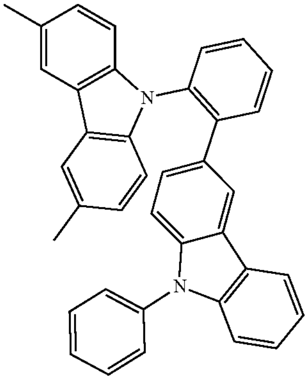

-continued
J10
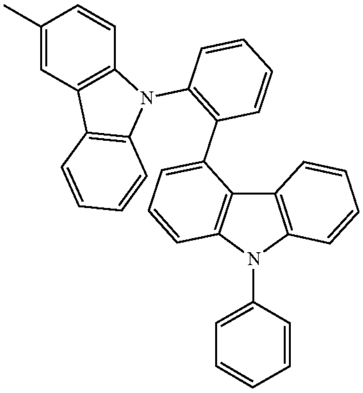
J11
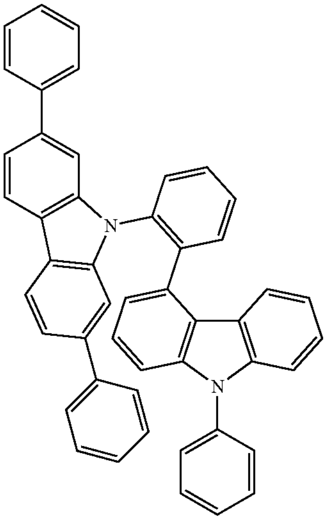
J12
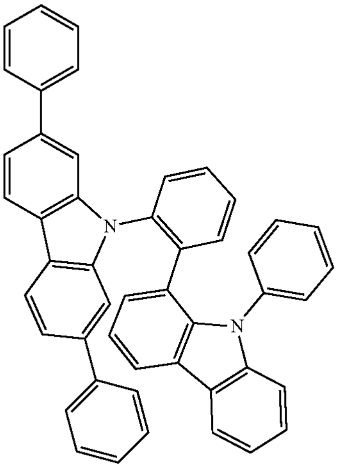
-continued
J13
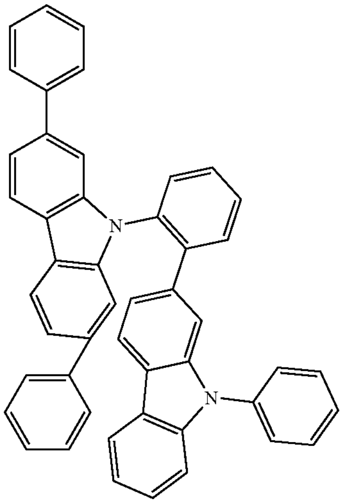
J14
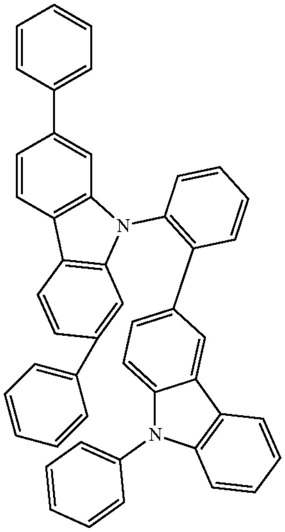
J15
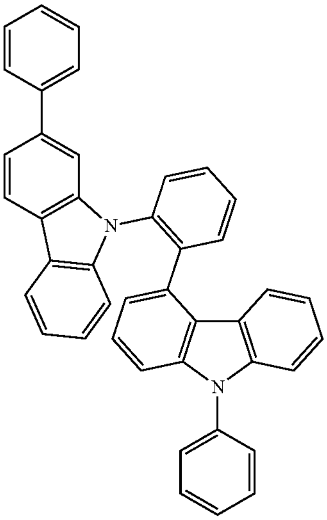

-continued
J16
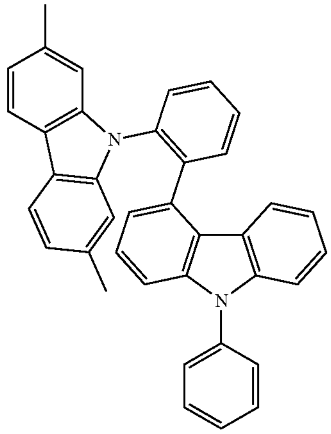
J17
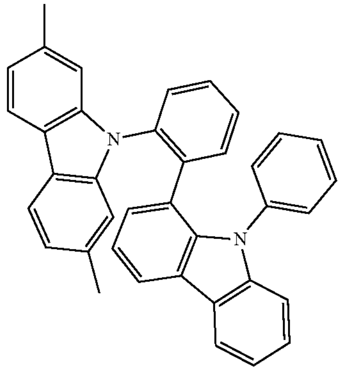
J18
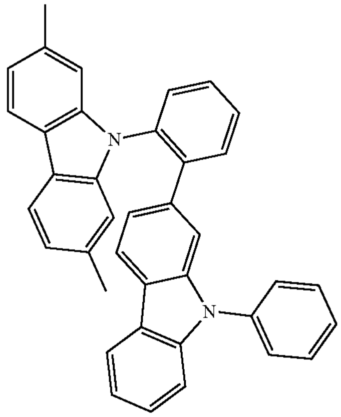
-continued
J19
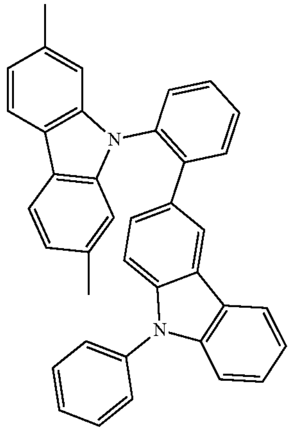
J20
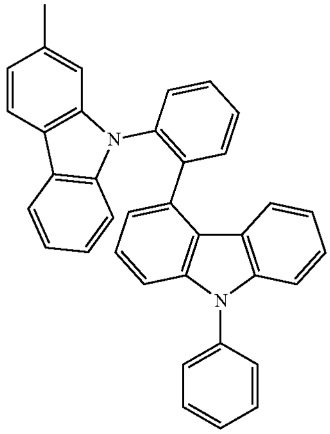
J21
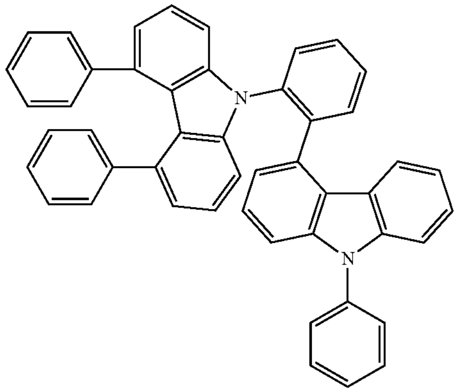
J22
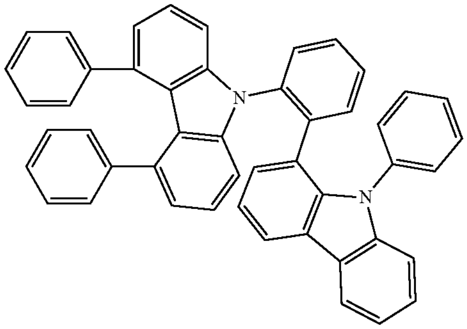

-continued
J23
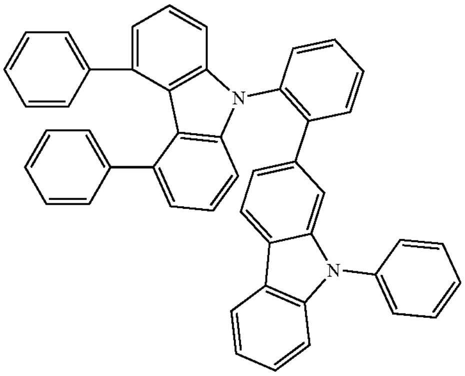
J24
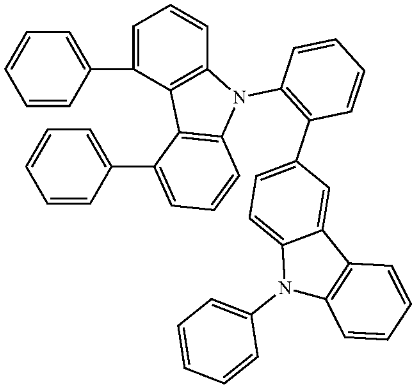
J25
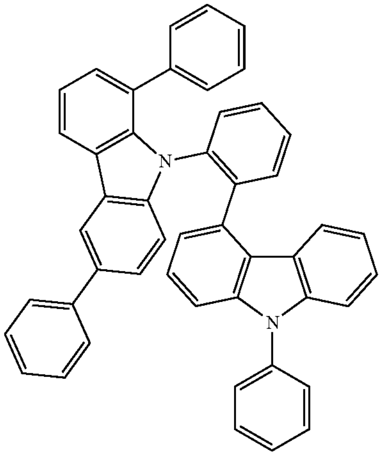
-continued
J26
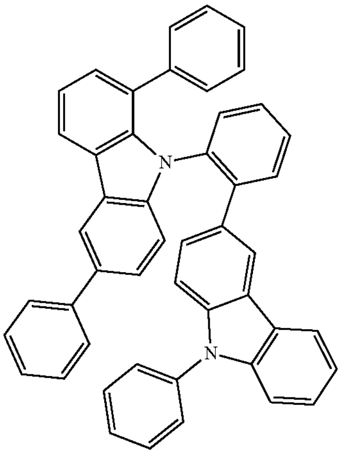
J27
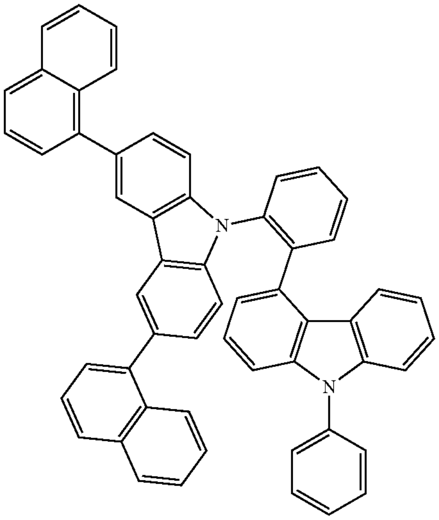

-continued
J28
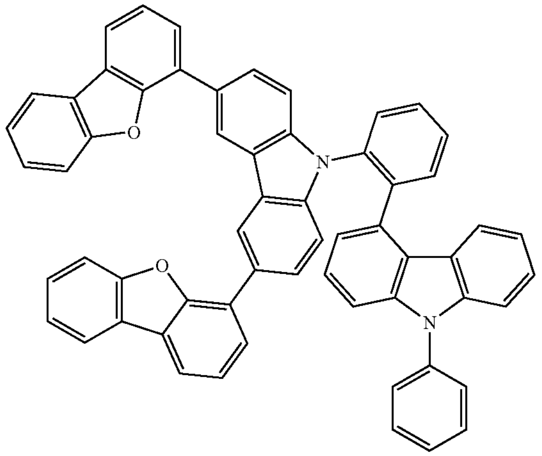
J29
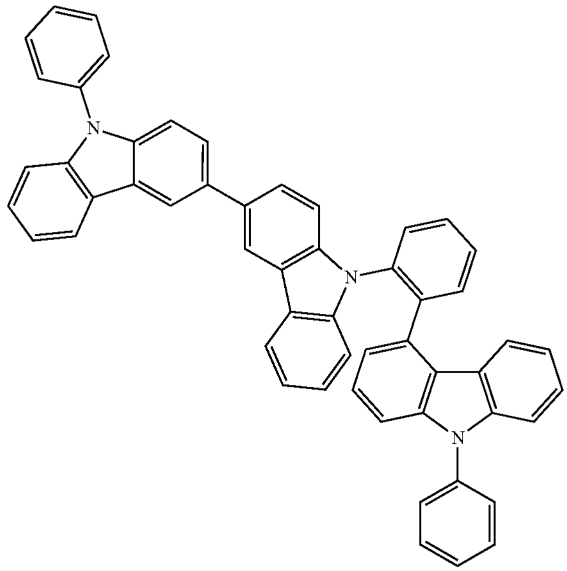
-continued
J30
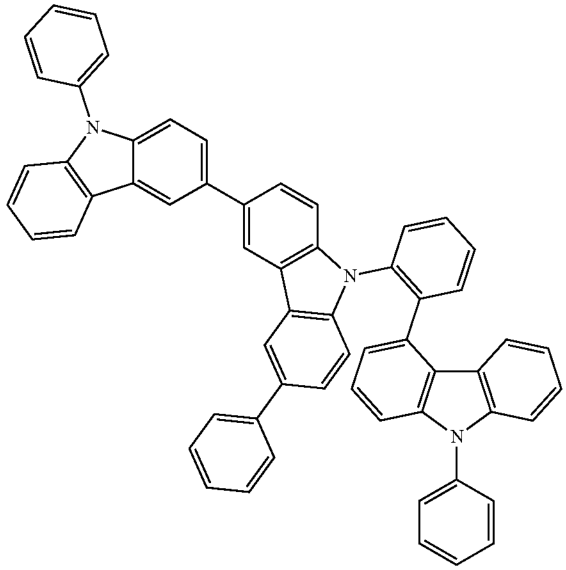
J31
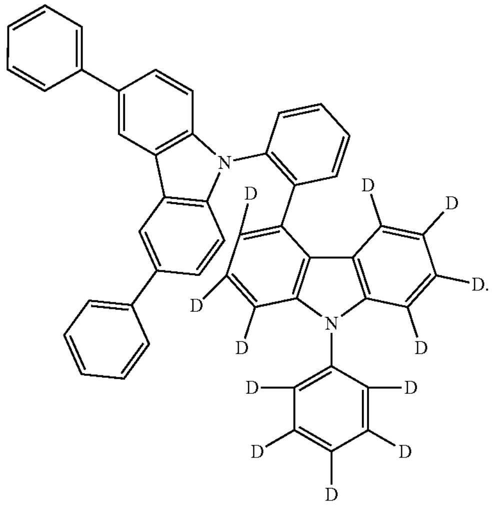
* * * * *